US012097307B2

(12) United States Patent
Vegas et al.

(10) Patent No.: US 12,097,307 B2
(45) Date of Patent: *Sep. 24, 2024

(54) MODIFIED ALGINATES FOR ANTI-FIBROTIC MATERIALS AND APPLICATIONS

(71) Applicants: Massachusetts Institute of Technology, Cambridge, MA (US); The Children's Medical Center Corporation, Boston, MA (US)

(72) Inventors: Arturo Vegas, Belmont, MA (US); Joshua C. Doloff, Quincy, MA (US); Omid Veiseh, Bellaire, TX (US); Minglin Ma, Ithaca, NY (US); Robert S. Langer, Newton, MA (US); Daniel G. Anderson, Framingham, MA (US)

(73) Assignees: MASSACHUSETTS INSTITUTE OF TECHNOLOGY, Cambridge, MA (US); THE CHILDREN'S MEDICAL CENTER CORPORATION, Boston, MA (US)

( * ) Notice: Subject to any disclaimer, the term of this patent is extended or adjusted under 35 U.S.C. 154(b) by 114 days.

This patent is subject to a terminal disclaimer.

(21) Appl. No.: 17/377,124

(22) Filed: Jul. 15, 2021

(65) Prior Publication Data

US 2022/0031913 A1 Feb. 3, 2022

Related U.S. Application Data

(63) Continuation of application No. 16/289,390, filed on Feb. 28, 2019, now Pat. No. 11,090,413, which is a continuation of application No. 15/588,475, filed on May 5, 2017, now Pat. No. 10,729,818, which is a continuation of application No. 15/341,110, filed on Nov. 2, 2016, now Pat. No. 10,709,818, which is a continuation of application No. PCT/US2016/059967, filed on Nov. 1, 2016.

(60) Provisional application No. 62/249,335, filed on Nov. 1, 2015.

(51) Int. Cl.
| | |
|---|---|
| A61K 9/50 | (2006.01) |
| A61K 9/00 | (2006.01) |
| A61K 9/48 | (2006.01) |
| A61K 35/39 | (2015.01) |
| A61K 47/36 | (2006.01) |
| A61L 29/08 | (2006.01) |
| A61L 31/10 | (2006.01) |
| A61L 33/08 | (2006.01) |
| C07D 487/04 | (2006.01) |
| C08B 37/00 | (2006.01) |
| C12N 5/00 | (2006.01) |
| C12N 5/071 | (2010.01) |

(52) U.S. Cl.
CPC .......... *A61L 29/085* (2013.01); *A61K 9/0024* (2013.01); *A61K 9/4816* (2013.01); *A61K 9/5036* (2013.01); *A61K 35/39* (2013.01); *A61K 47/36* (2013.01); *A61L 31/10* (2013.01); *A61L 33/08* (2013.01); *C07D 487/04* (2013.01); *C08B 37/0084* (2013.01); *C12N 5/0012* (2013.01); *C12N 5/0677* (2013.01)

(58) Field of Classification Search
CPC ........ A61L 29/085; A61L 31/10; A61L 33/08; A61K 9/0024; A61K 9/4816; A61K 9/5036; A61K 35/39; A61K 47/36; C07D 487/04; C08F 37/0084; C12N 5/0012; C12N 5/0677
See application file for complete search history.

(56) References Cited

U.S. PATENT DOCUMENTS

| | | | |
|---|---|---|---|
| 2,881,161 A | 4/1959 | Kohler | |
| 4,352,883 A | 10/1982 | Lim | |
| 2,860,130 A | 11/1985 | McNeely | |
| 4,816,567 A | 3/1989 | Cabilly | |
| 4,868,121 A | 9/1989 | Scharp | |
| 5,273,904 A | 12/1993 | Langley | |
| 5,322,790 A | 6/1994 | Scharp | |
| 5,336,668 A | 8/1994 | Dellavalle | |
| 5,443,505 A | 8/1995 | Wong | |
| 5,447,863 A | 9/1995 | Langley | |
| 5,605,835 A | 2/1997 | Hu | |
| 5,624,821 A | 4/1997 | Winter | |
| 5,821,121 A | 10/1998 | Brothers | |

(Continued)

FOREIGN PATENT DOCUMENTS

| | | |
|---|---|---|
| CN | 101565469 | 10/2009 |
| DE | 102005049833 | 4/2007 |

(Continued)

OTHER PUBLICATIONS

Aebischer, et al, "Transplantation of polymer encapsulated neurotransmitter secreting cells: effect of the encapsulation technique", J Biorech Eng., 113(2):178-83 (1991).

(Continued)

*Primary Examiner* — Alma Pipic
(74) *Attorney, Agent, or Firm* — PABST PATENT GROUP LLP

(57) ABSTRACT

Covalently modified alginate polymers, possessing enhanced biocompatibility and tailored physiochemical properties, as well as methods of making and use thereof, are disclosed herein. The covalently modified alginates are useful as a matrix for coating of any material where reduced fibrosis is desired, such as encapsulated cells for transplantation and medical devices implanted or used in the body.

22 Claims, 10 Drawing Sheets

Specification includes a Sequence Listing.

(56) References Cited

U.S. PATENT DOCUMENTS

| | | | |
|---|---|---|---|
| 5,876,452 | A | 3/1999 | Athanasiou |
| 6,129,761 | A | 10/2000 | Hubbell |
| 6,159,531 | A | 12/2000 | Dang |
| 6,194,551 | B1 | 2/2001 | Idusogie |
| 7,682,699 | B2 | 3/2010 | Wind |
| 7,807,150 | B2 | 10/2010 | Griffith |
| 10,709,818 | B2 * | 7/2020 | Vegas |
| 11,090,413 | B2 * | 8/2021 | Vegas |
| 2003/0068308 | A1 * | 4/2003 | Rozga |
| 2003/0113478 | A1 | 6/2003 | Dang |
| 2004/0253532 | A1 | 12/2004 | Wu |
| 2006/0286141 | A1 | 12/2006 | Campbell |
| 2008/0044900 | A1 | 2/2008 | Mooney |
| 2008/0177021 | A1 | 7/2008 | Berlin |
| 2008/0199914 | A1 | 8/2008 | Skjak-Braek |
| 2008/0242738 | A1 | 10/2008 | Marks |
| 2008/0268189 | A1 | 10/2008 | Sun |
| 2009/0148591 | A1 | 6/2009 | Wang |
| 2009/0197791 | A1 | 8/2009 | Balastre |
| 2010/0272776 | A1 * | 10/2010 | Harlow |
| 2011/0111004 | A1 | 5/2011 | Barbieri |
| 2011/0319569 | A1 | 12/2011 | Emrick |
| 2012/0009159 | A1 | 1/2012 | Humayun |
| 2012/0041546 | A1 | 2/2012 | Belcheva |
| 2012/0121657 | A1 | 5/2012 | Zhou |
| 2013/0149351 | A1 | 6/2013 | Lee |
| 2014/0094671 | A1 | 4/2014 | Boock |
| 2015/0183939 | A1 | 7/2015 | Lequeux |
| 2015/0368713 | A1 | 12/2015 | Bharti |
| 2016/0030360 | A1 | 2/2016 | Vegas |
| 2017/0014776 | A1 | 1/2017 | Li |
| 2019/0290170 | A1 | 9/2019 | Chen |

FOREIGN PATENT DOCUMENTS

| | | | |
|---|---|---|---|
| EP | 1614696 | | 1/2006 |
| FR | 2699545 | | 6/1994 |
| GB | 676618 | | 7/1952 |
| GB | 768309 | | 2/1957 |
| WO | 9107951 | | 6/1991 |
| WO | 9900070 | | 1/1999 |
| WO | 99/05989 | * | 2/1999 |
| WO | 9958572 | | 11/1999 |
| WO | 2003010354 | | 2/2003 |
| WO | 2003085372 | | 10/2003 |
| WO | 2005/056026 | A1 * | 6/2005 |
| WO | 2005058382 | | 6/2005 |
| WO | 2005063147 | | 7/2005 |
| WO | 2009032158 | | 3/2009 |
| WO | 2010090767 | | 8/2010 |
| WO | 2012167223 | | 12/2012 |
| WO | 2013121983 | | 8/2013 |
| WO | 2014044597 | | 3/2014 |
| WO | 2014044697 | | 3/2014 |
| WO | 2014052080 | | 4/2014 |
| WO | 2015054484 | | 4/2015 |
| WO | 2015187204 | | 12/2015 |
| WO | 2016019391 | | 3/2017 |

OTHER PUBLICATIONS

Ahad, et al., "Surface modification of polymers for biocompatibility via exposure to extreme ultraviolet radiation", Society for Biomaterials, 3296-3310 (2013).

Anderson, "Biological Repsonses to Materials", Annu. Rev. Mater. Res.,31:81-110 (2001).

Anderson, et al., "Conotoxins: Potential weapons from the sea", J. Bioterr. Biodef., 3:120 (2012).

Anderson, et al., "Foreign body reaction to biomaterials", Semin. Immunol., 20:86-100 (2008).

Angal, et al., "A single amino acid substitution abolishes the heterogeneity of chimeric mouse/human (IgG4) antibody", Mol. Immunol., 30:105-08 (1993).

Basta, et al., "Long-term metabolic and immunological follow-up of nonimmunosuppressed patients with type 1 diabetes treated with microencapsulated islet allografts: four cases", Diabetes Care, 34:2406-9 (2011).

Belikov, et al., Pharmaceutical Chemistry, Moscow, Higher School, 43-47 (1993).

Bell and Peppas, "Biomedical membranes from hydrogels and interpolymer complexes", Adv. Polym. Sci., 122:125-175 (1995).

Calafiore, et al., "Microencapsulated pancreatic islet allografts into nonimmunosuppressed patients with type 1 diabetes: first two cases", Diabetes Care, 29:137-8, (2006).

Chem. Europe "Hexazine", https://www.chemeurope.com/en/encylopedia/Hexazine.html, 2 pages, retrieved from Internet Nov. 4, 2020.

Chen, "Assessment of treatment response after chemoradiation of head and neck cancer", Macromolecules, 45:119-127 (2013).

Chen, "Differentiation of rat marrow mesenchymal stem cells into pancreatic islet beta-cells", World Journal of Gastroenterology, 10(20): 3016-3020 (2004).

Chen, et al., "Multifunctional Biocompatible Membrane and its application to fabricate a miniaturized glucose sensor with potential for us in vivo", Biomedical Microdevices, 1(2):155-166 (1998).

Chien, et al., "Surface conjugation of zwitterionic polymers to inhibit cell adhesion and protein adsorption", Colloids Surfaces B, 107:152-9 (2013).

Chu, et al., "A soft and flexible biosensor using phospholipid polymer for continuous glucose monitoring", Biomedical Microdevices, 11(4): 837-842 (2009).

Costa, et al., "Covalent immobilization of antimicrobial peptides (AMPs) onto biomaterial surfaces", Acta Biomaterialia, 7(5): 1431-1440 (2010).

Dai, et al., "Swelling characteristics and drug delivery properties of nifedipine-loaded pH sensitive alginate-chitosan hydrogel beads", Journal of Biomedical Materials Research Part B: Applied biomaterials 86(2):493-500 (2008).

Dang, et al., "Spatiotemporal effects of a controlled-release anti-inflammatory drug on the cellular dynamics of host response", Biomaterials, 32:4464-70 (2011).

De Groot, et al., "Causes of limited survival of microencapsulated pancreatic islet grafts", J Surg Res., 121:141-50 (2004).

de Vos, et al., "Improved biocompatibility but limited graft survival after purification of alginate for microencapsulation of pancreatic islets", Diabetologia, 40(3):262-270 (1997).

de Vos, et al., "Alginate-based microcapsules for immunoisolation of pancreatic islets", Biomaterials, 27:5603-17 (2006).

Dolgin, "Encapsulate this", Nat. Med. 20:9-11 (2014).

Dusseault, "Evaluation of alginate purification methods: effect on polyphenol, endotoxin, and protein contamination", J Biomed Mater Res A., 76(2):243-251 (2006).

Elliot, et al., "Intraperitoneal alginate-encapsulated neonatal porcine islets in a placebo-controlled study with 16 diabetic cynomolgus primates", Transplant Proc., 37:3505-8 (2005).

Elliot, et al., "Live encapsulated porcine islets from a type 1 diabetic patient 9.5 yr after xenotransplantation",. Xenotransplantation., 14(2):157-61 (2007).

Extended European Search Report issued for EP 18 16 2427 mailed Jun. 19, 2018.

Ferreira, et al., "Biocompatibility of chemoenzymatically derived dextran-acrylate hydrogels"., J. Biomed. Mater. Res., 68A :584-96 (2004).

Ferreira, et al., "Enzymatic synthesis of dextran-containing hydrogels". Biomaterials, 23: 3957-67 (2002).

Field, et al., "Improved islet isolation from rat pancreas using 35% bovine serum albumin in combination with Dextran gradient separation", Transplantation, 61(10):1554-6 (1996).

Garrett, et al., "New observations on peptide bond formation using CDMT", Tetrahedron Lett., 43(23):4161-4 (2002).

Gattas-Asfura, "Chemoselective cross-linking and functionalization of alginate via Staudinger ligation", Biomacromolecules, 10:3122-3129 (2009).

Gibly, et al., "Advancing islet transplantation: from engraftment to the immune response" Diabetologia, 54:2494-2505 (2011).

(56) References Cited

OTHER PUBLICATIONS

Grainger, "All charged up about implanted biomaterials", Nat. Biotechnol. 31:507-9 (2013).
Gruber, et al., "Efficient tumor cell lysis mediated by a bispecific single chain antibody expressed in *Escherichia coli*.", J. Immunol., 152(11):5368 (1994).
Gulino, et al., "Tissue Response to Neural Implant: The Use of Model Systems Toward New Design Solutions of Implantable Microelectrodes", Frontiers in Neuroscience, 13:689:1-24 (2019).
Hall, "Microencapsulation of islets within alginate/poly(ethylene glycol) gels cross-linked via Staudinger ligation", Acta Biomaterialia, 7:614-624 (2011).
Harding and Reynolds, "Combating medical device fouling", Trends Biotechnol. 32:140-6 (2014).
Hetrick, et al., "Reduced foreign body response at nitric oxide-releasing subcutaneous implants" Biomaterials 28:457-80 (2007).
Hirshberg, "Lessons learned from the international trial of the Edmonton protocol for islet transplantation", Curr Diab Rep., 7:301-3 (2007).
Hollinger, et al., "Diabodies": small bivalent and bispecific antibody fragments, PNAS, 90:6444-8 (1993).
Hudalla, et al., "Immobilization of peptides with distinct biological activities onto stem cell culture substrates using orthogonal chemistries", Langmuir, 26(9):6449-6456 (2010).
Huh et al., "From 3D cell culture to organs-on-chips" Trends in Cell Biology, 21(12):745-754 (2011).
International Search Report for PCT/US2016/059967 mailed Feb. 20, 2017.
Jacobs-Tulleneers-Thevissen, et al., "Sustained function of alginate-encapsulated human islet cell implants in the peritoneal cavity of mice leading to a pilot study in a type 1 diabetic patient", Diabetologia 56:1605-14 (2013).
King, et al., "The effect of host factors and capsule composition on the cellular overgrowth on implanted alginate capsules", J. Biomed. Mater. Res., 57:374-83 (2001).
Klock, et al., "Production of purified alginates suitable for use in immunoisolated transplantation", Appl Microbiol Biotechnol., 40:638-43 (1994).
Kolb, et al., "Differences in the fibrogenic response after transfer of active transforming growth factor-beta1 gene to lungs of "fibrosis-prone" and "fibrosis-resistant" mouse strains", J. Respir. Cell. Mol. Biol., 27:141-50 (2002).
Kovach, et al., "The Effects of PEG-based surface modification of PDMS microchannels on long-term hemocompatibility", J. of Biomedical Research Pt. A, 102A:4195-4205 (2014).
Langer, "Perspectives and Challenges in Tissue Engineering and Regenerative Medicine", Adv. Mater. 21:3235-3236 (2009).
Lee and Mooney, "Hydrogels for tissue engineering", Chem. Rev. 101:1869-79 (2001).
Lee, et al., "An aqueous=Based surface Modification of Poly(dimethylsiloxane) with Polyethylene glycol) to Prevent Blofouling", Langmuir, 21:11957-11962 (2005).
Lee, et al., "Development and characterization of an alginate-impregnated polyester vascular graft", Journal of Biomedical Materials Research, 36(2):200-208 (1997).
Lesney, "Going Cellular", Modern Drug Discovery 4(3), 45-46, 49, 50 (2001).
Lim and Sun, "Microencapsulated islets as bioartificial endocrine pancreas", Science, 210:908-10 (1980).
Lin, et al., "Photoreactive Polymers Bearing a Zwitterionic Phosphorylcholine Group for Surface Modification of Biomaterials", Applied Materials & Interfaces, 7(31):17489-17498 (2015).
Linetsky, et al., "Improved human islet isolation using a new enzyme blend, liberase", Diabetes 46:1120-3 (1997).
Massia and Stark, "Immobilized RGD peptides on surface-grafted dextran promote biospecific cell attachment", Biomed. Mater. Res., 56 :390-9 (2001).
Mehvar, "Dextrans for targeted and sustained delivery of therapeutic and imaging agents", J. Control. Rel., 69:1-25 (2000).

Morch, "Effect of Ca2+, Ba2+, and Sr2+ on alginate microbeads", Biomacromolecules 7(5): 1471-1480 (2006).
Morrison, et al., "Chimeric human antibody molecules: mouse antigen-binding domains with human constant region domains.", PNAS, 81:6851-5 (1984).
O'Sullivan, et al., "Islets transplanted in immunoisolation devices: a review of the progress and the challenges that remain", Endocrine Reviews, 32:827-44 (2011).
Omer, et al., "Survival and maturation of microencapsulated porcine neonatal pancreatic cell clusters transplanted into immunocompetent diabetic mice", Diabetes, 52:69-75 (2003).
Osterberg, et al., "Protein-rejecting ability of surface-bound dextran in end-on and side-on configurations: comparison to PEG", J. Biomed. Mat. Res., 29:741-7 (1995).
Pedraza, "Engineering an optimal bioartificial pancreas for islet transplantation using bioactive scaffolds", Dissertation (Ph.D.) University of Miami, (2011).
Pedraza, et al., "Macroporous three-dimensional PDMS scaffolds for extrahepatic islet transplantation", Cell Transplantation, 22:1123-1135 (2013).
Pedraza, et al., "Preventing hypoxia-induced cell death", PNAS, 109(11):4245-4250 (2012).
Peppas, et al., "Hydrogels in pharmaceutical formulations", Eur. J. Pharm. Biopharm. 50:27-46 (2000).
Pickup, "Insulin-pump therapy for type 1 diabetes mellitus", N. Engl. J. Med. 366:1616-24 (2012).
Prichard, et al., "Bioluminescence imaging of glucose in tissue surrounding polyurethane and glucose sensor implants", J. Diabetes Sci. Technol., 4:1055-1062 (2010).
Qi, et al., "Five-year follow-up of patients with type 1 diabetes transplanted with allogeneic islets: the UIC experience", Acta Diabetol., 51:833-43 (2014).
Ratner, "A pore way to heal and regenerate: 21st century thinking on biocompatibility". Regenerative Biomaterials, 107-110 (2016).
Ratner, "Reducing capsular thickness and enhancing angiogenesis around implant drug release systems" J. Controlled Release 78:211-218 (2002).
Robertson, "Islet transplantation as a treatment for diabetes—a work in progress", N. Engl. J. Med., 350:694-705 (2004).
Rodriguez, et al., "Quantitative in vivo cytokine analysis at synthetic biomaterial implant sites", J. Biomed. Mater. Res. A ,89:152-9 (2009).
Scharp, et al., "Encapsulated islets for diabetes therapy: history, current progress, and critical issues requiring solution", Adv Drug Deliv Rev., 67-68:35-73 (2014).
Schneider, et al., "Long-term graft function of adult rat and human islets encapsulated in novel alginate-based microcapsules after transplantation in immunocompetent diabetic mice", Diabetes 54:687-93 (2005).
Sharpiro , et al., "Islet transplantation in type 1 diabetes: ongoing challenges, refined procedures, and long-term outcome", Rev Diabet Stud., 9:385-406 (2012).
Shapiro, et al., "International trial of the Edmonton protocol for islet transplantation", N. Engl. J. Med., 355:1318-30 (2006).
Shapiro, et al., "Islet transplantation in seven patients with type 1 diabetes mellitus using a glucocorticoid-free immunosuppressive regimen", N. Engl. J. Med. 343:230-8 (2000).
Shaw, et al., "Global estimates of the prevalence of diabetes for 2010 and 2030", Diabetes Res. Clin. Pract. 87:4-14 (2010).
Skousen, et al. "A strategy to passively reduce inflammation surrounding devices implanted chronically brain tissue by manipulating device surface permeability", Biomaterials, 36:33-43 (2015).
Stowell and Widlanski, "A new method for the phosphorylation of alcohols and phenols", Tetrahedron Lett., 36(11):1825-6 (1995).
Sun, "Microencapsulation of pancreatic islet cells: a bioartificial endocrine pancreas", Methods in Enzymology, 137:575-580 (1988).
Sussman, et al., "Porous implants modulate healing and induce shifts in local macrophage polarization in foreign body reaction", Ann. Biomed. Eng., 42(7):1508-16 (2013).
Tang, et al., "Reprogramming liver-stem WB cells into functional insulin-prodcuing cells by persistent expression of Pdx1-and Pdx1-VP16 mediated by lentiviral vectors", Lab Invest 86(1)83-93 (2006).

(56) References Cited

OTHER PUBLICATIONS

Thevenot, et al., "Surface chemistry influences implant biocompatibility", Curr Top Med Chem., 8(4):270-80 (2008).
Tuch, et al., "Safety and viability of microencapsulated human islets transplanted into diabetic humans", Diabetes Care, 32:1887-9 (2009).
Vallee, et al., "Synthesis and rheological properties of hydrogels based on amphiphilic alginate-amide derivatives", Carbohydrate Research, 344(2):223-228 (2009).
Vegas, et al., "Combinatorial hydrogel library enables identification of materials that mitigate the foreign body response in primates", Nat Biotechnol., 34(3):345-52 (2016).
Veiseh, et al., "Size- and shape-dependent foreign body immune response to materials implanted in rodents and non-human primates", Nat. Mater., 14(6):643-51 (2015).
Vogelm, et al., "Sustained function of alignate-encapsulated human islet cell implants in theperitoneal cavity of mice leading to a pilot study in a type 1 diabetic pateient", Diabetologica, 56:1605-1514 (2013).
Wang, et al., "Significantly reduced absorption and activation of blood components in a membrane oxygenator system coated with crosslinkable zwitterionic copolymer", Acta Biomaterialia, 40(8):153-161 (2016).
Ward, "A review of the foreign-body response to subcutaneously-implanted devices: the role of macrophages and cytokines in biofouling and fibrosis", Diabetes Sci. Technol. Online 2(5):768-77 (2008).
Williams, "On the mechanisms of biocompatibility", Biomaterials 29:2941-53 (2008).
Wynn and Ramalingam, "Mechanisms of fibrosis: therapeutic translation for fibrotic disease", Nat. Med. 18:1028-40 (2012).
Yang, et al., "Research progress on chemical modification of alginate: A review", Carbohydrate Polymers, 84(1):33-39 (2011).
Yang, et al., "Zwitterionic poly(carboxybetaine) hydrogels for glucose biosensors in complex media", Biosensors and Bioelectronics, 26(5): 2454-2459 (2011a).
Yimin, et al., "Alginic Acid", China Light Industry Press Ltd., 137-140 (2008).

\* cited by examiner

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
catgttcagc tttgtggacc t                                      21

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2

```
gcagctgact tcagggatgt                                              20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
gcaggttcac ctactctgtc ct                                           22

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
cttgccccat tcatttgtct                                              20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
cgcttccgct gcccagagac t                                            21

<210> SEQ ID NO 6
<211> LENGTH: 26
<212> TYPE: DNA
<213> ORGANISM: Artificial Sequence
<220> FEATURE:
<223> OTHER INFORMATION: Synthetic Primer

<400> SEQUENCE: 6
tataggtggt ttcgtggatg cccgct                                       26

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
ccaagagaat gcaaaaggct tt                                           22

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8 gggggggctgc aacaaccaca                                             20

<210> SEQ ID NO 9
<211> LENGTH: 21
<212> TYPE: DNA
<213> ORGANISM: Artificial Sequence
```

<220> FEATURE:
<223> OTHER INFORMATION: Synthetic Primer

<400> SEQUENCE: 9
gcccgagtac agtctacctg g                                           21

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
agagatgaat tctgcgccat                                             20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tgccccttct ctgatggatt                                             20

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
tgctcttgac ttgcttctgt ga                                          22

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
gcttctttgc agctccttcg tt                                          22

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cggagccgtt ctcgacgacc                                             20

<210> SEQ ID NO 15
<211> LENGTH: 21
<212> TYPE: DNA
<213> ORGANISM: Artificial Sequence
<220> FEATURE:
<223> OTHER INFORMATION: Synthetic Primer

<400> SEQUENCE: 15
catgttcagc tttgtggacc t                                           21

```
<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gcagctgact tcagggatgt                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic Primer

<400> SEQUENCE: 17
cctggctctc gaggtgaac                                               19

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
caatgcccag aggaccag                                                18

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
tgccatgtat gtggctattc a                                            21

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
accagttgta cgtccagaag c                                            21

<210> SEQ ID NO 21
<211> LENGTH: 19
<212> TYPE: DNA
<213> ORGANISM: Artificial Sequence
<220> FEATURE:
<223> OTHER INFORMATION: Synthetic Primer

<400> SEQUENCE: 21
ctctcgtgcc atgtgaacc                                               19

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 22
ttctctaaat tggtcccagg aa                                      22

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
accttcttgc agctcctccg tc                                      22

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
cggagccgtt gtcgacgacg                                         20
```

MODIFIED ALGINATES FOR ANTI-FIBROTIC MATERIALS AND APPLICATIONS

CROSS-REFERENCE TO RELATED APPLICATIONS

This application is a continuation of PCT Application No. PCT/US2016/059967, filed Nov. 1, 2016, which claims the benefit of and priority to U.S. Provisional Application No. 62/249,335, filed Nov. 1, 2015, the entire contents of which is incorporated by reference in its entirety.

STATEMENT REGARDING FEDERALLY SPONSORED RESEARCH

This application is a continuation of U.S. application Ser. No. 16/289,390, filed Feb. 28, 2019, which is a continuation of U.S. application Ser. No. 15/588,475, filed May 5, 2017, now U.S. Pat. No. 10,729,818, issued Aug. 4, 2020, which is a continuation of U.S. application Ser. No. 15/341,110, filed Nov. 2, 2016, now U.S. Pat. No. 10,709,818, issued Jul. 14, 2020, which is a continuation of PCT Application No. PCT/US2016/059967, filed Nov. 1, 2016, which claims the benefit of and priority to U.S. Provisional Application No. 62/249,335, filed Nov. 1, 2015, the entire contents of which are incorporated by reference in their entirety.

REFERENCE TO SEQUENCE LISTING

The Sequence Listing submitted as a text file named "MIT_16906_CIP_ST25.txt," created on Nov. 1, 2016, and having a size of 4,994 bytes is hereby incorporated by reference pursuant to 37 C.F.R. § 1.52(e)(5).

FIELD OF THE INVENTION

The present invention relates to the use of alginates, chemically modified to enhance their properties, e.g., biocompatibility and anti-fibrotic properties; to their use to coat or encapsulate materials, products, and devices, such as cells, implants, and medical devices; and to methods of treating diseases or disorders, including diabetes, by implantation of the modified alginates and materials coated or encapsulated with the modified alginates.

BACKGROUND OF THE INVENTION

The foreign body response is an immune-mediated reaction that impacts the fidelity of implanted biomedical devices (Anderson et al., *Semin. Immunol.* 20:86-100 (2008); Langer, *Adv. Mater.* 21:3235-3236 (2009); Ward, *J. Diabetes Sci. Technol. Online* 2:768-777 (2008); Harding & Reynolds, *Trends Biotechnol.* 32:140-146 (2014)). Macrophage recognition of biomaterial surfaces in these devices initiate a cascade of inflammatory events that result in the fibrous and collagenous encapsulation of these foreign materials (Anderson et al. (2008); Ward (2008); Harding & Reynolds (2014); Grainger, *Nat. Biotechnol.* 31:507-509 (2013); Williams, *Biomaterials* 29:2941-2953 (2008)). This encapsulation, over time, often leads to device failure and can result in discomfort for the recipient (Anderson et al. (2008); Harding & Reynolds (2014); Williams (2008)). These adverse outcomes emphasize the critical need for biomaterials that do not elicit foreign body responses to overcome this key challenge to long-term biomedical device function.

The foreign body response to implanted biomaterials is the culmination of inflammatory events and wound-healing processes resulting in implant encapsulation (Anderson et al. (2008)). The final pathological product of this response is fibrosis, which is characterized by the accumulation of excessive extracellular matrix at sites of inflammation and is a key obstacle for implantable medical devices as the cellular and collagenous deposition isolate the device from the host (Anderson et al. (2008); Wick et al., *Annu. Rev. Immunol.* 31:107-135 (2013); Wynn & Ramalingam. *Nat. Med.* 18:1028-1040 (2012)). This device isolation can interfere with sensing of the host environment, lead to painful tissue distortion, cut off nourishment (for implants containing living, cellular components), and ultimately lead to device failure. Materials commonly used for medical device manufacture today elicit a foreign body response that results in fibrous encapsulation of the implanted material (Langer (2009); Ward (2008); Harding & Reynolds (2014); Williams (2008); Zhang et al., *Nat. Biotechnol.* 31:553-556 (2013)). Overcoming the foreign body response to implanted devices could pave the way for implementing new medical advances, making the development of materials with both anti-inflammatory and anti-fibrotic properties a critical medical need (Anderson et al. (2008); Langer (2009); Harding & Reynolds (2014)).

Macrophages are a key component of material recognition and actively adhere to the surface of foreign objects (Anderson et al. (2008); Ward (2008); Grainger, *Nat. Biotechnol.* 31:507-509 (2013); Sussman et al., *Ann. Biomed. Eng.* 1-9 (2013) (doi:10.1007/s10439-013-0933-0)). Objects too large for macrophage phagocytosis initiate processes that result in the fusion of macrophages into foreign-body giant cells. These multi-nucleated bodies amplify the immune response by secreting cytokines and chemokines that result in the recruitment of fibroblasts that actively deposit matrix to isolate the foreign material (Anderson et al. (2008); Ward (2008); Rodriguez et al., *J. Biomed. Mater. Res. A* 89:152-159 (2009); Hetrick et al., *Biomaterials* 28:4571-4580 (2007)). This response has been described for materials of both natural and synthetic origins that encompass a wide range of physicochemical properties, including alginate, chitosan, dextran, collagen, hyaluronan, poly(ethylene glycol) (PEG), poly(methyl methacrylate) (PMMA), poly(2-hydroxyethyl methacrylate) (PHEMA), polyurethane, polyethylene, silicone rubber, Teflon, gold, titanium, silica, and alumina (Ward (2008); Ratner, J. *Controlled Release* 78:211-218 (2002)).

The transplantation of hormone- or protein-secreting cells from genetically non-identical members of the same species (i.e. allotransplantation) or from other species (i.e. xenotransplantion) is a promising strategy for the treatment of many diseases and disorders. Using alginate microcapsules to provide immunoisolation, hormone- or protein-secreting cells can be transplanted into a patient without the need for extensive treatment with immunosuppressant drugs. This principle has been successfully demonstrated by the transplantation of alginate-encapsulated pancreatic β-cells in diabetic rat models (Lim, F, and Sun, A. M. *Science.* 210, 908-910 (1980)). Methods of encapsulating biological material in alginate gels are described, for example, in U.S. Pat. No. 4,352,883 to Lim. In the Lim process, an aqueous solution containing the biological materials to be encapsulated is suspended in a solution of a water soluble polymer. The suspension is formed into droplets which are configured into discrete microcapsules by contact with multivalent cations such as $Ca^{2+}$. The surface of the microcapsules is subsequently crosslinked with polyamino acids, forming a semipermeable membrane around the encapsulated materials.

The Lim method employs conditions which are mild enough to encapsulate cells without adversely affecting their subsequent survival and function. The resulting alginate microcapsules are semipermeable, possessing sufficient porosity to permit nutrients, waste, and the hormones and/or proteins secreted from encapsulated cells to diffuse freely into and out of the microcapsules, and, when implanted into an animal host, the alginate microcapsules effectively isolate the encapsulated cells from the host's immune system. See also U.S. Pat. No. 7,807,150 to Vacanti, el al.

Many other synthetic materials have been tried, including block copolymers such as poly ethyleneglycol-diacrylate polymers, polyacrylates, and thermoplastic polymers, as reported by U.S. Pat. No. 6,129,761 to Hubbell and by Aebischer, et al, J Biomech Eng. 1991 May 113(2): 178-83. See Lesney Modern Drug Discovery 4(3), 45-46, 49, 50 (2001) for review of these materials.

Since Lim first reported on the transplantation of encapsulated cells, many other have tried to create "bioreactors" for cells that could maintain viability of the cells in the absence of vascularization, by diffusion of nutrients, gases and wastes through the encapsulating materials, and still protect the cells from the body's immune defenses against foreign cells and materials. Unfortunately, efforts to translate these therapies into human subjects have proven difficult. For example, alginate-encapsulated porcine islet cells transplanted into a human subject suffering from Type 1 diabetes initially demonstrated significant improvement and required decreased insulin dosing. However, by week 49, the patient's insulin dose retuned to pre-transplant levels (Elliot, R. B. et al. *Xenotransplantation*. 2007; 14(2): 157-161).

In some cases, it is desirable to elicit fibrosis, for example, when the cells are implanted as a bulking material, as described in U.S. Pat. No. 6,060,053 and as subsequently approved by the Food and Drug Administration for treatment of vesicoureteral reflux.

The diminished efficacy of the implanted cells over time is the result of fibroblastic overgrowth of the alginate capsules. The alginate gel matrix provokes an inflammatory response upon implantation, resulting in the encapsulation of the alginate matrix with fibrous tissue. The fibrous tissue on the alginate capsule surface reduces the diffusion of nutrients and oxygen to the encapsulated cells, causing them to die. No better results have been obtained with the other materials.

Therefore, it is an object of the invention to provide polymers suitable for coating products, devices, and surfaces where the polymers have optimized properties, e.g., greater long-term biocompatibility, following implantation of the products, devices, and surfaces.

It is also an object of the invention to provide polymers suitable for coating products, devices, and surfaces where the polymers have less foreign body response following implantation of the products, devices, and surfaces.

It is also an object of the invention to provide polymers suitable for encapsulation and implantation of cells where the polymers have optimized properties, e.g., greater long-term biocompatibility, following implantation.

It is also an object of the invention to provide polymers suitable for encapsulation and implantation of cells where the polymers have less foreign body response following implantation.

It is also an object of the invention to provide chemically modified, ionically crosslinkable alginates with optimized properties, e.g., improved biocompatibility and tailored physiochemical properties, including gel stability, pore size, and hydrophobicity/hydrophilicity.

It is also an object of the invention to provide chemically modified, ionically crosslinkable alginates with less foreign body response.

It is also an object of the invention to provide methods for the coating of products, devices, and surfaces using modified alginate polymers.

It is also an object of the invention to provide methods for the encapsulation of cells using modified alginate polymers.

It is also an object of the invention to provide methods for treating a disorder or disease in a human or animal patient by transplanting or implanting products, devices, and surfaces coated with a modified alginate polymer.

It is also an object of the invention to provide methods for treating a disorder or disease in a human or animal patient by transplanting exogenous biological material encapsulated in a modified alginate polymer.

It is also an object of the invention to provide high-throughput methods for the characterization of modified alginate polymers.

SUMMARY OF THE INVENTION

Alginates, chemically modified to tailor their biocompatibility and physical properties, have been developed. The modified alginates described herein provide enhanced properties relative to unmodified alginates. Moreover, based on the discovery that the starting materials, as well as chemically modified and reacted materials, must be exhaustively purified to remove contaminants prior to implantation to prevent encapsulation, these materials are less likely to elicit fibrous capsule formation following implantation.

In some embodiments, modified alginates are alginate polymers that contain one or more covalently modified monomers defined by Formula I

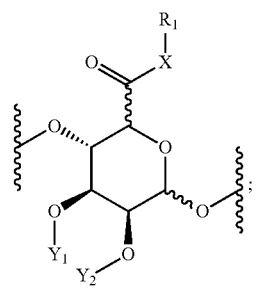

Formula I wherein, in some embodiments, the modified alginate is defined by Formula Ia, Formula Ib, or a combination of Formula Ia and Formula Ib

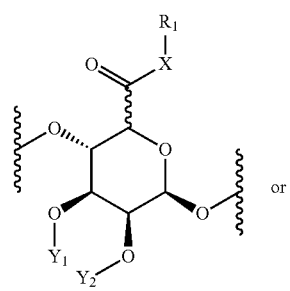

Formula Ia or

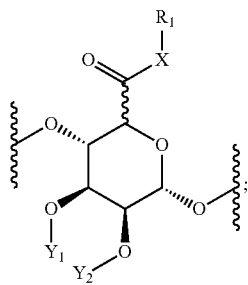

Formula Ib wherein, independently for Formula I, Formula Ia, and Formula Ib,

X is oxygen, sulfur, or $NR_4$;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$;

$Y_1$ and $Y_2$ independently are hydrogen or $-PO(OR_5)_2$; or $Y_2$ is absent, and $Y_1$. together with the two oxygen atoms to which $Y_1$ and $Y_2$ are attached to form a cyclic structure as shown in Formula II, Formula IIa, Formula IIb, or a combination of Formula IIa and Formula IIb,

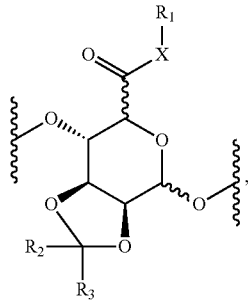

Formula II

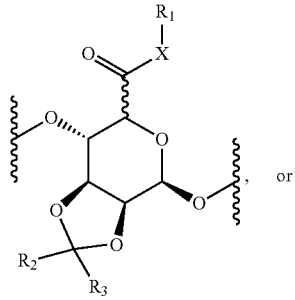

Formula IIa or

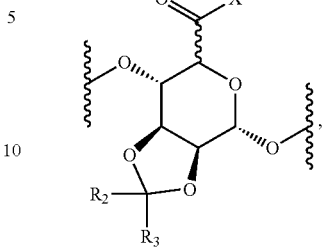

Formula IIb wherein, independently for Formula II, Formula IIa, and Formula IIb, $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_2$ and $R_3$ groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_4$ and $R_5$ groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain a mixture of monomers defined by Formula Ia and Formula Ib. In some embodiments, the mixture of monomers in the modified alginate are in percent compositions (Formula Ia: Formula Ib) of 1: 99, 5: 95, 10: 90, 15:85, 20:80, 25:75, 30:70, 35:65, 40:60, 45:55, 50:50, 55:45, 60:40, 65:35, 70:30, 75:25, 80:20, 85:15, 90:10, 95:5, 99:1. In some embodiments the percent composition of Formula Ia and Formula Ib in the modified alginate is 1-99% Formula Ia: 1-99% Formula Ib, with the understanding that the sum of the percent compositions is equal to 100%. Individual integers between each of these ranges are contemplated and disclosed.

In some embodiments, the modified alginates are alginate polymers that contain a mixture of monomers defined by Formula Ia, Formula Ib, Formula IIa and Formula IIb. In some embodiments, the mixture of monomers in the modified alginate are in percent compositions (Formula Ia: Formula Ib: Formula IIa: Formula IIb) of 1-99:1-99:1-99:1-99 with the understanding that the sum of the percent compositions is equal to 100%. Individual integers between each these ranges are contemplated and disclosed.

In some embodiments, R is, independently in one or more sites of chemical modification, -A-B(—C)$_b$,   Formula XVI wherein A is hydrogen or an organic grouping containing any number of carbon atoms, 1-carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_4+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

B, and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and δ is an integer from, as valency permits, 0 to 30.

In some embodiments, $R_1$ is, independently in one or more sites of chemical modification,

, Formula XVIII wherein $R_6$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_6$ organic groupings being $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and $R^b$ is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, C, and $R^b$, and independently in combination with any embodiments of any other relevant substituent classes, B, C, and $R^b$ can be, independently, absent, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_x+Q_3$.

Independently in some embodiments of A and $R_6$, and independently in combination with any other relevant substituent classes, A and $R_6$ can be, independently, hydrogen, amino, hydroxyl, thiol, oxo, phosphate, or $J_1$.

Independently in some embodiments of A and $R_6$, and independently in combination with any embodiments of any other relevant substituent classes, A and $R_6$ can be, independently, hydrogen, amino, hydroxyl, thiol, oxo, phosphate, or $J_2$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_1$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_2$.

Independently in some embodiments of A and $R_6$, and independently in combination with any embodiments of any other relevant substituent classes, A and $R_6$ can be, independently,

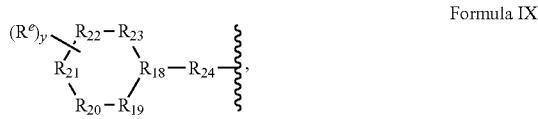  Formula IX

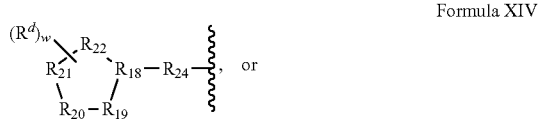  Formula XIV

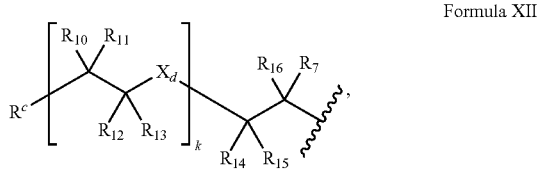  Formula XII wherein y is an integer from 0-11; wherein w is an integer from 0-9; wherein k is an integer from 0 to 20;

wherein $R^d$ and $R^e$ are independently B, C, —B(—C)$_δ$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is B, C, —B(—C)$_δ$, $R^b$, absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently B, C, absent, hydrogen, =O, =S, —OH, —SH, or —NR$_4$, wherein R$_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently B, C, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of B, and independently in combination with any embodiments of any other relevant substituent classes, B can be

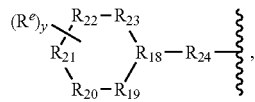

Formula IX

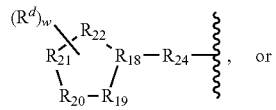

Formula XIV or

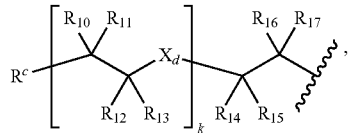

Formula XII wherein y is an integer from 0-11; wherein w is an integer from 0-9; wherein k is an integer from 0 to 20;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is C, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, $R^b$, absent, hydrogen, =O, =S, —OH, —SH, or —NR$_4$, wherein IQ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

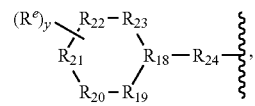

Formula IX

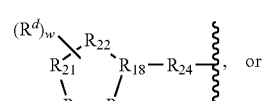

Formula XIV or

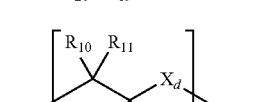

Formula XII wherein y is an integer from 0-11; wherein w is an integer from 0-9; wherein k is an integer from 0 to 20;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is C, absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, absent, hydrogen, =O, =S, —OH, —SH, or —NR$_4$, wherein R$_4$ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes C can be

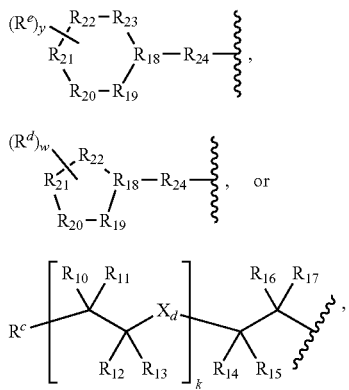

Formula IX

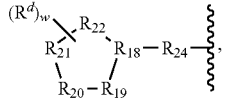

Formula XIV

Formula XII

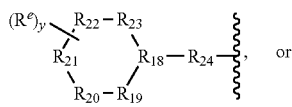

wherein y is an integer from 0-11; wherein w is an integer from 0-9; wherein k is an integer from 0 to 20;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently absent, hydrogen, =O, =S, —OH, —SH, or —$NR_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently, Formula IX

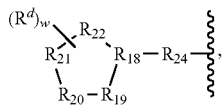

Formula XIV

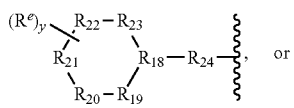

wherein y is an integer from 0-11; wherein w is an integer from 0-9;

wherein $R^d$ and $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently B, C, absent, hydrogen, =O, =S, —OH, —SH, or —$NR_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be Formula IX

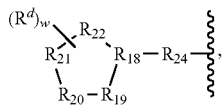

Formula XIV

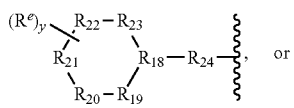

wherein y is an integer from 0-11; wherein w is an integer from 0-9;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently C, $R^b$, absent, hydrogen, =O, =S, —OH, —SH, or —$NR_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

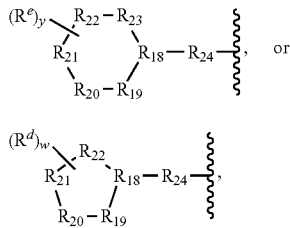

Formula IX or

Formula XIV wherein y is an integer from 0-11; wherein w is an integer from 0-9;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or $NR_4$, wherein each $R_{25}$ is, as valency permits, independently C, absent, hydrogen, =O, =S, —OH, —SH, or —$NR_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

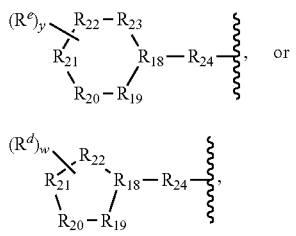

Formula IX or

Formula XIV wherein y is an integer from 0-11; wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or $NR_4$, wherein each $R_{25}$ is, as valency permits, independently absent, hydrogen, =O, =S, —OH, —SH, or —$NR_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently,

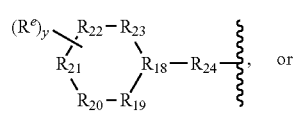

Formula IX or wherein y is an integer from 0-11;

wherein $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or $NR_4$, wherein each $R_{25}$ is, as valency permits, independently B, C, absent, hydrogen, =O, =S, —OH, —SH, or —$NR_4$, wherein $R_4$ is $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be

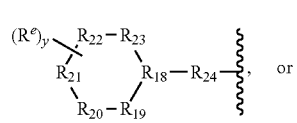

Formula IX or wherein y is an integer from 0-11;

wherein $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-S(O)-$, or $-S(O)_2-$, or $NR_4$, wherein each $R_{25}$ is, as valency permits, independently C, $R^b$, absent, hydrogen, $=O$, $=S$, $-OH$, $-SH$, or $-NR_4$, wherein $R_4$ is $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

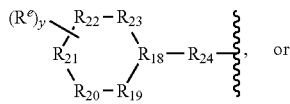

Formula IX or wherein y is an integer from 0-11;

wherein $R^c$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_4+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-S(O)-$, or $-S(O)_2-$, or $NR_4$, wherein each $R_{25}$ is, as valency permits, independently C, absent, hydrogen, $=O$, $=S$, $-OH$, $-SH$, or $-NR_4$, wherein $R_1$ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

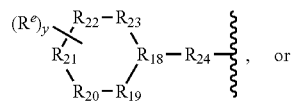

Formula IX or wherein y is an integer from 0-11;

wherein $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-S(O)-$, or $-S(O)_2-$, or $NR_4$, wherein each $R_{25}$ is, as valency permits, independently absent, hydrogen, $=O$, $=S$, $-OH$, $-SH$, or $-NR_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_x+Q_3$.

Independently in some embodiments of A and $R_6$, and independently in combination with any embodiments of any other relevant substituent classes, A and $R_6$ can be, independently,

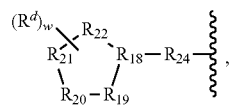

Formula XIV wherein w is an integer from 0-9;

wherein $R^d$ and $R^e$ are independently B, C, $-B(-C)_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or $S(O)_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-S(O)-$, or $-S(O)_2-$, or $NR_4$, wherein each $R_{25}$ is, as valency permits, independently B, C, absent, hydrogen, $=O$, $=S$, $-OH$, $-SH$, or $-NR_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_1+Q_3$, $U_1+Q_2+Q_4$, $U_4+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be

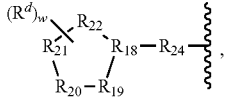
Formula XIV wherein w is an integer from 0-9;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, $R^b$, absent, hydrogen, =O, =S, —OH, —SH, or —NR$_4$, wherein IQ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_1+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

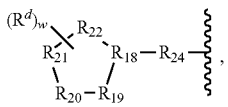
Formula XIV wherein w is an integer from 0-9;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$. preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

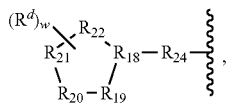
Formula XIV wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently,

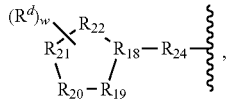
Formula XIV wherein w is an integer from 0-9;

wherein $R^d$ and $R^e$ are independently B, C, —B(—C)$_8$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently B, C, absent, hydrogen, =O, =S, —OH, —SH, or —$NR_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be

Formula XIV wherein w is an integer from 0-9;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently C, $R^b$, absent, hydrogen, =O, =S, —OH, —SH, or —$NR_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

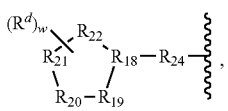

Formula XIV wherein w is an integer from 0-9;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently C, absent, hydrogen, =O, =S, —OH, —SH, or —$NR_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_4+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

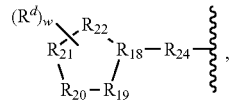

Formula XIV wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —$S(O)_2$—, or $NR_4$, wherein each $R_{25}$ is, as valency permits, independently absent, hydrogen, =O, =S, —OH, —SH, or —$NR_4$, wherein $R_4$ is $U_1$; $U_2+Q_1$; $U_2+Q_2$, $U_2+Q_3$, $U_2+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently,

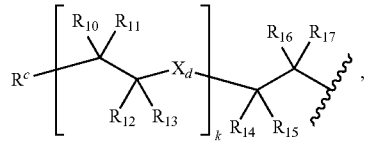

Formula XII wherein k is an integer from 0 to 20;
wherein $X_d$ are independently absent, O, or S;

wherein $R^c$ is B, C, —B(—C)$_\delta$, $R^b$, absent, hydrogen, $U_3$, $U_3+Q_1$; $U_3+Q_2$, $U_3+Q_3$, $U_3+Q_4$, $U_3+Q_1+Q_2$, $U_3+Q_1+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

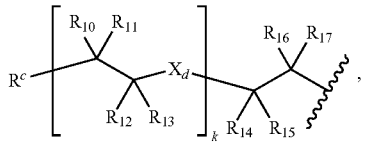

Formula XII wherein k is an integer from 0 to 20;
wherein $X_d$ are independently absent, O, or S;
wherein $R^c$ is C, $R^b$, absent, hydrogen, $U_3$, $U_3+Q_1$, $U_3+Q_2$, $U_3+Q_3$, $U_3+Q_4$, $U_3+Q_1+Q_2$, $U_3+Q_1+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

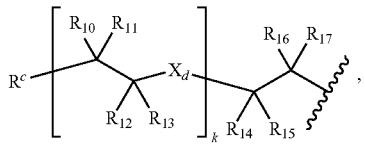

Formula XII wherein k is an integer from 0 to 20;
wherein $X_4$ are independently absent, O, or S;
wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

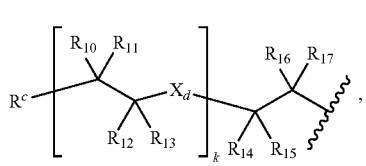

Formula XII wherein k is an integer from 0 to 20;
wherein $X_d$ are independently absent, O, or S;
wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently,

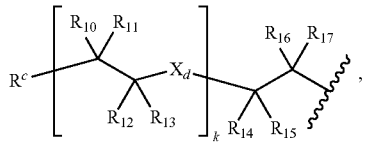

Formula XII wherein k is an integer from 0 to 20;
wherein $X_4$ are independently O or S;
wherein $R^c$ is B, C, —B(—C)$_\delta$, $R^b$, absent, hydrogen, $U_3$,$U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

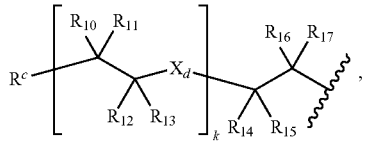

Formula XII wherein k is an integer from 0 to 20;
wherein $X_d$ are independently O or S;
wherein $R^c$ is C, $R^b$, absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_4+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

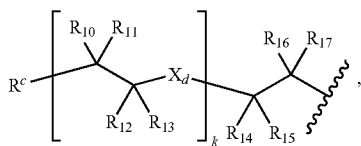

Formula XII wherein k is an integer from 0 to 20;
wherein $X_d$ are independently O or S;
wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$, $U_1+Q_1$, $U_1+Q_2$, $U_1+Q_3$, $U_1+Q_4$, $U_4+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

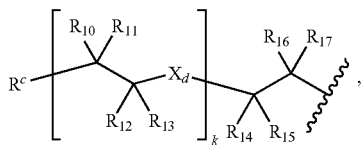

Formula XII wherein k is an integer from 0 to 20;
wherein $X_d$ are independently O or S;
wherein $R^c$ is absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently,

Formula XII wherein k is an integer from 1 to 20;
wherein $X_d$ are O;
wherein $R^c$ is B, C, —B(—C)$_\delta$, $R^b$, $U_3+U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$; and wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

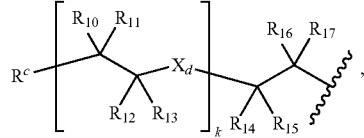

Formula XII wherein k is an integer from 1 to 20;
wherein $X_d$ are O;
wherein $R^c$ is C, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of $R^b$, and independently in combination with any embodiments of any other relevant substituent classes, $R^b$ can be

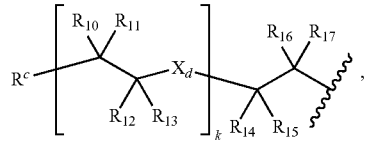

Formula XII wherein k is an integer from 1 to 20;
wherein $X_d$ are O;
wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

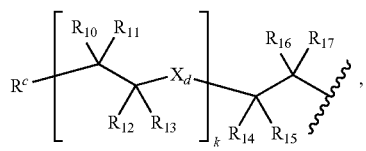

Formula XII wherein k is an integer from 1 to 20;

wherein $X_d$ are O;

wherein $R^c$ is absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, Up $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, modified alginates are alginate polymers that contain one or more covalently modified monomers defined by Formula I

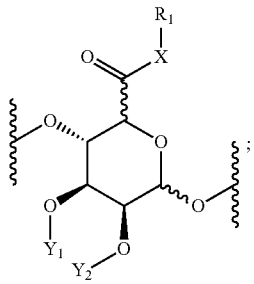

Formula I wherein, in some embodiments, the modified alginate is defined by Formula Ia, Formula Ib, or a combination of Formula Ia and Formula Ib

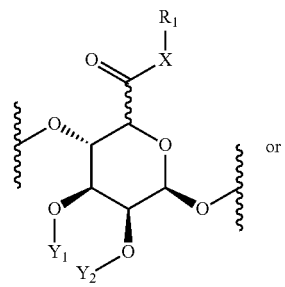

Formula Ia or

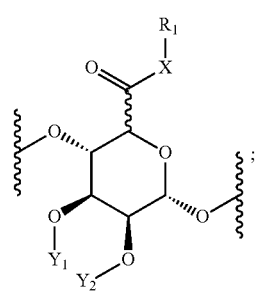

Formula Ib wherein, independently for Formula I, Formula Ia, and Formula Ib,

X is oxygen, sulfur, or $NR_4$;

$R_1$ is, independently in the one or more modified monomers

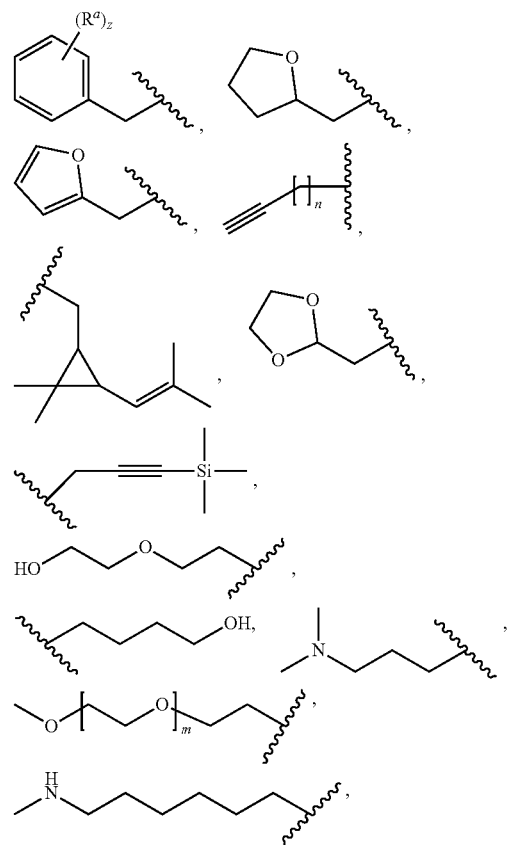

-continued

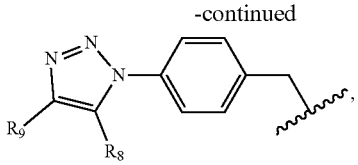

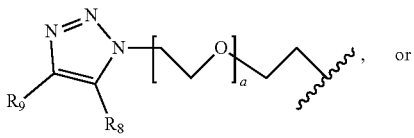

—$R_6$—$R^b$, wherein a is an integer from 1 to 30, z is an integer from 0 to 5, n is an integer from 1 to 12, m is an integer from 3 to 16, and $R^a$ and $R^b$ are independently selected from $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_2+Q_3$; or together with the carbon atom to which they are attached, form a 3- to 8-membered unsubstituted or substituted carbocyclic or heterocyclic ring;

wherein $Y_1$ and $Y_2$ independently are hydrogen or —$PO(OR_5)_2$; or $Y_2$ is absent, and $Y_1$. together with the two oxygen atoms to which $Y_1$ and $Y_2$ are attached form a cyclic structure as shown in Formula II, Formula IIa, Formula IIb, or a combination of Formula IIa and Formula IIb, Formula II

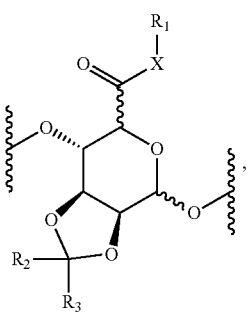

Formula IIa

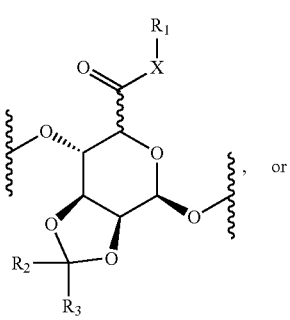

Formula IIb

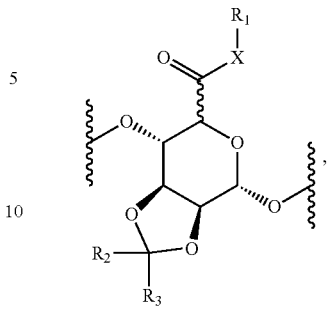

wherein, independently for Formula II, Formula IIa, and Formula IIb, $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being those present in $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$: or $R_2$ and $R_3$, together with the carbon atom to which they are attached, form a 3- to 8-membered unsubstituted or substituted carbocyclic or heterocyclic ring; and $R_4$, $R_5$, $R_6$, $R_8$, and $R_{10}$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Modified alginate polymers can contain any ratio of mannuronate monomers, guluronate monomers, and covalently modified monomers. In preferred embodiments, greater than 5%, greater than 10%, greater than 15%, greater than 20%, more preferably greater than 25%, and most preferably greater than 30%, of the monomers in the modified alginate polymer are covalently modified monomers.

In preferred embodiments, the modified alginate polymer can be ionically crosslinked to form hydrogels using a polyvalent ion, such as $Ca^{2+}$, $Sr^{2+}$, or $Ba^{2+}$. The ability of modified alginates to form stable hydrogels in physiological conditions can be quantified using the hydrogel formation assay described herein. In preferred embodiments, the modified alginate polymer forms hydrogels such that the fluorescence intensity measured using the high throughput assay described herein is between 15,000 and 55,000, preferably between 20,000 and 55,000, more preferably between 25,000 and 55,000.

In preferred embodiments, the modified alginate is biocompatible, and induces a lower foreign body response than unmodified alginate. The biocompatibility of modified alginates can be quantitatively determined using in vitro and in vivo assays known in the field, including the in vivo biocompatibility assay described herein. In preferred embodiments, the modified alginate polymer is biocompatible such that the fluorescence response normalized to unmodified alginate measured using the in vivo biocompatibility assay described herein is less than 75%, 70%, 65%, 60%, 55%, or 50%. Also described are assays for the characterization of modified alginate polymers.

A high throughput assay useful to characterize the ability of modified alginate polymers to form hydrogels is also described. In some embodiments, the hydrogel formation assay described herein is used to quantify the stability of hydrogels formed from alginates or modified alginates. In preferred embodiments, the hydrogel formation assay described herein is used as a screening tool to identify modified alginates capable of forming stable hydrogels. The high throughput in vivo biocompatibility assay described herein is used to identify modified alginates which induce a lower foreign body response than unmodified alginate. Assays are also provided for quantifying the biocompatibility of modified alginates.

In some embodiments, the disclosed capsules and products can include a cargo or payload, such as a biological material. For example, the biological material can be cells or tissue. In some embodiments, the cargo is disposed within an outer member (e.g. a coating or encapsulating layer) that includes compounds as described herein on its surface.

Further described herein are methods of coating medical products, devices, and surfaces using modified alginate polymers. In particular embodiments, the modified alginate polymers described herein are used to coat products, devices, and surfaces for use in methods of treating a disease or disorder in a human or animal patient. In some embodiments, a disease or disorder in a human or animal patient is treated by transplanting or implanting products, devices, and surfaces coated with a modified alginate polymer. In particular embodiments, a disease or disorder in a human or animal patient is treated by transplanting or implanting products, devices, and surfaces coated with a modified alginate polymer.

Further described herein are methods of encapsulating biological materials using modified alginate polymers. In particular embodiments, the modified alginate polymers described herein are used to encapsulate cells for use in methods of treating a disease or disorder in a human or animal patient. In some embodiments, a disease or disorder in a human or animal patient is treated by transplanting exogenous biological material encapsulated in a modified alginate polymer. In particular embodiments, a disease or disorder in a human or animal patient is treated by transplanting cells encapsulated in a modified alginate polymer. In a more particular embodiment, diabetes is treated by transplanting pancreatic islet cells encapsulated in a modified alginate polymer.

Cells suitable for encapsulation and transplantation are preferably secretory or metabolic cells (i.e., they secrete a therapeutic factor or metabolize toxins, or both) or structural cells (e.g., skin, muscle, blood vessel), or metabolic cells (e.g., they metabolize toxic substances). In some embodiments, the cells are naturally secretory, such as islet cells that naturally secrete insulin, or naturally metabolic, such as hepatocytes that naturally detoxify and secrete. In some embodiments, the cells are bioengineered to express a recombinant protein, such as a secreted protein or metabolic enzyme. Depending on the cell type, the cells may be organized as single cells, cell aggregates, spheroids, or even natural or bioengineered tissue.

In some embodiments, modified alginates are alginate polymers that contain one or more covalently modified monomers defined by Formula I

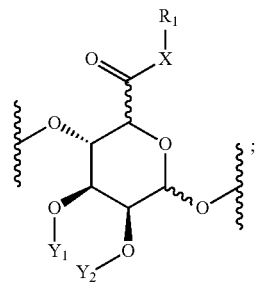

Formula I wherein, in some embodiments, the modified alginate is defined by Formula Ia, Formula Ib, or a combination of Formula Ia and Formula Ib

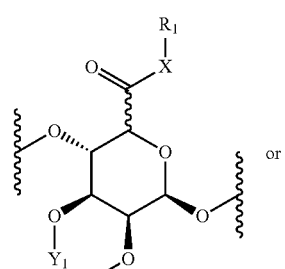

Formula Ia or

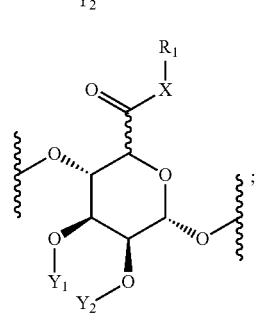

Formula Ib wherein, independently for Formula I, Formula Ia, and Formula Ib, $Y_1$ and $Y_2$ independently are hydrogen;

X is oxygen, sulfur, or $NR_4$; wherein $R_4$ is hydrogen, alkyl, or substituted alkyl;

$R_1$ is, independently in one or more sites of chemical modification,

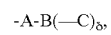

Formula XVI wherein
A is

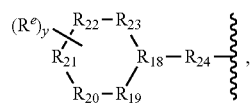

Formula IX in A, $R_{24}$ is $—(CR_{25}R_{25})_p$; each $R_{25}$ is hydrogen; p is an integer from 0 to 5; each $R^e$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; y is an integer from 0-11; $R_{18}$, $R_{19}$, $R_{20}$, $R_{21}$, $R_{22}$, and $R_{23}$ are independently C or N, wherein the bonds between adjacent $R_{12}$ to $R_{17}$ are double or single according to valency, and wherein $R_{18}$ to $R_{23}$ are bound to none, one, or two hydrogens according to valency; and $R_{21}$ is connected to B;

B is

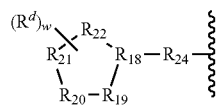

Formula XIV in B, $R_{24}$ is —$(CR_{25}R_{25})_p$—; each $R_{25}$ is hydrogen; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; $R_{18}$, $R_{19}$, $R_{20}$, $R_{21}$, and $R_{22}$ are independently C or N, wherein the bonds between adjacent $R_{18}$ to $R_{22}$ are double or single according to valency, and wherein $R_{18}$ to $R_{22}$ are bound to none, one, or two hydrogens according to valency; and $R_{20}$ is connected to C;

C is

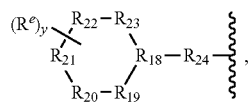

Formula IX in C, $R_{24}$ is —$(CR_{25}R_{25})_p$— or —$(CR_{25}R_{25})_p$—$X_b$—$(CR_{25}R_{25})_q$—; p and q are independently integers from 0 to 5; $X_b$ is absent, —O—, —S—, —S(O)—, or —S(O)$_2$—, or $NR_4$; each $R_{25}$ is hydrogen; $R_4$ is alkyl or substituted alkyl; $R^e$ are independently independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; y is an integer from 0 to 11; each $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and δ is 1.

In some embodiments, modified alginates are alginate polymers that contain one or more covalently modified monomers defined by Formula I

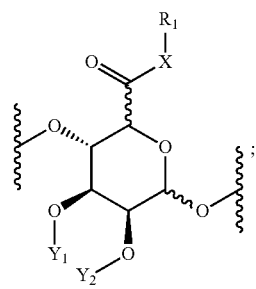

Formula I wherein, in some embodiments, the modified alginate is defined by Formula Ia, Formula Ib, or a combination of Formula Ia and Formula Ib

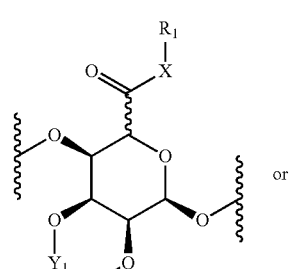

Formula Ia or

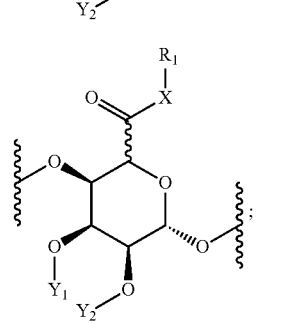

Formula Ib wherein, independently for Formula I, Formula Ia, and Formula Ib;

$Y_1$ and $Y_2$ independently are hydrogen;

X is oxygen, sulfur, or $NR_4$; wherein $R_4$ is hydrogen, alkyl, or substituted alkyl;

$R_1$ is, independently in one or more sites of chemical modification,

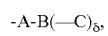  -A-B(—C)$_δ$,    Formula XVI wherein
A is

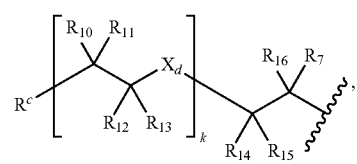

Formula XII in A, $R_{10}$, $R_{11}$, $R_{12}$, $R_{13}$, $R_{14}$, $R_{15}$, $R_{16}$, and $R_{17}$ are independently hydrogen, alkyl, substituted alkyl, alkenyl, substituted alkenyl, alkynyl, substituted alkynyl, phenyl, substituted phenyl, aryl, substituted aryl, heteroaryl, substituted heteroaryl, arylalkyl, substituted arylalkyl, alkoxy, substituted alkoxy, aroxy, substituted aroxy, carbonyl, substituted carbonyl, carboxyl, substituted carboxyl, amino, substituted amino, amido, substituted amido, $C_3$-$C_{20}$ cyclic, substituted $C_3$-$C_{20}$ cyclic, heterocyclic, substituted heterocyclic, poly(ethylene glycol), or poly(lactic-co-glycolic acid); k is an integer from 0 to 20; each $X_d$ is independently absent, O, or S; and $R^e$ is B;

B is

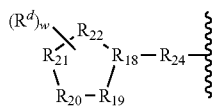

Formula XIV in B, $R_{24}$ is $-(CR_{25}R_{25})_p-$; each $R_{25}$ is hydrogen; p is an integer from 0 to 5; each $R^d$ is independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; w is an integer from 0 to 4; $R_{18}$, $R_{19}$, $R_{20}$, $R_{21}$, and $R_{22}$ are independently C or N, wherein the bonds between adjacent $R_{18}$ to $R_{22}$ are double or single according to valency, and wherein $R_{18}$ to $R_{22}$ are bound to none, one, or two hydrogens according to valency; and $R_{20}$ is connected to C;

C is

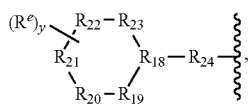

Formula IX in C, $R_{24}$ is $-(CR_{25}R_{25})_p-$ or $-(CR_{25}R_{25})_p-X_b-(CR_{25}R_{25})_q-$; p and q are independently integers from 0 to 5; $X_b$ is absent, $-O-$, $-S-$, $-S(O)-$, or $-S(O)_2-$, or $NR_4$; each $R_{25}$ is hydrogen; $R_4$ is alkyl or substituted alkyl; $R^e$ are independently independently alkyl, alkenyl, alkynyl, substituted alkyl, substituted alkenyl, substituted alkynyl, alkoxy, alkylamino, dialkylamino, hydroxy, aryl, substituted aryl, heteroaryl, substituted heteroaryl, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, or substituted heterocyclic; y is an integer from 0 to 11; each $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and
δ is 1.

In some embodiment, the capsules or product includes cells or tissues encapsulated or coated with a modified polymer, where the polymer includes compounds as described herein. In some embodiments:

(a) the polymer comprises modified alginate;

(b) the compound comprises the formula -A-B($-$C)$_δ$ (Formula XVI), where A is Formula VII or Formula IX, B is Formula XIV, δ is 1, C is Formula IX;

(c) the capsule or product is spherical or spheroidal in shape;

(d) the capsule or product has an average diameter of 1.5 mm;

(e) the cell is a cell producing a recombinant product; and, optionally, (f) the capsule or product has a pore size of 0.1 to 1 μm.

In some embodiments, the capsule or product is provided as a preparation of capsules or products and the capsules or products in the preparation have one or more of the following characteristics:

(1) at least 50% of the capsules or products in the preparation have a surface with a concentration of 1 to 5% surface modifications as measured by X-ray photoelectron spectroscopy (XPS);

(2) at least 50% of the capsules or products in the preparation have a the shape specified in (c);

(3) at least 50% of the capsules or products in the preparation have a the diameter specified in (d); and (4) at least 50% of the capsules or products in the preparation have the pore size of (f).

In some embodiments, the capsule or product has properties (1) and (2).

In some embodiments, the capsule or product has properties (1) and (3).

In some embodiments, the capsule or product has properties (1) and (4).

In some embodiments, the capsule or product has properties (2) and (3).

In some embodiments, the capsule or product has properties (2) and (4).

In some embodiments, the capsule or product has properties (3) and (4).

In some embodiments, the capsule or product has properties (1), (2), and (3).

In some embodiments, the capsule or product has properties (1), (2), (3), and (4).

In some embodiments, when implanted into the subject, at least 5% of the cells are alive after 30 days.

In some embodiments, when implanted into the subject, the cells respond to an increase in blood glucose by secreting insulin.

In some embodiments, the polymer is singulary modified with the compound of (b).

In some embodiments, the polymer is multiply modified with the compound of (b) and another compound of different structure (for example, another compound as disclosed herein).

DETAILED DESCRIPTION OF THE INVENTION

Figure 1:
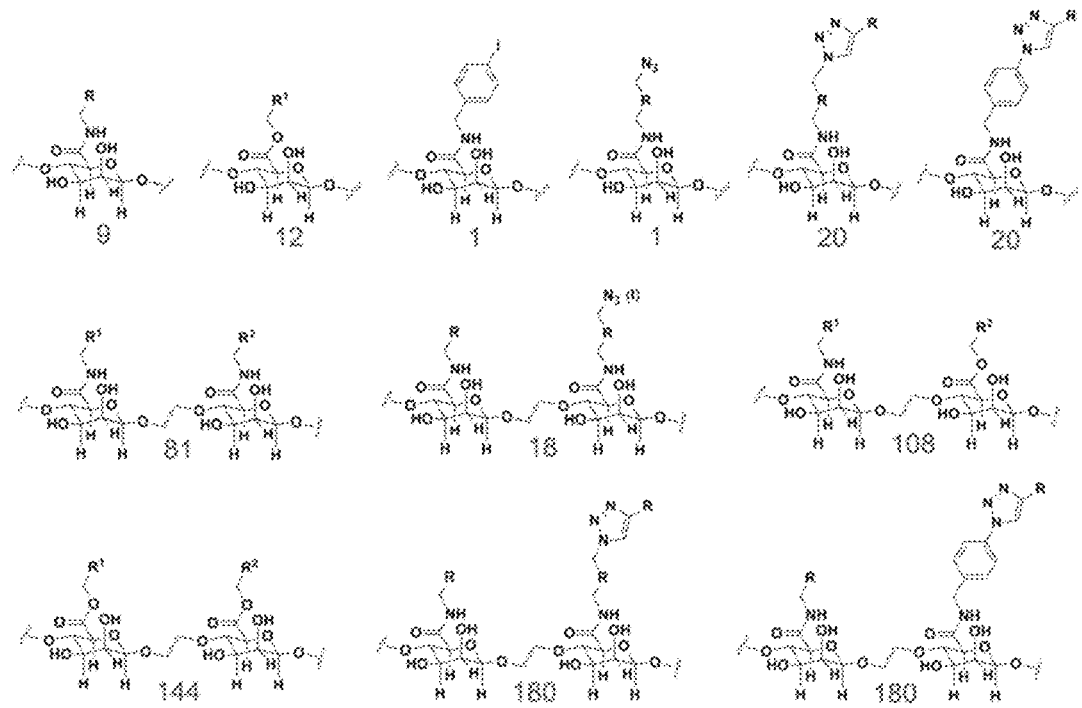
FIG. 1 shows the general structure of the modified alginates obtained using the combinatorial synthetic approach described in Example 1. The number of alginates prepared with each general structure is indicated below.
Figure 2:
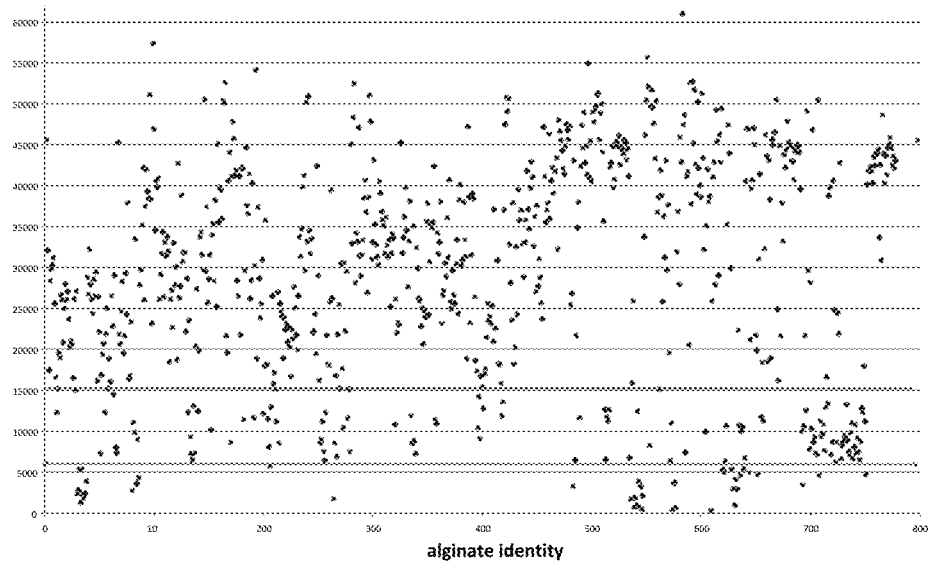
FIG. 2 is a plot obtained from the hydrogel formation assay described in Example 2. The average fluorescence intensity values measured for modified alginates are plotted. Modified alginates yielding fluorescence values below 15,000 were considered unusable for applications where hydrogel formation is critical (i.e. the encapsulation of cells).

Alginates are a class of linear polysaccharide copolymers formed from 1-4-glycosidically linked β-D-mannuronate (M) and its C-5 epimer α-L-guluronate (G). In some embodiments, alginates are formed from α-D-mannuronate (M) and β-L-guluronate (G). The M and G residues are present in any ratio. Alginates are naturally occurring biopolymers produced by a variety of organisms, including marine brown algae and at least two genera of bacteria (*Pseudomonas* and *Azotobacter*). Typically, commercial alginates are isolated from marine algae, including *Macrocystis pyrifera, Ascophyllum nodosum*, and various types of *Laminaria*. Monomers of alginates are represented by the general formulae shown below:

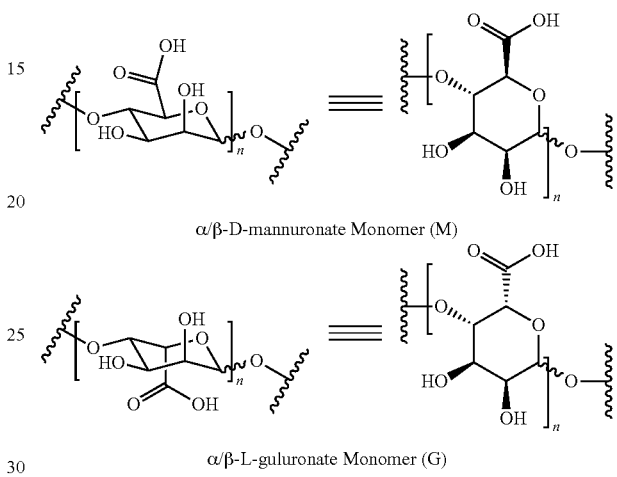

α/β-D-mannuronate Monomer (M)

α/β-L-guluronate Monomer (G)

In some embodiments, the monomers of alginates are represented by

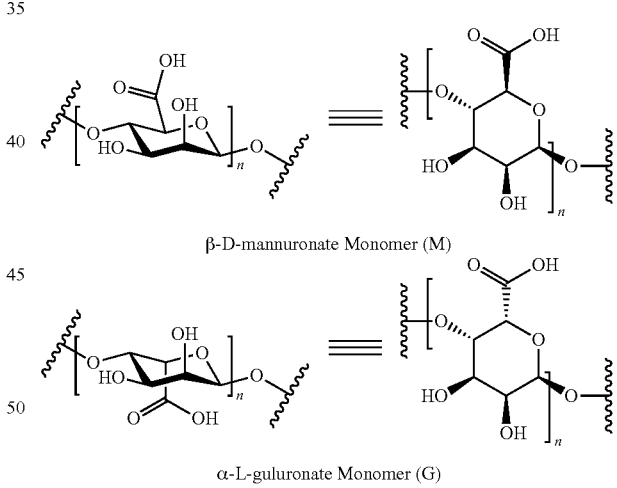

β-D-mannuronate Monomer (M)

α-L-guluronate Monomer (G)

Three types of primary structure define the polysaccharide backbone of alginates: homopolymeric regions of consecutive guluronate monomers (G-blocks), homopolymeric regions of consecutive mannuronate monomers (M-blocks), and regions containing alternating mannuronate and guluronate monomers (MG-blocks). The monomer blocks possess different conformations in solution, ranging from a flexible extended structure (M-blocks) to a rigid compact structure (G-blocks). In the case of G-blocks, the compact conformation facilitates the chelation of multivalent ions, notably $Ca^{2+}$ ions, such that G-blocks in one alginate chain can be ionically crosslinked with G-blocks in another alginate chain, forming stable gels. As a result, the proportion, length, and distribution of the monomer blocks influence the physiochemical properties of the alginate polymer.

In the case of commercially produced alginates obtained from algae, the molecular weight, primary structure, and overall molar ratio of uronic acid monomers (M/G ratio) in the alginate polymer depends on a number of factors, including the species producing the alginate, the time of year in which the species is collected, and the location and age of the algal body. As a result, alginates possessing a range of physiochemical properties, such as molecular weight and viscosity, are commercially available.

Alginates can be ionically crosslinked at room temperature and neutral pH to form hydrogels. The ability of alginates to form stable gels in physiologically compatible conditions renders alginate gels useful in a number of biomedical applications. For example, alginate gels have be used as a matrix for drug delivery to modulate the pharmacokinetics of therapeutic, diagnostic, and prophylactic agents.

I. Definitions

"Alginate," as used herein, is a collective term used to refer to linear polysaccharides formed from β-D-mannuronate, α-L-guluronate, α-D-mannuronate, and β-L-guluronate in any M/G ratio, as well as salts and derivatives thereof. M and G refer to the mannuronate and guluronate residues in any of their anomeric configuration. $M_{bD}$, $G_{aL}$, $M_{aD}$ and $G_{bL}$ may be used to distinguish between β-D-mannuronate, α-L-guluronate, α-D-mannuronate, and β-L-guluronate, respectively. The term "alginate," as used herein, encompasses any polymer having the structure shown below, as well as salts thereof.

The salts of the alginates contain monovalent, divalent, polyvalent cations and combinations thereof, including, but not limited to $Li^+$, $Na^+$, $K^+$, $Rb^+$, $Cs^+$, $Mg^{2+}$, $Ca^{2+}$, $Sr^{2+}$, $Ba^{2+}$, $Al^{3+}$, $Ga^{3+}$, $Zn^{2+}$, $Fe^{2+}$, $Fe^{3+}$, $Pb^{2+}$, $Cu^{2+}$, $Pb^{2+}$, $Co^{2+}$ and $Ni^{2+}$.

"Biocompatible," as used herein, refers to a material which performs its desired function when introduced into an organism without inducing significant inflammatory response, immunogenicity, or cytotoxicity to native cells, tissues, or organs. Biocompatibility, as used herein, can be quantified using the in vivo biocompatibility assay described herein in Example 5.

In this assay, a material or product as disclosed can be considered biocompatible if it produces, in a test of biocomptibilty related to immune system reaction less than 50%, 45%, 40%, 35%, 30%, 25%, 20%, 15%, 10%, 8%, 6%, 5%, 4%, 3%, 2%, or 1% of the reaction, in the same test of biocompatibility, produced by a material or product the same as the test material or product except for a lack of the surface modification on the test material or product. Examples of useful biocompatibility tests include measuring and assessing cytotoxicity in cell culture, inflammatory response after implantation (such as by fluorescence detection of cathepsin activity), and immune system cells recruited to implant (for example, macrophages and neutrophils).

"Foreign Body Response," as used herein, refers to the immunological response of biological tissue to the presence of any foreign material in the tissue which can include protein adsorption, macrophages, multinucleated foreign body giant cells, fibroblasts, and angiogenesis.

"Chemically Modified Alginate" or "Modified Alginate," are used herein interchangeably, and refer to alginate polymers which contain one or more covalently modified monomers.

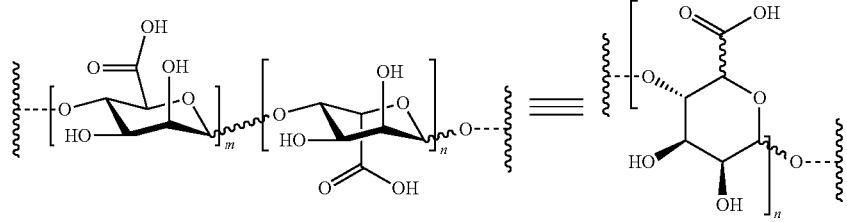 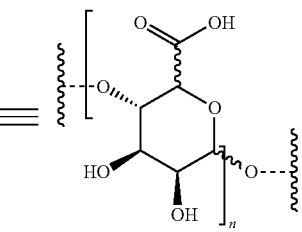

In some embodiments, the alginate is represented by the formula shown below, as well as salts thereof.

"Covalently Modified Monomer," as used herein, refers to a monomer which is an analog or derivative of a mannuro-

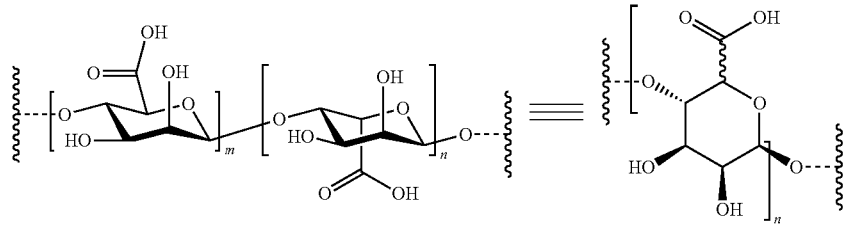 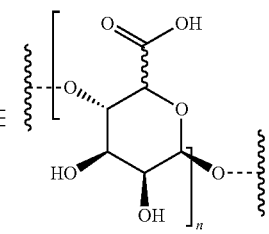

The modified alginate polymer exists in various charged states. In some embodiments, 1%, 2%, 5%, 10%, 15%, 20%, 25%, 30%, 35%, 40%, 45%, 50%, 55%, 60%, 65%, 70%, 75%, 80%, 85%, 90%, 90% and 99% of the monomers are charged. In some embodiments, the charges arise from any unmodified carboxylic acid groups, chemical modifications, or both, of the modified alginate polymer.

nate and/or guluronate monomer obtained from a mannuronate and/or guluronate monomer via a chemical process.

"Contacting" as used herein in the context of coating refers to any way for coating a polymer, such as the modified alginate polymers disclosed herein, on a substrate or surface. Contacting can include, but is not limited to, intraoperative dip-coating, spraying, wetting, immersing, dipping, painting, bonding or adhering, stepwise surface derivatization, or otherwise providing a substrate or surface with a compound with the hydrophobic, poly cationic polymer. The polymer can be covalently or non-covalently attached to the substrate or surface. In some embodiments, the polymer is non-covalently associated with the surface.

"Coating" as used herein refers to any temporary, semi-permanent or permanent layer, covering or surface. A coating can be applied as a gas, vapor, liquid, paste, semi-solid, or solid. In addition a coating can be applied as a liquid and solidified into a hard coating. Elasticity can be engineered into coatings to accommodate pliability, e.g. swelling or shrinkage, of the substrate or surface to be coated. Preferred coatings are modified alginate polymers disclosed herein.

"Surface" or "surfaces," as used herein, refers to any surface of any solid or semi-solid material, including glass, plastics, metals, polymers, and like. This includes surfaces constructed out of more than one material, including coated surfaces.

"Corresponding material" and "similar material," as used herein, refers a material that has, as far as is practical or possible, the same composition, structure, and construction as a reference material. The terms "corresponding" and "similar" can be used for the same meaning with any particular or subgroup of materials described herein. For example, a "similar surface modification" refers a surface modification that has, as far as is practical or possible, the same composition, structure, and construction as a reference surface modification.

"Control corresponding material" and "control similar material," as used herein, refers a material that has, as far as is practical or possible, the same composition, structure, and construction as a reference material except for one or more specified parameters. For example, a control corresponding material that lacks the chemical modification in reference to a chemically modified material refers to a material that has, as far as is practical or possible, the same composition, structure, and construction as a reference material except for the chemical modification. Generally, a material prior to chemical modification constitutes a control corresponding material to the chemically modified form of the material. The terms "control corresponding" and "control similar" can be used for the same meaning with any particular or subgroup of materials described herein. For example, a "control similar surface modification" refers a surface modification that has, as far as is practical or possible, the same composition, structure, and construction as a reference surface modification except for one or more specified parameters. Components that are "control corresponding" or "control similar" relative to a reference component are useful as controls in assays assessing the effect of independent variables.

"Preparation," as used herein in reference to capsules, compounds, and other objects and components themselves (as opposed to their production or preparation), refers to a plurality of the capsule, compound, or other object or component, each such capsule, compound, or other object or component having a set of common properties and structure but also having some differences in properties or structure. For example, a preparation of capsules with capsules having the same composition, structure, and functional properties, can include, for example, capsules having a variance in shape, size, pore size, generally around a desired mean. It is not necessary that such variance be intended or purposely designed, although that is contemplated. Rather, such variance generally is a consequence of the variability in production or preparation of the capsules, compounds, and other objects and components (as is exemplified by production of capsules).

"Implanting," as used herein, refers to the insertion or grafting into the body of a subject a product or material.

"Administering," as used herein, refers to contacting a substance, material, or product to the body of a subject. For example, administering a substance, material, or a product includes contacting the skin of a subject and injecting or implanting a substance, material, or product into the subject.

"Chemical compound," as used herein, refers to an organic compound. The disclosed compounds for chemically modifying alginates are examples of chemical compounds.

"High," "higher," "increases," "elevates," and "elevation," as used herein, refer to increases above a reference level, e.g., a basal level, e.g., as compared to a control. "Low," "lower," "reduces," and "reduction," as used herein, refer to decreases below a reference level, e.g., a basal level, e.g., as compared to a control. "Improved," as used herein, refers to a change that is desirable, which may be a higher or lower value of some measure.

"Long-term," as used herein, refers to a state or situation that extends for longer than days or weeks. Preferred long-term effects last several months or years.

"Monitoring" as used herein refers to any method in the art by which an activity can be measured.

"Providing," as used herein, refers to any method, device, or means of adding a compound or molecule to something, e.g., a method or device known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

"Preventing," as used herein, refers to administering or applying a treatment or therapy prior to the onset of clinical symptoms of a disease or conditions so as to prevent a physical manifestation of aberrations associated with the disease or condition.

"In need of treatment," as used herein, refers to a subject that would benefit from the treatment. In some embodiments, it comprises a judgment made by a caregiver (e.g. physician, nurse, nurse practitioner, or individual in the case of humans; veterinarian in the case of animals, including non-human mammals) that a subject requires or will benefit from treatment. This judgment can be made based on a variety of factors that are in the realm of a care giver's expertise, but that includes the knowledge that the subject is ill, or will be ill, as the result of a condition that is treatable by the compounds of the invention.

"Subject," as used herein, includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

"Treatment" and "treating," as used herein, refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitiative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

"Beneficial effect," as used herein, refers to any effect that is desired. In the context of the disclosed chemically modified alginates, beneficial effects include lower foreign body response, improved biocompatibility, and reduced immune response or reaction.

"Independently," as used herein in the context of chemical formulae (and unless the context clearly indicates otherwise), means that each instance of the group referred to is chosen independently of the other instances of that group. For example, each instance of the group could be different from every other instance, some other instances, or no other instances of the group. Where multiple groups are referred to, "independently" means that each instance of each given group is chosen independently of the other instances of the respective group and that each of the groups are chosen independently of the other groups. For example, each instance of a first group could be different from every instance, some other instances, or no other instances of a second group (or third, or fourth, etc., group).

"Component" as used herein in the context of a product, e.g., medical products, such as medical devices, is a part of a product that is structurally integrated with that product. A component may be applied to a substrate or to the surface of a product, contained within the substance of the product, retained in the interior of the product, or any other arrangement whereby that part is an integral element of the structure of the product. As an example, the silicone covering surrounding the mechanical part of a pacemaker is a component of the pacemaker. A component may be the lumen of a product where the lumen performs some function essential to the overall function of the product. The lumen of a tissue expander port is a component of the tissue expander. A component can refer to a reservoir or a discrete area within the product specifically adapted for the delivery of a fluid to a surface of the product. A reservoir within an implantable drug delivery device is a component of that device.

The phrase "effective amount," as used herein in the context of a coating, generally refers to the amount of the coating applied to the implant in order to provide one or more clinically measurable endpoints, such as reduced foreign body response compared to an uncoated implant, an implant coated with an unmodified coating, or another suitable control. The phrase "effective amount," as used herein in the context of a cell, capsule, product, device, material, composition, or compound, refers to a nontoxic but sufficient amount of the cell, capsule, product, device, material, composition, or compound to provide the desired result. The exact amount required may vary from subject to subject, depending on the species, age, and general condition of the subject; the severity of the disease that is being treated; the particular cell, capsule, product, device, material, composition, or compound used; its mode of administration; and other routine variables. An appropriate effective amount can be determined by one of ordinary skill in the art using only routine experimentation.

"Singularly Modified Alginate Polymer," as used herein, refers to modified alginates that contain one or more covalently modified monomers, wherein substantially all of the covalently modified monomers possess the same covalent modification (i.e. the polymer contains one 'type' or species of covalently modified monomer). Singularly modified alginate polymers include, for example, modified alginate polymers wherein substantially all of the monomers in the modified alginate polymer are represented by mannuronate monomers, guluronate monomers, and a covalently modified monomer defined by Formula I. Not all of the monomers are necessarily covalently modified.

"Capsule," as used herein, refers to a particle having a mean diameter of about 150 µm to about 5 cm, formed of a cross-linked hydrogel, having a cross-linked hydrogel core that is surrounded by one or more polymeric shells, having one or more cross-linked hydrogel layers, having a cross-linked hydrogel coating, or a combination thereof. The capsule may have any shape suitable for, for example, cell encapsulation. The capsule may contain one or more cells dispersed in the cross-linked hydrogel, thereby "encapsulating" the cells. Reference to "capsules" herein refers to and includes microcapsules unless the context clearly indicates otherwise. Preferred capsules have a mean diameter of about 150 µm to about 8 mm.

"Microcapsule" and "microgel," as used herein, are used interchangeably to refer to a particle or capsule having a mean diameter of about 150 µm to about 1000 µm.

"Biological material," as used herein, refers to any biological substance, including, but not limited to, tissue, cells, biological micromolecules, such as a nucleotides, amino acids, cofactors, and hormones, biological macromolecules, such as nucleic acids, polypeptides, proteins (for example enzymes, receptors, secretory proteins, structural and signaling proteins, hormones, ligands, etc.), polysaccharides, and/or any combination thereof.

"Cell," as used herein, refers to individual cells, cell lines, primary cultures, or cultures derived from such cells unless specifically indicated. "Culture," as used herein, refers to a composition including cells, such as isolated cells, which can be of the same or a different type. "Cell line," as used herein, refers to a permanently established cell culture that will proliferate indefinitely given appropriate fresh medium and space, thus making the cell line "immortal." "Cell strain," as used herein, refers to a cell culture having a plurality of cells adapted to culture, but with finite division potential. "Cell culture," as used herein, is a population of cells grown on a medium such as agar.

Cells can be, for example, xenogeneic, autologous, or allogeneic. Cells can also be primary cells. Cells can also be cells derived from the culture and expansion of a cell obtained from a subject. For example, cells can also be stem cells or derived from stem cells. Cells can also be immortalized cells. Cells can also be genetically engineered to express or produce a protein, nucleic acid, or other product.

"Mammalian cell," as used herein, refers to any cell derived from a mammalian subject.

"Autologous," as used herein, refers to a transplanted biological material, such as cells, taken from the same individual.

"Allogeneic," as used herein, refers to a transplanted biological material, such as cells, taken from a different individual of the same species.

"Xenogeneic," as used herein, refers to a transplanted biological material, such as cells, taken from a different species.

"Endocrine cell," as used herein, refers to a cell of the endocrine system. "Secreting endocrine cell," as used herein, refers to an endocrine cell that secretes one or more hormones.

"Islet cell," as used herein, refers to an endocrine cell derived from a mammalian pancreas. Islet cells include alpha cells that secrete glucagon, beta cells that secrete insulin and amylin, delta cells that secrete somatostatin, PP cells that secrete pancreatic polypeptide, or epsilon cells that secrete ghrelin. The term includes homogenous and heterogeneous populations of these cells. In preferred embodiments, a population of islet cells contains at least beta cells. In an embodiment, an islet cell is a human islet cell.

"Hormone-producing cell," as used herein, refers to a cell that produces one or more hormones. Preferred hormone-producing cells produce hormone in response to physiological stimulus, such as the physiological stimulus that cause secretion of the hormone from an endocrine cell that naturally secretes the hormone. Secreting endocrine cells, hormone-producing cells derived from stem cells, and cells genetically engineered to produce hormone are examples of hormone-producing cells.

"Insulin-producing cell," as used herein, refers to a cell that produces insulin. Preferred insulin-producing cells produce insulin in response to glucose levels. Islet beta cells, insulin-producing cells derived from stem cells, and cells genetically engineered to produce insulin are examples of insulin-producing cells.

"Transplant," as used herein, refers to the transfer of a cell, tissue, or organ to a subject from another source. The term is not limited to a particular mode of transfer. Encapsulated cells may be transplanted by any suitable method, such as by injection or surgical implantation.

"Primary cells," "primary cell lines," and "primary cultures," as used herein, are used interchangeably to refer to cells and cells cultures that have been derived from a subject and allowed to grow in vitro for a limited number of passages, that is, splittings, of the culture.

"Mesenchymal stem cell" or "MSC," as used herein, refer to multipotent stem cells present in or derived from mesenchymal tissue that can differentiate into a variety of cell types, including: osteoblasts, chondrocytes, and adipocytes.

"Derived from," as used herein, with respect to cells, refer to cells obtained from tissue, cell lines, or cells, which optionally are then cultured, passaged, differentiated, induced, etc., to produce the derived cells. For example, induced pluripotent stem cells are derived from somatic cells.

"Pluripotency," as used herein, refers to the ability of cells to differentiate into multiple types of cells in an organism. By "pluripotent stem cells," it is meant cells that can self-renew and differentiate to produce all types of cells in an organism. By "multipotency" it is meant the ability of cells to differentiate into some types of cells in an organism but not all, typically into cells of a particular tissue or cell lineage.

"Multi-potent cells" and "adult stem cells," as used herein, refer to any type of stem cell that is not derived from an embryo or fetus and generally has a limited capacity to generate new cell types (referred to as "multipotency") and being committed to a particular lineage.

"Induced pluripotent stem cell," as used herein, encompasses pluripotent stem cells, that, like embryonic stem (ES) cells, can be cultured over a long period of time while maintaining the ability to differentiate into all types of cells in an organism, but that, unlike ES cells (which are derived from the inner cell mass of blastocysts), are derived from somatic cells.

For clarity of discussion herein, singularly modified alginates are defined using formulae illustrating the structure of the covalently modified monomers incorporated in the backbone and omitting the mannuronate and guluronate monomers. For example, a singularly modified alginate polymer composed of mannuronate monomers, guluronate monomers, and a covalently modified monomer defined by Formula I, wherein X is $NR_4$, $R_1$ is methyl, and $R_4$, $Y_1$, and $Y_2$ are hydrogen, is illustrated herein by the structure below.

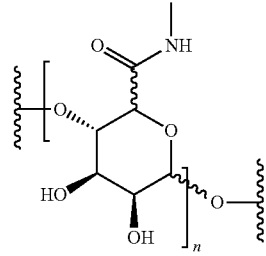

Formula I

In some embodiments, the covalently modified monomer is derived from Formula Ia or Formula Ib, shown below.

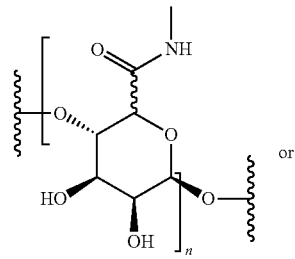

Formula Ia

Formula Ib

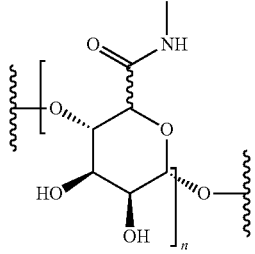

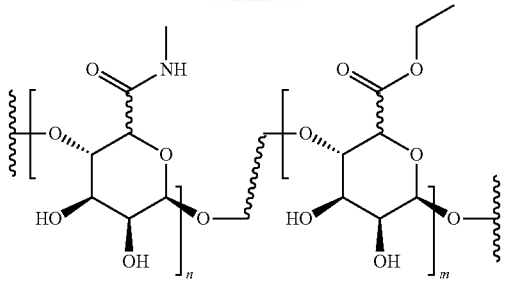

Derived from Formula Ia

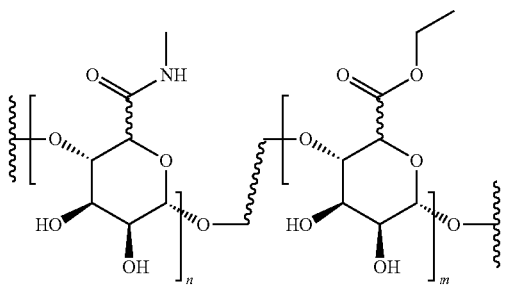

Derived from Formula Ib

"Multiply Modified Alginate Polymer," as used herein, refers to modified alginates that contain covalently modified monomers, wherein substantially all of the covalently modified monomers do not possess the same covalent modification (i.e. the polymer contains two or more different 'types' or species of covalently modified monomers). Multiply modified alginate polymers include, for example, modified alginate polymers wherein substantially all of the monomers in the modified alginate polymer are represented by mannuronate monomers, guluronate monomers, and two or more different types of covalently modified monomers defined by Formula I. As used in this context, a 'type' or 'species' of covalently modified monomer refers to a covalent monomer defined by Formula I, wherein all possible variable positions are chemically defined. Not all the monomers are covalently modified.

For clarity of discussion herein, modified alginates are defined using formulae illustrating the covalently modified monomers incorporated in the backbone and omitting the mannuronate and guluronate monomers. For example, a multiply modified alginate polymer composed of mannuronate monomers, guluronate monomers, and two different types of covalently modified monomers, wherein the first type of covalently modified monomer is defined by Formula I, Formula Ia, Formula Ib, or a combination of Formula Ia and Formula Ib, as described above, wherein X is $NR_4$, $R_1$ is methyl, and $R_4$, $Y_1$; and $Y_2$ are hydrogen and the second type of covalently modified monomer is defined by Formula I, Formula Ia, or Formula Ib, wherein X is oxygen, $R_1$ is ethyl, and $Y_1$ and $Y_2$ are hydrogen, is illustrated by the structures below.

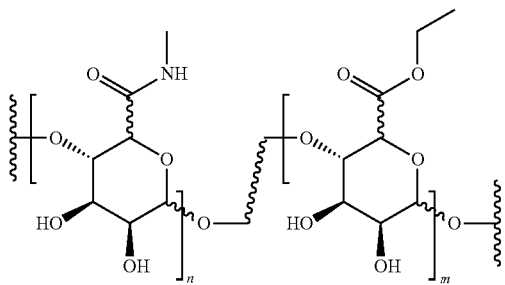

Derived from Formula I

"Analog" and "Derivative," in the context of chemical compounds, are used herein interchangeably, and refer to a compound having a structure similar to that of a parent compound, but varying from the parent compound by a difference in one or more certain components. Analogs or derivatives differ from the parent compound in one or more atoms, functional groups, or substructures, which are replaced with other atoms, groups, or substructures. An analog or derivative can be imagined to be formed, at least theoretically, from the parent compound via some chemical or physical process. The terms analog and derivative encompass compounds which retain the same basic ring structure as the parent compound, but possess one or more different substituents on the ring(s). For example, analog or derivative of mannuronate or guluronate refers to compounds which retain the core of the monomer, e.g., the pyranose ring, but differ in or more substitutents on the ring. In some embodiments, an analog or derivative retains at least, 20, 30, 40, 50, 60, 70, 80, 90, or 100% of a selected activity of a reference compound, e.g., a parent compound.

"Mannuronate" and "Mannuronate Monomer," as used herein, refer to mannuronic acid monomers as well as salts thereof.

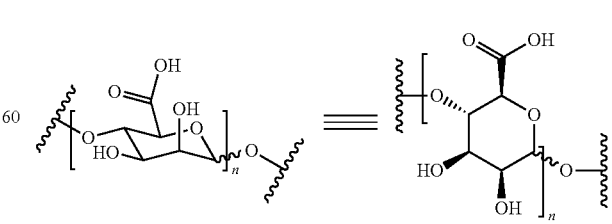

In some embodiments, the mannuronate is the structure shown below.

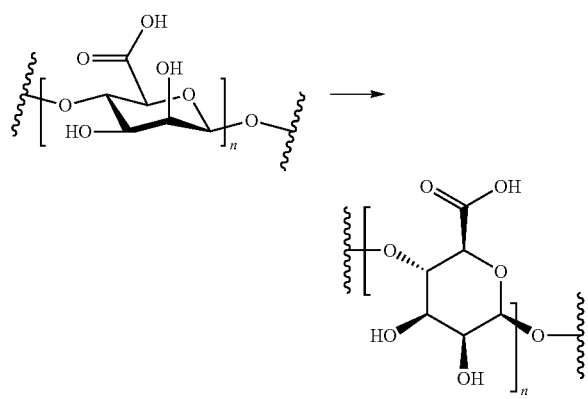

"Guluronate" and "Guluronate Monomer," as used herein, refer to guluronic acid monomers as well as salts thereof.

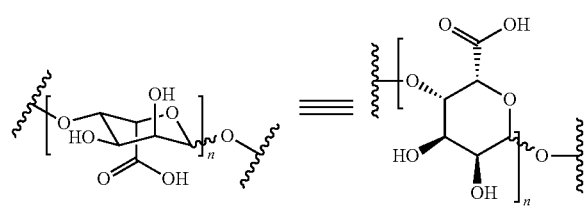

In some embodiments, the guluronate is the structure shown below.

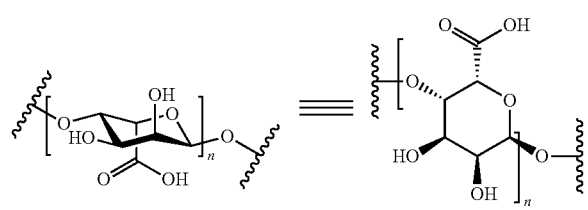

"Substantially," as used herein, specifies an amount of 95% or more, 96% or more, 97% or more, 98% or more, or 99% or more.

"Glass Transition Temperature" ($T_g$), as used herein, refers to the temperature at which a reversible transition is observed in amorphous materials from a hard and relatively brittle state into a molten or rubber-like state. $T_g$ values for alginate polymers can be experimentally determined using differential scanning calorimetry (DSC, heated and cooled at a rate of 10 K/min). In all cases herein, values of $T_g$ are measured using powder polymer samples.

"Click Chemistry," as used herein, refers to chemical reactions used to couple two compounds together which are high yielding, wide in scope, create only byproducts that can be removed without chromatography, are stereospecific, simple to perform, and can be conducted in easily removable or benign solvents. Examples of reactions which fulfill these criteria include the nucleophilic ring opening of epoxides and aziridines, non-aldol type carbonyl reactions, including the formation of hydrazones and heterocycles, additions to carbon-carbon multiple bonds, including Michael Additions, and cycloaddition reactions, such as a 1,3-dipolar cycloaddition reaction (i.e. a Huisgen cycloaddition reaction). See, for example, Moses, and Moorhouse, Chem Soc. Rev. 36:1249-1262 (2007); Kolb and Sharpless, Drug Discovery Today. 8(24): 1128-1137 (2003); and Kolb et al., Angew. Chem. Int. Ed. 40:2004-2021 (2001).

"Polyvalent Cation," as used herein, refers to cations which have a positive charge greater than 1. Examples include, but are not limited to, $Ca^{2+}$, $Ba^{2+}$, and $Sr^{2+}$.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups that may include from zero to four heteroatoms, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl."

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$ wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$; —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenyl" is art recognized, and refers to the aromatic moiety —C$_6$H$_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

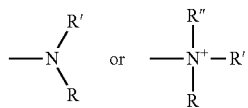

wherein, R, R', and R" each independently represent a hydrogen, substituted or unsubstituted alkyl, substituted or unsubstituted alkenyl, substituted or unsubstituted alkynyl, substituted or unsubstituted carbonyl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —(CH$_2$)$_m$—R'''. Thus, the term 'alkylamine' as used herein refers to an amine group, as defined above, having a substituted or unsubstituted alkyl attached thereto (i.e. at least one of R, R', or R" is an alkyl group).

"Carbonyl," as used herein, is art-recognized and includes such moieties as can be represented by the general formula:

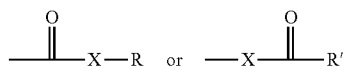

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —(CH$_2$)$_m$—R"; R" represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. Where X is oxygen and R is defines as above, the moiety is also referred to as a carboxyl group. When X is oxygen and R is hydrogen, the formula represents a 'carboxylic acid.' Where X is oxygen and R' is hydrogen, the formula represents a 'formate.' Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

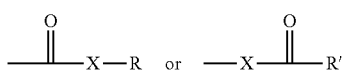

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

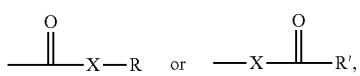

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy," "aroxy" or "aryloxy," generally describe compounds represented by the formula —$OR^v$, wherein $R^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenylthio" is art recognized, and refers to —S—C$_6$H$_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

The terms "amide" or "amido" are used interchangeably, refer to both "unsubstituted amido" and "substituted amido" and are represented by the general formula:

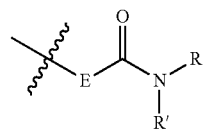

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —(CH$_2$)$_m$—R'' When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

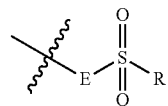

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E and R are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

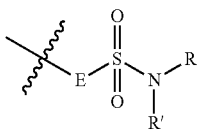

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

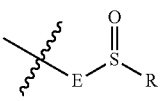

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8.

The term "phosphonyl" is represented by the formula

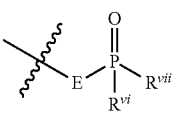

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, R$^{vi}$ and R$^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a poly cycle; and m is zero or an integer ranging from 1 to 8.

The term "substituted phosphonyl" represents a phosphonyl in which E, R$^{vi}$ and R$^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, R$^{vi}$ and R$^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, R$^{vi}$ and R$^{vii}$ are substituted, the substituents include, but are not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxy carbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "C$_3$-C$_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —NO$_2$.

The term "phosphate" refers to —O—PO$_3$.

The term "azide" or "azido" are used interchangeably to refer to —N$_3$.

The term "substituted C$_1$-C$_x$ alkyl" refers to alkyl groups having from one to x carbon atoms, wherein at least one carbon atom is substituted, wherein "x" is an integer from one and ten. The term "unsubstituted C$_1$-C$_x$ alkyl" refers to alkyl groups having from one to x carbon atoms that are not substituted, wherein "x" is an integer from one to ten.

The term "substituted C$_1$-C$_x$ alkylene" refers to alkylene groups having from one to x carbon atoms, wherein at least one carbon atom is substituted, wherein "x" is an integer from one to ten. The term "unsubstituted C$_1$-C$_x$ alkylene" refers to alkylene groups having from one to x carbon atoms that are not substituted, wherein "x" is an integer from one to ten. The term "alkylene" as used herein, refers to a moiety with the formula —(CH$_2$)$_a$—, wherein "a" is an integer from one to 10.

The term "substituted C$_2$-C$_x$ alkenyl" refers to alkenyl groups having from two to x carbon atoms, wherein at least one carbon atom is substituted, wherein "x" is an integer from two to ten. The term "unsubstituted C$_2$-C$_x$ alkenyl" refers to alkenyl groups having from two to x carbon atoms that are not substituted, wherein "x" is an integer from two to ten.

The term "substituted C$_2$-C$_x$ alkynyl" refers to alkynyl groups having from two to x carbon atoms, wherein at least one carbon atom is substituted, wherein "x" is an integer from two to ten. The term "unsubstituted C$_2$-C$_x$ alkynyl" refers to alkynyl groups having from two to x carbon atoms that are not substituted, wherein "x" is an integer from two to ten.

The term "substituted C$_1$-C$_x$ alkoxy" refers to alkoxy groups having from one to x carbon atoms, wherein at least one carbon atom is substituted, wherein "x" is an integer from one to ten. The term "unsubstituted C$_1$-C$_x$ alkoxy" refers to alkoxy groups having from one to x carbon atoms that are not substituted, wherein "x" is an integer from one to ten.

The term "substituted C$_1$-C$_x$ alkylamino" refers to alkylamino groups having from one to x carbon atoms, wherein at least one carbon atom is substituted, wherein "x" is an integer from one to ten. The term "unsubstituted C$_1$-C$_x$ alkylamino" refers to alkylamino groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quaternary nitrogen atom, respectively.

The term "substituted C$_1$-C$_x$ alkylthio" refers to alkylthio groups having from one to x carbon atoms, wherein at least one carbon atom is substituted, wherein "x" is an integer from one to ten. The term "unsubstituted C$_1$-C$_x$ alkylthio" refers to alkylthio groups having from one to x carbon atoms that are not substituted, wherein "x" is an integer from one to ten.

The term "substituted C$_1$-C$_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

The term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

The term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

The term "substituted $C_1$-$C_x$ sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x carbon atoms that are not substituted, wherein "x" is an integer from one to ten.

The term "substituted $C_1$-$C_x$ sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

The term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

The term "substituted $C_1$-$C_x$ sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

The term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

The term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

The term "substituted $C_0$-$C_x$ sulfonyl" refers to sulfonyl groups having from zero to x carbon atoms, wherein at least one carbon atom is substituted, wherein "x" is an integer from zero to ten. The term "unsubstituted $C_0$-$C_x$ sulfonyl" refers to sulfonyl groups having from zero to ten carbon atoms that are not substituted, wherein "x" is an integer from zero to ten.

The term "substituted $C_0$-$C_x$ sulfonic acid" refers to sulfonic acid groups having from zero to ten carbon atoms, wherein at least one carbon atom is substituted, wherein "x" is an integer from zero to ten. The term "unsubstituted $C_0$-$C_x$ sulfonic acid" refers to sulfonic acid groups having from zero to ten carbon atoms that are not substituted, wherein "x" is an integer from zero to ten.

The term "substituted $C_0$-$C_x$ sulfamoyl" refers to sulfamoyl groups having from zero to ten carbon atoms, wherein at least one carbon atom is substituted, wherein "x" is an integer from zero to ten. The term "unsubstituted $C_0$-$C_x$ sulfamoyl" refers to alkenyl groups having from two to nine carbon atoms that are not substituted, wherein "x" is an integer from zero to ten.

The term "substituted $C_0$-$C_x$ sulfoxide" refers to sulfoxide groups having from zero to ten carbon atoms, wherein at least one carbon atom is substituted, wherein "x" is an integer from zero to ten. The term "unsubstituted $C_0$-$C_x$ sulfoxide" refers to sulfoxide groups having from two to nine carbon atoms that are not substituted, wherein "x" is an integer from zero to ten.

The term "substituted $C_0$-$C_x$ phosphoryl" refers to phosphoryl groups having from zero to ten carbon atoms, wherein at least one carbon atom is substituted, wherein "x" is an integer from zero to ten. The term "unsubstituted $C_0$-$C_x$ phosphoryl" refers to phosphoryl groups having from zero to ten carbon atoms that are not substituted, wherein "x" is an integer from zero to ten.

The term "substituted $C_0$-$C_x$ phosphonyl" refers to phosphonyl groups having from zero to x carbon atoms, wherein at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein x is an integer from one to ten. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein x is an integer from one to ten.

The terms unsubstituted "$C_0$ sulfonyl," "$C_0$ sulfonic acid," "$C_0$ sulfamoyl," "$C_0$ phosphoryl," and "$C_0$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having zero carbon atoms that are not substituted.

"Halogen," as used herein, refers to fluorine, chlorine, bromine, or iodine.

As used herein, $U_1$, represents the organic groups alkyl, substituted alkyl, alkenyl, substituted alkenyl, alkynyl, substituted alkynyl, phenyl, substituted phenyl, aryl, substituted aryl, heteroaryl, substituted heteroaryl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, poly aryl, substituted poly aryl, $C_3$-$C_{20}$ cyclic, substituted $C_3$-$C_{20}$ cyclic, heterocyclic, substituted heterocyclic, amino acid, poly(ethylene glycol), peptide, and polypeptide group.

As used herein, $U_2$ represents the organic groups alkylamino, dialkylamino, hydroxy, alkenyl, alkynyl, substituted alkyl, substituted alkenyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), and polypeptide group.

As used herein, $U_3$ represents the organic groups alkylamino, dialkylamino, hydroxy, alkyl, alkenyl, alkynyl, substituted alkyl, substituted alkenyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, amino acid, poly(ethylene glycol), peptide, and polypeptide group.

As used herein, $U_4$ represents the organic groups alkyl, substituted alkyl, alkenyl, substituted alkenyl, alkynyl, substituted alkynyl, aryl, substituted aryl, heteroaryl, substituted heteroaryl, alkoxy, substituted alkoxy, carboxyl, substituted carboxyl, amino, substituted amino, amido, substituted amido, $C_3$-$C_{20}$ cyclic, substituted $C_3$-$C_{20}$ cyclic, heterocyclic, and substituted heterocyclic.

As used herein, $Q_1$ represents the organic groups arylalkyl and substituted arylalkyl.

As used herein, $Q_2$ represents the organic groups sulfonyl, substituted sulfonyl, sulfonic acid, phosphoryl, substituted phosphoryl, phosphonyl, and substituted phosphonyl.

As used herein, $Q_3$ represents the organic group poly (lactic-co-glycolic acid).

As used herein, $Q_4$ represents organic groups substituted alkylene and unsubstituted alkylene.

As used herein, $Q_5$ represents the organic groups alkylamino, dialkylamino, and hydroxy.

As used herein, $Q_6$ represents the organic groups aroxy, substituted aroxy, carbonyl, substituted carbonyl, and poly (ethylene glycol).

As used herein, $Q_7$ represents the organic groups alkylthio, substituted alkylthio, arylthio, substituted arylthio, phenoxy, substituted phenoxy, phenylthio, substituted phenylthio, polyaryl, and substituted polyaryl.

As used herein, $Q_8$ represents the organic groups amino acid, peptide, and polypeptide group.

As used herein, $Q_9$ represents the organic groups phenyl and substituted phenyl.

In some embodiments, groups $Q_1$; $Q_2$, $Q_3$, $Q_4$, or any combination thereof, can be used along with any one of $U_1$; $U_2$, and $U_3$. For example, $U_1$ can be combined with $Q_1$, with $Q_2$, with $Q_3$, with $Q_4$, with $Q_1$ and $Q_2$, with $Q_1$ and $Q_3$, with $Q_1$ and $Q_4$, with $Q_2$ and $Q_3$, with $Q_2$ and $Q_4$, with $Q_3$, and $Q_4$, with $Q_1$; $Q_2$, and $Q_3$, with $Q_1$; $Q_2$, and $Q_4$, with $Q_1$; $Q_3$, and $Q_4$, with $Q_2$, $Q_3$, and $Q_4$, and with with $Q_1$; $Q_2$, $Q_3$, and $Q_4$. Such combinations are referred to as $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, respectively. Similarly, $U_2$ can be combined with $Q_1$, with $Q_2$, with $Q_3$, with $Q_4$, with $Q_1$ and $Q_2$, with $Q_1$ and $Q_3$, with $Q_1$ and $Q_4$, with $Q_2$ and $Q_3$, with $Q_2$ and $Q_4$, with $Q_3$, and $Q_4$, with $Q_1$; $Q_2$, and $Q_3$, with $Q_1$; $Q_2$, and $Q_4$, with $Q_1$; $Q_3$, and $Q_4$, with $Q_2$, $Q_3$, and $Q_4$, and with with $Q_1$, $Q_2$, $Q_3$, and $Q_4$. Such combinations are referred to as $U_2+Q_1$; $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, respectively. Similarly, $U_3$ can be combined with $Q_1$; with $Q_2$, with $Q_3$, with $Q_4$, with $Q_1$ and $Q_2$, with $Q_1$ and $Q_3$, with $Q_1$ and $Q_4$, with $Q_2$ and $Q_3$, with $Q_2$ and $Q_4$, with $Q_3$, and $Q_4$, with $Q_1$; $Q_2$, and $Q_3$, with $Q_1$; $Q_2$, and $Q_4$, with $Q_1$; $Q_3$, and $Q_4$, with $Q_2$, $Q_3$, and $Q_4$, and with with $Q_1$; $Q_2$, $Q_3$, and $Q_4$. Such combinations are referred to as $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, respectively.

In some embodiments, groups $Q_1$; $Q_2$, $Q_3$, $Q_4$, $Q_5$, or any combination thereof, can be used along with 1% For example, $U_1$ can be combined with $Q_1$, with $Q_2$, with $Q_3$, with $Q_4$, with $Q_5$, with $Q_1$ and $Q_2$, with $Q_1$ and $Q_3$, with $Q_1$ and $Q_4$, with $Q_1$ and $Q_5$, with $Q_2$ and $Q_3$, with $Q_2$ and $Q_4$, with $Q_2$ and $Q_5$, with $Q_3$ and $Q_4$, with $Q_3$ and $Q_5$, with $Q_4$ and $Q_5$, with $Q_b$ $Q_2$, and $Q_3$, with $Q_1$; $Q_2$, and $Q_4$, with $Q_1$; $Q_2$, and $Q_5$, with $Q_1$; $Q_3$, and $Q_4$, with $Q_1$, $Q_3$, and $Q_5$, with $Q_1$; $Q_4$, and $Q_5$, with $Q_2$, $Q_3$, and $Q_4$, with $Q_2$, $Q_3$, and $Q_5$, with $Q_2$, $Q_4$, and $Q_5$, with $Q_3$, $Q_4$, and $Q_5$, with $Q_1$; $Q_2$, $Q_3$, and $Q_4$, with $Q_1$; $Q_2$, $Q_3$, and $Q_5$, with $Q_b$ $Q_2$, $Q_4$, and $Q_5$, with $Q_1$; $Q_3$, $Q_4$, and $Q_5$, with $Q_2$, $Q_3$, $Q_4$, and $Q_5$, with $Q_1$; $Q_2$, $Q_3$, $Q_4$, and $Q_5$. Such combinations can be referred to as $U_1+Q_1$, $U_1+Q_2$, $U_1+Q_3$, $U_1+Q_4$, $U_1+Q_5$, $U_1+Q_1+Q_2$, $U_1+Q_1+Q_3$, $U_1+Q_1+Q_4$, $U_1+Q_1+Q_5$, $U_1+Q_2+Q_3$, $U_1+Q_2+Q_4$, $U_1+Q_2+Q_5$, $U_1+Q_3+Q_4$, $U_1+Q_3+Q_5$, $U_1+Q_4+Q_5$, $U_1+Q_1+Q_2+Q_3$, $U_1+Q_1+Q_2+Q_4$, $U_1+Q_1+Q_2+Q_5$, $U_1+Q_1+Q_3+Q_4$, $U_1+Q_1+Q_3+Q_5$, $U_1+Q_1+Q_4+Q_5$, $U_1+Q_2+Q_3+Q_4$, $U_1+Q_2+Q_3+Q_5$, $U_1+Q_2+Q_4+Q_5$, $U_1+Q_3+Q_4+Q_5$, $U_1+Q_1+Q_2+Q_3+Q_4$, $U_1+Q_1+Q_2+Q_3+Q_5$, $U_1+Q_1+Q_2+Q_4+Q_5$, $U_1+Q_1+Q_3+Q_4+Q_5$, $U_1+Q_2+Q_3+Q_4+Q_5$, $U_1+Q_1+Q_2+Q_3+Q_4$, $+Q_8$, respectively.

In some embodiments, groups $Q_1$, $Q_2$, $Q_3$, $Q_4$, $Q_5$, $Q_6$, $Q_7$, $Q_8$, $Q_9$ or any combination thereof, can be used along with $U_4$. For example, $U_4$ can be combined with $Q_1$, with $Q_2$, with $Q_3$, with $Q_4$, with $Q_5$, with $Q_6$, with $Q_7$, with $Q_8$, with $Q_9$, with $Q_1+Q_2$, with $Q_1+Q_3$, with $Q_1+Q_4$, with $Q_1+Q_5$, with $Q_1+Q_6$, with $Q_1+Q_7$, with $Q_1+Q_8$, with $Q_1+Q_9$, with $Q_2+Q_3$, with $Q_2+Q_4$, with $Q_2+Q_5$, with $Q_2+Q_6$, with $Q_2+Q_7$, with $Q_2+Q_8$, with $Q_2+Q_9$, with $Q_3+Q_4$, with $Q_3+Q_5$, with $Q_3+Q_6$, with $Q_3+Q_7$, with $Q_3+Q_8$, with $Q_3+Q_9$, with $Q_4+Q_5$, with $Q_4+Q_6$, with $Q_4+Q_7$, with $Q_4+Q_8$, with $Q_4+Q_9$, with $Q_5+Q_6$, with $Q_5+Q_7$, with $Q_5+Q_8$, with $Q_5+Q_9$, with $Q_6+Q_7$, with $Q_6+Q_8$, with $Q_6+Q_9$, with $Q_7+Q_8$, with $Q_7+Q_9$, with $Q_8+Q_9$, with $Q_1+Q_2+Q_3$, with $Q_1+Q_2+Q_4$, with $Q_1+Q_2+Q_5$, with $Q_1+Q_2+Q_6$, with $Q_1+Q_2+Q_7$, with $Q_1+Q_2+Q_8$, with $Q_1+Q_2+Q_9$, with $Q_1+Q_3+Q_4$, with $Q_1+Q_3+Q_5$, with $Q_1+Q_3+Q_6$, with $Q_1+Q_3+Q_7$, with $Q_1+Q_3+Q_8$, with $Q_1+Q_3+Q_9$, with $Q_1+Q_4+Q_5$, with $Q_1+Q_4+Q_6$, with $Q_1+Q_4+Q_7$, with $Q_1+Q_4+Q_8$, with $Q_1+Q_4+Q_9$, with $Q_1+Q_5+Q_9$, with $Q_1+Q_5+Q_7$, with $Q_1+Q_5+Q_8$, with $Q_1+Q_5+Q_9$, with $Q_2+Q_3+Q_7$, with $Q_1+Q_6+Q_8$, with $Q_1+Q_6+Q_9$, with $Q_1+Q_7+Q_8$, with $Q_1+Q_7+Q_9$, with $Q_1+Q_8+Q_9$, with $Q_2+Q_3+Q_4$, with $Q_2+Q_3+Q_5$, with $Q_2+Q_3+Q_6$, with $Q_2+Q_3+Q_7$, with $Q_2+Q_3+Q_8$, with $Q_2+Q_3+Q_9$, with $Q_2+Q_4+Q_5$, with $Q_2+Q_4+Q_6$, with $Q_2+Q_4+Q_7$, with $Q_2+Q_4+Q_8$, with $Q_2+Q_4+Q_9$, with $Q_2+Q_5+Q_6$, with $Q_2+Q_5+Q_7$, with $Q_2+Q_8+Q_8$, with $Q_2+Q_5+Q_9$, with $Q_2+Q_6+Q_7$, with $Q_2+Q_6+Q_8$, with $Q_2+Q_6+Q_9$, with $Q_2+Q_7+Q_8$, with $Q_2+Q_7+Q_9$, with $Q_2+Q_8+Q_9$, with $Q_3+Q_4+Q_5$, with $Q_3+Q_4+Q_6$, with $Q_3+Q_4+Q_7$, with $Q_3+Q_4+Q_8$, with $Q_3+Q_4+Q_9$, with $Q_3+Q_5+Q_6$, with $Q_3+Q_5+Q_7$, with $Q_3+Q_5+Q_8$, with $Q_3+Q_5+Q_9$, with $Q_3+Q_6+Q_7$, with $Q_3+Q_3+Q_8$, with $Q_3+Q_6+Q_9$, with $Q_3+Q_7+Q_8$, with $Q_3+Q_7+Q_9$, with $Q_3+Q_8+Q_9$, with $Q_4+Q_5+Q_9$, with $Q_4+Q_5+Q_7$, with $Q_4+Q_5+Q_8$, with $Q_4+Q_5+Q_9$, with $Q_4+Q_6+Q_7$, with $Q_4+Q_6+Q_8$, with $Q_4+Q_6+Q_9$, with $Q_4+Q_7+Q_8$, with $Q_4+Q_7+Q_9$, with $Q_4+Q_8+Q_9$, with $Q_5+Q_3+Q_7$, with $Q_5+Q_3+Q_8$, with $Q_5+Q_3+Q_9$, with $Q_5+Q_7+Q_8$, with $Q_5+Q_7+Q_9$, with $Q_5+Q_8+Q_9$, with $Q_6+Q_7+Q_8$, with $Q_6+Q_7+Q_9$, with $Q_3+Q_8+Q_9$, with $Q_1+Q_2+Q_3+Q_4$, with $Q_1+Q_2+Q_3+Q_5$, with $Q_1+Q_2+Q_3+Q_6$, with $Q_1+Q_2+Q_3+Q_7$, with $Q_1+Q_2+Q_3+Q_8$, with $Q_1+Q_2+Q_3+Q_9$, with $Q_1+Q_3+Q_4+Q_8$, with $Q_1+Q_3+Q_4+Q_6$, with $Q_1+Q_3+Q_4+Q_7$, with $Q_1+Q_3+Q_4+Q_8$, with $Q_1+Q_3+Q_4+Q_9$, with $Q_1+Q_4+Q_5+Q_9$, with $Q_1+Q_4+Q_5+Q_7$, with $Q_x+Q_4+Q_5+Q_8$, with $Q_1+Q_4+Q_5+Q_9$, with $Q_1+Q_5+Q_6+Q_7$, with $Q_1+Q_5+Q_6+Q_8$, with $Q_1+Q_5+Q_3+Q_9$, with $Q_1+Q_6+Q_7+Q_8$, with $Q_1+Q_6+Q_7+Q_9$, with $Q_x+Q_7+Q_8+Q_9$, with $Q_2+Q_3+Q_4+Q_8$, with $Q_2+Q_3+Q_4+Q_6$, with $Q_2+Q_3+Q_4+Q_7$, with $Q_2+Q_3+Q_4+Q_8$, with $Q_2+Q_3+Q_4+Q_9$, with $Q_2+Q_4+Q_5+Q_9$, with $Q_2+Q_4+Q_5+Q_7$, with $Q_2+Q_4+Q_5+Q_8$, with $Q_2+Q_4+Q_5+Q_9$, with $Q_2+Q_5+Q_6+Q_7$, with $Q_2+Q_5+Q_3+Q_8$, with $Q_2+Q_5+Q_3+Q_9$, with $Q_2+Q_6+Q_7+Q_8$, with $Q_2+Q_6+Q_7+Q_9$, with $Q_2+Q_7+Q_8+Q_9$, with $Q_3+Q_4+Q_5+Q_6$, with $Q_3+Q_4+Q_5+Q_7$, with $Q_3+Q_4+Q_5+Q_8$, with $Q_3+Q_4+Q_5+Q_9$, with $Q_3+Q_5+Q_3+Q_7$, with $Q_3+Q_5+Q_6+Q_8$, with $Q_3+Q_5+Q_3+Q_9$, with $Q_3+Q_6+Q_7+Q_8$, with $Q_3+Q_6+Q_7+Q_9$, with $Q_3+Q_7+Q_8+Q_9$, with $Q_4+Q_5+Q_3+Q_7$, with $Q_4+Q_5+Q_3+Q_8$, with $Q_4+Q_5+Q_6+Q_9$, with $Q_4+Q_3+Q_7+Q_8$, with $Q_4+Q_6+Q_7+Q_9$, with $Q_4+Q_7+Q_8+Q_9$, with $Q_5+Q_3+Q_7+Q_8$, with $Q_5+Q_3+Q_7+Q_9$, with $Q_5+Q_7+Q_8+Q_9$, with $Q_x+Q_2+Q_3+Q_4+Q_5$, with $Q_1+Q_2+Q_3+Q_4+Q_6$, with $Q_1+Q_2+Q_3+Q_4+Q_7$, with $Q_4+Q_2+Q_3+Q_4+Q_8$, with $Q_1+Q_2+Q_3+Q_4+Q_9$, with $Q_1+Q_3+Q_4+Q_5+Q_6$, with $Q_1+Q_3+Q_4+Q_5+Q_7$, with $Q_1+Q_3+Q_4+Q_5+Q_8$, with $Q_1+Q_3+Q_4+Q_5+Q_9$, with $Q_1+Q_4+Q_8+Q_6+Q_7$, with $Q_1+Q_4+Q_5+Q_6+Q_8$, with $Q_1+Q_4+Q_5+Q_6+Q_9$, with $Q_1+Q_5+Q_6+Q_7+Q_8$, with $Q_1+Q_5+Q_6+Q_7+Q_9$, with $Q_1+Q_6+Q_7+Q_8+Q_9$, with $Q_2+Q_3+Q_4+Q_5+Q_6$, with $Q_2+Q_3+Q_4+Q_5+Q_7$, with $Q_2+Q_3+Q_4+Q_5+Q_8$, with $Q_2+Q_3+Q_4+Q_8+Q_9$, with $Q_2+Q_4+Q_5+Q_6+Q_7$, with $Q_2+Q_4+Q_5+Q_6+Q_8$, with $Q_2+Q_4+Q_8+Q_6+Q_9$, with $Q_2+Q_5+Q_6+Q_7+Q_8$, with $Q_2+Q_5+Q_6+Q_7+Q_9$, with $Q_2+Q_6+Q_7+Q_8+Q_9$, with $Q_3+Q_4+Q_5+Q_6+Q_7$, with $Q_3+Q_4+Q_5+Q_3+Q_8$, with $Q_3+Q_4+Q_5+Q_6+Q_9$, with $Q_3+Q_5+Q_6+Q_7+Q_9$, with $Q_3+Q_6+Q_7+Q_8+Q_9$, with $Q_4+Q_5+Q_6+Q_7+Q_8$, with $Q_4+Q_5+Q_6+Q_7+Q_9$, with $Q_4+Q_6+Q_7+Q_8+Q_9$ with $Q_5+Q_6+Q_7+Q_8+Q_9$, with $Q_1+Q_2+Q_3+Q_4+Q_5+Q_6$, with $Q_1+Q_2+Q_3+Q_4+Q_8+Q_7$, with $Q_1+Q_2+Q_3+Q_4+Q_5+Q_8$, with $Q_1+Q_2+Q_3+Q_4+Q_5+Q_9$, with $Q_1+Q_3+Q_4+Q_5+Q_6+Q_7$, with $Q_1+Q_3+Q_4+Q_8+Q_6+Q_8$, with $Q_1+Q_3+Q_4+Q_5+Q_6+Q_9$, with $Q_1+Q_4+Q_5+Q_6+Q_7+Q_8$, with $Q_1+Q_4+Q_5+Q_6+Q_7+Q_9$, with $Q_1+Q_5+Q_6+Q_7+Q_8+Q_9$, with $Q_2+Q_3+Q_4+Q_8+Q_6+Q_7$, with $Q_2+Q_3+Q_4+Q_8+Q_6+Q_8$, with $Q_2+Q_3+Q_4+Q_8+Q_6+Q_9$, with $Q_2+Q_4+Q_8+Q_6+Q_7+Q_8$, with $Q_2+Q_4+Q_5+Q_6+Q_7+Q_9$, with $Q_2+Q_5+Q_6+Q_7+Q_8+Q_9$, with $Q_3+Q_4+Q_5+Q_6+Q_7+Q_8$, with $Q_3+Q_4+Q_5+Q_6+Q_7+Q_9$, with $Q_3+Q_5+Q_6+Q_7+Q_8+Q$ % with $Q_4+Q_5+Q_6+Q_7+Q_8+Q$ % with $Q_1+Q_2+Q_3+Q_4+Q_5+Q_6+Q_7$, with $Q_1+Q_2+Q_3+Q_4+Q_5+Q_6+Q_8$, with $Q_1+Q_2+Q_3+Q_4+Q_8+Q_6+Q_9$, with $Q_1+Q_3+Q_4+Q_5+Q_6+Q_7+Q_8$, with $Q_1+Q_3+Q_4+Q_5+Q_6+Q_7+Q_9$, with $Q_1+Q_4+Q_5+Q_6+Q_7+Q_8+Q_9$, with $Q_2+Q_3+Q_4+Q_5+Q_6+Q_7+Q_8$, with $Q_2+Q_3+Q_4+Q_5+Q_8+Q_6+Q_7+Q_9$, with $Q_2+Q_3+Q_4+Q_8+Q_6+Q_7+Q_9$, with $Q_2+Q_4+Q_5+Q_6+Q_7+Q_8+Q_9$, with $Q_3+Q_4+Q_5+Q_6+Q_7+Q_8+Q_9$, with $Q_1+Q_2+Q_3+Q_4+Q_5+Q_6+Q_7+Q_8$, with $Q_1+Q_2+Q_3+Q_4+Q_5+Q_6+Q_7+Q_9$, with $Q_2+Q_3+Q_4+Q_5+Q_6+Q_7+Q_8+Q_9$, or with $Q_1+Q_2+Q_3+Q_4+Q_5+Q_6+Q_7+Q_8+Q_9$.

Such combinations can be referred to as $U4+Q_1$, $U4+Q_2$, $U4+Q_3$, $U4+Q_4$, $U4+Q_5$, $U4+Q_6$, $U4+Q_7$, $U4+Q_8$, $U4+Q_9$, $U4+Q_1+Q_2$, $U4+Q_1+Q_3$, $U4+Q_1+Q_4$, $U4+Q_1+Q_5$, $U4+Q_1+Q_6$, $U4+Q_1+Q_7$, $U4+Q_1+Q_8$, $U4+Q_1+Q_9$, $U4+Q_2+Q_3$, $U4+Q_2+Q_4$, $U4+Q_2+Q_5$, $U4+Q_2+Q_6$, $U4+Q_2+Q_7$, $U4+Q_2+Q_8$, $U4+Q_2+Q_9$, $U4+Q_3+Q_4$, $U4+Q_3+Q_5$, $U4+Q_3+Q_6$, $U4+Q_3+Q_7$, $U4+Q_3+Q_8$, $U4+Q_3+Q_9$, $U4+Q_4+Q_5$, $U4+Q_4+Q_6$, $U4+Q_4+Q_7$, $U4+Q_4+Q_8$, $U4+Q_4+Q_9$, $U4+Q_5+Q_6$, $U4+Q_5+Q_7$, $U4+Q_5+Q_8$, $U4+Q_5+Q_9$, $U4+Q_6+Q_7$, $U4+Q_6+Q_8$, $U4+Q_6+Q_9$, $U4+Q_7+Q_8$, $U4+Q_7+Q_9$, $U4+Q_8+Q_9$, $U4+Q_4+Q_2+Q_3$, $U4+Q_4+Q_2+Q_4$, $U4+Q_1+Q_2+Q_5$, $U4+Q_1+Q_2+Q_6$, $U4+Q_4+Q_2+Q_7$, $U4+Q_4+Q_2+Q_8$, $U4+Q_1+Q_2+Q_9$, $U4+Q_1+Q_3+Q_4$, $U4+Q_1+Q_3+Q_5$, $U4+Q_4+Q_3+Q_6$, $U4+Q_4+Q_3+Q_7$, $U4+Q_1+Q_3+Q_8$, $U4+Q_1+Q_3+Q_9$, $U4+Q_4+Q_4+Q_5$, $U4+Q_4+Q_4+Q_6$, $U4+Q_1+Q_4+Q_7$, $U4+Q_1+Q_4+Q_8$, $U4+Q_1+Q_4+Q_9$, $U4+Q_1+Q_5+Q_6$, $U4+Q_4+Q_5+Q_7$, $U4+Q_1+Q_5+Q_8$, $U4+Q_1+Q_5+Q_9$, $U4+Q_1+Q_6+Q_7$, $U4+Q_1+Q_6+Q_8$, $U4+Q_1+Q_6+Q_9$, $U4+Q_1+Q_7+Q_8$, $U4+Q_1+Q_7+Q_9$, $U4+Q_1+Q_8+Q_9$, $U4+Q_2+Q_3+Q_4$, $U4+Q_2+Q_3+Q_5$, $U4+Q_2+Q_3+Q_6$, $U4+Q_2+Q_3+Q_7$, $U4+Q_2+Q_3+Q_8$, $U4+Q_2+Q_3+Q_9$, $U4+Q_2+Q_4+Q_5$, $U4+Q_2+Q_4+Q_6$, $U4+Q_2+Q_4+Q_7$, $U4+Q_2+Q_4+Q_8$, $U4+Q_2+Q_4+Q_9$, $U4+Q_2+Q_5+Q_6$, $U4+Q_2+Q_5+Q_7$, $U4+Q_2+Q_5+Q_8$, $U4+Q_2+Q_5+Q_9$, $U4+Q_2+Q_6+Q_7$, $U4+Q_2+Q_6+Q_8$, $U4+Q_2+Q_6+Q_9$, $U4+Q_2+Q_7+Q_8$, $U4+Q_2+Q_7+Q_9$, $U4+Q_2+Q_8+Q_9$, $U4+Q_3+Q_4+Q_5$, $U4+Q_3+Q_4+Q_6$, $U4+Q_3+Q_4+Q_7$, $U4+Q_3+Q_4+Q_8$, $U4+Q_3+Q_4+Q_9$, $U4+Q_3+Q_5+Q_6$, $U4+Q_3+Q_5+Q_7$, $U4+Q_3+Q_5+Q_8$, $U4+Q_3+Q_5+Q_9$, $U4+Q_3+Q_6+Q_7$, $U4+Q_3+Q_6+Q_8$, $U4+Q_3+Q_6+Q_9$, $U4+Q_3+Q_7+Q_8$, $U4+Q_3+Q_7+Q_9$, $U4+Q_3+Q_8+Q_9$, $U4+Q_4+Q_5+Q_6$, $U4+Q_4+Q_5+Q_7$, $U4+Q_4+Q_5+Q_8$, $U4+Q_4+Q_5+Q_9$, $U4+Q_4+Q_6+Q_7$, $U4+Q_4+Q_6+Q_8$, $U4+Q_4+Q_6+Q_9$, $U4+Q_4+Q_7+Q_8$, $U4+Q_4+Q_7+Q_9$, $U4+Q_4+Q_8+Q_9$, $U4+Q_5+Q_6+Q_7$, $U4+Q_5+Q_6+Q_8$, $U4+Q_5+Q_6+Q_9$, $U4+Q_5+Q_7+Q_8$, $U4+Q_5+Q_7+Q_9$, $U4+Q_5+Q_8+Q_9$, $U4+Q_6+Q_7+Q_8$, $U4+Q_6+Q_7+Q_9$, $U4+Q_6+Q_8+Q_9$, $U4+Q_1+Q_2+Q_3+Q_4$, $U4+Q_1+Q_2+Q_3+Q_5$, $U4+Q_1+Q_2+Q_3+Q_6$, $U4+Q_1+Q_2+Q_3+Q_7$, $U4+Q_1+Q_2+Q_3+Q_8$, $U4+Q_1+Q_2+Q_3+Q_9$, $U4+Q_1+Q_3+Q_4+Q_5$, $U4+Q_1+Q_3+Q_4+Q_6$, $U4+Q_1+Q_3+Q_4+Q_7$, $U4+Q_1+Q_3+Q_4+Q_8$, $U4+Q_1+Q_3+Q_4+Q_9$, $U4+Q_1+Q_4+Q_5+Q_6$, $U4+Q_1+Q_4+Q_5+Q_7$, $U4+Q_1+Q_4+Q_5+Q_8$, $U4+Q_1+Q_5+Q_6+Q_7$, $U4+Q_1+Q_5+Q_6+Q_8$, $U4+Q_1+Q_5+Q_6+Q_9$, $U4+Q_1+Q_6+Q_7+Q_8$, $U4+Q_1+Q_6+Q_7+Q_9$, $U4+Q_1+Q_7+Q_8+Q_9$, $U4+Q_2+Q_3+Q_4+Q_5$, $U4+Q_2+Q_3+Q_4+Q_6$, $U4+Q_2+Q_3+Q_4+Q_7$, $U4+Q_2+Q_3+Q_4+Q_8$, $U4+Q_2+Q_3+Q_4+Q_9$, $U4+Q_2+Q_4+Q_5+Q_6$, $U4+Q_2+Q_4+Q_5+Q_7$, $U4+Q_2+Q_4+Q_5+Q_8$, $U4+Q_2+Q_4+Q_5+Q_9$, $U4+Q_2+Q_5+Q_6+Q_7$, $U4+Q_2+Q_5+Q_6+Q_8$, $U4+Q_2+Q_5+Q_6+Q_9$, $U4+Q_2+Q_6+Q_7+Q_8$, $U4+Q_2+Q_6+Q_7+Q_9$, $U4+Q_2+Q_7+Q_8+Q_9$, $U4+Q_3+Q_4+Q_5+Q_6$, $U4+Q_3+Q_4+Q_5+Q_7$, $U4+Q_3+Q_4+Q_5+Q_8$, $U4+Q_3+Q_4+Q_5+Q_9$, $U4+Q_3+Q_5+Q_6+Q_7$, $U4+Q_3+Q_5+Q_6+Q_8$, $U4+Q_3+Q_5+Q_6+Q_9$, $U4+Q_3+Q_6+Q_7+Q_8$, $U4+Q_3+Q_6+Q_7+Q_9$, $U4+Q_3+Q_7+Q_8+Q_9$, $U4+Q_4+Q_5+Q_6+Q_7$, $U4+Q_4+Q_8+Q_6+Q_8$, $U4+Q_4+Q_5+Q_6+Q_9$, $U4+Q_4+Q_6+Q_7+Q_8$, $U4+Q_4+Q_6+Q_7+Q_9$, $U4+Q_4+Q_7+Q_8+Q_9$, $U4+Q_5+Q_6+Q_7+Q_8$, $U4+Q_5+Q_6+Q_7+Q_9$, $U4+Q_5+Q_7+Q_8+Q_9$, $U4+Q_1+Q_2+Q_3+Q_4+Q_5$, $U4+Q_1+Q_2+Q_3+Q_4+Q_6$, $U4+Q_4+Q_2+Q_3+Q_4+Q_7$, $U4+Q_1+Q_2+Q_3+Q_4+Q_8$, $U4+Q_1+Q_2+Q_3+Q_4+Q_9$, $U4+Q_1+Q_3+Q_4+Q_5+Q_6$, $U4+Q_1+Q_3+Q_4+Q_5+Q_7$, $U4+Q_4+Q_3+Q_4+Q_5+Q_8$, $U4+Q_1+Q_3+Q_4+Q_5+Q_9$, $U4+Q_1+Q_4+Q_5+Q_6+Q_7$, $U4+Q_1+Q_4+Q_5+Q_6+Q_8$, $U4+Q_1+Q_4+Q_5+Q_6+Q_9$, $U4+Q_1+Q_5+Q_6+Q_7+Q_8$, $U4+Q_1+Q_5+Q_6+Q_7+Q_9$, $U4+Q_1+Q_6+Q_7+

$Q_8+Q_9$, $U4+Q_2+Q_3+Q_4+Q_5+Q_6$, $U4+Q_2+Q_3+Q_4+Q_5+Q_7$, $U4+Q_2+Q_3+Q_4+Q_5+Q_8$, $U4+Q_2+Q_3+Q_4+Q_5+Q_9$, $U4+Q_2+Q_4+Q_5+Q_6+Q_7$, $U4+Q_2+Q_4+Q_5+Q_6+Q_8$, $U4+Q_2+Q_4+Q_5+Q_6+Q_9$, $U4+Q_2+Q_5+Q_6+Q_7+Q_8$, $U4+Q_2+Q_5+Q_6+Q_7+Q_9$, $U4+Q_2+Q_6+Q_7+Q_8+Q_9$, $U4+Q_3+Q_4+Q_5+Q_6+Q_7$, $U4+Q_3+Q_4+Q_5+Q_6+Q_8$, $U4+Q_3+Q_4+Q_5+Q_6+Q_9$, $U4+Q_3+Q_8+Q_6+Q_7+Q_8$, $U4+Q_3+Q_5+Q_6+Q_7+Q_9$, $U4+Q_3+Q_6+Q_7+Q_8+Q_9$, $U4+Q_4+Q_5+Q_6+Q_7+Q_8$, $U4+Q_4+Q_5+Q_6+Q_7+Q_9$, $U4+Q_4+Q_6+Q_7+Q_8+Q_9$, $U4+Q_5+Q_6+Q_7+Q_8+Q_9$, $U4+Q_1+Q_2+Q_3+Q_4+Q_5+Q_6$, $U4+Q_1+Q_2+Q_3+Q_4+Q_8+Q_7$, $U4+Q_1+Q_2+Q_3+Q_4+Q_5+Q_8$, $U4+Q_1+Q_2+Q_3+Q_4+Q_5+Q_9$, $U4+Q_1+Q_3+Q_4+Q_5+Q_6+Q_7$, $U4+Q_1+Q_3+Q_4+Q_5+Q_6+Q_8$, $U4+Q_1+Q_3+Q_4+Q_8+Q_6+Q_9$, $U4+Q_1+Q_4+Q_5+Q_6+Q_7+Q_8$, $U4+Q_1+Q_4+Q_5+Q_6+Q_7+Q_9$, $U4+Q_1+Q_5+Q_6+Q_7+Q_8+Q_9$, $U4+Q_2+Q_3+Q_4+Q_5+Q_6+Q_7$, $U4+Q_2+Q_3+Q_4+Q_5+Q_6+Q_8$, $U4+Q_2+Q_3+Q_4+Q_5+Q_6+Q_9$, $U4+Q_2+Q_4+Q_5+Q_6+Q_7+Q_8$, $U4+Q_2+Q_4+Q_5+Q_6+Q_7+Q_9$, $U4+Q_2+Q_5+Q_6+Q_7+Q_8+Q_9$, $U4+Q_3+Q_4+Q_5+Q_6+Q_7+Q_8$, $U4+Q_3+Q_4+Q_5+Q_6+Q_7+Q_9$, $U4+Q_3+Q_5+Q_6+Q_7+Q_8+Q_9$, $U4+Q_4+Q_5+Q_6+Q_7+Q_8+Q_9$, $U4+Q_1+Q_2+Q_3+Q_4+Q_5+Q_6+Q_7$, $U4+Q_1+Q_2+Q_3+Q_4+Q_5+Q_6+Q_8$, $U4+Q_1+Q_2+Q_3+Q_4+Q_5+Q_6+Q_9$, $U4+Q_1+Q_3+Q_4+Q_5+Q_6+Q_7+Q_8$, $U4+Q_1+Q_3+Q_4+Q_5+Q_6+Q_7+Q_9$, $U4+Q_1+Q_4+Q_5+Q_6+Q_7+Q_8+Q_9$, $U4+Q_2+Q_3+Q_4+Q_5+Q_6+Q_7+Q_8$, $U4+Q_2+Q_3+Q_4+Q_5+Q_6+Q_7+Q_9$, $U4+Q_2+Q_3+Q_4+Q_5+Q_6+Q_8+Q_9$, $U4+Q_2+Q_4+Q_5+Q_6+Q_7+Q_8+Q_9$, $U4+Q_3+Q_4+Q_5+Q_6+Q_7+Q_8+Q_9$, $U4+Q_1+Q_2+Q_3+Q_4+Q_6+Q_7+Q_8$, $U4+Q_1+Q_2+Q_3+Q_4+Q_5+Q_6+Q_7+Q_9$, $U4+Q_2+Q_3+Q_4+Q_8+Q_6+Q_7+Q_8+Q_9$, and $U4+Q_1+Q_2+Q_3+Q_4+Q_5+Q_6+Q_7+Q_8+Q_9$, respectively.

As used herein, $J_1$ represents the groups substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_1$-$C_{10}$ carbonyl, $C_1$-$C_{10}$ carboxyl, $C_1$-$C_{10}$ amido, $C_1$-$C_{10}$ sulfonyl, $C_1$-$C_{10}$ sulfonic acid, $C_1$-$C_{10}$ sulfamoyl, $C_1$-$C_{10}$ sulfoxide, $C_1$-$C_{10}$ phosphoryl, $C_1$-$C_{10}$ phosphonyl, $C_1$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_9$ carbonyl, $C_1$-$C_9$ carboxyl, $C_1$-$C_9$ amido, $C_1$-$C_9$ sulfonyl, $C_1$-$C_9$ sulfonic acid, $C_1$-$C_9$ sulfamoyl, $C_1$-$C_9$ sulfoxide, $C_1$-$C_9$ phosphoryl, $C_1$-$C_9$ phosphonyl, $C_1$-$C_8$ alkyl, $C_1$-$C_8$ alkylene, $C_2$-$C_8$ alkenyl, $C_2$-$C_8$ alkynyl, $C_1$-$C_8$ alkoxy, $C_1$-$C_8$ alkylamino, $C_1$-$C_8$ alkylthio, $C_1$-$C_8$ carbonyl, $C_1$-$C_8$ carboxyl, $C_1$-$C_8$ amido, $C_1$-$C_8$ sulfonyl, $C_1$-$C_8$ sulfonic acid, $C_1$-$C_8$ sulfamoyl, $C_1$-$C_8$ sulfoxide, $C_1$-$C_8$ phosphoryl, $C_1$-$C_8$ phosphonyl, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_7$ carbonyl, $C_1$-$C_7$ carboxyl, $C_1$-$C_7$ amino, $C_1$-$C_7$ amido, $C_1$-$C_7$ sulfonyl, $C_1$-$C_7$ sulfonic acid, $C_1$-$C_7$ sulfamoyl, $C_1$-$C_7$ sulfoxide, $C_1$-$C_7$ phosphoryl, $C_1$-$C_7$ phosphonyl, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $C_1$-$C_6$ alkylamino, $C_1$-$C_6$ alkylthio, $C_1$-$C_6$ carbonyl, $C_1$-$C_6$ carboxyl, $C_1$-$C_6$ amido, $C_1$-$C_6$ sulfonyl, $C_1$-$C_6$ sulfonic acid, $C_1$-$C_6$ sulfamoyl, $C_1$-$C_6$ sulfoxide, $C_2$-$C_6$ phosphoryl, $C_2$-$C_6$ phosphonyl, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_5$ carbonyl, $C_1$-$C_5$ carboxyl, $C_1$-$C_5$ amido, $C_1$-$C_5$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_{10}$ sulfonyl, $C_0$-$C_{10}$ sulfonic acid, $C_0$-$C_{10}$ sulfamoyl, $C_0$-$C_{10}$ sulfoxide, $C_0$-$C_{10}$ phosphoryl, $C_0$-$C_{10}$ phosphonyl, $C_0$-$C_9$ sulfonyl, $C_0$-$C_9$ sulfonic acid, $C_0$-$C_9$ sulfamoyl, $C_0$-$C_9$ sulfoxide, $C_0$-$C_9$ phosphoryl, $C_0$-$C_9$ phosphonyl, $C_0$-$C_8$ sulfonyl, $C_0$-$C_8$ sulfonic acid, $C_0$-$C_8$ sulfamoyl, $C_0$-$C_8$ sulfoxide, $C_0$-$C_8$ phosphoryl, $C_0$-$C_8$ phosphonyl, $C_0$-$C_7$ sulfonyl, $C_0$-$C_7$ sulfonic acid, $C_0$-$C_7$ sulfamoyl, $C_0$-$C_7$ sulfoxide, $C_0$-$C_7$ phosphoryl, $C_0$-$C_7$ phosphonyl, $C_0$-$C_6$ sulfonyl, $C_0$-$C_6$ sulfonic acid, $C_0$-$C_6$ sulfamoyl, $C_0$-$C_6$ sulfoxide, $C_0$-$C_6$ phosphoryl, $C_0$-$C_6$ phosphonyl, $C_0$-$C_5$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_{10}$ carbonyl, $C_{10}$ carboxyl, $C_{10}$ amido, $C_{10}$ sulfonyl, $C_{10}$ sulfonic acid, $C_{10}$ sulfamoyl, $C_{10}$ sulfoxide, $C_{10}$ phosphoryl, $C_{10}$ phosphonyl, $C_9$ alkyl, $C_9$ alkylene, $C_9$ alkenyl, $C_9$ alkynyl, $C_9$ alkoxy, $C_9$ alkylamino, $C_9$ alkylthio, $C_9$ carbonyl, $C_9$ carboxyl, $C_9$ amido, $C_9$ sulfonyl, $C_9$ sulfonic acid, $C_9$ sulfamoyl, $C_9$ sulfoxide, $C_9$ phosphoryl, $C_9$ phosphonyl, $C_8$ alkyl, $C_8$ alkylene, $C_8$ alkenyl, $C_8$ alkynyl, $C_8$ alkoxy, $C_8$ alkylamino, $C_8$ alkylthio, $C_8$ carbonyl, $C_8$ carboxyl, $C_8$ amido, $C_8$ sulfonyl, $C_8$ sulfonic acid, $C_8$ sulfamoyl, $C_8$ sulfoxide, $C_8$ phosphoryl, $C_8$ phosphonyl, $C_7$ alkyl, $C_7$ alkylene, $C_7$ alkenyl, $C_7$ alkynyl, $C_7$ alkoxy, $C_7$ alkylamino, $C_7$ alkylthio, $C_7$ carbonyl, $C_7$ carboxyl, $C_7$ amido, $C_7$ sulfonyl, $C_7$ sulfonic acid, $C_7$ sulfamoyl, $C_7$ sulfoxide, $C_7$ phosphoryl, $C_7$ phosphonyl, $C_6$ alkyl, $C_6$ alkylene, $C_6$ alkenyl, $C_6$ alkynyl, $C_6$ alkoxy, $C_6$ alkylamino, $C_6$ alkylthio, $C_6$ carbonyl, $C_6$ carboxyl, $C_6$ amido, $C_6$ sulfonyl, $C_6$ sulfonic acid, $C_6$ sulfamoyl, $C_6$ sulfoxide, $C_6$ phosphoryl, $C_6$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, and $C_0$ phosphonyl.

As used herein, $J_2$ represents the organic groups substituted or unsubstituted $C_1$-$C_{10}$ alkyl, $C_1$-$C_{10}$ alkylene, $C_2$-$C_{10}$ alkenyl, $C_2$-$C_{10}$ alkynyl, $C_1$-$C_{10}$ alkoxy, $C_1$-$C_{10}$ alkylamino, $C_1$-$C_{10}$ alkylthio, $C_4$-$C_9$ alkyl, $C_1$-$C_9$ alkylene, $C_2$-$C_9$ alkenyl, $C_2$-$C_9$ alkynyl, $C_1$-$C_9$ alkoxy, $C_1$-$C_9$ alkylamino, $C_1$-$C_9$ alkylthio, $C_1$-$C_8$ alkyl, $C_1$-$C_8$ alkylene, $C_2$-$C_8$ alkenyl, $C_2$-$C_8$ alkynyl, $C_1$-$C_8$ alkoxy, $C_1$-$C_8$ alkylamino, $C_1$-$C_8$ alkylthio, $C_1$-$C_7$ alkyl, $C_1$-$C_7$ alkylene, $C_2$-$C_7$ alkenyl, $C_2$-$C_7$ alkynyl, $C_1$-$C_7$ alkoxy, $C_1$-$C_7$ alkylamino, $C_1$-$C_7$ alkylthio, $C_1$-$C_6$ alkyl, $C_1$-$C_6$ alkylene, $C_2$-$C_6$ alkenyl, $C_2$-$C_6$ alkynyl, $C_1$-$C_6$ alkoxy, $Cr$ $C_6$ alkylamino, $C_1$-$C_6$ alkylthio, $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $Cr$ $C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_1$ alkylene, $C_1$ alkoxy, $C_1$ alkylamino, and $C_1$ alkylthio.

II. Modified Alginates

Described herein are alginate polymers that have been chemically modified to alter their biocompatibility and physical properties, as well as methods of making thereof.

A. Structure of Modified Alginate Polymers

Modified alginates contain one or more covalently modified monomers defined by Formula I Formula I

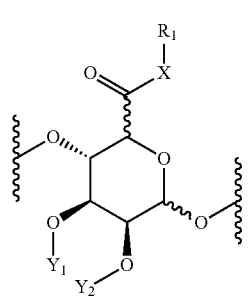

In some embodiments, the modified alginate is defined by Formula Ia, Formula Ib, or a combination of Formula Ia and Formula Ib Formula Ia

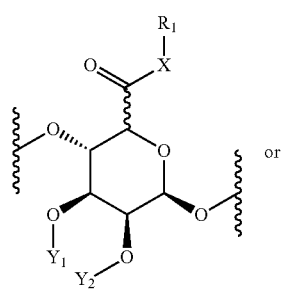

or

Formula Ib

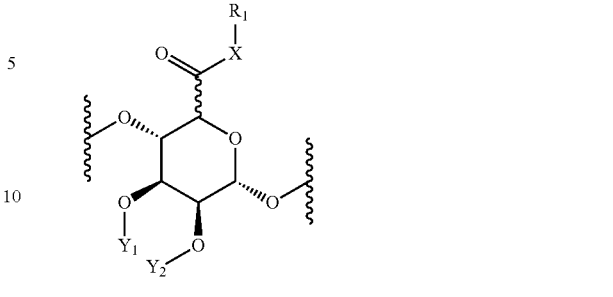

wherein, for Formula I, Formula Ia or Formula Ib,

X is oxygen, sulfur, or $NR_4$;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being those present in $U_1$, $U_1+Q_1$; $Q_1+Q_2$, $Q_1+Q_3$, $Q_1+Q_4$, $Q_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$;

$Y_1$ and $Y_2$ independently are hydrogen or —$PO(OR_5)_2$; or $Y_2$ is absent, and $Y_{2,j}$ together with the two oxygen atoms to which $Y_1$ and $Y_2$ are attached form a cyclic structure as shown in Formula II, Formula IIa, Formula IIb, or a combination of Formula IIa and Formula IIb Formula II Formula IIa -continued

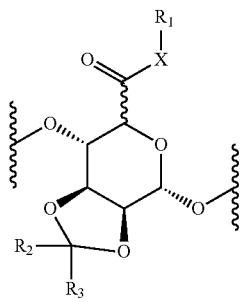

Formula IIb wherein for Formula II, Formula IIa or Formula IIb, $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_2$ and $R_3$ groupings being those present in U. $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_4+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_4$ and $R_5$ groupings being those present in U. $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, $R_1$ is, independently in one or more sites of chemical modification, -A-B(—C)$_\delta$,    Formula XVI wherein A is hydrogen or an organic grouping containing any number of carbon atoms, 1-carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_x+Q_x+Q_2+Q_3+Q_4$, preferably $U_x+Q_x+Q_3$;

B, and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and δ is an integer from, as valency permits, 0 to 30.

In some embodiments, R is, independently in one or more sites of chemical modification, —$R_6$—$R^b$,    Formula XVIII wherein $R_6$ is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_6$ organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and $R^b$ is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being those present in $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments of $R_1$; $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_6$, —B(—C)$_6$, —B, and independently in combination with any embodiments of any other relevant substituent classes, $R_1$; $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_\delta$, —B(—C)$_\delta$, —B can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative R. $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_6$, —B(—C)$_6$, —B organic groupings being those present in $U_1+Q_1$; $U_1+Q_2$, $U_1+Q_3$, $U_1+Q_4$, $U_1+Q_5$, $U_1+Q_1+Q_2$, $U_1+Q_1+Q_3$, $U_1+Q_1+Q_4$, $U_1+Q_1+Q_5$, $U_1+Q_2+Q_3$, $U_1+Q_2+Q_4$, $U_1+Q_2+Q_5$, $U_1+Q_3+Q_4$, $U_1+Q_3+Q_5$, $U_1+Q_4+Q_5$, $U_1+Q_1+Q_2+Q_3$, $U_1+Q_1+Q_2+Q_4$, $U_1+Q_1+Q_2+Q_5$, $U_1+Q_1+Q_3+Q_4$, $U_1+Q_1+Q_3+Q_5$, $U_1+Q_1+Q_4+Q_5$, $U_1+Q_2+Q_3+Q_4$, $U_1+Q_2+Q_3+Q_5$, $U_1+Q_2+Q_4+Q_5$, $U_1+Q_3+Q_4+Q_5$, $U_1+Q_1+Q_2+Q_3+Q_4$, $U_1+Q_1+Q_2+Q_3+Q_5$, $U_1+Q_1+Q_2+Q_4+Q_5$, $U_1+Q_1+Q_3+Q_4+Q_5$, $U_1+Q_2+Q_3+Q_4+Q_5$, or $U_1+Q_1+Q_2+Q_3+Q_4$, +$Q_8$.

In some embodiments of $R_1$; $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_6$, —B(—C)$_6$, —B, and independently in combination with any embodiments of any other relevant substituent classes, $R_1$; $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_\delta$, —B(—C)$_\delta$, —B can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative R. $R_2$, $R_3$, $R_4$, $R_5$, $R_6$, $R_7$, $R_8$, $R_9$, $R^a$, $R^b$, $R^c$, $R^d$, $R^e$, A, B, C, -A-B(—C)$_6$, —B(—C)$_6$, —B organic groupings being those present in U4+$Q_1$; U4+$Q_2$, U4+$Q_3$, U4+$Q_4$, U4+$Q_5$, U4+$Q_6$, U4+$Q_7$, U4+$Q_8$, U4+$Q_9$, U4+$Q_1+Q_2$, U4+$Q_1+Q_3$, U4+$Q_1+Q_4$, U4+$Q_1+Q_5$, U4+$Q_1+Q_6$, U4+$Q_1+Q_7$, U4+$Q_1+$ $Q_8$, U4+$Q_1$+$Q_9$, U4+$Q_2$+$Q_3$, U4+$Q_2$+$Q_4$, U4+$Q_2$+$Q_5$, U4+$Q_2$+$Q_6$, U4+$Q_2$+$Q_7$, U4+$Q_2$+$Q_8$, U4+$Q_2$+$Q_9$, U4+$Q_3$+$Q_4$, U4+$Q_3$+$Q_5$, U4+$Q_3$+$Q_6$, U4+$Q_3$+$Q_7$, U4+$Q_3$+$Q_8$, U4+$Q_3$+$Q_9$, U4+$Q_4$+$Q_5$, U4+$Q_4$+$Q_6$, U4+$Q_4$+$Q_7$, U4+$Q_4$+$Q_8$, U4+$Q_4$+$Q_9$, U4+$Q_5$+$Q_6$, U4+$Q_5$+$Q_7$, U4+$Q_5$+$Q_8$, U4+$Q_5$+$Q_9$, U4+$Q_6$+$Q_7$, U4+$Q_6$+$Q_8$, U4+$Q_6$+$Q_9$, U4+$Q_7$+$Q_8$, U4+$Q_7$+$Q_9$, U4+$Q_8$+$Q_9$, U4+$Q_4$+$Q_2$+$Q_3$, U4+$Q_1$+$Q_4$, U4+$Q_1$+$Q_2$+$Q_5$, U4+$Q_4$+$Q_2$+$Q_6$, U4+$Q_4$+$Q_2$+$Q_7$, U4+$Q_1$+$Q_2$+$Q_8$, U4+$Q_1$+$Q_2$+$Q_9$, U4+$Q_4$+$Q_3$+$Q_4$, U4+$Q_4$+$Q_3$+$Q_5$, U4+$Q_4$+$Q_3$+$Q_6$, U4+$Q_1$+$Q_3$+$Q_7$, U4+$Q_1$+$Q_3$+$Q_8$, U4+$Q_4$+$Q_3$+$Q_9$, U4+$Q_4$+$Q_4$+$Q_5$, U4+$Q_1$+$Q_4$+$Q_6$, U4+$Q_1$+$Q_4$+$Q_7$, U4+$Q_4$+$Q_4$+$Q_8$, U4+$Q_4$+$Q_4$+$Q_9$, U4+$Q_1$+$Q_5$+$Q_6$, U4+$Q_1$+$Q_5$+$Q_7$, U4+$Q_1$+$Q_5$+$Q_8$, U4+$Q_1$+$Q_5$+$Q_9$, U4+$Q_1$+$Q_6$+$Q_7$, U4+$Q_1$+$Q_6$+$Q_8$, U4+$Q_1$+$Q_6$+$Q_9$, U4+$Q_1$+$Q_7$+$Q_8$, U4+$Q_1$+$Q_7$+$Q_9$, U4+$Q_1$+$Q_8$+$Q_9$, U4+$Q_2$+$Q_3$+$Q_4$, U4+$Q_2$+$Q_3$+$Q_5$, U4+$Q_2$+$Q_3$+$Q_6$, U4+$Q_2$+$Q_3$+$Q_7$, U4+$Q_2$+$Q_3$+$Q_8$, U4+$Q_2$+$Q_3$+$Q_9$, U4+$Q_2$+$Q_4$+$Q_5$, U4+$Q_2$+$Q_4$+$Q_6$, U4+$Q_2$+$Q_4$+$Q_7$, U4+$Q_2$+$Q_4$+$Q_8$, U4+$Q_2$+$Q_4$+$Q_9$, U4+$Q_2$+$Q_5$+$Q_6$, U4+$Q_2$+$Q_5$+$Q_7$, U4+$Q_2$+$Q_5$+$Q_8$, U4+$Q_2$+$Q_5$+$Q_9$, U4+$Q_2$+$Q_6$+$Q_7$, U4+$Q_2$+$Q_6$+$Q_8$, U4+$Q_2$+$Q_6$+$Q_9$, U4+$Q_2$+$Q_7$+$Q_8$, U4+$Q_2$+$Q_7$+$Q_9$, U4+$Q_2$+$Q_8$+$Q_9$, U4+$Q_3$+$Q_4$+$Q_5$, U4+$Q_3$+$Q_4$+$Q_9$, U4+$Q_3$+$Q_4$+$Q_7$, U4+$Q_3$+$Q_4$+$Q_8$, U4+$Q_3$+$Q_4$+$Q_9$, U4+$Q_3$+$Q_5$+$Q_6$, U4+$Q_3$+$Q_5$+$Q_7$, U4+$Q_3$+$Q_5$+$Q_8$, U4+$Q_3$+$Q_5$+$Q_9$, U4+$Q_3$+$Q_6$+$Q_7$, U4+$Q_3$+$Q_6$+$Q_8$, U4+$Q_3$+$Q_6$+$Q_9$, U4+$Q_3$+$Q_7$+$Q_8$, U4+$Q_3$+$Q_7$+$Q_9$, U4+$Q_3$+$Q_8$+$Q_9$, U4+$Q_4$+$Q_5$+$Q_6$, U4+$Q_4$+$Q_5$+$Q_7$, U4+$Q_4$+$Q_5$+$Q_8$, U4+$Q_4$+$Q_5$+$Q_9$, U4+$Q_4$+$Q_6$+$Q_7$, U4+$Q_4$+$Q_6$+$Q_8$, U4+$Q_4$+$Q_6$+$Q_9$, U4+$Q_4$+$Q_7$+$Q_8$, U4+$Q_4$+$Q_7$+$Q_9$, U4+$Q_4$+$Q_8$+$Q_9$, U4+$Q_5$+$Q_6$+$Q_7$, U4+$Q_5$+$Q_6$+$Q_8$, U4+$Q_5$+$Q_6$+$Q_9$, U4+$Q_5$+$Q_7$+$Q_8$, U4+$Q_5$+$Q_7$+$Q_9$, U4+$Q_5$+$Q_8$+$Q_9$, U4+$Q_6$+$Q_7$+$Q_8$, U4+$Q_6$+$Q_7$+$Q_9$, U4+$Q_6$+$Q_8$+$Q_9$, U4+$Q_1$+$Q_2$+$Q_3$+$Q_4$, U4+$Q_1$+$Q_2$+$Q_3$+$Q_5$, U4+$Q_1$+$Q_2$+$Q_3$+$Q_6$, U4+$Q_1$+$Q_2$+$Q_3$+$Q_7$, U4+$Q_1$+$Q_2$+$Q_3$+$Q_8$, U4+$Q_1$+$Q_2$+$Q_3$+$Q_9$, U4+$Q_1$+$Q_3$+$Q_4$+$Q_5$, U4+$Q_1$+$Q_3$+$Q_4$+$Q_6$, U4+$Q_1$+$Q_3$+$Q_4$+$Q_7$, U4+$Q_1$+$Q_3$+$Q_4$+$Q_8$, U4+$Q_1$+$Q_3$+$Q_4$+$Q_9$, U4+$Q_1$+$Q_4$+$Q_5$+$Q_6$, U4+$Q_1$+$Q_4$+$Q_5$+$Q_7$, U4+$Q_1$+$Q_4$+$Q_5$+$Q_8$, U4+$Q_1$+$Q_4$+$Q_5$+$Q_9$, U4+$Q_1$+$Q_5$+$Q_6$+$Q_7$, U4+$Q_1$+$Q_5$+$Q_6$+$Q_8$, U4+$Q_1$+$Q_5$+$Q_6$+$Q_9$, U4+$Q_1$+$Q_6$+$Q_7$+$Q_8$, U4+$Q_1$+$Q_6$+$Q_7$+$Q_9$, U4+$Q_1$+$Q_7$+$Q_8$+$Q_9$, U4+$Q_2$+$Q_3$+$Q_4$+$Q_5$, U4+$Q_2$+$Q_3$+$Q_4$+$Q_6$, U4+$Q_2$+$Q_3$+$Q_4$+$Q_7$, U4+$Q_2$+$Q_3$+$Q_4$+$Q_8$, U4+$Q_2$+$Q_3$+$Q_4$+$Q_9$, U4+$Q_2$+$Q_4$+$Q_8$+$Q_9$, U4+$Q_2$+$Q_4$+$Q_5$+$Q_7$, U4+$Q_2$+$Q_4$+$Q_5$+$Q_8$, U4+$Q_2$+$Q_4$+$Q_5$+$Q_9$, U4+$Q_2$+$Q_5$+$Q_6$+$Q_7$, U4+$Q_2$+$Q_5$+$Q_6$+$Q_8$, U4+$Q_2$+$Q_5$+$Q_6$+$Q_9$, U4+$Q_2$+$Q_6$+$Q_7$+$Q_8$, U4+$Q_2$+$Q_6$+$Q_7$+$Q_9$, U4+$Q_2$+$Q_7$+$Q_8$+$Q_9$, U4+$Q_3$+$Q_4$+$Q_5$+$Q_6$, U4+$Q_3$+$Q_4$+$Q_5$+$Q_7$, U4+$Q_3$+$Q_4$+$Q_5$+$Q_8$, U4+$Q_3$+$Q_4$+$Q_5$+$Q_9$, U4+$Q_3$+$Q_5$+$Q_6$+$Q_7$, U4+$Q_3$+$Q_5$+$Q_6$+$Q_8$, U4+$Q_3$+$Q_5$+$Q_6$+$Q_9$, U4+$Q_3$+$Q_6$+$Q_7$+$Q_8$, U4+$Q_3$+$Q_6$+$Q_7$+$Q_9$, U4+$Q_3$+$Q_7$+$Q_8$+$Q_9$, U4+$Q_4$+$Q_5$+$Q_6$+$Q_7$, U4+$Q_4$+$Q_5$+$Q_6$+$Q_8$, U4+$Q_4$+$Q_5$+$Q_6$+$Q_9$, U4+$Q_4$+$Q_6$+$Q_7$+$Q_8$, U4+$Q_4$+$Q_6$+$Q_7$+$Q_9$, U4+$Q_4$+$Q_7$+$Q_8$+$Q_9$, +U4+$Q_5$+$Q_6$+$Q_7$+$Q_8$, +U4+$Q_5$+$Q_6$+$Q_7$+$Q_9$, U4+$Q_5$+$Q_7$+$Q_8$+$Q_9$, U4+$Q_1$+$Q_2$+$Q_3$+$Q_4$+$Q_5$, U4+$Q_1$+$Q_2$+$Q_3$+$Q_4$+$Q_6$, U4+$Q_1$+$Q_2$+$Q_3$+$Q_4$+$Q_7$+U4+$Q_1$+$Q_2$+$Q_3$+$Q_4$+$Q_8$, U4+$Q_1$+$Q_2$+$Q_3$+$Q_4$+$Q_9$, U4+$Q_1$+$Q_3$+$Q_4$+$Q_5$+$Q_6$+U4+$Q_1$+$Q_3$+$Q_4$+$Q_5$+$Q_7$+U4+$Q_1$+$Q_3$+$Q_4$+$Q_5$+$Q_8$+U4+$Q_1$+$Q_3$+$Q_4$+$Q_5$+$Q_9$, U4+$Q_1$+$Q_4$+$Q_5$+$Q_6$+$Q_7$, U4+$Q_1$+$Q_4$+$Q_5$+$Q_6$+$Q_8$, U4+$Q_1$+$Q_4$+$Q_5$+$Q_6$+$Q_9$, U4+$Q_1$+$Q_5$+$Q_6$+$Q_7$+$Q_8$, U4+$Q_1$+$Q_5$+$Q_6$+$Q_7$+$Q_9$, +U4+$Q_1$+$Q_6$+$Q_7$+$Q_8$+$Q_9$, U4+$Q_2$+$Q_3$+$Q_4$+$Q_5$+$Q_6$, U4+$Q_2$+$Q_3$+$Q_4$+$Q_5$+$Q_7$, U4+$Q_2$+$Q_3$+$Q_4$+$Q_5$+$Q_8$+U4+$Q_2$+$Q_3$+$Q_4$+$Q_5$+$Q_9$, U4+$Q_2$+$Q_4$+$Q_5$+$Q_8$+$Q_7$, U4+$Q_2$+$Q_4$+$Q_5$+$Q_6$+$Q_8$, U4+$Q_2$+$Q_4$+$Q_5$+$Q_6$+$Q_9$, U4+$Q_2$+$Q_5$+$Q_6$+$Q_7$+$Q_8$, U4+$Q_2$+$Q_5$+$Q_6$+$Q_7$+$Q_9$, U4+$Q_2$+$Q_6$+$Q_7$+$Q_8$+$Q_9$, U4+$Q_3$+$Q_4$+$Q_5$+$Q_6$+$Q_7$, U4+$Q_3$+$Q_4$+$Q_5$+$Q_6$+$Q_8$, U4+$Q_3$+$Q_4$+$Q_5$+$Q_6$+$Q_9$, U4+$Q_3$+$Q_5$+$Q_6$+$Q_7$+$Q_8$, U4+$Q_3$+$Q_5$+$Q_6$+$Q_7$+$Q_9$, U4+$Q_3$+$Q_6$+$Q_7$+$Q_8$+$Q_9$, U4+$Q_4$+$Q_5$+$Q_6$+$Q_7$+$Q_8$, U4+$Q_4$+$Q_5$+$Q_6$+$Q_7$+$Q_9$, U4+$Q_4$+$Q_6$+$Q_7$+$Q_8$+$Q_9$, U4+$Q_5$+$Q_6$+$Q_7$+$Q_8$+$Q_9$, U4+$Q_1$+$Q_2$+$Q_3$+$Q_4$+$Q_5$+$Q_6$, U4+$Q_1$+$Q_2$+$Q_3$, $Q_4$+$Q_5$+$Q_7$, U4+$Q_1$+$Q_2$+$Q_3$+$Q_4$+$Q_5$+$Q_8$, U4+$Q_1$+$Q_2$, $Q_3$+$Q_4$+$Q_5$+$Q_9$, U4+$Q_1$+$Q_3$+$Q_4$+$Q_5$+$Q_6$+$Q_7$, U4+$Q_1$+$Q_3$+$Q_4$+$Q_5$+$Q_6$+$Q_8$, U4+$Q_1$+$Q_3$+$Q_4$+$Q_5$+$Q_6$+$Q_9$, U4+$Q_1$+$Q_4$+$Q_5$+$Q_6$+$Q_7$+$Q_8$, U4+$Q_1$+$Q_4$+$Q_5$+$Q_6$+$Q_7$+$Q_9$, U4+$Q_1$+$Q_5$+$Q_6$+$Q_7$+$Q_8$+$Q_9$, U4+$Q_2$+$Q_3$+$Q_4$+$Q_5$+$Q_6$+$Q_7$, U4+$Q_2$+$Q_3$+$Q_4$+$Q_5$+$Q_6$+$Q_8$, U4+$Q_2$+$Q_3$+$Q_4$+$Q_5$++$Q_6$+$Q_9$, U4+$Q_2$+$Q_4$+$Q_5$+$Q_6$+$Q_7$+$Q_8$, U4+$Q_2$+$Q_4$+$Q_5$+$Q_6$+$Q_7$+$Q_9$, U4+$Q_2$+$Q_5$+$Q_6$+$Q_7$+$Q_8$+$Q_9$, U4+$Q_3$+$Q_4$+$Q_5$+$Q_6$+$Q_7$+$Q_8$, U4+$Q_3$+$Q_4$+$Q_5$+$Q_6$+$Q_7$+$Q_9$, +U4+$Q_3$+$Q_5$+$Q_6$+$Q_7$+$Q_8$+$Q_9$, U4+$Q_4$+$Q_5$+$Q_6$+$Q_7$+$Q_8$+$Q_9$, U4+$Q_{1+}$$Q_2$+$Q_3$+$Q_4$+$Q_5$+$Q_6$+$Q_7$, U4+$Q_1$+$Q_2$+$Q_3$+$Q_4$+$Q_5$+$Q_6$+$Q_8$+U4+$Q_1$+$Q_2$+$Q_3$+$Q_{4+}$$Q_5$+$Q_6$+$Q_9$, U4+$Q_1$+$Q_3$+$Q_4$+$Q_5$+$Q_6$+$Q_7$+$Q_8$, U4+$Q_1$+$Q_3$+$Q_4$+$Q_5$+$Q_6$+$Q_7$+$Q_9$, U4+$Q_1$+$Q_4$+$Q_5$+$Q_6$+$Q_7$+$Q_8$+$Q_9$, U4+$Q_2$+$Q_3$+$Q_4$+$Q_5$+$Q_6$+$Q_7$+$Q_8$+, U4+$Q_2$+$Q_3$+$Q_4$+$Q_5$+$Q_6$+$Q_7$+$Q_9$, U4+$Q_2$+$Q_3$+$Q_4$+$Q_5$+$Q_6$+$Q_8$+$Q_9$, U4+$Q_2$+$Q_4$+$Q_5$+$Q_6$+$Q_7$+$Q_8$+$Q_9$, U4+$Q_3$+$Q_4$+$Q_5$+$Q_6$+$Q_7$+$Q_8$+$Q_9$, U4+$Q_1$+$Q_2$+$Q_3$+$Q_4$+$Q_5$+$Q_6$+$Q_7$+$Q_8$, U4+$Q_1$+$Q_2$+$Q_3$+$Q_4$+$Q_5$+$Q_6$+$Q_7$+$Q_9$, U4+$Q_2$+$Q_3$+$Q_4$+$Q_5$+$Q_6$+$Q_7$+$Q_8$+$Q_9$, or U4+$Q_1$+$Q_2$+$Q_3$+$Q_4$+$Q_5$+$Q_6$+$Q_7$+$Q_8$+$Q_9$, Independently in some embodiments of A and $R_6$, and independently in combination with any embodiments of any other relevant substituent classes, A and $R_6$ can be, independently, hydrogen, $U_1$, $U_1$+$Q_1$, $U_1$+$Q_2$, $U_1$+$Q_3$, $U_1$+$Q_4$, $U_1$+$Q_1$+$Q_2$, $U_1$+$Q_1$+$Q_3$, $U_1$+$Q_1$+$Q_4$, $U_1$+$Q_2$+$Q_3$, $U_1$+$Q_2$+$Q_4$, $U_1$+$Q_3$+$Q_4$, $U_1$+$Q_1$+$Q_2$+$Q_3$, $U_1$+$Q_1$+$Q_2$+$Q_4$, $U_1$+$Q_1$+$Q_3$+$Q_4$, $U_1$+$Q_2$+$Q_3$+$Q_4$, and $U_1$+$Q_1$+$Q_2$+$Q_3$+$Q_4$, preferably $U_1$+$Q_1$+$Q_3$.

Independently in some embodiments of B, C, and $R^b$, and independently in combination with any embodiments of any other relevant substituent classes, B, C, and $R^b$ can be, independently, absent, hydrogen, $U_1$; $U_1$+$Q_1$, $U_1$+$Q_2$, $U_1$+$Q_3$, $U_1$+$Q_4$, $U_1$+$Q_1$+$Q_2$, $U_1$+$Q_1$+$Q_3$, $U_1$+$Q_1$+$Q_4$, $U_1$+$Q_2$+$Q_3$, $U_1$+$Q_2$+$Q_4$, $U_1$+$Q_3$+$Q_4$, $U_1$+$Q_1$+$Q_2$+$Q_3$, $U_1$+$Q_1$+$Q_2$+$Q_4$, $U_1$+$Q_1$+$Q_3$+$Q_4$, $U_1$+$Q_2$+$Q_3$+$Q_4$, and $U_1$+$Q_1$+$Q_2$+$Q_3$+$Q_4$, preferably $U_1$+$Q_1$+$Q_3$.

Independently in some embodiments of A and $R_6$, and independently in combination with any embodiments of any other relevant substituent classes, A and $R_6$ can be, independently, hydrogen, amino, hydroxyl, thiol, oxo, phosphate, or $J_1$, Independently in some embodiments of A and $R_6$, and independently in combination with any embodiments of any other relevant substituent classes, A and $R_6$ can be, independently, hydrogen, amino, hydroxyl, thiol, oxo, phosphate, or $J_2$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_1$.

Independently in some embodiments of B, C, and $R^b$, and independently in combination with any embodiments of any other relevant substituent classes, B, C, and $R^b$ can be, independently, absent, hydrogen, amino, hydroxyl, thiol, oxo, phosphate, or $J_2$.

Independently in some embodiments of A and $R_6$, and independently in combination with any embodiments of any other relevant substituent classes, A and $R_6$ can be, independently,

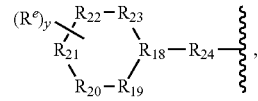

Formula IX

-continued

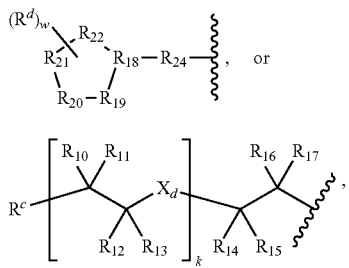

Formula XIV

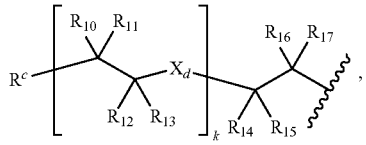

Formula XII wherein y is an integer from 0-11; wherein w is an integer from 0-9; wherein k is an integer from 0 to 20;

wherein $R^d$ and $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is B, C, —B(—C)$_\delta$, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently B, C, absent, hydrogen, =O, =S, —OH, —SH, or —NR$_4$, wherein IQ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_4+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently B, C, hydrogen, $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

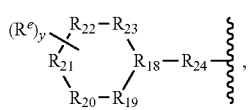

Formula IX

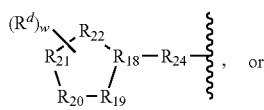

Formula XIV wherein y is an integer from 0-11; wherein w is an integer from 0-9; wherein k is an integer from 0 to 20;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is C, $R^b$, absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, $R^b$, absent, hydrogen, =O, =S, —OH, —SH, or —NR$_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

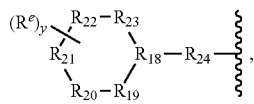

Formula IX

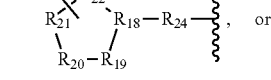

Formula XIV

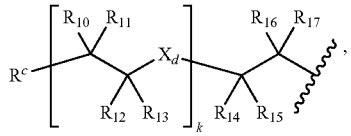

Formula XII wherein y is an integer from 0-11; wherein w is an integer from 0-9; wherein k is an integer from 0 to 20;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$. preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, absent, hydrogen, =O, =S, —OH, —SH, or —NR$_4$, wherein IQ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_4+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes C can be

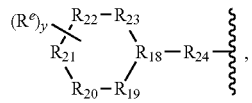

Formula IX

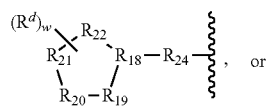

Formula XIV

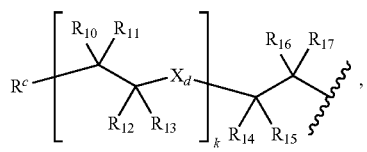

Formula XII wherein y is an integer from 0-11; wherein w is an integer from 0-9; wherein k is an integer from 0 to 20;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_4+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently,

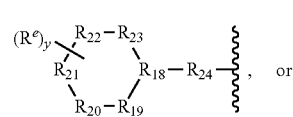

Formula IX

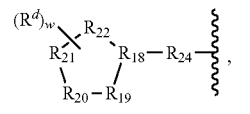

Formula XIV wherein y is an integer from 0-11; wherein w is an integer from 0-9;

wherein $R^d$ and $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently B, C, absent, hydrogen, =O, =S, —OH, —SH, or —NR$_4$, wherein R$_4$ is U$_1$, U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_3$.

Independently in some embodiments of B, and independently in combination with any embodiments of any other relevant substituent classes, B can be

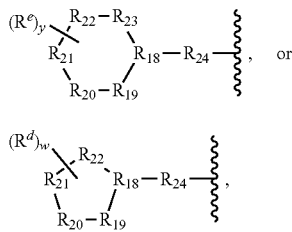

Formula IX

Formula XIV wherein y is an integer from 0-11; wherein w is an integer from 0-9;

wherein R$^d$ and R$^e$ are independently C, R$^b$, U$_2$, U$_2$+Q$_1$, U$_2$+Q$_2$, U$_2$+Q$_3$, U$_2$+Q$_4$, U$_2$+Q$_1$+Q$_2$, U$_2$+Q$_1$+Q$_3$, U$_2$+Q$_1$+Q$_4$, U$_2$+Q$_2$+Q$_3$, U$_2$+Q$_2$+Q$_4$, U$_2$+Q$_3$+Q$_4$, U$_2$+Q$_1$+Q$_2$+Q$_3$, U$_2$+Q$_1$+Q$_2$+Q$_4$, U$_2$+Q$_1$+Q$_3$+Q$_4$, U$_2$+Q$_2$+Q$_3$+Q$_4$, and U$_2$+Q$_1$+Q$_2$+Q$_3$+Q$_4$, preferably U$_2$+Q$_1$+Q$_3$; or together with the carbon atom to which they are attached, form a 3- to 8-membered unsubstituted or substituted carbocyclic or heterocyclic ring;

wherein R$_{18}$, R$_{19}$, R$_{20}$, R$_{21}$, R$_{22}$, and R$_{23}$ are independently C, O, N, S, S(O), or S(O)$_2$, wherein the bonds between adjacent R$_{18}$ to R$_{23}$ are double or single according to valency, and wherein R$_{18}$ to R$_{23}$ are bound to none, one, or two hydrogens according to valency; and wherein R$_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each R$_{25}$ is, as valency permits, independently C, R$^b$, absent, hydrogen, =O, =S, —OH, —SH, or —NR$_4$, wherein IG is U$_1$; U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_3$.

Independently in some embodiments of R$^b$, and independently in combination with any embodiments of any other relevant substituent classes, R$^b$ can be

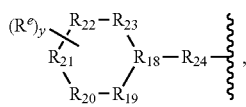

Formula IX or

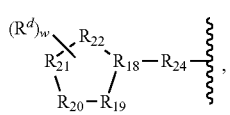

Formula XIV wherein y is an integer from 0-11; wherein w is an integer from 0-9;

wherein R$^d$ and R$^e$ are independently C, U$_2$, U$_2$+Q$_1$, U$_2$+Q$_2$, U$_2$+Q$_3$, U$_2$+Q$_4$, U$_2$+Q$_1$+Q$_2$, U$_2$+Q$_1$+Q$_3$, U$_2$+Q$_1$+Q$_4$, U$_2$+Q$_2$+Q$_3$, U$_2$+Q$_2$+Q$_4$, U$_2$+Q$_3$+Q$_4$, U$_2$+Q$_1$+Q$_2$+Q$_8$, U$_2$+Q$_1$+Q$_2$+Q$_4$, U$_2$+Q$_1$+Q$_3$+Q$_4$, U$_2$+Q$_2$+Q$_3$+Q$_4$, and U$_2$+Q$_1$+Q$_2$+Q$_3$+Q$_4$. preferably U$_2$+Q$_1$+Q$_3$; or together with the carbon atom to which they are attached, form a 3- to 8-membered unsubstituted or substituted carbocyclic or heterocyclic ring;

wherein R$_{18}$, R$_{19}$, R$_{20}$, R$_{21}$, R$_{22}$, and R$_{23}$ are independently C, O, N, S, S(O), or S(O)$_2$, wherein the bonds between adjacent R$_{18}$ to R$_{23}$ are double or single according to valency, and wherein R$_{18}$ to R$_{23}$ are bound to none, one, or two hydrogens according to valency; and wherein R$_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each R$_{25}$ is, as valency permits, independently C, absent, hydrogen, =O, =S, —OH, —SH, or —NR$_4$, wherein R$_4$ is U$_1$, U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_3$.

Independently in some embodiments of C, and independently in combination with any embodiments of any other relevant substituent classes, C can b

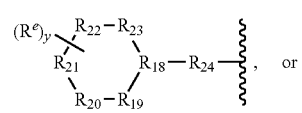

Formula IX or

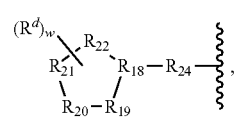

Formula XIV wherein y is an integer from 0-11; wherein w is an integer from 0-9;

wherein R$^d$ and R$^e$ are independently U$_2$, U$_2$+Q$_1$, U$_2$+Q$_2$, U$_2$+Q$_3$, U$_2$+Q$_4$, U$_2$+Q$_1$+Q$_2$, U$_2$+Q$_1$+Q$_3$, U$_2$+Q$_1$+Q$_4$, U$_2$+Q$_2$+Q$_3$, U$_2$+Q$_2$+Q$_4$, U$_2$+Q$_3$+Q$_4$, U$_2$+Q$_1$+Q$_2$+Q$_3$, U$_2$+Q$_1$+Q$_2$+Q$_4$, U$_2$+Q$_1$+Q$_3$+Q$_4$, U$_2$+Q$_2$+Q$_3$+Q$_4$, and U$_2$+Q$_1$+Q$_2$+Q$_3$+Q$_4$, preferably U$_2$+Q$_1$+Q$_3$; or together with the carbon atom to which they are attached, form a 3- to 8-membered unsubstituted or substituted carbocyclic or heterocyclic ring;

wherein R$_{18}$, R$_{19}$, R$_{20}$, R$_{21}$, R$_{22}$, and R$_{23}$ are independently C, O, N, S, S(O), or S(O)$_2$, wherein the bonds between adjacent R$_{18}$ to R$_{23}$ are double or single according to valency, and wherein R$_{18}$ to R$_{23}$ are bound to none, one, or two hydrogens according to valency; and wherein R$_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each R$_{25}$ is, as valency permits, independently absent, hydrogen, =O, =S, —OH, —SH, or —NR$_4$, wherein IG is U$_1$; U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_3$.

Independently in some embodiments of A and IG, and independently in combination with any embodiments of any other relevant substituent classes, A and IG can be, independently,

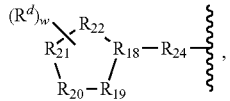

Formula XIV wherein w is an integer from 0-9;

wherein $R^d$ and $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each $R_{25}$ is, as valency permits, independently B, C, absent, hydrogen, =O, =S, —OH, —SH, or —NR$_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be

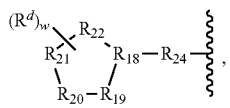

Formula XIV wherein w is an integer from 0-9;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each $R_{25}$ is, as valency permits, independently C, $R^b$, absent, hydrogen, =O, =S, —OH, —SH, or —NR$_4$, wherein $R_4$ is 1% $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

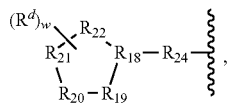

Formula XIV wherein w is an integer from 0-9;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each $R_{25}$ is, as valency permits, independently C, absent, hydrogen, =O, =S, —OH, —SH, or —NR$_4$, wherein $R_4$ is $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_4+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

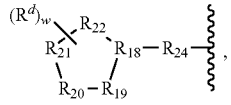

Formula XIV wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$; $U_2+Q_1$; $U_2+Q_2$, $U_2+Q_3$, $U_2+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently,

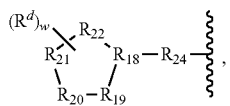

Formula XIV wherein w is an integer from 0-9;

wherein $R^d$ and $R^e$ are independently B, C, —B(—C)$_\delta$, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently B, C, absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_2+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of B, and independently in combination with any embodiments of any other relevant substituent classes, B can be

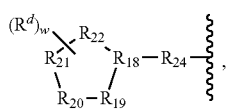

Formula XIV wherein w is an integer from 0-9;

wherein $R^d$ and $R^e$ are independently C, $R^b$, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, $R^b$, absent, hydrogen, =O, =S, —OH, —SH, or —NR$_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R^b$, and independently in combination with any embodiments of any other relevant substituent classes, $R^b$ can be

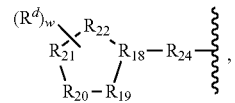

Formula XIV wherein w is an integer from 0-9;

wherein $R^d$ and $R^e$ are independently C, $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently C, absent, hydrogen, =O, =S, —OH, —SH, or —NR$_4$, wherein $R_4$ is 1% $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of C, and independently in combination with any embodiments of any other relevant substituent classes, C can be

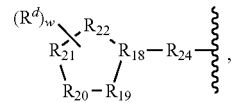

Formula XIV wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and wherein $R_{24}$ are independently absent, $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-S(O)-$, or $-S(O)_2-$, or $NR_4$, wherein each $R_{25}$ is, as valency permits, independently absent, hydrogen, $=O$, $=S$, $-OH$, $-SH$, or $-NR_4$, wherein $R_4$ is $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of A and $R_6$, and independently in combination with any embodiments of any other relevant substituent classes, A and $R_6$ can be, independently,

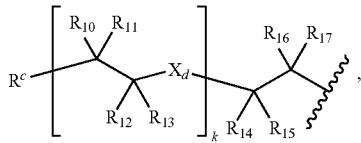

Formula XII wherein k is an integer from 0 to 20;
wherein $X_d$ are independently absent, O, or S;
wherein $R^c$ is B, C, $-B(-C)_\delta$, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

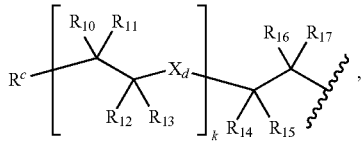

Formula XII wherein k is an integer from 0 to 20;
wherein $X_d$ are independently absent, O, or S;
wherein $R^c$ is C, $R^b$, absent, hydrogen $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_4+Q_3$; and wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

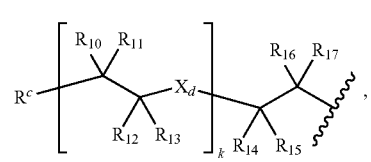

Formula XII wherein k is an integer from 0 to 20;
wherein $X_d$ are independently absent, O, or S;
wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, Rn, $R_{13}$, $R_{14}$, $R_{15}$, $R_{16}$, and $R_{17}$ are independently C, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

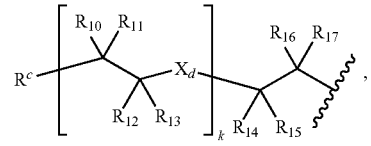

Formula XII wherein k is an integer from 0 to 20;
wherein $X_d$ are independently absent, O, or S;
wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently,

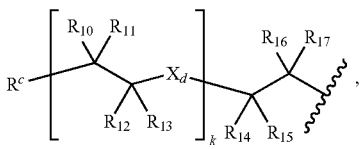

Formula XII wherein k is an integer from 0 to 20;
wherein $X_4$ are independently O or S;
wherein $R^c$ is B, C, —B(—C)$_8$, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

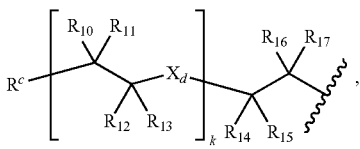

Formula XII wherein k is an integer from 0 to 20;
wherein $X_4$ are independently O or S;
wherein $R^c$ is C, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

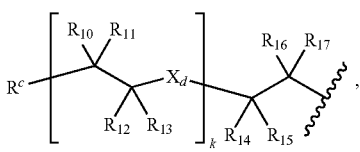

Formula XII wherein k is an integer from 0 to 20;
wherein $X_d$ are independently O or S;
wherein $R^c$ is C, absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently C, hydrogen, $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

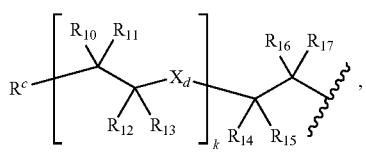

Formula XII wherein k is an integer from 0 to 20;
wherein $X_4$ are independently O or S;
wherein $R^c$ is absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of A and $R_6$, and independently in combination with any embodiments of any other relevant substituent classes, A and $R_6$ can be, independently,

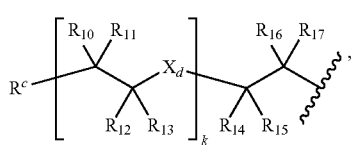

Formula XII wherein k is an integer from 1 to 20;
wherein $X_d$ are O;
wherein $R^c$ is B, C, —B(—C)$_8$, $R^b$, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$; and wherein $R_{10}$, $R_{11}$, $R_{12}$, $R_{13}$, $R_{14}$, $R_{15}$, $R_{16}$, and $R_{17}$ are independently B, C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of B, and independently in combination with any embodiments of any other relevant substituent classes, B can be

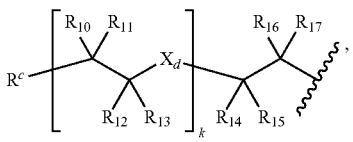

Formula XII wherein k is an integer from 1 to 20;
wherein $X_4$ are O;
wherein $R^c$ is C, $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, $R_{11}$, $R_{12}$, $R_{13}$, $R_{14}$, $R_{15}$, $R_{16}$, and $R_{17}$ are independently C, $R^b$, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$ Independently in some embodiments of $R^b$, and independently in combination with any embodiments of any other relevant substituent classes, $R^b$ can be

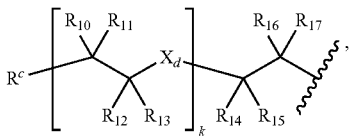

Formula XII wherein k is an integer from 1 to 20;
wherein $X_4$ are O;
wherein $R^c$ is C, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, $R_{11}$, $R_{12}$, $R_{13}$, $R_{14}$, $R_{15}$, $R_{16}$, and $R_{17}$ are independently C, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of C, and independently in combination with any embodiments of any other relevant substituent classes, C can be

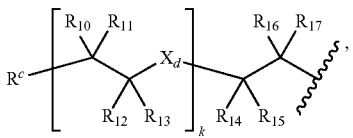

Formula XII wherein k is an integer from 1 to 20;
wherein $X_d$ are O;
wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, A is

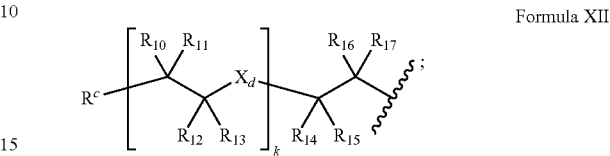

Formula XII wherein each k is, independently, an integer from 0 to 20;
wherein $R^c$ is B;
wherein each $X_4$ is, independently, absent, O, or S; and
wherein each $R_{10}$, $R_{11}$, $R_{12}$, $R_{13}$, $R_{14}$, $R_{15}$, $R_{16}$, and $R_{17}$ is, independently, hydrogen, amino, hydroxyl, thiol, oxo, phosphate, or U;
wherein preferably k is 1, 2, 3, 4, 5, 6, or 7; each $X_4$ is O; and each $R_{10}$, $R_{11}$, $R_{12}$, $R_{13}$, $R_{14}$, $R_{15}$, $R_{16}$, and $R_{17}$ is, independently, hydrogen, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio;
wherein more preferably k is 2, 3, or 4; each $X_4$ is O; and each $R_{10}$, $R_{11}$, $R_{12}$, $R_{13}$, $R_{14}$, $R_{15}$, $R_{16}$, and $R_{17}$ is hydrogen; and
wherein most preferably A is —$CH_2$—$CH_2$-(0-$CH_2$—$CH_2$)$_3$—; and B and C are, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, B is

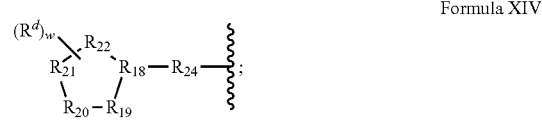

Formula XIV wherein each w is, independently, an integer from 0-9;
wherein $R^d$ is C;
wherein each $R_{18}$, $R_{19}$, $R_{20}$, $R_{21}$, and $R_{22}$ is, independently, C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency;
preferably w is 1, 2, 3, or 4; and none, one, two, three, four, or five of $R_{18}$, $R_{10}$, $R_{20}$, $R_{21}$, and $R_{22}$ are N, none, one, two, three, four, or five of $R_{18}$, $R_{10}$, $R_{20}$, $R_{21}$, and $R_{22}$ is O, and the others are C;
more preferably w is 1 or 2; and one, two, or three of $R_{18}$, $R_{10}$, $R_{20}$, $R_{21}$, and $R_{22}$ are N, none or one of $R_{18}$, $R_{10}$, $R_{20}$, $R_{21}$, and $R_{22}$ is O, and the others are C;

even more preferably w is 1 or 2; and three of $R_{18}$, $R_{10}$, $R_{20}$, $R_{21}$, and $R_{22}$ are N, none of $R_{18}$, $R_{10}$, $R_{20}$, $R_{21}$, and $R_{22}$ is O, and the others are C; and
most preferably

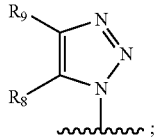

wherein $R_8$ is hydrogen and $R_9$ is C;

A is hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and each C is, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, C is

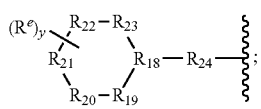

Formula IX wherein y is an integer from 0-11;

wherein each $R_{18}$, $R_{19}$, $R_{20}$, $R_{21}$, $R_{22}$, and $R_{23}$ is, independently, C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency;

wherein each $R_{24}$ is, independently, absent, $-(CR_{25}R_{25})_p-$, or $-(CR_{25}R_{25})_p-X_b-(CR_{25}R_{25})_q-$, wherein each p and q is, independently, an integer from 0 to 5, wherein $X_b$ is absent, $-O-$, $-S-$, $-S(O)-$, $-S(O)_2-$, or $NR_4$, wherein each $R_{25}$ is, as valency permits, independently absent, hydrogen, $=O$, $=S$, $-OH$, $-SH$, or $-NR_4$, wherein each $R_4$ is, independently, $J_2$;

wherein each $R^e$ is, independently, $J_1$;

preferably y is 0, 1, 2, 3, 4, or 5; none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ is O, none or one is $S(O)_2$, and the others are C; each $R_{24}$ is, independently, absent, $-(CR_{25}R_{25})_p-$, or $-(CR_{25}R_{25})_p-X_b-(CR_{25}R_{25})_q-$, wherein each p is, independently, 0, 1, 2, or 3, each q is, independently, 0, 1, or 2, and $X_b$ is O; and $R^e$ is, independently, $C_1$-$C_2$ carbonyl, $C_1$-$C_2$ carboxyl, $C_1$-$C_2$ amino, $C_1$-$C_2$ amido, $C_1$-$C_2$ sulfonyl, $C_1$-$C_2$ sulfonic acid, $C_2$-$C_3$ phosphoryl, or $C_2$-$C_3$ phosphonyl;

more preferably y is 0, 1, 2, or 3; none, one, two, or three of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ is O, none or one is $S(O)_2$, and the others are C; each $R_{24}$ is, independently, absent, $-(CR_{25}R_{25})_p-$, or $-(CR_{25}R_{25})_p-X_b-(CR_{25}R_{25})_q-$, wherein each p is, independently, 0 or 1, each q is, independently, 0 or 1, and $X_b$ is O; and $R^e$ is, independently, $C_1$ carbonyl, $C_1$ carboxyl, $C_1$ amino, $C_1$ amido, $C_1$ sulfonyl, $C_1$ sulfonic acid, $C_2$ phosphoryl, or $C_2$ phosphonyl; and even more preferably y is 0 or 1; none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ is O, none or one is $S(O)_2$, and the others are C; each $R_{24}$ is, independently, absent, $-(CR_{25}R_{25})_p-$, or $-(CR_{25}R_{25})_p-X_b-(CR_{25}R_{25})_q-$, wherein each p is, independently, 0 or 1, each q is, independently, 0 or 1, and $X_b$ is O; and $R^e$ is, independently, $C_1$ carbonyl, $C_1$ carboxyl, $C_1$ amino, or $C_1$ sulfonyl; and most preferably C is

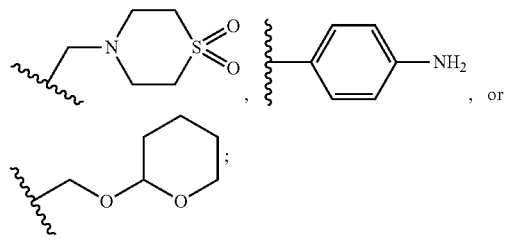

A is hydrogen or an organic grouping containing any number of carbon atoms, 1-carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_x+Q_2+Q_3+Q_4$, preferably $U_1+Q_x+Q_3$; and B is absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments
A is
B is

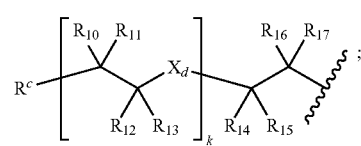

Formula XII

-continued

Formula XIV

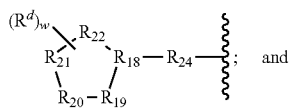

and each $R_8$, $R_9$, and C are, independently,

Formula IX

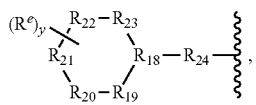

Formula XIV

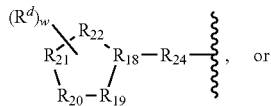
, or

Formula XII

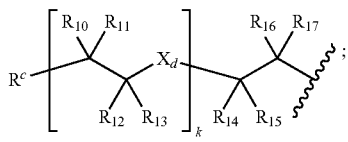
;

wherein each y is, independently, an integer from 0-11; wherein each w is, independently, an integer from 0-9; wherein each k is, independently, an integer from 0 to 20;
wherein in A, $R^c$ is B,
wherein in B, $R^c$, $R^d$, and $R^e$ are C,
wherein each $X_4$ is, independently, absent, O, or S;
wherein each $R_{18}$, $R_{19}$, $R_{20}$, $R_{21}$, $R_{22}$, and $R_{23}$ is, independently, C, O, N, S, S(O), or $S(O)_2$, wherein the bonds between adjacent $R_{18}$ to $R_{23}$ are double or single according to valency, and wherein $R_{18}$ to $R_{23}$ are bound to none, one, or two hydrogens according to valency; and
wherein each $R_{24}$ is, independently, absent, $-(CR_{25}R_{25})_p-$, or $-(CR_{25}R_{25})_p-X_b-(CR_{25}R_{25})_q-$, wherein each p and q is, independently, an integer from 0 to 5, wherein $X_b$ is absent, $-O-$, $-S-$, $-S(O)-$, $-S(O)_2-$, or $NR_4$, wherein each $R_{25}$ is, as valency permits, independently absent, hydrogen, $=O$, $=S$, $-OH$, $-SH$, or $-NR_4$, wherein each $R_4$ is, independently, $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, preferably $U_1+Q_1+Q_3$; and
wherein each $R_{10}$, $R_{11}$, $R_{12}$, $R_{13}$, $R_{14}$, $R_{15}$, $R_{16}$, and $R_{17}$ is, independently, hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, each $R_4$ is, independently, $J_2$.

In some embodiments, each $R_{10}$, $R_{11}$, $R_{12}$, $R_{13}$, $R_{14}$, $R_{15}$, $R_{16}$, and $R_{17}$ is, independently, hydrogen, amino, hydroxyl, thiol, oxo, phosphate, or $J_1$.

In some embodiments, independently in each Formula IX, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ is O, and the others are C. In some embodiments, independently in each Formula XIV, none, one, two, three, four, or five of $R_{18}$, $R_{19}$, $R_{20}$, $R_{21}$, and $R_{22}$ are N, none, one, two, three, four, or five of $R_{18}$, $R_{19}$, $R_{20}$, $R_{21}$, and $R_{22}$ is O, and the others are C.

In some embodiments, independently in each C, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ is O, and the others are C. In some embodiments, in B, three of $R_{18}$, $R_{19}$, $R_{20}$, $R_{21}$, and $R_{22}$ are N, none of $R_{18}$, $R_{19}$, $R_{20}$, $R_{21}$, and $R_{22}$ is O, and the others are C.

In some embodiments, $R_6$ and A are $-CH_2-Ar-$ or $-CH_2-CH_2-(O-CH_2-CH_2)_3-$; $R_2$ is hydrogen; $R_8$ and C are hydrogen, methyl, or $-CH_2-OH$; and $R_9$ and C are methyl, $-COCH_3$, $-CH_2-N(CH_2-CH_3)_2$,

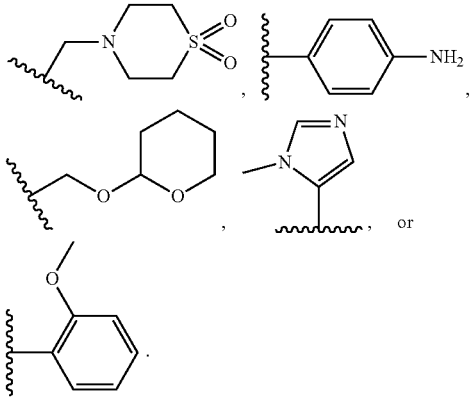

In some embodiments, $R_8$ is hydrogen; and $R_9$ and C are

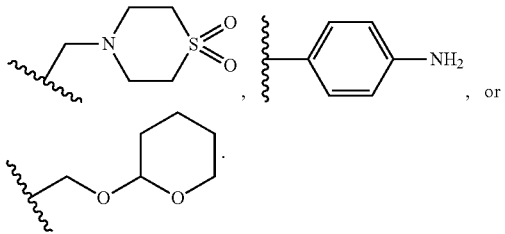

In some embodiments, $R_8$ is hydrogen; and $R_9$ and C are

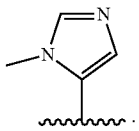

In some embodiments, $R_9$ and C are methyl, $-COCH_3$, or $-CH_2-N(CH_2-CH_3)_2$.

In some embodiments, X is oxygen or $NR_2$, wherein $R_2$ is hydrogen, methyl, or $-CH_2-CH_3$; and $R_1$ is $-CH_2-CH_2-CH_2-CH_2-OH$, $-CH_2-CH_2-(O-CH_2-CH_2)_n-O-CH_3$, $-CH_2-CH_2-O-CH_2-CH_2-OH$, $-(CH_2-CH_2)_3-NH-CH_3$,

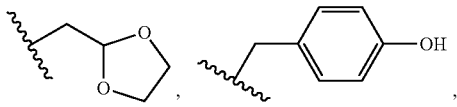

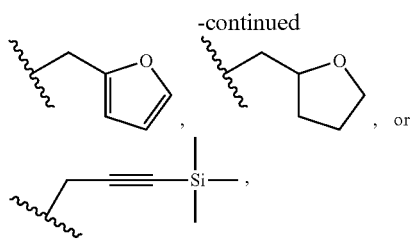

, or where n is an integer from 3 to 16.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or J.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or $J_2$.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, Cr $C_5$ alkylthio, $C_1$-$C_5$ carbonyl, $C_1$-$C_5$ carboxyl, $C_1$-$C_5$ amido, $C_1$-$C_5$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_5$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phos-
phonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, $C_1$-$C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_4$ alkylene, $C_4$ alkoxy, $C_4$ alkylamino, or $C_4$ alkylthio.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, Cr $C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_4$ alkylthio, $C_4$ carbonyl, $C_4$ carboxyl, $C_4$ amido, $C_4$ sulfonyl, $C_4$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, Cr $C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_1$ alkyl, $C_1$ alkylene, $C_1$ alkoxy, $C_1$ alkylamino, or $C_1$ alkylthio.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_3$ alkyl, $C_4$-$C_3$ alkylene, $C_2$-$C_3$ alkenyl, $C_2$-$C_3$ alkynyl, $C_1$-$C_3$ alkoxy, $C_1$-$C_3$ alkylamino, Cr $C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R^c$, and independently in combination with any embodiments of any other relevant substituent classes, $R^c$ can be B, C, —B(—C)$_8$, $R^b$, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, Cr $C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_1$ alkylene, $C_1$ alkoxy, $C_1$ alkylamino, or $C_1$ alkylthio.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{11}$, $R_{16}$, and $R_{17}$ can be, independently, $R^b$, hydrogen, amino, hydroxyl, thiol, oxo, phosphate, or $J_1$.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or $J_2$.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, Cr $C_5$ alkylthio, $C_1$-$C_5$ carbonyl, $C_1$-$C_5$ carboxyl, $C_1$-$C_5$ amido, $C_1$-$C_5$ sulfonyl, $C_1$-$C_5$ sulfonic acid, $C_1$-$C_5$ sulfamoyl, $C_1$-$C_5$ sulfoxide, $C_1$-$C_5$ phosphoryl, $C_1$-$C_5$ phosphonyl, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_5$ sulfonyl, $C_0$-$C_5$ sulfonic acid, $C_0$-$C_5$ sulfamoyl, $C_0$-$C_5$ sulfoxide, $C_0$-$C_5$ phosphoryl, $C_0$-$C_5$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_5$ alkyl, $C_5$ alkylene, $C_5$ alkenyl, $C_5$ alkynyl, $C_5$ alkoxy, $C_5$ alkylamino, $C_5$ alkylthio, $C_5$ carbonyl, $C_5$ carboxyl, $C_5$ amido, $C_5$ sulfonyl, $C_5$ sulfonic acid, $C_5$ sulfamoyl, $C_5$ sulfoxide, $C_5$ phosphoryl, $C_5$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_4$ alkyl, $C_4$ alkylene, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_5$ alkyl, $C_1$-$C_5$ alkylene, $C_2$-$C_5$ alkenyl, $C_2$-$C_5$ alkynyl, $C_1$-$C_5$ alkoxy, $C_1$-$C_5$ alkylamino, Cr $C_5$ alkylthio, $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_4$ alkylene, $C_4$ alkoxy, $C_4$ alkylamino, or $C_4$ alkylthio.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, Cr $C_4$ alkylthio, $C_1$-$C_4$ carbonyl, $C_1$-$C_4$ carboxyl, $C_1$-$C_4$ amino, $C_1$-$C_4$ amido, $C_1$-$C_4$ sulfonyl, $C_1$-$C_4$ sulfonic acid, $C_1$-$C_4$ sulfamoyl, $C_1$-$C_4$ sulfoxide, $C_1$-$C_4$ phosphoryl, $C_1$-$C_4$ phosphonyl, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_4$ sulfonyl, $C_0$-$C_4$ sulfonic acid, $C_0$-$C_4$ sulfamoyl, $C_0$-$C_4$ sulfoxide, $C_0$-$C_4$ phosphoryl, $C_0$-$C_4$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_4$ alkyl, $C_4$ alkylene, $C_4$ alkenyl, $C_4$ alkynyl, $C_4$ alkoxy, $C_4$ alkylamino, $C_4$ alkylthio, $C_4$ carbonyl, $C_4$ carboxyl, $C_4$ amido, $C_4$ sulfonyl, $C_4$ sulfonic acid, $C_4$ sulfamoyl, $C_4$ sulfoxide, $C_4$ phosphoryl, $C_4$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_4$ alkyl, $C_1$-$C_4$ alkylene, $C_2$-$C_4$ alkenyl, $C_2$-$C_4$ alkynyl, $C_1$-$C_4$ alkoxy, $C_1$-$C_4$ alkylamino, $C_1$-$C_4$ alkylthio, $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, $C_1$-$C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_4$ alkylene, $C_4$ alkoxy, $C_4$ alkylamino, or $C_1$ alkylthio.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, Cr $C_3$ alkylthio, $C_1$-$C_3$ carbonyl, $C_1$-$C_3$ carboxyl, $C_1$-$C_3$ amino, $C_1$-$C_3$ amido, $C_1$-$C_3$ sulfonyl, $C_1$-$C_3$ sulfonic acid, $C_1$-$C_3$ sulfamoyl, $C_1$-$C_3$ sulfoxide, $C_1$-$C_3$ phosphoryl, $C_1$-$C_3$ phosphonyl, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_1$-$C_2$ carbonyl, $C_1$-$C_2$ carboxyl, $C_1$-$C_2$ amido, $C_1$-$C_2$ sulfonyl, $C_1$-$C_2$ sulfonic acid, $C_1$-$C_2$ sulfamoyl, $C_1$-$C_2$ sulfoxide, $C_1$-$C_2$ phosphoryl, $C_1$-$C_2$ phosphonyl, $C_0$-$C_3$ sulfonyl, $C_0$-$C_3$ sulfonic acid, $C_0$-$C_3$ sulfamoyl, $C_0$-$C_3$ sulfoxide, $C_0$-$C_3$ phosphoryl, $C_0$-$C_3$ phosphonyl, $C_0$-$C_2$ sulfonyl, $C_0$-$C_2$ sulfonic acid, $C_0$-$C_2$ sulfamoyl, $C_0$-$C_2$ sulfoxide, $C_0$-$C_2$ phosphoryl, $C_0$-$C_2$ phosphonyl, $C_0$-$C_1$ sulfonyl, $C_0$-$C_1$ sulfonic acid, $C_0$-$C_1$ sulfamoyl, $C_0$-$C_1$ sulfoxide, $C_0$-$C_1$ phosphoryl, $C_0$-$C_1$ phosphonyl, $C_3$ alkyl, $C_3$ alkylene, $C_3$ alkenyl, $C_3$ alkynyl, $C_3$ alkoxy, $C_3$ alkylamino, $C_3$ alkylthio, $C_3$ carbonyl, $C_3$ carboxyl, $C_3$ amido, $C_3$ sulfonyl, $C_3$ sulfonic acid, $C_3$ sulfamoyl, $C_3$ sulfoxide, $C_3$ phosphoryl, $C_3$ phosphonyl, $C_2$ alkyl, $C_2$ alkylene, $C_2$ alkenyl, $C_2$ alkynyl, $C_2$ alkoxy, $C_2$ alkylamino, $C_2$ alkylthio, $C_2$ carbonyl, $C_2$ carboxyl, $C_2$ amido, $C_2$ sulfonyl, $C_2$ sulfonic acid, $C_2$ sulfamoyl, $C_2$ sulfoxide, $C_2$ phosphoryl, $C_2$ phosphonyl, $C_1$ alkyl, $C_1$ alkylene, $C_1$ alkoxy, $C_1$ alkylamino, $C_1$ alkylthio, $C_1$ carbonyl, $C_1$ carboxyl, $C_1$ amido, $C_1$ sulfonyl, $C_1$ sulfonic acid, $C_1$ sulfamoyl, $C_1$ sulfoxide, $C_1$ phosphoryl, $C_1$ phosphonyl, $C_0$ sulfonyl, $C_0$ sulfonic acid, $C_0$ sulfamoyl, $C_0$ sulfoxide, $C_0$ phosphoryl, or $C_0$ phosphonyl.

Independently in some embodiments of $R_{10}$, $R_{11}$, $R_{12}$, $R_{13}$, $R_{14}$, $R_{15}$, $R_{16}$, and $R_{17}$, and independently in combination with any embodiments of any other relevant substituent classes, $R_{10}$, $R_{11}$, $R_{12}$, $R_{13}$, $R_{14}$, $R_{15}$, $R_{16}$, and $R_{17}$ can be, independently, $R^b$, hydrogen, amino, hydroxyl, thiol, oxo, phosphate, or substituted or unsubstituted $C_1$-$C_3$ alkyl, $C_1$-$C_3$ alkylene, $C_2$-$C_3$ alkenyl, $C_2$-$C_3$ alkynyl, $C_1$-$C_3$ alkoxy, $C_1$-$C_3$ alkylamino, Cr $C_3$ alkylthio, $C_1$-$C_2$ alkyl, $C_1$-$C_2$ alkylene, $C_1$-$C_2$ alkoxy, $C_1$-$C_2$ alkylamino, $C_1$-$C_2$ alkylthio, $C_{10}$ alkyl, $C_{10}$ alkylene, $C_{10}$ alkenyl, $C_{10}$ alkynyl, $C_{10}$ alkoxy, $C_{10}$ alkylamino, $C_{10}$ alkylthio, $C_9$ alkyl, $C_9$ alkylene, $C_9$ alkenyl, $C_9$ alkynyl, $C_9$ alkoxy, $C_9$ alkylamino, $C_9$ alkylthio, $C_8$ alkyl, $C_8$ alkylene, $C_8$ alkenyl, $C_8$ alkynyl, $C_8$ alkoxy, $C_8$ alkylamino, $C_8$ alkylthio, $C_7$ alkyl, $C_7$ alkylene, $C_7$ alkenyl, $C_7$ alkynyl, $C_7$ alkoxy, $C_7$ alkylamino, $C_7$ alkylthio, $C_6$ alkyl, $C_6$ alkylene, $C_6$ alkenyl, $C_6$ alkynyl, $C_6$ alkoxy, $C_6$ alkylamino, $C_6$ alkylthio, $C_5$ alkyl, $C_5$ alkylene, $C_5$ alkenyl, $C_5$ alkynyl, $C_5$ alkoxy, $C_5$ alkylamino, $C_5$ alkylthio, $C_4$ alkyl, $C_4$ alkylene, $C_4$ alkenyl, $C_4$ alkynyl, $C_4$ alkoxy, $C_4$ alkylamino, $C_4$ alkylthio, $C_3$ alkyl, $C_3$ alkylene, $C_3$ alkenyl, $C_3$ alkynyl, $C_3$ alkoxy, $C_3$ alkylamino, $C_3$ alkylthio, $C_2$ alkyl, $C_2$ alkylene, $C_2$ alkenyl, $C_2$ alkynyl, $C_2$ alkoxy, $C_2$ alkylamino, $C_2$ alkylthio, $C_4$ alkyl, $C_1$ alkylene, $C_1$ alkoxy, $C_1$ alkylamino, or $C_1$ alkylthio.

Independently in some embodiments of 5, and independently in combination with any embodiments of any other relevant substituent classes, 5 can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, 5 is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of 5, and independently in combination with any embodiments of any other relevant substituent classes, 5 can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of 5, and independently in combination with any embodiments of any other relevant substituent classes, 5 can be 1, 2, 3, 4, 5, 6, 7, 8, 9, or 10.

Independently in some embodiments of 5, and independently in combination with any embodiments of any other relevant substituent classes, 5 can be an integer from 1 to 5, 2 to 5, 3 to 5, 4 to 5, 1 to 4, 2 to 4, 3 to 4, 1 to 3, 2 to 3, or 1 to 2. Independently in some embodiments of 5, and independently in combination with any other relevant substituent classes, 5 can be 1, 2, 3, 4, or 5.

Independently in some embodiments of k, and independently in combination with any embodiments of any other relevant substituent classes, k can be an integer from 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, to 18, 6 to 18, 7 to 18, 8 to 18, 9 to 18, 10 to 18, 11 to 18, 12 to 18, 13 to 18, 14 to 18, to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, k is 1, 2, 3, 4, 5, 6, 7, 8, 9, 10, 11, 12, 13, 14, 15, 16, 17, 18, 19, or 20.

Independently in some embodiments of k, and independently in combination with any embodiments of any other relevant substituent classes, k can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of k, and independently in combination with any embodiments of any other relevant substituent classes, k can be 1, 2, 3, 4, 5, 6, 7, 8, 9, or 10.

Independently in some embodiments of w, and independently in combination with any embodiments of any other relevant substituent classes, w can be an integer from 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of w, and independently in combination with any embodiments of any other relevant substituent classes, w can be 1, 2, 3, 4, 5, 6, 7, 8, or 9.

Independently in some embodiments of w, and independently in combination with any embodiments of any other relevant substituent classes, w can be an integer from 1 to 5, 2 to 5, 3 to 5, 4 to 5, 1 to 4, 2 to 4, 3 to 4, 1 to 3, 2 to 3, or 1 to 2. In preferred embodiments, w is 1, 2, 3, 4, or 5.

Independently in some embodiments of y, and independently in combination with any embodiments of any other relevant substituent classes, y can be an integer from 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of y, and independently in combination with any embodiments of any other relevant substituent classes, y can be 1, 2, 3, 4, 5, 6, 7, 8, 9, 10, or 11.

Independently in some embodiments of y, and independently in combination with any embodiments of any other relevant substituent classes, y can be an integer from 1 to 5, 2 to 5, 3 to 5, 4 to 5, 1 to 4, 2 to 4, 3 to 4, 1 to 3, 2 to 3, or 1 to 2. Independently in some embodiments of y, and independently in combination with any embodiments of any other relevant substituent classes, y can be 1, 2, 3, 4, or 5.

Independently in some embodiments of p and q, and independently in combination with any embodiments of any other relevant substituent classes, p and q can be, independently, an integer from 1 to 5, 2 to 5, 3 to 5, 4 to 5, 1 to 4, 2 to 4, 3 to 4, 1 to 3, 2 to 3, or 1 to 2. Independently in some embodiments of p and q, and independently in combination with any embodiments of any other relevant substituent classes, p and q can be, independently, 1, 2, 3, 4, or 5.

In some embodiments, modified alginates are alginate polymers that contain one or more covalently modified monomers defined by Formula I

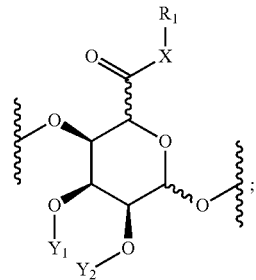

Formula I

In some embodiments, the modified alginate is defined by Formula Ia, Formula Ib, or a combination of Formula Ia and Formula Ib,

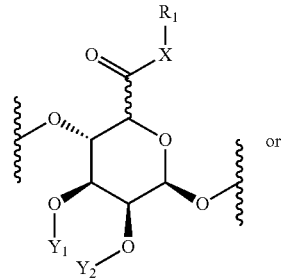

Formula Ia

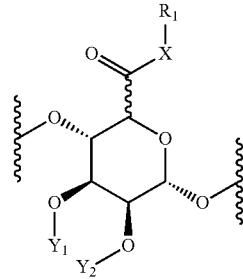

Formula Ib wherein, for Formula I, Formula Ia or Formula Ib,
X is oxygen, sulfur, or $NR_4$;
$R_1$ is independently in the one or more modified monomers

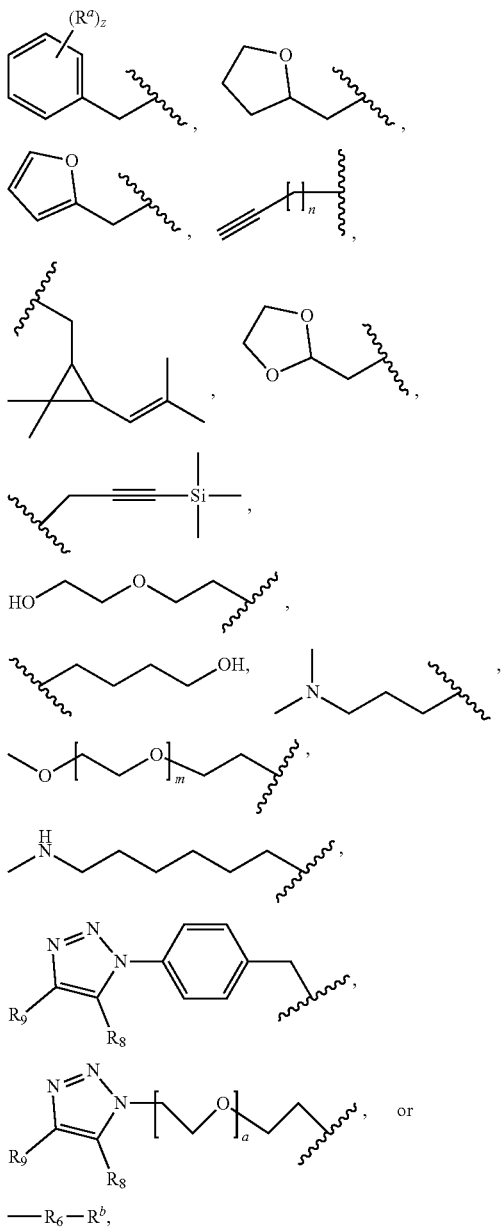

wherein a is an integer from 1 to 30, z is an integer from 0 to 5, n is an integer from 1 to 12, m is an integer from 3 to 16, and $R^a$ and $R^b$ are independently selected from $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_2+Q_3$; or together with the carbon atom to which they are attached, form a 3- to 8-membered unsubstituted or substituted carbocyclic or heterocyclic ring; wherein Y and $Y_2$ independently are hydrogen or —$PO(OR_5)_2$; or $Y_2$ is absent, and $Y_1$. together with the two oxygen atoms to which $Y_1$ and $Y_2$ are attached form a cyclic structure as shown in Formula II, Formula IIa, Formula IIb, or a combination of Formula IIa and Formula IIb Formula II Formula IIa Formula IIb wherein, for Formula II, Formula IIa or Formula IIb, $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being those present in $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+$ $Q_3+Q_4$, $U_1+Q_2+Q_3+Q_4$, and $U_1+Q_1+Q_2+Q_3+Q_4$, preferably $U_1+Q_1+Q_3$: or $R_2$ and $R_3$, together with the carbon atom to which they are attached, form a 3- to 8-membered unsubstituted or substituted carbocyclic or heterocyclic ring; and $R_4$, $R_5$, $R_6$, $R_8$, and $R_9$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of a, and independently in combination with any embodiments of any other relevant substituent classes, a can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, a is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of a, and independently in combination with any embodiments of any other relevant substituent classes, a can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of a, and independently in combination with any embodiments of any other relevant substituent classes, a can be 1, 2, 3, 4, 5, 6, 7, 8, 9, or 10.

Independently in some embodiments of a, and independently in combination with any embodiments of any other relevant substituent classes, a can be an integer from 1 to 5, 2 to 5, 3 to 5, 4 to 5, 1 to 4, 2 to 4, 3 to 4, 1 to 3, 2 to 3, or 1 to 2. In preferred embodiments, a is 1, 2, 3, 4, or 5.

Independently in some embodiments of m, and independently in combination with any embodiments of any other relevant substituent classes, m can be an integer from 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 3 to 15, 4 to 15, 5 to 15, 6 to 15, 7 to 15, 8 to 15, 9 to 15, 10 to 15, 11 to 15, 12 to 15, 13 to 15, 14 to 15, 3 to 14, 4 to 14, 5 to 14, 6 to 14, 7 to 14, 8 to 14, 9 to 14, 10 to 14, 11 to 14, 12 to 14, 13 to 14, 3 to 13, 4 to 13, 5 to 13, 6 to 13, 7 to 13, 8 to 13, 9 to 13, 10 to 13, 11 to 13, 12 to 13, 3 to 12, 4 to 12, 5 to 12, 6 to 12, 7 to 12, 8 to 12, 9 to 12, 10 to 12, 11 to 12, 3 to 11, 4 to 11, 5 to 11, 6 to 11, 7 to 11, 8 to 11, 9 to 11, 10 to 11, 3 to 10, 4 to 10, 5 to 10, 6 to 10, 7 to 10, 8 to 10, 9 to 10, 3 to 9, 4 to 9, 5 to 9, 6 to 9, 7 to 9, 8 to 9, 3 to 8, 4 to 8, 5 to 8, 6 to 8, 7 to 8, 3 to 7, 4 to 7, 5 to 7, 6 to 7, 3 to 6, 4 to 6, 5 to 6, 3 to 5, 4 to 5, and 3 to 4. In some embodiments, m is 3, 4, 5, 6, 7, 8, 9, 10, 11, 12, 13, 14, 15, or 16.

Independently in some embodiments of m, and independently in combination with any embodiments of any other relevant substituent classes, m can be an integer from 3 to 10, 4 to 10, 5 to 10, 6 to 10, 7 to 10, 8 to 10, 9 to 10, 3 to 9, 4 to 9, 5 to 9, 6 to 9, 7 to 9, 8 to 9, 3 to 8, 4 to 8, 5 to 8, 6 to 8, 7 to 8, 3 to 7, 4 to 7, 5 to 7, 6 to 7, 3 to 6, 4 to 6, 5 to 6, 3 to 5, 4 to 5, and 3 to 4. Independently in some embodiments of m, and independently in combination with any embodiments of any other relevant substituent classes, m can be 3, 4, 5, 6, 7, 8, 9, or 10.

Independently in some embodiments of m, and independently in combination with any embodiments of any other relevant substituent classes, m can be an integer from 3 to 5, 4 to 5, or 3 to 4. In preferred embodiments, m is 3, 4, or 5.

Independently in some embodiments of n, and independently in combination with any embodiments of any other relevant substituent classes, n can be an integer from 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, n is 1, 2, 3, 4, 5, 6, 7, 8, 9, 10, 11, 12, 13, 14, 15, 16, 17, 18, 19, or 20.

Independently in some embodiments of n, and independently in combination with any embodiments of any other relevant substituent classes, n can be an integer from 1 to 5, 2 to 5, 3 to 5, 4 to 5, 1 to 4, 2 to 4, 3 to 4, 1 to 3, 2 to 3, or 1 to 2. In preferred embodiments, n is 1, 2, 3, 4, or 5.

In some embodiments, modified alginates are alginate polymers that contain one or more covalently modified monomers defined by Formula I

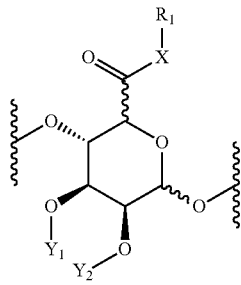

Formula I

In some embodiments, the modified alginate is defined by Formula Ia or Formula Ib

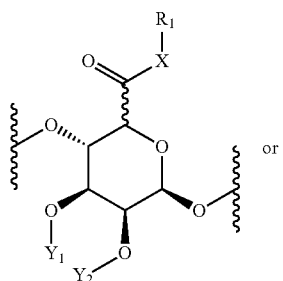

Formula Ia or

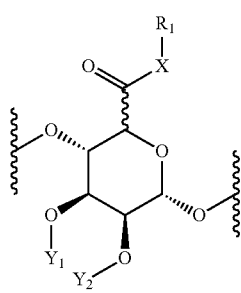

Formula Ib wherein, for Formula I, Formula Ia or Formula Ib,

X is oxygen, sulfur, or $NR_4$;

$R_1$ is, independently in the one or more modified monomers,

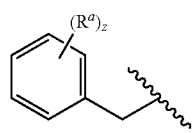

Formula X

-continued

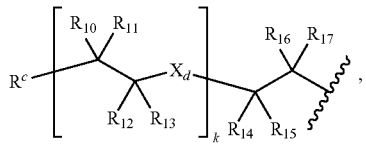

Formula XII

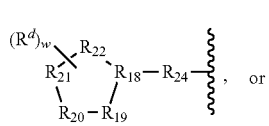

Formula XIV

, or

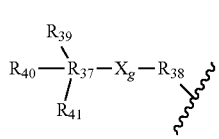

Formula XV wherein k is an integer from 1 to 10; wherein z is an integer from 0 to 5; wherein w is an integer from 0 to 4; wherein $X_4$ is absent, O or S;

wherein $R_{10}$, $R_{11}$, $R_{12}$, $R_{13}$, $R_{14}$, $R_{15}$, $R_{16}$, $R_{11}$, $R_{39}$, $R_{40}$, and $R_{41}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$;

wherein $R_{37}$ is C or Si;

wherein $X_g$ and $R_{38}$ are independently $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3+Q_4$; and wherein $R^a$ and $R^c$ are independently $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic, heterocyclic ring or

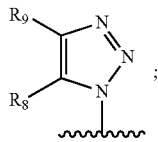

Formula XIII

;

wherein $R_8$, $R_9$, or both are, independently, hydrogen, alkyl, substituted alkyl, alkoxy, amino, alkylamino, dialkylamino, hydroxy, alkenyl, alkynyl, substituted alkyl, substituted alkenyl, substituted alkynyl, carbonyl, substituted carbonyl, carbinol,

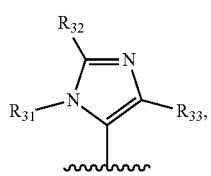

Formula VII

Formula VIII

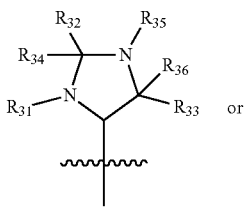

or

Formula IX

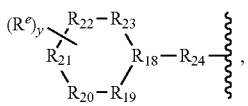

wherein $R_{31}$, $R_{32}$, $R_{33}$, $R_{34}$, $R_{35}$, and $R_{36}$ are, independently, hydrogen, U. $U_1+Q_1$; $U_1+Q_2$, $U_1+Q_3$, $U_1+Q_4$, $U_4+Q_1+Q_2$, $U_1+Q_1+Q_3$, $U_1+Q_4+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency;

wherein in $R_x$ or $R_9$:

y is an integer from 0 to 11;

$R^e$ are each independently $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring;

$R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and $R_{24}$ is independently —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —SO$_2$—, or NR$_4$, wherein each $R_{25}$ is, as valency permits, independently absent, hydrogen, =O, =S, —OH, —SH, —NR$_4$, wherein $R_4$ is 1% $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$:

wherein $R_8$, and $R_9$ are not both hydrogen; wherein at least one $R^b$ or $R^c$ is defined by Formula XIII;

wherein $Y_1$ and $Y_2$ independently are hydrogen or —PO(OR$_5$)$_2$; or $Y_2$ is absent, and $Y_1$. together with the two oxygen atoms to which $Y_1$ and $Y_2$ are attached form a cyclic structure as shown in Formula II, Formula IIa, Formula IIb, or a combination of Formula IIa and Formula IIb Formula II

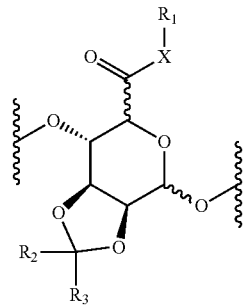

Formula IIa

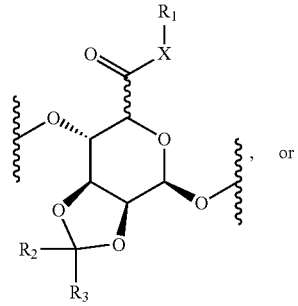

, or

Formula IIb

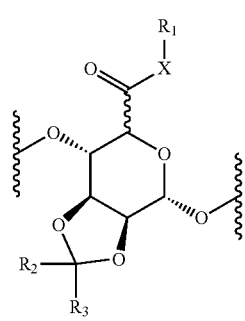

wherein, for Formula II, Formula IIa or Formula IIb, $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being those present in $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$: or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of $R_8$ and $R_9$, and independently in combination with any embodiments of any other relevant substituent classes, $R_8$ and $R_9$ can be, independently, Formula XII $$\left[ R^c \diagdown \begin{matrix} R_{10} & R_{11} \\ & \\ R_{12} & R_{13} \end{matrix} \diagdown X_d \diagdown \begin{matrix} R_{16} & R_{17} \\ & \\ R_{14} & R_{15} \end{matrix} \diagdown \right]_k ,$$

wherein k is an integer from 1 to 20;
wherein $X_4$ are O;
wherein $R^c$ is $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$; and
wherein $R_{10}$, $R_{11}$, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of Formula IX, and independently in combination with any embodiments of any other relevant substituent classes, all of $R_{18}$, $R_{19}$, $R_{20}$, $R_{21}$, $R_{22}$, and $R_{23}$ are C. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is C.

Independently in some embodiments of Formula XIV, and independently in combination with any embodiments of any other relevant substituent classes, all of $R_{18}$, $R_{19}$, $R_{20}$, $R_{21}$, and $R_{22}$ are C. Independently in some embodiments of Formula XIV, and independently in combination with any embodiments of any other relevant substituent classes, one, two, three, or four of $R_{18}$, $R_{19}$, $R_{20}$, $R_{21}$; and $R_{22}$ are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are C. Independently in some embodiments of Formula XIV, and independently in combination with any embodiments of any other relevant substituent classes, one of $R_{18}$, $R_{19}$, $R_{20}$, $R_{21}$, and $R_{22}$ is C.

Independently in some embodiments of Formula IX, and independently in combination with any embodiments of any other relevant substituent classes, all of $R_{18}$, $R_{19}$, $R_{20}$, $R_{21}$, $R_{22}$, and $R_{23}$ are N. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N.

Independently in some embodiments of Formula XIV, and independently in combination with any embodiments of any other relevant substituent classes, all of $R_{18}$, $R_{19}$, $R_{20}$, $R_{21}$, and $R_{22}$ are N. Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N. Independently in some embodiments of Formula XIV, and independently in combination with any embodiments of any other relevant substituent classes, one or two of $R_{18}$, $R_{19}$, $R_{20}$, $R_{21}$, and $R_{22}$ are N. Independently in some embodiments of Formula XIV, and independently in combination with any embodiments of any other relevant substituent classes, one of $R_{18}$, $R_{19}$, $R_{20}$, $R_{21}$, and $R_{22}$ is N.

Independently in some embodiments of Formula IX, and independently in combination with any embodiments of any other relevant substituent classes, all of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O. Independently in some embodiments of Formula IX, and independently in combination with any other relevant substituent classes, one, two, or three of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are O. Independently in some embodiments of Formula IX, and independently in combination with any other relevant substituent classes, one of $R_{18}$, $R_{19}$, $R_{20}$, $R_{21}$, $R_{22}$, and $R_{23}$ is O.

Independently in some embodiments of Formula XIV, and independently in combination with any embodiments of any other relevant substituent classes, all of $R_{18}$, $R_{19}$, $R_{20}$, $R_{21}$, and $R_{22}$ are O. Independently in some embodiments of Formula XIV, and independently in combination with any embodiments of any other relevant substituent classes, one, two, three, or four of $R_{18}$, $R_{19}$, $R_{20}$, $R_{21}$; and $R_{22}$ are O. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are O. Independently in some embodiments of Formula XIV, and independently in combination with any embodiments of any other relevant substituent classes, one or two of $R_{18}$, $R_{19}$, $R_{20}$, $R_{21}$, and $R_{22}$ are O. Independently in some embodiments of Formula XIV, and independently in combination with any embodiments of any other relevant substituent classes, one of $R_{18}$, $R_{19}$, $R_{20}$, $R_{21}$, and $R_{22}$ is O.

Independently in some embodiments of Formula IX, and independently in combination with any embodiments of any other relevant substituent classes, all of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are S. Independently in some embodiments of Formula IX, and independently in combination with any other relevant substituent classes, one, two, three, or four of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is S.

Independently in some embodiments of Formula XIV, and independently in combination with any embodiments of any other relevant substituent classes, all of $R_{18}$, $R_{19}$, $R_{20}$, $R_{21}$, and $R_{22}$ are S. Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are S. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are S. Independently in some embodiments of Formula XIV, and independently in combination with any embodiments of any other relevant substituent classes, one or two of $R_{18}$, $R_{19}$, $R_{20}$, $R_{21}$, and $R_{22}$ are S. Independently in some embodiments of Formula XIV, and independently in combination with any embodiments of any other relevant substituent classes, one of $R_{18}$, $R_{19}$, $R_{20}$, $R_{21}$, and $R_{22}$ is S.

Independently in some embodiments of Formula IX, and independently in combination with any embodiments of any other relevant substituent classes, all of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are $S(O)_2$. Independently in some embodiments of Formula IX, and independently in combination with any other relevant substituent classes, one, two, or three of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is $S(O)_2$.

Independently in some embodiments of Formula XIV, and independently in combination with any embodiments of any other relevant substituent classes, all of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one or two of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one of $R_{18}$, Rw, $R_{20}$, $R_{21}$, and $R_{22}$ is $S(O)_2$.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N and one of $R_{18}$, $R_{19}$, $R_{20}$, $R_{21}$, $R_{22}$, and $R_{23}$ is O. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N and one or two of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N and one, two, or three of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N and one, two, three, or four of $R_{18}$, $R_{19}$, $R_{20}$, $R_{21}$, $R_{22}$, and $R_{23}$ are O. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N and one, two, three, four, or five of $R_{18}$, $R_{19}$, $R_{20}$, $R_{21}$, $R_{22}$, and $R_{23}$ are O. Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N and one of $R_{18}$, $R_{19}$, $R_{20}$, $R_{21}$, and $R_{22}$ is O. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N and one or two of $R_{18}$, $R_{19}$, $R_{20}$, $R_{21}$, and $R_{22}$ are O. Independently in some embodiments of Formula XIV, and independently in combination with any embodiments of any other relevant substituent classes, one or two of $R_{18}$, $R_{19}$, $R_{20}$, $R_{21}$, and $R_{22}$ are N and one, two, or three of $R_{18}$, $R_{19}$, $R_{20}$, $R_{21}$, and $R_{22}$ are O. Independently in some embodiments of Formula XIV, and independently in combination with any embodiments of any other relevant substituent classes, one of $R_{18}$, $R_{19}$, $R_{20}$, $R_{21}$, and $R_{22}$ is N and one, two, three, or four of $R_{18}$, $R_{19}$, $R_{20}$, $R_{21}$, and $R_{22}$ are O.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N and one of $R_{18}$, $R_{19}$, $R_{20}$, $R_{21}$, $R_{22}$, and $R_{23}$ is S. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N and one or two of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N and one, two, or three of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N and one, two, three, or four of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N and one, two, three, four, or five of $R_{18}$, $R_{19}$, $R_{20}$, $R_{21}$, $R_{22}$, and $R_{23}$ are S.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N and one of $R_{18}$, $R_{19}$, $R_{20}$, $R_{21}$, and $R_{22}$ is S. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N and one or two of $R_{18}$, $R_{19}$, $R_{20}$, $R_{21}$, and $R_{22}$ are S. Independently in some embodiments of Formula XIV, and independently in combination with any embodiments of any other relevant substituent classes, one or two of $R_{18}$, $R_{19}$, $R_{20}$, $R_{21}$, and $R_{22}$ are N and one, two, or three of $R_{18}$, $R_{19}$, $R_{20}$, $R_{21}$, and $R_{22}$ are S. Independently in some embodiments of Formula XIV, and independently in combination with any embodiments of any other relevant substituent classes, one of $R_{18}$, $R_{19}$, $R_{20}$, $R_{21}$, and $R_{22}$ is N and one, two, three, or four of $R_{18}$, $R_{19}$, $R_{20}$, $R_{21}$, and $R_{22}$ are S.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N and one of $R_{18}$, $R_{19}$, $R_{20}$, $R_{21}$, $R_{22}$, and $R_{23}$ is $S(O)_2$. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N and one or two of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N and one, two, or three of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N and one, two, three, or four of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N and one, two, three, four, or five of $R_{18}$, $R_{19}$, $R_{20}$, $R_{21}$, $R_{22}$, and $R_{23}$ are $S(O)_2$.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N and one of $R_{18}$, $R_{19}$, $R_{20}$, $R_{21}$, and $R_{22}$ is $S(O)_2$. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N and one or two of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one or two of $R_{18}$, $R_{19}$, $R_{20}$, $R_{21}$, and $R_{22}$ are N and one, two, or three of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one of $R_{18}$, $R_{19}$, $R_{20}$, $R_{21}$, and $R_{22}$ is N and one, two, three, or four of $R_{18}$, $R_{19}$, $R_{20}$, $R_{21}$, and $R_{22}$ are $S(O)_2$.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O and one of $R_{18}$, $R_{19}$, $R_{20}$, $R_{21}$, $R_{22}$, and $R_{23}$ is S. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O and one or two of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are O and one, two, or three of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are O and one, two, three, or four of $R_{18}$, $R_{19}$, $R_{20}$, $R_{21}$, $R_{22}$, and $R_{23}$ are S. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N and one, two, three, four, or five of $R_{18}$, $R_{19}$, $R_{20}$, $R_{21}$, $R_{22}$, and $R_{23}$ are S.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are O and one of $R_{18}$, $R_{19}$, $R_{20}$, $R_{21}$, and $R_{22}$ is S. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are O and one or two of $R_{18}$, $R_{19}$, $R_{20}$, $R_{21}$, and $R_{22}$ are S. Independently in some embodiments of Formula XIV, and independently in combination with any embodiments of any other relevant substituent classes, one or two of $R_{18}$, $R_{19}$, $R_{20}$, $R_{21}$, and $R_{22}$ are O and one, two, or three of $R_{18}$, $R_{19}$, $R_{20}$, $R_{21}$, and $R_{22}$ are S. Independently in some embodiments of Formula XIV, and independently in combination with any embodiments of any other relevant substituent classes, one of $R_{18}$, $R_{19}$, $R_{20}$, $R_{21}$, and $R_{22}$ is O and one, two, three, or four of $R_{18}$, $R_{19}$, $R_{20}$, $R_{21}$, and $R_{22}$ are S.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O and one of $R_{18}$, $R_{19}$, $R_{20}$, $R_{21}$, $R_{22}$, and $R_{23}$ is $S(O)_2$. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O and one or two of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are O and one, two, or three of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are O and one, two, three, or four of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is O and one, two, three, four, or five of $R_{18}$, $R_{19}$, $R_{20}$, $R_{21}$, $R_{22}$, and $R_{23}$ are $S(O)_2$.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are O and one of $R_{18}$, $R_{19}$, $R_{20}$, $R_{21}$, and $R_{22}$ is $S(O)_2$. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are O and one or two of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one or two of $R_{18}$, $R_{19}$, $R_{20}$, $R_{21}$, and $R_{22}$ are O and one, two, or three of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one of $R_{18}$, $R_{19}$, $R_{20}$, $R_{21}$, and $R_{22}$ is O and one, two, three, or four of $R_{18}$, $R_{19}$, $R_{20}$, $R_{21}$, and $R_{22}$ are $S(O)_2$.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are S and one of $R_{18}$, $R_{19}$, $R_{20}$, $R_{21}$, $R_{22}$, and $R_{23}$ is $S(O)_2$. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are S and one or two of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are S and one, two, or three of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are S and one, two, three, or four of $R_{18}$, $R_{19}$, $R_{20}$, $R_{21}$, $R_{22}$, and $R_{23}$ are $S(O)_2$. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is S and one, two, three, four, or five of $R_{18}$, $R_{19}$, $R_{20}$, $R_{21}$, $R_{22}$, and $R_{23}$ are $S(O)_2$.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are S and one of $R_{18}$, $R_{19}$, $R_{20}$, $R_{21}$, and $R_{22}$ is $S(O)_2$. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are S and one or two of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one or two of $R_{18}$, $R_{19}$, $R_{20}$, $R_{21}$, and $R_{22}$ are S and one, two, or three of $R_{18}$, $R_{19}$, $R_{20}$, $R_{21}$, and $R_{22}$ are $S(O)_2$. Independently in some embodiments of Formula XIV, and independently in combination with any embodiments of any other relevant substituent classes, one of $R_{18}$, $R_{19}$, $R_{20}$, $R_{21}$, and $R_{22}$ is S and one, two, three, or four of $R_{18}$, $R_{19}$, $R_{20}$, $R_{21}$, and $R_{22}$ are $S(O)_2$.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are N and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is N and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O and the others are C. Independently in some embodiments of Formula IX, and independently in combination with any embodiments of any other relevant substituent classes, one, two, or three of $R_{18}$, $R_{10}$, $R_{20}$, $R_{21}$, $R_{22}$, and $R_{23}$ are O and the others are C. Independently in some embodiments of Formula IX, and independently in combination with any embodiments of any other relevant substituent classes, one or two of $R_{18}$, $R_{10}$, $R_{20}$, $R_{21}$, $R_{22}$, and $R_{23}$ are O and the others are C. Independently in some embodiments of Formula IX, and independently in combination with any embodiments of any other relevant substituent classes, one of $R_{18}$, $R_{10}$, $R_{20}$, $R_{21}$, $R_{22}$, and $R_{23}$ is O and the others are C.

Independently in some embodiments of Formula XIV, and independently in combination with any embodiments of any other relevant substituent classes, one, two, three, or four of $R_{18}$, $R_{10}$, $R_{20}$, $R_{21}$, and $R_{22}$ are O and the others are C. Independently in some embodiments of Formula XIV, and independently in combination with any embodiments of any other relevant substituent classes, one, two, or three of $R_{18}$, $R_{10}$, $R_{20}$, $R_{21}$, and $R_{22}$ are O and the others are C. Independently in some embodiments of Formula XIV, and independently in combination with any embodiments of any other relevant substituent classes, one or two of $R_{18}$, $R_{10}$, $R_{20}$, $R_{21}$, and $R_{22}$ are O and the others are C. Independently in some embodiments of Formula XIV, and independently in combination with any embodiments of any other relevant substituent classes, one of $R_{18}$, $R_{10}$, $R_{20}$, $R_{21}$, and $R_{22}$ is O and the others are C.

Independently in some embodiments of Formula IX, and independently in combination with any embodiments of any other relevant substituent classes, one, two, three, four, or five of $R_{18}$, $R_{10}$, $R_{20}$, $R_{21}$, $R_{22}$, and $R_{23}$ are S and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are S and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are S and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are S and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is S and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are S and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are S and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are S and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is S and the others are C. Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are $S(O)_2$ and the others are C.

Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are $S(O)_2$ and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are $S(O)_2$ and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are $S(O)_2$ and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is $S(O)_2$ and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are $S(O)_2$ and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are $S(O)_2$ and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are $S(O)_2$ and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is $S(O)_2$ and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ is O, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are N, none, one, two, three, four, or five of $R_{18}$, $R_{19}$, $R_{20}$, $R_{21}$, and $R_{22}$ is O, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are N, none, one, two, three, or four of $R_{18}$, $R_{19}$, $R_{20}$, $R_{21}$, and $R_{22}$ is O, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are N, none, one, two, or three of $R_{18}$, $R_{19}$, $R_{20}$, $R_{21}$, and $R_{22}$ are O, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are N, none, one or two of $R_{18}$, $R_{19}$, $R_{20}$, $R_{21}$, and $R_{22}$ are O, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is N, none or one of $R_{18}$, $R_{19}$, $R_{20}$, $R_{21}$, and $R_{22}$ are O, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N, one of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N, one or two of $R_{18}$, $R_{19}$, $R_{20}$, $R_{21}$, $R_{22}$, and $R_{23}$ are O, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N, one, two, or three of $R_{18}$, $R_{19}$, $R_{20}$, $R_{21}$, $R_{22}$, and $R_{23}$ are O, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N, one, two, three, or four of $R_{18}$, $R_{19}$, $R_{20}$, $R_{21}$, $R_{22}$, and $R_{23}$ are O, and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N, one, two, three, four, or five of $R_{18}$, $R_{19}$, $R_{20}$, $R_{21}$, $R_{22}$, and $R_{23}$ are O, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N, one of $R_{18}$, $R_{19}$, $R_{20}$, $R_{21}$, and $R_{22}$ is O, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N, one or two of $R_{18}$, $R_{19}$, $R_{20}$, $R_{21}$, and $R_{22}$ are O, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are N, one, two, or three of $R_{18}$, $R_{19}$, $R_{20}$, $R_{21}$, and $R_{22}$ are O, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is N, one, two, three, or four of $R_{18}$, $R_{19}$, $R_{20}$, $R_{21}$, and $R_{22}$ are O, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ is S, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are N, none, one, two, three, four, or five of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are N, none, one, two, three, or four of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are N, none, one, two, or three of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are N, none, one or two of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is N, none or one of $R_{18}$, $R_{19}$, $R_{20}$, $R_{21}$, and $R_{22}$ are S, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N, one of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N, one or two of $R_{18}$, $R_{19}$, $R_{20}$, $R_{21}$, $R_{22}$, and $R_{23}$ are S, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N, one, two, or three of $R_{18}$, $R_{19}$, $R_{20}$, $R_{21}$, $R_{22}$, and $R_{23}$ are S, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N, one, two, three, or four of $R_{18}$, $R_{19}$, $R_{20}$, $R_{21}$, $R_{22}$, and $R_{23}$ are S, and the others are C.

Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N, one, two, three, four, or five of $R_{18}$, $R_{19}$, $R_{20}$, $R_{21}$, $R_{22}$, and $R_{23}$ are S, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N, one of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N, one or two of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are N, one, two, or three of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is N, one, two, three, or four of $R_{18}$, $R_{19}$, $R_{20}$, $R_{21}$, and $R_{22}$ are S, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ is $S(O)_2$, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are N, none, one, two, three, four, or five of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are N, none, one, two, three, or four of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are N, none, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are N, none, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is N, none or one of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are N, one of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are N, one or two of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are N, one, two, or three of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are N, one, two, three, or four of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N, one, two, three, four, or five of $R_{18}$, $R_{19}$, $R_{20}$, $R_{21}$, $R_{22}$, and $R_{23}$ are $S(O)_2$, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are N, one of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are N, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are N, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is N, one, two, three, or four of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are O, none, one, two, three, four, five, or six of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are O, none, one, two, three, four, or five of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are O, none, one, two, three, or four of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are O, none, one, two, or three of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are O, none, one, or two of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are O, none or one of $R_{18}$, $R_{19}$, $R_{20}$, $R_{21}$, $R_{22}$, and $R_{23}$ is S, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are O, none, one, two, three, four, or five of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are O, none, one, two, three, or four of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are O, none, one, two, or three of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are O, none, one or two of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is O, none or one of $R_{18}$, $R_{19}$, $R_{20}$, $R_{21}$, and $R_{22}$ are S, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O, one of $R_{18}$, $R_{19}$, $R_{20}$, $R_{21}$, $R_{22}$, and $R_{23}$ is S, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O, one or two of $R_{18}$, $R_{19}$, $R_{20}$, $R_{21}$, $R_{22}$, and $R_{23}$ are S, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are O, one, two, or three of $R_{18}$, $R_{19}$, $R_{20}$, $R_{21}$, $R_{22}$, and $R_{23}$ are S, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are O, one, two, three, or four of $R_{18}$, $R_{19}$, $R_{20}$, $R_{21}$, $R_{22}$, and $R_{23}$ are S, and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is N, one, two, three, four, or five of $R_{18}$, $R_{19}$, $R_{20}$, $R_{21}$, $R_{22}$, and $R_{23}$ are S, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are O, one of $R_{18}$, $R_{19}$, $R_{20}$, $R_{21}$, and $R_{22}$ is S, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are O, one or two of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are O, one, two, or three of $R_{18}$, $R_{19}$, $R_{20}$, $R_{21}$, and $R_{22}$ are S, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is O, one, two, three, or four of $R_{18}$, $R_{19}$, $R_{20}$, $R_{21}$, and $R_{22}$ are S, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are O, none, one, two, three, four, five, or six of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are O, none, one, two, three, four, or five of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are O, none, one, two, three, or four of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are O, none, one, two, or three of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are O, none, one, or two of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are O, none or one of $R_{18}$, $R_{19}$, $R_{20}$, $R_{21}$, $R_{22}$, and $R_{23}$ is $S(O)_2$, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are O, none, one, two, three, four, or five of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are O, none, one, two, three, or four of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are O, none, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are O, none, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is O, none or one of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are O, one of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are O, one or two of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are O, one, two, or three of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are O, one, two, three, or four of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is O, one, two, three, four, or five of $R_{18}$, $R_{19}$, $R_{20}$, $R_{21}$, $R_{22}$, and $R_{23}$ are $S(O)_2$, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are O, one of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are O, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are O, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is O, one, two, three, or four of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are S, none, one, two, three, four, five, or six of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are S, none, one, two, three, four, or five of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are S, none, one, two, three, or four of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are S, none, one, two, or three of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are S, none, one, or two of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are S, none or one of $R_{18}$, $R_{19}$, $R_{20}$, $R_{21}$, $R_{22}$, and $R_{23}$ is $S(O)_2$, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, and $R_{22}$ are S, none, one, two, three, four, or five of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, and $R_{22}$ are S, none, one, two, three, or four of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, none, one, two, or three of $R_{18}$, $R_{19}$, $R_{20}$, $R_{21}$, and $R_{22}$ are S, none, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none, one or two of $R_{18}$, $R_{19}$, $R_{20}$, $R_{21}$, and $R_{22}$ are S, none, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, none or one of $R_{18}$, $R_{19}$, $R_{20}$, $R_{21}$, and $R_{22}$ is S, none or one of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, one, two, three, four, or five of $R_{18}$, $R_{19}$, $R_{20}$, $R_{21}$, $R_{22}$, and $R_{23}$ are S, one of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, one, two, three, or four of $R_{18}$, $R_{19}$, $R_{20}$, $R_{21}$, $R_{22}$, and $R_{23}$ are S, one or two of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one, two, or three of $R_{18}$, $R_{19}$, $R_{20}$, $R_{21}$, $R_{22}$, and $R_{23}$ are S, one, two, or three of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one or two of $R_{18}$, $R_{19}$, $R_{20}$, $R_{21}$, $R_{22}$, and $R_{23}$ are S, one, two, three, or four of $R_{18}$, $R_{19}$, $R_{20}$, $R_{21}$, $R_{22}$, and $R_{23}$ are $S(O)_2$, and the others are C. Independently in some embodiments of Formula IX, and independently in combination with any embodiments of any other relevant substituent classes, one of $R_{18}$, $R_{19}$, $R_{20}$, $R_{21}$, $R_{22}$, and $R_{23}$ is S, one, two, three, four, or five of $R_{18}$, $R_{19}$, $R_{20}$, $R_{21}$, $R_{22}$, and $R_{23}$ are $S(O)_2$, and the others are C.

Independently in some embodiments of Formula XIV, and independently in combination with any embodiments of any other relevant substituent classes, one, two, three, or four of $R_{18}$, $R_{19}$, $R_{20}$, $R_{21}$, and $R_{22}$ are S, one of $R_{18}$, $R_{19}$, $R_{20}$, $R_{21}$, and $R_{22}$ is $S(O)_2$, and the others are C. Independently in some embodiments of Formula XIV, and independently in combination with any embodiments of any other relevant substituent classes, one, two, or three of $R_{18}$, $R_{19}$, $R_{20}$, $R_{21}$, and $R_{22}$ are S, one or two of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one or two of $R_{18}$, $R_{19}$, $R_{20}$, $R_{21}$, and $R_{22}$ are S, one, two, or three of $R_{18}$, $R_{19}$, $R_{20}$, $R_{21}$, and $R_{22}$ are $S(O)_2$, and the others are C. Independently in some embodiments of Formula XIV, and independently in combination with any embodiments of any other relevant substituent classes, one of $R_{18}$, $R_{19}$, $R_{20}$, $R_{21}$, and $R_{22}$ is S, one, two, three, or four of $R_{18}$, $R_{19}$, $R_{20}$, $R_{21}$, and $R_{22}$ are $S(O)_2$, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ are S, none, one, two, three, four, five, or six of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ are S, none, one, two, three, four, or five of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ are S, none, one, two, three, or four of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ are S, none, one, two, or three of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ are S, none, one, or two of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ are S, none or one of $R_{18}$, $R_{19}$, $R_{20}$, $R_{21}$, $R_{22}$, and $R_{23}$ is O, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, or $R_{22}$ are N, none, one, two, three, four, or five of $R_{18}$, $R_{19}$, $R_{20}$, $R_{21}$, or $R_{22}$ are S, none, one, two, three, four, or five of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, or $R_{22}$ are N, none, one, two, three, or four of $R_{18}$, $R_{19}$, $R_{20}$, $R_{21}$, or $R_{22}$ are S, none, one, two, three, or four of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, or three of $R_{18}$, $R_{19}$, $R_{20}$, $R_{21}$, or $R_{22}$ are N, none, one, two, or three of $R_{18}$, $R_{19}$, $R_{20}$, $R_{21}$, or $R_{22}$ are S, none, one, two, or three of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, or two of $R_{18}$, $R_{19}$, $R_{20}$, $R_{21}$, or $R_{22}$ are N, none, one, or two of $R_{18}$, $R_{19}$, $R_{20}$, $R_{21}$, or $R_{22}$ are S, none, one, or two of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none or one of $R_{18}$, $R_{19}$, $R_{20}$, $R_{21}$, or $R_{22}$ are N, none or one of $R_{18}$, $R_{19}$, $R_{20}$, $R_{21}$, or $R_{22}$ are S, none or one of $R_{18}$, $R_{19}$, $R_{20}$, $R_{21}$, or $R_{22}$ is O, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ are $S(O)_2$, none, one, two, three, four, five, or six of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ are $S(O)_2$, none, one, two, three, four, or five of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ are $S(O)_2$, none, one, two, three, or four of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ are $S(O)_2$, none, one, two, or three of $R_{18}$, $R_{19}$, $R_{20}$, $R_{21}$, $R_{22}$, and $R_{23}$ is O, and the others are C. Independently in some embodiments of Formula IX, and independently in combination with any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ are $S(O)_2$, none, one, or two of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ are $S(O)_2$, none or one of $R_{18}$, $R_{19}$, $R_{20}$, $R_{21}$, $R_{22}$, and $R_{23}$ is O, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, or $R_{22}$ are N, none, one, two, three, four, or five of $R_{18}$, $R_{19}$, $R_{20}$, $R_{21}$, or $R_{22}$ are $S(O)_2$, none, one, two, three, four, or five of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, or $R_{22}$ are N, none, one, two, three, or four of $R_{18}$, $R_{19}$, $R_{20}$, $R_{21}$, or $R_{22}$ are $S(O)_2$, none, one, two, three, or four of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, or three of $R_{18}$, $R_{19}$, $R_{20}$, $R_{21}$, or $R_{22}$ are N, none, one, two, or three of $R_{18}$, $R_{19}$, $R_{20}$, $R_{21}$, or $R_{22}$ are $S(O)_2$, none, one, two, or three of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, or two of $R_{18}$, $R_{19}$, $R_{20}$, $R_{21}$, or $R_{22}$ are N, none, one, or two of $R_{18}$, $R_{19}$, $R_{20}$, $R_{21}$, or $R_{22}$ are $S(O)_2$, none, one, or two of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none or one of $R_{18}$, $R_{19}$, $R_{20}$, $R_{21}$, or $R_{22}$ are N, none or one of $R_{18}$, $R_{19}$, $R_{20}$, $R_{21}$, or $R_{22}$ are $S(O)_2$, none or one of $R_{18}$, $R_{19}$, $R_{20}$, $R_{21}$, or $R_{22}$ is O, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ are S, none, one, two, three, four, five, or six of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ are S, none, one, two, three, four, or five of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ are S, none, one, two, three, or four of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ are S, none, one, two, or three of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ are S, none, one, or two of $R_{18}$, $R_{19}$, $R_{20}$, $R_{21}$, $R_{22}$, and $R_{23}$ is $S(O)_2$, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ are S, none or one of $R_{18}$, $R_{19}$, $R_{20}$, $R_{21}$, $R_{22}$, and $R_{23}$ is $S(O)_2$, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, or $R_{22}$ are N, none, one, two, three, four, or five of $R_{18}$, $R_{19}$, $R_{20}$, $R_{21}$, or $R_{22}$ are S, none, one, two, three, four, or five of $R_{18}$, $R_{19}$, $R_{20}$, $R_{21}$, or $R_{22}$ is $S(O)_2$, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, or $R_{22}$ are N, none, one, two, three, or four of $R_{18}$, $R_{19}$, $R_{20}$, $R_{21}$, or $R_{22}$ are S, none, one, two, three, or four of $R_{18}$, $R_{19}$, $R_{20}$, $R_{21}$, or $R_{22}$ is $S(O)_2$, and the others are C. Independently in some embodiments of Formula XIV, and independently in combination with any embodiments of any other relevant substituent classes, none, one, two, or three of $R_{18}$, $R_{19}$, $R_{20}$, $R_{21}$, or $R_{22}$ are N, none, one, two, or three of $R_{18}$, $R_{19}$, $R_{20}$, $R_{21}$, or $R_{22}$ are S, none, one, two, or three of $R_{18}$, $R_{19}$, $R_{20}$, $R_{21}$, or $R_{22}$ is $S(O)_2$, and the others are C. Independently in some embodiments of Formula XIV, and independently in combination with any embodiments of any other relevant substituent classes, none, one, or two of $R_{18}$, $R_{19}$, $R_{20}$, $R_{21}$, or $R_{22}$ are N, none, one, or two of $R_{18}$, $R_{19}$, $R_{20}$, $R_{21}$, or $R_{22}$ are S, none, one, or two of $R_{18}$, $R_{19}$, $R_{20}$, $R_{21}$, or $R_{22}$ is $S(O)_2$, and the others are C. Independently in some embodiments of Formula XIV, and independently in combination with any embodiments of any other relevant substituent classes, none or one of $R_{18}$, $R_{19}$, $R_{20}$, $R_{21}$, or $R_{22}$ are N, none or one of $R_{18}$, $R_{19}$, $R_{20}$, $R_{21}$, or $R_{22}$ are S, none or one of $R_{18}$, $R_{19}$, $R_{20}$, $R_{21}$, or $R_{22}$ is $S(O)_2$, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are $S(O)_2$, none, one, two, three, four, five, or six of $R_{18}$, $R_{19}$, $R_{20}$, $R_{21}$, $R_{22}$, and $R_{23}$ are S, none, one, two, three, four, five, or six of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are $S(O)_2$, none, one, two, three, four, or five of $R_{18}$, $R_{19}$, $R_{20}$, $R_{21}$, $R_{22}$, and $R_{23}$ are S, none, one, two, three, four, or five of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are $S(O)_2$, none, one, two, three, or four of $R_{18}$, $R_{19}$, $R_{20}$, $R_{21}$, $R_{22}$, and $R_{23}$ are S, none, one, two, three, or four of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are $S(O)_2$, none, one, two, or three of $R_{18}$, $R_{19}$, $R_{20}$, $R_{21}$, $R_{22}$, and $R_{23}$ are S, none, one, two, or three of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are $S(O)_2$, none, one, or two of $R_{18}$, $R_{19}$, $R_{20}$, $R_{21}$, $R_{22}$, and $R_{23}$ are S, none, one, or two of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are $S(O)_2$, none or one of $R_{18}$, $R_{19}$, $R_{20}$, $R_{21}$, $R_{22}$, and $R_{23}$ are S, none or one of $R_{18}$, $R_{19}$, $R_{20}$, $R_{21}$, $R_{22}$, and $R_{23}$ is O, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, or $R_{22}$ are $S(O)_2$, none, one, two, three, four, or five of $R_{18}$, $R_{19}$, $R_{20}$, $R_{21}$, or $R_{22}$ are S, none, one, two, three, four, or five of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, or $R_{22}$ are $S(O)_2$, none, one, two, three, or four of $R_{18}$, $R_{19}$, $R_{20}$, $R_{21}$, or $R_{22}$ are S, none, one, two, three, or four of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, or three of $R_{18}$, $R_{19}$, $R_{20}$, $R_{21}$, or $R_{22}$ are $S(O)_2$, none, one, two, or three of $R_{18}$, $R_{19}$, $R_{20}$, $R_{21}$, or $R_{22}$ are S, none, one, two, or three of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, or two of $R_{18}$, $R_{19}$, $R_{20}$, $R_{21}$, or $R_{22}$ are $S(O)_2$, none, one, or two of $R_{18}$, $R_{19}$, $R_{20}$, $R_{21}$, or $R_{22}$ are S, none, one, or two of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none or one of $R_{18}$, $R_{19}$, $R_{20}$, $R_{21}$, or $R_{22}$ are $S(O)_2$, none or one of $R_{18}$, $R_{19}$, $R_{20}$, $R_{21}$, or $R_{22}$ are S, none or one of $R_{18}$, $R_{19}$, $R_{20}$, $R_{21}$, or $R_{22}$ is O, and the others are C.

Independently in some embodiments of Formula IX, and independently in combination with any embodiments of any other relevant substituent classes, none, one, two, three, four, five, or six of $R_{18}$, $R_{19}$, $R_{20}$, $R_{21}$, $R_{22}$, and $R_{23}$ are N, none, one, two, three, four, five, or six of $R_{18}$, $R_{19}$, $R_{20}$, $R_{21}$, $R_{22}$, and $R_{23}$ are S, none, one, two, three, four, five, or six of $R_{18}$, $R_{19}$, $R_{20}$, $R_{21}$, $R_{22}$, and $R_{23}$ are $S(O)_2$, none, one, two, three, four, five, or six of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, four, or five of $R_{18}$, $R_{19}$, $R_{20}$, $R_{21}$, $R_{22}$, and $R_{23}$ are N, none, one, two, three, four, or five of $R_{18}$, $R_{19}$, $R_{20}$, $R_{21}$, $R_{22}$, and $R_{23}$ are S, none, one, two, three, four, or five of $R_{18}$, $R_{19}$, $R_{20}$, $R_{21}$, $R_{22}$, and $R_{23}$ are $S(O)_2$, none, one, two, three, four, or five of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, three, or four of $R_{18}$, $R_{19}$, $R_{20}$, $R_{21}$, $R_{22}$, and $R_{23}$ are N, none, one, two, three, or four of $R_{18}$, $R_{19}$, $R_{20}$, $R_{21}$, $R_{22}$, and $R_{23}$ are S, none, one, two, three, or four of $R_{18}$, $R_{19}$, $R_{20}$, $R_{21}$, $R_{22}$, and $R_{23}$ are $S(O)_2$, none, one, two, three, or four of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, two, or three of $R_{18}$, $R_{19}$, $R_{20}$, $R_{21}$, $R_{22}$, and $R_{23}$ are N, none, one, two, or three of $R_{18}$, $R_{19}$, $R_{20}$, $R_{21}$, $R_{22}$, and $R_{23}$ are S, none, one, two, or three of $R_{18}$, $R_{19}$, $R_{20}$, $R_{21}$, $R_{22}$, and $R_{23}$ are $S(O)_2$, none, one, two, or three of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none, one, or two of $R_{18}$, $R_{19}$, $R_{20}$, $R_{21}$, $R_{22}$, and $R_{23}$ are N, none, one, or two of $R_{18}$, $R_{19}$, $R_{20}$, $R_{21}$, $R_{22}$, and $R_{23}$ are S, none, one, or two of $R_{18}$, $R_{19}$, $R_{20}$, $R_{21}$, $R_{22}$, and $R_{23}$ are $S(O)_2$, none, one, or two of $R_{18}$, $R_{19}$, $R_{20}$, $R_{21}$, $R_{22}$, and $R_{23}$ is O, and the others are C. Independently in some embodiments of Formula IX, and independently in combination with any embodiments of any other relevant substituent classes, none or one of $R_{18}$, $R_{19}$, $R_{20}$, $R_{21}$, $R_{22}$, and $R_{23}$ are N, none or one of $R_{18}$, $R_{19}$, $R_{20}$, $R_{21}$, $R_{22}$, and $R_{23}$ are S, none or one of $R_{18}$, $R_{19}$, $R_{20}$, $R_{21}$, $R_{22}$, and $R_{23}$ are $S(O)_2$, none or one of $R_{18}$, $R_{19}$, $R_{20}$, $R_{21}$, $R_{22}$, and $R_{23}$ is O, and the others are C.

Independently in some embodiments of Formula XIV, and independently in combination with any embodiments of any other relevant substituent classes, none, one, two, three, four, or five of $R_{18}$, $R_{19}$, $R_{20}$, $R_{21}$, or $R_{22}$ are N, none, one, two, three, four, or five of $R_{18}$, $R_{19}$, $R_{20}$, $R_{21}$, or $R_{22}$ are S, none, one, two, three, four, or five of $R_{18}$, $R_{19}$, $R_{20}$, $R_{21}$, or $R_{22}$ are $S(O)_2$, none, one, two, three, four, or five of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, three, or four of $R_{18}$, $R_{19}$, $R_{20}$, $R_{21}$, or $R_{22}$ are N, none, one, two, three, or four of $R_{18}$, $R_{19}$, $R_{20}$, $R_{21}$, or $R_{22}$ are S, none, one, two, three, or four of $R_{18}$, $R_{19}$, $R_{20}$, $R_{21}$, or $R_{22}$ are $S(O)_2$, none, one, two, three, or four of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, two, or three of $R_{18}$, $R_{19}$, $R_{20}$, $R_{21}$, or $R_{22}$ are N, none, one, two, or three of $R_{18}$, $R_{19}$, $R_{20}$, $R_{21}$, or $R_{22}$ are S, none, one, two, or three of $R_{18}$, $R_{19}$, $R_{20}$, $R_{21}$, or $R_{22}$ are $S(O)_2$, none, one, two, or three of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none, one, or two of $R_{18}$, $R_{19}$, $R_{20}$, $R_{21}$, or $R_{22}$ are N, none, one, or two of $R_{18}$, $R_{19}$, $R_{20}$, $R_{21}$, or $R_{22}$ are S, none, one, or two of $R_{18}$, $R_{19}$, $R_{20}$, $R_{21}$, or $R_{22}$ are $S(O)_2$, none, one, or two of $R_{18}$, $R_{19}$, $R_{20}$, $R_{21}$, or $R_{22}$ is O, and the others are C. Independently in some embodiments of Formula XIV, and independently in combination with any embodiments of any other relevant substituent classes, none or one of $R_{18}$, $R_{19}$, $R_{20}$, $R_{21}$, or $R_{22}$ are N, none or one of $R_{18}$, $R_{19}$, $R_{20}$, $R_{21}$, or $R_{22}$ are S, none or one of $R_{18}$, $R_{19}$, $R_{20}$, $R_{21}$, or $R_{22}$ are $S(O)_2$, none or one of $R_{18}$, $R_{19}$, $R_{20}$, $R_{21}$, or $R_{22}$ is O, and the others are C.

Independently in some embodiments of $R_{24}$, and independently in combination with any embodiments of any other relevant substituent classes, $R_{24}$ can be

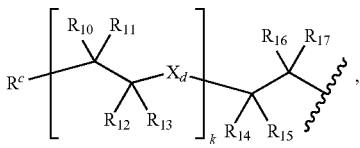

Formula XII wherein k is an integer from 0 to 20;
wherein $X_d$ are absent or O;
wherein $R^c$ is $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_4+Q_3$; and
wherein $R_{10}$, $R_{11}$, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of $R_{24}$, and independently in combination with any embodiments of any other relevant substituent classes, $R_{24}$ can be

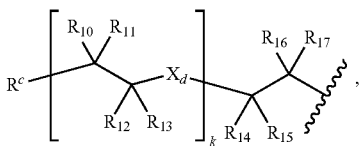

Formula XII wherein k is an integer from 1 to 20;
wherein $X_4$ are O;
wherein $R^c$ is $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, $R_{11}$, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_4+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of $R_{24}$, and independently in combination with any embodiments of any other relevant substituent classes, $R_{24}$ can be

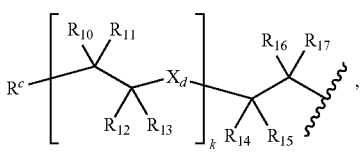

Formula XII wherein k is an integer from 1 to 20;
wherein $X_d$ are absent;
wherein $R^c$ is $R^b$, absent, hydrogen, $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and wherein $R_{10}$, $R_{11}$, $R_{12}$, $R_{13}$, $R_{14}$, $R_{15}$, $R_{16}$, and $R_{17}$ are independently $R^b$, hydrogen $U_b$ $U_1+Q_b$ $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of $R_{24}$, and independently in combination with any embodiments of any other relevant substituent classes, $R_{24}$ can be absent or —$(CR_{25}R_{25})_p$—, wherein p is 1.

Independently in some embodiments of -A-B(—C)$_\delta$, —B(—C)$_\delta$, —B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, —B, C, $R_6$, $R_8$, $R_9$, $R^a$, $R^b$, $R^c$, $R^d$, and $R^e$ can be, independently, an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R^b$ organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of -A-B(—C)$_\delta$, —B(—C)$_\delta$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_6$, $R_8$, $R_9$, $R^a$, $R^b$, $R^c$, $R^d$, and $R^e$ can be, independently, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of -A-B(—C)$_\delta$, —B(—C)$_\delta$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_6$, $R_8$, $R_9$, $R^a$, $R^b$, $R^c$, $R^d$, and $R^e$ can be, independently, amino, hydroxyl, thiol, oxo, phosphate, or $J_1$.

Independently in some embodiments of -A-B(—C)$_\delta$, —B(—C)$_\delta$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_6$, $R_8$, $R_9$, $R^a$, $R^b$, $R^c$, $R^d$, and $R^e$ can be, independently, amino, hydroxyl, thiol, oxo, phosphate, or $J_2$.

Independently in some embodiments of -A-B(—C)$_\delta$, —B(—C)$_\delta$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, $R_6$, $R_8$, $R_9$, $R^a$, $R^b$, $R^c$, $R^d$, and $R^e$ can be, independently,

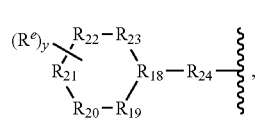

Formula IX

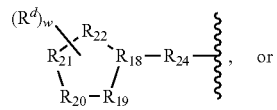

Formula XIV

, or

-continued

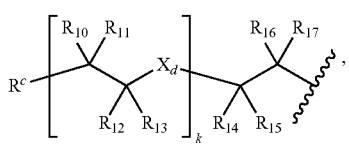

Formula XII wherein y is an integer from 0-11; wherein w is an integer from 0-9; wherein k is an integer from 0 to 20;

wherein $R^d$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, $R_{11}$, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

Independently in some embodiments of -A-B(—C)$_δ$, —B(—C)$_δ$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_δ$, —B(—C)$_δ$, A, B, C, $R_6$, $R_8$, $R_9$, $R^a$, $R^b$, $R^c$, $R^d$, and $R^e$ can be, independently,

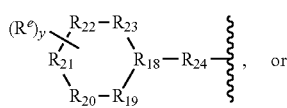

Formula IX

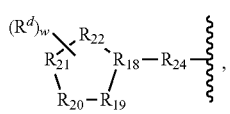

Formula XIV wherein y is an integer from 0-11; wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of -A-B(—C)$_δ$, —B(—C)$_δ$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_δ$, —B(—C)$_δ$, A, B, C, $R_6$, $R_8$, $R_9$, $R^a$, $R^b$, $R^c$, $R^d$, and $R^e$ can be, independently,

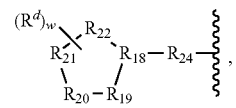

Formula XIV wherein w is an integer from 0-9;

wherein $R^d$ and $R^e$ are independently $U_2$, $U_2+Q_1$, $U_2+Q_2$, $U_2+Q_3$, $U_2+Q_4$, $U_2+Q_1+Q_2$, $U_2+Q_1+Q_3$, $U_2+Q_1+Q_4$, $U_2+Q_2+Q_3$, $U_2+Q_2+Q_4$, $U_2+Q_3+Q_4$, $U_2+Q_1+Q_2+Q_3$, $U_2+Q_1+Q_2+Q_4$, $U_2+Q_1+Q_3+Q_4$, $U_2+Q_2+Q_3+Q_4$, and $U_2+Q_1+Q_2+Q_3+Q_4$, preferably $U_2+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, or —S(O)$_2$—, or NR$_4$, wherein each $R_{25}$ is, as valency permits, independently absent, hydrogen, =O, =S, —OH, —SH, or —NR$_4$, wherein $R_4$ is $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

Independently in some embodiments of -A-B(—C)$_δ$, —B(—C)$_δ$, A, B, C, $R_6$, $R_8$, $R_9$, $R^a$, $R^b$, $R^c$, $R^d$, and $R^e$, and independently in combination with any embodiments of any other relevant substituent classes, -A-B(—C)$_\delta$, —B(—C)$_\delta$, A, B, C, R$_6$, R$_8$, R$_9$, R$^a$, R$^b$, R$^c$, R$^d$, and R$^e$ can be, independently,

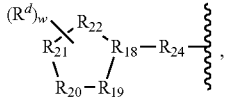

Formula XIV wherein w is an integer from 0-9;

wherein R$^d$ and R$^e$ are independently U$_2$, U$_2$+Q$_1$, U$_2$+Q$_2$, U$_2$+Q$_3$, U$_2$+Q$_4$, U$_2$+Q$_1$+Q$_2$, U$_2$+Q$_1$+Q$_3$, U$_2$+Q$_1$+Q$_4$, U$_2$+Q$_2$+Q$_3$, U$_2$+Q$_2$+Q$_4$, U$_2$+Q$_3$+Q$_4$, U$_2$+Q$_1$+Q$_2$+Q$_3$, U$_2$+Q$_1$+Q$_2$+Q$_4$, U$_2$+Q$_1$+Q$_3$+Q$_4$, U$_2$+Q$_2$+Q$_3$+Q$_4$, and U$_2$+Q$_1$+Q$_2$+Q$_3$+Q$_4$, preferably U$_2$+Q$_1$+Q$_3$; or together with the carbon atom to which they are attached, form a 3- to 8-membered unsubstituted or substituted carbocyclic or heterocyclic ring;

wherein R$_{18}$, R$_{19}$, R$_{20}$, R$_{21}$, and R$_{22}$ are independently C or N, wherein the bonds between adjacent R$_{18}$ to R$_{22}$ are double or single according to valency, wherein one, two, three, or four of R$_{18}$, R$_{19}$, R$_{20}$, R$_{21}$, and R$_{22}$ are N and the others are C, and wherein R$_{18}$ to R$_{22}$ are bound to none, one, or two hydrogens according to valency; and wherein R$_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein X$_b$ is absent, —O—, —S—, —S(O)—, or —S(O)$_2$—, or NR$_4$, wherein each R$_{25}$ is, as valency permits, independently absent, hydrogen, =O, =S, —OH, —SH, or —NR$_4$, wherein R$_4$ is U$_1$; U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_3$.

Independently in some embodiments of -A-B(—C)$_\delta$, —B(—C)$_\delta$, A, B, C, R$_6$, R$_8$, R$_9$, R$^a$, R$^b$, R$^c$, R$^d$, and R$^e$, and independently in combination with any embodiments of any other relevant substituent classes, -A-B(—C)$_\delta$, —B(—C)$_\delta$, A, B, C, R$_6$, R$_8$, R$_9$, R$^a$, R$^b$, R$^c$, R$^d$, and R$^e$ can be, independently,

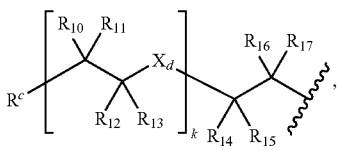

Formula XII wherein k is an integer from 0 to 20;

wherein X$_d$ are independently absent, O, or S;

wherein R$^c$ is absent, hydrogen, U$_3$, U$_3$+Q$_1$; U$_3$+Q$_2$, U$_3$+Q$_3$, U$_3$+Q$_4$, U$_3$+Q$_2$+Q$_2$, U$_3$+Q$_2$+Q$_3$, U$_3$+Q$_1$+Q$_4$, U$_3$+Q$_2$+Q$_3$, U$_3$+Q$_2$+Q$_4$, U$_3$+Q$_3$+Q$_4$, U$_3$+Q$_1$+Q$_2$+Q$_3$, U$_3$+Q$_1$+Q$_2$+Q$_4$, U$_3$+Q$_1$+Q$_3$+Q$_4$, U$_3$+Q$_2$+Q$_3$+Q$_4$, and U$_3$+Q$_1$+Q$_2$+Q$_3$+Q$_4$, preferably U$_3$+Q$_1$+Q$_3$; and wherein R$_{10}$, R$_{11}$, R$_{12}$, R$_{13}$, R$_{14}$, R$_{15}$, R$_{16}$, and R$_{17}$ are independently hydrogen, U$_1$, U$_1$+Q$_1$; U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_2$+Q$_3$.

Independently in some embodiments of -A-B(—C)$_\delta$, —B(—C)$_\delta$, A, B, C, R$_6$, R$_8$, R$_9$, R$^a$, R$^b$, R$^c$, R$^d$, and R$^e$, and independently in combination with any embodiments of any other relevant substituent classes, -A-B(—C)$_\delta$, —B(—C)$_\delta$, A, B, C, R$_6$, R$_8$, R$_9$, R$^a$, R$^b$, R$^c$, R$^d$, and R$^e$ can be, independently,

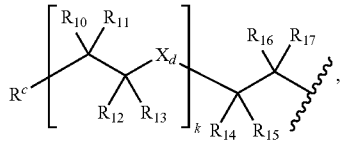

Formula XII wherein k is an integer from 0 to 20;

wherein X$_d$ are independently O or S;

wherein R$^c$ is absent, hydrogen, U$_3$, U$_3$+Q$_1$, U$_3$+Q$_2$, U$_3$+Q$_3$, U$_3$+Q$_4$, U$_3$+Q$_2$+Q$_2$, U$_3$+Q$_2$+Q$_3$, U$_3$+Q$_1$+Q$_4$, U$_3$+Q$_2$+Q$_3$, U$_3$+Q$_2$+Q$_4$, U$_3$+Q$_3$+Q$_4$, U$_3$+Q$_1$+Q$_2$+Q$_3$, U$_3$+Q$_1$+Q$_2$+Q$_4$, U$_3$+Q$_1$+Q$_3$+Q$_4$, U$_3$+Q$_2$+Q$_3$+Q$_4$, and U$_3$+Q$_1$+Q$_2$+Q$_3$+Q$_4$, preferably U$_3$+Q$_1$+Q$_3$; and wherein R$_{10}$, R$_{11}$, R$_{12}$, R$_{13}$, R$_{14}$, R$_{15}$, R$_{16}$, and R$_{17}$ are independently hydrogen, U$_1$, U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_2$+Q$_3$.

Independently in some embodiments of -A-B(—C)$_\delta$, —B(—C)$_\delta$, A, B, C, R$_6$, R$_8$, R$_9$, R$^a$, R$^b$, R$^c$, R$^d$, and R$^e$, and independently in combination with any embodiments of any other relevant substituent classes, -A-B(—C)$_\delta$, —B(—C)$_\delta$, A, B, C, R$_6$, R$_8$, R$_9$, R$^a$, R$^b$, R$^c$, R$^d$, and R$^e$ can be, independently,

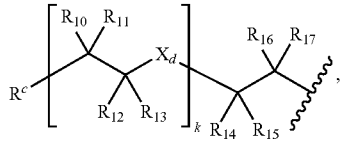

Formula XII wherein k is an integer from 1 to 20;

wherein X$_d$ are O;

wherein R$^c$ is absent, hydrogen, U$_3$, U$_3$+Q$_1$, U$_3$+Q$_2$, U$_3$+Q$_3$, U$_3$+Q$_4$, U$_3$+Q$_2$+Q$_2$, U$_3$+Q$_2$+Q$_3$, U$_3$+Q$_1$+Q$_4$, U$_3$+Q$_2$+Q$_3$, U$_3$+Q$_2$+Q$_4$, U$_3$+Q$_3$+Q$_4$, U$_3$+Q$_1$+Q$_2$+Q$_3$, U$_3$+Q$_1$+Q$_2$+Q$_4$, U$_3$+Q$_1$+Q$_3$+Q$_4$, U$_3$+Q$_2$+Q$_3$+Q$_4$, and U$_3$+Q$_1$+Q$_2$+Q$_3$+Q$_4$, preferably U$_3$+Q$_1$+Q$_3$; and wherein R$_{10}$, R$_{11}$, R$_{12}$, R$_{13}$, R$_{14}$, R$_{15}$, R$_{16}$, and R$_{17}$ are independently hydrogen, U$_1$, U$_1$+Q$_1$, U$_1$+Q$_2$, U$_1$+Q$_3$, U$_1$+Q$_4$, U$_1$+Q$_1$+Q$_2$, U$_1$+Q$_1$+Q$_3$, U$_1$+Q$_1$+Q$_4$, U$_1$+Q$_2$+Q$_3$, U$_1$+Q$_2$+Q$_4$, U$_1$+Q$_3$+Q$_4$, U$_1$+Q$_1$+Q$_2$+Q$_3$, U$_1$+Q$_1$+Q$_2$+Q$_4$, U$_1$+Q$_1$+Q$_3$+Q$_4$, U$_1$+Q$_2$+Q$_3$+Q$_4$, and U$_1$+Q$_1$+Q$_2$+Q$_3$+Q$_4$, preferably U$_1$+Q$_1$+Q$_2$+Q$_3$.

In some embodiments, y in Formula IX is an integer from 0-3; R$^e$ is independently amino, hydroxyl, thiol, oxo, phosphate, or substituted or unsubstituted Cr C$_6$ alkyl, C$_1$-C$_6$ alkoxy, C$_1$-C$_6$ alkylamino, or C$_1$-C$_6$ alkylthio;

where R$_{18}$, R$_{19}$, R$_{20}$, R$_{21}$, R$_{22}$, and R$_{23}$ are independently C, O, N, or S, where the bonds between adjacent R$_{18}$ to R$_{23}$ are double or single according to valency, and where R$_{18}$ to R$_{23}$ are bound to none, one, or two hydrogens according to valency; and where R$_{24}$ is independently —(CR$_{25}$R$_{25}$)$_p$— or —(CR$_{25}$R$_{25}$)$_p$—X$_b$—(CR$_{25}$R$_{25}$)$_q$—, where p and q are independently integers from 0 to 3, where $X_b$ is absent, —O—, —S—, —SO$_2$—, or NR$_4$, where each $R_{25}$ is, as valency permits, independently absent, hydrogen, =O, =S, —OH, —SH, —NR$_4$, where R$_4$ is substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, y in Formula IX is 2, $R_{18}$ is N, $R_{19}$, $R_{20}$, $R_{21}$, $R_{22}$, or $R_{23}$ is S, both $R^e$ are oxo and are bonded to the S, and all of the bonds between adjacent $R_{18}$ to $R_{23}$ are single.

In some embodiments, y in Formula IX is 2, both $R^e$ are oxo and are bonded to $R_{21}$, $R_{18}$ is N, $R_{21}$ is S, and all of the bonds between adjacent $R_{18}$ to $R_{23}$ are single.

In some embodiments, y in Formula IX is 2, both $R^e$ are oxo and are bonded to $R_{21}$, $R_{18}$ is N, $R_{21}$ is S, and all of the bonds between adjacent $R_{18}$ to $R_{23}$ are single, $X_b$ is absent, q is 0, p is 1, and each $R_{25}$ is hydrogen.

In some embodiments, y in Formula IX is 1, $R^e$ is amino, and three of the bonds between adjacent $R_{18}$ to $R_{23}$ are double and three of the bonds between adjacent $R_{18}$ to $R_{23}$ are single.

In some embodiments, y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single.

In some embodiments, y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula IX is 0, $R_{19}$, $R_{20}$, $R_{21}$, $R_{22}$, or $R_{23}$ is O, and all of the bonds between adjacent $R_{18}$ to $R_{23}$ are single.

In some embodiments, y in Formula IX is 0, $R_{19}$ is O, and all of the bonds between adjacent $R_{18}$ to $R_{23}$ are single.

In some embodiments, y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments, $R_{19}$ and $R_{23}$ of Formula IX are O and all of the bonds between adjacent $R_{18}$ to $R_{23}$ are single.

In some embodiments, $R_{19}$ and $R_{23}$ of Formula IX are O, the bonds between $R_{18}$ and $R_{19}$, and between $R_{21}$ and $R_{22}$ are double bonds, and the rest of the bonds in the ring are single bonds.

In some embodiments, y in Formula IX is 1, $R^e$ is alkoxy and is bonded to $R_{19}$, $R_{20}$, $R_{21}$, $R_{21}$, $R_{22}$, or $R_{23}$, three of the bonds between adjacent $R_{18}$ to $R_{23}$ are double and three of the bonds between adjacent $R_{18}$ to $R_{23}$ are single.

In some embodiments, y in Formula IX is 1, $R^e$ is alkoxy and is bonded to $R_{19}$, three of the bonds between adjacent $R_{18}$ to $R_{23}$ are double and three of the bonds between adjacent $R_{18}$ to $R_{23}$ are single.

In some embodiments, y in Formula IX is 1, $R^e$ is methoxy, and is bonded to $R_{19}$, $R_{18}$ to $R_{23}$ are carbon atoms, three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula IX is 1, $R^e$ is hydroxyl.

In some embodiments, y in Formula IX is 1 and $R^e$ is hydroxyl bonded at the position para- to the methylene group.

In some embodiments, y in Formula IX is 1, $R^e$ is Formula XIII shown below:

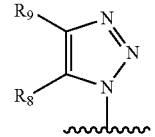

Formula XIII wherein $R_8$ is a substituted alkyl and $R_9$ is a dialkylamino, or $R_8$ is a dialkylamino and $R_9$ is a substituted alkyl, wherein the substituted alkyl is hydroxymethyl and the dialkylamino is XX-diethylamino.

In some embodiments, y in Formula IX is 1, $R^e$ is Formula XIII, wherein $R_8$ is hydrogen and $R_9$ is Formula IX shown below:

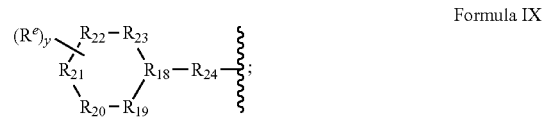

Formula IX or $R_8$ is Formula IX and $R_9$ is hydrogen. In some embodiments, y in Formula IX is 0, $R_{19}$, $R_{20}$, $R_{21}$, $R_{22}$, or $R_{23}$ is O, and all of the bonds between adjacent $R_{18}$ to $R_{23}$ are single. In some embodiments, y in Formula IX is 0, $R_{19}$ is O, and all of the bonds between adjacent $R_{18}$ to $R_{23}$ are single. In some embodiments, y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments, y in Formula IX is 1, $R^e$ is Formula XIII, wherein $R_8$ is hydrogen and $R_9$ is Formula VII or Formula VIII shown below:

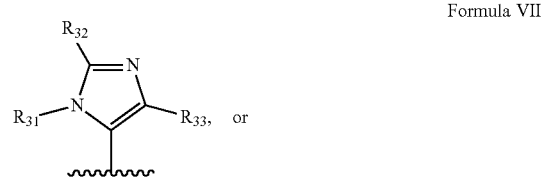

Formula VII

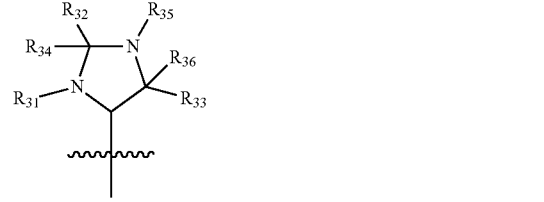

Formula VIII wherein $R_{31}$, $R_{32}$, $R_{33}$, $R_{34}$, $R_{35}$, and $R_{36}$ are, independently, hydrogen, U. $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency.

In some embodiments $R_{31}$ of Formula VII is alkyl. In some embodiments, $R_{31}$ is methyl.

In some embodiments $R_{31}$ of Formula VII is methyl, $R_{32}$ and $R_{33}$ are hydrogen.

In some embodiments, y in Formula IX is 1 and $R^e$ is hydroxyl bonded at the position para- to the methylene group.

In some embodiments of Formula XII, k is 1 and $R^c$ is hydroxyl.

In some embodiments of Formula XII, k is 1, $R^c$ is hydroxyl, and $X_d$ is absent.

In some embodiments of Formula XII, k is 1, $R^c$ is hydroxyl, $X_d$ is absent, and $R_{10}$-$R_{17}$ are hydrogen.

In some embodiments of Formula XII, $R^c$ is alkoxy.

In some embodiments of Formula XII, $R^c$ is methoxy and $X_d$ is O.

In some embodiments of Formula XII, $R^c$ is methoxy, $X_d$ is O, and $R_{10}$-$R_{17}$ are hydrogen.

In some embodiments of Formula XII, k is 2 and $R^c$ is alkylamino.

In some embodiments of Formula XII, k is 2, $R^c$ is methylamino, and $X_d$ is absent.

In some embodiments of Formula XII, k is 2, $R^c$ is methylamino, $X_d$ is absent, and $R_{10}$-$R_{17}$ are hydrogen.

In some embodiments of Formula XII, k is 3, $X_d$ is O and $R^c$ is Formula XIII shown below:

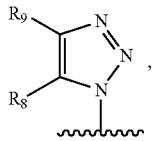

Formula XIII wherein $R_8$ and $R_9$ are alkyl.

In some embodiments of Formula XII, k is 3, $X_4$ is O, and $R^c$ is Formula XIII, wherein $R_8$ and $R_9$ are methyl.

In some embodiments of Formula XII, k is 3, $X_4$ is O and $R_c$ is Formula XIII, wherein $R_8$ is hydrogen, and $R_9$ is carbonyl, or $R_8$ is carbonyl, and $R_9$ is hydrogen.

In some embodiments of Formula XII, k is 3, $X_4$ is O and $R_c$ is Formula XIII, wherein $R_8$ is hydrogen, and $R_9$ is acetyl, or $R_8$ is acetyl, and $R_9$ is hydrogen.

In some embodiments of Formula XII, k is 3 and $R_c$ is Formula XIII, $R_8$ is hydrogen, and $R_9$ is Formula IX shown below:

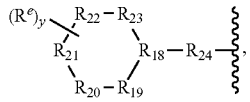

Formula IX or $R_8$ is hydrogen and $R_9$ is Formula IX.

In some embodiments of Formula XII, k is 3 and $R_c$ is Formula XIII, wherein $R_8$ is hydrogen, and $R_9$ is Formula IX, or $R_8$ is hydrogen and $R_9$ is Formula IX, wherein y in Formula IX is 2, $R_{18}$ is N, $R_{19}$, $R_{20}$, $R_{21}$, $R_{22}$, or $R_{23}$ is S, both $R_e$ are oxo and are bonded to the S, and all of the bonds between adjacent $R_{18}$ to $R_{23}$ are single.

In some embodiments of Formula XII, k is 3 and $R_c$ is Formula XIII, wherein $R_8$ is hydrogen, and $R_9$ is Formula IX, or $R_8$ is hydrogen and $R_9$ is Formula IX, wherein y in Formula IX is 2, both $R_e$ are oxo and are bonded to $R_{21}$, $R_{18}$ is N, $R_{21}$ is S, and all of the bonds between adjacent $R_{18}$ to $R_{23}$ are single.

In some embodiments of Formula XII, k is 3 and $R_c$ is Formula XIII, wherein $R_8$ is hydrogen, and $R_9$ is Formula IX, or $R_8$ is hydrogen and $R_9$ is Formula IX, wherein y in Formula IX is 2, both $R_e$ are oxo and are bonded to $R_{21}$, $R_{18}$ is N, $R_{21}$ is S, and all of the bonds between adjacent $R_{18}$ to $R_{23}$ are single, $X_b$ is absent, q is 0, p is 1, and each $R_{25}$ is hydrogen.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino, and three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is amino and is bonded to $R_{21}$, and three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 0, $R_{19}$, $R_{20}$, $R_{21}$, $R_{22}$, or $R_{23}$ is O, and all of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 0, $R_{19}$ is O, and all of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 0, $R_{19}$ is O, all of the bonds between adjacent $R_{18}$ to $R_{23}$ are single, $X_b$ is oxygen, p is 1, q is 0 and each $R_{25}$ is hydrogen.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy and is bonded to $R_{19}$, $R_{20}$, $R_{21}$, $R_{21}$, $R_{22}$, or $R_{23}$, three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy and is bonded to $R_{19}$, three of the bonds between adjacent $R_{18}$ to $R_{23}$ are double and three of the bonds between adjacent $R_{18}$ to $R_{23}$ are single.

In some embodiments of Formula XII, k is 3 and $R^c$ is Formula XIII, wherein $R_8$ is hydrogen, and $R_9$ is Formula IX, or $R_8$ is hydrogen and $R_9$ is Formula IX, wherein y in Formula IX is 1, $R^e$ is alkoxy such as methoxy, and is bonded to $R_{19}$, $R_{18}$ to $R_{23}$ are carbon atoms, three of the bonds between adjacent $R_{18}$ to $R_{23}$ are double and three of the bonds between adjacent $R_{18}$ to $R_{23}$ are single, $X_b$ is absent, p is 0 and q is 0.

In some embodiments, y in Formula XIV is 0, $R_{19}$, $R_{20}$, $R_{21}$, $R_{21}$, or $R_{22}$ is O, and, as valency permits, two of the bonds between adjacent $R_{18}$ to $R_{22}$ are double bonds, and three of the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, the bonds between $R_{18}$ and $R_{22}$, and between $R_{20}$ and $R_{21}$, are double bonds, and the rest of the bonds in the ring are single bonds.

In some embodiments, y in Formula XIV is 0, $R_{19}$ is O, $R_{18}$, $R_{20}$, $R_{21}$ and $R_{22}$ are C, the bonds between $R_{18}$ and $R_{22}$, and between $R_{20}$ and $R_{21}$, are double bonds, the rest of the bonds in the ring are single bonds, $X_b$ is absent, p is 1, q is 0, and each $R_{25}$ is hydrogen.

In some embodiments, y in Formula XIV is 0, $R_{19}$, $R_{20}$, $R_{21}$, or $R_{22}$ is O, and, the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, and the bonds between adjacent $R_{18}$ to $R_{22}$ are single bonds.

In some embodiments, y in Formula XIV is 0, $R_{19}$ is O, $R_{18}$, $R_{20}$, $R_{21}$ and $R_{22}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$ and $R_{22}$ are O, and the bonds between adjacent $R_{18}$ to $R_{22}$ are single bonds.

In some embodiments, y in Formula XIV is 0, $R_{19}$ and $R_{22}$ are O, $R_{18}$, $R_{20}$ and $R_{21}$ are C, the bonds between adjacent $R_{18}$ to $R_{22}$ are single bonds.

In some embodiments, y in Formula XIV is 0, $R_{19}$ and $R_{22}$ are O, $R_{18}$, $R_{20}$ and $R_{21}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$, $R_{20}$, $R_{21}$, $R_{21}$, or $R_{22}$ is N, and, as valency permits, two of the bonds between adjacent $R_{18}$ to $R_{22}$ are double bonds, and three of the bonds between adjacent $R_{18}$ to $R_{22}$ are single bonds.

In some embodiments, y in Formula XIV is 0, $R_{19}$ is N, $R_{18}$, $R_{20}$, $R_{21}$ and $R_{22}$ are C, the bonds between $R_{18}$ and $R_{22}$, and between $R_{20}$ and $R_{21}$, are double bonds, and the rest of the bonds in the ring are single bonds.

In some embodiments, y in Formula XIV is 0, $R_{19}$ is N, $R_{18}$, $R_{20}$, $R_{21}$ and $R_{22}$ are C, the bonds between $R_{18}$ and $R_{22}$, and between $R_{20}$ and $R_{21}$, are double bonds, the rest of the bonds in the ring are single bonds, $X_b$ is absent, p is 1, q is 0, and each $R_{25}$ is hydrogen.

In some embodiments, y in Formula XIV is 0, $R_{19}$, $R_{20}$, $R_{21}$, or $R_{22}$ is N, and, the bonds between adjacent $R_{18}$ to $R_{22}$ are single bonds.

In some embodiments, y in Formula XIV is 0, $R_{19}$ is N, $R_{18}$, $R_{20}$, $R_{21}$ and $R_{22}$ are C, and the bonds between adjacent $R_{18}$ to $R_{22}$ are single bonds.

In some embodiments, y in Formula XIV is 0, $R_{19}$ is N, $R_{18}$, $R_{20}$, $R_{21}$ and $R_{22}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$ and $R_{22}$ are N, and the bonds between adjacent $R_{18}$ to $R_{22}$ are single bonds.

In some embodiments, y in Formula XIV is 0, $R_{19}$ and $R_{22}$ are N, $R_{18}$, $R_{20}$ and $R_{21}$ are C, the bonds between adjacent $R_{18}$ to $R_{22}$ are single bonds.

In some embodiments, y in Formula XIV is 0, $R_{19}$ and $R_{22}$ are N, $R_{18}$, $R_{20}$ and $R_{21}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$, $R_{20}$, $R_{21}$, $R_{21}$, or $R_{22}$ is S, and, as valency permits, two of the bonds between adjacent $R_{18}$ to $R_{22}$ are double bonds, and three of the bonds between adjacent $R_{18}$ to $R_{22}$ are single bonds.

In some embodiments, y in Formula XIV is 0, $R_{19}$ is S, $R_{18}$, $R_{20}$, $R_{21}$ and $R_{22}$ are C, the bonds between $R_{18}$ and $R_{22}$, and between $R_{20}$ and $R_{21}$, are double bonds, and the rest of the bonds in the ring are single bonds.

In some embodiments, y in Formula XIV is 0, $R_{19}$ is S, $R_{18}$, $R_{20}$, $R_{21}$ and $R_{22}$ are C, the bonds between $R_{18}$ and $R_{22}$, and between $R_{20}$ and $R_{21}$, are double bonds, the rest of the bonds in the ring are single bonds, $X_b$ is absent, p is 1, q is 0, and each $R_{25}$ is hydrogen.

In some embodiments, y in Formula XIV is 0, $R_{19}$, $R_{20}$, $R_{21}$, or $R_{22}$ is S, and, the bonds between adjacent $R_{18}$ to $R_{22}$ are single bonds.

In some embodiments, y in Formula XIV is 0, $R_{19}$ is S, $R_{18}$, $R_{20}$, $R_{21}$ and $R_{22}$ are C, and the bonds between adjacent $R_{18}$ to $R_{22}$ are single bonds.

In some embodiments, y in Formula XIV is 0, $R_{19}$ is S, $R_{18}$, $R_{20}$, $R_{21}$ and $R_{22}$ are C, the bonds between adjacent $R_{18}$ to $R_{22}$ are single bonds, $X_b$ is absent, p is 1, q is 0, and each $R_{25}$ is hydrogen.

In some embodiments, y in Formula XIV is 0, $R_{19}$ and $R_{22}$ are S, and the bonds between adjacent $R_{18}$ to $R_{22}$ are single bonds.

In some embodiments, y in Formula XIV is 0, $R_{19}$ and $R_{22}$ are S, $R_{18}$, $R_{20}$ and $R_{21}$ are C, the bonds between adjacent $R_{18}$ to $R_{22}$ are single bonds.

In some embodiments, y in Formula XIV is 0, $R_{19}$ and $R_{22}$ are S, $R_{18}$, $R_{20}$ and $R_{21}$ are C, the bonds between adjacent $R_{18}$ to $R_{22}$ are single bonds, $X_b$ is absent, p is 1, q is 0, and each $R_{25}$ is hydrogen.

In some embodiments $R_{37}$ of Formula XV is Si, and $X_g$ is alkynyl.

In some embodiments $R_{37}$ of Formula XV is Si, $X_g$ is ethynyl, and $R_{38}$ is alkylene.

In some embodiments $R_{37}$ of Formula XV is Si, $X_g$ is ethynyl, $R_{38}$ is methylene, and $R_{39}$, $R_{40}$, and $R_{41}$ are alkyl.

In some embodiments $R_{37}$ of Formula XV is Si, $X_g$ is ethynyl, $R_{38}$ is methylene, and $R_{39}$, $R_{40}$, and $R_{41}$ are methyl.

Modified alginates can be either singularly modified alginate polymers or multiply modified alginate polymers. Singularly modified alginate polymers are alginate polymers that contain one or more covalently modified monomers, wherein substantially all of the covalently modified monomers possess the same covalent modification (i.e. the polymer contains one 'type' or species of covalently modified monomer). Multiply modified alginate polymers are alginate polymers that contain covalently modified monomers, wherein substantially all of the covalently modified monomers do not possess the same covalent modification (i.e. the polymer contains two or more 'types' or species of covalently modified monomers).

In some embodiments, the modified alginate polymer is a singularly modified alginate polymer. In some embodiments, the modified alginate polymer is one of the singularly modified alginate polymers shown below:

O11
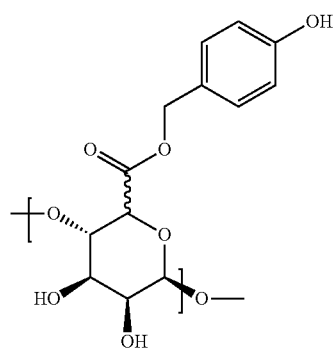
N8
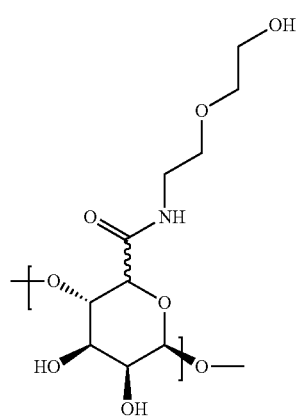
N7
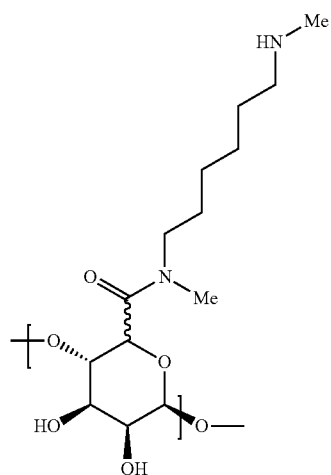
O6
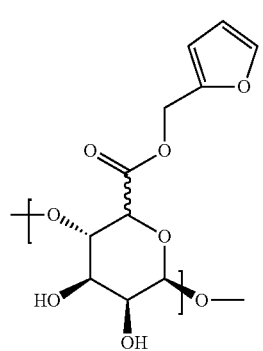
O3
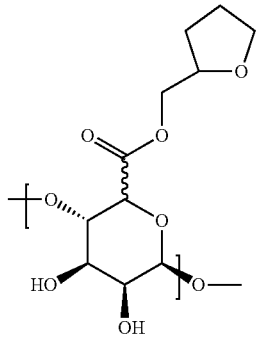
O9
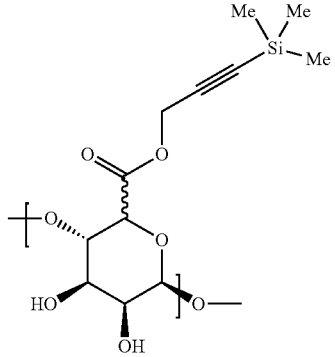
Z2-Y12
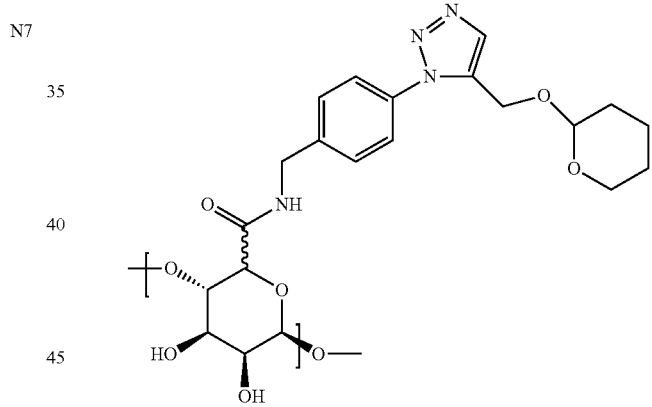
Z1-Y19
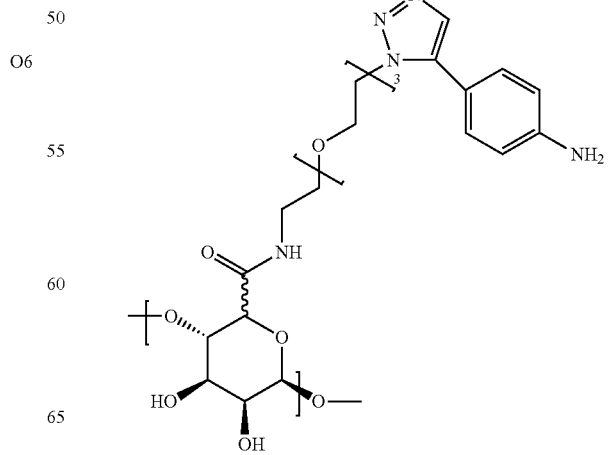

151

-continued

Z1-Y15

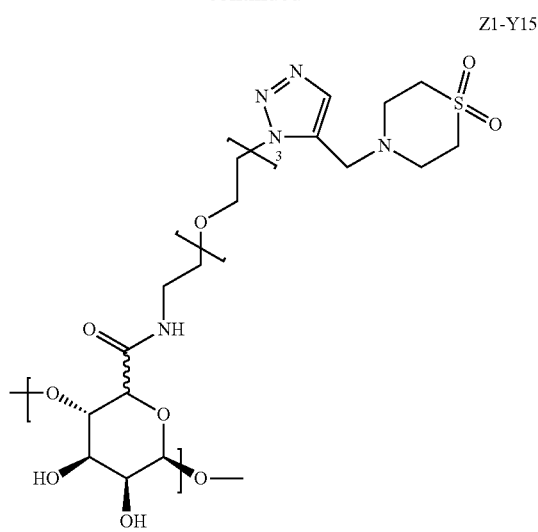

Z2-Y3

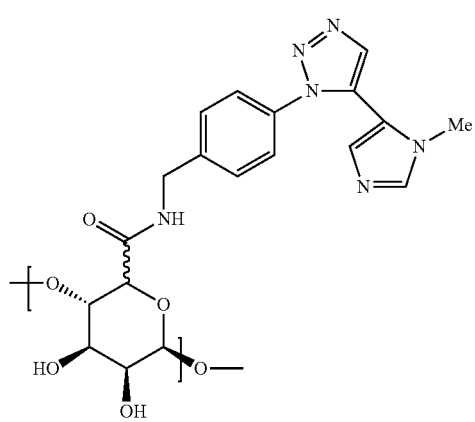

Z1-Y3

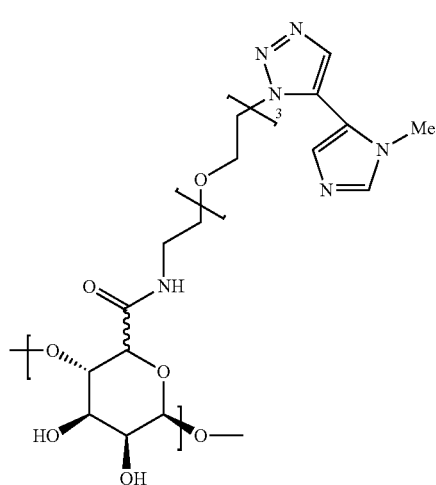

152

-continued

Z1-Y2

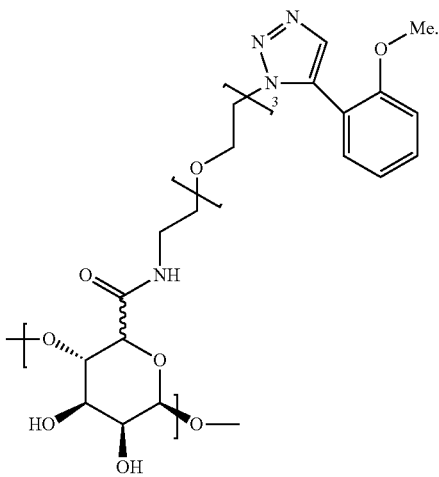

In preferred embodiments, the modified alginate polymer is a multiply modified alginate polymer possessing a polysaccharide backbone containing mannuronate monomers, guluronate monomers, a first species or type of covalently modified monomer defined by Formula I, and a second species or type of covalently modified monomer defined by Formula I. In some embodiments, the modified alginate polymer is one of the multiply modified alginate polymers shown below.

PF_N263_A7

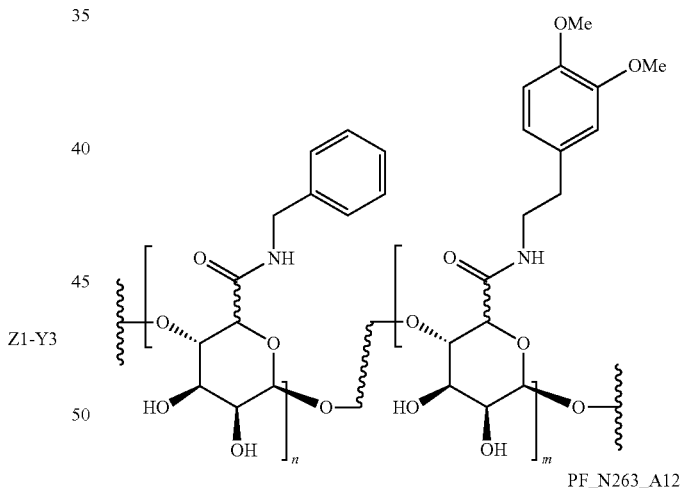

PF_N263_A12

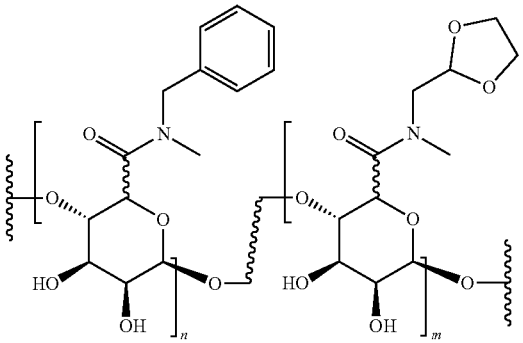

-continued
PF_N263_C6
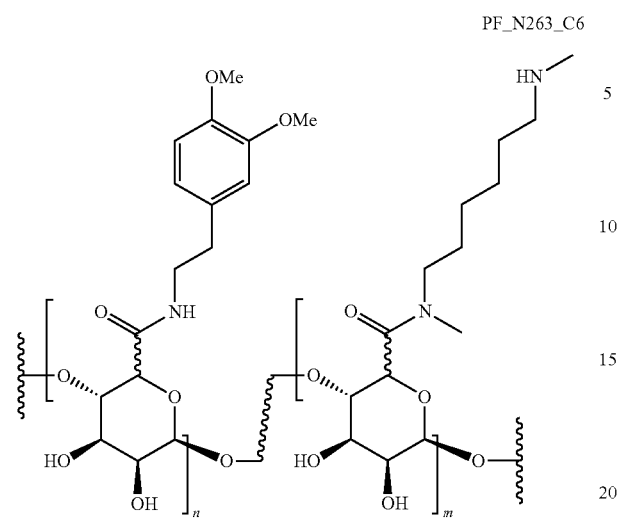
PF_N263_C12
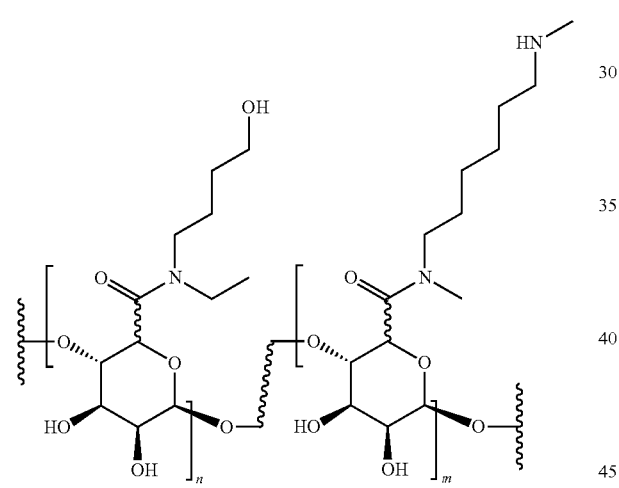
PF_N287_A4
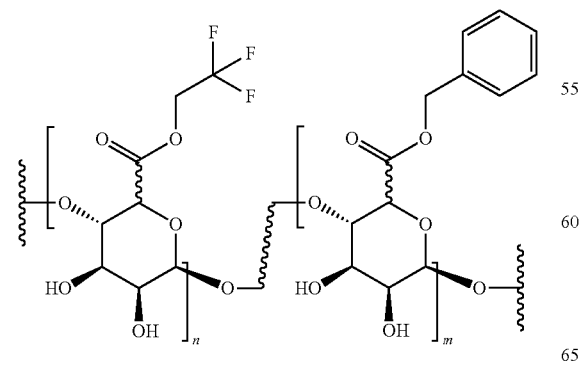
-continued
PF_N287_B1
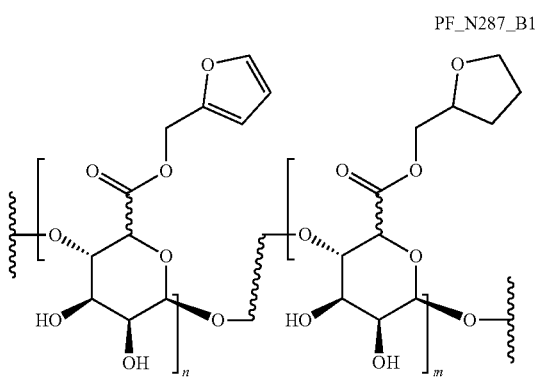
PF_N287_B3
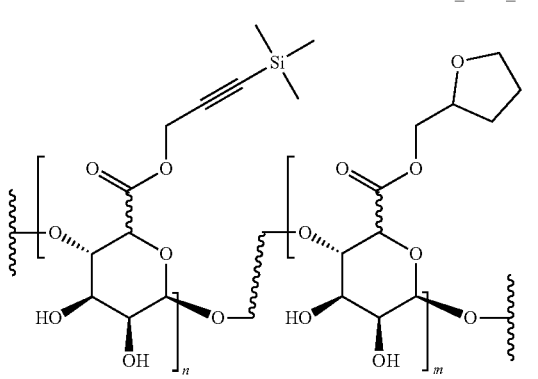
PF_N287_D3
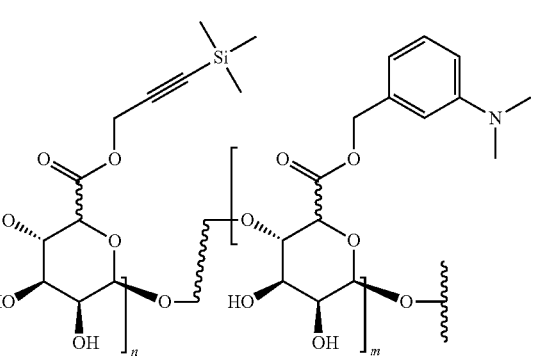
PF_N263_E1
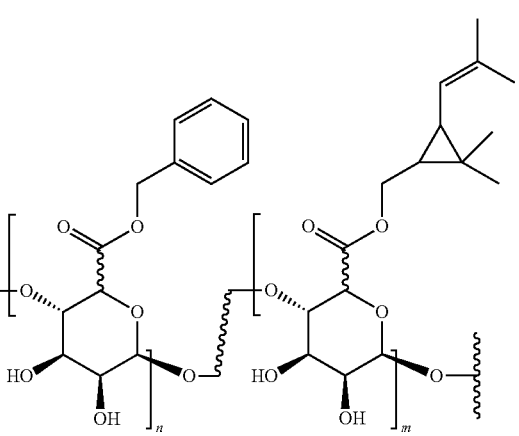

-continued
PF_N287_G5
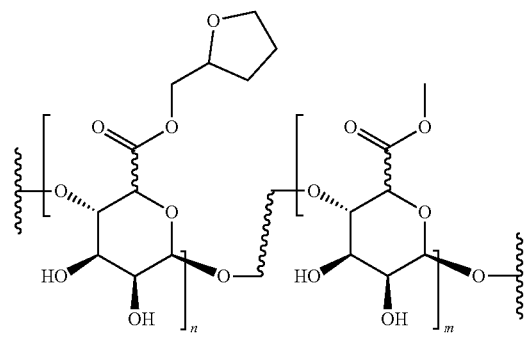
PF_N287_F4
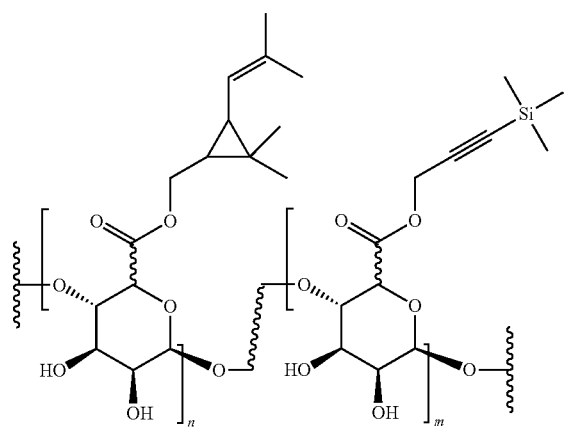
PF_N287_B_A3
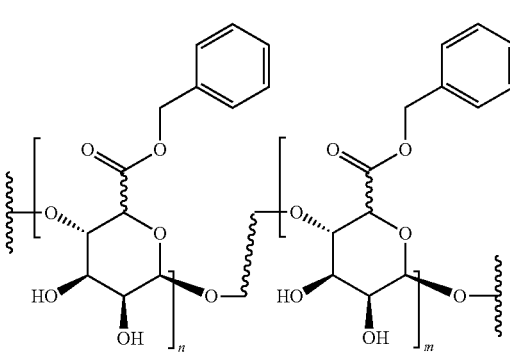
PF_N287_B_B10
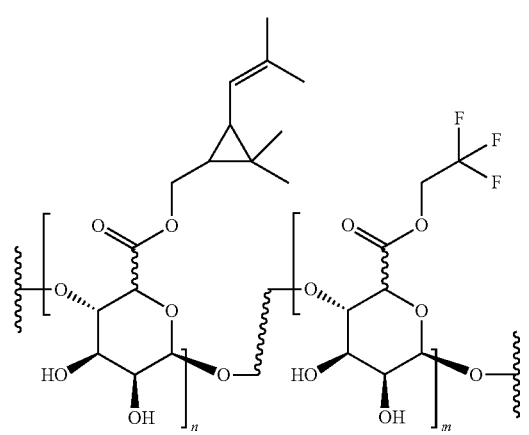
-continued
PF_N287_B_B4
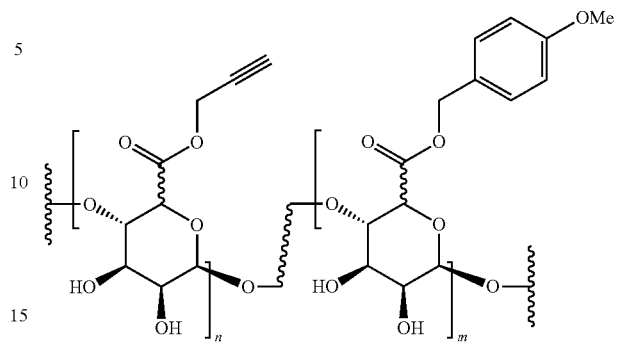
PF_N287_B_B5
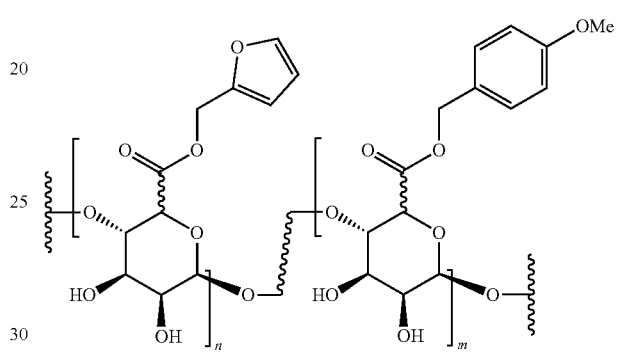
PF_N287_B_B8
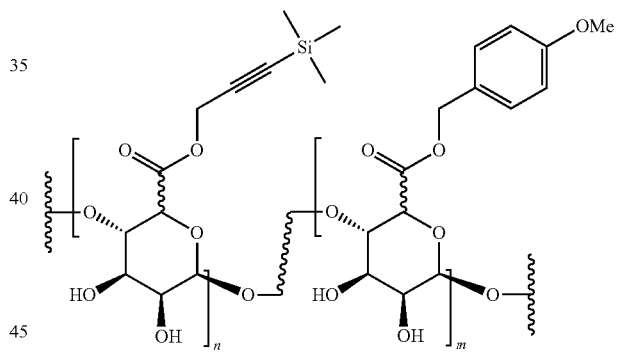
PF_N287_B_C5
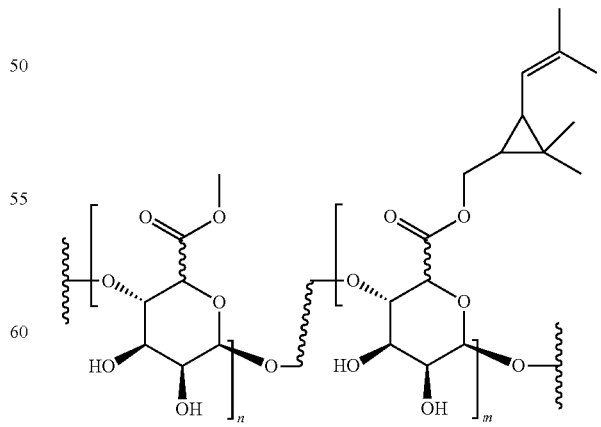

157
-continued
PF_N287_B_C10
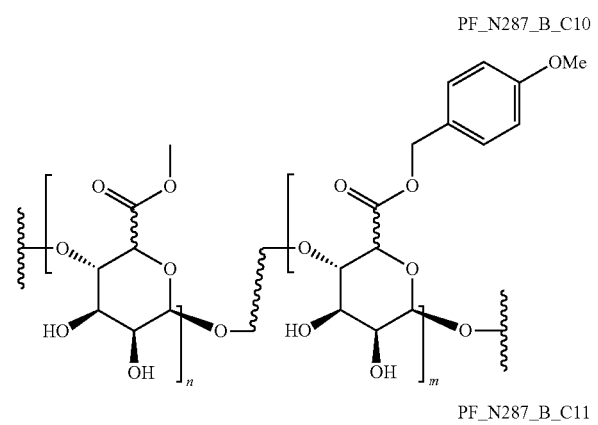
PF_N287_B_C11
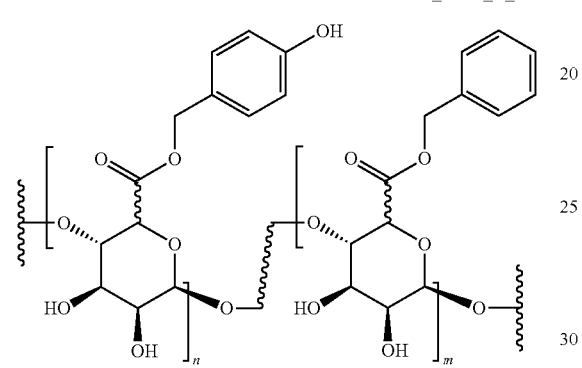
PF_N327_A8
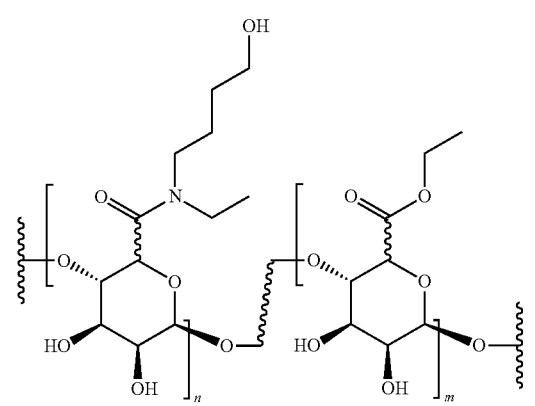
PF_N327_B8
158
-continued
PF_N327_B10
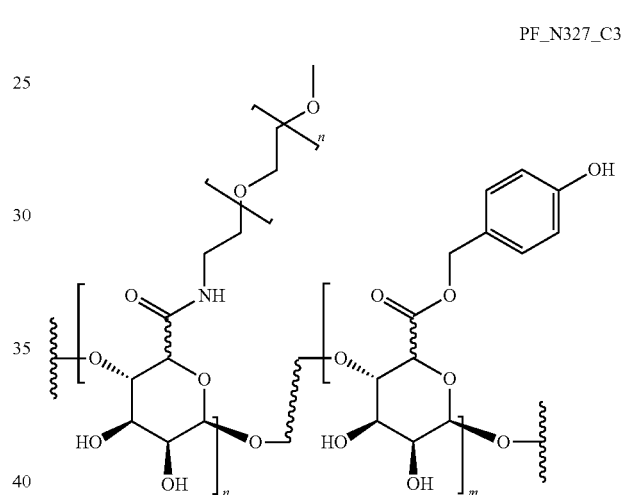
PF_N327_C3
PF_N327_D10
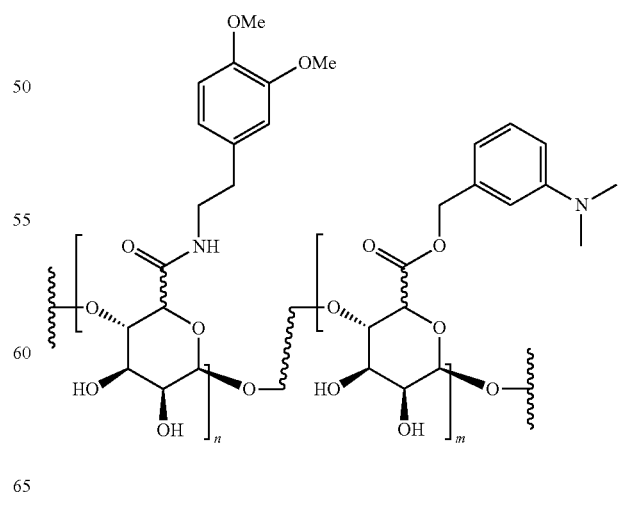
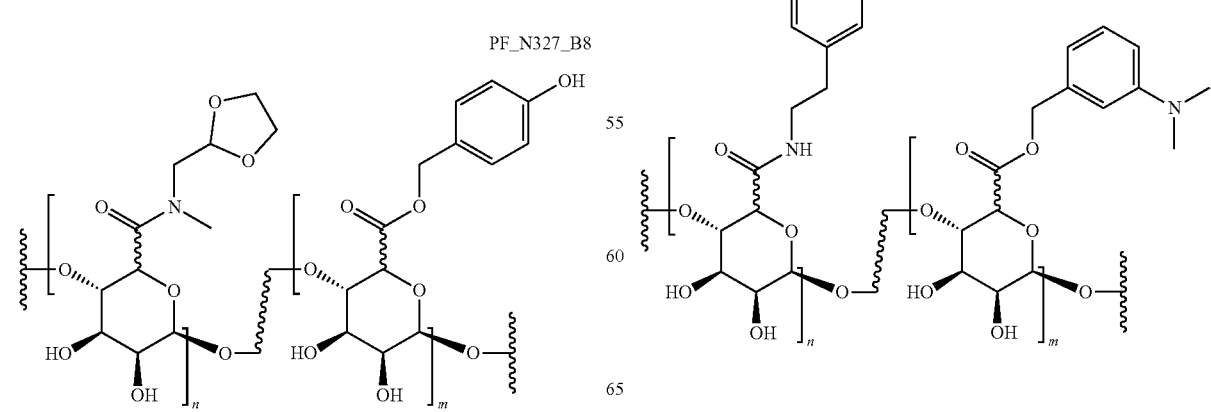

-continued
PF_N287_E3
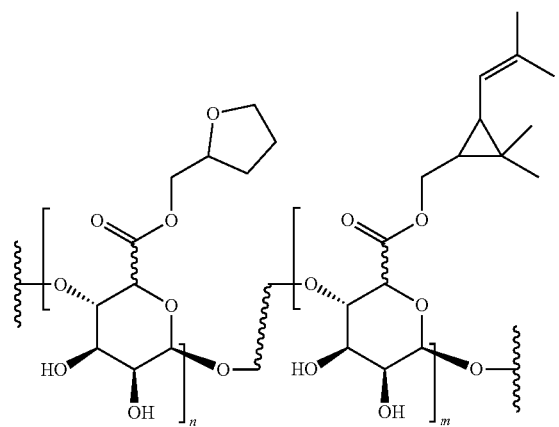
PF_N287_E4
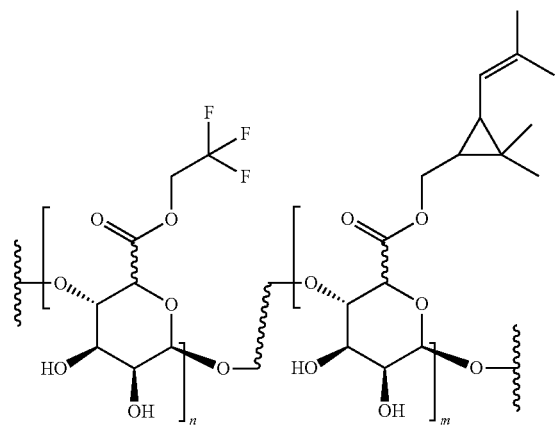
PF_N287_F2
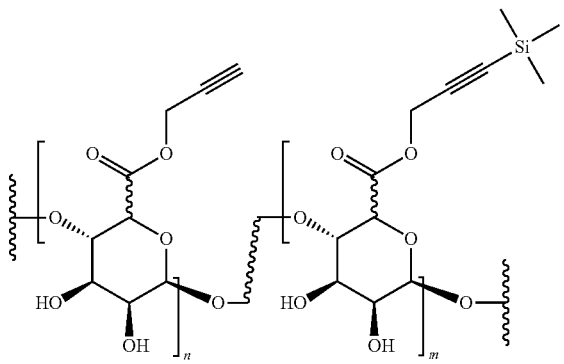
-continued
N9-Z1-Y16
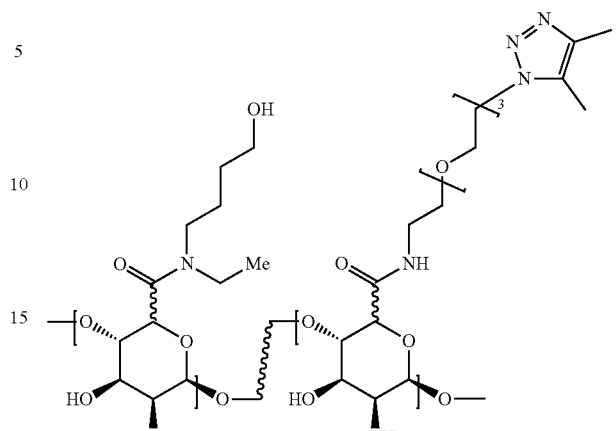
N6-Z1-Y18
N2-Z2-Y6
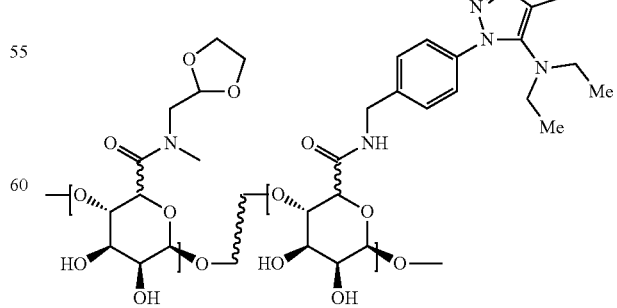

N9-Z1-Y18

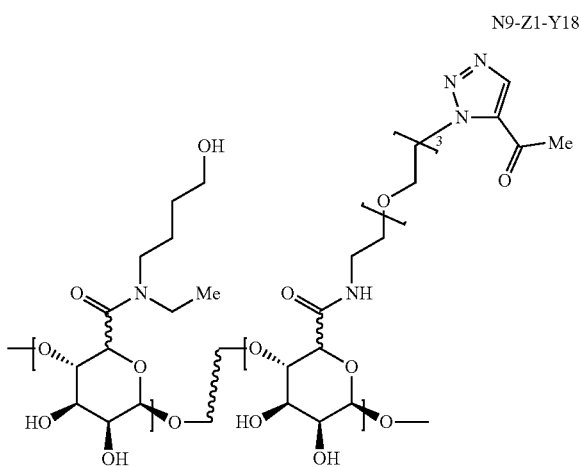

In some embodiments, multiply modified alginates are alginate polymers that contain one or more covalently modified monomers having a structure according to Formula III, Formula IIIa, Formula IIIb, or a combination of Formula IIIa and Formula IIIb Formula III Formula IIIa

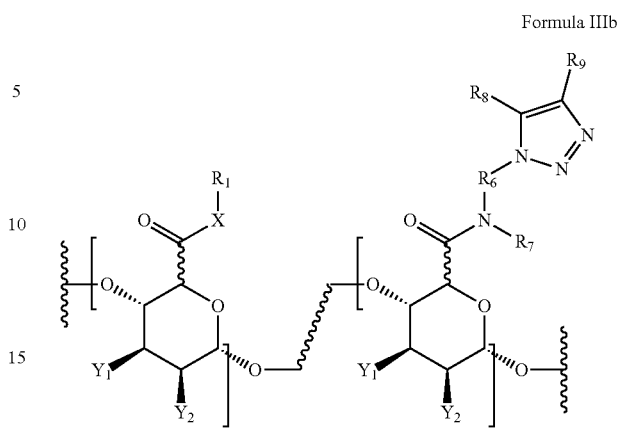

Formula IIIb wherein, for Formula III, Formula IIIa or Formula IIIb,

X is oxygen, sulfur, or $NR_4$;

$R_1$; $R_6$, $R_7$, $R_8$, and $R_9$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$;

wherein $Y_1$ and $Y_2$ independently are hydrogen or —$PO(OR_5)_2$; or $Y_2$ is absent, and $Y_1$, together with the two oxygen atoms to which $Y_1$ and $Y_2$ are attached form a cyclic structure as shown in Formula IV, Formula IVa, Formula IVb, or a combination of Formula IVa and Formula IVb Formula IV Formula IVa or -continued Formula IVb

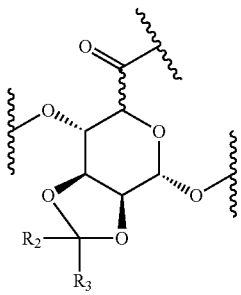

wherein, for Formula IV, Formula IVa and Formula IVb $R_2$ and $R_3$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_2$ and $R_3$ groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and $R_4$ and $R_5$ are, independently, hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_4$ and $R_5$ groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, $R_8$, $R_9$, or both are, independently, hydrogen,

Formula VII

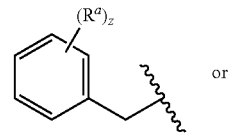

Formula VIII

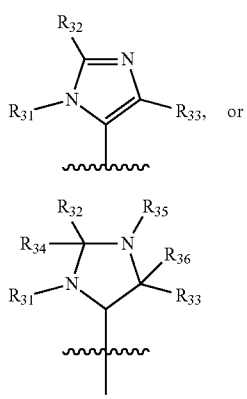

wherein $R_{31}$, $R_{32}$, $R_{33}$, $R_{34}$, $R_{35}$, and $R_{36}$ are, independently, hydrogen, U. $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency.

In some embodiments, R is (A)

Formula X

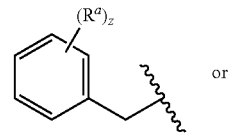

or

Formula XII

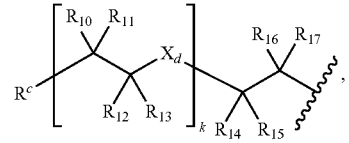

wherein k is independently an integer from 1 to 30; wherein z is an integer from 0 to 4; wherein $X_4$ is O or S; wherein $R_{10}$, $R_{11}$, $R_{12}$, $R_{13}$, $R_{14}$, $R_{15}$, $R_{16}$, and $R_{17}$ are independently hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$; and wherein $R^a$ and $R^c$ are independently $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic, heterocyclic ring or Formula XIII

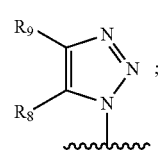

wherein $R_8$, $R_9$, or both are, independently, hydrogen,

Formula VII

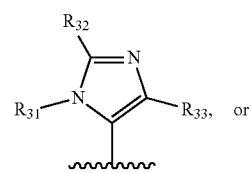

or

Formula VIII

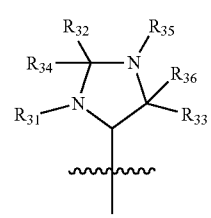

wherein $R_{31}$, $R_{32}$, $R_{33}$, $R_{34}$, $R_{35}$, and $R_{36}$ are, independently, hydrogen, U. $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency.

It should be understood that Formula III, Formula IIIa, and Formula IIIb also represent a singly modified alginate, such as when X is —$NR_7$ and $R_1$ is

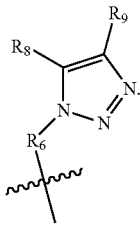

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_2$, $R_3$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_4$, $U_4+Q_1+Q_2$, $U_1+Q_1+Q_3$, $U_1+Q_1+Q_4$, $U_1+Q_2+Q_3$, $U_1+Q_2+Q_4$, $Q_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_1$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_3$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_4+Q_2+Q_3$, $U_4+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_2$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_4$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_3$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_5$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_4$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_4$, $R_6$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_5$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_4$, $R_5$, $R_7$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_6$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_4$, $R_5$, $R_6$, $R_8$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_7$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_4$, $R_5$, $R_6$, $R_7$, and $R_9$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_4+Q_2+Q_3$, $U_4+Q_2+Q_4$, $U_4+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_8$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginates are alginate polymers that contain one or more covalently modified alginates units described by Formula I, Formula Ia, Formula Ib, combinations of Formula Ia and Formula Ib, Formula II, Formula IIa, Formula IIb, combinations of Formula IIa and Formula IIb, Formula III, Formula IIIa, Formula IIIb, combinations of Formula IIIa and Formula IIIb, Formula IV, Formula IVa, Formula IVb or combinations of Formula IVa and Formula IVb, wherein for each formula $R_1$; $R_2$, $R_3$, $R_4$, $R_5$, $R_6$, $R_7$, and $R_8$ are independently hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; or $R_2$ and $R_3$, together with the carbon atom to which they are attached, form a 3- to 8-membered unsubstituted or substituted carbocyclic or heterocyclic ring; and wherein $R_9$ is not hydrogen or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative organic groupings being those present in $U_1$, $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, the modified alginate polymer is a singularly modified alginate polymer. In specific embodiments, the singularly modified alginate polymer contains one or more covalently modified monomers defined by Formula I, Formula Ia, Formula Ib, or combinations of Formula Ia and Formula Ib, wherein IQ includes an azide group, an alkyne group, or a 1,2,3-triazole ring. In certain embodiments, the singularly modified alginate polymer contains one or more covalently modified monomers defined by Formula I, Formula Ia, Formula Ib, or combinations of Formula Ia and Formula Ib, wherein X is not oxygen and IQ is not an unsubstituted $C_1$-$C_{18}$ alkyl group, polyethylene glycol) chain, or cholesteryl moiety. In certain additional embodiments, the singularly modified alginate polymer contains one or more covalently modified monomers defined by Formula I, Formula Ia, Formula Ib, or combinations of Formula Ia and Formula Ib, wherein X is not $NR_4$ and R is not a substituted or unsubstituted $C_1$-$C_6$ alkyl group, or a poly(ethylene glycol) chain.

In alternative embodiments, the modified alginate polymer is a multiply modified alginate polymer. In preferred embodiments, the multiply modified alginate polymer possesses a polysaccharide backbone containing mannuronate monomers, guluronate monomers, a first species or type of covalently modified monomer defined by Formula I, Formula Ia, Formula Ib, or combinations of Formula Ia and Formula Ib, and a second species or type of covalently modified monomer defined by Formula I, Formula Ia, Formula Ib, or combinations of Formula Ia and Formula Ib. In other embodiments, the multiply modified alginate polymer possesses a polysaccharide backbone containing mannuronate monomers, guluronate monomers, and three or more different types of covalently modified monomers defined by Formula I, Formula Ia, Formula Ib, or combinations of Formula Ia and Formula Ib.

In some embodiments, the multiply modified alginate polymer contains two different species of covalently modified monomers defined by Formula I, Formula Ia, Formula Ib, or combinations of Formula Ia and Formula Ib, wherein in both species of monomer, X is $NR_4$. In other embodiments, the multiply modified alginate polymer contains two different species of covalently modified monomers defined by Formula I, Formula Ia, Formula Ib, or combinations of Formula Ia and Formula Ib, wherein in both species of monomer, X is oxygen. In further embodiments, the multiply modified alginate polymer contains two different species of covalently modified monomers defined by Formula I, Formula Ia, Formula Ib, or combinations of Formula Ia and Formula Ib, wherein in one species of monomer X is oxygen, and in the second species of monomer, X is $NR_4$.

In some embodiments, the multiply modified alginate polymer contains two different species of covalently modified monomers defined by Formula I, Formula Ia, Formula Ib, or combinations of Formula Ia and Formula Ib, wherein in at least one species of monomer, $R_4$ includes one or more cyclic moieties. In preferred embodiments, the multiply modified alginate polymer contains two different species of covalently modified monomers defined by Formula I, Formula Ia, Formula Ib, or combinations of Formula Ia and Formula Ib, wherein in at least one species of monomer, $R_4$ includes a phenyl ring, furan ring, oxolane ring, dioxolane ring, or a 1,2,3-triazole ring.

In certain embodiments, the multiply modified alginate polymer contains two different species of covalently modified monomers defined by Formula I, Formula Ia, Formula Ib, or combinations of Formula Ia and Formula Ib, wherein in at least one species of monomer, $R_4$ includes one or more halogen moieties, an azide group, or an alkyne.

In preferred embodiments, the multiply modified alginate polymer is one of the multiply modified alginate polymers shown below.

-continued
PF_N263_A7
PF_N263_A12
PF_N263_C6
PF_N263_C12
PF_N287_A4
PF_N287_B1
PF_N287_B3
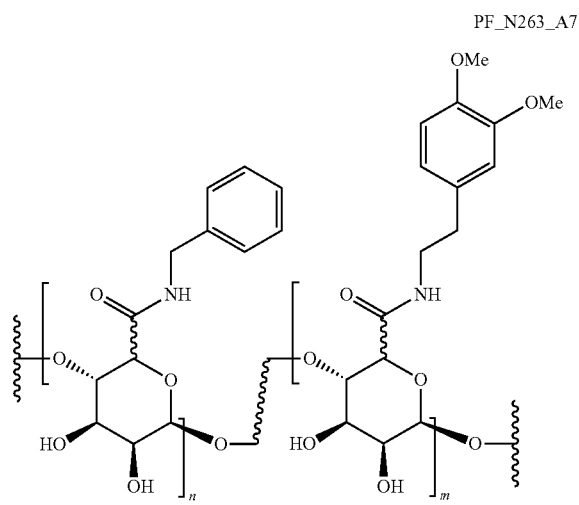

-continued
PF_N287_D3
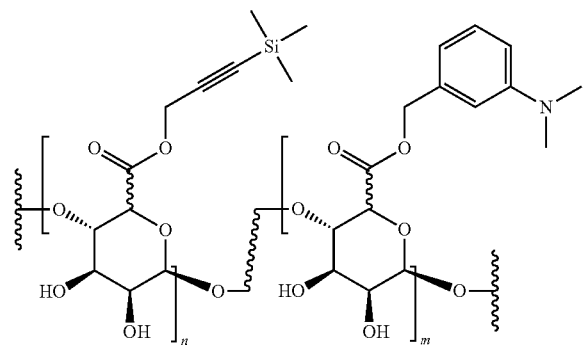
PF_N263_E1
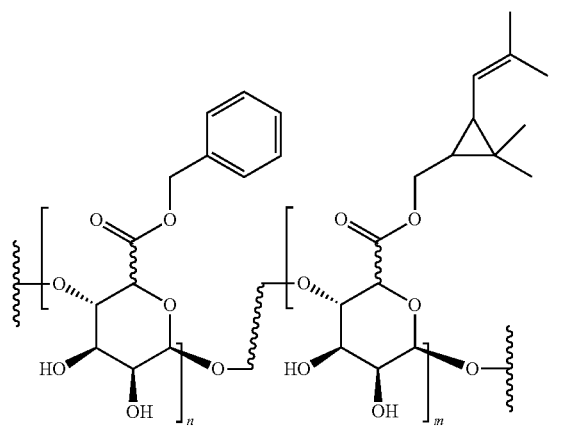
PF_N287_G5
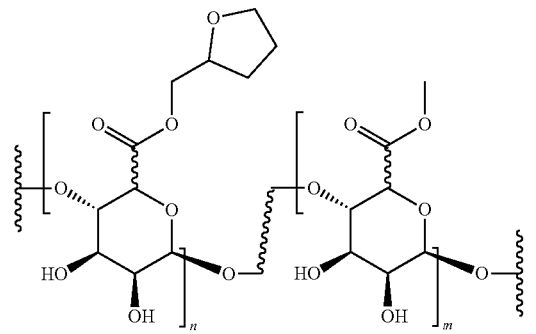
PF_N287_F4
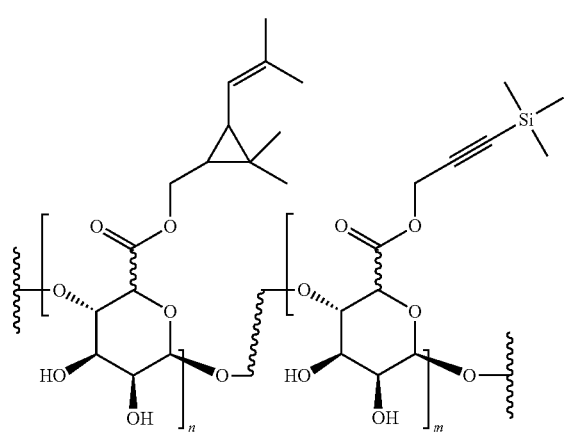
-continued
PF_N287_B_A3
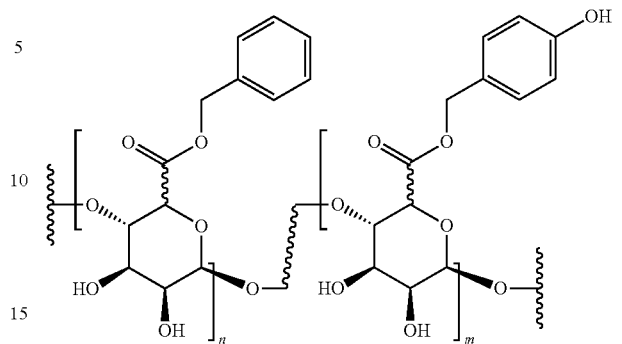
PF_N287_B_B10
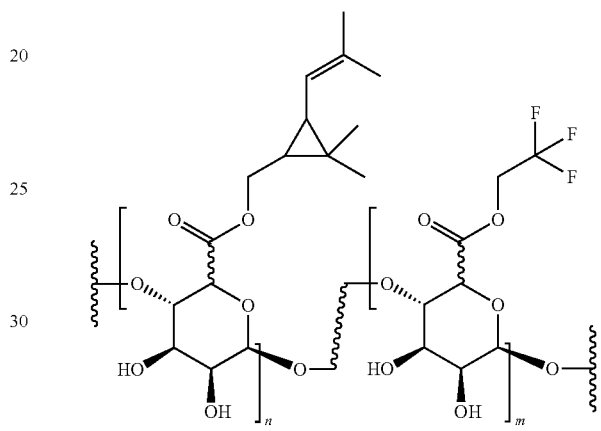
PF_N287_B_B4
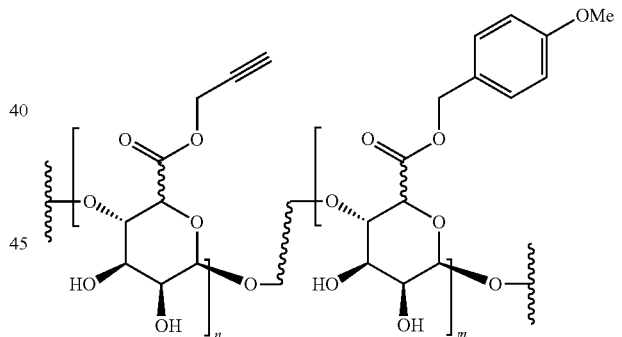
PF_N287_B_B5
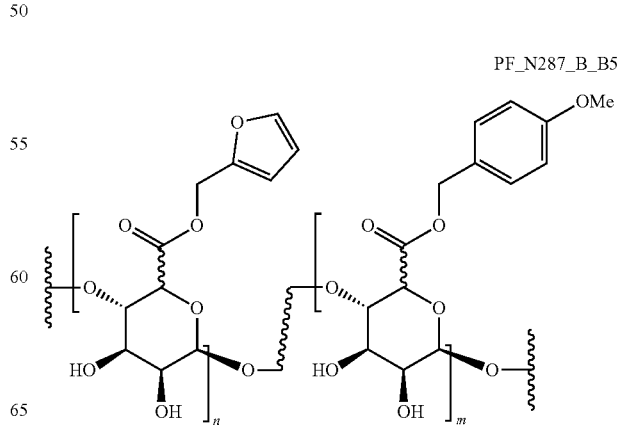

175
-continued
PF_N287_B_B8
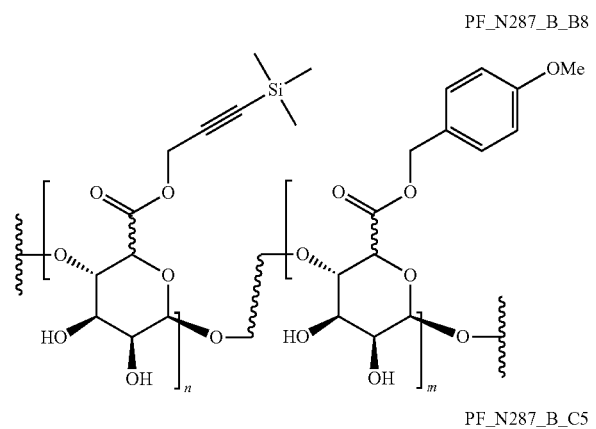
PF_N287_B_C5
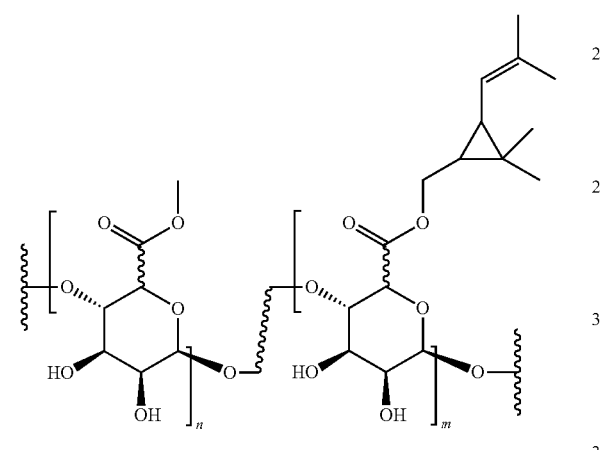
PF_N287_B_C10
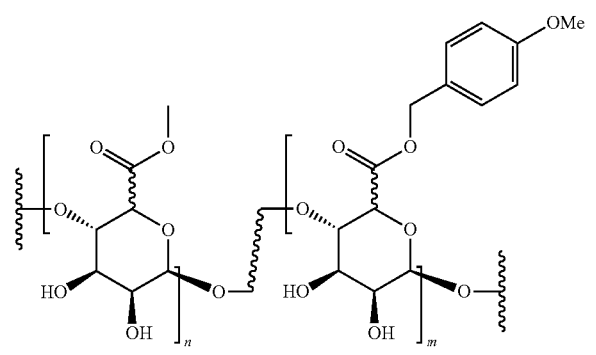
PF_N287_B_C11
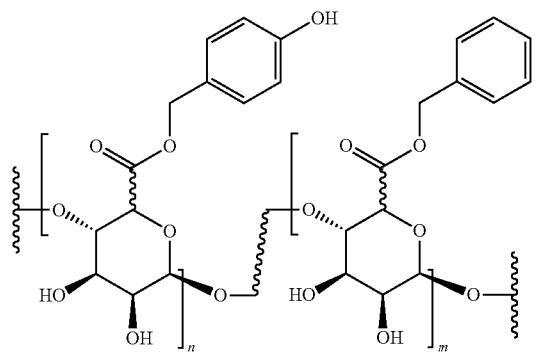
176
-continued
PF_N327_A8
PF_N327_B8
PF_N327_B10
PF_N327_C3
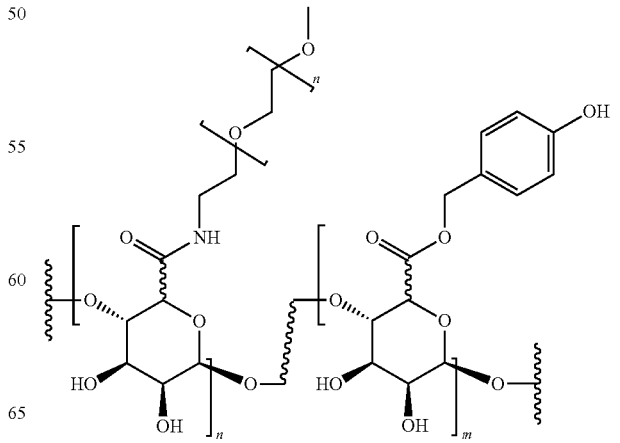

-continued

PF_N327_D10

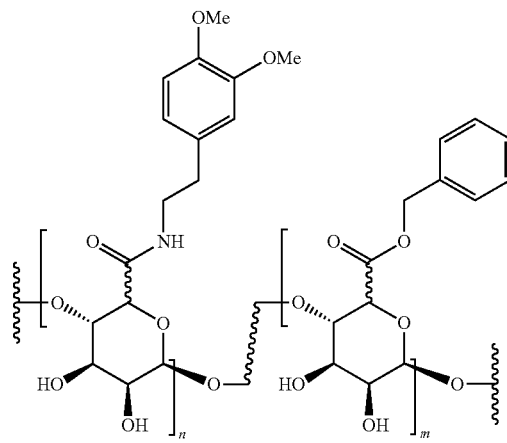

PF_N287_E3

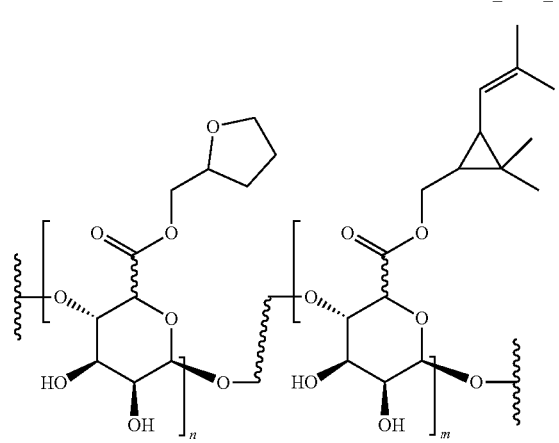

PF_N287_E4

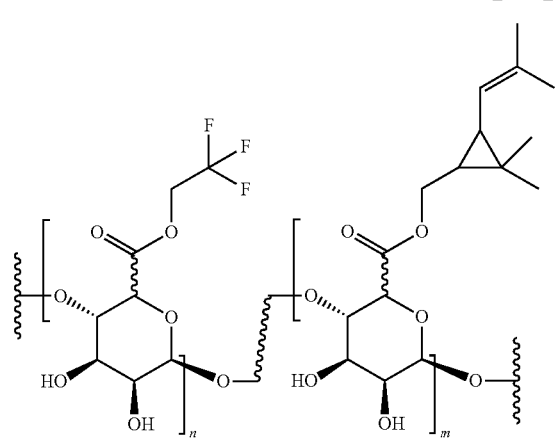

-continued

PF_N287_F2

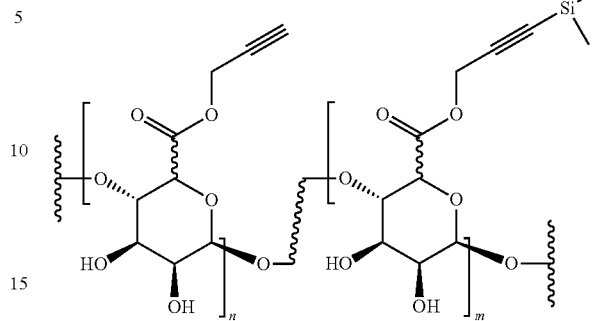

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or $J_1$.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_{10}$ alkyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkoxy, $C_1$-$C_9$ alkylamino, $C_1$-$C_9$ alkylthio, $C_1$-$C_8$ alkyl, $C_1$-$C_8$ alkoxy, $C_1$-$C_8$ alkylamino, $C_1$-$C_8$ alkylthio, $C_1$-$C_7$ alkyl, $C_1$-$C_7$ alkoxy, $C_1$-$C_7$ alkylamino, $C_1$-$C_7$ alkylthio, $C_1$-$C_6$ alkyl, $C_1$-$C_6$ alkoxy, $C_1$-$C_6$ alkylamino, $C_1$-$C_6$ alkylthio, $C_1$-$C_5$ alkyl, $C_1$-$C_5$ alkoxy, $C_1$-$C_5$ alkylamino, $C_1$-$C_5$ alkylthio, $C_1$-$C_4$ alkyl, $C_1$-$C_4$ alkoxy, $C_1$-$C_4$ alkylamino, $C_1$-$C_4$ alkylthio, $C_1$-$C_3$ alkyl, $C_1$-$C_3$ alkoxy, $C_1$-$C_3$ alkylamino, $C_1$-$C_3$ alkylthio, $C_1$-$C_2$ alkyl, $C_1$-$C_2$ alkoxy, $C_1$-$C_2$ alkylamino, $C_1$-$C_2$ alkylthio, $C_{10}$ alkyl, $C_{10}$ alkoxy, $C_{10}$ alkylamino, $C_{10}$ alkylthio, $C_9$ alkyl, $C_9$ alkoxy, $C_9$ alkylamino, $C_9$ alkylthio, $C_8$ alkyl, $C_8$ alkoxy, $C_8$ alkylamino, $C_8$ alkylthio, $C_7$ alkyl, $C_7$ alkoxy, $C_7$ alkylamino, $C_7$ alkylthio, $C_6$ alkyl, $C_6$ alkoxy, $C_6$ alkylamino, $C_6$ alkylthio, $C_5$ alkyl, $C_5$ alkoxy, $C_5$ alkylamino, $C_5$ alkylthio, $C_4$ alkyl, $C_4$ alkoxy, $C_4$ alkylamino, $C_4$ alkylthio, $C_3$ alkyl, $C_3$ alkoxy, $C_3$ alkylamino, $C_3$ alkylthio, $C_2$ alkyl, $C_2$ alkoxy, $C_2$ alkylamino, $C_2$ alkylthio, $C_1$ alkyl, $C_4$ alkoxy, $C_4$ alkylamino, or $C_4$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_{10}$ alkyl, $C_1$-$C_{10}$ alkoxy, $C_1$-$C_{10}$ alkylamino, or $C_1$-$C_{10}$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_9$ alkyl, $C_1$-$C_9$ alkoxy, $C_1$-$C_9$ alkylamino, or $C_1$-$C_9$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_8$ alkyl, $C_1$-$C_8$ alkoxy, $C_1$-$C_8$ alkylamino, or $C_1$-$C_8$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_7$ alkyl, $C_1$-$C_7$ alkoxy, $C_1$-$C_7$ alkylamino, or $C_1$-$C_7$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_6$ alkyl, $C_1$-$C_6$ alkoxy, $C_1$-$C_6$ alkylamino, or $C_1$-$C_6$ alkylthio.

In some embodiments, $R_1$ through $R_{17}$, $R_{31}$ through $R_{36}$, $R^a$, $R^b$, $R^c$, and $R^d$ are independently hydrogen, amino, hydroxyl, thiol, oxo, phosphate, or substituted or unsubstituted $C_1$-$C_5$ alkyl, $C_1$-$C_5$ alkoxy, $C_1$-$C_5$ alkylamino, or $C_1$-$C_5$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_4$ alkyl, $C_1$-$C_4$ alkoxy, $C_1$-$C_4$ alkylamino, or $C_1$-$C_4$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_3$ alkyl, $C_1$-$C_3$ alkoxy, $C_1$-$C_3$ alkylamino, or $C_1$-$C_3$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$-$C_2$ alkyl, $C_1$-$C_2$ alkoxy, $C_1$-$C_2$ alkylamino, or $C_1$-$C_2$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_{10}$ alkyl, $C_{10}$ alkoxy, $C_{10}$ alkylamino, or $C_{10}$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_9$ alkyl, $C_0$ alkoxy, $C_0$ alkylamino, or $C_0$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_8$ alkyl, $C_8$ alkoxy, $C_8$ alkylamino, or $C_8$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_7$ alkyl, $C_7$ alkoxy, $C_7$ alkylamino, or $C_7$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_6$ alkyl, $C_6$ alkoxy, $C_6$ alkylamino, or $C_6$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_5$ alkyl, $C_5$ alkoxy, $C_5$ alkylamino, or $C_5$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_4$ alkyl, $C_4$ alkoxy, $C_4$ alkylamino, or $C_4$ alkylthio.

In some embodiments, $R_1$ through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_3$ alkyl, $C_3$ alkoxy, $C_3$ alkylamino, or $C_3$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_2$ alkyl, $C_2$ alkoxy, $C_2$ alkylamino, or $C_2$ alkylthio.

In some embodiments, R through $R_{17}$, $R_{31}$ through $R_{36}$, $R^a$, $R^b$, $R^c$, $R^d$, and $R^e$ are independently hydrogen, amino, hydroxyl, thiol, oxo, phosphate, or substituted or unsubstituted $C_1$ alkyl, $C_1$ alkoxy, $C_1$ alkylamino, or $C_1$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or h.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_{10}$ alkyl, $C_1$-$C_{10}$ alkoxy, $C_1$-$C_{10}$ alkylamino, $C_1$-$C_{10}$ alkylthio, $C_1$-$C_9$ alkyl, $C_1$-$C_9$ alkoxy, $C_1$-$C_9$ alkylamino, $C_1$-$C_9$ alkylthio, $C_1$-$C_8$ alkyl, $C_1$-$C_8$ alkoxy, $C_1$-$C_8$ alkylamino, $C_1$-$C_8$ alkylthio, $C_1$-$C_7$ alkyl, $C_1$-$C_7$ alkoxy, $C_1$-$C_7$ alkylamino, $C_1$-$C_7$ alkylthio, $C_1$-$C_6$ alkyl, Cr $C_6$ alkoxy, $C_1$-$C_6$ alkylamino, $C_1$-$C_6$ alkylthio, $C_1$-$C_5$ alkyl, $C_1$-$C_5$ alkoxy, $C_1$-$C_5$ alkylamino, $C_1$-$C_5$ alkylthio, $C_1$-$C_4$ alkyl, $C_1$-$C_4$ alkoxy, $C_1$-$C_4$ alkylamino, $C_1$-$C_4$ alkylthio, $C_1$-$C_3$ alkyl, $C_1$-$C_3$ alkoxy, $C_1$-$C_3$ alkylamino, $C_1$-$C_3$ alkylthio, $C_1$-$C_2$ alkyl, $C_1$-$C_2$ alkoxy, $C_1$-$C_2$ alkylamino, $C_1$-$C_2$ alkylthio, $C_{10}$ alkyl, $C_{10}$ alkoxy, $C_{10}$ alkylamino, $C_{10}$ alkylthio, $C_9$ alkyl, $C_9$ alkoxy, $C_9$ alkylamino, $C_9$ alkylthio, $C_8$ alkyl, $C_8$ alkoxy, $C_8$ alkylamino, $C_8$ alkylthio, $C_7$ alkyl, $C_7$ alkoxy, $C_7$ alkylamino, $C_7$ alkylthio, $C_6$ alkyl, $C_6$ alkoxy, $C_6$ alkylamino, $C_6$ alkylthio, $C_5$ alkyl, $C_5$ alkoxy, $C_5$ alkylamino, $C_5$ alkylthio, $C_4$ alkyl, $C_4$ alkoxy, $C_4$ alkylamino, $C_4$ alkylthio, $C_3$ alkyl, $C_3$ alkoxy, $C_3$ alkylamino, $C_3$ alkylthio, $C_2$ alkyl, $C_2$ alkoxy, $C_2$ alkylamino, $C_2$ alkylthio, $C_1$ alkyl, $C_1$ alkoxy, $C_1$ alkylamino, or $C_1$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_1$-$C_{10}$ alkyl, $C_1$-$C_{10}$ alkoxy, $C_1$-$C_{10}$ alkylamino, or $C_1$-$C_{10}$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_9$ alkyl, $C_1$-$C_9$ alkoxy, $C_1$-$C_9$ alkylamino, or $C_1$-$C_9$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_8$ alkyl, $C_1$-$C_8$ alkoxy, $C_1$-$C_8$ alkylamino, or $C_1$-$C_8$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_1$-$C_7$ alkyl, $C_1$-$C_7$ alkoxy, $C_1$-$C_7$ alkylamino, or $C_1$-$C_7$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_6$ alkyl, $C_1$-$C_6$ alkoxy, $C_1$-$C_6$ alkylamino, or $C_1$-$C_6$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_5$ alkyl, $C_1$-$C_5$ alkoxy, $C_1$-$C_5$ alkylamino, or $C_1$-$C_5$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_4$ alkyl, $C_1$-$C_4$ alkoxy, $C_1$-$C_4$ alkylamino, or $C_1$-$C_4$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_3$ alkyl, $C_1$-$C_3$ alkoxy, $C_1$-$C_3$ alkylamino, or $C_1$-$C_3$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted Cr $C_2$ alkyl, $C_1$-$C_2$ alkoxy, $C_1$-$C_2$ alkylamino, or $C_1$-$C_2$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_{10}$ alkyl, $C_{10}$ alkoxy, $C_{10}$ alkylamino, or $C_{10}$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_9$ alkyl, $C_9$ alkoxy, $C_9$ alkylamino, or $C_9$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_8$ alkyl, $C_8$ alkoxy, $C_8$ alkylamino, or $C_8$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_7$ alkyl, $C_7$ alkoxy, $C_7$ alkylamino, or $C_7$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_6$ alkyl, $C_6$ alkoxy, $C_6$ alkylamino, or $C_6$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_5$ alkyl, $C_5$ alkoxy, $C_5$ alkylamino, or $C_5$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_4$ alkyl, $C_4$ alkoxy, $C_4$ alkylamino, or $C_4$ alkylthio.

In some embodiments, $R_1$ through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_3$ alkyl, $C_3$ alkoxy, $C_3$ alkylamino, or $C_3$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_2$ alkyl, $C_2$ alkoxy, $C_2$ alkylamino, or $C_2$ alkylthio.

In some embodiments, R through $R_{17}$, $R_{31}$ through $R_{36}$, $R^a$, $R^b$, $R^c$, $R^d$, and $R^e$ are independently amino, hydroxyl, thiol, oxo, phosphate, or substituted or unsubstituted $C_1$ alkyl, $C_4$ alkoxy, $C_4$ alkylamino, or $C_4$ alkylthio.

In some embodiments, -A-B(—C)$_\delta$, —B(—C)$_\delta$, A, B, C, $R_1$; $R_4$, $R_6$, $R_8$, $R_9$, $R_{31}$, $R_{32}$, $R_{33}$, $R_{34}$, $R_{35}$, $R_{36}$, $R_{59}$, Reo, $R^a$, $R^e$, $R^d$, and $R^e$ are independently —$R_h$—($R_g$)$_j$—$R_f$, wherein $R_h$ is absent, $C(R_{59}R_{60})$, O, S, $SO_2$, $SO_3$, or $NR_{61}$; wherein each $R_g$ is independently absent (i.e., j is 0), $C(R_{42}R_{43})$, O, S, $SO_2$, $SO_3$, or $NR_{44}$; and wherein $R_f$ is hydrogen, $C(R_{45}R_{46}R_{47})$, OH, SH, $SO_2$, $SO_3$, $Si(R_{100}R_{101}R_{102})$, or $NR_{48}R_{49}R_{50}$;

wherein j is an integer from 0 to 30, wherein $R_{59}$, $R_{60}$, $R_{61}$, $R_{42}$, $R_{43}$, and $R_{44}$ are each independently, as valency permits, absent, hydrogen, =O, —$OR_{51}$, —$SR_{52}$, —$NR_{53}R_{54}R_{55}$, —$C(R_{56}R_{57}R_{58})$, or —$R_{hx}$—($R_{gx}$)$_{jx}$—$R_{fx}$, wherein $R_{45}$, $R_{46}$, $R_{47}$, $R_{48}$, $R_{49}$, $R_{50}$, $R_{51}$, $R_{52}$, $R_{53}$, $R_{54}$, $R_{55}$, $R_{56}$, $R_{57}$, and $R_{58}$ are each independently, as valency permits, absent, hydrogen, fluorine, —OH, =O, —SH, =NH, —$NH_2$, —$NH_3$, —$CH_3$, or —COOH, wherein $R_{100}$, $R_{101}$, and $R_{102}$ are each independently alkyl, phenyl, aryl, or $C_3$-$C_{20}$ cyclic, wherein the bond between $R_h$ and $R_g$, if present, is single, double, or triple depending on the valency, wherein the bond between $R_g$ and $R_f$, if present, is single, double, or triple depending on the valency, wherein the bond between each adjacent $R_g$ is single, double, or triple depending on the valency, wherein the bond between $R_h$ and $R_f$, if present, is single, double, or triple depending on the valency; wherein when $R_h$ is O, S, $SO_2$, or $SO_3$, the bond between $R_h$ and $R_g$ is not a double or triple bond; wherein when $R_h$ is $NR_{61}$, the bond between $R_h$ and $R_g$ is not a triple bond; wherein when $R_g$ is O, S, $SO_2$, or $SO_3$, the bond between $R_g$ and $R_h$ is not a double or triple bond; wherein when $R_h$ is $NR_{44}$, the bond between $R_g$ and $R_h$ is not a triple bond; wherein when $R_g$ is O, S, $SO_2$, or $SO_3$, the bond between $R_g$ and $R_f$ is not a double or triple bond; wherein when $R_g$ is $NR_{44}$, the bond between $R_g$ and $R_f$ is not a triple bond; wherein when $R_h$ is O, $R_g$ is not O, S, or $NR_{44}$ and vice versa; wherein when $R_h$ is S, $R_g$ is not O, $SO_2$, $SO_3$, or $NR_{44}$, and vice versa; wherein when $R_h$ is $SO_2$, $R_g$ is not S, $SO_2$, or $SO_3$, and vice versa; wherein when $R_h$ is $SO_3$, $R_g$ is not S, $SO_2$, or $SO_3$, and vice versa; wherein when $R_h$ is $SO_2$, $R_g$ is not S, $SO_2$, or $SO_3$, and vice versa; wherein when $R_h$ is $SO_3$, $R_g$ is not S, $SO_2$, or $SO_3$, and vice versa; wherein when $R_h$ is $NR_{61}$, $R_g$ is not O, or S, and vice versa; wherein when $R_g$ is O, $R_f$ is not OH, SH, or $NR_{48}R_{49}R_{50}$, and vice versa; wherein when $R_g$ is S, $R_f$ is not OH, SH, $SO_2$ or $NR_{48}R_{49}R_{50}$, and vice versa; wherein when $R_g$ is $SO_2$, $R_f$ is not SH, $SO_2$, or $SO_3$, and vice versa; wherein when $R_g$ is $SO_3$, $R_f$ is not SH, $SO_2$, or $SO_3$, and vice versa; and wherein when $R_g$ is $NR_{44}$, $R_f$ is not OH, SH, or $SO_2$, and vice versa;

wherein each $R_{hx}$ is independently absent, $C(R_{59x}R_{60x})$, O, S, $SO_2$, $SO_3$, or $NR_{61x}$; wherein each $R_{gx}$ is independently absent (i.e., jx is 0), $C(R_{42x}R_{43x})$, O, S, $SO_2$, $SO_3$, or $NR_{44x}$; and wherein each $R_{fx}$ is independently hydrogen, $C(R_{45x}R_{46x}R_{47x})$, OH, SH, $SO_2$, $SO_3$, $Si(R_{100x}R_{101x}R_{102x})$, or $NR_{48x}R_{49x}R_{50x}$;

wherein jx is an integer from 0 to 20, wherein $R_{59x}$, $R_{60x}$, $R_{61x}$, $R_{42x}$, $R_{43x}$, and $R_{44x}$ are each independently, as valency permits, absent, hydrogen, =O, —$OR_{51x}$, —$SR_{52x}$, —$NR_{53x}R_{54x}R_{55x}$, —$C(R_{56x}R_{57x}R_{58x})$, or —$R_{hy}$—($R_{gy}$)$_{jy}$—$R_{fy}$, wherein $R_{45x}$, $R_{46x}$, $R_{47x}$, $R_{48x}$, $R_{49x}$, $R_{50x}$, $R_{51x}$, $R_{52x}$, $R_{53x}$, $R_{54x}$, $R_{55x}$, $R_{56x}$, $R_{57x}$, and $R_{58x}$ are each independently, as valency permits, absent, hydrogen, —OH, =O, —SH, =NH, —$NH_2$, —$NH_3$, —$CH_3$, or —COOH, wherein $R_{100x}$, $R_{101x}$, and $R_{102x}$ are each independently alkyl, phenyl, aryl, or $C_3$-$C_{20}$ cyclic, wherein the bond between each $R_{hx}$ and each respective $R_{gx}$, if present, is single, double, or triple depending on the valency, wherein the bond between each $R_{gx}$ and each respective $R_{fx}$, if present, is single, double, or triple depending on the valency, wherein the bond between each adjacent $R_{gx}$ is single, double, or triple depending on the valency, wherein the bond between each $R_{hx}$ and each respective $R_{fx}$, if present, is single, double, or triple depending on the valency; wherein when $R_{hx}$ is O, S, $SO_2$, or $SO_3$, the bond between $R_{hx}$ and $R_{gx}$ is not a double or triple bond; wherein when $R_{hx}$ is $NR_{61x}$, the bond between $R_{hx}$ and $R_{gx}$ is not a triple bond; wherein when $R_{gx}$ is O, S, $SO_2$, or $SO_3$, the bond between $R_{gx}$ and $R_{hx}$ is not a double or triple bond; wherein when $R_{hx}$ is $NR_{44x}$, the bond between $R_{gx}$ and $R_{hx}$ is not a triple bond; wherein when $R_{gx}$ is O, S, $SO_2$, or $SO_3$, the bond between $R_{gx}$ and $R_{fx}$ is not a double or triple bond; wherein when $R_{gx}$ is $NR_{44x}$, the bond between $R_{gx}$ and $R_{fx}$ is not a triple bond; wherein when $R_{hx}$ is O, $R_{gx}$ is not O, S, or $NR_{44x}$ and vice versa; wherein when $R_{hx}$ is S, $R_{gx}$ is not O, $SO_2$, $SO_3$, or $NR_{44x}$, and vice versa; wherein when $R_{hx}$ is $SO_2$, $R_{gx}$ is not S, $SO_2$, or $SO_3$, and vice versa; wherein when $R_{hx}$ is $SO_3$, $R_{gx}$ is not S, $SO_2$, or $SO_3$, and vice versa; wherein when $R_{hx}$ is $NR_{61x}$, $R_{gx}$ is not O, or S, and vice versa; wherein when $R_{gx}$ is O, $R_{fx}$ is not OH, SH, or $NR_{48x}R_{49x}R_{50x}$, and vice versa; wherein when $R_{gx}$ is S, $R_{fx}$ is not OH, SH, $SO_2$ or $NR_{48x}R_{49x}R_{50x}$, and vice versa; wherein when $R_{gx}$ is $SO_2$, $R_{fx}$ is not SH, $SO_2$, or $SO_3$, and vice versa; wherein when $R_{gx}$ is $SO_3$, $R_{fx}$ is not SH, $SO_2$, or $SO_3$, and vice versa; and wherein when $R_{gx}$ is $NR_{44x}$, $R_{fx}$ is not OH, SH, or $SO_2$, and vice versa;

wherein each $R_{hy}$ is independently absent, $C(R_{59y}R_{60y})$, O, S, $SO_2$, $SO_3$, or $NR_{61y}$; wherein each $R_{gy}$ is independently absent (i.e., jy is 0), $C(R_{42y}R_{43y})$, O, S, $SO_2$, $SO_3$, or $NR_{44y}$; and wherein each $R_{fy}$ is independently hydrogen, $C(R_{45y}R_{46y}R_{47y})$, OH, SH, $SO_2$, $SO_3$, $Si(R_{100y}R_{101y}R_{102y})$, or $NR_{48y}R_{49y}R_{50y}$;

wherein jy is an integer from 0 to 10, wherein $R_{59y}$, $R_{60y}$, $R_{61y}$, $R_{42y}$, $R_{43y}$, and $R_{44y}$ are each independently, as valency permits, absent, hydrogen, =O, —$OR_{51y}$, —$SR_{52y}$, —$NR_{53y}R_{54y}R_{55y}$, —$C(R_{56y}R_{57y}R_{58y})$, or —$R_{hz}$—($R_{gz}$)$_{jz}$—$R_{fz}$, wherein $R_{45y}$, $R_{46y}$, $R_{47y}$, $R_{48y}$, $R_{49y}$, $R_{50y}$, $R_{51y}$, $R_{52y}$, $R_{53y}$, $R_{54y}$, $R_{55y}$, $R_{56y}$, $R_{57y}$, and $R_{58y}$ are each independently, as valency permits, absent, hydrogen, —OH, =O, —SH, =NH, —NH$_2$, —NH$_3$, —CH$_3$, or —COOH, wherein $R_{100y}$, $R_{101y}$, and $R_{102y}$ are each independently alkyl, phenyl, aryl, or $C_3$-$C_{20}$ cyclic, wherein the bond between each $R_{hy}$ and each respective $R_{gy}$, if present, is single, double, or triple depending on the valency, wherein the bond between each $R_{gy}$ and each respective $R_{fy}$, if present, is single, double, or triple depending on the valency, wherein the bond between each adjacent $R_{gy}$ is single, double, or triple depending on the valency, wherein the bond between each $R_{hy}$ and each respective $R_{fy}$, if present, is single, double, or triple depending on the valency; wherein when $R_{hy}$ is O, S, SO$_2$, or SO$_3$, the bond between $R_{hy}$ and $R_{gy}$ is not a double or triple bond; wherein when $R_{hy}$ is NR$_{61y}$, the bond between $R_{hy}$ and $R_{gy}$ is not a triple bond; wherein when $R_{gy}$ is O, S, SO$_2$, or SO$_3$, the bond between $R_{gy}$ and $R_{hy}$ is not a double or triple bond; wherein when $R_{hy}$ is NR$_{44y}$, the bond between $R_{gy}$ and $R_{hy}$ is not a triple bond; wherein when $R_{gy}$ is O, S, SO$_2$, or SO$_3$, the bond between $R_{gy}$ and $R_{fy}$ is not a double or triple bond; wherein when $R_{gy}$ is NR$_{44y}$, the bond between $R_{gy}$ and $R_{fy}$ is not a triple bond; wherein when $R_{hy}$ is O, $R_{gy}$ is not O, S, or NR$_{44y}$, and vice versa; wherein when $R_{hy}$ is S, $R_{gy}$ is not O, SO$_2$, SO$_3$, or NR$_{44y}$, and vice versa; wherein when $R_{hy}$ is SO$_2$, $R_{gy}$ is not S, SO$_2$, or SO$_3$, and vice versa; wherein when $R_{hy}$ is SO$_3$, $R_{gy}$ is not S, SO$_2$, or SO$_3$, and vice versa; wherein when $R_{hy}$ is NR$_{61y}$, $R_{gy}$ is not O, or S, and vice versa; wherein when $R_{gy}$ is O, $R_{fy}$ is not OH, SH, or NR$_{48y}$R$_{49y}$R$_{50y}$, and vice versa; wherein when $R_{gy}$ is S, $R_{fy}$ is not OH, SH, SO$_2$ or NR$_{48y}$R$_{49y}$R$_{50y}$, and vice versa; wherein when $R_{gy}$ is SO$_2$, $R_{fy}$ is not SH, SO$_2$, or SO$_3$, and vice versa; wherein when $R_{gy}$ is SO$_3$, $R_{fy}$ is not SH, SO$_2$, or SO$_3$, and vice versa; and wherein when $R_{gy}$ is NR$_{44y}$, $R_{fy}$ is not OH, SH, or SO$_2$, and vice versa;

wherein each $R_{hz}$ is independently absent, C(R$_{59z}$R$_{60z}$), O, S, SO$_2$, SO$_3$, or NR$_{61z}$; wherein each $R_{gz}$ is independently absent (i.e., jz is 0), C(R$_{42z}$R$_{43z}$), O, S, SO$_2$, SO$_3$, or NR$_{44z}$; and wherein each $R_{fz}$ is independently hydrogen, C(R$_{45z}$R$_{46z}$R$_{47z}$), OH, SH, SO$_2$, SO$_3$, Si(R$_{100z}$R$_{101z}$R$_{102z}$), or NR$_{48z}$R$_{49z}$R$_{50z}$;

wherein jz is an integer from 0 to 6, wherein $R_{59z}$, $R_{60z}$, $R_{61z}$, $R_{42z}$, $R_{43z}$, and $R_{44z}$ are each independently, as valency permits, absent, hydrogen, =O, —OR$_{51z}$, —SR$_{52z}$, —NR$_{53z}$R$_{54z}$R$_{55z}$, or —C(R$_{56z}$R$_{57z}$R$_{58z}$), wherein $R_{45z}$, $R_{46z}$, $R_{47z}$, $R_{48z}$, $R_{49z}$, $R_{50z}$, $R_{51z}$, $R_{52z}$, $R_{53z}$, $R_{54z}$, $R_{55z}$, $R_{56z}$, $R_{57z}$, and $R_{58z}$ are each independently, as valency permits, absent, hydrogen, —OH, =O, —SH, =NH, —NH$_2$, —NH$_3$, —CH$_3$, or —COOH, wherein $R_{100z}$, $R_{101z}$, and $R_{102z}$ are each independently alkyl, phenyl, aryl, or $C_3$-$C_{20}$ cyclic, wherein the bond between each $R_{hz}$ and each respective $R_{gz}$, if present, is single, double, or triple depending on the valency, wherein the bond between each $R_{gz}$ and each respective $R_{fz}$, if present, is single, double, or triple depending on the valency, wherein the bond between each adjacent $R_{gz}$ is single, double, or triple depending on the valency, wherein the bond between each $R_{hz}$ and each respective $R_{fz}$, if present, is single, double, or triple depending on the valency; wherein when $R_{hz}$ is O, S, SO$_2$, or SO$_3$, the bond between $R_{hz}$ and $R_{gz}$ is not a double or triple bond; wherein when $R_{hz}$ is NR$_{61z}$, the bond between $R_{hz}$ and $R_{gz}$ is not a triple bond; wherein when $R_{gz}$ is O, S, SO$_2$, or SO$_3$, the bond between $R_{gz}$ and $R_{hz}$ is not a double or triple bond; wherein when $R_{hz}$ is NR$_{44z}$, the bond between $R_{gz}$ and $R_{hz}$ is not a triple bond; wherein when $R_{gz}$ is O, S, SO$_2$, or SO$_3$, the bond between $R_{gz}$ and $R_{fz}$ is not a double or triple bond; wherein when $R_{gz}$ is NR$_{44z}$, the bond between $R_{gz}$ and $R_{fz}$ is not a triple bond; wherein when $R_{hz}$ is O, $R_{gz}$ is not O, S, or NR$_{44z}$ and vice versa; wherein when $R_{hz}$ is S, $R_{gz}$ is not O, SO$_2$, SO$_3$, or NR$_{44z}$, and vice versa; wherein when $R_{hz}$ is SO$_2$, $R_{gz}$ is not S, SO$_2$, or SO$_3$, and vice versa; wherein when $R_{hz}$ is SO$_3$, $R_{gz}$ is not S, SO$_2$, or SO$_3$, and vice versa; wherein when $R_{hz}$ is NR$_{61z}$, $R_{gz}$ is not O, or S, and vice versa; wherein when $R_{gz}$ is O, $R_{fz}$ is not OH, SH, or NR$_{48z}$R$_{49z}$R$_{50z}$, and vice versa; wherein when $R_{gz}$ is S, $R_{fz}$ is not OH, SH, SO$_2$ or NR$_{48z}$R$_{49z}$R$_{50z}$, and vice versa; wherein when $R_{gz}$ is SO$_2$, $R_{fz}$ is not SH, SO$_2$, or SO$_3$, and vice versa; wherein when $R_{gz}$ is SO$_3$, $R_{fz}$ is not SH, SO$_2$, or SO$_3$, and vice versa; and wherein when $R_{gz}$ is NR$_{44z}$, $R_{fz}$ is not OH, SH, or SO$_2$, and vice versa.

Independently in some embodiments of j, and independently in combination with any embodiments of any other relevant substituent classes, j can be an integer from 1 to 30, 2 to 30, 3 to 30, 4 to 30, 5 to 30, 6 to 30, 7 to 30, 8 to 30, 9 to 30, 10 to 30, 11 to 30, 12 to 30, 13 to 30, 14 to 30, 15 to 30, 16 to 30, 17 to 30, 18 to 30, 19 to 30, 20 to 30, 21 to 30, 22 to 30, 23 to 30, 24 to 30, 25 to 30, 26 to 30, 27 to 30, 28 to 30, 29 to 30, 1 to 29, 2 to 29, 3 to 29, 4 to 29, 5 to 29, 6 to 29, 7 to 29, 8 to 29, 9 to 29, 10 to 29, 11 to 29, 12 to 29, 13 to 29, 14 to 29, 15 to 29, 16 to 29, 17 to 29, 18 to 29, 19 to 29, 20 to 29, 21 to 29, 22 to 29, 23 to 29, 24 to 29, 25 to 29, 26 to 29, 27 to 29, 28 to 29, 1 to 28, 2 to 28, 3 to 28, 4 to 28, 5 to 28, 6 to 28, 7 to 28, 8 to 28, 9 to 28, 10 to 28, 11 to 28, 12 to 28, 13 to 28, 14 to 28, 15 to 28, 16 to 28, 17 to 28, 18 to 28, 19 to 28, 20 to 28, 21 to 28, 22 to 28, 23 to 28, 24 to 28, 25 to 28, 26 to 28, 27 to 28, 1 to 27, 2 to 27, 3 to 27, 4 to 27, 5 to 27, 6 to 27, 7 to 27, 8 to 27, 9 to 27, 10 to 27, 11 to 27, 12 to 27, 13 to 27, 14 to 27, 15 to 27, 16 to 27, 17 to 27, 18 to 27, 19 to 27, 20 to 27, 21 to 27, 22 to 27, 23 to 27, 24 to 27, 25 to 27, 26 to 27, 1 to 26, 2 to 26, 3 to 26, 4 to 26, 5 to 26, 6 to 26, 7 to 26, 8 to 26, 9 to 26, 10 to 26, 11 to 26, 12 to 26, 13 to 26, 14 to 26, 15 to 26, 16 to 26, 17 to 26, 18 to 26, 19 to 26, 20 to 26, 21 to 26, 22 to 26, 23 to 26, 24 to 26, 25 to 26, 1 to 25, 2 to 25, 3 to 25, 4 to 25, 5 to 25, 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25, 24 to 25, 1 to 24, 2 to 24, 3 to 24, 4 to 24, 5 to 24, 6 to 24, 7 to 24, 8 to 24, 9 to 24, 10 to 24, 11 to 24, 12 to 24, 13 to 24, 14 to 24, 15 to 24, 16 to 24, 17 to 24, 18 to 24, 19 to 24, 20 to 24, 21 to 24, 22 to 24, 23 to 24, 1 to 23, 2 to 23, 3 to 23, 4 to 23, 5 to 23, 6 to 23, 7 to 23, 8 to 23, 9 to 23, 10 to 23, 11 to 23, 12 to 23, 13 to 23, 14 to 23, 15 to 23, 16 to 23, 17 to 23, 18 to 23, 19 to 23, 20 to 23, 21 to 23, 22 to 23, 1 to 22, 2 to 22, 3 to 22, 4 to 22, 5 to 22, 6 to 22, 7 to 22, 8 to 22, 9 to 22, 10 to 22, 11 to 22, 12 to 22, 13 to 22, 14 to 22, 15 to 22, 16 to 22, 17 to 22, 18 to 22, 19 to 22, 20 to 22, 21 to 22, 1 to 21, 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, j is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Independently in some embodiments of j, and independently in combination with any embodiments of any other relevant substituent classes, j can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of j, and independently in combination with any embodiments of any other relevant substituent classes, j can be 1, 2, 3, 4, 5, 6, 7, 8, 9, or 10.

Independently in some embodiments of j, and independently in combination with any embodiments of any other relevant substituent classes, j can be an integer from 1 to 5, 2 to 5, 3 to 5, 4 to 5, 1 to 4, 2 to 4, 3 to 4, 1 to 3, 2 to 3, or 1 to 2. In preferred embodiments, j is 1, 2, 3, 4, or 5.

Independently in some embodiments of jx, and independently in combination with any embodiments of any other relevant substituent classes, jx can be an integer from 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, 19 to 20, 1 to 19, 2 to 19, 3 to 19, 4 to 19, 5 to 19, 6 to 19, 7 to 19, 8 to 19, 9 to 19, 10 to 19, 11 to 19, 12 to 19, 13 to 19, 14 to 19, 15 to 19, 16 to 19, 17 to 19, 18 to 19, 1 to 18, 2 to 18, 3 to 18, 4 to 18, 5 to 18, 6 to 18, 7 to 18, 8 to 18, 9 to 18, 10 to 18, 11 to 18, 12 to 18, 13 to 18, 14 to 18, 15 to 18, 16 to 18, 17 to 18, 1 to 17, 2 to 17, 3 to 17, 4 to 17, 5 to 17, 6 to 17, 7 to 17, 8 to 17, 9 to 17, 10 to 17, 11 to 17, 12 to 17, 13 to 17, 14 to 17, 15 to 17, 16 to 17, 1 to 16, 2 to 16, 3 to 16, 4 to 16, 5 to 16, 6 to 16, 7 to 16, 8 to 16, 9 to 16, 10 to 16, 11 to 16, 12 to 16, 13 to 16, 14 to 16, 15 to 16, 1 to 15, 2 to 15, 3 to 15, 4 to 15, 5 to 15, 6 to 15, 7 to 15, 8 to 15, 9 to 15, 10 to 15, 11 to 15, 12 to 15, 13 to 15, 14 to 15, 1 to 14, 2 to 14, 3 to 14, 4 to 14, 5 to 14, 6 to 14, 7 to 14, 8 to 14, 9 to 14, 10 to 14, 11 to 14, 12 to 14, 13 to 14, 1 to 13, 2 to 13, 3 to 13, 4 to 13, 5 to 13, 6 to 13, 7 to 13, 8 to 13, 9 to 13, 10 to 13, 11 to 13, 12 to 13, 1 to 12, 2 to 12, 3 to 12, 4 to 12, 5 to 12, 6 to 12, 7 to 12, 8 to 12, 9 to 12, 10 to 12, 11 to 12, 1 to 11, 2 to 11, 3 to 11, 4 to 11, 5 to 11, 6 to 11, 7 to 11, 8 to 11, 9 to 11, 10 to 11, 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In some embodiments, jx is 1, 2, 3, 4, 5, 6, 7, 8, 9, 10, 11, 12, 13, 14, 15, 16, 17, 18, 19, or 20.

Independently in some embodiments of jx, and independently in combination with any embodiments of any other relevant substituent classes, jx can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of jx, and independently in combination with any embodiments of any other relevant substituent classes, jx can be 1, 2, 3, 4, 5, 6, 7, 8, 9, or 10.

Independently in some embodiments of jx, and independently in combination with any embodiments of any other relevant substituent classes, jx can be an integer from 1 to 5, 2 to 5, 3 to 5, 4 to 5, 1 to 4, 2 to 4, 3 to 4, 1 to 3, 2 to 3, or 1 to 2. In preferred embodiments, jx is 1, 2, 3, 4, or 5.

Independently in some embodiments of jy, and independently in combination with any embodiments of any other relevant substituent classes, jy can be an integer from 1 to 10, 2 to 10, 3 to 10, 4 to 10, 5 to 10, 6 to 10, 7 to 10, 8 to 10, 9 to 10, 1 to 9, 2 to 9, 3 to 9, 4 to 9, 5 to 9, 6 to 9, 7 to 9, 8 to 9, 1 to 8, 2 to 8, 3 to 8, 4 to 8, 5 to 8, 6 to 8, 7 to 8, 1 to 7, 2 to 7, 3 to 7, 4 to 7, 5 to 7, 6 to 7, 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. Independently in some embodiments of jy, and independently in combination with any embodiments of any other relevant substituent classes, jy can be 1, 2, 3, 4, 5, 6, 7, 8, 9, or 10.

Independently in some embodiments of jy, and independently in combination with any embodiments of any other relevant substituent classes, jy can be an integer from 1 to 5, 2 to 5, 3 to 5, 4 to 5, 1 to 4, 2 to 4, 3 to 4, 1 to 3, 2 to 3, or 1 to 2. In preferred embodiments, jy is 1, 2, 3, 4, or 5.

Independently in some embodiments of jz, and independently in combination with any embodiments of any other relevant substituent classes, jz can be an integer from 1 to 6, 2 to 6, 3 to 6, 4 to 6, 5 to 6, 1 to 5, 2 to 5, 3 to 5, 4 to 5, 1 to 4, 2 to 4, 3 to 4, 1 to 3, 2 to 3, or 1 to 2. In preferred embodiments, jz is 1, 2, 3, 4, or 5.

N1

Independently in some embodiments of Formula IX, and independently in combination with any embodiments of any other relevant substituent classes, $R_{18}$, $R_{19}$, $R_{20}$, $R_{21}$, $R_{22}$, and $R_{23}$ are carbon, y is 1 to 5, at least one $R^e$ is —O—CH$_3$, and other $R^e$ are independently hydrogen, $C_1$-$C_3$ alkyl, or $C_1$-$C_3$ alkoxy, the ring of Formula IX is aromatic, $R_{24}$ is —(CR$_{25}$R$_{25}$)$_p$—, $R_{25}$ are independently hydrogen, $C_1$-$C_3$ alkyl, or $C_1$-$C_3$ alkoxy, and p is 1 to 6. In some embodiments, at least two $R^e$ are —O—CH$_3$. In some embodiments, at least three $R^e$ are —O—CH$_3$. In some embodiments, at least four $R^e$ are —O—CH$_3$. In some embodiments, at least five $R^e$ are —O—CH$_3$. In some embodiments, p is 1. In some embodiments, p is 2, In some embodiments, p is 3. In some embodiments, p is 4. In some embodiments, p is 5. In some embodiments, p is 6. In some embodiments, y is 1 and $R^e$ is at position $R_{19}$, $R_{20}$, $R_{21}$, $R_{22}$, or $R_{23}$. In some embodiments, y is 2 and $R^e$ are at positions $R_{19}$ and $R_{20}$, $R_{19}$ and $R_{21}$, $R_{19}$ and $R_{22}$, $R_{19}$ and $R_{23}$, $R_{20}$ and $R_{21}$, $R_{20}$ and $R_{22}$, $R_{20}$ and $R_{23}$, $R_{21}$ and $R_{22}$, $R_{21}$ and $R_{23}$, or $R_{22}$ and $R_{23}$. In some embodiments, y is 3 and $R^e$ are at positions $R_{19}$, $R_{20}$, and $R_{21}$, $R_{19}$, $R_{20}$, and $R_{22}$, $R_{19}$, $R_{20}$, and $R_{23}$, $R_{19}$, $R_{21}$, and $R_{22}$, $R_{19}$, $R_{21}$, and $R_{23}$, $R_{19}$, $R_{22}$, and $R_{23}$, $R_{20}$, $R_{21}$, and $R_{22}$, $R_{20}$, $R_{21}$, and $R_{23}$, $R_{20}$, $R_{22}$, and $R_{23}$, or $R_{21}$, $R_{22}$, and $R_{23}$. In some embodiments, y is 4 and $R^e$ are at positions $R_{19}$, $R_{20}$, $R_{21}$, and $R_{22}$, $R_{19}$, $R_{20}$, $R_{21}$, and $R_{23}$, $R_{19}$, $R_{20}$, $R_{22}$, and $R_{23}$, $R_{19}$, $R_{21}$, $R_{22}$, and $R_{23}$, or $R_{20}$, $R_{21}$, $R_{22}$, and $R_{23}$. In some embodiments, y is 5 and $R^e$ are at positions $R_{19}$, $R_{20}$, $R_{21}$, $R_{22}$, and $R_{23}$.

Independently in some embodiments of $R_1$; and independently in combination with any embodiments of any other relevant substituent classes, R is Formula IX, wherein in Formula IX, $R_{18}$, $R_{19}$, $R_{20}$, $R_{21}$, $R_{22}$, and $R_{23}$ are carbon, y is 2, $R^e$ is —O—$CH_3$, $R^e$ is at positions $R_{20}$ and $R_{21}$, the ring of Formula IX is aromatic, $R_{24}$ is —$(CR_{25}R_{25})_p$—, both $R_{25}$ are hydrogen, and p is 2.

Independently in some embodiments of Formula IX, and independently in combination with any embodiments of any other relevant substituent classes, $R_{18}$, $R_{19}$, $R_{20}$, $R_{21}$, $R_{22}$, and $R_{23}$ are carbon, y is 2, $R^e$ is —O—$CH_3$, $R^e$ is at positions $R_{20}$ and $R_{21}$, the ring of Formula IX is aromatic, $R_{24}$ is —$(CR_{25}R_{25})_p$—, both $R_{25}$ are hydrogen, and p is 2.

Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 2, $R^e$ is —O—$CH_3$, $R^e$ is at positions $R_{20}$ and $R_{21}$, the ring of Formula IX is aromatic, $R_{24}$ is —$(CR_{25}R_{25})_p$—, and both $R_{25}$ are hydrogen, then p is not 2. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 2, $R^e$ is —O—$CH_3$, $R^e$ is at positions $R_{20}$ and $R_{21}$, the ring of Formula IX is aromatic, $R_{24}$ is —$(CR_{25}R_{25})_p$—, and p is 2, then at least one $R_{25}$ is not hydrogen. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 2, $R^e$ is —O—$CH_3$, $R^e$ is at positions $R_{20}$ and $R_{21}$, $R_{24}$ is —$(CR_{25}R_{25})_p$—, both $R_{25}$ are hydrogen, and p is 2, then the ring of Formula IX is not aromatic. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 2, $R^e$ is —O—$CH_3$, the ring of Formula IX is aromatic, $R_{24}$ is —$(CR_{25}R_{25})_p$—, both $R_{25}$ are hydrogen, and p is 2, then $R^e$ is not at positions $R_{20}$ and $R_{21}$. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 2, $R^e$ is at positions $R_{20}$ and $R_{21}$, the ring of Formula IX is aromatic, $R_{24}$ is —$(CR_{25}R_{25})_p$—, both $R_{25}$ are hydrogen, and p is 2, then at least one $R^e$ is not —O—$CH_3$. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, $R^e$ is —O—$CH_3$, $R^e$ is at positions $R_{20}$ and $R_{21}$, the ring of Formula IX is aromatic, $R_{24}$ is —$(CR_{25}R_{25})_p$—, both $R_{25}$ are hydrogen, and p is 2, then y is not 2. Independently in some embodiments of Formula IX, and independently in combination with any embodiments of any other relevant substituent classes, if y is 2, $R^e$ is —O—$CH_3$, $R^e$ is at positions $R_{20}$ and $R_{21}$, the ring of Formula IX is aromatic, $R_{24}$ is —$(CR_{25}R_{25})_p$—, both $R_{25}$ are hydrogen, and p is 2, then at least one of $R_{18}$, $R_{19}$, $R_{20}$, $R_{21}$, $R_{22}$, and $R_{23}$ is not carbon and the rest of $R_{18}$, $R_{19}$, $R_{20}$, $R_{21}$, $R_{22}$, and $R_{23}$ are carbon.

N2

Independently in some embodiments, and independently in combination with any embodiments of any other relevant substituent classes, X is O, S, or $NR_4$, $R_4$ is hydrogen, $C_1$-$C_N$ alkyl, or $C_1$-$C_N$ alkoxy, and R is Formula XIV, wherein $R_{19}$, $R_{20}$, $R_{21}$, and $R_{22}$ are, independently, oxygen or carbon, $R_{18}$ is carbon, w is 0 to 3, $R^e$ are independently hydrogen, $C_1$-$C_3$ alkyl, or $C_1$-$C_3$ alkoxy, the ring of Formula XIV has zero, one, or two double bonds, $R_{24}$ is —$(CR_{25}R_{25})_p$—, $R_{25}$ are independently hydrogen, $C_1$-$C_3$ alkyl, or $C_1$-$C_3$ alkoxy, and p is 1 to 5. In some embodiments, one of $R_{19}$, $R_{20}$, $R_{21}$, and $R_{22}$ is oxygen. In some embodiments, two of $R_{19}$, $R_{20}$, $R_{21}$, and $R_{22}$ are oxygen. In some embodiments, three of $R_{19}$, $R_{20}$, $R_{21}$, and $R_{22}$ are oxygen. In some embodiments, each of $R_{19}$, $R_{20}$, $R_{21}$, and $R_{22}$ is oxygen. In some embodiments, w is 1 and $R^e$ is at position $R_{19}$, $R_{20}$, $R_{21}$, or $R_{22}$. In some embodiments, w is 2 and $R^e$ are at positions $R_{19}$ and $R_{20}$, $R_{19}$ and $R_{21}$, $R_{19}$ and $R_{22}$, $R_{20}$ and $R_{21}$, $R_{20}$ and $R_{22}$, or $R_{21}$ and $R_{22}$. In some embodiments, w is 3 and $R^e$ are at positions $R_{19}$, $R_{20}$, and $R_{21}$, $R_{19}$, $R_{20}$, and $R_{22}$, $R_{19}$, $R_{21}$, and $R_{22}$, or $R_{20}$, $R_{21}$, and $R_{22}$.

Independently in some embodiments of Formula XIV, and independently in combination with any embodiments of any other relevant substituent classes, $R_{19}$, $R_{20}$, $R_{21}$, and $R_{22}$ are, independently, oxygen or carbon, $R_{18}$ is carbon, w is 0 to 3, $R^e$ are independently hydrogen, $C_1$-$C_3$ alkyl, or $C_1$-$C_3$ alkoxy, the ring of Formula XIV has zero, one, or two double bonds, $R_{24}$ is —$(CR_{25}R_{25})_p$—, $R_{25}$ are independently hydrogen, $C_1$-$C_3$ alkyl, or $C_1$-$C_3$ alkoxy, and p is 1 to 5. In some embodiments, one of $R_{19}$, $R_{20}$, $R_{21}$, and $R_{22}$ is oxygen. In some embodiments, two of $R_{19}$, $R_{20}$, $R_{21}$, and $R_{22}$ are oxygen. In some embodiments, three of $R_{19}$, $R_{20}$, $R_{21}$, and $R_{22}$ are oxygen. In some embodiments, each of $R_{19}$, $R_{20}$, $R_{21}$, and $R_{22}$ is oxygen. In some embodiments, w is 1 and $R^e$ is at position $R_{19}$, $R_{20}$, $R_{21}$, or $R_{22}$. In some embodiments, w is 2 and $R^e$ are at positions $R_{19}$ and $R_{20}$, $R_{19}$ and $R_{21}$, $R_{19}$ and $R_{22}$, $R_{20}$ and $R_{21}$, $R_{20}$ and $R_{22}$, or $R_{21}$ and $R_{22}$. In some embodiments, w is 3 and $R^e$ are at positions $R_{19}$, $R_{20}$, and $R_{21}$, $R_{19}$, $R_{20}$, and $R_{22}$, $R_{19}$, $R_{21}$, and $R_{22}$, or $R_{20}$, $R_{21}$, and $R_{22}$.

Independently in some embodiments, and independently in combination with any embodiments of any other relevant substituent classes, X is $NR_4$, $R_4$ is methyl, and $R_1$ is Formula XIV, wherein $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1.

Independently in some embodiments of Formula XIV, and independently in combination with any embodiments of any other relevant substituent classes, $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1.

Independently in some embodiments, and independently in combination with any embodiments of any other relevant substituent classes, if X is $NR_4$, $R_4$ is methyl, $R_1$ is Formula XIV, $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, and both $R_{25}$ are hydrogen, then p is not 1. Independently in some embodiments, and independently in combination with any embodiments of any other relevant substituent classes, if X is $NR_4$, $R_4$ is methyl, $R_1$ is Formula XIV, $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, and p is 1, then at least one $R_{25}$ is not hydrogen. Independently in some embodiments, and independently in combination with any embodiments of any other relevant substituent classes, if X is $NR_4$, $R_4$ is methyl, $R_1$ is Formula XIV, $R_{19}$ and $R_{22}$ are oxygen, $R_{18}$, $R_{20}$, and $R_{21}$ are carbon, w is 0, $R_{24}$ is —$(CR_{25}R_{25})_p$—, both $R_{25}$ are hydrogen, and p is 1, then the ring of Formula XIV has at least one double bonds. Independently in some embodiments, and independently in combination with any embodiments of any other relevant substituent classes, if X is $NR_4$, $R_4$ is methyl, $R_1$ is Formula XIV, $R_{19}$ and $R_{22}$ are oxygen, $R_{18}$, $R_{20}$, and $R_{21}$ are carbon, the ring of Formula XIV has no double bonds, $R_{24}$ is —$(CR_{25}R_{25})_p$—, both $R_{25}$ are hydrogen, and p is 1, then w is not 0. Independently in some embodiments, and independently in combination with any embodiments of any other relevant substituent classes, if X is $NR_4$, $R_4$ is methyl, $R_4$ is Formula XIV, $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then at least one of $R_{18}$, $R_{20}$, and $R_{21}$ is not carbon. Independently in some embodiments, and independently in combination with any embodiments of any other relevant substituent classes, if X is $NR_4$, $R_4$ is methyl, $R_1$ is Formula XIV, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then at least one of $R_{19}$ and $R_{22}$ is not oxygen. Independently in some embodiments, and independently in combination with any embodiments of any other relevant substituent classes, if X is $NR_4$, $R_1$ is Formula XIV, $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then $R_4$ is not methyl. Independently in some embodiments, and independently in combination with any embodiments of any other relevant substituent classes, if $R_4$ is methyl, $R_4$ is Formula XIV, wherein $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then X is not $NR_4$.

Independently in some embodiments of Formula XIV, and independently in combination with any embodiments of any other relevant substituent classes, if $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, and both $R_{25}$ are hydrogen, then p is not 1. Independently in some embodiments of Formula XIV, and independently in combination with any embodiments of any other relevant substituent classes, if $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, and p is 1, then at least one $R_{25}$ is not hydrogen. Independently in some embodiments of Formula XIV, and independently in combination with any embodiments of any other relevant substituent classes, if $R_{19}$ and $R_{22}$ are oxygen, $R_{18}$, $R_{20}$, and $R_{21}$ are carbon, w is 0, $R_{24}$ is —$(CR_{25}R_{25})_p$—, both $R_{25}$ are hydrogen, and p is 1, then the ring of Formula XIV has at least one double bonds. Independently in some embodiments of Formula XIV, and independently in combination with any embodiments of any other relevant substituent classes, if $R_{19}$ and $R_{22}$ are oxygen, $R_{18}$, $R_{20}$, and $R_{21}$ are carbon, the ring of Formula XIV has no double bonds, $R_{24}$ is —$(CR_{25}R_{25})_p$—, both $R_{25}$ are hydrogen, and p is 1, then w is not 0. Independently in some embodiments of Formula XIV, and independently in combination with any embodiments of any other relevant substituent classes, if $R_{19}$ and $R_{22}$ are oxygen, $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then at least one of $R_{18}$, $R_{20}$, and $R_{21}$ is not carbon. Independently in some embodiments of Formula XIV, and independently in combination with any embodiments of any other relevant substituent classes, if $R_{18}$, $R_{20}$, and $R_{21}$ are carbon, w is 0, the ring of Formula XIV has no double bonds, $R_{24}$ is —$(CR_{25}R_{25})_p$—, both $R_{25}$ are hydrogen, and p is 1, then at least one of $R_{10}$ and $R_{22}$ is not oxygen.

N3

Independently in some embodiments of —$R_h$—$(R_g)_j$—$R_f$, and independently in combination with any embodiments of any other relevant substituent classes, $R_h$ is absent, j is 0 to 10, each $R_g$ is $C(R_{42}R_{43})$, and $R_f$ is $NR_{48}R_{49}R_{50}$, wherein $R_{42}$, $R_{43}$, $R_{48}$, and $R_{49}$ are, independently, hydrogen, $C_1$-$C_3$ alkyl, or $C_1$-$C_3$ alkoxy, and $R_{50}$ is absent. In some embodiments, all but one, all but two, all but three, all but four, all but five, all but six, all but seven, all but eight, all but none, or all but ten of $R_{42}$ and $R_{43}$ are hydrogen. In some embodiments, at least one of $R_{42}$ and $R_{43}$ is $C_1$-$C_3$ alkyl. In some embodiments, both $R_{42}$ and $R_{43}$ are $C_1$-$C_3$ alkyl. In some embodiments, at least one of $R_{42}$ and $R_{43}$ is —$CH_3$. In some embodiments, both $R_{42}$ and $R_{43}$ are —$CH_3$. In some embodiments $R_h$ is absent, j is 3, and each $R_g$ is $C(R_{42}R_{43})$, wherein $R_{42}$ and $R_{43}$ are hydrogen. In some embodiments $R_h$ is absent, j is 0 to 10, and each $R_g$ is $C(R_{42}R_{43})$, wherein $R_{42}$ and $R_{43}$ are hydrogen. In some embodiments j is 0. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

Independently in some embodiments of $R_1$; and independently in combination with any embodiments of any other relevant substituent classes, $R_1$ is —$R_h$—$(R_g)_j$—$R_f$, $R_h$ is absent, j is 3, each $R_g$ is $C(R_{42}R_{43})$, and $R_f$ is $NR_{48}R_{49}R_{50}$, wherein $R_{48}$ and $R_{49}$ are —$CH_3$, $R_{50}$ is absent, and $R_{42}$ and $R_{43}$ are hydrogen.

Independently in some embodiments of —$R_h$—$(R_g)_j$—$R_f$, and independently in combination with any embodiments of any other relevant substituent classes, $R_h$ is absent, j is 3, each $R_g$ is $C(R_{42}R_{43})$, and $R_f$ is $NR_{48}R_{49}R_{50}$, wherein $R_{48}$ and $R_{49}$ are —$CH_3$, $R_{50}$ is absent, and $R_{42}$ and $R_{43}$ are hydrogen.

Independently in some embodiments of —$R_h$—$(R_g)_j$—$R_f$, and independently in combination with any embodiments of any other relevant substituent classes, if $R_h$ is absent, j is 3, each $R_g$ is $C(R_{42}R_{43})$, and $R_f$ is $NR_{48}R_{49}R_{50}$, $R_{48}$ and $R_{49}$ are —$CH_3$, and $R_{50}$ is absent, then $R_{42}$ and $R_{43}$ are not both hydrogen. Independently in some embodiments of —$R_h$—$(R_g)_j$—$R_f$, and independently in combination with any embodiments of any other relevant substituent classes, $R_h$ is absent, j is 3, each $R_g$ is $C(R_{42}R_{43})$, and $R_f$ is $NR_{48}R_{49}R_{50}$, $R_{50}$ is absent, and $R_{42}$ and $R_{43}$ are hydrogen, then $R_{48}$ and $R_{49}$ are not both —$CH_3$. Independently in some embodiments of —$R_h$—$(R_g)_j$—$R_f$, and independently in combination with any embodiments of any other relevant substituent classes, $R_h$ is absent, each $R_g$ is $C(R_{42}R_{43})$, and $R_f$ is $NR_{48}R_{49}R_{50}$, wherein $R_{48}$ and $R_{49}$ are —$CH_3$, $R_{50}$ is absent, and $R_{42}$ and $R_{43}$ are hydrogen, then j is not 3.

N4 and N5

Independently in some embodiments, and independently in combination with any embodiments of any other relevant substituent classes, X is $NR_4$, $R_4$ is methyl, and R is Formula IX, wherein in Formula IX, $R_{18}$, $R_{19}$, $R_{20}$, $R_{21}$, $R_{22}$, and $R_{23}$ are carbon, y is 0 to 5, at least one $R^e$ is —O—$CH_3$, and other $R^e$ are independently hydrogen, $C_1$-$C_3$ alkyl, or $C_1$-$C_3$ alkoxy, the ring of Formula IX is aromatic, $R_{24}$ is —$(CR_{25}R_{25})_p$—, $R_{25}$ are independently hydrogen, $C_1$-$C_3$ alkyl, or $C_1$-$C_3$ alkoxy, and p is 1 to 6. Independently in some embodiments of Formula IX, and independently in combination with any embodiments of any other relevant substituent classes, $R_{18}$, $R_{19}$, $R_{20}$, $R_{21}$, $R_{22}$, and $R_{23}$ are carbon, y is 0 to 5, at least one $R^e$ is —O—$CH_3$, and other $R^e$ are independently hydrogen, $C_1$-$C_3$ alkyl, or $C_1$-$C_3$ alkoxy, the ring of Formula IX is aromatic, $R_{24}$ is —$(CR_{25}R_{25})_p$—, $R_{25}$ are independently hydrogen, $C_1$-$C_3$ alkyl, or $C_1$-$C_3$ alkoxy, and p is 1 to 6. In some embodiments, p is 1. In some embodiments, p is 2, In some embodiments, p is 3. In some embodiments, p is 4. In some embodiments, p is 5. In some embodiments, p is 6. In some embodiments, y is 1 and $R^e$ is at position $R_{19}$, $R_{20}$, $R_{21}$, $R_{22}$, or $R_{23}$. In some embodiments, y is 2 and $R^e$ are at positions $R_{19}$ and $R_{20}$, $R_{19}$ and $R_{21}$, $R_{19}$ and $R_{22}$, $R_{19}$ and $R_{23}$, $R_{20}$ and $R_{21}$, $R_{20}$ and $R_{22}$, $R_{20}$ and $R_{23}$, $R_{21}$ and $R_{22}$, $R_{21}$ and $R_{23}$, or $R_{22}$ and $R_{23}$. In some embodiments, y is 3 and $R^e$ are at positions $R_{19}$, $R_{20}$, and $R_{21}$, $R_{19}$, $R_{20}$, and $R_{22}$, $R_{19}$, $R_{20}$, and $R_{23}$, $R_{19}$, $R_{21}$, and $R_{22}$, $R_{19}$, $R_{21}$, and $R_{23}$, $R_{19}$, $R_{22}$, and $R_{23}$, $R_{20}$, $R_{21}$, and $R_{22}$, $R_{20}$, $R_{21}$, and $R_{23}$, $R_{20}$, $R_{22}$, and $R_{23}$, or $R_{21}$, $R_{22}$, and $R_{23}$. In some embodiments, y is 4 and $R^e$ are at positions $R_{19}$, $R_{20}$, $R_{21}$, and $R_{22}$, $R_{19}$, $R_{20}$, $R_{21}$, and $R_{23}$, $R_{19}$, $R_{20}$, $R_{22}$, and $R_{23}$, $R_{19}$, $R_{21}$, $R_{22}$, and $R_{23}$, or $R_{20}$, $R_{21}$, $R_{22}$, and $R_{23}$. In some embodiments, y is 5 and $R^e$ are at positions $R_{19}$, $R_{20}$, $R_{21}$, $R_{22}$, and $R_{23}$.

Independently in some embodiments, and independently in combination with any embodiments of any other relevant substituent classes, X is $NR_4$, $R_4$ is methyl, and $R_1$ is Formula IX, wherein in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, both $R_{25}$ are hydrogen, and p is 1.

Independently in some embodiments of Formula IX, and independently in combination with any embodiments of any other relevant substituent classes, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, both $R_{25}$ are hydrogen, and p is 1.

Independently in some embodiments, and independently in combination with any embodiments of any other relevant substituent classes, if X is $NR_4$, $R_4$ is methyl, $R_1$ is Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and both $R_{25}$ are hydrogen, then p is not 1. Independently in some embodiments, and independently in combination with any embodiments of any other relevant substituent classes, if X is $NR_4$, $R_4$ is methyl, $R_1$ is Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and p is 1, then at least one both $R_{25}$ is not hydrogen. Independently in some embodiments, and independently in combination with any embodiments of any other relevant substituent classes, if X is $NR_4$, $R_4$ is methyl, $R_1$ is Formula IX, $R_{18}$, $R_{19}$, $R_{20}$, $R_{21}$, $R_{22}$, and $R_{23}$ are carbon, y is 0, $R_{24}$ is —$(CR_{25}R_{25})_p$—, both $R_{25}$ are hydrogen, and p is 1, then the ring of Formula IX is not aromatic. Independently in some embodiments, and independently in combination with any embodiments of any other relevant substituent classes, if X is $NR_4$, $R_4$ is methyl, $R_4$ is Formula IX, $R_{18}$, $R_{19}$, $R_{20}$, $R_{21}$, $R_{22}$, and $R_{23}$ are carbon, the ring of Formula IX is aromatic, $R_{24}$ is —$(CR_{25}R_{25})_p$—, both $R_{25}$ are hydrogen, and p is 1, then y is not 0. Independently in some embodiments, and independently in combination with any embodiments of any other relevant substituent classes, if X is $NR_4$, $R_4$ is methyl, $R_1$ is Formula IX, y is 0, the ring of Formula IX is aromatic, $R_{24}$ is —$(CR_{25}R_{25})_p$—, both $R_{25}$ are hydrogen, and p is 1, then at least one of $R_{18}$, $R_{19}$, $R_{20}$, $R_{21}$, $R_{22}$, and $R_{23}$ is not carbon. Independently in some embodiments, and independently in combination with any embodiments of any other relevant substituent classes, if X is $NR_4$, $R_1$ is Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, both $R_{25}$ are hydrogen, and p is 1, then $R_4$ is not methyl. Independently in some embodiments, and independently in combination with any embodiments of any other relevant substituent classes, if $R_4$ is methyl, $R_1$ is Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, both $R_{25}$ are hydrogen, and p is 1, then X is not $NR_4$. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and both $R_{25}$ are hydrogen, then p is not 1. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and p is 1, then at least one both $R_{25}$ is not hydrogen. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, y is 0, $R_{24}$ is —$(CR_{25}R_{25})_p$—, both $R_{25}$ are hydrogen, and p is 1, then the ring of Formula IX is not aromatic. Independently in some embodiments of Formula IX, and independently in combination with any embodiments of any other relevant substituent classes, if $R_{18}$, $R_{19}$, $R_{20}$, $R_{21}$, $R_{22}$, and $R_{23}$ are carbon, the ring of Formula IX is aromatic, $R_{24}$ is —$(CR_{25}R_{25})_p$—, both $R_{25}$ are hydrogen, and p is 1, then y is not 0. Independently in some embodiments of Formula IX, and independently in combination with any embodiments of any other relevant substituent classes, if y is 0, the ring of Formula IX is aromatic, $R_{24}$ is —$(CR_{25}R_{25})_p$—, both $R_{25}$ are hydrogen, and p is 1, then at least one of $R_{18}$, $R_{19}$, $R_{20}$, $R_{21}$, $R_{22}$, and $R_{23}$ is not carbon.

N6

Independently in some embodiments of —$R_h$—$(R_g)_j$—$R_f$, and independently in combination with any embodiments of any other relevant substituent classes, $R_h$ is $C(R_{59}R_{60})$, j is 2 to 32, and $R_f$ is $C(R_{45}R_{46}R_{47})$, and every other, every third, or every fourth $R_g$, if present, is O, wherein every other $R_g$, is $C(R_{42}R_{43})$, wherein $R_{59}$, $R_{60}$, $R_{42}$, and $R_{43}$ are independently hydrogen, $C_1$-$C_3$ alkyl, or $C_1$-$C_3$ alkoxy, wherein $R_{45}$, $R_{46}$, $R_{47}$, $R_{48}$, $R_{49}$, and $R_{50}$ are independently, as valency permits, absent, hydrogen, —OH, =O, —SH, =N, —$NH_2$, —$NH_3$, —$CH_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$alkyl, phenyl, aryl, or $C_5$-$C_6$ cyclic.

Independently in some embodiments of —$R_h$—$(R_g)_j$—$R_f$, and independently in combination with any embodiments of any other relevant substituent classes, $R_h$ is $C(R_{59}R_{60})$, and j is 5, 8, 11, 14, 17, 20, 23, 26, 29, or 32, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{59}$, $R_{60}$, $R_{42}$, and $R_{43}$ are independently hydrogen, $C_1$-$C_3$ alkyl, or $C_1$-$C_3$ alkoxy.

Independently in some embodiments of —$R_h$—$(R_g)_j$—$R_f$, and independently in combination with any embodiments of any other relevant substituent classes, $R_h$ is $C(R_{59}R_{60})$, j is 5, 8, 11, 14, 17, 20, 23, 26, 29, or 32, and $R_f$ is $C(R_{45}R_{46}R_{47})$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{59}$, $R_{60}$, $R_{42}$, $R_{43}$, $R_{45}$, $R_{46}$, and $R_{47}$ are independently hydrogen, $C_1$-$C_3$ alkyl, or $C_1$-$C_3$ alkoxy, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently G-G, alkyl, phenyl, aryl, or $C_5$-$C_6$ cyclic.

Independently in some embodiments of —$R_h$—$(R_g)_j$—$R_f$, and independently in combination with any embodiments of any other relevant substituent classes, $R_h$ is $C(R_{59}R_{60})$, and j is 11, wherein the first, third, fourth, sixth, seventh, ninth, and tenth $R_g$ are $C(R_{42}R_{43})$ and the second, fifth, eighth, and eleventh $R_g$ are O, wherein $R_{59}$, $R_{60}$, $R_{42}$, and $R_{43}$ are independently hydrogen, $C_1$-$C_3$ alkyl, or $C_1$-$C_3$ alkoxy.

Independently in some embodiments of —$R_h$—$(R_g)_j$—$R_f$, and independently in combination with any embodiments of any other relevant substituent classes, $R_h$ is $C(R_{59}R_{60})$, j is 11, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, and tenth $R_g$ are $C(R_{42}R_{43})$ and the second, fifth, eighth, and eleventh $R_g$ are O, wherein $R_{59}$, $R_{60}$, $R_{42}$, and $R_{43}$ are independently hydrogen, $C_1$-$C_3$ alkyl, or $C_1$-$C_3$ alkoxy, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently G-G, alkyl, phenyl, aryl, or $C_5$-$C_6$ cyclic.

Independently in some embodiments of —$R_h$—$(R_g)_j$—$R_f$, and independently in combination with any embodiments of any other relevant substituent classes, $R_h$ is $C(R_{59}R_{60})$, and j is 5, 8, 11, 14, 17, 20, 23, 26, 29, or 32, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{59}$, $R_{60}$, $R_{42}$, and $R_{43}$ are independently hydrogen, $C_1$-$C_3$ alkyl, or $C_1$-$C_3$ alkoxy.

Independently in some embodiments of —$R_h$—$(R_g)_j$—$R_f$, and independently in combination with any embodiments of any other relevant substituent classes, $R_h$ is $C(R_{59}R_{60})$, j is 5, 8, 11, 14, 17, 20, 23, 26, 29, or 32, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, twenty-ninth, and thirty-second $R_g$, if present, are O, wherein $R_{59}$, $R_{60}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

Independently in some embodiments of —$R_h$—$(R_g)_j$—$R_f$, and independently in combination with any embodiments of any other relevant substituent classes, $R_h$ is $C(R_{59}R_{60})$, and j is 11, wherein the first, third, fourth, sixth, seventh, ninth, and tenth $R_g$ are $C(R_{42}R_{43})$ and the second, fifth, eighth, and eleventh $R_g$ are O, wherein $R_{59}$, $R_{60}$, $R_{42}$, and $R_{43}$ are hydrogen.

Independently in some embodiments of $R_1$; and independently in combination with any embodiments of any other relevant substituent classes, $R_1$ is —$R_h$—$(R_g)_j$—$R_f$, $R_h$ is $C(R_{59}R_{60})$, j is 11, and $R_f$ is $C(R_{45}R_{46}R_{47})$, wherein the first, third, fourth, sixth, seventh, ninth, and tenth $R_g$ are $C(R_{42}R_{43})$ and the second, fifth, eighth, and eleventh $R_g$ are O, wherein $R_{59}$, $R_{60}$, $R_{42}$, $R_{43}$, $R_{45}$, $R_{46}$, and $R_{47}$ are hydrogen.

Independently in some embodiments of —$R_h$—$(R_g)_j$—$R_f$, and independently in combination with any embodiments of any other relevant substituent classes, $R_h$ is $C(R_{59}R_{60})$, j is 11, and $R_f$ is $C(R_{45}R_{46}R_{47})$, wherein the first, third, fourth, sixth, seventh, ninth, and tenth $R_g$ are $C(R_{42}R_{43})$ and the second, fifth, eighth, and eleventh $R_g$ are O, wherein $R_{59}$, $R_{60}$, $R_{42}$, $R_{43}$, $R_{45}$, $R_{46}$, and $R_{43}$ are hydrogen.

Independently in some embodiments of —$R_h$—$(R_g)_j$—$R_f$, and independently in combination with any embodiments of any other relevant substituent classes, if $R_h$ is $C(R_{59}R_{60})$, j is 11, $R_f$ is $C(R_{45}R_{46}R_{47})$, the first, third, fourth, sixth, seventh, ninth, and tenth $R_g$ are $C(R_{42}R_{43})$, the second, fifth, eighth, and eleventh $R_g$ are O, then at least one of $R_{59}$, $R_{60}$, $R_{42}$, $R_{43}$, $R_{45}$, $R_{46}$, and $R_{47}$ is not hydrogen. Independently in some embodiments of —$R_h$—$(R_g)_j$—$R_f$, and independently in combination with any embodiments of any other relevant substituent classes, if $R_h$ is $C(R_{59}R_{60})$, j is 11, $R_f$ is $C(R_{45}R_{46}R_{47})$, the first, third, fourth, sixth, seventh, ninth, and tenth $R_g$ are $C(R_{42}R_{43})$, and $R_{50}$, $R_{60}$, $R_{42}$, $R_{43}$, $R_{45}$, $R_{46}$, and $R_{47}$ are hydrogen, then at least one of the second, fifth, eighth, and eleventh $R_g$ is not O. Independently in some embodiments of —$R_h$—$(R_g)_j$—$R_f$, and independently in combination with any embodiments of any other relevant substituent classes, if $R_h$ is $C(R_{59}R_{60})$, j is 11, $R_f$ is $C(R_{45}R_{46}R_{47})$, the second, fifth, eighth, and eleventh $R_g$ are O, and $R_{59}$, $R_{60}$, $R_{42}$, $R_{43}$, $R_{45}$, $R_{46}$, and $R_{47}$ are hydrogen, then at least one of the first, third, fourth, sixth, seventh, ninth, and tenth $R_g$ is not $C(R_{42}R_{43})$. Independently in some embodiments of —$R_h$—$(R_g)_j$—$R_f$, and independently in combination with any embodiments of any other relevant substituent classes, if $R_h$ is $C(R_{59}R_{60})$, $R_f$ is $C(R_{45}R_{46}R_{47})$, the first, third, fourth, sixth, seventh, ninth, and tenth $R_g$ are $C(R_{42}R_{43})$, the second, fifth, eighth, and eleventh $R_g$ are O, and $R_{59}$, $R_{60}$, $R_{42}$, $R_{43}$, $R_{45}$, $R_{46}$, and $R_{47}$ are hydrogen, them j is not 11.

N7

Independently in some embodiments, and independently in combination with any embodiments of any other relevant substituent classes, X is O, S, or $NR_4$, $R_4$ is hydrogen, $C_1$-$C_3$ alkyl, or $C_1$-$C_3$ alkoxy, $R_4$ is —$R_h$—$(R_g)_j$—$R_f$, $R_h$ is absent, $C(R_{59}R_{60})$, O, S, $S(O)_2$, $S(O)_3$, or $NR_{61}$, j is 0 to 12, each $R_g$ is $C(R_{42}R_{43})$, $R_f$ is hydrogen, $C(R_{45}R_{46}R_{47})$, OH, SH, or $NR_{48}R_{49}R_{50}$, $R_{59}$, $R_{60}$, $R_{61}$, $R_{42}$, $R_{43}$, $R_{45}$, $R_{46}$, $R_{48}$, $R_{49}$, $R_{48}$, and $R_{43}$ are independently hydrogen, $C_1$-$C_3$ alkyl, or $C_1$-$C_3$ alkoxy, $R_{47}$ and $R_{50}$ are independently absent, hydrogen, $C_1$-$C_3$ alkyl, or $C_1$-$C_3$ alkoxy. Independently in some embodiments of —$R_h$—$(R_g)_j$—$R_f$, and independently in combination with any embodiments of any other relevant substituent classes, $R_h$ is absent, $C(R_{59}R_{60})$, O, S, $S(O)_2$, $S(O)_3$, or $NR_{61}$, j is 0 to 12, each $R_g$ is $C(R_{42}R_{43})$, $R_f$ is hydrogen, $C(R_{45}R_{46}R_{47})$, OH, SH, or $NR_{48}R_{49}R_{50}$, $R_{59}$, $R_{60}$, $R_{61}$, $R_{42}$, $R_{43}$, $R_{45}$, $R_{46}$, $R_{48}$, $R_{49}$, $R_{48}$, and $R_{49}$ are independently hydrogen, $C_1$-$C_3$ alkyl, or $C_1$-$C_3$ alkoxy, $R_{47}$ and $R_{50}$ are independently absent, hydrogen, $C_1$-$C_3$ alkyl, or $C_1$-$C_3$ alkoxy. In some embodiments, X is O. In some embodiments, X is S. In some embodiments, X is $NR_4$, $R_4$ is hydrogen, $C_1$-$C_3$ alkyl, or $C_1$-$C_3$ alkoxy. In some embodiments, $R_4$ is hydrogen. In some embodiments, $R_4$ is $C_1$-$C_3$ alkyl. In some embodiments, $R_4$ is $C_1$-$C_3$ alkoxy. In some embodiments, $R_4$ is methyl. In some embodiments, $R_4$ is —O—$CH_3$. In some embodiments, $R_h$ is absent. In some embodiments, $R_h$ is $C(R_{59}R_{60})$. In some embodiments, $R_h$ is O. In some embodiments, $R_h$ is S. In some embodiments, $R_h$ is $S(O)_2$. In some embodiments, $R_h$ is $S(O)_3$. In some embodiments, $R_h$ is $NR_{61}$. In some embodiments, at least one $R_{42}$ or $R_{43}$ is not hydrogen. In some embodiments, at least one $R_{48}$ or $R_{49}$ is not hydrogen. In some embodiments j is 0. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10. In some embodiments j is 11. In some embodiments j is 12. In some embodiments $R_4$ is hydrogen, methyl, ethyl, or butyl.

Independently in some embodiments, and independently in combination with any embodiments of any other relevant substituent classes, X is $NR_4$, $R_4$ is methyl, $R_1$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{48}$ is —$CH_3$, $R_{42}$, $R_{43}$, and $R_{49}$ are hydrogen, $R_{50}$ is absent.

Independently in some embodiments of —$R_h$—$(R_g)_j$—$R_f$, and independently in combination with any embodiments of any other relevant substituent classes, $R_h$ is absent, j is 6, $R_g$ are $C(R_{42}R_{43})$, $R_f$ is $NR_{48}R_{49}R_{50}$, $R_{48}$ is —$CH_3$, $R_{42}$, $R_{43}$, and $R_{49}$ are hydrogen, $R_{50}$ is absent.

Independently in some embodiments, and independently in combination with any embodiments of any other relevant substituent classes, if X is $NR_4$, $R_4$ is methyl, $R_1$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{48}$ is —$CH_3$, and $R_{42}$, $R_{43}$, and $R_{43}$ are hydrogen, then $R_{50}$ is present. Independently in some embodiments, and independently in combination with any embodiments of any other relevant substituent classes, if X is $NR_4$, $R_4$ is methyl, $R_1$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{43}$ is —$CH_3$, and $R_{50}$ is absent, then at least one of $R_{42}$, $R_{43}$, and $R_{49}$ is not hydrogen. Independently in some embodiments, and independently in combination with any embodiments of any other relevant substituent classes, if X is $NR_4$, $R_4$ is methyl, $R_1$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{42}$, $R_{43}$, and $R_{49}$ are hydrogen, and $R_{50}$ is absent, then $R_{48}$ is not —$CH_3$. Independently in some embodiments, and independently in combination with any embodiments of any other relevant substituent classes, if X is $NR_4$, $R_4$ is methyl, $R_4$ is —$R_h$—$(R_g)_j$—$R_f$, $R_h$ is absent, j is 6, $R_g$ are $C(R_{42}R_{43})$, $R_{48}$ is —$CH_3$, $R_{42}$, $R_{43}$, and $R_{49}$ are hydrogen, and $R_{50}$ is absent, then $R_f$ is not $NR_{48}R_{49}R_{50}$. Independently in some embodiments, and independently in combination with any embodiments of any other relevant substituent classes, if X is $NR_4$, $R_4$ is methyl, $R_1$ is —$R_h$—$(R_g)_j$—$R_f$, $R_h$ is absent, j is 6, $R_f$ is $NR_{48}R_{49}R_{50}$, $R_{48}$ is —$CH_3$, $R_{42}$, $R_{43}$, and $R_{49}$ are hydrogen, and $R_{50}$ is absent, then at least one $R_g$ is not $C(R_{42}R_{43})$. Independently in some embodiments, and independently in combination with any embodiments of any other relevant substituent classes, if X is $NR_4$, $R_4$ is methyl, $R_1$ is —$R_h$—$(R_g)_j$—$R_f$, $R_h$ is absent, $R_g$ are $C(R_{42}R_{43})$, $R_f$ is $NR_{48}R_{49}R_{50}$, $R_{43}$ is —$CH_3$, $R_{42}$, $R_{43}$, and $R_{49}$ are hydrogen, and $R_{50}$ is absent, then j is not 6. Independently in some embodiments, and independently in combination with any embodiments of any other relevant substituent classes, if X is $NR_4$, $R_1$ is —$R_h$—$(R_g)_j$—$R_f$, j is 6, $R_g$ are $C(R_{42}R_{43})$, $R_f$ is $NR_{48}R_{49}R_{50}$, $R_{48}$ is —$CH_3$, $R_{42}$, $R_{43}$, and $R_{49}$ are hydrogen, and $R_{50}$ is absent, then $R_h$ is present. Independently in some embodiments of $R_1$; and independently in combination with any embodiments of any other relevant substituent classes, if X is $NR_4$, $R_1$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{48}$ is —$CH_3$, $R_{42}$, $R_{43}$, and $R_{43}$ are hydrogen, and $R_{50}$ is absent, then $R_4$ is not methyl. Independently in some embodiments of $R_1$; and independently in combination with any embodiments of any other relevant substituent classes, if $R_4$ is —$R_h$—$(R_g)_j$—$R_f$, $R_h$ is absent, j is 6, $R_g$ are $C(R_{42}R_{43})$, $R_f$ is $NR_{48}R_{49}R_{50}$, $R_{43}$ is —$CH_3$, $R_{42}$, $R_{43}$, and $R_{49}$ are hydrogen, and $R_{50}$ is absent, then X is not $NR_4$. Independently in some embodiments of —$R_h$—$(R_g)_j$—$R_f$, and independently in combination with any embodiments of any other relevant substituent classes, if $R_h$ is absent, j is 6, $R_g$ are $C(R_{42}R_{43})$, $R_f$ is $NR_{48}R_{49}R_{50}$, $R_{48}$ is —$CH_3$, and $R_{42}$, $R_{43}$, and $R_{49}$ are hydrogen, then $R_{50}$ is present. Independently in some embodiments of —$R_h$—$(R_g)_j$—$R_f$ and independently in combination with any embodiments of any other relevant substituent classes, if $R_h$ is absent, j is 6, $R_g$ are $C(R_{42}R_{43})$, $R_f$ is $NR_{48}R_{49}R_{50}$, $R_{48}$ is —$CH_3$, and $R_{50}$ is absent, then at least one of $R_{42}$, $R_{43}$, and $R_{49}$ is not hydrogen. Independently in some embodiments of —$R_h$—$(R_g)_j$—$R_f$ and independently in combination with any embodiments of any other relevant substituent classes, if $R_h$ is absent, j is 6, $R_g$ are $C(R_{42}R_{43})$, $R_f$ is $NR_{48}R_{49}R_{50}$, $R_{42}$, $R_{43}$, and $R_{43}$ are hydrogen, and $R_{50}$ is absent, then $R_{48}$ is not —$CH_3$. Independently in some embodiments of —$R_h$—$(R_g)_j$—$R_f$, and independently in combination with any embodiments of any other relevant substituent classes, if $R_h$ is absent, j is 6, $R_g$ are $C(R_{42}R_{43})$, $R_{48}$ is —$CH_3$, $R_{42}$, $R_{43}$, and $R_{49}$ are hydrogen, and $R_{50}$ is absent, then $R_f$ is not $NR_{48}R_{49}R_{50}$. Independently in some embodiments of —$R_h$—$(R_g)_j$—$R_f$ and independently in combination with any embodiments of any other relevant substituent classes, if $R_h$ is absent, j is 6, $R_f$ is $NR_{48}R_{49}R_{50}$, $R_{48}$ is —$CH_3$, $R_{42}$, $R_{43}$, and $R_{19}$ are hydrogen, and $R_{50}$ is absent, then at least one $R_g$ is not $C(R_{42}R_{43})$. Independently in some embodiments of —$R_h$—$(R_g)_j$—$R_f$, and independently in combination with any embodiments of any other relevant substituent classes, if $R_h$ is absent, $R_g$ are $C(R_{42}R_{43})$, $R_f$ is $NR_{48}R_{49}R_{50}$, $R_{48}$ is —$CH_3$, $R_{42}$, $R_{43}$, and $R_{43}$ are hydrogen, and $R_{50}$ is absent, then j is not 6. Independently in some embodiments of —$R_h$—$(R_g)_j$—$R_f$, and independently in combination with any embodiments of any other relevant substituent classes, if j is 6, $R_g$ are $C(R_{42}R_{43})$, $R_f$ is $NR_{48}R_{49}R_{50}$, $R_{48}$ is —$CH_3$, $R_{42}$, $R_{43}$, and $R_{49}$ are hydrogen, and $R_{50}$ is absent, then $R_h$ is present.

N8

Independently in some embodiments of —$R_h$—$(R_g)_j$—$R_f$, and independently in combination with any embodiments of any other relevant substituent classes, $R_h$ is $C(R_{59}R_{60})$, j is 1, 4, 7, 10, 13, or 16, the first, third, fourth, sixth, seventh, ninth, tenth, twelfth, thirteenth, fifteenth, and sixteenth $R_g$, if present, are $C(R_{42}R_{43})$, and the second, fifth, eighth, eleventh, and fourteenth $R_g$, if present, are O, wherein $R_{59}$, $R_{60}$, $R_{42}$, and $R_{43}$ are hydrogen.

Independently in some embodiments of —$R_h$—$(R_g)_j$—$R_f$, and independently in combination with any embodiments of any other relevant substituent classes, $R_h$ is $C(R_{59}R_{60})$, j is 1, 4, 7, 10, 13, or 16, the first, third, fourth, sixth, seventh, ninth, tenth, twelfth, thirteenth, fifteenth, and sixteenth $R_g$, if present, are $C(R_{42}R_{43})$, the second, fifth, eighth, eleventh, and fourteenth $R_g$, if present, are O, and $R_f$ is OH, wherein $R_{59}$, $R_{60}$, $R_{42}$, and $R_{43}$ are hydrogen.

Independently in some embodiments of —$R_h$—$(R_g)_j$—$R_f$, and independently in combination with any embodiments of any other relevant substituent classes, $R_h$ is $C(R_{59}R_{60})$, j is 4 to 16, one $R_g$ is O, and the other $R_g$ are $C(R_{42}R_{43})$, wherein $R_{59}$, $R_{60}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the sixth $R_g$ is O.

In some embodiments the fifth from the last $R_g$ is O. In some embodiments the fourth from the last $R_g$ is O. In some embodiments the antepenultimate $R_g$ is O. In some embodiments the penultimate $R_g$ is not O. In some embodiments the last $R_g$ is not O. In some embodiments neither the penultimate $R_g$ nor the last $R_g$ is O.

Independently in some embodiments of $—R_h—(R_g)_j—R_f$, and independently in combination with any embodiments of any other relevant substituent classes, $R_h$ is $C(R_{59}R_{60})$, j is 4 to 16, one $R_g$ is O, the other $R_g$ are $C(R_{42}R_{43})$, and $R_f$ is OH, wherein $R_{59}$, $R_{60}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the sixth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is not O. In some embodiments the last $R_g$ is not O. In some embodiments neither the penultimate $R_g$ nor the last $R_g$ is O.

Independently in some embodiments of $—R_h—(R_g)_j—R_f$, and independently in combination with any embodiments of any other relevant substituent classes, $R_h$ is $C(R_{59}R_{60})$, j is 4, the first, third, and fourth $R_g$ are $C(R_{42}R_{43})$, and the second $R_g$ is O, wherein $R_{59}$, $R_{60}$, $R_{42}$, and $R_{43}$ are hydrogen.

Independently in some embodiments of $R_1$; and independently in combination with any embodiments of any other relevant substituent classes, $R_1$ is $—R_h—(R_g)_j—R_f$, $R_h$ is $C(R_{59}R_{60})$, j is 4, the first, third, and fourth $R_g$ are $C(R_{42}R_{43})$, the second $R_g$ is O, and $R_f$ is OH, wherein $R_{59}$, $R_{60}$, $R_{42}$, and $R_{43}$ are hydrogen.

Independently in some embodiments of $—R_h—(R_g)_j—R_f$, and independently in combination with any embodiments of any other relevant substituent classes, $R_h$ is $C(R_{59}R_{60})$, j is 4, the first, third, and fourth $R_g$ are $C(R_{42}R_{43})$, the second $R_g$ is O, and $R_f$ is OH, wherein $R_{59}$, $R_{60}$, $R_{42}$, and $R_{43}$ are hydrogen.

Independently in some embodiments of $—R_h—(R_g)_j—R_f$, and independently in combination with any embodiments of any other relevant substituent classes, if $R_h$ is $C(R_{59}R_{60})$, j is 4, the first, third, and fourth $R_g$ are $C(R_{42}R_{43})$, the second $R_g$ is O, and $R_f$ is OH, then at least one of $R_{59}$, $R_{60}$, $R_{42}$, and $R_{43}$ is not hydrogen. Independently in some embodiments of $—R_h—(R_g)_j—R_f$, and independently in combination with any embodiments of any other relevant substituent classes, if $R_h$ is $C(R_{59}R_{60})$, j is 4, the first, third, and fourth $R_g$ are $C(R_{42}R_{43})$, the second $R_g$ is O, and $R_{59}$, $R_{60}$, $R_{42}$, and $R_{43}$ are hydrogen, then $R_f$ is not OH. Independently in some embodiments of $—R_h—(R_g)_j—R_f$, and independently in combination with any embodiments of any other relevant substituent classes, if $R_h$ is $C(R_{59}R_{60})$, j is 4, the first, third, and fourth $R_g$ are $C(R_{42}R_{43})$, $R_f$ is OH, and $R_{59}$, $R_{60}$, $R_{42}$, and $R_{43}$ are hydrogen, then the second $R_g$ is not O. Independently in some embodiments of $—R_h—(R_g)_j—R_f$, and independently in combination with any other relevant substituent classes, if $R_h$ is $C(R_{59}R_{60})$, j is 4, the second $R_g$ is O, $R_f$ is OH, and $R_{59}$, $R_{60}$, $R_{42}$, and $R_{43}$ are hydrogen, then at least one of the first, third, and fourth $R_g$ is not $C(R_{42}R_{43})$. Independently in some embodiments of $—R_h—(R_g)_j—R_f$, and independently in combination with any embodiments of any other relevant substituent classes, if $R_h$ is $C(R_{59}R_{60})$, the first, third, and fourth $R_g$ are $C(R_{42}R_{43})$, the second $R_g$ is O, $R_f$ is OH, and $R_{59}$, $R_{60}$, $R_{42}$, and $R_{43}$ are hydrogen, then j is not 4.

N9

In some embodiments $R_4$ is methyl, $R_h$ is $NR_{61}$, j is 4, and $R_g$ is $C(R_{42}R_{43})$, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0, and $R_{fx}$ is $C(R_{45x}R_{46x}R_{47x})$, and wherein $R_{59x}$, $R_{60x}$, $R_{45x}$, $R_{46x}$, $R_{47x}$ are hydrogen.

In some embodiments $R_4$ is methyl, $R_h$ is $NR_{61}$, j is 4, $R_g$ is $C(R_{42}R_{43})$, and $R_f$ is OH, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0, and $R_{fx}$ is $C(R_{45x}R_{46x}R_{47x})$, and wherein $R_{59x}$, $R_{60x}$, $R_{45x}$, $R_{46x}$, $R_{47x}$ are hydrogen.

In some embodiments $R_4$ is methyl, $R_h$ is $NR_{61}$, j is 0 to 10, and $R_g$ is $C(R_{42}R_{43})$, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0 to 10, and $R_{fx}$ is $C(R_{45x}R_{46x}R_{47x})$, and wherein $R_{59x}$, $R_{60x}$, $R_{45x}$, $R_{46x}$, $R_{47x}$ are hydrogen. In some embodiments $R_4$ is methyl, $R_h$ is $NR_{61}$, j is 0 to 10, $R_g$ is $C(R_{42}R_{43})$, and $R_f$ is OH, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0 to 10, and $R_{fx}$ is $C(R_{45x}R_{46x}R_{47x})$, and wherein $R_{59x}$, $R_{60x}$, $R_{45x}$, $R_{46x}$, $R_{47x}$ are hydrogen. In some embodiment j is 0. In some embodiments j is 1. In some embodiment j is 2. In some embodiments j is 3. In some embodiment j is 4. In some embodiments j is 5. In some embodiments j is 6. In some embodiments j is 7. In some embodiment j is 8. In some embodiments j is 9. In some embodiments j is 10. In some embodiment jx is 0. In some embodiment jx is 1. In some embodiment jx is 2. In some embodiments jx is 3. In some embodiment jx is 4. In some embodiments jx is 5. In some embodiment jx is 6. In some embodiments jx is 7. In some embodiment jx is 8. In some embodiments jx is 9. In some embodiments jx is 10. In some embodiments j=jx. In some embodiments j=jx+4. In some embodiments j=2*jx. In some embodiments $R_4$ is hydrogen, methyl, ethyl, or butyl.

In some embodiments $R_4$ is methyl, $R_h$ is $NR_{61}$, j is 0 to 10, and $R_g$ is $C(R_{42}R_{43})$, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0 to 10, and $R_{fx}$ is hydrogen, and wherein $R_{59x}$, $R_{60x}$, $R_{45x}$, $R_{46x}$, $R_{47x}$ are hydrogen. In some embodiments $R_4$ is methyl, $R_h$ is $NR_{61}$, j is 0 to 10, $R_g$ is $C(R_{42}R_{13})$, and $R_f$ is OH, wherein $NR_{61}$ is $—R_{hx}—(R_{gx})_{jx}—R_{fx}$ and $R_{42}$ and $R_{43}$ are hydrogen, wherein $R_{hx}$ is $C(R_{59x}R_{60x})$, jx=0 to 10, and $R_{fx}$ is hydrogen, and wherein $R_{59x}$, $R_{60x}$, $R_{45x}$, $R_{46x}$, $R_{47x}$ are hydrogen. In some embodiment j is 0. In some embodiments j is 1. In some embodiment j is 2. In some embodiments j is 3. In some embodiment j is 4. In some embodiments j is 5. In some embodiments j is 6. In some embodiments j is 7. In some embodiments j is 8. In some embodiments j is 9. In some embodiments j is 10. In some embodiment jx is 0. In some embodiment jx is 1. In some embodiment jx is 2. In some embodiment jx is 3. In some embodiment jx is 4. In some embodiment jx is 5. In some embodiments jx is 6. In some embodiment jx is 7. In some embodiment jx is 8. In some embodiment jx is 9. In some embodiments jx is 10. In some embodiments j=jx. In some embodiments j=jx+4. In some embodiments j=2*jx. In some embodiments $R_4$ is hydrogen, methyl, ethyl, or butyl.

O1

In some embodiments, in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, both $R_{25}$ are hydrogen, and p is 1.

O3

In some embodiments, in Formula XIV, $R_{19}$ is oxygen, $R_{18}$, $R_{20}$, $R_{21}$, and $R_{22}$ are carbon, w is 0, the ring of Formula XIV has no double bonds, $R_{24}$ is —$(CR_{25}R_{25})_p$—, both $R_{25}$ are hydrogen, and p is 1.

O4

In some embodiments, $R_h$ is $C(R_{59}R_{60})$, j is 0, $R_f$ is $C(R_{45}R_{46}R_{47})$, wherein $R_{45}$, $R_{46}$, and $R_{47}$ are fluorine, wherein $R_{59}$ and $R_{60}$ are hydrogen. In some embodiments, j is an integer from 0 to 5, wherein each $R_g$ is $C(R_{42}R_{43})$, wherein $R_{42}$ and $R_{43}$ are hydrogen. In some embodiments, j is 1. In some embodiments, j is 2. In some embodiments, j is 3. In some embodiments, j is 4. In some embodiments, j is 5.

O5

In some embodiments $R_h$ is $C(R_{59}R_{60})$, j is 2, and $R_g$ is $C(R_{42}R_{43})$, wherein $R_{42}$ and $R_{43}$ are absent and $R_{59}$ and $R_{60}$ are hydrogen. In some embodiments $R_h$ is $C(R_{59}R_{60})$, j is 2, $R_g$ is $C(R_{42}R_{43})$, and $R_f$ is hydrogen, wherein $R_{42}$ and $R_{43}$ are absent and $R_{59}$ and $R_{60}$ are hydrogen. In some embodiments $R_h$ is $C(R_{59}R_{60})$, j is 2 to 12, and $R_g$ is $C(R_{42}R_{43})$, wherein $R_{42}$ and $R_{43}$ are absent on one pair of adjacent $R_g$, $R_{42}$ and $R_{43}$ are hydrogen on the other $R_g$, and $R_{59}$ and $R_{60}$ are hydrogen. In some embodiments $R_h$ is $C(R_{59}R_{60})$, j is 2 to 12, $R_g$ is $C(R_{42}R_{43})$, and $R_f$ is hydrogen, wherein $R_{42}$ and $R_{43}$ are absent on one pair of adjacent $R_g$, $R_{42}$ and $R_{43}$ are hydrogen on the other $R_g$, and $R_{59}$ and $R_{60}$ are hydrogen. In some embodiments $R_{42}$ and $R_{43}$ are absent on the first and second $R_g$. In some embodiments $R_{42}$ and $R_{43}$ are absent on the second and third $R_g$. In some embodiments $R_{42}$ and $R_{43}$ are absent on the third and fourth $R_g$. In some embodiments $R_{42}$ and $R_{43}$ are absent on the fourth and fifth $R_g$. In some embodiments $R_{42}$ and $R_{43}$ are absent on the fifth and sixth $R_g$. In some embodiments $R_{42}$ and $R_{43}$ are absent on the sixth and seventh $R_g$. In some embodiments $R_{42}$ and $R_{43}$ are absent on the seventh and eighth $R_g$. In some embodiments $R_{42}$ and $R_{43}$ are absent on the eighth and ninth $R_g$. In some embodiments $R_{42}$ and $R_{43}$ are absent on the ninth and tenth $R_g$. In some embodiments $R_{42}$ and $R_{43}$ are absent on the tenth and eleventh $R_g$. In some embodiments $R_{42}$ and $R_{43}$ are absent on the eleventh and twelfth $R_g$.

O6

In some embodiments, in Formula XIV, $R_{19}$ is oxygen, $R_{18}$, $R_{20}$, $R_{21}$, and $R_{22}$ are carbon, w is 0, the ring of Formula XIV has double bonds between $R_{20}$ and $R_{21}$ and between $R_{22}$ and $R_{18}$, $R_{24}$ is —$(CR_{25}R_{25})_p$—, both $R_{25}$ are hydrogen, and p is 1.

O7

Independently in some embodiments of Formula XIV, and independently in combination with any embodiments of any other relevant substituent classes, $R_{21}$ and $R_{22}$ are absent, $R_{18}$, $R_{19}$, and $R_{20}$ are carbon, w is 3, the ring of Formula XIV has no double bonds, $R_{24}$ is —$(CR_{25}R_{25})_p$—, and p is 1, two $R^e$ are —$CH_3$ and one $R^e$ is —$R_h$—$(R_g)_j$—$R_f$, $R_h$ is $C(R_{59}R_{60})$, $R_{59}$ is hydrogen, $R_{60}$ is absent, j is 0, $R_f$ is $C(R_{45}R_{46}R_{47})$, $R_{45}$ and $R_{46}$ are —$CH_3$, $R_{47}$ is absent, and there is a double bond between $R_h$ and $R_f$, the two $R^e$ that are —$CH_3$ are both on $R_{19}$ or $R_{20}$.

In some embodiments, one $R^e$ is —$CH_3$ and two $R^e$ are —$R_h$—$(R_g)_j$—$R_f$. In some embodiments, one $R^e$ is —$R_h$—$(R_g)_j$—$R_f$, and two $R^e$ are —$CH_3$. In some embodiments, each $R^e$ is —$R_h$—$(R_g)_j$—$R_f$. In some embodiments, each $R^e$ is —$CH_3$. In some embodiments, w is 4. In some embodiments, w is 3. In some embodiments, w is 2. In some embodiments, w is 1. In some embodiments, w is 0.

O8

In some embodiments $R_h$ is $C(R_{59}R_{60})$, and j is 0, wherein $R_{59}$ and $R_{60}$ are hydrogen. In some embodiments $R_h$ is $C(R_{59}R_{60})$, and j is 0 to 10, wherein $R_{59}$ and $R_{60}$ are hydrogen. In some embodiments $R_h$ is $C(R_{59}R_{60})$, j is 0, and $R_f$ is $C(R_{45}R_{46}R_{47})$, wherein $R_{59}$, $R_{60}$, $R_{45}$, $R_{46}$, and $R_{47}$ are hydrogen. In some embodiments $R_h$ is $C(R_{59}R_{60})$, j is 0 to 10, and $R_f$ is $C(R_{45}R_{46}R_{47})$, wherein $R_{59}$, $R_{60}$, $R_{45}$, $R_{46}$, and $R_{47}$ are hydrogen. In some embodiment) is 0. In some embodiments) is 1. In some embodiment) is 2. In some embodiments) is 3. In some embodiment) is 4. In some embodiments) is 5. In some embodiments) is 6. In some embodiments) is 7. In some embodiment) is 8. In some embodiments) is 9. In some embodiments) is 10.

O9

In some embodiments $R_h$ is $C(R_{59}R_{60})$, j is 2, and $R_g$ is $C(R_{42}R_{43})$, wherein $R_{42}$ and $R_{43}$ are absent and $R_{50}$ and $R_{60}$ are hydrogen. In some embodiments $R_h$ is $C(R_{59}R_{60})$, j is 2 to 12, and $R_g$ is $C(R_{42}R_{43})$, wherein $R_{42}$ and $R_{43}$ are absent on one pair of adjacent $R_g$, $R_{42}$ and $R_{43}$ are hydrogen on the other $R_g$, and $R_{59}$ and $R_{60}$ are hydrogen. In some embodiments, $R_{100}$, $R_{101}$, and $R_{102}$ are each independently $C_1$-$C_6$ alkyl, phenyl, aryl, or $C_5$-$C_6$ cyclic. In some embodiments $R_h$ is $C(R_{59}R_{60})$, j is 2, $R_g$ is $C(R_{42}R_{43})$, and $R_f$ is $Si(R_{100}R_{101}R_{102})$, wherein $R_{100}$, $R_{101}$, and $R_{102}$ are methyl, $R_{42}$ and $R_{43}$ are absent and $R_{59}$ and $R_{60}$ are hydrogen. In some embodiments $R_h$ is $C(R_{59}R_{60})$, j is 2 to 12, $R_g$ is $C(R_{42}R_{43})$, and $R_f$ is $Si(R_{100}R_{101}R_{102})$, wherein $R_{100}$, $R_{101}$, and $R_{102}$ are each independently alkyl, phenyl, aryl, or $C_3$-$C_{20}$ cyclic, $R_{42}$ and $R_{43}$ are absent on one pair of adjacent $R_g$, $R_{42}$ and $R_{43}$ are hydrogen on the other $R_g$, and $R_{59}$ and $R_{60}$ are hydrogen.

In some embodiments, $R_{100}$, $R_{101}$, and $R_{102}$ are each independently $C_1$-$C_3$ alkyl. In some embodiments $R_{42}$ and $R_{43}$ are absent on the first and second $R_g$. In some embodiments, $R_{100}$, $R_{101}$, and $R_{102}$ are each independently $C_1$-$C_6$ alkyl, phenyl, aryl, or $C_5$-$C_6$ cyclic. In some embodiments, $R_{100}$, $R_{101}$, and $R_{102}$ are each independently $C_1$-$C_3$ alkyl.

In some embodiments $R_{42}$ and $R_{43}$ are absent on the first and second $R_g$. In some embodiments $R_{42}$ and $R_{43}$ are absent on the second and third $R_g$. In some embodiments $R_{42}$ and $R_{43}$ are absent on the third and fourth $R_g$. In some embodiments $R_{42}$ and $R_{43}$ are absent on the fourth and fifth $R_g$. In some embodiments $R_{42}$ and $R_{43}$ are absent on the fifth and sixth $R_g$. In some embodiments $R_{42}$ and $R_{43}$ are absent on the sixth and seventh $R_g$. In some embodiments $R_{42}$ and $R_{43}$ are absent on the seventh and eighth $R_g$. In some embodiments $R_{42}$ and $R_{43}$ are absent on the eighth and ninth $R_g$. In some embodiments $R_{42}$ and $R_{43}$ are absent on the ninth and tenth $R_g$. In some embodiments $R_{42}$ and $R_{43}$ are absent on the tenth and eleventh $R_g$. In some embodiments $R_{42}$ and $R_{43}$ are absent on the eleventh and twelfth $R_g$.

O10

In some embodiments $R_h$ is $C(R_{59}R_{60})$, and j is 0, wherein $R_{59}$ and $R_{60}$ are hydrogen. In some embodiments $R_h$ is $C(R_{59}R_{60})$, and j is 0, wherein $R_{59}$ and $R_{60}$ are —$C(R_{56}R_{57}R_{58})$, and $R_{56}$, $R_{57}$, and $R_{58}$ are hydrogen. In some embodiments $R_h$ is $C(R_{59}R_{60})$, j is 0, and $R_f$ is hydrogen, wherein $R_{59}$ and $R_{60}$ are hydrogen. In some embodiments $R_h$ is $C(R_{59}R_{60})$, j is 0, and $R_f$ is $C(R_{45}R_{46}R_{47})$, wherein $R_{59}$, $R_{60}$, $R_{45}$, $R_{46}$, and $R_{43}$ are hydrogen. In some embodiments $R_h$ is $C(R_{59}R_{60})$, j is 0, and $R_f$ is $C(R_{45}R_{46}R_{47})$, wherein $R_{59}$ and $R_{60}$ are —$C(R_{56}R_{57}R_{58})$, and $R_{45}$, $R_{46}$, Rn, $R_{56}$, $R_{57}$, and $R_{58}$ are hydrogen.

O11

In some embodiments, in Formula IX, $R_{18}$, $R_{19}$, $R_{20}$, $R_{21}$, $R_{22}$, and $R_{23}$ are carbon, y is 1, $R^e$ is —OH, the ring of Formula IX is aromatic, $R_{24}$ is —$(CR_{25}R_{25})_p$—, both $R_{25}$ are hydrogen, and p is 1. In some embodiments, $R^e$ is at position $R_{21}$.

O12 In some embodiments, in Formula IX, $R_{18}$, $R_{19}$, $R_{20}$, $R_{21}$, $R_{22}$, and $R_{23}$ are carbon, y is 1, $R^e$ is —O—$CH_3$, the ring of Formula IX is aromatic, $R_{24}$ is —$(CR_{25}R_{25})_p$—, both $R_{25}$ are hydrogen, and p is 1. In some embodiments, $R^e$ is at position $R_{21}$.

Y1

In some embodiments, in Formula IX, $R_{18}$, $R_{19}$, $R_{20}$, $R_{21}$, $R_{22}$, and $R_{23}$ are carbon, y is 1, $R^e$ is hydroxy, the ring of Formula IX has no double bonds, $R_{24}$ is —$(CR_{25}R_{25})_p$—, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Y2

In some embodiments, in Formula IX, $R_{18}$, $R_{19}$, $R_{20}$, $R_{21}$, $R_{22}$, and $R_{23}$ are carbon, y is 1, $R^e$ is —O—$CH_3$, the ring of Formula IX is aromatic, $R_{24}$ is —$(CR_{25}R_{25})_p$—, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Y3

Independently in some embodiments of Formula XIV, and independently in combination with any embodiments of any other relevant substituent classes, $R_{19}$ and $R_{21}$ are nitrogen, $R_{18}$, $R_{20}$, and $R_{22}$ are carbon, w is 1, the ring of Formula XIV has double bonds between $R_{20}$ and $R_{21}$ and between $R_{22}$ and $R_{18}$, $R_{24}$ is —$(CR_{25}R_{25})_p$—, and p is 0.

Y4

In some embodiments, in Formula IX, $R_{18}$, $R_{19}$, $R_{20}$, $R_{21}$, $R_{22}$, and $R_{23}$ are carbon, y is 1, $R^e$ is —$CH_2$—OH, the ring of Formula IX is aromatic, $R_{24}$ is —$(CR_{25}R_{25})_p$—, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Y5

In some embodiments, in Formula IX, $R_{18}$, $R_{19}$, $R_{20}$, $R_{21}$, $R_{22}$, and $R_{23}$ are carbon, y is 1, $R^e$ is methyl, the ring of Formula IX is aromatic, $R_{24}$ is —$(CR_{25}R_{25})_p$—$X_b$—$(CR_{25}R_{25})_q$—, p is 0, q is 0, and $X_b$ is $S(O)_2$.

Y6 Left

In some embodiments $R_h$ is $NR_{61}$, j is 1, and $R_g$ is $C(R_{42}R_{43})$, wherein $R_{61}$ is —$R_{hx}$—$(R_{gx})_{jx}$—$R_{fx}$, and $R_{42}$ and $R_{43}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen. In some embodiments $R_h$ is $NR_{61}$, j is 1, $R_g$ is $C(R_{42}R_{43})$, and $R_f$ is $C(R_{45}R_{46}R_{47})$, wherein $R_{61}$ is —$R_{hx}$—$(R_{gx})_{jx}$—$R_{fx}$, and $R_{42}$, $R_{43}$, $R_{45}$, $R_{46}$, and $R_{47}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen.

In some embodiments $R_h$ is $NR_{61}$, j is 0 to 10, and each $R_g$ is $C(R_{42}R_{43})$, wherein Ru is —$R_{hx}$—$(R_{gx})_{jx}$—$R_{fx}$, and $R_{42}$ and $R_{43}$ are hydrogen, wherein $R_{hx}$ is $C(R_{59x}R_{60x})$, jx=0 to 10, $R_{gx}$ is $C(R_{42x}R_{43x})$, and $R_{fx}$ is $C(R_{45x}R_{46x}R_{47x})$, and wherein $R_{59x}$, $R_{60x}$, $R_{42x}$, $R_{43x}$, $R_{45x}$, $R_{46x}$, $R_{47x}$ are hydrogen. In some embodiments $R_h$ is $NR_{61}$, j is 0 to 10, each $R_g$ is $C(R_{42}R_{43})$, and $R_f$ is $C(R_{45}R_{46}R_{47})$, wherein $R_{61}$ is —$R_{hx}$—$(R_{gx})_{jx}$—$R_{fx}$, and $R_{42}$, $R_{43}$, $R_{45}$, $R_{46}$, and $R_{47}$ are hydrogen, wherein $R_{hx}$ is $C(R_{59x}R_{60x})$, jx=0 to 10, $R_{gx}$ is $C(R_{42x}R_{43x})$, and $R_{fx}$ is $C(R_{45x}R_{46x}R_{47x})$, and wherein $R_{59x}$, $R_{60x}$, $R_{42x}$, $R_{43x}$, $R_{45x}$, $R_{46x}$, $R_{47x}$ are hydrogen. In some embodiments j=jx. In some embodiments j and jx are 0. In some embodiment j and jx are 2. In some embodiments j and jx are 3. In some embodiments j and jx are 4.

Y6 Right

In some embodiments $R_h$ is $C(R_{59}R_{60})$, and j is 0, wherein $R_{59}$ and $R_{60}$ are hydrogen. In some embodiments $R_h$ is $C(R_{59}R_{60})$, j is 0 to 10, and each $R_g$ is $C(R_{42}R_{43})$, wherein $R_{59}$, $R_{60}$, $R_{42}$, $R_{43}$ are hydrogen. In some embodiments $R_h$ is $C(R_{59}R_{60})$, j is 0, and $R_f$ is OH, wherein $R_{59}$ and $R_{60}$ are hydrogen. In some embodiments $R_h$ is $C(R_{59}R_{60})$, j is 0 to 10, each $R_g$ is $C(R_{42}R_{43})$, and $R_f$ is OH, wherein $R_{59}$, $R_{60}$, $R_{42}$, $R_{43}$ are hydrogen. In some embodiments j is 1. In some embodiment j is 2. In some embodiments j is 3. In some embodiments j is 4.

Y7

In some embodiments $R_h$ is $C(R_{59}R_{60})$, j is 1, and $R_g$ is O, wherein $R_{59}$, $R_{60}$, $R_{45}$, $R_{46}$, and $R_{47}$ are hydrogen. In some embodiments $R_h$ is absent, j is 1, and $R_g$ is O. In some embodiments $R_h$ is $C(R_{59}R_{60})$, j is 1, $R_g$ is O, and $R_f$ is $C(R_{45}R_{46}R_{47})$, wherein $R_{59}$, $R_{60}$, $R_{45}$, $R_{46}$, and $R_{47}$ are hydrogen. In some embodiments $R_h$ is absent, j is 1, $R_g$ is O, and $R_f$ is $C(R_{45}R_{46}R_{47})$, wherein $R_{45}$, $R_{46}$, and $R_{47}$ are hydrogen.

In some embodiments $R_h$ is $C(R_{59}R_{60})$, j is 1 to 10, one $R_g$ is O, and the other $R_g$ are $C(R_{42}R_{43})$, wherein $R_{59}$, $R_{60}$, $R_{42}$, and $R_{43}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

In some embodiments $R_h$ is $C(R_{59}R_{60})$, j is 1 to 10, one $R_g$ is O, the other $R_g$ are $C(R_{42}R_{43})$, and $R_f$ is $C(R_{45}R_{46}R_{47})$, wherein $R_{59}$, $R_{60}$, $R_{42}$, $R_{43}$, $R_{45}$, $R_{46}$, and $R_{43}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

Y9 Left

In some embodiments, $R_8$ is —COOH and in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and p is 0.

Y9 Right

In some embodiments $R_h$ is $C(R_{59}R_{60})$, and j is 0, wherein $R_{59}$ is =O and $R_{60}$ is —OH. In some embodiments $R_h$ is absent, j is 0 to 10, and each $R_g$ is $C(R_{42}R_{43})$, wherein $R_{42}$ and $R_{43}$ are hydrogen. In some embodiments $R_h$ is absent, j is 0, and $R_f$ is $C(R_{45}R_{46}R_{47})$, wherein $R_{45}$ is =O, $R_{43}$ is —OH, and $R_{47}$ is absent. In some embodiments $R_h$ is absent, j is 0 to 10, each $R_g$ is $C(R_{42}R_{43})$, and $R_f$ is $C(R_{45}R_{46}R_{47})$, wherein $R_{43}$ is =O, $R_{46}$ is —OH, $R_{47}$ is absent, and $R_{42}$ and $R_{43}$ are hydrogen.

Y10

In some embodiments $R_h$ is absent, j is 6, and each $R_g$ is $C(R_{42}R_{43})$, wherein $R_{42}$ and $R_{43}$ are hydrogen. In some embodiments $R_h$ is absent, j is 1 to 10, and each $R_g$ is $C(R_{42}R_{43})$, wherein $R_{42}$ and $R_{43}$ are hydrogen. In some embodiments $R_h$ is absent, j is 6, each $R_g$ is $C(R_{42}R_{43})$, and $R_f$ is $C(R_{45}R_{46}R_{47})$, wherein $R_{42}$, $R_{43}$, $R_{45}$, $R_{46}$, and $R_{43}$ are hydrogen. In some embodiments $R_h$ is absent, j is 1 to 10, each $R_g$ is $C(R_{42}R_{43})$, and $R_f$ is $C(R_{45}R_{46}R_{47})$, wherein $R_{42}$, $R_{43}$, $R_{45}$, $R_{46}$, and $R_{47}$ are hydrogen. In some embodiments j is 3. In some embodiments j is 4. In some embodiments j is 5. In some embodiments j is 7. In some embodiment j is 8. In some embodiments j is 9. In some embodiments j is 10.

Y11

In some embodiments $R_h$ is $C(R_{59}R_{60})$, j is 3, the first $R_g$ is O, and the second and third $R_g$ are $C(R_{42}R_{43})$, wherein $R_{59}$, $R_{60}$, $R_{42}$, and $R_{43}$ are hydrogen. In some embodiments $R_h$ is $C(R_{59}R_{60})$, j is 1 to 10, one $R_g$ is O, and the other $R_g$ are $C(R_{42}R_{43})$, wherein $R_{59}$, $R_{60}$, $R_{42}$, and $R_{43}$ are hydrogen. In some embodiments $R_h$ is $C(R_{59}R_{60})$, j is 3, the first $R_g$ is O, the second and third $R_g$ are $C(R_{42}R_{43})$, and $R_f$ is OH, wherein $R_{59}$, $R_{60}$, $R_{42}$, and $R_{43}$ are hydrogen. In some embodiments $R_h$ is $C(R_{59}R_{60})$, j is 1 to 10, one $R_g$ is O, the other $R_g$ are $C(R_{42}R_{43})$, and $R_f$ is OH, wherein $R_{59}$, $R_{60}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is O. In some embodiments the last $R_g$ is O.

In some embodiments $R_h$ is $C(R_{59}R_{60})$, j is 4 to 16, two $R_g$ are O, and the other $R_g$ are $C(R_{42}R_{43})$, wherein $R_{59}$, $R_{60}$, $R_{42}$, and $R_{43}$ are hydrogen. In some embodiments $R_h$ is $C(R_{59}R_{60})$, j is 4 to 16, two $R_g$ are O, the other $R_g$ are $C(R_{42}R_{43})$, and $R_f$ is OH, wherein $R_{59}$, $R_{60}$, $R_{42}$, and $R_{43}$ are hydrogen.

In some embodiments the first and third $R_g$ are O. In some embodiments the first and fourth $R_g$ are O. In some embodiments the first and fifth $R_g$ are O. In some embodiments the first and sixth $R_g$ are O. In some embodiments the first and seventh $R_g$ are O. In some embodiments the first and eighth $R_g$ are O. In some embodiments the first and ninth $R_g$ are O. In some embodiments the first and tenth $R_g$ are O. In some embodiments the first and eleventh $R_g$ are O. In some embodiments the first and twelfth $R_g$ are O. In some embodiments the first and thirteenth $R_g$ are O. In some embodiments the first and fourteenth $R_g$ are O. In some embodiments the first and fifteenth $R_g$ are O. In some embodiments the second and fourth $R_g$ are O. In some embodiments the second and fifth $R_g$ are O. In some embodiments the second and sixth $R_g$ are O. In some embodiments the second and seventh $R_g$ are O. In some embodiments the second and eighth $R_g$ are O. In some embodiments the second and ninth $R_g$ are O. In some embodiments the second and tenth $R_g$ are O. In some embodiments the second and eleventh $R_g$ are O. In some embodiments the second and twelfth $R_g$ are O. In some embodiments the second and thirteenth $R_g$ are O. In some embodiments the second and fourteenth $R_g$ are O. In some embodiments the second and fifteenth $R_g$ are O. In some embodiments the third and fifth $R_g$ are O. In some embodiments the third and sixth $R_g$ are O. In some embodiments the third and seventh $R_g$ are O. In some embodiments the third and eighth $R_g$ are O. In some embodiments the third and ninth $R_g$ are O. In some embodiments the third and tenth $R_g$ are O. In some embodiments the third and eleventh $R_g$ are O. In some embodiments the third and twelfth $R_g$ are O. In some embodiments the third and thirteenth $R_g$ are O. In some embodiments the third and fourteenth $R_g$ are O. In some embodiments the third and fifteenth $R_g$ are O. In some embodiments the fourth and sixth $R_g$ are O. In some embodiments the fourth and seventh $R_g$ are O. In some embodiments the fourth and eighth $R_g$ are O. In some embodiments the fourth and ninth $R_g$ are O. In some embodiments the fourth and tenth $R_g$ are O. In some embodiments the fourth and eleventh $R_g$ are O. In some embodiments the fourth and twelfth $R_g$ are O. In some embodiments the fourth and thirteenth $R_g$ are O. In some embodiments the fourth and fourteenth $R_g$ are O. In some embodiments the fourth and fifteenth $R_g$ are O. In some embodiments the fifth and seventh $R_g$ are O. In some embodiments the fifth and eighth $R_g$ are O. In some embodiments the fifth and ninth $R_g$ are O. In some embodiments the fifth and tenth $R_g$ are O. In some embodiments the fifth and eleventh $R_g$ are O. In some embodiments the fifth and twelfth $R_g$ are O. In some embodiments the fifth and thirteenth $R_g$ are O. In some embodiments the fifth and fourteenth $R_g$ are O. In some embodiments the fifth and fifteenth $R_g$ are O. In some embodiments the sixth and eighth $R_g$ are O. In some embodiments the sixth and ninth $R_g$ are O. In some embodiments the sixth and tenth $R_g$ are O. In some embodiments the sixth and eleventh $R_g$ are O. In some embodiments the sixth and twelfth $R_g$ are O. In some embodiments the sixth and thirteenth $R_g$ are O. In some embodiments the sixth and fourteenth $R_g$ are O. In some embodiments the sixth and fifteenth $R_g$ are O. In some embodiments the seventh and ninth $R_g$ are O. In some embodiments the seventh and tenth $R_g$ are O. In some embodiments the seventh and eleventh $R_g$ are O. In some embodiments the seventh and twelfth $R_g$ are O. In some embodiments the seventh and thirteenth $R_g$ are O. In some embodiments the seventh and fourteenth $R_g$ are O. In some embodiments the seventh and fifteenth $R_g$ are O. In some embodiments the eighth and tenth $R_g$ are O. In some embodiments the eighth and eleventh $R_g$ are O. In some embodiments the eighth and twelfth $R_g$ are O. In some embodiments the eighth and thirteenth $R_g$ are O. In some embodiments the eighth and fourteenth $R_g$ are O. In some embodiments the eighth and fifteenth $R_g$ are O. In some embodiments the ninth and eleventh $R_g$ are O. In some embodiments the ninth and twelfth $R_g$ are O. In some embodiments the ninth and thirteenth $R_g$ are O. In some embodiments the ninth and fourteenth $R_g$ are O. In some embodiments the ninth and fifteenth $R_g$ are O. In some embodiments the tenth and twelfth $R_g$ are O. In some embodiments the tenth and thirteenth $R_g$ are O. In some embodiments the tenth and fourteenth $R_g$ are O. In some embodiments the tenth and fifteenth $R_g$ are O. In some embodiments the eleventh and thirteenth $R_g$ are O. In some embodiments the eleventh and fourteenth $R_g$ are O. In some embodiments the eleventh and fifteenth $R_g$ are O. In some embodiments the twelfth and fourteenth $R_g$ are O. In some embodiments the twelfth and fifteenth $R_g$ are O. In some embodiments the thirteenth and fifteenth $R_g$ are O.

Y12

In some embodiments, in Formula IX, $R_{19}$ is O, $R_{18}$, $R_{20}$, $R_{21}$, $R_{22}$, and $R_{23}$ are carbon, y is 0, the ring of Formula IX has no double bonds, $R_{24}$ is —$(CR_{25}R_{25})_p$—$X_b$—$(CR_{25}R_{25})_q$—, p is 0, q is 1, both $R_{25}$ are hydrogen, and $X_b$ is O.

Y13

In some embodiments, in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, one $R_{25}$ is —OH, the other $R_{25}$ is hydrogen, and p is 1.

Y14

In some embodiments, in Formula IX, $R_{20}$ is N, $R_{18}$, $R_{19}$, $R_{21}$, $R_{22}$, and $R_{23}$ are carbon, y is 0, the ring of Formula IX is aromatic, $R_{24}$ is —$(CR_{25}R_{25})_p$—, and p is 0).

Y15

In some embodiments, in Formula IX, $R_{18}$ is N, $R_{21}$ is $S(O)_2$, $R_{19}$, $R_{20}$, $R_{22}$, and $R_{23}$ are carbon, the ring of Formula IX has no double bonds, $R_{24}$ is —$(CR_{25}R_{25})_p$—, p is 1, both $R_{25}$ are hydrogen.

Y16

In some embodiments $R_h$ is $C(R_{59}R_{60})$, and j is 0, wherein $R_{59}$ and $R_{60}$ are hydrogen. In some embodiments $R_h$ is $C(R_{59}R_{60})$, j is 0 to 10, and each $R_g$ is $C(R_{42}R_{43})$, wherein $R_{59}$, $R_{60}$, $R_{42}$, and $R_{43}$ are hydrogen. In some embodiments $R_h$ is $C(R_{59}R_{60})$, j is 0, and $R_f$ is hydrogen, wherein $R_{59}$ and $R_{60}$ are hydrogen. In some embodiments $R_h$ is $C(R_{59}R_{60})$, j is 0 to 10, each $R_g$ is $C(R_{42}R_{43})$, and $R_f$ is hydrogen, wherein $R_{59}$, $R_{60}$, $R_{42}$, and $R_{43}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{59}R_{60})$, j is 0 to 10, and each $R_g$ is $C(R_{42}R_{43})$, wherein $R_{59}$ is —$R_{hx}$—$(R_{gx})_{jx}$—$R_{fx}$, and $R_{60}$, $R_{42}$, and $R_{43}$ are hydrogen, wherein $R_{hx}$ is $C(R_{59x}R_{60x})$, jx is 0, and $R_{fx}$ is hydrogen, wherein $R_{59x}$ and $R_{60x}$ are hydrogen. In some embodiments j is 0. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{59}R_{60})$, j is 0 to 10, and each $R_g$ is $C(R_{42}R_{43})$, wherein $R_{59}$ is —$R_{hx}$—$(R_{gx})_{jx}$—$R_{fx}$, and $R_{60}$, $R_{42}$, and $R_{43}$ are hydrogen, wherein $R_{hx}$ is $C(R_{59x}R_{60x})$, jx is 0, and $R_{fx}$ is hydrogen, wherein $R_{59x}$ and $R_{60x}$ are hydrogen. In some embodiments $R_h$ is $C(R_{59}R_{60})$, j is 0 to 10, each $R_g$ is $C(R_{42}R_{43})$, and $R_f$ is hydrogen, wherein $R_{59}$ is —$R_{hx}$—$(R_{gx})_{jx}$—$R_{fx}$, and $R_{60}$, $R_{42}$, and $R_{43}$ are hydrogen, wherein $R_{hx}$ is $C(R_{59x}R_{60x})$, jx is 0, and $R_{fx}$ is hydrogen, wherein $R_{59x}$ and $R_{60x}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10. In some embodiments jx is 1. In some embodiment jx is 2. In some embodiments jx is 3. In some embodiment jx is 4. In some embodiments jx is 5. In some embodiments jx is 7. In some embodiment jx is 8. In some embodiments jx is 9. In some embodiments jx is 10. In some embodiments j=jx.

Y17

In some embodiments, in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —$(CR_{25}R_{25})_p$—, and p is 0.

Y18

In some embodiments $R_h$ is $C(R_{59}R_{60})$, and j is 0, wherein $R_{59}$ is =O, and $R_{60}$ is absent. In some embodiments $R_h$ is $C(R_{59}R_{60})$, j is 0, and $R_f$ is $C(R_{45}R_{46}R_{47})$, wherein $R_{59}$ is =O, $R_{60}$ is absent, and $R_{45}$, $R_{46}$, and $R_{47}$ are hydrogen. In some embodiments $R_h$ is $C(R_{59}R_{60})$, j is 0 to 10, and each $R_g$ is $C(R_{42}R_{43})$, wherein $R_{59}$ is =O, $R_{60}$ is absent, and $R_{42}$ and $R_{43}$ are hydrogen. In some embodiments $R_h$ is $C(R_{59}R_{60})$, j is 0 to 10, each $R_g$ is $C(R_{42}R_{43})$, and $R_f$ is $C(R_{45}R_{46}R_{47})$, wherein $R_{59}$ is =O, $R_{60}$ is absent, and $R_{42}$, $R_{43}$, $R_{45}$, $R_{46}$, and $R_{47}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{59}R_{60})$, j is 1 to 10, and each $R_g$ is $C(R_{42}R_{43})$, wherein $R_{43}$ is =O and $R_{43}$ is absent for one $R_g$, $R_{42}$ and $R_{43}$ are hydrogen for the other $R_g$, and $R_{59}$ and $R_{60}$ are hydrogen. In some embodiments $R_h$ is $C(R_{59}R_{60})$, j is 1 to 10, each $R_g$ is $C(R_{42}R_{43})$, and $R_f$ is $C(R_{45}R_{46}R_{47})$, wherein $R_{42}$ is =O and $R_{43}$ is absent for one $R_g$, $R_{42}$ and $R_{43}$ are hydrogen for the other $R_g$, and $R_{59}$, $R_{60}$, $R_{45}$, $R_{46}$, and $R_{47}$ are hydrogen. In some embodiments $R_{43}$ is =O and $R_{43}$ is absent for the last $R_g$. In some embodiments $R_{43}$ is =O and $R_{43}$ is absent for the penultimate $R_g$. In some embodiments $R_{42}$ is =O and $R_{43}$ is absent for the antepenultimate $R_g$. In some embodiments $R_{42}$ is =O and $R_{43}$ is absent for the fourth from the last $R_g$. In some embodiments $R_{43}$ is =O and $R_{43}$ is absent for the fifth from the last $R_g$. In some embodiments $R_{42}$ is =O and $R_{43}$ is absent for the first $R_g$. In some embodiments $R_{43}$ is =O and $R_{43}$ is absent for the second $R_g$. In some embodiments $R_{43}$ is =O and $R_{43}$ is absent for the third $R_g$. In some embodiments $R_{42}$ is =O and $R_{43}$ is absent for the fourth $R_g$. In some embodiments $R_{43}$ is =O and $R_{43}$ is absent for the fifth $R_g$.

In some embodiments $R_h$ is $C(R_{59}R_{60})$, j is 1 to 15, and each $R_g$ is $C(R_{42}R_{43})$, wherein $R_{42}$ is =O and $R_{43}$ is absent for two $R_g$, $R_{42}$ and $R_{43}$ are hydrogen for the other $R_g$, and $R_{59}$ and $R_{60}$ are hydrogen. In some embodiments $R_h$ is $C(R_{59}R_{60})$, j is 1 to 15, each $R_g$ is $C(R_{42}R_{43})$, and $R_f$ is $C(R_{45}R_{46}R_{47})$, wherein $R_{43}$ is =O and $R_{43}$ is absent for two $R_g$, $R_{42}$ and $R_{43}$ are hydrogen for the other $R_g$, and $R_{59}$, $R_{60}$, $R_{45}$, $R_{46}$, and $R_{47}$ are hydrogen. In some embodiments $R_{43}$ is =O and $R_{43}$ is absent the first and third $R_g$. In some embodiments $R_{43}$ is =O and $R_{43}$ is absent the first and fourth $R_g$. In some embodiments $R_{43}$ is =O and $R_{43}$ is absent the first and fifth $R_g$. In some embodiments $R_{42}$ is =O and $R_{43}$ is absent the first and sixth $R_g$. In some embodiments $R_{43}$ is =O and $R_{43}$ is absent the first and seventh $R_g$. In some embodiments $R_{43}$ is =O and $R_{43}$ is absent the first and eighth $R_g$. In some embodiments $R_{43}$ is =O and $R_{43}$ is absent the first and ninth $R_g$. In some embodiments $R_{42}$ is =O and $R_{43}$ is absent the first and tenth $R_g$. In some embodiments $R_{43}$ is =O and $R_{43}$ is absent the first and eleventh $R_g$. In some embodiments $R_{42}$ is =O and $R_{43}$ is absent the first and twelfth $R_g$. In some embodiments $R_{43}$ is =O and $R_{43}$ is absent the first and thirteenth $R_g$. In some embodiments $R_{42}$ is =O and $R_{43}$ is absent the first and fourteenth $R_g$. In some embodiments $R_{43}$ is =O and $R_{43}$ is absent the first and fifteenth $R_g$. In some embodiments $R_{42}$ is =O and $R_{43}$ is absent the second and fourth $R_g$. In some embodiments $R_{42}$ is =O and $R_{43}$ is absent the second and fifth $R_g$. In some embodiments $R_{42}$ is =O and $R_{43}$ is absent the second and sixth $R_g$. In some embodiments $R_{42}$ is =O and $R_{43}$ is absent the second and seventh $R_g$. In some embodiments $R_{42}$ is =O and $R_{43}$ is absent the second and eighth $R_g$. In some embodiments $R_{42}$ is =O and $R_{43}$ is absent the second and ninth $R_g$. In some embodiments $R_{42}$ is =O and $R_{43}$ is absent the second and tenth $R_g$. In some embodiments $R_{42}$ is =O and $R_{43}$ is absent the second and eleventh $R_g$. In some embodiments $R_{42}$ is =O and $R_{43}$ is absent the second and twelfth $R_g$. In some embodiments $R_{42}$ is =O and $R_{43}$ is absent the second and thirteenth $R_g$. In some embodiments $R_{42}$ is =O and $R_{43}$ is absent the second and fourteenth $R_g$. In some embodiments $R_{42}$ is =O and $R_{43}$ is absent the second and fifteenth $R_g$. In some embodiments $R_{42}$ is =O and $R_{43}$ is absent the third and fifth $R_g$. In some embodiments $R_{42}$ is =O and $R_{43}$ is absent the third and sixth $R_g$. In some embodiments $R_{42}$ is =O and $R_{43}$ is absent the third and seventh $R_g$. In some embodiments $R_{42}$ is =O and $R_{43}$ is absent the third and eighth $R_g$. In some embodiments $R_{42}$ is =O and $R_{43}$ is absent the third and ninth $R_g$. In some embodiments $R_{42}$ is =O and $R_{43}$ is absent the third and tenth $R_g$. In some embodiments $R_{42}$ is =O and $R_{43}$ is absent the third and eleventh $R_g$. In some embodiments $R_{42}$ is =O and $R_{43}$ is absent the third and twelfth $R_g$. In some embodiments $R_{42}$ is =O and $R_{43}$ is absent the third and thirteenth $R_g$. In some embodiments $R_{42}$ is =O and $R_{43}$ is absent the third and fourteenth $R_g$. In some embodiments $R_{42}$ is =O and $R_{43}$ is absent the third and fifteenth $R_g$. In some embodiments $R_{42}$ is =O and $R_{43}$ is absent the fourth and sixth $R_g$. In some embodiments $R_{42}$ is =O and $R_{43}$ is absent the fourth and seventh $R_g$. In some embodiments $R_{42}$ is =O and $R_{43}$ is absent the fourth and eighth $R_g$. In some embodiments $R_{42}$ is =O and $R_{43}$ is absent the fourth and ninth $R_g$. In some embodiments $R_{42}$ is =O and $R_{43}$ is absent the fourth and tenth $R_g$. In some embodiments $R_{42}$ is =O and $R_{43}$ is absent the fourth and eleventh $R_g$. In some embodiments $R_{42}$ is =O and $R_{43}$ is absent the fourth and twelfth $R_g$. In some embodiments $R_{42}$ is =O and $R_{43}$ is absent the fourth and thirteenth $R_g$. In some embodiments $R_{42}$ is =O and $R_{43}$ is absent the fourth and fourteenth $R_g$. In some embodiments $R_{42}$ is =O and $R_{43}$ is absent the fourth and fifteenth $R_g$. In some embodiments $R_{42}$ is =O and $R_{43}$ is absent the fifth and seventh $R_g$. In some embodiments $R_{42}$ is =O and $R_{43}$ is absent the fifth and eighth $R_g$. In some embodiments $R_{42}$ is =O and $R_{43}$ is absent the fifth and ninth $R_g$. In some embodiments $R_{42}$ is =O and $R_{43}$ is absent the fifth and tenth $R_g$. In some embodiments $R_{42}$ is =O and $R_{43}$ is absent the fifth and eleventh $R_g$. In some embodiments $R_{42}$ is =O and $R_{43}$ is absent the fifth and twelfth $R_g$. In some embodiments $R_{42}$ is =O and $R_{43}$ is absent the fifth and thirteenth $R_g$. In some embodiments $R_{42}$ is =O and $R_{43}$ is absent the fifth and fourteenth $R_g$. In some embodiments $R_{42}$ is =O and $R_{43}$ is absent the fifth and fifteenth $R_g$. In some embodiments $R_{42}$ is =O and $R_{43}$ is absent the sixth and eighth $R_g$. In some embodiments $R_{42}$ is =O and $R_{43}$ is absent the sixth and ninth $R_g$. In some embodiments $R_{42}$ is =O and $R_{43}$ is absent the sixth and tenth $R_g$. In some embodiments $R_{42}$ is =O and $R_{43}$ is absent the sixth and eleventh $R_g$. In some embodiments $R_{42}$ is =O and $R_{43}$ is absent the sixth and twelfth $R_g$. In some embodiments $R_{42}$ is =O and $R_{43}$ is absent the sixth and thirteenth $R_g$. In some embodiments $R_{42}$ is =O and $R_{43}$ is absent the sixth and fourteenth $R_g$. In some embodiments $R_{42}$ is =O and $R_{43}$ is absent the sixth and fifteenth $R_g$. In some embodiments $R_{42}$ is =O and $R_{43}$ is absent the seventh and ninth $R_g$. In some embodiments $R_{42}$ is =O and $R_{43}$ is absent the seventh and tenth $R_g$. In some embodiments $R_{42}$ is =O and $R_{43}$ is absent the seventh and eleventh $R_g$. In some embodiments $R_{42}$ is =O and $R_{43}$ is absent the seventh and twelfth $R_g$. In some embodiments $R_{42}$ is =O and $R_{43}$ is absent the seventh and thirteenth $R_g$. In some embodiments $R_{42}$ is =O and $R_{43}$ is absent the seventh and fourteenth $R_g$. In some embodiments $R_{42}$ is =O and $R_{43}$ is absent the seventh and fifteenth $R_g$. In some embodiments $R_{42}$ is =O and $R_{43}$ is absent the eighth and tenth $R_g$. In some embodiments $R_{42}$ is =O and $R_{43}$ is absent the eighth and eleventh $R_g$. In some embodiments $R_{42}$ is =O and $R_{43}$ is absent the eighth and twelfth $R_g$. In some embodiments $R_{42}$ is =O and $R_{43}$ is absent the eighth and thirteenth $R_g$. In some embodiments $R_{42}$ is =O and $R_{43}$ is absent the eighth and fourteenth $R_g$. In some embodiments $R_{42}$ is =O and $R_{43}$ is absent the eighth and fifteenth $R_g$. In some embodiments $R_{42}$ is =O and $R_{43}$ is absent the ninth and eleventh $R_g$. In some embodiments $R_{42}$ is =O and $R_{43}$ is absent the ninth and twelfth $R_g$. In some embodiments $R_{42}$ is =O and $R_{43}$ is absent the ninth and thirteenth $R_g$. In some embodiments $R_{42}$ is =O and $R_{43}$ is absent the ninth and fourteenth $R_g$. In some embodiments $R_{42}$ is =O and $R_{43}$ is absent the ninth and fifteenth $R_g$. In some embodiments $R_{42}$ is =O and $R_{43}$ is absent the tenth and twelfth $R_g$. In some embodiments $R_{42}$ is =O and $R_{43}$ is absent the tenth and thirteenth $R_g$. In some embodiments $R_{42}$ is =O and $R_{43}$ is absent the tenth and fourteenth $R_g$. In some embodiments $R_{42}$ is =O and $R_{43}$ is absent the tenth and fifteenth $R_g$. In some embodiments $R_{42}$ is =O and $R_{43}$ is absent the eleventh and thirteenth $R_g$. In some embodiments $R_{42}$ is =O and $R_{43}$ is absent the eleventh and fourteenth $R_g$. In some embodiments $R_{42}$ is =O and $R_{43}$ is absent the eleventh and fifteenth $R_g$. In some embodiments $R_{42}$ is =O and $R_{43}$ is absent the twelfth and fourteenth $R_g$. In some embodiments $R_{42}$ is =O and $R_{43}$ is absent the twelfth and fifteenth $R_g$. In some embodiments the thirteenth and fifteenth $R_g$.

Y19

In some embodiments, in Formula IX, $R_{18}$, $R_{19}$, $R_{20}$, $R_{21}$, $R_{22}$, and $R_{23}$ are carbon, y is 1, $R^e$ is —NH$_2$, the ring of Formula IX is aromatic, $R_{24}$ is —(CR$_{25}$R$_{25}$)$_p$—, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Y20

In some embodiments $R_h$ is $C(R_{59}R_{60})$, j is 6, each $R_g$ is $C(R_{42}R_{43})$, and $R_f$ is $C(R_{45}R_{46}R_{47})$, wherein $R_{59}$, $R_{60}$, $R_{45}$, $R_{46}$, and $R_{47}$ are hydrogen, wherein $R_{43}$ of the first $R_g$ is $C(R_{56}R_{57}R_{58})$, $R_{43}$ of the first through sixth $R_g$ are hydrogen, and $R_{42}$ of the second through sixth $R_g$ are hydrogen, wherein $R_{56}$ is =O, $R_{57}$ is —OH, and $R_{58}$ is absent. In some embodiments $R_h$ is $C(R_{59}R_{60})$, j is 6, and each $R_g$ is $C(R_{42}R_{43})$, wherein $R_{59}$ and Reo are hydrogen, wherein $R_{43}$ of the first $R_g$ is $C(R_{56}R_{57}R_{58})$, $R_{43}$ of the first through sixth $R_g$ are hydrogen, and $R_{42}$ of the second through sixth $R_g$ are hydrogen, wherein $R_{56}$ is =O, $R_{57}$ is —OH, and $R_{58}$ is absent.

In some embodiments $R_h$ is $C(R_{59}R_{60})$, j is 1 to 10, each $R_g$ is $C(R_{42}R_{43})$, and $R_f$ is $C(R_{45}R_{46}R_{47})$, wherein $R_{59}$, $R_{60}$, $R_{45}$, $R_{46}$, and $R_{47}$ are hydrogen, wherein $R_{43}$ of one $R_g$ is $C(R_{56}R_{57}R_{58})$, $R_{42}$ of the other $R_g$ are hydrogen, and $R_{43}$ is hydrogen, and, wherein $R_{56}$ is =O, $R_{57}$ is —OH, and $R_{58}$ is absent. In some embodiments $R_{42}$ of the first $R_g$ is $C(R_{56}R_{57}R_{58})$. In some embodiments $R_h$ is $C(R_{59}R_{60})$, j is 1 to 10, and each $R_g$ is $C(R_{42}R_{43})$, wherein $R_{59}$ and Reo are hydrogen, wherein $R_{43}$ of one $R_g$ is $C(R_{56}R_{57}R_{58})$, $R_{42}$ of the other $R_g$ are hydrogen, and $R_{43}$ is hydrogen, and, wherein $R_{56}$ is =O, $R_{57}$ is —OH, and $R_{58}$ is absent. In some embodiments $R_{43}$ of the first $R_g$ is $C(R_{56}R_{57}R_{58})$. In some embodiments $R_{42}$ of the second $R_g$ is $C(R_{56}R_{57}R_{58})$. In some embodiments $R_{42}$ of the third $R_g$ is $C(R_{56}R_{57}R_{58})$. In some embodiments $R_{42}$ of the fourth $R_g$ is $C(R_{56}R_{57}R_{58})$. In some embodiments $R_{42}$ of the fifth $R_g$ is $C(R_{56}R_{57}R_{58})$. In some embodiments $R_{42}$ of the sixth $R_g$ is $C(R_{56}R_{57}R_{58})$. In some embodiments $R_{42}$ of the seventh $R_g$ is $C(R_{56}R_{57}R_{58})$. In some embodiments $R_{43}$ of the eighth $R_g$ is $C(R_{56}R_{57}R_{58})$. In some embodiments $R_{43}$ of the ninth $R_g$ is $C(R_{56}R_{57}R_{58})$. In some embodiments $R_{42}$ of the tenth $R_g$ is $C(R_{56}R_{57}R_{58})$.

Z1

In some embodiments $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, wherein $R_{59}$, $R_{60}$, $R_{42}$, $R_{43}$, $R_{45}$, $R_{46}$, and $R_{47}$ are hydrogen. In some embodiments $R_h$ is $C(R_{59}R_{60})$, j is 10, and $R_f$ is $C(R_{45}R_{46}R_{47})$, wherein the first, third, fourth, sixth, seventh, ninth, and tenth $R_g$ are $C(R_{42}R_{43})$ and the second, fifth, and eighth $R_g$ are O, wherein $R_{59}$, $R_{60}$, $R_{42}$, $R_{43}$, $R_{45}$, $R_{46}$, and $R_{47}$ are hydrogen.

In some embodiments $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen. In some embodiments $R_h$ is $C(R_{59}R_{60})$, j is 4 to 31, and $R_f$ is $C(R_{45}R_{46}R_{47})$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, $R_{43}$, $R_{45}$, $R_{46}$, and $R_{43}$ are hydrogen.

In some embodiments $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, wherein $R_{59}$, $R_{60}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{59}R_{60})$, j is 10, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, and tenth $R_g$ are $C(R_{42}R_{43})$ and the second, fifth, and eighth $R_g$ are O, wherein $R_{59}$, $R_{60}$, $R_{42}$, and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen.

In some embodiments $R_h$ is $C(R_{59}R_{60})$, j is 4 to 31, and $R_f$ is hydrogen, $C(R_{45}R_{46}R_{47})$, OH, SH, $S(O)_2$, $S(O)_3$, $Si(R_{100}R_{101}R_{102})$, or $NR_{48}R_{49}R_{50}$, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, $R_{43}$ and $R_{43}$ are hydrogen, wherein $R_{45}$, $R_{46}$, $R_{47}$, $R_{48}$, $R_{49}$, and $R_{50}$ are independently, as valency permits, absent, hydrogen, —OH, =O, —SH, =N, —NH$_2$, —NH$_3$, —CH$_3$, or —COOH, and wherein $R_{100}$, $R_{101}$, and $R_{102}$ are each independently alkyl, phenyl, aryl, or $C_3$-$C_{20}$ cyclic. In some embodiments, $R_{100}$, $R_{101}$, and $R_{102}$ are each independently $C_1$-$C_6$ alkyl, phenyl, aryl, or $C_5$-$C_6$ cyclic.

In some embodiments, A, $R_6$, $R_{24}$, and $R^b$ are independently —$R_h$—$(R_g)_j$, wherein $R_h$ is $C(R_{59}R_{60})$, O, S, $S(O)_2$, $S(O)_3$, or $NR_{61}$; and wherein each $R_g$ is independently absent (i.e., j is 0), $C(R_{42}R_{43})$, O, S, $S(O)_2$, $S(O)_3$, or $NR_{44}$;

wherein j is an integer from 0 to 30, wherein $R_{59}$, $R_{60}$, $R_{61}$, $R_{42}$, $R_{43}$, and $R_{44}$ are each independently, as valency permits, absent, hydrogen, =O, —OR$_{51}$, —SR$_{52}$, —NR$_{53}$R$_{54}$R$_{55}$, —C(R$_{56}$R$_{57}$R$_{58}$), or —R$_{hx}$—(R$_{gx}$)$_{jx}$—R$_{fx}$, wherein $R_{51}$, $R_{52}$, $R_{53}$, $R_{54}$, $R_{55}$, $R_{56}$, $R_{57}$, and $R_{58}$ are each independently, as valency permits, absent, hydrogen, —OH, =O, —SH, =NH, —NH$_2$, —NH$_3$, —CH$_3$, or —COOH, wherein the bond between $R_h$ and $R_g$, if present, is single, double, or triple depending on the valency, wherein the bond between each adjacent $R_g$ is single, double, or triple depending on the valency; wherein when $R_h$ is O, S, $S(O)_2$, or $S(O)_3$, the bond between $R_h$ and $R_g$ is not a double or triple bond; wherein when $R_h$ is $NR_{61}$, the bond between $R_h$ and $R_g$ is not a triple bond; wherein when $R_g$ is O, S, $S(O)_2$, or $S(O)_3$, the bond between $R_g$ and $R_h$ is not a double or triple bond; wherein when $R_h$ is $NR_{44}$, the bond between $R_g$ and $R_h$ is not a triple bond; wherein when $R_h$ is O, $R_g$ is not O, S, or $NR_{44}$, and vice versa; wherein when $R_h$ is S, $R_g$ is not O, $S(O)_2$, $S(O)_3$, or $NR_{44}$, and vice versa; wherein when $R_h$ is $S(O)_2$, $R_g$ is not S, $S(O)_2$, or $S(O)_3$, and vice versa; wherein when $R_h$ is $S(O)_3$, $R_g$ is not S, $S(O)_2$, or $S(O)_3$, and vice versa; and wherein when $R_h$ is $NR_{61}$, $R_g$ is not O, or S, and vice versa.

Z2

In some embodiments where A or $R_6$ is Formula IX, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —$(CR_{25}R_{25})_p$—, p is 0 to 10, and $R_{25}$ are independently hydrogen or $C_1$-$C_3$ alkyl. In some embodiments, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —$(CR_{25}R_{25})_p$—, p is 1, and $R_{25}$ are hydrogen.

In some embodiments where A or $R_6$ is Formula IX, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$. In some embodiments, p is 0. In some embodiments p is 1. In some embodiment p is 2. In some embodiments p is 3. In some embodiments p is 4. In some embodiments p is 5. In some embodiments p is 7. In some embodiment p is 8. In some embodiments p is 9. In some embodiments p is 10. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

Z1-Y18

In some embodiments, compounds are represented by the general formula:

—X—R$_1$ wherein X is oxygen, sulfur, or $NR_4$;
wherein $R_4$ is -A-B(—C)$_\delta$ or —$R_6$—$R^b$;
wherein A and $R_6$ are —$R_h$—$(R_g)_j$,
wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;

wherein B and $R^b$ are:

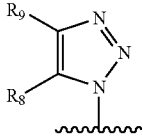

Formula XIII wherein each C, $R_8$, and $R_9$ are independently hydrogen or —$R_h$—$(R_g)_j$, wherein $R_h$ is $C(R_{59}R_{60})$, j is 1 to 15, and each $R_g$ is $C(R_{42}R_{43})$, wherein $R_{42}$ is =O and $R_{43}$ is absent for two $R_g$, $R_{42}$ and $R_{43}$ are hydrogen for the other $R_g$, and $R_{50}$ and $R_{60}$ are hydrogen;

wherein $R_8$ and $R_9$ are not both hydrogen, wherein at least one of C is not hydrogen.

In some embodiments where A or $R_6$ is —$R_h$—$(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and $R_{60}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is —$R_h$—$(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments $R_h$ is $C(R_{59}R_{60})$, and j is 0, wherein $R_{59}$ is =O, and $R_{60}$ is absent. In some embodiments $R_h$ is $C(R_{59}R_{60})$, j is 0 to 10, and each $R_g$ is $C(R_{42}R_{43})$, wherein $R_{59}$ is =O, $R_{60}$ is absent, and $R_{42}$ and $R_{43}$ are hydrogen. In some embodiments j is 1. In some embodiment j is 2. In some embodiments j is 3. In some embodiment j is 4. In some embodiments j is 5. In some embodiments j is 7. In some embodiment j is 8. In some embodiments j is 9. In some embodiments j is 10.

In some embodiments $R_h$ is $C(R_{59}R_{60})$, j is 1 to 10, and each $R_g$ is $C(R_{42}R_{43})$, wherein $R_{42}$ is =O and $R_{43}$ is absent for one $R_g$, $R_{42}$ and $R_{43}$ are hydrogen for the other $R_g$, and $R_{59}$ and $R_{60}$ are hydrogen. In some embodiments $R_{43}$ is =O and $R_{43}$ is absent for the last $R_g$. In some embodiments $R_{43}$ is =O and $R_{43}$ is absent for the penultimate $R_g$. In some embodiments $R_{43}$ is =O and $R_{43}$ is absent for the antepenultimate $R_g$. In some embodiments $R_{43}$ is =O and $R_{43}$ is absent for the fourth from the last $R_g$. In some embodiments $R_{43}$ is =O and $R_{43}$ is absent for the fifth from the last $R_g$. In some embodiments $R_{43}$ is =O and $R_{43}$ is absent for the first $R_g$. In some embodiments $R_{43}$ is =O and $R_{43}$ is absent for the second $R_g$. In some embodiments $R_{43}$ is =O and $R_{43}$ is absent for the third $R_g$. In some embodiments $R_{42}$ is =O and $R_{43}$ is absent for the fourth $R_g$. In some embodiments $R_{43}$ is =O and $R_{43}$ is absent for the fifth $R_g$.

In some embodiments $R_h$ is $C(R_{59}R_{60})$, j is 1 to 15, and each $R_g$ is $C(R_{42}R_{43})$, wherein $R_{43}$ is =O and $R_{43}$ is absent for two $R_g$, $R_{42}$ and $R_{43}$ are hydrogen for the other $R_g$, and $R_{59}$ and $R_{60}$ are hydrogen. In some embodiments $R_{43}$ is =O and $R_{43}$ is absent the first and third $R_g$. In some embodiments $R_{43}$ is =O and $R_{43}$ is absent the first and fourth $R_g$. In some embodiments $R_{42}$ is =O and $R_{43}$ is absent the first and fifth $R_g$. In some embodiments $R_{43}$ is =O and $R_{43}$ is absent the first and sixth $R_g$. In some embodiments $R_{42}$ is =O and $R_{43}$ is absent the first and seventh $R_g$. In some embodiments $R_{43}$ is =O and $R_{43}$ is absent the first and eighth $R_g$. In some embodiments $R_{43}$ is =O and $R_{43}$ is absent the first and ninth $R_g$. In some embodiments $R_{43}$ is =O and $R_{43}$ is absent the first and tenth $R_g$. In some embodiments $R_{42}$ is =O and $R_{43}$ is absent the first and eleventh $R_g$. In some embodiments $R_{43}$ is =O and $R_{43}$ is absent the first and twelfth $R_g$. In some embodiments $R_{42}$ is =O and $R_{43}$ is absent the first and thirteenth $R_g$. In some embodiments $R_{42}$ is =O and $R_{43}$ is absent the first and fourteenth $R_g$. In some embodiments $R_{43}$ is =O and $R_{43}$ is absent the first and fifteenth $R_g$. In some embodiments $R_{43}$ is =O and $R_{43}$ is absent the second and fourth $R_g$. In some embodiments $R_{43}$ is =O and $R_{43}$ is absent the second and fifth $R_g$. In some embodiments $R_{43}$ is =O and $R_{43}$ is absent the second and sixth $R_g$. In some embodiments $R_{43}$ is =O and $R_{43}$ is absent the second and seventh $R_g$. In some embodiments $R_{43}$ is =O and $R_{43}$ is absent the second and eighth $R_g$. In some embodiments $R_{43}$ is =O and $R_{43}$ is absent the second and ninth $R_g$. In some embodiments $R_{42}$ is =O and $R_{43}$ is absent the second and tenth $R_g$. In some embodiments $R_{42}$ is =O and $R_{43}$ is absent the second and eleventh $R_g$. In some embodiments $R_{43}$ is =O and $R_{43}$ is absent the second and twelfth $R_g$. In some embodiments $R_{42}$ is =O and $R_{43}$ is absent the second and thirteenth $R_g$. In some embodiments $R_{42}$ is =O and $R_{43}$ is absent the second and fourteenth $R_g$. In some embodiments $R_{43}$ is =O and $R_{43}$ is absent the second and fifteenth $R_g$. In some embodiments $R_{42}$ is =O and $R_{43}$ is absent the third and fifth $R_g$. In some embodiments $R_{43}$ is =O and $R_{43}$ is absent the third and sixth $R_g$. In some embodiments $R_{43}$ is =O and $R_{43}$ is absent the third and seventh $R_g$. In some embodiments $R_{42}$ is =O and $R_{43}$ is absent the third and eighth $R_g$. In some embodiments $R_{42}$ is =O and $R_{43}$ is absent the third and ninth $R_g$. In some embodiments $R_{43}$ is =O and $R_{43}$ is absent the third and tenth $R_g$. In some embodiments $R_{42}$ is =O and $R_{43}$ is absent the third and eleventh $R_g$. In some embodiments $R_{42}$ is =O and $R_{43}$ is absent the third and twelfth $R_g$. In some embodiments $R_{42}$ is =O and $R_{43}$ is absent the third and thirteenth $R_g$. In some embodiments $R_{43}$ is =O and $R_{43}$ is absent the third and fourteenth $R_g$. In some embodiments $R_{43}$ is =O and $R_{43}$ is absent the third and fifteenth $R_g$. In some embodiments $R_{43}$ is =O and $R_{43}$ is absent the fourth and sixth $R_g$. In some embodiments $R_{42}$ is =O and $R_{43}$ is absent the fourth and seventh $R_g$. In some embodiments $R_{42}$ is =O and $R_{43}$ is absent the fourth and eighth $R_g$. In some embodiments $R_{42}$ is =O and $R_{43}$ is absent the fourth and ninth $R_g$. In some embodiments $R_{42}$ is =O and $R_{43}$ is absent the fourth and tenth $R_g$. In some embodiments $R_{42}$ is =O and $R_{43}$ is absent the fourth and eleventh $R_g$. In some embodiments $R_{42}$ is =O and $R_{43}$ is absent the fourth and twelfth $R_g$. In some embodiments $R_{42}$ is =O and $R_{43}$ is absent the fourth and thirteenth $R_g$. In some embodiments $R_{43}$ is =O and $R_{43}$ is absent the fourth and fourteenth $R_g$. In some embodiments $R_{43}$ is =O and $R_{43}$ is absent the fourth and fifteenth $R_g$. In some embodiments $R_{43}$ is =O and $R_{43}$ is absent the fifth and seventh $R_g$. In some embodiments $R_{42}$ is =O and $R_{43}$ is absent the fifth and eighth $R_g$. In some embodiments $R_{42}$ is =O and $R_{43}$ is absent the fifth and ninth $R_g$. In some embodiments $R_{42}$ is =O and $R_{43}$ is absent the fifth and tenth $R_g$. In some embodiments $R_{42}$ is =O and $R_{43}$ is absent the fifth and eleventh $R_g$. In some embodiments $R_{42}$ is =O and $R_{43}$ is absent the fifth and twelfth $R_g$. In some embodiments $R_{42}$ is =O and $R_{43}$ is absent the fifth and thirteenth $R_g$. In some embodiments $R_{42}$ is =O and $R_{43}$ is absent the fifth and fourteenth $R_g$. In some embodiments $R_{42}$ is =O and $R_{43}$ is absent the fifth and fifteenth $R_g$. In some embodiments $R_{42}$ is =O and $R_{43}$ is absent the sixth and eighth $R_g$. In some embodiments $R_{42}$ is =O and $R_{43}$ is absent the sixth and ninth $R_g$. In some embodiments $R_{42}$ is =O and $R_{43}$ is absent the sixth and tenth $R_g$. In some embodiments $R_{42}$ is =O and $R_{43}$ is absent the sixth and eleventh $R_g$. In some embodiments $R_{42}$ is =O and $R_{43}$ is absent the sixth and twelfth $R_g$. In some embodiments $R_{42}$ is =O and $R_{43}$ is absent the sixth and thirteenth $R_g$. In some embodiments $R_{42}$ is =O and $R_{43}$ is absent the sixth and fourteenth $R_g$. In some embodiments $R_{42}$ is =O and $R_{43}$ is absent the sixth and fifteenth $R_g$. In some embodiments $R_{42}$ is =O and $R_{43}$ is absent the seventh and ninth $R_g$. In some embodiments $R_{42}$ is =O and $R_{43}$ is absent the seventh and tenth $R_g$. In some embodiments $R_{42}$ is =O and $R_{43}$ is absent the seventh and eleventh $R_g$. In some embodiments $R_{42}$ is =O and $R_{43}$ is absent the seventh and twelfth $R_g$. In some embodiments $R_{42}$ is =O and $R_{43}$ is absent the seventh and thirteenth $R_g$. In some embodiments $R_{42}$ is =O and $R_{43}$ is absent the seventh and fourteenth $R_g$. In some embodiments $R_{42}$ is =O and $R_{43}$ is absent the seventh and fifteenth $R_g$. In some embodiments $R_{42}$ is =O and $R_{43}$ is absent the eighth and tenth $R_g$. In some embodiments $R_{42}$ is =O and $R_{43}$ is absent the eighth and eleventh $R_g$. In some embodiments $R_{42}$ is =O and $R_{43}$ is absent the eighth and twelfth $R_g$. In some embodiments $R_{42}$ is =O and $R_{43}$ is absent the eighth and thirteenth $R_g$. In some embodiments $R_{42}$ is =O and $R_{43}$ is absent the eighth and fourteenth $R_g$. In some embodiments $R_{42}$ is =O and $R_{43}$ is absent the eighth and fifteenth $R_g$. In some embodiments $R_{42}$ is =O and $R_{43}$ is absent the ninth and eleventh $R_g$. In some embodiments $R_{42}$ is =O and $R_{43}$ is absent the ninth and twelfth $R_g$. In some embodiments $R_{42}$ is =O and $R_{43}$ is absent the ninth and thirteenth $R_g$. In some embodiments $R_{42}$ is =O and $R_{43}$ is absent the ninth and fourteenth $R_g$. In some embodiments $R_{42}$ is =O and $R_{43}$ is absent the ninth and fifteenth $R_g$. In some embodiments $R_{42}$ is =O and $R_{43}$ is absent the tenth and twelfth $R_g$. In some embodiments $R_{42}$ is =O and $R_{43}$ is absent the tenth and thirteenth $R_g$. In some embodiments $R_{42}$ is =O and $R_{43}$ is absent the tenth and fourteenth $R_g$. In some embodiments $R_{42}$ is =O and $R_{43}$ is absent the tenth and fifteenth $R_g$. In some embodiments $R_{42}$ is =O and $R_{43}$ is absent the eleventh and thirteenth $R_g$. In some embodiments $R_{42}$ is =O and $R_{43}$ is absent the eleventh and fourteenth $R_g$. In some embodiments $R_{42}$ is =O and $R_{43}$ is absent the eleventh and fifteenth $R_g$. In some embodiments $R_{43}$ is =O and $R_{43}$ is absent the twelfth and fourteenth $R_g$. In some embodiments $R_{43}$ is =O and $R_{43}$ is absent the twelfth and fifteenth $R_g$. In some embodiments the thirteenth and fifteenth $R_g$.

Z1-Y12

In some embodiments, compounds are represented by the general formula:

wherein X is oxygen, sulfur, or $NR_4$;
wherein $R_4$ is -A-B(—C)$_\delta$ or —$R_6$—$R^b$;
wherein A and $R_6$ are —$R_h$—$(R_g)_j$,
wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;

wherein B and $R^b$ are:

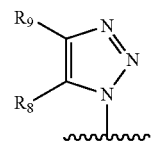

Formula XIII wherein each C, $R_8$, and $R_0$ are independently hydrogen or

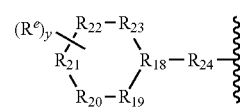

Formula IX wherein for C, $R_8$, and $R_0$, $R_{18}$ is carbon, one or two of nonadjacent $R_{19}$, $R_{20}$, $R_{21}$, $R_{22}$, and $R_{23}$ are O, the rest of $R_{19}$, $R_{20}$, $R_{21}$, $R_{22}$, and $R_{23}$ are carbon, y is 0 to 3, $R^e$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX has no double bonds, $R_{24}$ is —$(CR_{25}R_{25})_p$—$X_b$—$(CR_{25}R_{25})_q$—, p is 0 to 5, q is 0 to 5, $R_{25}$ are independently hydrogen or $C_1$-$C_3$ alkyl, and $X_b$ is O;

wherein $R_8$ and $R_0$ are not both hydrogen, wherein at least one of C is not hydrogen.

In some embodiments where A or $R_6$ is —$R_h$—$(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and Rbo are $C_1$-$C_3$ alkyl. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{43}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments where one or more of C, $R_8$, and $R_0$ are Formula IX, in such C, $R_8$, and $R_9$: $R_{18}$ is carbon, one or two of nonadjacent $R_{19}$, $R_{20}$, $R_{21}$, $R_{22}$, and $R_{23}$ are O, the rest of $R_{19}$, $R_{20}$, $R_{21}$, $R_{22}$, and $R_{23}$ are carbon, y is 0 to 3, $R^e$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX has no double bonds, $R_{24}$ is $-(CR_{25}R_{25})_p-X_b-(CR_{25}R_{25})_q-$, p is 0 to 5, q is 0 to 5, $R_{25}$ are independently hydrogen or $C_1$-$C_3$ alkyl, and $X_b$ is O.

In some embodiments where one or more of C, $R_8$, and $R_0$ are Formula IX, in such C, $R_8$, and $R_0$: $R_{18}$ is carbon, one or two of nonadjacent $R_{19}$, $R_{20}$, $R_{21}$, $R_{22}$, and $R_{23}$ are O, the rest of $R_{19}$, $R_{20}$, $R_{21}$, $R_{22}$, and $R_{23}$ are carbon, y is 0 to 3, $R^e$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX has no double bonds, $R_{24}$ is $-(CR_{25}R_{25})_p-X_b-(CR_{25}R_{25})_q-$, p is 0 to 5, q is 0 to 5, $R_{25}$ are independently hydrogen or $C_1$-$C_3$ alkyl, and $X_b$ is O. In some embodiments $R_8$ is hydrogen. In some embodiments, $R_0$ is hydrogen. In some embodiments, $R_{19}$ is O and $R_{20}$, $R_{21}$, $R_{22}$, and $R_{23}$ are carbon. In some embodiments, $R_{20}$ is O and $R_{19}$, $R_{21}$, $R_{22}$, and $R_{23}$ are carbon. In some embodiments, $R_{21}$ is O and $R_{19}$, $R_{20}$, $R_{22}$, and $R_{23}$ are carbon. In some embodiments, $R_{22}$ is O and $R_{19}$, $R_{20}$, $R_{21}$, and $R_{23}$ are carbon. In some embodiments, $R_{23}$ is O and $R_{19}$, $R_{20}$, $R_{21}$, and $R_{22}$ are carbon. In some embodiments, $R_{19}$ and $R_{21}$ are O. In some embodiments, $R_{19}$ and $R_{22}$ are O. In some embodiments, $R_{19}$ and $R_{23}$ are O. In some embodiments, $R_{20}$ and $R_{22}$ are O. In some embodiments, $R_{20}$ and $R_{23}$ are O. In some embodiments, $R_{21}$ and $R_{23}$ are O. In some embodiments y is 0. In some embodiments y is 1. In some embodiments y is 2. In some embodiments y is 3. In some embodiments $R^e$ is independently methyl, ethyl, methoxy, ethoxy, amino methyl, amino ethyl, hydroxyl, or amino. In some embodiments, p is 0. In some embodiments p is 1. In some embodiment p is 2. In some embodiments p is 3. In some embodiments p is 4. In some embodiments p is 5. In some embodiments, q is 0. In some embodiments q is 1. In some embodiment q is 2. In some embodiments q is 3. In some embodiments q is 4. In some embodiments q is 5. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

In some embodiments where at least one C is Formula IX, $R_8$ is hydrogen, and $R_9$ is Formula IX, in such C and $R_9$: $R_{19}$ is O, $R_{18}$, $R_{20}$, $R_{21}$, $R_{22}$, and $R_{23}$ are carbon, y is 0, the ring of Formula IX has no double bonds, $R_{24}$ is $-(CR_{25}R_{25})_p-X_b-(CR_{25}R_{25})_q-$, p is 0, q is 1, both $R_{25}$ are hydrogen, and $X_b$ is O.

Z1-Y17

In some embodiments, compounds are represented by the general formula:

—X—$R_1$ wherein X is oxygen, sulfur, or $NR_4$;

wherein $R_4$ is -A-B(—C)$_\delta$ or —$R_6$—$R^b$;

wherein A and $R_6$ are —$R_h$—$(R_g)_j$, wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;

wherein B and $R^b$ are:

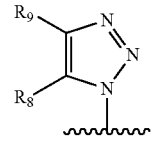

Formula XIII wherein each C, $R_8$, and $R_0$ are independently hydrogen or

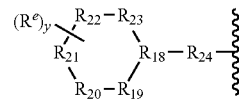

Formula IX wherein for C, $R_8$, and $R_9$, $R_{18}$, $R_{19}$, $R_{20}$, $R_{21}$, $R_{22}$, and $R_{23}$ are carbon, y is 0 to 3, $R^e$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX is aromatic, $R_{24}$ is $-(CR_{25}R_{25})_p-$, and p is 0;

wherein $R_8$ and $R_0$ are not both hydrogen, wherein at least one of C is not hydrogen.

In some embodiments where A or $R_6$ is —$R_h$—$(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{50}$ and $R_{60}$ are hydrogen. In some embodiments $R_{59}$ is hydrogen and $R_{60}$ is $C_1$-$C_3$ alkyl. In some embodiments $R_{59}$ and Reo are $C_1$-$C_3$ alkyl. In some embodiments all $R_{42}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{43}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments, in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is $-(CR_{25}R_{25})_p-$, and p is 0.

In some embodiments, in Formula IX, $R_{18}$, $R_{19}$, $R_{20}$, $R_{21}$, $R_{22}$, and $R_{23}$ are carbon, y is 1, $R^e$ are independently $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX is aromatic, $R_{24}$ is $-(CR_{25}R_{25})_p-$, and p is 0.

Z1-Y1

In some embodiments, compounds are represented by the general formula:

wherein X is oxygen, sulfur, or $NR_4$;

wherein $R_4$ is -A-B(—C)$_\delta$ or $-R_6-R^b$;

wherein A and $R_6$ are $-R_h-(R_g)_j$, wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;

wherein B and $R^b$ are:

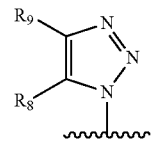

Formula XIII wherein each C, $R_8$, and $R_0$ are independently hydrogen or

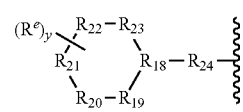

Formula IX wherein for C, $R_8$, and $R_9$, $R_{18}$, $R_{19}$, $R_{20}$, $R_{21}$, $R_{22}$, and $R_{23}$ are carbon, y is 1, $R^e$ is hydroxy, $C_1$-$C_3$ alkyl, $C_1$-$C_3$ alkoxy, amino, $C_1$-$C_3$ alkylamino, $C_1$-$C_3$ dialkylamino, hydroxy, $C_1$-$C_3$ alkenyl, or $C_1$-$C_3$ alkynyl, the ring of Formula IX has no double bonds, $R_{24}$ is $-(CR_{25}R_{25})_p-$, and p is 0;

wherein $R_8$ and $R_0$ are not both hydrogen, wherein at least one of C is not hydrogen.

In some embodiments where A or $R_6$ is $-R_h-(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{50}$ and $R_{60}$ are hydrogen. In some embodiments $R_{59}$ is hydrogen and $R_{60}$ is $C_1$-$C_3$ alkyl. In some embodiments $R_{59}$ and Reo are $C_1$-$C_3$ alkyl. In some embodiments all $R_{42}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{43}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments, in Formula IX, $R_{18}$, $R_{19}$, $R_{20}$, $R_{21}$, $R_{22}$, and $R_{23}$ are carbon, y is 1, $R^e$ is hydroxy, the ring of Formula IX has no double bonds, $R_{24}$ is $-(CR_{25}R_{25})_p-$, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Z1-Y9

In some embodiments, compounds are represented by the general formula:

wherein X is oxygen, sulfur, or $NR_4$;
wherein $R_1$ is -A-B(—C)$_\delta$ or $-R_6-R^b$;
wherein A and $R_6$ are $-R_h-(R_g)_j$,
wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;
wherein B and $R^b$ are:

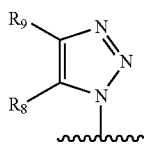

Formula XIII wherein C and $R_9$ are independently hydrogen or

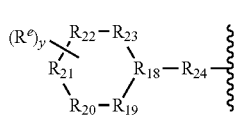

Formula IX wherein C and $R_8$, independently hydrogen or $-R_h-(R_g)_j$, wherein for C and $R_9$, $R_{18}$, $R_{19}$, $R_{20}$, $R_{21}$, $R_{22}$, and $R_{23}$ are carbon, y is 0, the ring of Formula IX is aromatic, $R_{24}$ is $-(CR_{25}R_{25})_p-$, and p is 0; wherein $R_h$ is $C(R_{59}R_{60})$, and j is 0, wherein $R_{59}$ is =O and $R_{60}$ is —OH. In some embodiments $R_h$ is absent, j is 0 to 10, and each $R_g$ is $C(R_{42}R_{43})$, wherein $R_{42}$ and $R_{43}$ are hydrogen;
wherein $R_8$ and $R_9$ are not both hydrogen, wherein at least one of C is not hydrogen.

In some embodiments where A or $R_6$ is $-R_h-(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and $R_{60}$ are $C_1$-$C_3$ alkyl. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments, one C or $R_8$ is $-R_h-(R_g)_j$, and one C or $R_9$ is, wherein in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is $-(CR_{25}R_{25})_p-$, and p is 0, wherein $R_h$ is $C(R_{59}R_{60})$, and j is 0, wherein $R_{59}$ is =O and $R_{60}$ is —OH. In some embodiments $R_h$ is absent, j is 0 to 10, and each $R_g$ is $C(R_{42}R_{43})$, wherein $R_{42}$ and $R_{43}$ are hydrogen.

Z1-Y2

In some embodiments, compounds are represented by the general formula:

wherein X is oxygen, sulfur, or $NR_4$;
wherein $R_1$ is -A-B(—C)$_\delta$ or $-R_6-R^b$;
wherein A and $R_6$ are $-R_h-(R_g)_j$,
wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;
wherein B and $R^b$ are:

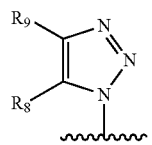

Formula XIII wherein each C, $R_8$, and $R_0$ are independently hydrogen or

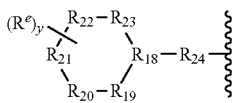

Formula IX wherein for C, $R_8$, and $R_9$, $R_{18}$, $R_{19}$, $R_{20}$, $R_{21}$, $R_{22}$, and $R_{23}$ are carbon, y is 1, $R^e$ is —O—CH$_3$, the ring of Formula IX is aromatic, $R_{24}$ is —(CR$_{25}$R$_{25}$)$_p$—, and p is 0. In some embodiments, $R^e$ is at $R_{21}$;

wherein $R_8$ and $R_9$ are not both hydrogen, wherein at least one of C is not hydrogen.

In some embodiments where A or $R_6$ is —R$_h$—(R$_g$)$_j$, R$_h$ is C(R$_{59}$R$_{60}$), and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are C(R$_{42}$R$_{43}$) and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or C$_1$-C$_3$ alkyl. In some embodiments $R_{59}$ and $R_{60}$ are hydrogen. In some embodiments $R_{59}$ is hydrogen and $R_{60}$ is C$_1$-C$_3$ alkyl. In some embodiments $R_{59}$ and Reo are C$_1$-C$_3$ alkyl. In some embodiments all $R_{43}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{42}$ are hydrogen. In some embodiments all but three $R_{42}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{42}$ are hydrogen. In some embodiments all but twelve $R_{43}$ are hydrogen.

In some embodiments where A or $R_6$ is —R$_h$—(R$_g$)$_j$, R$_h$ is C(R$_{59}$R$_{60}$), and j is 10, wherein the first, third, fourth, sixth, seventh, ninth, and tenth $R_g$ are C(R$_{42}$R$_{43}$) and the second, fifth, and eighth $R_g$ are O, and wherein $R_{59}$, $R_{60}$, $R_{42}$, and $R_{43}$ are hydrogen.

In some embodiments, in Formula IX, $R_{18}$, $R_{19}$, $R_{20}$, $R_{21}$, $R_{22}$, and $R_{23}$ are carbon, y is 1, $R^e$ is —O—CH$_3$, the ring of Formula IX is aromatic, $R_{24}$ is —(CR$_{25}$R$_{25}$)$_p$—, and p is 0. In some embodiments, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$.

Z2-Y13

In some embodiments, the compounds are represented by the general formula:

wherein X is oxygen, sulfur, or NR$_4$;

wherein $R_1$ is -A-B(—C)$_\delta$ or —R$_6$—R$^b$;
wherein A and $R_6$ are

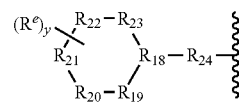

Formula IX wherein for A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 0 to 10, and $R_{25}$ are independently hydrogen or C$_1$-C$_3$ alkyl;

wherein B and $R^b$

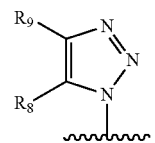

Formula XIII wherein each C, $R_8$, and $R_0$ are independently hydrogen or

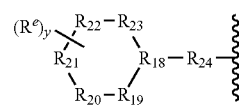

Formula IX wherein for C, $R_8$, and $R_9$, $R_{18}$, $R_{19}$, $R_{20}$, $R_{21}$, $R_{22}$, and $R_{23}$ are carbon, y is 0, the ring of Formula IX is aromatic, $R_{24}$ is —(CR$_{25}$R$_{25}$)$_p$—, one $R_{25}$ is —OH, the other $R_{25}$ is hydrogen, and p is 1;

wherein $R_8$ and $R_9$ are not both hydrogen, wherein at least one of C is not hydrogen.

In some embodiments where A or $R_6$ is Formula IX, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

In some embodiments where A or $R_6$ is Formula IX, in such A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 1, and $R_{25}$ are hydrogen.

In some embodiments, in Formula IX, $R_{18}$, $R_{19}$, $R_{20}$, $R_{21}$, $R_{22}$, and $R_{23}$ are carbon, y is 0, the ring of Formula IX is aromatic, $R_{24}$ is —(CR$_{25}$R$_{25}$)$_p$—, one $R_{25}$ is —OH, the other $R_{25}$ is hydrogen, and p is 1.

Z2-Y5

In some embodiments, the compounds are represented by the general formula:

wherein X is oxygen, sulfur, or NR$_4$;

wherein $R_4$ is -A-B(—C)$_\delta$ or —$R_6$—$R^b$;
wherein A and, $R_6$ are

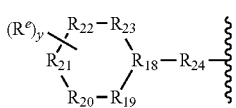

Formula IX wherein for A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 0 to 10, and $R_{25}$ are independently hydrogen or $C_1$-$C_3$ alkyl;
wherein B and $R^b$ are:

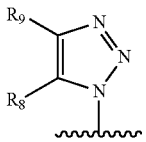

Formula XIII wherein each C, $R_8$, and $R_9$ are independently hydrogen or

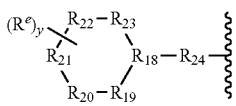

Formula IX wherein for C, $R_8$, and $R_9$, $R_{18}$, $R_{19}$, $R_{20}$, $R_{21}$, $R_{22}$, and $R_{23}$ are carbon, y is 1, $R^e$ is methyl, the ring of Formula IX is aromatic, $R_{24}$ is —(CR$_{25}$R$_{25}$)$_p$—X$_b$—(CR$_{25}$R$_{25}$)$_q$—, p is 0, q is 0, and X$_b$ is S(O)$_2$;
wherein $R_8$ and $R_9$ are not both hydrogen, wherein at least one of C is not hydrogen.

In some embodiments where A or $R_6$ is Formula IX, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

In some embodiments where A or $R_6$ is Formula IX, in such A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 1, and $R_{25}$ are hydrogen.

In some embodiments, in Formula IX, $R_{18}$, $R_{19}$, $R_{20}$, $R_{21}$, $R_{22}$, and $R_{23}$ are carbon, y is 1, $R^e$ is methyl, the ring of Formula IX is aromatic, $R_{24}$ is —(CR$_{25}$R$_{25}$)$_p$—X$_b$—(CR$_{25}$R$_{25}$)$_q$—, p is 0, q is 0, and X$_b$ is S(O)$_2$.
Z2-Y7

In some embodiments, the compounds are represented by the general formula:

wherein X is oxygen, sulfur, or NR$_4$;

wherein $R_4$ is -A-B(—C)$_\delta$ or —$R_6$—$R^b$;
wherein A and $R_6$ are

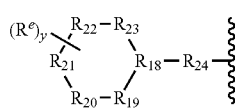

Formula IX wherein for A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 0 to 10, and $R_{25}$ are independently hydrogen or $C_1$-$C_3$ alkyl;
wherein B and $R^b$ are:

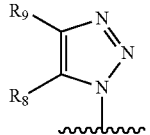

Formula XIII wherein each C, $R_8$, and $R_9$ are independently hydrogen or —$R_h$—($R_g$)$_j$,
wherein $R_h$ is C($R_{59}R_{60}$), j is 1 to 10, one $R_g$ is O, the other $R_g$ are C($R_{42}R_{43}$), and $R_f$ is C($R_{45}R_{46}R_{47}$), wherein $R_{59}$, $R_{60}$, $R_{42}$, $R_{43}$, $R_{45}$, $R_{46}$, and $R_{43}$ are hydrogen;
wherein $R_8$ and $R_9$ are not both hydrogen, wherein at least one of C is not hydrogen.

In some embodiments where A or $R_6$ is Formula IX, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

In some embodiments where A or $R_6$ is Formula IX, in such A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —(CR$_{25}$R$_{25}$)$_p$—, p is 1, and $R_{25}$ are hydrogen.

In some embodiments $R_h$ is C($R_{59}R_{60}$), j is 1, $R_g$ is O, and $R_f$ is C($R_{45}R_{46}R_{47}$), wherein $R_{59}$, $R_{60}$, $R_{45}$, $R_{46}$, and $R_{47}$ are hydrogen. In some embodiments $R_h$ is absent, j is 1, $R_g$ is O, and $R_f$ is C($R_{45}R_{46}R_{47}$), wherein $R_{45}$, $R_{46}$, and $R_{47}$ are hydrogen.

In some embodiments $R_h$ is C($R_{59}R_{60}$), j is 1 to 10, one $R_g$ is O, the other $R_g$ are C($R_{42}R_{43}$), and $R_f$ is C($R_{45}R_{46}R_{47}$), wherein $R_{59}$, $R_{60}$, $R_{42}$, $R_{43}$, $R_{45}$, $R_{46}$, and $R_{47}$ are hydrogen. In some embodiments the last $R_g$ is O. In some embodiments the penultimate $R_g$ is O. In some embodiments the antepenultimate $R_g$ is O. In some embodiments the fourth from the last $R_g$ is O. In some embodiments the fifth from the last $R_g$ is O. In some embodiments the first $R_g$ is O. In some embodiments the second $R_g$ is O. In some embodiments the third $R_g$ is O. In some embodiments the fourth $R_g$ is O. In some embodiments the fifth $R_g$ is O.

Z2-Y6

In some embodiments, the compounds are represented by the general formula:

wherein X is oxygen, sulfur, or $NR_4$;
wherein $R_4$ is -A-B(—C)$_\delta$ or —$R_6$—$R^b$;
wherein A and $R_6$ are

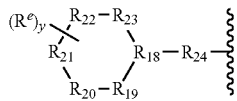

Formula IX wherein for A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —$(CR_{25}R_{25})_p$—, p is 0 to 10, and $R_{25}$ are independently hydrogen or $C_1$-$C_3$ alkyl;
wherein B and $R^b$ are:

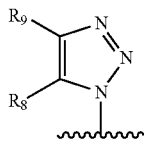

Formula XIII wherein each C, $R_8$, and $R_9$ are independently hydrogen or —$R_h$—$(R_g)_j$,
wherein for C and $R_9$, $R_h$ is $NR_{61}$, j is 0 to 10, and each $R_g$ is $C(R_{42}R_{43})$, wherein $R_{61}$ is —$R_{hx}$—$(R_{gx})_{jx}$—$R_{fx}$, and $R_{42}$ and $R_{43}$ are hydrogen, wherein $R_{hx}$ is $C(R_{59x}R_{60x})$, jx=0 to 10, $R_{gx}$ is $C(R_{42x}R_{43x})$, and $R_{fx}$ is $C(R_{45x}R_{46x}R_{47x})$, and wherein $R_{59x}$, $R_{60x}$, $R_{42x}$, $R_{43x}$, $R_{45x}$, $R_{46x}$, $R_{47x}$ are hydrogen; wherein for C and $R_8$, $R_h$ is $C(R_{59}R_{60})$, j is 0 to 10, and each $R_g$ is $C(R_{42}R_{43})$, wherein $R_{59}$, $R_{60}$, $R_{42}$, $R_{43}$ are hydrogen;
wherein $R_8$ and $R_9$ are not both hydrogen, wherein at least one of C is not hydrogen.

In some embodiments where A or $R_6$ is Formula IX, $R^e$ is at $R_{21}$. In some embodiments, $R^e$ is at $R_{19}$. In some embodiments, $R^e$ is at $R_{20}$. In some embodiments, $R^e$ is at $R_{22}$. In some embodiments, $R^e$ is at $R_{23}$. In some embodiments, p is 0. In some embodiments p is 1. In some embodiment p is 2. In some embodiments p is 3. In some embodiment p is 4. In some embodiments p is 5. In some embodiments p is 7. In some embodiment p is 8. In some embodiments p is 9. In some embodiments p is 10. In some embodiments all $R_{25}$ are hydrogen. In some embodiments all but one $R_{25}$ are hydrogen. In some embodiments all but two $R_{25}$ are hydrogen. In some embodiments all but three $R_{25}$ are hydrogen. In some embodiments all but four $R_{25}$ are hydrogen.

In some embodiments where A or $R_6$ is Formula IX, in such A and $R_6$, $R_{18}$, $R_{19}$, $R_{20}$, $R_{21}$, $R_{22}$, and $R_{23}$ are carbon, y is 1, $R^e$ is $R^b$, the ring of Formula IX is aromatic, $R_{24}$ is —$(CR_{25}R_{25})_p$—, p is 1, and $R_{25}$ are hydrogen.

In some embodiments $R_h$ is $NR_{61}$, j is 1, and $R_g$ is $C(R_{42}R_{43})$, wherein $R_{61}$ is —$R_{hx}$—$(R_{gx})_{jx}$—$R_{fx}$, and $R_{42}$ and $R_{43}$ are hydrogen, wherein $R_{hx}$ is absent, jx=1, $R_{gx}$ is $C(R_{42x}R_{43x})$, and $R_{fx}$ is $C(R_{45x}R_{46x}R_{47x})$, and wherein $R_{42x}$, $R_{43x}$, $R_{45x}$, $R_{46x}$, $R_{47x}$ are hydrogen.

In some embodiments $R_h$ is $NR_{61}$, j is 0 to 10, and each $R_g$ is $C(R_{42}R_{43})$, wherein $R_{61}$ is —$R_{hx}$—$(R_{gx})_{jx}$—$R_{fx}$, and $R_{42}$ and $R_{43}$ are hydrogen, wherein $R_{hx}$ is $C(R_{59x}R_{60x})$, jx=0 to 10, $R_{gx}$ is $C(R_{42x}R_{43x})$, and $R_{fx}$ is $C(R_{45x}R_{46x}R_{47x})$, and wherein $R_{59x}$, $R_{60x}$, $R_{42x}$, $R_{43x}$, $R_{45x}$, $R_{46x}$, $R_{47x}$ are hydrogen. In some embodiments j=jx. In some embodiments j and jx are 0. In some embodiment j and jx are 2. In some embodiments j and jx are 3. In some embodiments j and jx are 4.

In some embodiments $R_h$ is $C(R_{59}R_{60})$, and j is 0, wherein $R_{59}$ and $R_{60}$ are hydrogen. In some embodiments $R_h$ is $C(R_{59}R_{60})$, j is 0 to 10, and each $R_g$ is $C(R_{42}R_{43})$, wherein $R_{59}$, $R_{60}$, $R_{42}$, $R_{43}$ are hydrogen. In some embodiments j is 1. In some embodiment j is 2. In some embodiments j is 3. In some embodiments j is 4.

Z1-Y10

In some embodiments, compounds are represented by the general formula:

wherein X is oxygen, sulfur, or $NR_4$;
wherein $R_1$ is -A-B(—C)$_\delta$ or —$R_6$—$R^b$;
wherein A and $R_6$ are —$R_h$—$(R_g)_j$,
wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;
wherein B and $R^b$ are:

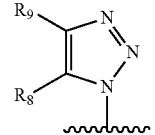

Formula XIII wherein each C, $R_8$, and $R_0$ are independently hydrogen or —$R_h$—$(R_g)_j$,
wherein $R_h$ is absent, j is 1 to 10, and each $R_g$ is $C(R_{42}R_{43})$, wherein $R_{42}$ and $R_{43}$ are hydrogen;
wherein $R_8$ and $R_0$ are not both hydrogen, wherein at least one of C is not hydrogen.

In some embodiments where A or $R_6$ is —$R_h$—$(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and $R_{60}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{43}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments $R_h$ is absent, j is 6, and each $R_g$ is $C(R_{42}R_{43})$, wherein $R_{42}$ and $R_{43}$ are hydrogen. In some embodiments $R_h$ is absent, j is 1 to 10, and each $R_g$ is $C(R_{42}R_{43})$, wherein $R_{42}$ and $R_{43}$ are hydrogen. In some embodiments j is 3. In some embodiment j is 4. In some embodiments j is 5. In some embodiments j is 7. In some embodiment j is 8. In some embodiments j is 9. In some embodiments j is 10.

Z1-Y11

In some embodiments, compounds are represented by the general formula:

wherein X is oxygen, sulfur, or $NR_4$;
wherein $R_4$ is -A-B(—C)$_\delta$ or $-R_6-R^b$;
wherein A and $R_5$ are $-R_h-(R_g)_j$;
wherein $R_h$ is $C(R_{59}R_{50})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;
wherein B and $R^b$ are;

Formula XIII

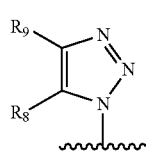

wherein each C, $R_8$, and $R_9$ are independently hydrogen or $-R_h-(R_g)_j$,
wherein $R_h$ is $C(R_{59}R_{60})$, j is 1 to 10, one $R_g$ is O, and the other $R_g$ are $C(R_{42}R_{43})$, wherein $R_{59}$, $R_{60}$, $R_{42}$, and $R_{43}$ are hydrogen;
wherein $R_8$ and $R_9$ are not both hydrogen, wherein at least one of C is not hydrogen.

In some embodiments where A or $R_6$ is $-R_h-(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and $R_{60}$ are $C_1$-$C_3$ alkyl. In some embodiments all $R_{42}$ are hydrogen. In some embodiments all but one $R_{42}$ are hydrogen. In some embodiments all but two $R_{42}$ are hydrogen. In some embodiments all but three $R_{42}$ are hydrogen. In some embodiments all but four $R_{42}$ are hydrogen. In some embodiments all but five $R_{42}$ are hydrogen. In some embodiments all but six $R_{42}$ are hydrogen. In some embodiments all but seven $R_{42}$ are hydrogen. In some embodiments all but eight $R_{42}$ are hydrogen. In some embodiments all but nine $R_{42}$ are hydrogen. In some embodiments all but ten $R_{42}$ are hydrogen. In some embodiments all but eleven $R_{42}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is $-R_h-(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments $R_h$ is $C(R_{59}R_{60})$, j is 3, the first $R_g$ is O, and the second and third $R_g$ are $C(R_{42}R_{43})$, wherein $R_{59}$, $R_{60}$, $R_{42}$, and $R_{43}$ are hydrogen. In some embodiments $R_h$ is $C(R_{59}R_{60})$, j is 1 to 10, one $R_g$ is O, and the other $R_g$ are $C(R_{42}R_{43})$, wherein $R_{59}$, $R_{50}$, $R_{42}$, and $R_{43}$ are hydrogen. In some embodiments the first $R_g$ is O. In some embodiments the second $R_g$ is O. In some embodiments the third $R_g$ is O. In some embodiments the fourth $R_g$ is O. In some embodiments the fifth $R_g$ is O. In some embodiments the fifth from the last $R_g$ is O. In some embodiments the fourth from the last $R_g$ is O. In some embodiments the antepenultimate $R_g$ is O. In some embodiments the penultimate $R_g$ is O. In some embodiments the last $R_g$ is O.

In some embodiments $R_h$ is $C(R_{59}R_{60})$, j is 4 to 16, two $R_g$ are O, and the other $R_g$ are $C(R_{42}R_{43})$, wherein $R_{59}$, $R_{50}$, $R_{42}$, and $R_{43}$ are hydrogen. In some embodiments the first and third $R_g$ are O. In some embodiments the first and fourth $R_g$ are O. In some embodiments the first and fifth $R_g$ are O. In some embodiments the first and sixth $R_g$ are O. In some embodiments the first and seventh $R_g$ are O. In some embodiments the first and eighth $R_g$ are O. In some embodiments the first and ninth $R_g$ are O. In some embodiments the first and tenth $R_g$ are O. In some embodiments the first and eleventh $R_g$ are O. In some embodiments the first and twelfth $R_g$ are O. In some embodiments the first and thirteenth $R_g$ are O. In some embodiments the first and fourteenth $R_g$ are O. In some embodiments the first and fifteenth $R_g$ are O. In some embodiments the second and fourth $R_g$ are O. In some embodiments the second and fifth $R_g$ are O. In some embodiments the second and sixth $R_g$ are O. In some embodiments the second and seventh $R_g$ are O. In some embodiments the second and eighth $R_g$ are O. In some embodiments the second and ninth $R_g$ are O. In some embodiments the second and tenth $R_g$ are O. In some embodiments the second and eleventh $R_g$ are O. In some embodiments the second and twelfth $R_g$ are O. In some embodiments the second and thirteenth $R_g$ are O. In some embodiments the second and fourteenth $R_g$ are O. In some embodiments the second and fifteenth $R_g$ are O. In some embodiments the third and fifth $R_g$ are O. In some embodiments the third and sixth $R_g$ are O. In some embodiments the third and seventh $R_g$ are O. In some embodiments the third and eighth $R_g$ are O. In some embodiments the third and ninth $R_g$ are O. In some embodiments the third and tenth $R_g$ are O. In some embodiments the third and eleventh $R_g$ are O. In some embodiments the third and twelfth $R_g$ are O. In some embodiments the third and thirteenth $R_g$ are O. In some embodiments the third and fourteenth $R_g$ are O. In some embodiments the third and fifteenth $R_g$ are O. In some embodiments the fourth and sixth $R_g$ are O. In some embodiments the fourth and seventh $R_g$ are O. In some embodiments the fourth and eighth $R_g$ are O. In some embodiments the fourth and ninth $R_g$ are O. In some embodiments the fourth and tenth $R_g$ are O. In some embodiments the fourth and eleventh $R_g$ are O. In some embodiments the fourth and twelfth $R_g$ are O. In some embodiments the fourth and thirteenth $R_g$ are O. In some embodiments the fourth and fourteenth $R_g$ are O. In some embodiments the fourth and fifteenth $R_g$ are O. In some embodiments the fifth and seventh $R_g$ are O. In some embodiments the fifth and eighth $R_g$ are O. In some embodiments the fifth and ninth $R_g$ are O. In some embodiments the fifth and tenth $R_g$ are O. In some embodiments the fifth and eleventh $R_g$ are O. In some embodiments the fifth and twelfth $R_g$ are O. In some embodiments the fifth and thirteenth $R_g$ are O. In some embodiments the fifth and fourteenth $R_g$ are O. In some embodiments the fifth and fifteenth $R_g$ are O. In some embodiments the sixth and eighth $R_g$ are O. In some embodiments the sixth and ninth $R_g$ are O. In some embodiments the sixth and tenth $R_g$ are O. In some embodiments the sixth and eleventh $R_g$ are O. In some embodiments the sixth and twelfth $R_g$ are O. In some embodiments the sixth and thirteenth $R_g$ are O. In some embodiments the sixth and fourteenth $R_g$ are O. In some embodiments the sixth and fifteenth $R_g$ are O. In some embodiments the seventh and ninth $R_g$ are O. In some embodiments the seventh and tenth $R_g$ are O. In some embodiments the seventh and eleventh $R_g$ are O. In some embodiments the seventh and twelfth $R_g$ are O. In some embodiments the seventh and thirteenth $R_g$ are O. In some embodiments the seventh and fourteenth $R_g$ are O. In some embodiments the seventh and fifteenth $R_g$ are O. In some embodiments the eighth and tenth $R_g$ are O. In some embodiments the eighth and eleventh $R_g$ are O. In some embodiments the eighth and twelfth $R_g$ are O. In some embodiments the eighth and thirteenth $R_g$ are O. In some embodiments the eighth and fourteenth $R_g$ are O. In some embodiments the eighth and fifteenth $R_g$ are O. In some embodiments the ninth and eleventh $R_g$ are O. In some embodiments the ninth and twelfth $R_g$ are O. In some embodiments the ninth and thirteenth $R_g$ are O. In some embodiments the ninth and fourteenth $R_g$ are O. In some embodiments the ninth and fifteenth $R_g$ are O. In some embodiments the tenth and twelfth $R_g$ are O. In some embodiments the tenth and thirteenth $R_g$ are O. In some embodiments the tenth and fourteenth $R_g$ are O. In some embodiments the tenth and fifteenth $R_g$ are O. In some embodiments the eleventh and thirteenth $R_g$ are O. In some embodiments the eleventh and fourteenth $R_g$ are O. In some embodiments the eleventh and fifteenth $R_g$ are O. In some embodiments the twelfth and fourteenth $R_g$ are O. In some embodiments the twelfth and fifteenth $R_g$ are O. In some embodiments the thirteenth and fifteenth $R_g$ are O.

Z1-Y2

In some embodiments, compounds are represented by the general formula:

wherein X is oxygen, sulfur, or $NR_4$;

wherein $R_4$ is -A-B(—C)$_\delta$ or —$R_6$—$R^b$;

wherein A and $R_6$ are —$R_h$—$(R_g)_j$, wherein $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are independently hydrogen or $C_1$-$C_3$ alkyl;

wherein B and $R^b$ are:

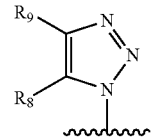

Formula XIII wherein each C, $R_8$, and $R_0$ are independently hydrogen or

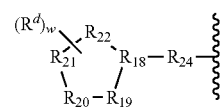

Formula XIV wherein for C, $R_8$, and $R_0$, $R_{19}$ and $R_{20}$ are oxygen, $R_{18}$, $R_{21}$, and $R_{22}$ are carbon, w is 0, the ring of Formula XIV has no double bonds, $R_{24}$ is —$(CR_{25}R_{25})_p$—, both $R_{25}$ are hydrogen, and p is 1;

wherein $R_8$ and $R_0$ are not both hydrogen, wherein at least one of C is not hydrogen.

In some embodiments where A or $R_6$ is —$R_h$—$(R_g)_j$, $R_h$ is $C(R_{59}R_{60})$, and j is 4 to 31, wherein the first, third, fourth, sixth, seventh, ninth, tenth, twelfth, thirteenth, fifteenth, sixteenth, eighteenth, nineteenth, twenty-first, twenty-second, twenty-fourth, twenty-fifth, twenty-seventh, twenty-eighth, thirtieth, and thirty-first $R_g$, if present, are $C(R_{42}R_{43})$ and the second, fifth, eighth, eleventh, fourteenth, seventeenth, twentieth, twenty-third, twenty-sixth, and twenty-ninth, $R_g$, if present, are O, wherein $R_{59}$, $R_{60}$, $R_{42}$, and $R_{43}$ are hydrogen or $C_1$-$C_3$ alkyl. In some embodiments $R_{59}$ and $R_{60}$ are hydrogen. In some embodiments $R_{59}$ is hydrogen and $R_{60}$ is $C_1$-$C_3$ alkyl. In some embodiments $R_{59}$ and $R_{60}$ are $C_1$-$C_3$ alkyl. In some embodiments all $R_{42}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{42}$ are hydrogen. In some embodiments all but five $R_{43}$ are hydrogen. In some embodiments all but six $R_{43}$ are hydrogen. In some embodiments all but seven $R_{42}$ are hydrogen. In some embodiments all but eight $R_{43}$ are hydrogen. In some embodiments all but nine $R_{43}$ are hydrogen. In some embodiments all but ten $R_{42}$ are hydrogen. In some embodiments all but eleven $R_{43}$ are hydrogen. In some embodiments all but twelve $R_{42}$ are hydrogen. In some embodiments all $R_{43}$ are hydrogen. In some embodiments all but one $R_{43}$ are hydrogen. In some embodiments all but two $R_{43}$ are hydrogen. In some embodiments all but three $R_{43}$ are hydrogen. In some embodiments all but four $R_{43}$ are hydrogen. In some embodiments all but five $R_{43}$ are hydrogen. In some embodiments all but six $R_{43}$ are hydrogen. In some embodiments all but seven $R_{43}$ are hydrogen. In some embodiments all but eight $R_{43}$ are hydrogen. In some embodiments all but nine $R_{43}$ are hydrogen. In some embodiments all but ten $R_{43}$ are hydrogen. In some embodiments all but eleven $R_{43}$ are hydrogen. In some embodiments all but twelve $R_{43}$ are hydrogen.

In some embodiments where A or $R_6$ is —$R_h$—$(R_g)_j$, $R_h$ is $C(R_{59}R_{60})$, and j is 10, wherein the first, third, fourth, sixth, seventh, ninth, and tenth $R_g$ are $C(R_{42}R_{43})$ and the second, fifth, and eighth $R_g$ are O, and wherein $R_{59}$, $R_{60}$, $R_{42}$, and $R_{43}$ are hydrogen.

In some embodiments, in Formula XIV, $R_{19}$ and $R_{20}$ are oxygen, $R_{18}$, $R_{21}$, and $R_{22}$ are carbon, w is 0, the ring of Formula XIV has no double bonds, $R_{24}$ is —$(CR_{25}R_{25})_p$—, both $R_{25}$ are hydrogen, and p is 1.

Modified alginate polymers can be of any desired molecular weight. The weight average molecular weight of the alginates is preferably between 1,000 and 1,000,000 Daltons, more preferably between 10,000 and 500,000 Daltons as determined by gel permeation chromatography.

Modified alginate polymers can contain any ratio of mannuronate monomers, guluronate monomers, and covalently modified monomers. In some embodiments, greater than 2.5%, 5%, 7.5%, 10%, 12%, 14%, 15%, 16%, 18%, 20%, 22%, 24%, 25%, 26%, 28%, 30%, 32.5%, 35%, 37.5%, 40%, 45%, 50%, 55%, or 60% of the monomers in the modified alginate polymer are covalently modified monomers. Preferably greater than 10%, more preferably greater than 20%, and most preferably greater than 30% of the monomers in the modified alginate polymer are covalently modified monomers.

Modified alginate polymers can be produced incorporating covalently modified monomers possessing a range of different hydrogen bonding potentials, hydrophobicities/hydrophilicities, and charge states. The inclusion of covalently modified monomers into an alginate polymer alters the physiochemical properties of alginate polymer. Accordingly, the physiochemical properties of alginates can be tuned for desired applications by the selective incorporation of covalently modified monomers.

For example, the glass transition temperature ($T_g$), can be varied by the incorporation of covalently modified monomers. In some embodiments, the modified alginate polymer powder possess a $T_g$, as measured by differential scanning calorimetry (DSC), of greater than 50° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 160° C., 175° C., 190° C., or 200° C.

The hydrophobicity/hydrophilicity of alginates can be varied by the incorporation of hydrophobic and/or hydrophilic covalently modified monomers. In preferred embodiments, the modified alginate polymer contains one or more hydrophobic covalently modified monomers. The relative hydrophobicity/hydrophilicity of modified alginates can be quantitatively assessed by measuring the contact angle of a water droplet on a film of the modified alginate polymer using a goniometer. In some embodiments, the modified alginate has a contact angle of less than 90° (i.e. it is hydrophilic). In preferred embodiments, the modified alginate has a contact angle of more than 90° (i.e. it is hydrophobic). In some embodiments, the modified alginate has a contact angle of more than 95°, 100°, 105°, 110°, 115°, or 120°.

In embodiments used for cell encapsulation, the modified alginate polymer can be ionically crosslinked by a polyvalent cation such as $Ca^{2+}$, $Sr^{2+}$, or $Ba^{2+}$ to form hydrogels. The ability of modified alginates to form stable hydrogels in physiological conditions can be quantified using the hydrogel formation assay described in Example 2.

In some embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, preferably between 20,000 and 55,000, more preferably between 25,000 and 55,000.

In embodiments used for cell encapsulation, the modified alginate polymer forms a hydrogel with sufficient porosity to permit nutrients, waste, and the hormones and/or proteins secreted from encapsulated cells to diffuse freely into and out of the capsules, while simultaneously preventing the incursion of immune cells into the gel matrix. The porosity and surface area of modified alginate hydrogels can be measured using BET analysis. Prior to BET analysis, solvent and volatile impurities are removed by prolonged heating of the modified alginate gel under vacuum. Subsequently, the hydrogel samples are cooled under vacuum, for example by liquid nitrogen, and analyzed by measuring the volume of gas (typically $N_2$, Kr, $CO_2$, or Ar gas) adsorbed to the hydrogel at specific pressures. Analysis of the physisorption of the gas at variable pressures is used to characterize the total surface area and porosity of gels formed by the modified alginate polymers. The preferred method of determining hydrogel porosity is BET analysis.

In preferred embodiments, the modified alginate forms a hydrogel with sufficient porosity to permit nutrients, waste, and the hormones and/or proteins secreted from encapsulated cells to diffuse freely into and out of the capsules, while simultaneously preventing the incursion of immune cells into the gel matrix. In some embodiments, the porosity of the hydrogel formed by the modified alginate polymer is increased by 5%, 10%, 15%, or 20% relative to the porosity of a hydrogel formed from the unmodified alginate polymer. In alternative embodiments, the porosity of the hydrogel formed by the modified alginate polymer is decreased by 5%, 10%, 15%, or 20% relative to the porosity of a hydrogel formed from the unmodified alginate polymer.

In preferred embodiments used for cell encapsulation, the modified alginate is biocompatible. The biocompatibility of modified alginates can be quantitatively determined using the fluorescence-based in vivo biocompatibility assay described in Example 5. In this assay, cathepsin activity was measured using an in vivo fluorescence assay to quantify the foreign body response to the modified alginate.

In some embodiments, the modified alginate polymer is biocompatible such that the fluorescence response normalized to unmodified alginate measured using the in vivo biocompatibility assay described herein is less than 100%, 95%, 90%, 85%, 80%, 75%, 70%, 65%, 60%, 55%, 50%, 45%, or 40%. In preferred embodiments, the modified alginate polymer induces a lower foreign body response than unmodified alginate. This is indicated by fluorescence response normalized to unmodified alginate of less than 100%. In some embodiments, the modified alginate polymer is biocompatible such that the fluorescence response normalized to unmodified alginate measured using the in vivo biocompatibility assay described herein is less than 75%, more preferably less than 65%, and most preferably less than 50%.

The modified alginates can be chemically modified as described herein to any desired density of modifications. The density of modifications is the average number of modifications (that is, attached compounds) per a given weight, volume, or area of the surface of a capsule or product that includes the modified alginate. Generally, a density at or above a threshold density can provide a beneficial effect, such as lower foreign body response. In some embodiments, a high density is not required. Without being bound to any particular theory of operation, it is believed that the chemical modifications signal to, indicate to, or are identified by, one or more immune system or other body components to result in a beneficial effect, such as a lower foreign body response. In some embodiments, a lower density of modifications can be effective for this purpose.

Useful densities include densities of at least, of less than, of about, or of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, and 1000 modifications per square μm, per μg, or per cubic μm. All ranges defined by any pair of these densities are also specifically contemplated and disclosed.

In some embodiments, the density of the modifications on a surface, surfaces, or portions of a surface(s) of a capsule or product that, when the product is administered to (e.g., implanted in the body of) a subject, would be in contact with fluid(s), cell(s), tissue(s), other component(s), or a combination thereof of the subject's body is greater than the density of the modifications on other surfaces of the product.

Density can also be expressed in terms of the concentration of the surface modifications as measured by X-ray photoelectron spectroscopy (XPS). XPS is a surface-sensitive quantitative spectroscopic technique that measures the elemental composition at the parts per thousand range of the elements that exist within a material. XPS spectra are obtained by irradiating a material with a beam of X-rays while simultaneously measuring the kinetic energy and number of electrons that escape from the top 0 to 10 nm of the material being analyzed. By measuring all elements present on the surface, the percentage of the elements that come from the surface modifications can be calculated. This can be accomplished by, for example, taking the percentage of nitrogen (and/or other elements in the surface modifications) in the total elemental signal measured. Nitrogen is a useful indicator for the surface modification because many substrated and materials forming the capsule or product contain little nitrogen. For convenience, the percent of the element(s) used to indicate the surface modifications can be stated as the percent surface modifications. Also for convenience, the percent surface modifications can be referred to as the concentration of surface modifications.

Useful percent surface modifications include concentrations of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

Useful percent surface modifications also include concentrations of less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

Useful percent surface modifications also include concentrations of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent surface modifications. All ranges defined by any pair of these concentrations are also specifically contemplated and disclosed.

B. Capsules and Particle Morphology

Capsules are particles having a mean diameter of about 150 μm to about 5 cm. The disclosed capsules can be formed of cross-linked hydrogel. Other than the encapsulated material, the capsules, for example, can be formed solely of cross-linked hydrogel, can have a cross-linked hydrogel core that is surrounded by one or more polymeric shells, can have one or more cross-linked hydrogel layers, can have a cross-linked hydrogel coating, or a combination thereof. The capsule may have any shape suitable for, for example, cell encapsulation. The capsule may contain one or more cells dispersed in the cross-linked hydrogel, thereby "encapsulating" the cells. Preferred capsules are formed of or include one or more of the disclosed modified alginates. Preferred capsules have a mean diameter of about 150 μm to about 8 mm.

The capsules can have any mean diameter from about 150 μm to about 5 cm. Preferably the capsules have a mean diameter that is greater than 1 mm, preferably 1.5 mm or greater. In some embodiments, the capsules can be as large as about 8 mm in diameter. For example, the capsule can be in a size range of about 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, or 1.5 mm to 2 mm.

The rate of molecules entering the capsule necessary for cell viability and the rate of therapeutic products and waste material exiting the capsule membrane can be selected by modulating capsule permeability. Capsule permeability can also be modified to limit entry of immune cells, antibodies, and cytokines into the capsule. Generally, as shown by the examples, known methods of forming hydrogel capsules can produce capsules the permeability of which limit entry of immune cells, antibodies, and cytokines into the capsule. Since different cell types have different metabolic requirements, the permeability of the membrane can be optimized based on the cell type encapsulated in the hydrogel. The diameter of the capsules is an important factor that influences both the immune response towards the cell capsules as well as the mass transport across the capsule membrane.

The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

The unmodified alginate typically has a weight average molecular weight of about 50,000 Daltons to about 500,000 Daltons; however, unmodified alginates having molecular weights can also be used. In some embodiments, the weight average molecular weight is from about 50,000 to about 250,000 Daltons, more preferably from about 50,000 to about 150,000 Daltons. In some embodiments, the weight average molecular weight is about 100,000 Daltons.

In other embodiments, one or more additional hydrogel-forming polymers are used in combination with unmodified alginate or in place of unmodified alginate. Such polymers are known in the art. Examples include, but are not limited to, PEG, chitosan, dextran, hyaluronic acid, silk, fibrin, poly(vinyl alcohol) and poly(hydroxyl ethyl methacrylate).

In some embodiments, the alginate is made up of β-D-mannuronic acid (M) and α-L-guluronic acid (G) linked together. In some embodiments, alginate is a high guluronic acid (G) alginate. In some embodiments, the alginate is a high mannuronic acid (M) alginate. In some embodiments, the ratio of M:G is about 1. In some embodiments, the ratio of M:G is less than 1. In some embodiments, the ratio of M:G is greater than 1.

For example, particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations in terms of shape and size as evaluated by scanning electron microscopy (SEM). Quantitative fluorescence analysis with prosense at several time points with modified alginates blended with SLG100 showed that several reformulated modified alginates display less inflammatory response at day 7 compared to the control alginate. Initial experiments with large capsules (1.5 mm diameter) were comparably clean capsules after 2 weeks in the IP space of immunocompetent C57BL6 mice. Subsequent experiments (Example 9) show that encapsulated human cells can achieve glucose-responsive, long-term glycemic correction (over 170 days) in an immune-competent diabetic animal with no immunosuppression. This result was accomplished using a modified alginate as disclosed to encapsulate the human cells. The resulting capsule mitigates immunological responses to human cell implants, effectively delaying the fibrotic deposition that leads to implant tissue necrosis. This formulation provided sufficient immunoprotection to enable long-term glycemic correction, in spite of the xenogeneic stimulation that these human cells manifest in an immunocompetent rodent recipient.

In some embodiments, the hydrogel capsules can have any suitable shape. Useful shapes include spheres, sphere-like shapes, spheroids, spheroid-like shapes, ellipsoids, ellipsoid-like shapes, stadiumoids, stadiumoid-like shapes, disks, disk-like shapes, cylinders, cylinder-like shapes, rods, rod-like shapes, cubes, cube-like shapes, cuboids, cuboid-like shapes, toruses, torus-like shapes, and flat and curved surfaces. Products, devices, and surfaces that have been or will be coated can have any of these shapes or any shape suitable for the product or device.

Spheres, spheroids, and ellipsoids are shapes with curved surfaces that can be defined by rotation of circles, ellipses, or a combination around each of the three perpendicular axes, a, b, and c. For a sphere, the three axes are the same length. For oblate spheroids (also referred to as oblate ellipsoids of rotation), the length of the axes are a=b>c. For prolate spheroids (also referred to as prolate ellipsoids of rotation), the length of the axes are a=b<c. For tri-axial ellipsoids (also referred to as scalene ellipsoids), the length of the axes are a>b>c. Stadiumoids are rotational shapes of stadiums. Cylinders are rotational shapes of rectangles rotated on the long axis. Disks are squashed cylinders where the diameter is greater than the height. Rods are elongated cylinders where the long axis is ten or more times the diameter.

"Sphere-like shape," "spheroid-like shape," "ellipsoid-like shape," "stadiumoid-like shape," "cylinder-like shape," "rod-like shape," "cube-like shape," "cuboid-like shape," and "torus-like shape" refers to an object having a surface that roughly forms a sphere, spheroid, ellipsoid, stadiumoid, cylinder, rod, cube, cuboid, or torus, respectively. Beyond a perfect or classical form of the shape, a sphere-like shape, spheroid-like shape, ellipsoid-like shape, stadiumoid-like shape, cylinder-like shape, rod-like shape, cube-like shape, cuboid-like shape, and torus-like shape can have waves and undulations.

Generally, a sphere-like shape is an ellipsoid (for its averaged surface) with semi-principal axes within 10% of each other. The diameter of a sphere or sphere-like shape is the average diameter, such as the average of the semi-principal axes. Generally, a spheroid-like shape is an ellipsoid (for its averaged surface) with semi-principal axes within 100% of each other. The diameter of a spheroid or spheroid-like shape is the average diameter, such as the average of the semi-principal axes. Generally, an ellipsoid-like shape is an ellipsoid (for its averaged surface) with semi-principal axes within 100% of each other. The diameter of an ellipsoid or ellipsoid-like shape is the average diameter, such as the average of the semi-principal axes. Generally, a stadiumoid-like shape is a stadiumoid (for its averaged surface) with semi-principal axes of the ends within 20% of each other. The diameter of a stadiumoid or stadiumoid-like shape is the average diameter, such as the average of the semi-principal axes. Alternatively, the size of a stadiumoid or stadiumoid-like shape can be given as the average of the long axis. Generally, a cylinder-like shape is a cylinder (for its averaged surface) with semi-principal axes within 20% of each other. The diameter of a cylinder or cylinder-like shape is the average diameter, such as the average of the semi-principal axes. Alternatively, the size of a cylinder or cylinder-like shape can be given as the average of the long axis. Generally, a rod-like shape is a rod (for its averaged surface) with semi-principal axes within 10% of each other. The diameter of a rod or rod-like shape is the average diameter, such as the average of the semi-principal axes. Alternatively, the size of a rod or rod-like shape can be given as the average of the long axis. Generally, a cube-like shape is a cube (for its averaged surface) with sides within 10% of each other. The diameter of a cube or cube-like shape is the average side length. Generally, a cuboid-like shape is a cuboid (for its averaged surface) with matching sides within 10% of each other. The diameter of a cuboid or cuboid-like shape is the average side length. Generally, a torus-like shape is a torus (for its averaged surface) with semi-principal axes within 10% of each other. The diameter of atoms or torus-like shape is the average diameter, such as the average of the semi-principal axes. Alternatively, the size of a torus or toms-like shape can be given as the diameter across the ring.

"Flat side" refers to a contiguous area of more than 5% of a surface that has a curvature of 0.

"Sharp angle" refers to a location on a surface across which the tangent to the surface changes by more than 10% over a distance of 2% or less of the circumference of the surface. Edges, corners, grooves, and ridges in a surface are all forms of sharp angles.

Preferred capsules can be made of biocompatible materials, have a diameter of at least 1 mm and less than 10 mm, has a spheroid-like shape, and have one or more of the additional characteristics: surface pores of the capsules greater than 0 nm and less than 10 µm; surface of the capsules neutral or hydrophilic; curvature of the surface of the capsules at least 0.2 and is not greater than 2 on all points of the surface; and surface of the capsules lacking flat sides, sharp angles, grooves, or ridges. Generally, the capsules elicit less of a fibrotic reaction after implantation than the same capsules lacking one or more of these characteristics that are present on the capsules.

In some embodiments, the capsule s are provided as a preparation and at least 30%, 35%, 40%, 45%, 50%, 55%, 60%, 65%, 70%, 75%, 80%, 85%, 90%, 95% or 100% of the capsules in the preparation have a shape characteristic described herein, e.g., have a spheroid-like shape, or have a curvature of the surface of at least 0.2 to 2.0 on all points of the surface.

In some embodiments, the hydrogel capsules have a mean diameter that is greater than 1 mm, preferably 1.5 mm or greater. In some embodiments, the hydrogel capsules can be as large as 8 mm in diameter. For example, the hydrogel capsules is in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm. In some embodiments, the capsule has a mean diameter or size between 1 mm to 8 mm. In some embodiments, the capsule has a mean diameter or size between 1 mm to 4 mm. In some embodiments, the capsule has a mean diameter or size between 1 mm to 2 mm.

In some embodiments, the capsules are provided as a preparation and at least 30%, 35%, 40%, 45%, 50%, 55%, 60%, 65%, 70%, 75%, 80%, 85%, 90%, 95% or 100% of the hydrogel capsules in the preparation have a diameter in a size range described herein In some embodiments, the hydrogel capsules have a mean pore size ranging from 0.1 µm to 10 µm. For example, the pores is in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to, 0.85 µm to 9 µm, 0.9 µm to 10 µm, 0.95 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to, 8 µm to 9 µm, 8.5 µm to 10 µm, 8.5 µm to 9 µm, 9 µm to 10 µm, or 9.5 µm to 10 µm. In some embodiments, the capsule has a mean pore size ranging from 0.1 µm to 10 µm. In some embodiments, the capsule has a mean pore size ranging from 0.1 µm to 5 µm. In some embodiments, the capsule has a mean pore size ranging from 0.1 µm to 1 µm.

In some embodiments, the capsules are provided as a preparation and at least 30%, 35%, 40%, 45%, 50%, 55%, 60%, 65%, 70%, 75%, 80%, 85%, 90%, 95% or 100% of the hydrogel capsules in the preparation have pores in a size range described herein.

In some embodiments, the chemical modifications of the residues within the hydrogel capsules are expressed as a density, i.e., average number of attached modifications per given area. In some embodiments, the density is at least, is less than, or is 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical modifications per µm$^2$ on the surface of the hydrogel capsules, in the interior of the hydrogel capsules, or both.

In some embodiments, the density is at least 100 chemical derivatizations per $\mu m^2$ on the surface of the hydrogel capsules, in the interior of the hydrogel capsules, or both. In some embodiments, the density is at least 1000 chemical derivatizations per $\mu m^2$ on the surface of the hydrogel capsules, in the interior of the hydrogel capsules, or both.

In some embodiments the density is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, and 0.1 to 1000 chemical derivatizations per $\mu m^2$ on the surface of the hydrogel capsules, in the interior of the hydrogel capsules, or both.

In some embodiments, the density is in the range of 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, and 0.2 to 1000 chemical derivatizations per $\mu m^2$ on the surface of the hydrogel capsules, in the interior of the hydrogel capsules, or both.

In some embodiments the density is in the range of 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, and 0.5 to 1000 chemical derivatizations per $\mu m^2$ on the surface of the hydrogel capsules, in the interior of the hydrogel capsules, or both.

In some embodiments the density is in the range of 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, and 1 to 1000 chemical derivatizations per $\mu m^2$ on the surface of the hydrogel capsules, in the interior of the hydrogel capsules, or both.

In some embodiments the density is in the range of 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, and 2 to 1000 chemical derivatizations per $\mu m^2$ on the surface of the hydrogel capsules, in the interior of the hydrogel capsules, or both.

In some embodiments the density is in the range of 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, and 3 to 1000 chemical derivatizations per $\mu m^2$ on the surface of the hydrogel capsules, in the interior of the hydrogel capsules, or both.

In some embodiments the density is in the range of 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, and 4 to 1000 chemical derivatizations per $\mu m^2$ on the surface of the hydrogel capsules, in the interior of the hydrogel capsules, or both.

In some embodiments the density is in the range of 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, 5 to 380, to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, and 5 to 1000 chemical derivatizations per $\mu m^2$ on the surface of the hydrogel capsules, in the interior of the hydrogel capsules, or both.

In some embodiments the density is in the range of 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, and 6 to 1000 chemical derivatizations per $\mu m^2$ on the surface of the hydrogel capsules, in the interior of the hydrogel capsules, or both.

In some embodiments the density is in the range of 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, and 7 to 1000 chemical derivatizations per $\mu m^2$ on the surface of the hydrogel capsules, in the interior of the hydrogel capsules, or both.

In some embodiments the density is in the range of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, and 8 to 1000 chemical derivatizations per $\mu m^2$ on the surface of the hydrogel capsules, in the interior of the hydrogel capsules, or both.

In some embodiments the density is in the range of 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, and 9 to 1000 chemical derivatizations per $\mu m^2$ on the surface of the hydrogel capsules, in the interior of the hydrogel capsules, or both.

In some embodiments the density is in the range of 10 to 11, 10 to 12, 10 to 13, to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, and 10 to 1000 chemical derivatizations per $\mu m^2$ on the surface of the hydrogel capsules, in the interior of the hydrogel capsules, or both.

In some embodiments the density is in the range of 20 to 25, 20 to 30, 20 to 35, to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, and 20 to 1000 chemical derivatizations per $\mu m^2$ on the surface of the hydrogel capsules, in the interior of the hydrogel capsules, or both.

In some embodiments the density is in the range of 30 to 35, 30 to 40, 30 to 45, to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, and 30 to 1000 chemical derivatizations per $\mu m^2$ on the surface of the hydrogel capsules, in the interior of the hydrogel capsules, or both.

In some embodiments the density is in the range of 40 to 45, 40 to 50, 40 to 55, to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, and 40 to 1000 chemical derivatizations per $\mu m^2$ on the surface of the hydrogel capsules, in the interior of the hydrogel capsules, or both.

In some embodiments the density is in the range of 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, and 50 to 1000 chemical derivatizations per $\mu m^2$ on the surface of the hydrogel capsules, in the interior of the hydrogel capsules, or both.

In some embodiments the density is in the range of 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, and 60 to 1000 chemical derivatizations per $\mu m^2$ on the surface of the hydrogel capsules, in the interior of the hydrogel capsules, or both.

In some embodiments the density is in the range of 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, and 70 to 1000 chemical derivatizations per $\mu m^2$ on the surface of the hydrogel capsules, in the interior of the hydrogel capsules, or both.

In some embodiments the density is in the range of 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, and 80 to 1000 chemical derivatizations per $\mu m^2$ on the surface of the hydrogel capsules, in the interior of the hydrogel capsules, or both.

In some embodiments the density is in the range of 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, and 90 to 1000 chemical derivatizations per $\mu m^2$ on the surface of the hydrogel capsules, in the interior of the hydrogel capsules, or both.

In some embodiments the density is in the range of 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, and 100 to 1000 chemical derivatizations per $\mu m^2$ on the surface of the hydrogel capsules, in the interior of the hydrogel capsules, or both.

In some embodiments the density is in the range of 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, and 200 to 1000 chemical derivatizations per $\mu m^2$ on the surface of the hydrogel capsules, in the interior of the hydrogel capsules, or both.

In some embodiments the density is in the range of 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, and 300 to 1000 chemical derivatizations per $\mu m^2$ on the surface of the hydrogel capsules, in the interior of the hydrogel capsules, or both.

In some embodiments the density is in the range of 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, and 400 to 1000 chemical derivatizations per $\mu m^2$ on the surface of the hydrogel capsules, in the interior of the hydrogel capsules, or both.

In some embodiments the density is in the range of 500 to 550, 500 to 600, 500 to 650, 500 to 700, 500 to 750, 500 to 800, 500 to 850, 500 to 900, and 500 to 1000 chemical derivatizations per $\mu m^2$ on the surface of the hydrogel capsules, in the interior of the hydrogel capsules, or both.

In some embodiments the density is in the range of 600 to 650, 600 to 700, 600 to 750, 600 to 800, 600 to 850, 600 to 900, and 600 to 1000 chemical derivatizations per $\mu m^2$ on the surface of the hydrogel capsules, in the interior of the hydrogel capsules, or both.

In some embodiments the density is in the range of 700 to 750, 700 to 800, 700 to 850, 700 to 900, and 700 to 1000 chemical derivatizations per $\mu m^2$ on the surface of the hydrogel capsules, in the interior of the hydrogel capsules, or both.

In some embodiments the density is in the range of 800 to 850, 800 to 900, and 800 to 1000 chemical derivatizations per $\mu m^2$ on the surface of the hydrogel capsules, in the interior of the hydrogel capsules, or both.

In some embodiments the density is in the range of 900 to 1000 chemical derivatizations per $\mu m^2$ on the surface of the hydrogel capsules, in the interior of the hydrogel capsules, or both.

In some embodiments, the capsules are provided as a preparation and at least 30%, 35%, 40%, 45%, 50%, 55%, 60%, 65%, 70%, 75%, 80%, 85%, 90%, 95% or 100% of the capsules in the preparation have a combination of diameter and pore size described herein.

In some embodiments, density chemical derivatizations of the surface of the capsules or products are expressed as a percent surface modifications or concentration of surface modifications. In some embodiments, the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent.

In some embodiments the concentration of surface modifications is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100 percent surface modifications.

In some embodiments the concentration of surface modifications is in the range of 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100 percent surface modifications.

In some embodiments the concentration of surface modifications is in the range of 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100 percent surface modifications.

In some embodiments the concentration of surface modifications is in the range of 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100 percent surface modifications.

In some embodiments the concentration of surface modifications is in the range of 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100 percent surface modifications.

In some embodiments the concentration of surface modifications is in the range of 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100 percent surface modifications.

In some embodiments the concentration of surface modifications is in the range of 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100 percent surface modifications.

In some embodiments the concentration of surface modifications is in the range of 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100 percent surface modifications.

In some embodiments the concentration of surface modifications is in the range of 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100 percent surface modifications.

In some embodiments the concentration of surface modifications is in the range of 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100 percent surface modifications.

In some embodiments the concentration of surface modifications is in the range of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100 percent surface modifications.

In some embodiments the concentration of surface modifications is in the range of 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100 percent surface modifications.

In some embodiments the concentration of surface modifications is in the range of 10 to 11, 10 to 12, 10 to 13, 10 to 14, 10 to 15, 10 to 16, 10 to 17, 10 to 18, 10 to 19, to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100 percent surface modifications. In some embodiments, the concentration of surface modifications is in the range of 10 to 100 percent surface modifications.

In some embodiments the concentration of surface modifications is in the range of 20 to 25, 20 to 30, 20 to 35, 20 to 40, 20 to 45, 20 to 50, 20 to 55, 20 to 60, 20 to 65, to 70, 20 to 75, 20 to 80, 20 to 85, 20 to 90, 20 to 95, 20 to 100 percent surface modifications.

In some embodiments the concentration of surface modifications is in the range of 30 to 35, 30 to 40, 30 to 45, 30 to 50, 30 to 55, 30 to 60, 30 to 65, 30 to 70, 30 to 75, to 80, 30 to 85, 30 to 90, 30 to 95, 30 to 100 percent surface modifications.

In some embodiments the concentration of surface modifications is in the range of 40 to 45, 40 to 50, 40 to 55, 40 to 60, 40 to 65, 40 to 70, 40 to 75, 40 to 80, 40 to 85, to 90, 40 to 95, 40 to 100 percent surface modifications.

In some embodiments the concentration of surface modifications is in the range of 50 to 55, 50 to 60, 50 to 65, 50 to 70, 50 to 75, 50 to 80, 50 to 85, 50 to 90, 50 to 95, 50 to 100 percent surface modifications.

In some embodiments the concentration of surface modifications is in the range of 60 to 65, 60 to 70, 60 to 75, 60 to 80, 60 to 85, 60 to 90, 60 to 95, 60 to 100 percent surface modifications.

In some embodiments the concentration of surface modifications is in the range of 70 to 75, 70 to 80, 70 to 85, 70 to 90, 70 to 95, 70 to 100 percent surface modifications.

In some embodiments the concentration of surface modifications is in the range of 80 to 85, 80 to 90, 80 to 95, 80 to 100 percent surface modifications.

In some embodiments the concentration of surface modifications is in the range of 90 to 95, 90 to 100 percent surface modifications.

In some embodiments, the capsule or product is provided as a preparation and at least 30%, 35%, 40%, 45%, 50%, 55%, 60%, 65%, 70%, 75%, 80%, 85%, 90%, 95% or 100% of the capsules or products in the preparation have a concentration of attached compounds described herein.

In some embodiments, the hydrogel capsules have a mean diameter that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the hydrogel capsule is provided as a preparation and at least 30%, 35%, 40%, 45%, 50%, 55%, 60%, 65%, 70%, 75%, 80%, 85%, 90%, 95% or 100% of the hydrogel capsules in the preparation have a combination of diameter and pore size described herein.

In some embodiments, the hydrogel capsules have a mean diameter that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, the density is at least 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical modifications per µm² on the surface of the hydrogel capsules, in the interior of the hydrogel capsules, or both.

In some embodiments, the hydrogel capsules have a mean diameter or size in a range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, and a density in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per µm$^2$ on the surface of the hydrogel capsules, in the interior of the hydrogel capsules, or both In some embodiments, the hydrogel capsule is provided as a preparation and at least 30%, 35%, 40%, 45%, 50%, 55%, 60%, 65%, 70%, 75%, 80%, 85%, 90%, 95% or 100% of the hydrogel capsules in the preparation have a combination of hydrogel capsule size or diameter and derivatization density described herein.

In some embodiments, the capsules or products have a mean diameter or size that is greater than 1 mm and less than 8 mm, greater than 1.5 mm and less than 8 mm, greater than 2 mm and less than 8 mm, greater than 2.5 mm and less than 8 mm, greater than 3 mm and less than 8 mm, greater than 3.5 mm and less than 8 mm, greater than 4 mm and less than 8 mm, greater than 4.5 mm and less than 8 mm, greater than 5 mm and less than 8 mm, greater than 5.5 mm and less than 8 mm, greater than 6 mm and less than 8 mm, greater than 6.5 mm and less than 8 mm, greater than 7 mm and less than 8 mm, or greater than 7.5 mm and less than 8 mm, and, independently, the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, and 100 percent.

In some embodiments, the capsules or products have a mean diameter or size in a range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, and a concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, 10 to 16, 10 to 17, 10 to 18, 10 to 19, 10 to 20, to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, 20 to 60, 20 to 65, 20 to 70, 20 to 75, 20 to 80, to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, 40 to 70, 40 to 75, 40 to 80, 40 to 85, 40 to 90, to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent.

In some embodiments, the capsule or product is provided as a preparation and at least 30%, 35%, 40%, 45%, 50%, 55%, 60%, 65%, 70%, 75%, 80%, 85%, 90%, 95% or 100% of the capsules or products in the preparation have a combination of capsule or product size or diameter and concentrations of surface modifications described herein.

In some embodiments, the density of the chemical modifications is at least, is less than, oris 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical modifications per $\mu m^2$ on the surface of the hydrogel capsules, in the interior of the hydrogel capsules, or both, or the concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 percent, and, independently, the hydrogel capsules have pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 junto 10 µm, 0.55 µm to 9 µm, 0.55 µm to 8 µm, 0.55 µm to 7 µm, 0.55 µm to 6 µm, 0.6 µm to 10 µm, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to, 1 µm to 10 µm, 1 µm to 10 µm, 1 µm to 9 µm, 1 µm to 8 µm, 1 µm to 7 µm, 1 junto 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to µm, 8.5 µm to 9 µm, 9 µm to 10 µm, or 9.5 µm to 10 µm.

In some embodiments, the density of the chemical derivatizations is in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, to 300, 5 to 320, 5 to 340, 5 to 360, 5 to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, 10 to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per $\mu m^2$ on the surface of the hydrogel capsules, in the interior of the hydrogel capsules, or both, and the hydrogel capsules have pores in a size range of 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, to 60, 20 to 65, 20 to 70, 20 to 75, 20 to 80, 20 to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, to 70, 40 to 75, 40 to 80, 40 to 85, 40 to 90, 40 to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent, and the capsules or products have pores in a size range of 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, 5 µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8 µm to 9 µm, 8.5 µm to 10 µm, 8.5 µm to 9 µm, 9 µm to 10 µm, or 9.5 µm to 10 µm.

In some embodiments, the hydrogel capsule is provided as a preparation and at least 30%, 35%, 40%, 45%, 50%, 55%, 60%, 65%, 70%, 75%, 80%, 85%, 90%, 95% or 100% of the hydrogel capsules in the preparation have a combination of pore size and derivatization density or concentration of surface modifications described herein.

In some embodiments, the hydrogel capsules are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 0.1 µm to 10 µm, 0.1 µm to 9 µm, 0.1 µm to 8 µm, 0.1 µm to 7 µm, 0.1 µm to 6 µm, 0.1 µm to 5 µm, 0.1 µm to 4 µm, 0.1 µm to 3 µm, 0.1 µm to 2 µm, 0.15 µm to 10 µm, 0.15 µm to 9 µm, 0.15 µm to 8 µm, 0.15 µm to 7 µm, 0.15 µm to 6 µm, 0.15 µm to 5 µm, 0.15 µm to 4 µm, 0.15 µm to 3 µm, 0.15 µm to 2 µm, 0.2 µm to 10 µm, 0.2 µm to 9 µm, 0.2 µm to 8 µm, 0.2 µm to 7 µm, 0.2 µm to 6 µm, 0.2 µm to 5 µm, 0.2 µm to 4 µm, 0.2 µm to 3 µm, 0.25 µm to 10 µm, 0.25 µm to 9 µm, 0.25 µm to 8 µm, 0.25 µm to 7 µm, 0.25 µm to 6 µm, 0.25 µm to 5 µm, 0.25 µm to 4 µm, 0.25 µm to 3 µm, 0.3 µm to 10 µm, 0.3 µm to 9 µm, 0.3 µm to 8 µm, 0.3 µm to 7 µm, 0.3 µm to 6 µm, 0.3 µm to 5 µm, 0.3 µm to 4 µm, 0.35 µm to 10 µm, 0.35 µm to 9 µm, 0.35 µm to 8 µm, 0.35 µm to 7 µm, 0.35 µm to 6 µm, 0.35 µm to 5 µm, 0.35 µm to 4 µm, 0.4 µm to 10 µm, 0.4 µm to 9 µm, 0.4 µm to 8 µm, 0.4 µm to 7 µm, 0.4 µm to 6 µm, 0.4 µm to 5 µm, 0.45 µm to 10 µm, 0.45 µm to 9 µm, 0.45 µm to 8 µm, 0.45 µm to 7 µm, 0.45 µm to 6 µm, 0.45 µm to 5 µm, 0.5 µm to 10 µm, 0.5 µm to 9 µm, 0.5 µm to 8 µm, 0.5 µm to 7 µm, 0.5 µm to 6 µm, 0.55 µm to 10 µm, 0.55 µm to 9 µm, 0.55 µm to 8 µm, 0.55 µm to 7 µm, 0.55 µm to 6 µm, 0.6 µm to, 0.6 µm to 9 µm, 0.6 µm to 8 µm, 0.6 µm to 7 µm, 0.65 µm to 10 µm, 0.65 µm to 9 µm, 0.65 µm to 8 µm, 0.65 µm to 7 µm, 0.7 µm to 10 µm, 0.7 µm to 9 µm, 0.7 µm to 8 µm, 0.75 µm to 10 µm, 0.75 µm to 9 µm, 0.75 µm to 8 µm, 0.8 µm to 10 µm, 0.8 µm to 9 µm, 0.85 µm to 10 µm, 0.85 µm to 9 µm, 0.9 µm to 10 µm, 0.95 µm to 10 µm, 1 µm to 10 µm, 1 µm to 9 µm, 1 µm to 8 µm, 1 µm to 7 µm, 1 µm to 6 µm, 1 µm to 5 µm, 1 µm to 4 µm, 1 µm to 3 µm, 1 µm to 2 µm, 1.5 µm to 10 µm, 1.5 µm to 9 µm, 1.5 µm to 8 µm, 1.5 µm to 7 µm, 1.5 µm to 6 µm, 1.5 µm to 5 µm, 1.5 µm to 4 µm, 1.5 µm to 3 µm, 1.5 µm to 2 µm, 2 µm to 10 µm, 2 µm to 9 µm, 2 µm to 8 µm, 2 µm to 7 µm, 2 µm to 6 µm, 2 µm to 5 µm, 2 µm to 4 µm, 2 µm to 3 µm, 2.5 µm to 10 µm, 2.5 µm to 9 µm, 2.5 µm to 8 µm, 2.5 µm to 7 µm, 2.5 µm to 6 µm, 2.5 µm to 5 µm, 2.5 µm to 4 µm, 2.5 µm to 3 µm, 3 µm to 10 µm, 3 µm to 9 µm, 3 µm to 8 µm, 3 µm to 7 µm, 3 µm to 6 µm, 3 µm to 5 µm, 3 µm to 4 µm, 3.5 µm to 10 µm, 3.5 µm to 9 µm, 3.5 µm to 8 µm, 3.5 µm to 7 µm, 3.5 µm to 6 µm, 3.5 µm to 5 µm, 3.5 µm to 4 µm, 4 µm to 10 µm, 4 µm to 9 µm, 4 µm to 8 µm, 4 µm to 7 µm, 4 µm to 6 µm, 4 µm to 5 µm, 4.5 µm to 10 µm, 4.5 µm to 9 µm, 4.5 µm to 8 µm, 4.5 µm to 7 µm, 4.5 µm to 6 µm, 4.5 µm to 5 µm, µm to 10 µm, 5 µm to 9 µm, 5 µm to 8 µm, 5 µm to 7 µm, 5 µm to 6 µm, 5.5 µm to 10 µm, 5.5 µm to 9 µm, 5.5 µm to 8 µm, 5.5 µm to 7 µm, 5.5 µm to 6 µm, 6 µm to 10 µm, 6 µm to 9 µm, 6 µm to 8 µm, 6 µm to 7 µm, 6.5 µm to 10 µm, 6.5 µm to 9 µm, 6.5 µm to 8 µm, 6.5 µm to 7 µm, 7 µm to 10 µm, 7 µm to 9 µm, 7 µm to 8 µm, 7.5 µm to 10 µm, 7.5 µm to 9 µm, 7.5 µm to 8 µm, 8 µm to 10 µm, 8

μm to 9 μm, 8.5 μm to 10 μm, 8.5 μm to 9 μm, 9 μm to 10 μm, or 9.5 μm to 10 μm, and have a density of at least, of less than, or of 0.1, 0.2, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 550, 600, 650, 700, 750, 800, 850, 900, or 1000 chemical modifications per μm² on its surface, interior or both, or have a concentration of surface modifications is at least, is less than, or is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 percent.

In some embodiments, the hydrogel capsules are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 1 μm to 10 μm, 1 μm to 9 μm, 1 μm to 8 μm, 1 μm to 7 μm, 1 μm to 6 μm, 1 μm to 5 μm, 1 μm to 4 μm, 1 μm to 3 μm, 1 μm to 2 μm, 1.5 μm to 10 μm, 1.5 μm to 9 μm, 1.5 μm to 8 μm, 1.5 μm to 7 μm, 1.5 μm to 6 μm, 1.5 μm to 5 μm, 1.5 μm to 4 μm, 1.5 μm to 3 μm, 1.5 μm to 2 μm, 2 μm to 10 μm, 2 μm to 9 μm, 2 μm to 8 μm, 2 μm to 7 μm, 2 μm to 6 μm, 2 μm to μm, 2 μm to 4 μm, 2 μm to 3 μm, 2.5 μm to 10 μm, 2.5 μm to 9 μm, 2.5 μm to 8 μm, 2.5 μm to 7 μm, 2.5 μm to 6 μm, 2.5 μm to 5 μm, 2.5 μm to 4 μm, 2.5 μm to 3 μm, 3 μm to 10 μm, 3 μm to 9 μm, 3 μm to 8 μm, 3 μm to 7 μm, 3 μm to 6 μm, 3 μm to 5 μm, 3 μm to 4 μm, 3.5 μm to 10 μm, 3.5 μm to 9 μm, 3.5 μm to 8 μm, 3.5 μm to 7 μm, 3.5 μm to 6 μm, 3.5 μm to 5 μm, 3.5 μm to 4 μm, 4 μm to 10 μm, 4 μm to 9 μm, 4 μm to 8 μm, 4 μm to 7 μm, 4 μm to 6 μm, 4 μm to 5 μm, 4.5 μm to 10 μm, 4.5 μm to 9 μm, 4.5 μm to 8 μm, 4.5 μm to 7 μm, 4.5 μm to 6 μm, 4.5 μm to 5 μm, 5 μm to 10 μm, 5 μm to 9 μm, 5 μm to 8 μm, 5 μm to 7 μm, 5 μm to 6 μm, 5.5 μm to 10 μm, 5.5 μm to 9 μm, 5.5 μm to 8 μm, 5.5 μm to 7 μm, 5.5 μm to 6 μm, 6 μm to 10 μm, 6 μm to 9 μm, 6 μm to 8 μm, 6 μm to 7 μm, 6.5 μm to 10 μm, 6.5 μm to 9 μm, 6.5 μm to 8 μm, 6.5 μm to 7 μm, 7 μm to μm, 7 μm to 9 μm, 7 μm to 8 μm, 7.5 μm to 10 μm, 7.5 μm to 9 μm, 7.5 μm to 8 μm, 8 μm to 10 μm, 8 μm to 9 μm, 8.5 μm to 10 μm, 8.5 μm to 9 μm, 9 μm to 10 μm, or 9.5 μm to 10 μm, and have a density in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.1 to 110, 0.1 to 120, 0.1 to 130, 0.1 to 140, 0.1 to 150, 0.1 to 160, 0.1 to 170, 0.1 to 180, 0.1 to 190, 0.1 to 200, 0.1 to 210, 0.1 to 220, 0.1 to 230, 0.1 to 240, 0.1 to 250, 0.1 to 260, 0.1 to 270, 0.1 to 280, 0.1 to 290, 0.1 to 300, 0.1 to 320, 0.1 to 340, 0.1 to 360, 0.1 to 380, 0.1 to 400, 0.1 to 420, 0.1 to 440, 0.1 to 460, 0.1 to 480, 0.1 to 500, 0.1 to 550, 0.1 to 600, 0.1 to 650, 0.1 to 700, 0.1 to 750, 0.1 to 800, 0.1 to 850, 0.1 to 900, 0.1 to 1000, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.2 to 110, 0.2 to 120, 0.2 to 130, 0.2 to 140, 0.2 to 150, 0.2 to 160, 0.2 to 170, 0.2 to 180, 0.2 to 190, 0.2 to 200, 0.2 to 210, 0.2 to 220, 0.2 to 230, 0.2 to 240, 0.2 to 250, 0.2 to 260, 0.2 to 270, 0.2 to 280, 0.2 to 290, 0.2 to 300, 0.2 to 320, 0.2 to 340, 0.2 to 360, 0.2 to 380, 0.2 to 400, 0.2 to 420, 0.2 to 440, 0.2 to 460, 0.2 to 480, 0.2 to 500, 0.2 to 550, 0.2 to 600, 0.2 to 650, 0.2 to 700, 0.2 to 750, 0.2 to 800, 0.2 to 850, 0.2 to 900, 0.2 to 1000, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 0.5 to 110, 0.5 to 120, 0.5 to 130, 0.5 to 140, 0.5 to 150, 0.5 to 160, 0.5 to 170, 0.5 to 180, 0.5 to 190, 0.5 to 200, 0.5 to 210, 0.5 to 220, 0.5 to 230, 0.5 to 240, 0.5 to 250, 0.5 to 260, 0.5 to 270, 0.5 to 280, 0.5 to 290, 0.5 to 300, 0.5 to 320, 0.5 to 340, 0.5 to 360, 0.5 to 380, 0.5 to 400, 0.5 to 420, 0.5 to 440, 0.5 to 460, 0.5 to 480, 0.5 to 500, 0.5 to 550, 0.5 to 600, 0.5 to 650, 0.5 to 700, 0.5 to 750, 0.5 to 800, 0.5 to 850, 0.5 to 900, 0.5 to 1000, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 1 to 110, 1 to 120, 1 to 130, 1 to 140, 1 to 150, 1 to 160, 1 to 170, 1 to 180, 1 to 190, 1 to 200, 1 to 210, 1 to 220, 1 to 230, 1 to 240, 1 to 250, 1 to 260, 1 to 270, 1 to 280, 1 to 290, 1 to 300, 1 to 320, 1 to 340, 1 to 360, 1 to 380, 1 to 400, 1 to 420, 1 to 440, 1 to 460, 1 to 480, 1 to 500, 1 to 550, 1 to 600, 1 to 650, 1 to 700, 1 to 750, 1 to 800, 1 to 850, 1 to 900, 1 to 1000, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 2 to 110, 2 to 120, 2 to 130, 2 to 140, 2 to 150, 2 to 160, 2 to 170, 2 to 180, 2 to 190, 2 to 200, 2 to 210, 2 to 220, 2 to 230, 2 to 240, 2 to 250, 2 to 260, 2 to 270, 2 to 280, 2 to 290, 2 to 300, 2 to 320, 2 to 340, 2 to 360, 2 to 380, 2 to 400, 2 to 420, 2 to 440, 2 to 460, 2 to 480, 2 to 500, 2 to 550, 2 to 600, 2 to 650, 2 to 700, 2 to 750, 2 to 800, 2 to 850, 2 to 900, 2 to 1000, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 3 to 110, 3 to 120, 3 to 130, 3 to 140, 3 to 150, 3 to 160, 3 to 170, 3 to 180, 3 to 190, 3 to 200, 3 to 210, 3 to 220, 3 to 230, 3 to 240, 3 to 250, 3 to 260, 3 to 270, 3 to 280, 3 to 290, 3 to 300, 3 to 320, 3 to 340, 3 to 360, 3 to 380, 3 to 400, 3 to 420, 3 to 440, 3 to 460, 3 to 480, 3 to 500, 3 to 550, 3 to 600, 3 to 650, 3 to 700, 3 to 750, 3 to 800, 3 to 850, 3 to 900, 3 to 1000, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 4 to 110, 4 to 120, 4 to 130, 4 to 140, 4 to 150, 4 to 160, 4 to 170, 4 to 180, 4 to 190, 4 to 200, 4 to 210, 4 to 220, 4 to 230, 4 to 240, 4 to 250, 4 to 260, 4 to 270, 4 to 280, 4 to 290, 4 to 300, 4 to 320, 4 to 340, 4 to 360, 4 to 380, 4 to 400, 4 to 420, 4 to 440, 4 to 460, 4 to 480, 4 to 500, 4 to 550, 4 to 600, 4 to 650, 4 to 700, 4 to 750, 4 to 800, 4 to 850, 4 to 900, 4 to 1000, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 5 to 110, 5 to 120, 5 to 130, 5 to 140, 5 to 150, 5 to 160, 5 to 170, 5 to 180, 5 to 190, 5 to 200, 5 to 210, 5 to 220, 5 to 230, 5 to 240, 5 to 250, 5 to 260, 5 to 270, 5 to 280, 5 to 290, 5 to 300, 5 to 320, 5 to 340, 5 to 360, to 380, 5 to 400, 5 to 420, 5 to 440, 5 to 460, 5 to 480, 5 to 500, 5 to 550, 5 to 600, 5 to 650, 5 to 700, 5 to 750, 5 to 800, 5 to 850, 5 to 900, 5 to 1000, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 6 to 110, 6 to 120, 6 to 130, 6 to 140, 6 to 150, 6 to 160, 6 to 170, 6 to 180, 6 to 190, 6 to 200, 6 to 210, 6 to 220, 6 to 230, 6 to 240, 6 to 250, 6 to 260, 6 to 270, 6 to 280, 6 to 290, 6 to 300, 6 to 320, 6 to 340, 6 to 360, 6 to 380, 6 to 400, 6 to 420, 6 to 440, 6 to 460, 6 to 480, 6 to 500, 6 to 550, 6 to 600, 6 to 650, 6 to 700, 6 to 750, 6 to 800, 6 to 850, 6 to 900, 6 to 1000, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 7 to 110, 7 to 120, 7 to 130, 7 to 140, 7 to 150, 7 to 160, 7 to 170, 7 to 180, 7 to 190, 7 to 200, 7 to 210, 7 to 220, 7 to 230, 7 to 240, 7 to 250, 7 to 260, 7 to 270, 7 to 280, 7 to 290, 7 to 300, 7 to 320, 7 to 340, 7 to 360, 7 to 380, 7 to 400, 7 to 420, 7 to 440, 7 to 460, 7 to 480, 7 to 500, 7 to 550, 7 to 600, 7 to 650, 7 to 700, 7 to 750, 7 to 800, 7 to 850, 7 to 900, 7 to 1000, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 8 to 110, 8 to 120, 8 to 130, 8 to 140, 8 to 150, 8 to 160, 8 to 170, 8 to 180, 8 to 190, 8 to 200, 8 to 210, 8 to 220, 8 to 230, 8 to 240, 8 to 250, 8 to 260, 8 to 270, 8 to 280, 8 to 290, 8 to 300, 8 to 320, 8 to 340, 8 to 360, 8 to 380, 8 to 400, 8 to 420, 8 to 440, 8 to 460, 8 to 480, 8 to 500, 8 to 550, 8 to 600, 8 to 650, 8 to 700, 8 to 750, 8 to 800, 8 to 850, 8 to 900, 8 to 1000, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 9 to 110, 9 to 120, 9 to 130, 9 to 140, 9 to 150, 9 to 160, 9 to 170, 9 to 180, 9 to 190, 9 to 200, 9 to 210, 9 to 220, 9 to 230, 9 to 240, 9 to 250, 9 to 260, 9 to 270, 9 to 280, 9 to 290, 9 to 300, 9 to 320, 9 to 340, 9 to 360, 9 to 380, 9 to 400, 9 to 420, 9 to 440, 9 to 460, 9 to 480, 9 to 500, 9 to 550, 9 to 600, 9 to 650, 9 to 700, 9 to 750, 9 to 800, 9 to 850, 9 to 900, 9 to 1000, 10 to 11, 10 to 12, 10 to 13, 10 to 14, 10 to 15, 10 to 16, 10 to 17, 10 to 18, 10 to 19, 10 to 20, 10 to 25, 10 to 30, to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 10 to 110, 10 to 120, 10 to 130, 10 to 140, to 150, 10 to 160, 10 to 170, 10 to 180, 10 to 190, 10 to 200, 10 to 210, 10 to 220, 10 to 230, 10 to 240, 10 to 250, 10 to 260, 10 to 270, 10 to 280, 10 to 290, 10 to 300, 10 to 320, 10 to 340, 10 to 360, 10 to 380, 10 to 400, 10 to 420, 10 to 440, 10 to 460, 10 to 480, 10 to 500, 10 to 550, 10 to 600, 10 to 650, 10 to 700, 10 to 750, 10 to 800, 10 to 850, 10 to 900, 10 to 1000, 20 to 25, 20 to 30, 20 to 35, 20 to 40, 20 to 45, 20 to 50, 20 to 55, 20 to 60, 20 to 65, 20 to 70, 20 to 75, 20 to 80, 20 to 85, 20 to 90, 20 to 95, 20 to 100, 20 to 110, 20 to 120, 20 to 130, 20 to 140, 20 to 150, 20 to 160, 20 to 170, 20 to 180, 20 to 190, 20 to 200, 20 to 210, 20 to 220, 20 to 230, 20 to 240, 20 to 250, 20 to 260, 20 to 270, 20 to 280, 20 to 290, 20 to 300, 20 to 320, 20 to 340, 20 to 360, 20 to 380, 20 to 400, 20 to 420, 20 to 440, 20 to 460, 20 to 480, 20 to 500, 20 to 550, 20 to 600, 20 to 650, 20 to 700, 20 to 750, 20 to 800, 20 to 850, 20 to 900, 20 to 1000, 30 to 35, 30 to 40, to 45, 30 to 50, 30 to 55, 30 to 60, 30 to 65, 30 to 70, 30 to 75, 30 to 80, 30 to 85, 30 to 90, 30 to 95, 30 to 100, 30 to 110, 30 to 120, 30 to 130, 30 to 140, 30 to 150, 30 to 160, 30 to 170, 30 to 180, 30 to 190, 30 to 200, 30 to 210, 30 to 220, 30 to 230, 30 to 240, 30 to 250, 30 to 260, 30 to 270, 30 to 280, 30 to 290, 30 to 300, 30 to 320, 30 to 340, 30 to 360, 30 to 380, 30 to 400, 30 to 420, 30 to 440, 30 to 460, 30 to 480, 30 to 500, 30 to 550, 30 to 600, 30 to 650, 30 to 700, 30 to 750, 30 to 800, 30 to 850, 30 to 900, 30 to 1000, 40 to 45, 40 to 50, 40 to 55, 40 to 60, 40 to 65, 40 to 70, 40 to 75, 40 to 80, 40 to 85, 40 to 90, 40 to 95, 40 to 100, 40 to 110, 40 to 120, 40 to 130, 40 to 140, 40 to 150, 40 to 160, 40 to 170, 40 to 180, 40 to 190, 40 to 200, 40 to 210, 40 to 220, 40 to 230, 40 to 240, 40 to 250, 40 to 260, 40 to 270, 40 to 280, 40 to 290, 40 to 300, 40 to 320, 40 to 340, 40 to 360, 40 to 380, 40 to 400, 40 to 420, 40 to 440, 40 to 460, 40 to 480, 40 to 500, 40 to 550, 40 to 600, 40 to 650, 40 to 700, 40 to 750, 40 to 800, 40 to 850, 40 to 900, 40 to 1000, 50 to 55, 50 to 60, 50 to 65, 50 to 70, 50 to 75, 50 to 80, 50 to 85, 50 to 90, 50 to 95, 50 to 100, 50 to 110, 50 to 120, 50 to 130, 50 to 140, 50 to 150, 50 to 160, 50 to 170, 50 to 180, 50 to 190, 50 to 200, 50 to 210, 50 to 220, 50 to 230, 50 to 240, 50 to 250, 50 to 260, 50 to 270, 50 to 280, 50 to 290, 50 to 300, 50 to 320, 50 to 340, 50 to 360, 50 to 380, 50 to 400, 50 to 420, 50 to 440, 50 to 460, 50 to 480, 50 to 500, 50 to 550, 50 to 600, 50 to 650, 50 to 700, 50 to 750, 50 to 800, 50 to 850, 50 to 900, 50 to 1000, 60 to 65, 60 to 70, 60 to 75, 60 to 80, 60 to 85, 60 to 90, 60 to 95, 60 to 100, 60 to 110, 60 to 120, 60 to 130, 60 to 140, 60 to 150, 60 to 160, 60 to 170, 60 to 180, 60 to 190, 60 to 200, 60 to 210, 60 to 220, 60 to 230, 60 to 240, 60 to 250, 60 to 260, 60 to 270, 60 to 280, 60 to 290, 60 to 300, 60 to 320, 60 to 340, 60 to 360, 60 to 380, 60 to 400, 60 to 420, 60 to 440, 60 to 460, 60 to 480, 60 to 500, 60 to 550, 60 to 600, 60 to 650, 60 to 700, 60 to 750, 60 to 800, 60 to 850, 60 to 900, 60 to 1000, 70 to 75, 70 to 80, 70 to 85, 70 to 90, 70 to 95, 70 to 100, 70 to 110, 70 to 120, 70 to 130, 70 to 140, 70 to 150, 70 to 160, 70 to 170, 70 to 180, 70 to 190, 70 to 200, 70 to 210, 70 to 220, 70 to 230, 70 to 240, 70 to 250, 70 to 260, 70 to 270, 70 to 280, 70 to 290, 70 to 300, 70 to 320, 70 to 340, 70 to 360, 70 to 380, 70 to 400, 70 to 420, 70 to 440, 70 to 460, 70 to 480, 70 to 500, 70 to 550, 70 to 600, 70 to 650, 70 to 700, 70 to 750, 70 to 800, 70 to 850, 70 to 900, 70 to 1000, 80 to 85, 80 to 90, 80 to 95, 80 to 100, 80 to 110, 80 to 120, 80 to 130, 80 to 140, 80 to 150, 80 to 160, 80 to 170, 80 to 180, 80 to 190, 80 to 200, 80 to 210, 80 to 220, 80 to 230, 80 to 240, 80 to 250, 80 to 260, 80 to 270, 80 to 280, 80 to 290, 80 to 300, 80 to 320, 80 to 340, 80 to 360, 80 to 380, 80 to 400, 80 to 420, 80 to 440, 80 to 460, 80 to 480, 80 to 500, 80 to 550, 80 to 600, 80 to 650, 80 to 700, 80 to 750, 80 to 800, 80 to 850, 80 to 900, 80 to 1000, 90 to 95, 90 to 100, 90 to 110, 90 to 120, 90 to 130, 90 to 140, 90 to 150, 90 to 160, 90 to 170, 90 to 180, 90 to 190, 90 to 200, 90 to 210, 90 to 220, 90 to 230, 90 to 240, 90 to 250, 90 to 260, 90 to 270, 90 to 280, 90 to 290, 90 to 300, 90 to 320, 90 to 340, 90 to 360, 90 to 380, 90 to 400, 90 to 420, 90 to 440, 90 to 460, 90 to 480, 90 to 500, 90 to 550, 90 to 600, 90 to 650, 90 to 700, 90 to 750, 90 to 800, 90 to 850, 90 to 900, 90 to 1000, 100 to 110, 100 to 120, 100 to 130, 100 to 140, 100 to 150, 100 to 160, 100 to 170, 100 to 180, 100 to 190, 100 to 200, 100 to 210, 100 to 220, 100 to 230, 100 to 240, 100 to 250, 100 to 260, 100 to 270, 100 to 280, 100 to 290, 100 to 300, 100 to 320, 100 to 340, 100 to 360, 100 to 380, 100 to 400, 100 to 420, 100 to 440, 100 to 460, 100 to 480, 100 to 500, 100 to 550, 100 to 600, 100 to 650, 100 to 700, 100 to 750, 100 to 800, 100 to 850, 100 to 900, 100 to 1000, 200 to 210, 200 to 220, 200 to 230, 200 to 240, 200 to 250, 200 to 260, 200 to 270, 200 to 280, 200 to 290, 200 to 300, 200 to 320, 200 to 340, 200 to 360, 200 to 380, 200 to 400, 200 to 420, 200 to 440, 200 to 460, 200 to 480, 200 to 500, 200 to 550, 200 to 600, 200 to 650, 200 to 700, 200 to 750, 200 to 800, 200 to 850, 200 to 900, 200 to 1000, 300 to 320, 300 to 340, 300 to 360, 300 to 380, 300 to 400, 300 to 420, 300 to 440, 300 to 460, 300 to 480, 300 to 500, 300 to 550, 300 to 600, 300 to 650, 300 to 700, 300 to 750, 300 to 800, 300 to 850, 300 to 900, 300 to 1000, 400 to 420, 400 to 440, 400 to 460, 400 to 480, 400 to 500, 400 to 550, 400 to 600, 400 to 650, 400 to 700, 400 to 750, 400 to 800, 400 to 850, 400 to 900, 400 to 1000, 500 to 550, 500 to 600, 500 to 650, 500 to 700, 500 to 750, 500 to 800, 500 to 850, 500 to 900, 500 to 1000, 600 to 650, 600 to 700, 600 to 750, 600 to 800, 600 to 850, 600 to 900, 600 to 1000, 700 to 750, 700 to 800, 700 to 850, 700 to 900, 700 to 1000, 800 to 850, 800 to 900, 800 to 1000, and 900 to 1000 chemical derivatizations per $\mu m^2$ on the surface of the hydrogel capsules, in the interior of the hydrogel capsules, or both.

In some embodiments, the capsules or products are in a size range of 1 mm to 8 mm, 1 mm to 6 mm, 1 mm to 5 mm, 1 mm to 4 mm, 1 mm to 3 mm, 1 mm to 2 mm, 1 mm to 1.5 mm, 1.5 mm to 8 mm, 1.5 mm to 6 mm, 1.5 mm to 5 mm, 1.5 mm to 4 mm, 1.5 mm to 3 mm, 1.5 mm to 2 mm, 2 mm to 8 mm, 2 mm to 7 mm, 2 mm to 6 mm, 2 mm to 5 mm, 2 mm to 4 mm, 2 mm to 3 mm, 2.5 mm to 8 mm, 2.5 mm to 7 mm, 2.5 mm to 6 mm, 2.5 mm to 5 mm, 2.5 mm to 4 mm, 2.5 mm to 3 mm, 3 mm to 8 mm, 3 mm to 7 mm, 3 mm to 6 mm, 3 mm to 5 mm, 3 mm to 4 mm, 3.5 mm to 8 mm, 3.5 mm to 7 mm, 3.5 mm to 6 mm, 3.5 mm to 5 mm, 3.5 mm to 4 mm, 4 mm to 8 mm, 4 mm to 7 mm, 4 mm to 6 mm, 4 mm to 5 mm, 4.5 mm to 8 mm, 4.5 mm to 7 mm, 4.5 mm to 6 mm, 4.5 mm to 5 mm, 5 mm to 8 mm, 5 mm to 7 mm, 5 mm to 6 mm, 5.5 mm to 8 mm, 5.5 mm to 7 mm, 5.5 mm to 6 mm, 6 mm to 8 mm, 6 mm to 7 mm, 6.5 mm to 8 mm, 6.5 mm to 7 mm, 7 mm to 8 mm, or 7.5 mm to 8 mm, have pores in a size range of 1 $\mu m$ to 10 $\mu m$, 1 $\mu m$ to 9 $\mu m$, 1 $\mu m$ to 8 $\mu m$, 1 $\mu m$ to 7 $\mu m$, 1 $\mu m$ to 6 $\mu m$, 1 $\mu m$ to 5 $\mu m$, 1 $\mu m$ to 4 $\mu m$, 1 $\mu m$ to 3 $\mu m$, 1 $\mu m$ to 2 $\mu m$, 1.5 $\mu m$ to 10 $\mu m$, 1.5 $\mu m$ to 9 $\mu m$, 1.5 $\mu m$ to 8 $\mu m$, 1.5 $\mu m$ to 7 $\mu m$, 1.5 $\mu m$ to 6 $\mu m$, 1.5 $\mu m$ to 5 $\mu m$, 1.5 $\mu m$ to 4 $\mu m$, 1.5 $\mu m$ to 3 $\mu m$, 1.5 $\mu m$ to 2 $\mu m$, 2 $\mu m$ to 10 $\mu m$, 2 $\mu m$ to 9 $\mu m$, 2 $\mu m$ to 8 $\mu m$, 2 $\mu m$ to 7 $\mu m$, 2 $\mu m$ to 6 $\mu m$, 2 $\mu m$ to 5 $\mu m$, 2 $\mu m$ to 4 $\mu m$, 2 $\mu m$ to 3 $\mu m$, 2.5 $\mu m$ to 10 $\mu m$, 2.5 $\mu m$ to 9 $\mu m$, 2.5 $\mu m$ to 8 $\mu m$, 2.5 $\mu m$ to 7 $\mu m$, 2.5 $\mu m$ to 6 $\mu m$, 2.5 $\mu m$ to 5 $\mu m$, 2.5 $\mu m$ to 4 $\mu m$, 2.5 $\mu m$ to 3 $\mu m$, 3 $\mu m$ to 10 $\mu m$, 3 $\mu m$ to 9 $\mu m$, 3 $\mu m$ to 8 $\mu m$, 3 $\mu m$ to 7 $\mu m$, 3 $\mu m$ to 6 $\mu m$, 3 $\mu m$ to 5 $\mu m$, 3 $\mu m$ to 4 $\mu m$, 3.5 $\mu m$ to 10 $\mu m$, 3.5 $\mu m$ to 9 $\mu m$, 3.5 $\mu m$ to 8 $\mu m$, 3.5 $\mu m$ to 7 $\mu m$, 3.5 $\mu m$ to 6 $\mu m$, 3.5 $\mu m$ to 5 $\mu m$, 3.5 $\mu m$ to 4 $\mu m$, 4 $\mu m$ to 10 $\mu m$, 4 $\mu m$ to 9 $\mu m$, 4 $\mu m$ to 8 $\mu m$, 4 $\mu m$ to 7 $\mu m$, 4 $\mu m$ to 6 $\mu m$, 4 $\mu m$ to 5 $\mu m$, 4.5 $\mu m$ to 10 $\mu m$, 4.5 $\mu m$ to 9 $\mu m$, 4.5 $\mu m$ to 8 $\mu m$, 4.5 $\mu m$ to 7 $\mu m$, 4.5 $\mu m$ to 6 $\mu m$, 4.5 $\mu m$ to 5 $\mu m$, 5 $\mu m$ to 10 $\mu m$, 5 $\mu m$ to 9 $\mu m$, 5 $\mu m$ to 8 $\mu m$, 5 $\mu m$ to 7 $\mu m$, 5 $\mu m$ to 6 $\mu m$, 5.5 $\mu m$ to 10 $\mu m$, 5.5 $\mu m$ to 9 $\mu m$, 5.5 $\mu m$ to 8 $\mu m$, 5.5 $\mu m$ to 7 $\mu m$, 5.5 $\mu m$ to 6 $\mu m$, 6 $\mu m$ to 10 $\mu m$, 6 $\mu m$ to 9 $\mu m$, 6 $\mu m$ to 8 $\mu m$, 6 $\mu m$ to 7 $\mu m$, 6.5 $\mu m$ to 10 $\mu m$, 6.5 $\mu m$ to 9 $\mu m$, 6.5 $\mu m$ to 8 $\mu m$, 6.5 $\mu m$ to 7 $\mu m$, 7 $\mu m$ to 10 $\mu m$, 7 $\mu m$ to 9 $\mu m$, 7 $\mu m$ to 8 $\mu m$, 7.5 $\mu m$ to 10 $\mu m$, 7.5 $\mu m$ to 9 $\mu m$, 7.5 $\mu m$ to 8 $\mu m$, 8 $\mu m$ to 10 $\mu m$, 8 $\mu m$ to 9 $\mu m$, 8.5 $\mu m$ to 10 $\mu m$, 8.5 $\mu m$ to 9 $\mu m$, 9 $\mu m$ to 10 $\mu m$, or 9.5 $\mu m$ to 10 $\mu m$, and have a concentration of surface modifications in the range of 0.1 to 0.2, 0.1 to 0.5, 0.1 to 1, 0.1 to 2, 0.1 to 3, 0.1 to 4, 0.1 to 5, 0.1 to 6, 0.1 to 7, 0.1 to 8, 0.1 to 9, 0.1 to 10, 0.1 to 11, 0.1 to 12, 0.1 to 13, 0.1 to 14, 0.1 to 15, 0.1 to 16, 0.1 to 17, 0.1 to 18, 0.1 to 19, 0.1 to 20, 0.1 to 25, 0.1 to 30, 0.1 to 35, 0.1 to 40, 0.1 to 45, 0.1 to 50, 0.1 to 55, 0.1 to 60, 0.1 to 65, 0.1 to 70, 0.1 to 75, 0.1 to 80, 0.1 to 85, 0.1 to 90, 0.1 to 95, 0.1 to 100, 0.2 to 0.5, 0.0 to 1, 0.2 to 2, 0.2 to 3, 0.2 to 4, 0.2 to 5, 0.2 to 6, 0.2 to 7, 0.2 to 8, 0.2 to 9, 0.2 to 10, 0.2 to 11, 0.2 to 12, 0.2 to 13, 0.2 to 14, 0.2 to 15, 0.2 to 16, 0.2 to 17, 0.2 to 18, 0.2 to 19, 0.2 to 20, 0.2 to 25, 0.2 to 30, 0.2 to 35, 0.2 to 40, 0.2 to 45, 0.2 to 50, 0.2 to 55, 0.2 to 60, 0.2 to 65, 0.2 to 70, 0.2 to 75, 0.2 to 80, 0.2 to 85, 0.2 to 90, 0.2 to 95, 0.2 to 100, 0.5 to 1, 0.5 to 2, 0.5 to 3, 0.5 to 4, 0.5 to 5, 0.5 to 6, 0.5 to 7, 0.5 to 8, 0.5 to 9, 0.5 to 10, 0.5 to 11, 0.5 to 12, 0.5 to 13, 0.5 to 14, 0.5 to 15, 0.5 to 16, 0.5 to 17, 0.5 to 18, 0.5 to 19, 0.5 to 20, 0.5 to 25, 0.5 to 30, 0.5 to 35, 0.5 to 40, 0.5 to 45, 0.5 to 50, 0.5 to 55, 0.5 to 60, 0.5 to 65, 0.5 to 70, 0.5 to 75, 0.5 to 80, 0.5 to 85, 0.5 to 90, 0.5 to 95, 0.5 to 100, 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, 1 to 100, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 16, 2 to 17, 2 to 18, 2 to 19, 2 to 20, 2 to 25, 2 to 30, 2 to 35, 2 to 40, 2 to 45, 2 to 50, 2 to 55, 2 to 60, 2 to 65, 2 to 70, 2 to 75, 2 to 80, 2 to 85, 2 to 90, 2 to 95, 2 to 100, 3 to 4, 3 to 5, 3 to 6, 3 to 7, 3 to 8, 3 to 9, 3 to 10, 3 to 11, 3 to 12, 3 to 13, 3 to 14, 3 to 15, 3 to 16, 3 to 17, 3 to 18, 3 to 19, 3 to 20, 3 to 25, 3 to 30, 3 to 35, 3 to 40, 3 to 45, 3 to 50, 3 to 55, 3 to 60, 3 to 65, 3 to 70, 3 to 75, 3 to 80, 3 to 85, 3 to 90, 3 to 95, 3 to 100, 4 to 5, 4 to 6, 4 to 7, 4 to 8, 4 to 9, 4 to 10, 4 to 11, 4 to 12, 4 to 13, 4 to 14, 4 to 15, 4 to 16, 4 to 17, 4 to 18, 4 to 19, 4 to 20, 4 to 25, 4 to 30, 4 to 35, 4 to 40, 4 to 45, 4 to 50, 4 to 55, 4 to 60, 4 to 65, 4 to 70, 4 to 75, 4 to 80, 4 to 85, 4 to 90, 4 to 95, 4 to 100, 5 to 6, 5 to 7, 5 to 8, 5 to 9, 5 to 10, 5 to 11, 5 to 12, 5 to 13, 5 to 14, 5 to 15, 5 to 16, 5 to 17, 5 to 18, 5 to 19, 5 to 20, 5 to 25, 5 to 30, 5 to 35, 5 to 40, 5 to 45, 5 to 50, 5 to 55, 5 to 60, 5 to 65, 5 to 70, 5 to 75, 5 to 80, 5 to 85, 5 to 90, 5 to 95, 5 to 100, 6 to 7, 6 to 8, 6 to 9, 6 to 10, 6 to 11, 6 to 12, 6 to 13, 6 to 14, 6 to 15, 6 to 16, 6 to 17, 6 to 18, 6 to 19, 6 to 20, 6 to 25, 6 to 30, 6 to 35, 6 to 40, 6 to 45, 6 to 50, 6 to 55, 6 to 60, 6 to 65, 6 to 70, 6 to 75, 6 to 80, 6 to 85, 6 to 90, 6 to 95, 6 to 100, 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, 7 to 25, 7 to 30, 7 to 35, 7 to 40, 7 to 45, 7 to 50, 7 to 55, 7 to 60, 7 to 65, 7 to 70, 7 to 75, 7 to 80, 7 to 85, 7 to 90, 7 to 95, 7 to 100, 8 to 9, 8 to 10, 8 to 11, 8 to 12, 8 to 13, 8 to 14, 8 to 15, 8 to 16, 8 to 17, 8 to 18, 8 to 19, 8 to 20, 8 to 25, 8 to 30, 8 to 35, 8 to 40, 8 to 45, 8 to 50, 8 to 55, 8 to 60, 8 to 65, 8 to 70, 8 to 75, 8 to 80, 8 to 85, 8 to 90, 8 to 95, 8 to 100, 9 to 10, 9 to 11, 9 to 12, 9 to 13, 9 to 14, 9 to 15, 9 to 16, 9 to 17, 9 to 18, 9 to 19, 9 to 20, 9 to 25, 9 to 30, 9 to 35, 9 to 40, 9 to 45, 9 to 50, 9 to 55, 9 to 60, 9 to 65, 9 to 70, 9 to 75, 9 to 80, 9 to 85, 9 to 90, 9 to 95, 9 to 100, 10 to 11, 10 to 12, 10 to 13, 10 to 14, 10 to 15, to 16, 10 to 17, 10 to 18, 10 to 19, 10 to 20, 10 to 25, 10 to 30, 10 to 35, 10 to 40, 10 to 45, 10 to 50, 10 to 55, 10 to 60, 10 to 65, 10 to 70, 10 to 75, 10 to 80, 10 to 85, 10 to 90, 10 to 95, 10 to 100, 20 to 25, 20 to 30, 20 to 35, 20 to 40, 20 to 45, 20 to 50, 20 to 55, to 60, 20 to 65, 20 to 70, 20 to 75, 20 to 80, 20 to 85, 20 to 90, 20 to 95, 20 to 100, 30 to 35, 30 to 40, 30 to 45, 30 to 50, 30 to 55, 30 to 60, 30 to 65, 30 to 70, 30 to 75, 30 to 80, 30 to 85, 30 to 90, 30 to 95, 30 to 100, 40 to 45, 40 to 50, 40 to 55, 40 to 60, 40 to 65, to 70, 40 to 75, 40 to 80, 40 to 85, 40 to 90, 40 to 95, 40 to 100, 50 to 55, 50 to 60, 50 to 65, 50 to 70, 50 to 75, 50 to 80, 50 to 85, 50 to 90, 50 to 95, 50 to 100, 60 to 65, 60 to 70, 60 to 75, 60 to 80, 60 to 85, 60 to 90, 60 to 95, 60 to 100, 70 to 75, 70 to 80, 70 to 85, 70 to 90, 70 to 95, 70 to 100, 80 to 85, 80 to 90, 80 to 95, 80 to 100, 90 to 95, 90 to 100 percent.

In some embodiments, the hydrogel capsule is provided as a preparation and at least 30%, 35%, 40%, 45%, 50%, 55%, 60%, 65%, 70%, 75%, 80%, 85%, 90%, 95% or 100% of the hydrogel capsules in the preparation have a combination of hydrogel capsule size or diameter, pore size, and derivatization density or concentration of surface modifications described herein.

Because the disclosed modified alginates mediate the reduced fibrosis, capsules made of other materials but coated or encapsulated with the modified alginates is a useful form of capsule for achieving reduced fibrosis. This, the capsules can include capsules and particles made of a variety of materials that are then coated or encapsulated in alginate that is or included modified alginate.

The disclosed compositions may be fabricated into artificial organs, such as an artificial pancreas containing encapsulated islet cells. In some of these embodiments, the cells are encapsulated in a single hydrogel compartment. In other embodiments, the composition contains a plurality of encapsulated cells dispersed or encapsulated in a biocompatible structure.

C. Therapeutic Agents Included in Hydrogel Capsules

The disclosed hydrogel capsules can include one or more therapeutic agents. Therapeutic agents are any compound, composition, conjugate, or construct that can be used to treat a disease, disorder, condition, symptom, etc. Examples of therapeutic agents include cells, tissues, cell products, tissue products, proteins, antibodies, vaccines, vaccine components, antigens, epitopes, drugs, salts, nutrients, buffers, acids, and bases. In some embodiments, the therapeutic agent can be a biological material.

In some embodiments, the hydrogel capsule can include a cell or tissue, e.g., a living cell or tissue, which in some embodiments is encapsulated in, or coated with, a polymer. In such embodiments, the surface of the polymer encapsulation or coating is modified with moieties or compounds disclosed herein. In some embodiments, the cell can include an exogenous nucleic acid that encodes a therapeutic or diagnostic polypeptide. In some embodiments the cell or engineered cell is autologous, allogenic, or zenogeneic.

In some embodiments, the cell is a genetically engineered cell that secretes a therapeutic agent, such as a protein or hormone for treating a disease or other condition. In some embodiments, the cell is a genetically engineered cell that secretes a diagnostic agent. In some embodiments, the cell is a stem cell, e.g., an embryonic stem cell, mesenchymal stem cell, hepatic stem cell, or bone marrow stem cell.

1. Biological Materials

Biological material for inclusion in the disclosed hydrogel capsules can be any biological substance. For example, the biological material can be tissue, cells, biological micromolecules, or biological macromolecules. Examples of biological macromolecules include nucleotides, amino acids, cofactors, and hormones. Examples of biological macromolecules include nucleic acids, polypeptides, proteins, and polysaccharides. Examples of proteins include enzymes, receptors, secretory proteins, structural proteins, signaling proteins, hormones, and ligands. Any class, type, form, or particular biological material can be used together with any other classes, types, forms, or particular biological materials.

a. Cells

The cell type chosen for inclusion in the disclosed hydrogel capsules depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Any of these types of cells can be from natural sources, stem cells, derived cells, or genetically engineered cell.

In some embodiments, the cells secrete a therapeutically effective substance, such as a protein or nucleic acid. In some embodiments, the cells produce a metabolic product. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid. In some embodiments, the cells are genetically engineered to produce a new or different product, which can be an expression product of the engineered gene(s) or another product, such as a metabolite, produced because of the engineered gene(s).

Types of cells for inclusion in the disclosed hydrogel capsules include cells from natural sources, such as cells from xenotissue, cells from a cadaver, and primary cells; stem cells, such as embryonic stem cells, mesenchymal stem cells, and induced pluripotent stem cells; derived cells, such as cells derived from stem cells, cells from a cell line, reprogrammed cells, reprogrammed stem cells, and cells derived from reprogrammed stem cells; and genetically engineered cells, such as cells genetically engineered to express a protein or nucleic acid, cells genetically engineered to produce a metabolic product, and cells genetically engineered to metabolize toxic substances.

Types of cells for inclusion in the disclosed hydrogel capsules include liver cells (e.g., hepatoblasts liver stellate cells, biliary cells, or hepatocytes), insulin producing cells (e.g., pancreatic islet cells, isolated pancreatic beta cells, or insulinoma cells), kidney cells, epidermal cells, epithelial cells, neural cells, including neurons and glial cells (e.g., astrocytes), ganglion cells, retinal epithelial cells, adrenal medulla cells, lung cells, cardiac muscle cells, osteoblast cells, osteoclast cells, bone marrow cells, spleen cells, thymus cells, glandular cells, blood cells (e.g., T cells, B cells, macrophage lineage cells, lymphocytes, or monocytes), endocrine hormone-producing cells (e.g., parathyroid, thyroid, or adrenal cells), cells of intestinal origin and other cells acting primarily to synthesize and secret or to metabolize materials, endothelial cells (e.g., capillary endothelial cells), fibroblasts (e.g., dermal fibroblasts), myogenic cells, keratinocytes, smooth muscle cells, progenitor cells (e.g., bone marrow progenitor cells, adipose progenitor cells, hepatic precursor cells, endothelia progenitor cells, peripheral blood progenitor cells, or progenitor cells from muscle, skin) marrow stromal cells cell lines (e.g., CHO cells, MDCK cells and PC12 cells).

A preferred cell type is a pancreatic islet cell or other insulin-producing cell. Hormone-producing cells can produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. Genetically engineered cells are also suitable for inclusion in the disclosed hydrogel capsules. In some embodiments, the cells are engineered to produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. In some embodiments, the cells are engineered to secrete blood clotting factors (e.g., for hemophilia treatment) or to secrete growth hormones. In some embodiments, the cells are contained in natural or bioengineered tissue. For example, the cells for inclusion in the disclosed hydrogel capsules are in some embodiments a bioartificial renal glomerulus. In some embodiments, the cells are suitable for transplantation into the central nervous system for treatment of neurodegenerative disease.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell viability can be assessed using standard techniques, such as histology and fluorescent microscopy. The function of the implanted cells can be determined using a combination of these techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, pancreatic islet cells and other insulin-producing cells can be implanted to achieve glucose regulation by appropriate secretion of insulin. Other endocrine tissues and cells can also be implanted.

The site, or sites, where cells are to be implanted is determined based on individual need, as is the requisite number of cells. For cells replacing or supplementing organ or gland function (for example, hepatocytes or islet cells), the mixture can be injected into the mesentery, subcutaneous tissue, retroperitoneum, properitoneal space, and intramuscular space.

The amount and density of cells included in the disclosed hydrogel capsules will vary depending on the choice of cell and site of implantation. In some embodiments, the single cells are present in the hydrogel capsule at a concentration of $0.1 \times 10^6$ to $4 \times 10^6$ cells/ml, preferred $0.5 \times 10^6$ to $2 \times 10^6$ cells/ml. In other embodiments, the cells are present as cell aggregates. For example, islet cell aggregates (or whole islets) preferably contain about 1500-2000 cells for each aggregate of 150 μm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

i. Islet Cells and Other Insulin-Producing Cells

In preferred embodiments, the disclosed compositions contain islet cells or other insulin-producing cells. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to inclusion in the hydrogel capsule using any suitable method of culturing islet cells as is known in the art. See e.g., U.S. Pat. No. 5,821,121 to Brothers. Isolated cells may be cultured in a medium under conditions that helps to eliminate antigenic components. Insulin-producing cells can also be derived from stem cells and cell lines and can be cells genetically engineered to produce insulin.

2. Genetically Engineered Cells

In some embodiments, the disclosed compositions contain cells genetically engineered to produce a protein or nucleic acid (e.g., a therapeutic protein or nucleic acid). In these embodiments, the cell can be, for example, a stem cell (e.g., pluripotent), a progenitor cell (e.g., multipotent or oligopotent), or a terminally differentiated cell (i.e., unipotent). Any of the disclosed cell types can be genetically engineered. The cell can be engineered, for example, to contain a nucleic acid encoding, for example, a polynucleotide such miRNA or RNAi or a polynucleotide encoding a protein. The nucleic acid can be, for example, integrated into the cells genomic DNA for stable expression or can be, for example, in an expression vector (e.g., plasmid DNA). The polynucleotide or protein can be selected based on the disease to be treated (or effect to be achieved) and the site of transplantation or implantation. In some embodiments, the polynucleotide or protein is anti-neoplastic. In other embodiments, the polynucleotide or protein is a hormone, growth factor, or enzyme.

Therapeutic agents for secretion by genetically engineered cells include, for example, thyroid stimulating hormone; beneficial lipoproteins such as Apo1; prostacyclin and other vasoactive substances, anti-oxidants and free radical scavengers; soluble cytokine receptors, for example soluble transforming growth factor (TGF) receptor, or cytokine receptor antagonists, for example IL1ra; soluble adhesion molecules, for example ICAM-1; soluble receptors for viruses, e.g. CD4, CXCR4, CCR5 for HIV; cytokines; elastase inhibitors; bone morphogenetic proteins (BMP) and BMP receptors 1 and 2; endoglin; serotonin receptors; tissue inhibiting metaloproteinases; potassium channels or potassium channel modulators; anti-inflammatory factors; angiogenic factors including vascular endothelial growth factor (VEGF), transforming growth factor (TGF), hepatic growth factor, and hypoxia inducible factor (HIF); polypeptides with neurotrophic and/or anti-angiogenic activity including ciliary neurotrophic factor (CNTF), glial-derived neurotrophic factor (GDNF), nerve growth factor (NGF), brain-derived neurotrophic factor (BDNF), neurotrophin-3, nurturin, fibroblast growth factors (FGFs), endostatin, ATF, fragments of thrombospondin, variants thereof and the like. More preferred polypeptides are FGFs, such as acidic FGF (aFGF), basic FGF (bFGF), FGF-1 and FGF-2 and endostatin.

In some embodiments, the active agent is a protein or peptide. Examples of protein active agents include, but are not limited to, cytokines and their receptors, as well as chimeric proteins including cytokines or their receptors, including, for example tumor necrosis factor alpha and beta, their receptors and their derivatives; renin; lipoproteins; colchicine; prolactin; corticotrophin; vasopressin; somatostatin; lypressin; pancreozymin; leuprolide; alpha-1-antitrypsin; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of protein active agents also include CCL1, CCL2 (MCP-1), CCL3 (MIP-1α), CCL4 (MIP-1β), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, ILIA (IL1F1), IL1B (IL1F2), ILIRa (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, Clqtnf4, Ccl21a, Ccl27a, Cd70, Cerl, Cklf, Clcf1, Cmtm2a, Cmtm2b, Cmtm3, Cmtm4, Cmtm5, Cmtm6, Cmtm7, Cmtm8, Crlf1, Ctf2, Ebi3, Edn1, Fam3b, Fas1, Fgf2, Flt31, Gdf10, Gdf11, Gdf15, Gdf2, Gdf3, Gdf5, Gdf6, Gdf7, Gdf9, Gml2597, Gml3271, Gml3275, Gml3276, Gml3280, Gml3283, Gm2564, Gpi1, Grem1, Grem2, Gm, Hmgb1, Ifna11, Ifha12, Ifha9, Ifnab, Ifne, I117a, I123a, I125, I131, Iltifb, Inhba, Lefty 1, Lefty2, Mstn, Nampt, Ndp, Noda1, Pf4, Pglyrp1, Prl7dl, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, Epinephrine, Melatonin, Triiodothyronine, Thyroxine, Prostaglandins, Leukotrienes, Prostacyclin, Thromboxane, Islet Amyloid Polypeptide, Müllerian inhibiting factor or hormone, Adiponectin, Corticotropin, Angiotensin, vasopressin, arginine vasopressin, atriopeptin, Brain natriuretic peptide, Calcitonin, Cholecystokinin, Cortistatin, Enkephalin, Endothelin, Erythropoietin, Follicle-stimulating hormone, Galanin, Gastric inhibitory polypeptide, Gastrin, Ghrelin, Glucagon, Glucagon-like peptide-1, Gonadotropin-releasing hormone, Growth hormone-releasing hormone, Hepcidin, Human chorionic gonadotropin, Human placental lactogen, Growth hormone, Inhibin, Insulin, Somatomedin, Leptin, Lipotropin, Luteinizing hormone, Melanocyte stimulating hormone, Motilin, Orexin, Oxytocin, Pancreatic polypeptide, Parathyroid hormone, Pituitary adenylate cyclase-activating peptide, Prolactin, Prolactin releasing hormone, Relaxin, Renin, Secretin, Somatostatin, Thrombopoietin, Thyrotropin, Thyrotropin-releasing hormone, Vasoactive intestinal peptide, Androgen, Androgen, acid maltase (alpha-glucosidase), glycogen phosphorylase, glycogen debrancher enzyme, Phosphofructokinase, Phosphoglycerate kinase, Phosphoglycerate mutase, Lactate dehydrogenase, Carnitine palymityl transferase, Carnitine, and Myoadenylate deaminase.

b. Hormones

Hormones to be included in the disclosed hydrogel capsules or, most preferably, produced from cells included in the disclosed hydrogel capsules can be any hormone of interest.

Examples of endocrine hormones include Anti-diuretic Hormone (ADH), which is produced by the posterior pituitary, targets the kidneys, and affects water balance and blood pressure; Oxytocin, which is produced by the posterior pituitary, targets the uterus, breasts, and stimulates uterine contractions and milk secretion; Growth Hormone (GH), which is produced by the anterior pituitary, targets the body cells, bones, muscles, and affects growth and development; Prolactin, which is produced by the anterior pituitary, targets the breasts, and maintains milk secretions; Growth Hormone-Releasing Hormone (GHRH), which is a releasing hormone of GH and is produced in the arcuate nuclease of the hypothalamus; Thyroid Stimulating Hormone (TSH), which is produced by the anterior pituitary, targets the thyroid, and regulates thyroid hormones; Thyrotropin-Release Hormone (TRH), which is produced by the hypothalamus and stimulates the release of TSH and prolactin from the anterior pituitary; Adrenocorticotropic Hormone (ACTH), which is produced by the anterior pituitary, targets the adrenal cortex, and regulates adrenal cortex hormones; Follicle-Stimulating Hormone (FSH), which is produced by the anterior pituitary, targets the ovaries/testes, and stimulates egg and sperm production; Lutenizing Hormone (LH), which is produced by the anterior pituitary, targets the ovaries/testes, and stimulates ovulation and sex hormone release; Luteinizing Hormone-Releasing Hormone (LHRH), also known as Gonadotropin-Releasing Hormone (GnRH), which is synthesized and released from GnRH neurons within the hypothalamus and is a trophic peptide hormone responsible for the release of FSH and LH; Thyroxine, which is produced by the thyroid, targets the body cells, and regulates metabolism; Calcitonin, which is produced by the thyroid, targets the adrenal cortex, and lowers blood calcium; Parathyroid Hormone, which is produced by the parathyroid, targets the bone matrix, and raises blood calcium; Aldosterone, which is produced by the adrenal cortex, targets the kidney, and regulates water balance; Cortisol, which is produced by the adrenal cortex, targets the body cells, and weakens immune system and stress responses; Epinephrine, which is produced by the adrenal medulla, targets the heart, lungs, liver, and body cells, and affects primary "fight or flight" responses; Glucagon, which is produced by the pancreas, targets the liver body, and raises blood glucose level; Insulin, which is produced by the pancreas, targets body cells, and lowers blood glucose level; Estrogen, which is produced by the ovaries, targets the reproductive system, and affects puberty, menstrual, and development of gonads; Progesterone, which is produced by the ovaries, targets the reproductive system, and affects puberty, menstrual cycle, and development of gonads; and Testosterone, which is produced by the adrenal gland, testes, targets the reproductive system, and affects puberty, development of gonads, and sperm.

In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

c. Vaccines

The disclosed hydrogel capsules can also be used to provide vaccine components. For example, cells expressing vaccine antigens can be included in the hydrogel capsule. A vaccine is a biological preparation that provides active acquired immunity to a particular disease. A vaccine typically contains the same antigens (or parts of antigens) from a microorganism that causes disease. For example, measles vaccine contains measles virus. However, the antigens in vaccines are either killed, or weakened to the point that the do not cause disease but they are strong enough to stimulate the body's immune system so that the immune system can readily recognize and kill any of microorganisms that it later encounters (immunity).

An antigen can include any protein or peptide that is foreign to the subject organism. Preferred antigens can be presented at the surface of antigen presenting cells (APC) of a subject for surveillance by immune effector cells, such as leucocytes expressing the CD4 receptor (CD4 T cells) and Natural Killer (NK) cells. Typically, the antigen is of viral, bacterial, protozoan, fungal, or animal origin. In some embodiments the antigen is a cancer antigen. Cancer antigens can be antigens expressed only on tumor cells and/or required for tumor cell survival.

Certain antigens are recognized by those skilled in the art as immuno-stimulatory (i.e., stimulate effective immune recognition) and provide effective immunity to the organism or molecule from which they derive. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. Antigens may be provided as single antigens or may be provided in combination. Antigens may also be provided as complex mixtures of polypeptides or nucleic acids.

Viral Antigens

A viral antigen can be isolated from any virus including, but not limited to, a virus from any of the following viral families: Arenavmdae, Arterivirus, Astroviridae, Baculoviridae, Badnavirus, Barnaviridae, Birnaviridae, Bromoviridae, Bunyaviridae, Caliciviridae, CapiUovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Fiaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g, poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3. Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Bacterial Antigens

Bacterial antigens can originate from any bacteria including, but not limited to, *Actinomyces, Anabaena, Bacillus, Bacteroides, Bellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria,* Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi. Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, Plasmodian antigens, such as all or part of a Circumsporozoite protein, a Sporozoite surface protein, a liver stage antigen, an apical membrane associated protein, or a Merozoite surface protein.

Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagaies, Oleales, Pinoles and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodop, Dactylis, Holcus, Phalaris, Secale,* and *Sorghum,* the orders of Asterales and Urticales including i.a. herbs of the genera *Ambrosia, Artemisia,* and *Parietaria.* Other allergen antigens that may be used include allergens from house dust mites of the genus *Dermatophagoides* and *Euroglyphus,* storage mite e.g. *Lepidoglyphys, Glycyphagus* and *Tyrophagus,* those from cockroaches, midges and fleas e.g. *Blatella, Periplaneta, Chironomus* and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.*

Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, b-Catenin, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29YBCAA), CA 195, CA 242, CA-50, CAM43, CD68\KP1, CO-029, FGF-5, G250, Ga733 (EpCAM), HTgp-175, M344, MA-50, MG7-Ag, MOV 18, NB\70K, NY-CO-1, RCAS1, SDCCAG16, TA-90 (Mac-2 binding protein\cyclophibn C-associated protein), TAAL6, TAG72, TLP, and TPS.

d. Antibodies

The disclosed hydrogel capsules can also be used to provide antibodies. For example, cells expressing antibodies can be included in the hydrogel capsule. Antibodies that function by binding directly to one or more epitopes, other ligands or accessory molecules at the surface of eukaryote cells, are described. Typically, the antibody or antigen binding fragment thereof has affinity for a receptor at the surface of a specific cell type, such as a receptor expressed at the surface of macrophage cells.

In some embodiments, the antibody or antigen binding fragment binds specifically to an epitope. The epitope can be a linear epitope. The epitope can be specific to one cell type or can be expressed by multiple different cell types. In other embodiments, the antibody or antigen binding fragment thereof can bind a conformational epitope that includes a 3-D surface feature, shape, or tertiary structure at the surface of the target cell.

In some embodiments, the antibody or antigen binding fragment that binds specifically to an epitope on the target cell can only bind if the protein epitope is not bound by a ligand or small molecule.

Various types of antibodies and antibody fragments can be used in the described compositions and methods, including whole immunoglobulin of any class, fragments thereof, and synthetic proteins containing at least the antigen binding variable domain of an antibody. The antibody can be an IgG antibody, such as $IgG_1$; $IgG_2$, $IgG_3$, or $IgG_4$. An antibody can be in the form of an antigen binding fragment including a Fab fragment, F(ab')2 fragment, a single chain variable region, and the like. Antibodies can be polyclonal or monoclonal (mAb). Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and Morrison, et al., *Proc. Natl. Acad. Sci. USA,* 81: 6851-6855 (1984)). The described antibodies can also be modified by recombinant means, for example by deletions, additions or substitutions of amino acids, to increase efficacy of the antibody in mediating the desired function. Substitutions can be conservative substitutions. For example, at least one amino acid in the constant region of the antibody can be replaced with a different residue (see, e.g., U.S. Pat. Nos. 5,624,821; 6,194,551; WO 9958572; and Angal, et al., Mol. Immunol. 30:105-08 (1993)). In some cases changes are made to reduce undesired activities, e.g., complement-dependent cytotoxicity. The antibody can be a bi-specific antibody having binding specificities for at least two different antigenic epitopes. In one embodiment, the epitopes are from the same antigen. In another embodiment, the epitopes are from two different antigens. Bi-specific antibodies can include bi-specific antibody fragments (see, e.g., Hollinger, et al., *Proc. Natl. Acad. Sci. U.S.A.,* 90:6444-48 (1993); Gruber, et al., *J. Immunol.,* 152:5368 (1994)).

Antibodies can be generated by any means known in the art. Exemplary descriptions means for antibody generation and production include Delves, Antibody Production: Essential Techniques (Wiley, 1997); Shephard, et al., Monoclonal Antibodies (Oxford University Press, 2000); Goding, Monoclonal Antibodies: Principles And Practice (Academic Press, 1993); and Current Protocols In Immunology (John Wiley & Sons, most recent edition). Fragments of intact Ig molecules can be generated using methods well known in the art, including enzymatic digestion and recombinant means.

D. Preparation of Modified Alginate Polymers

Modified alginates can be prepared through covalent modification of any available alginate polymer. Covalently modified monomers can be introduced into alginate polymers using a variety of synthetic procedures known in the art. In some embodiments, mannuronate and guluronate monomers are covalently modified via esterification and/or amidation of their carboxylic acid moiety. In alternative embodiments, mannuronate and guluronate monomers are covalently modified via phosphorylation or acetal formation. Stoichiometric variation of the reactants during covalent modification can be used to vary the amount of covalently modified monomer incorporated into the modified alginate.

In addition to the reactions discussed below, alternative synthetic methodologies for the covalent modification of mannuronate and guluronate monomers are known in the art. (see, for example, March, "Advanced Organic Chemistry," 5th Edition, 2001, Wiley-Interscience Publication, New York).

I. Modification Via the Carboxylate Moiety of the Mannuronate and Guluronate Monomers

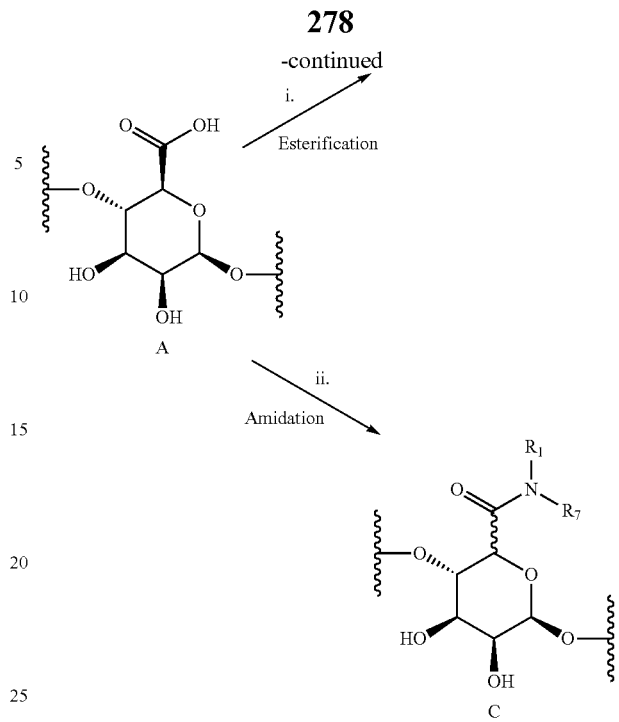

Scheme 1. Representative Reaction Conditions: i. HO—$R_1$, 2-Chloro-4,6-dimethoxy-1,3,5-triazine (CDMT), N-methyl morpholine (NMM); ii. $HNR_1R_7$, CDMT, NMM.

Mannuronate and guluronate monomers contain a carboxylic acid moiety which can serve as a point of covalent modification. In preferred embodiments, the carboxylic acid moiety present on one or more mannuronate and/or guluronate residues (1) are reacted as shown in Scheme 1.

Mannuronate and guluronate residues (A) can be readily esterified by a variety of methods known in the art, forming covalently modified monomer B. For example, using a Steglich Esterification, mannuronate and guluronate residues (A) can be esterified by reaction with any suitable alcohol (HO—$R_1$) in the presence of a carbodiimide (for example, N,N'-dicyclohexylcarbodiimide (DCC), N,N'-diisopropylcarbodiimide (DIC), or 1-ethyl-3-(3-dimethylaminopropyl) carbodiimide (EDC)) and dimethylaminopyridine (DMAP). In a preferred method, mannuronate and guluronate residues (A) were esterified by reaction with a large molar excess of an alcohol (HO—$R_1$) in the presence of 2-Chloro-4,6-dimethoxy-1,3,5-triazine (CDMT) and N-methyl morpholine (NMM). See, for example, Garrett, C. E. et al. *Tetrahedron Lett.* 2002; 43(23): 4161-4164. Preferred alcohols for use as reagents in esterification include those shown below.

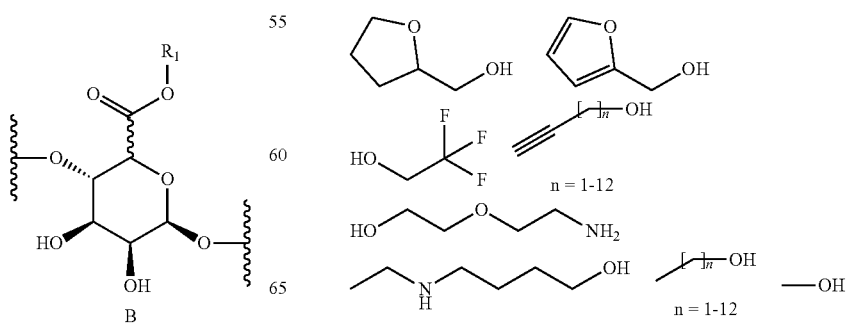

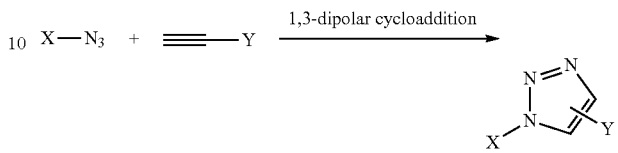

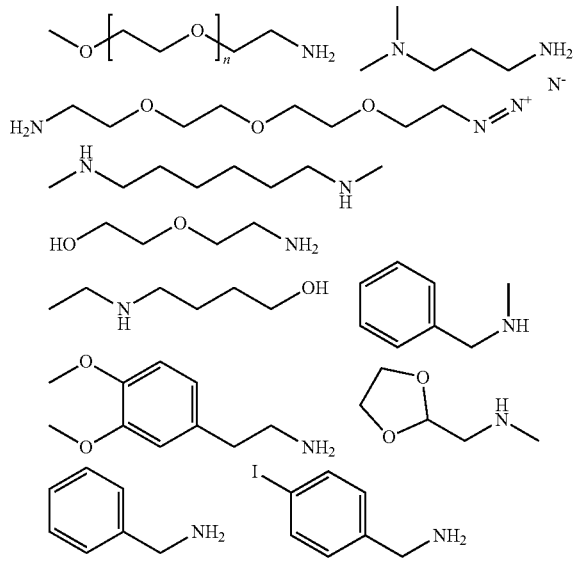

2. Modification of Mannuronate and Guluronate Monomers Via Click Chemistry

Mannuronate and guluronate residues (A) can also be covalently modified via amidation, forming modified monomer C. For example, mannuronate and guluronate residues (A) can amidated by reaction with any suitable amine ($R_1$—$NH_2$) in the presence of a carbodiimide and DMAP. In a preferred method, mannuronate and guluronate residues (A) were amidated by reaction with a stoichiometric amount of a suitable amine ($R_1$—$NH_2$) in the presence of CDMT and NMM. Preferred amines for use as reagents in amidation reactions include those shown below.

In some embodiments, mannuronate and guluronate monomers are covalently modified to introduce a functional group which can be further reacted via click chemistry.

In preferred embodiments, amidation and/or esterification is used to introduce a functional group which can further reacted using a 1,3-dipolar cycloaddition reaction (i.e. a Huisgen cycloaddition reaction). In a 1,3-dipolar cycloaddition reaction, a first molecule containing an azide moiety is reacted with a second molecule containing a terminal or internal alkyne. As shown below, the azide and the alkyne groups undergo an intramolecular 1,3-dipolar cycloaddition reaction, coupling the two molecules together and forming a 1,2,3-triazole ring.

$$X-N_3 \ + \ \equiv-Y \ \xrightarrow{\text{1,3-dipolar cycloaddition}} \ \begin{array}{c}\text{triazole}\end{array}$$

The regiochemistry of 1,3-dipolar cycloadditions reaction can be controlled by addition of a copper(I) catalyst (formed in situ by the reduction of $CuSO_4$ with sodium ascorbate) or a ruthenium catalyst (such as $Cp^*RuCl(PPh_3)_2$, $Cp^*Ru$ (COD), or $Cp^*[RuCl_4]$). For example, using a copper catalyst, azides and terminal alkynes can be reacted to exclusively afford the 1,4-regioisomers of 1,2,3-triazoles. Similarly, in the presence of a suitable ruthenium catalyst, azides can be reacted with internal or terminal alkynes to form exclusively the 1,5-regioisomers of 1,2,3-triazoles.

In some embodiments, amidation and/or esterification is used to form a covalently modified monomer containing an alkyne moiety. In these embodiments, the alkyne moiety present on the covalently modified monomer can be further reacted with a second molecule containing an azide functional group. Upon reaction, the azide and the alkyne groups undergo an intramolecular 1,3-dipolar cycloaddition reaction forming a 1,2,3-triazole ring, coupling the second molecule to the covalently modified monomer.

Examples of the alkyne-containing amidation/esterification reactant include $X_a$—$R_z$—$C\equiv C$—$R_x$; wherein $X_a$ is —OH or —$NH_2$; wherein $R_z$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$; and wherein $R_x$ is hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments,
(1) $R_z$ is hydrogen,
(A)

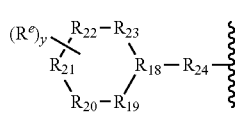

Formula IX wherein y is an integer from 1 to 11; wherein $R^e$ is $U_{3}$, $U_3+Q_1$; $U_3+Q_2$, $U_3+Q_3$, $U_3+Q_4$, $u_3+Q_2+Q_2$, $u_3+Q_2+Q_3$, $U_3+Q_1+Q_4$, $u_3+Q_2+Q_3$, $u_3+Q_2+Q_4$, $u_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring; wherein one instance of $R^e$ is or contains $X_a$; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-SO_2-$, or $NR_4$, wherein each $R_{25}$ is, as valency permits, independently absent, hydrogen, $=O$, $=S$, $-OH$, $-SH$, $-NR_4$, wherein $R_4$ is 1% $U_1+Q_1$, $U_1+Q2$, $U_1+Q_3$, $U_1+Q_4$, $U_1+Q_1+Q2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q2+Q_4$, $U_1+Q_1+Q_3+Q_4$, $U_1+Q_2+Q_3+Q_4$, and $U_1+Q_1+Q_2+Q_3+Q_4$, preferably $LJ1+Q1+Qv$ (B) $-(CH_2)_s-R_{26}$, wherein s is an integer from 0 to 20; wherein $R_{26}$ is $-X_a$, $-O-R_{27}$, $-S-R_{27}$, $-(CH_2)_r-R_{27}$, $-CO-R_{27}$, or $-CHR_{28}R_{29}$, wherein r is an integer from 0 to 19; wherein $R_{27}$ is $-X_a$, $-(CH_2)_U-R_{30}$, wherein u is an integer from 0 to 18; wherein $R_{28}$ is $-(CH_2)_t-R_{30}$, $R_{29}$ is $-(CH_2)_v-R_{30}$, and t and v are integers from 0 to 18, wherein t and v together total 0 to 18; wherein $R_{30}$ is $-X_a$, methyl, $-OH$, $-SH$, or $-COOH$; or (C)

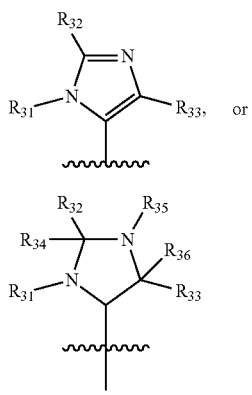

Formula VII or

Formula VIII

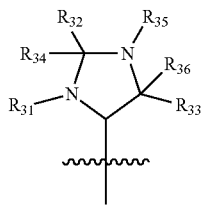

wherein $R_{31}$, $R_{32}$, $R_{33}$, $R_{34}$, $R_{35}$, and $R_{36}$ are, independently, hydrogen, $U_1$, $U_1+Q_1$, $U1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein one instance of $R_{31}$, $R_{32}$, $R_{33}$, $R_{34}$, $R_{35}$, or $R_{36}$ is or contains $X_a$;

wherein $R_{31}$, $R_{34}$, $R_{35}$, and $R_{36}$ are independently present or absent according to valency, and wherein the ring bonds are double or single according to valency;

(2) $R_x$ is hydrogen, (A)

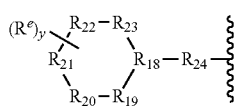

Formula IX wherein y is an integer from 0-11; wherein $R^e$ is independently $U_3$, $U_3+Q_1$, $U_3+Q_2$, $U_3+Q_3$, $U_3+Q_4$, $u_3+Q_2+Q_2$, $u_3+Q_2+Q_3$, $U_3+Q_1+Q_4$, $u_3+Q_2+Q_3$, $u_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently $-(CR_{25}R_{25})_p-$ or $-(CR_{25}R_{25})_p-X_b-(CR_{25}R_{25})_q-$, wherein p and q are independently integers from 0 to 5, wherein $X_b$ is absent, $-O-$, $-S-$, $-SO_2-$, or $NR_4$, wherein each $R_{25}$ is, as valency permits, independently absent, hydrogen, $=O$, $=S$, $-OH$, $-SH$, $-NR_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

(B) $-(CH_2)_s-R_{26}$, wherein s is an integer from 0 to 20; wherein $R_{26}$ is $-O-R_{27}$, $-S-R_{27}$, $-(CH_2)_r-R_{27}$, $-CO-R_{27}$, or $-CHR_{28}R_{29}$, wherein r is an integer from 0 to 19; wherein 5 $R_{27}$ is $-(CH_2)_U-R_{30}$, wherein u is an integer from 0 to 18; wherein $R_{28}$ is $-(CH_2)_t-R_{30}$, $R_{29}$ is $-(CH_2)_v-R_{30}$, and t and v are integers from 0 to 18, wherein t and v together total 0 to 18; wherein $R_{30}$ is methyl, $-OH$, $-SH$, or $-COOH$; or (C)

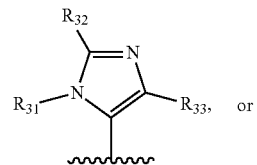

Formula VII or

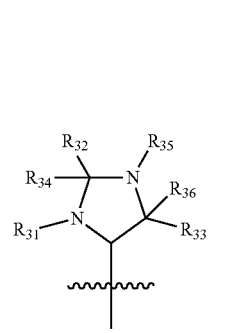

Formula VIII wherein $R_{31}$, $R_{32}$, $R_{33}$, $R_{34}$, $R_{35}$, and $R_{36}$ are, independently, hydrogen, $U_1$, $U_1+Q_1$, $U_1+Q2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency; and (3) wherein $R_z$ and $R_x$ are not both hydrogen.

Examples of the azide-containing second molecule include $R_w-N_3$, wherein $R_w$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $R_w$ is
(A)

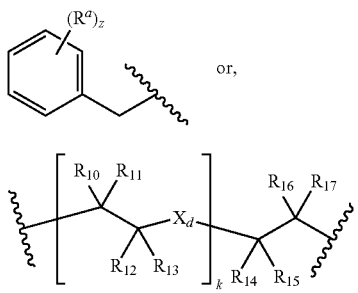

Formula X or,

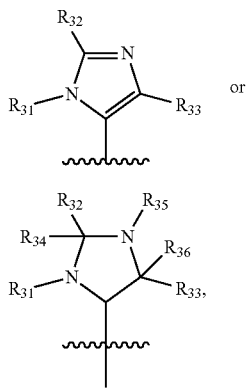

Formula XI wherein k are independently an integer from 1 to 30; wherein z is an integer from 0 to 4; wherein $X_4$ is O or S; wherein $R^a$ is independently $U_{3j}U_3+Q_1$; $U_3+Q_2$, $U_3+Q_3$, $U_3+Q_4$, $u_3+Q_2+Q_2$, $u_3+Q_2+Q_3$, $U_3+Q_1+Q_4$, $u_3+Q_2+Q_3$, $u_3+Q_2+Q_4$, $u_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic, or heterocyclic ring; and wherein $R_{10}$, Rn, $R_{12}$, $R_{13}$, $R_{14}$, $R_{15}$, $R_{16}$, $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$; or
(B)

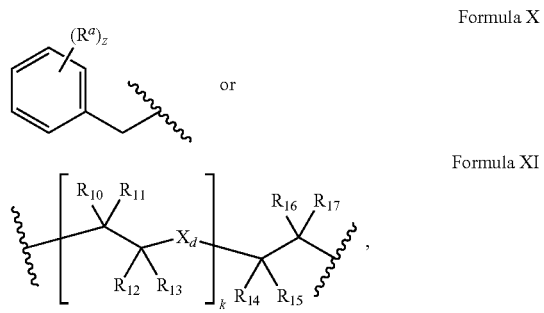

Formula VII or

Formula VIII wherein $R_{31}$, $R_{32}$, $R_{33}$, $R_{34}$, $R_{35}$, and $R_{36}$ are, independently, hydrogen, $U_1$, $U_1+Q_1$, $U_1+Q2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency.

In alternative embodiments, amidation and/or esterification is used to form a covalently modified monomer containing an azide moiety. In these embodiments, the azide moiety present on the covalently modified monomer can be further reacted with a second molecule containing a terminal or internal alkyne. Upon reaction, the azide and the alkyne groups undergo an intramolecular 1,3-dipolar cycloaddition reaction forming a 1,2,3-triazole ring, coupling the second molecule to the covalently modified monomer.

Examples of the azide-containing amidation/esterification reactant include $X_c$—$R_w$—$N_3$, where $X_c$ is —OH or —$NH_2$ and $R_w$ is $U_1$; $U_1+Q_1$, $U_1+Q_2$, $U_1+Q_3$, $U_1+Q_4$, $U_1+Q_1+Q2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $X_c$ is not —$NH_2$ and $R_w$ is not —$CH_2$—Ar— or —$CH_2$—$CH_2$—(O—$CH_2$—$CH_2$)$_3$.

In some embodiments, $R_w$ is
(A)

Formula X

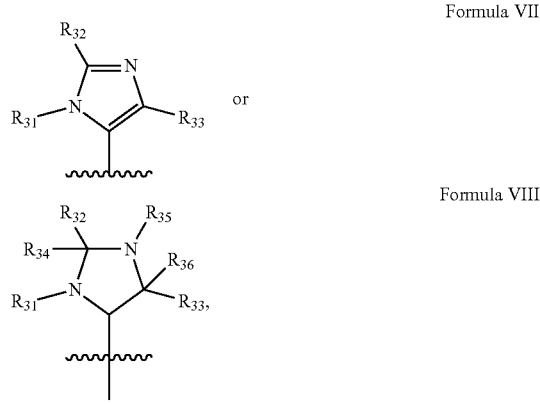

or

Formula XI wherein k are independently an integer from 1 to 30; wherein z is an integer from 0 to 4; wherein $X_4$ is O or S; wherein $R^a$ is independently $U_{3j}$ $U_3+Q_1$, $U_3+Q_2$, $U_3+Q_3$, $U_3+Q_4$, $u_3+Q_2+Q_2$, $u_3+Q_2+Q_3$, $U_3+Q_1+Q_4$, $u_3+Q_2+Q_3$, $u_3+Q_2+Q_4$, $u_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic, or heterocyclic ring; wherein one instance of $R^a$ is or contains $X_c$; wherein $R_{10}$, Rn, $R_{12}$, $R_{13}$, $R_{14}$, $R_{15}$, $R_{16}$, $R_{17}$ are independently $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$; and wherein one instance of $R_{10}$, $R_{11}$, $R_{12}$, $R_{13}$, $R_{14}$, $R_{15}$, $R_{16}$, or $R_{17}$ is or contains $X_c$; or
(B)

Formula VII

Formula VIII wherein $R_{31}$, $R_{32}$, $R_{33}$, $R_{34}$, $R_{35}$, and $R_{36}$ are, independently, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein one instance of $R_{31}$, $R_{32}$, $R_{33}$, $R_{34}$, $R_{35}$, or $R_{36}$ is or contains $X_c$;

wherein $R_{31}$, $R_{34}$, $R_{35}$, and $R_{36}$ are independently present or absent according to valency, and wherein the ring bonds are double or single according to valency.

Examples of the alkyne-containing second molecule include $R_z$—C≡C—$R_x$, wherein $R_z$ and $R_x$ are, independently, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $R_z$ and $R_x$ are independently hydrogen, (A)

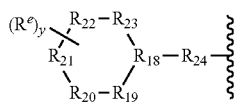

Formula IX wherein y is an integer from 0 to 11; wherein $R^e$ is independently $U_3$, $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring; wherein $R_{18}$, $R_{19}$, $R_{20}$, $R_{21}$, $R_{22}$, and $R_{23}$ are independently C, O, N, or S, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ is independently —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —SO$_2$—, or NR$_4$, wherein each $R_{25}$ is, as valency permits, independently absent, hydrogen, =O, =S, —OH, —SH, —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_x+Q_2+Q_3+Q_4$, preferably $U_1+Q_x+Q_3$;

(B) —$(CH_2)_s$—$R_{26}$, wherein s is an integer from 0 to 20; wherein $R_{26}$ is —O—$R_{27}$, —S—$R_{27}$, —$(CH_2)_r$—$R_{27}$, —CO—$R_{27}$, or —$CHR_{28}R_{29}$, wherein r is an integer from 0 to 19; wherein $R_{27}$ is —$(CH_2)_t$—$R_{30}$, wherein u is an integer from 0 to 18; wherein $R_{28}$ is —$(CH_2)_t$—$R_{30}$, $R_{29}$ is —$(CH_2)_v$—$R_{30}$, and t and v are integers from 0 to 18, wherein t and v together total 0 to 18; wherein $R_{30}$ is methyl, —OH, —SH, or —COOH; or

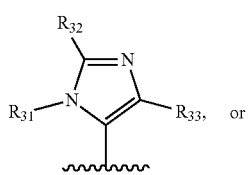

Formula VII

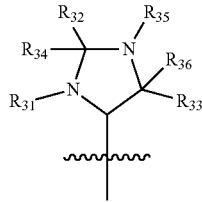

Formula VIII wherein $R_{31}$, $R_{32}$, $R_{33}$, $R_{34}$, $R_{35}$, and $R_{36}$ are, independently, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$;

wherein $R_{31}$, $R_{34}$, $R_{35}$, and $R_{36}$ are independently present or absent according to valency, and wherein the ring bonds are double or single according to valency; and wherein $R_z$ and $R_x$ are not both hydrogen.

In some embodiments, the azide moiety can be added to a covalently modified monomer containing a leaving group, such as I, Br, OTs, OMs. In some embodiments, amidation and/or esterification is used to form the covalently modified monomer containing the leaving group. Examples of the leaving group-containing amidation/esterification reactant include $X_c$—$R_w$-L, where $X_c$ is —OH or —NH$_2$, L is the leaving group, and $R_w$ is $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $X_c$ is not —NH$_2$ and $R_w$ is not —CH$_2$—Ar— or —CH$_2$—CH$_2$—(O—CH$_2$—CH$_2$)$_3$—.

In some embodiments, $R_w$ is (A)

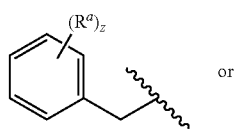

Formula X or

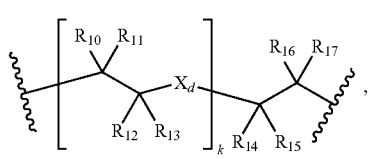

Formula XI wherein k are independently an integer from 1 to 30; wherein z is an integer from 0 to 4; wherein $X_4$ is O or S; wherein $R^a$ is independently $U_1$; $U_1+Q_1$; $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_3+Q_1+Q_3$; or together with the carbon atom to which they are attached, form a 3- to 8-membered unsubstituted or substituted carbocyclic, or heterocyclic ring; wherein one instance of $R^a$ is or contains $X_c$; wherein $R_{10}$, Rn, $R_{12}$, $R_{13}$, $R_{14}$, $R_{15}$, $R_{16}$, $R_{17}$ are independently hydrogen, $U_1$; $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+

$Q_3+Q_4$, and $U_1+Q_1+Q_2+Q_3+Q_4$, preferably $U_1+Q_1+Q_2+Q_3$; and wherein one instance of $R_{10}$, Rn, $R_{12}$, $R_{13}$, $R_{14}$, $R_{15}$, $R_{16}$, or $R_{17}$ is or contains $X_c$; or (B)

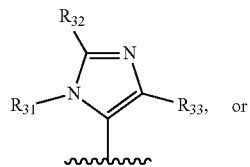

Formula VII

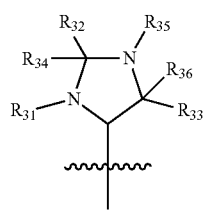

Formula VIII wherein $R_{31}$, $R_{32}$, $R_{33}$, $R_{34}$, $R_{35}$, and $R_{36}$ are, independently, hydrogen, $U_1$, $U_1+Q_1$, $U_1+Q2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein one instance of $R_{31}$, $R_{32}$, $R_{33}$, $R_{34}$, $R_{35}$, or $R_{36}$ is or contains $X_c$;

wherein $R_{31}$, $R_{34}$, $R_{35}$, and $R_{36}$ are independently present or absent according to valency, and wherein the ring bonds are double or single according to valency.

In some embodiments, $X_c$ is not —$NH_2$ and $R_w$ is not —$CH_2$—Ar— or —$CH_2$—$CH_2$—(O—$CH_2$—$CH_2$)$_3$—.

In preferred embodiments, amidation is used to form a covalently modified monomer containing an azide moiety. Subsequently, the azide moiety present on the covalently modified monomer is reacted with a second molecule containing a terminal or internal alkyne, forming a 1,2,3-triazole ring and coupling the second molecule to the covalently modified monomer.

As shown in Scheme 2, different strategies can be employed to prepare covalently modified monomers containing an azide moiety.

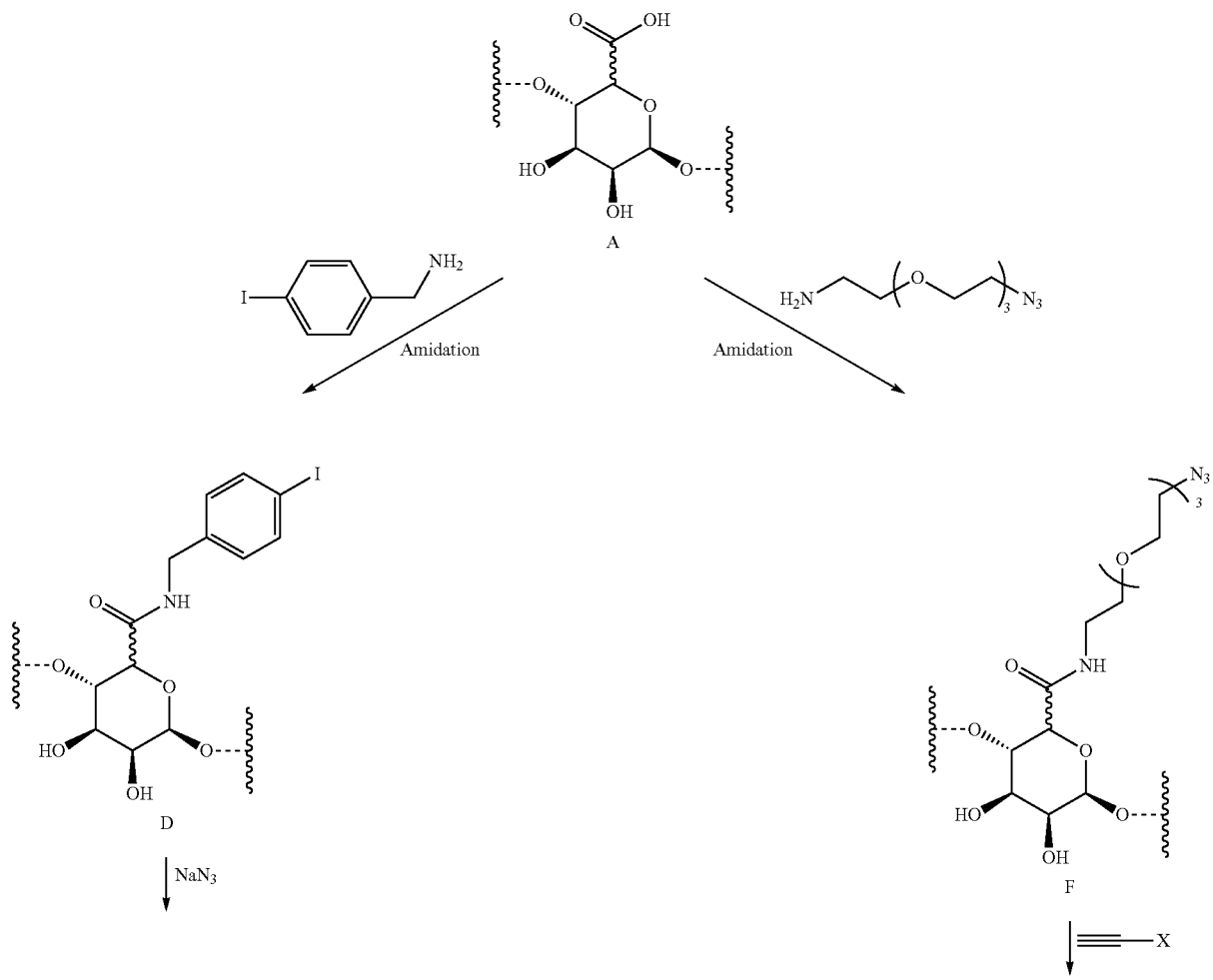

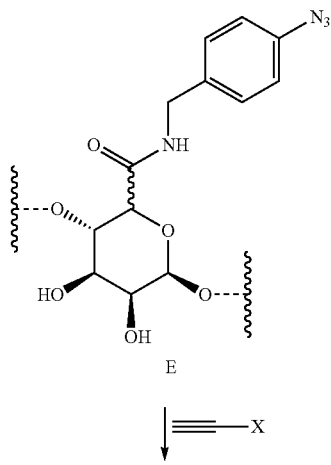

E

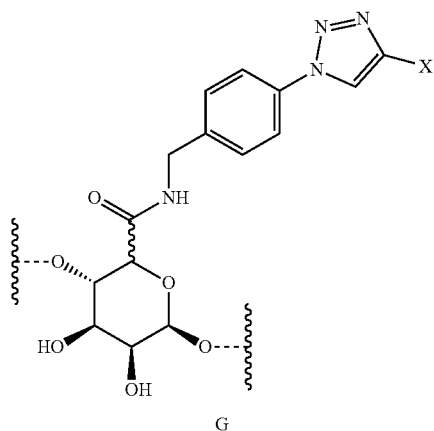

G

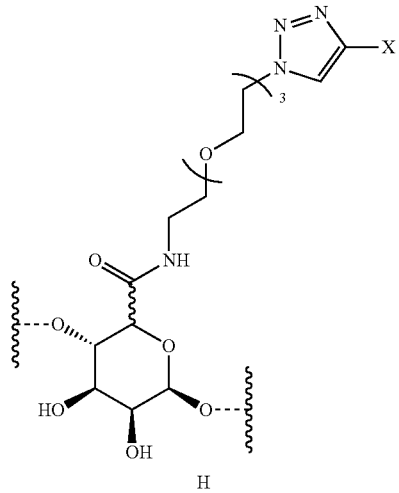

H

For example, mannuronate and guluronate residues (A) can amidated by reaction with an amine substituted with an azide moiety (for example, 11-Azido-3,6,9-trioxaundecan-1-amine) in the presence of a carbodiimide and DMAP, forming azide-functionalized modified monomer F in a single synthetic step. Alternatively, mannuronate and guluronate residues (A) can amidated by reaction with an amine substituted with any moiety which can be readily transformed into an azide. For example, mannuronate and guluronate residues can be amidated by reaction with 4-iodobenzylamine in the presence of a carbodiimide and DMAP, forming iodo-functionalized monomer D. The iodine moiety can then be readily converted to the azide, for example by treatment with sodium azide.

Subsequently, the azide-functionalized monomers can be reacted with a molecule containing an alkyne functionality. For example, azide-functionalized monomers F and E can be reacted with a molecule containing a terminal alkyne functionality in the presence of a copper(I) catalyst (formed in situ by the reduction of $CuSO_4$ with sodium ascorbate), forming covalently modified monomers G and H.

Alkynes for use as reagents in 1,3-dipolarcycloaddition reactions include alkynes having side groups corresponding to of the moieties described herein for any of the organic groups, R groups, and substituents. For example, the alkynes can have side groups corresponding to of the moieties described herein for $R_8$ and $R_0$.

In some embodiments, alkynes for use as reagents in 1,3-dipolarcycloaddition reactions can be $$R_{62}-C \equiv C-R_{63}, \quad \text{Formula XVII}$$

wherein $R_{62}$ and $R_{43}$ are independently hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_{62}$ and $R_{63}$ organic groupings being those present in $U_1$, $U_1+Q_1$; $U_1+Q_2$, $U_1+Q_3$, $U_1+Q_4$, $U_4+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, $R_{62}$ and $R_{43}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments, $R_{62}$ and $R_{63}$ are independently hydrogen, amino, hydroxyl, thiol, oxo, phosphate, or In some embodiments, $R_{62}$ and $R_{63}$ are independently hydrogen, amino, hydroxyl, thiol, oxo, phosphate, or $J_2$.

In some embodiments, $R_{62}$ and $R_{63}$ are independently,

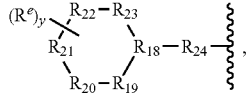
Formula IX

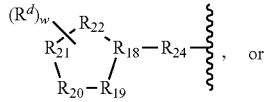, or
Formula XIV

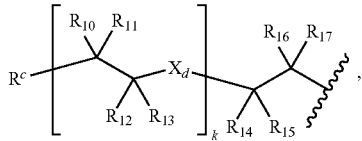,
Formula XII wherein y is an integer from 0-11; wherein w is an integer from 0-9; wherein k is an integer from 0 to 20;

wherein $R^d$ and $R^e$ are independently absent, $U_3$, $U_3+Q_1$; $U_3+Q_2$, $U_3+Q_3$, $U_3+Q_4$, $U_3+Q_2+Q_2$, $u_3+Q_2+Q_3$, $U_3+Q_1+Q_4$, $u_3+Q_2+Q_3$, $u_3+Q_2+Q_4$, $u_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring;

wherein $X_d$ are independently absent, O, or S;

wherein $R^c$ is absent, hydrogen, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$; and wherein $R_{10}$, Rn, $R_{12}$, $R_{13}$, $R_{14}$, $R_{15}$, $R_{16}$, and $R_{17}$ are independently hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_x+Q_2+Q_3+Q_4$, preferably $U_1+Q_x+Q_3$.

In some embodiments, $R_{62}$ and $R_{43}$ are independently,

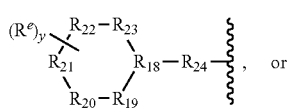, or
Formula IX

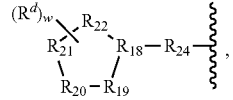,
Formula XIV wherein y is an integer from 0-11; wherein w is an integer from 0-9;

wherein $R^d$ and $R^e$ are independently absent, $U_3$, $U_3+Q_1$; $U_3+Q_2$, $U_3+Q_3$, $U_3+Q_4$, $u_3+Q_2+Q_2$, $u_3+Q_2+Q_3$, $U_3+Q_1+Q_4$, $u_3+Q_2+Q_3$, $u_3+Q_2+Q_4$, $u_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, $R_{22}$, and $R_{23}$ are independently C, O, N, S, S(O), or S(O)$_2$, wherein the bonds between adjacent $R_{18}$ to $R_{23}$ are double or single according to valency, and wherein $R_{18}$ to $R_{23}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_3$.

In some embodiments. $R_{67}$ and $R_{63}$ are independently.

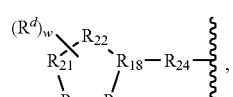,
Formula XIV wherein w is an integer from 0-9;

wherein $R^d$ and $R^e$ are independently absent, $U_3$, $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring;

wherein $R_{18}$, $R_{19}$, $R_{20}$, $R_{21}$, and $R_{22}$ are independently C, O, N, S, S(O), or S(O)$_2$, wherein the bonds between adjacent $R_{18}$ to $R_{22}$ are double or single according to valency, and wherein $R_{18}$ to $R_{22}$ are bound to none, one, or two hydrogens according to valency; and wherein $R_{24}$ are independently absent, —(CR$_{25}$R$_{25}$)$_p$— or —(CR$_{25}$R$_{25}$)$_p$—X$_b$—(CR$_{25}$R$_{25}$)$_q$—, wherein p and q are independently integers from 0 to 5, wherein $X_b$ is absent, —O—, —S—, —S(O)—, —S(O)$_2$—, or NR$_4$, wherein each $R_{25}$ is, as valency permits, independently absent, hydrogen, =O, =S, —OH, —SH, or —NR$_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q2+Q_4$, $U_4+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_x+Q_2+Q_3+Q_4$, preferably $U_1+Q_x+Q_3$.

In some embodiments, $R_{62}$ and $R_{63}$ are independently,

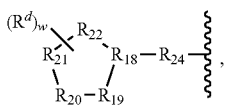

Formula XIV wherein w is an integer from 0-9;
wherein $R^d$ and $R^e$ are independently $U_{3j}$ $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q_2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; or together with the carbon atom to which they are attached, form a 3- to 8-membered unsubstituted or substituted carbocyclic or heterocyclic ring;
wherein $R_{18}$, $R_{19}$, $R_{20}$, $R_{21}$, and $R_{22}$ are independently C or N, wherein the bonds between adjacent $R_{18}$ to $R_{22}$ are double or single according to valency, wherein one, two, three, or four of $R_{18}$, $R_{19}$, $R_{20}$, $R_{21}$, and $R_{22}$ are N and the others are C, and wherein $R_{18}$ to $R_{22}$ are bound to none, one, or two hydrogens according to valency; and
wherein $R_{24}$ are independently absent, —$(CR_{25}R_{25})_p$— or —$(CR_{25}R_{25})_p$—$X_b$—$(CR_{25}R_{25})_q$—, wherein p and q are independently integers from 0 to 5, wherein $X_b$ is absent, —O—, —S—, —S(O)—, —S(O)$_2$—, or $NR_4$, wherein each $R_{25}$ is, as valency permits, independently absent, hydrogen, =O, =S, —OH, —SH, or —$NR_4$, wherein $R_4$ is $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_x+Q_2+Q_3+Q_4$, preferably $U_1+Q_1+Q_3$.

In some embodiments, $R_{62}$ and $R_{63}$ are independently,

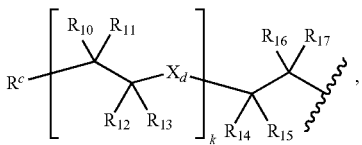

Formula XII wherein k is an integer from 0 to 20;
wherein $X_4$ are independently absent, O, or S;
wherein $R^c$ is $R^b$, absent, hydrogen, $U_{3j}$ $U_3+Q_1$; $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q2+Q_3$, $U_3+Q_1+Q_2+Q_4$, $U_3+Q_1+Q_3+Q_4$, $U_3+Q_2+Q_3+Q_4$, and $U_3+Q_4+Q_2+Q_3+Q_4$, preferably $U_3+Q_1+Q_3$; and
wherein $R_{10}$, Rn, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $R_{62}$ and $R_{63}$ are independently,

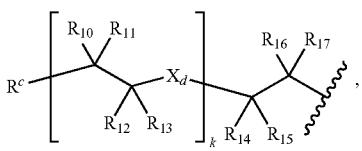

Formula XII wherein k is an integer from 1 to 20;
wherein $X_4$ are independently O or S;
wherein $R^c$ is $R^b$, absent, hydrogen, $U_{3j}$ $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, Rn, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_4+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments, $R_{62}$ and $R_{63}$ are independently,

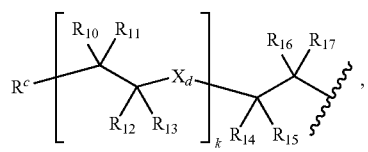

Formula XII wherein k is an integer from 1 to 20;
wherein $X_4$ are O;
wherein $R^c$ is $R^b$, absent, hydrogen, $U_{3j}$ $U_3+Q_1$, $U_3+Q_2$, $U_3+Q_3$, $U_3+Q_4$, $U_3+Q_2+Q_2$, $U_3+Q_2+Q_3$, $U_3+Q_1+Q_4$, $U_3+Q_2+Q_3$, $U_3+Q_2+Q_4$, $U_3+Q_3+Q_4$, $U_3+Q_1+Q2+Q_3$, $U_3+Q_1+Q_2+Q_4$, $U_3+Q_1+Q_3+Q_4$, $U_3+Q_2+Q_3+Q_4$, and $U_3+Q_1+Q_2+Q_3+Q_4$, preferably $U_3+Q_1+Q_3$; and
wherein $R_{10}$, Rn, $R_{12}$, $R_{13}$, $R_{14}$, $R_{15}$, $R_{16}$, and $R_{17}$ are independently $R^b$, hydrogen, $U_1$, $U_1+Q_1$, $U_1+Q_2$, $U_1+Q_3$, $U_1+Q_4$, $U_1+Q_1+Q_2$, $U_1+Q_1+Q_3$, $U_1+Q_1+Q_4$, $U_1+Q_2+Q_3$, $U_1+Q_2+Q_4$, $U_1+Q_3+Q_4$, $U_1+Q_1+Q_2+Q_3$, $U_1+Q_1+Q_2+Q_4$, $U_1+Q_1+Q_3+Q_4$, $U_1+Q_2+Q_3+Q_4$, and $U_1+Q_1+Q_2+Q_3+Q_4$, preferably $U_1+Q_1+Q_2+Q_3$.

In some embodiments of $R_{10}$, $R_n$, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$, and independently in combination with any embodiments of any other relevant substituent classes, $R_{10}$, Rn, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$ can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_{10}$, Rn, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$ organic groupings being those present in $U_1+Q_1$, $U_1+Q_2$, $U_1+Q3$, $U_1+Q_4$, $U_1+Q_5$, $U_1+Q_1+Q_2$, $U_1+Q_1+Q_3$, $U_1+Q_1+Q_4$, $U_1+Q_1+Q_5$, $U_1+Q_2+Q_3$, $U_1+Q_2+Q_4$, $U_1+Q_2+Q_5$, $U_1+Q_3+Q_4$, $U_1+Q_3+Q_5$, $U_1+Q_4+Q_5$, $U_1+Q_1+Q_2+Q_3$, $U_1+Q_1+Q2+Q_4$, $U_1+Q_1+Q_2+Q_5$, $U_1+Q_1+Q_3+Q_4$, $U_1+Q_1+Q_3+Q_5$, $U_1+Q_1+Q_4+Q_5$, $U_1+Q_2+Q_3+Q_4$, $U_1+Q_2+Q_3+Q_5$, $U_1+Q_2+Q_4+Q_5$, $U_1+Q_3+Q_4+Q_5$, $U_1+Q_1+Q_2+Q_3+Q_4$, $U_1+Q_1+Q_2+Q_3+Q_5$, $U_1+Q_1+Q_2+Q_4+Q_5$, $U_1+Q_1+Q_3+Q_4+Q_5$, $U_1+Q_2+Q_3+Q_4+Q5$, or $U_1+Q_1+Q_2+Q_3+Q_4$, $+Q_5$.

In some embodiments of $R_{10}$, Rn, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$, and independently in combination with any embodiments of any other relevant substituent classes, $R_{10}$, Rn, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$ can be, independently, absent, hydrogen, or an organic grouping containing any number of carbon atoms, 1-30 carbon atoms, 1-20 carbon atoms, or 1-14 carbon atoms, and optionally including one or more heteroatoms such as oxygen, sulfur, or nitrogen grouping in linear, branched, or cyclic structural formats, representative $R_{10}$, Rn, $R_{12}$, $R_{13}$, $R_{14}$, $R_{15}$, $R_{16}$, $R_{17}$, $R_{31}$, $R_{32}$, $R_{33}$, $R_{34}$, $R_{35}$, $R_{36}$, $R_{38}$, $R_{39}$, $R_{40}$, $X_g$ organic groupings being those present in $U4+Q_1$, $U4+Q_2$, $U4+Q_3$, $U4+Q_4$, $U4+Q_5$, $U4+Q_6$, $U4+Q_7$, $U4+Q_8$, $U4+Q_9$, $U4+Q_1+Q_2$, $U4+Q_1+Q_3$, $U4+Q_1+Q_4$, $U4+Q_1+Q_5$, $U4+Q_1+Q_6$, $U4+Q_1+Q_7$, $U4+Q_1+Q_8$, $U4+Q_1+Q_9$, $U4+Q_2+Q_3$, $U4+Q_2+Q_4$, $U4+Q_2+Q_5$, $U4+Q_2+Q_6$, $U4+Q_2+Q_7$, $U4+Q_2+Q_8$, $U4+Q_2+Q9$, $U4+Q_3+Q_4$, $U4+Q_3+Q_5$, $U4+Q_3+Q_6$, $U4+Q_3+Q_7$, $U4+Q_3+Q_8$, $U4+Q_3+Q9$, $U4+Q_4+Q_5$, $U4+Q_4+Q_6$, $U4+Q_4+Q_7$, $U4+Q_4+Q_8$, $U4+Q_4+Q_9$, $U4+Q_5+Q_6$, $U4+Q_5+Q_7$, $U4+Q_5+Q_8$, $U4+Q_5+Q_9$, $U4+Q_6+Q_7$, $U4+Q_6+Q_8$, $U4+Q_5+Q9$, $U4+Q_7+Q_8$, $U4+Q_7+Q_9$, $U4+Q_8+Q9$, $U4+Q_1+Q_2+Q_3$, $U4+Q_1+Q_2+Q_4$, $U4+Q_1+Q_2+Q_5$, $U4+Q_1+Q_2+Q_6$, $U4+Q_1+Q_2+Q_7$, $U4+Q_1+Q_2+Q_8$, $U4+Q_1+Q_2+Q9$, $U4+Q_1+Q_3+Q_4$, $U4+Q_1+Q_3+Q_5$, $U4+Q_1+Q_3+Q_6$, $U4+Q_1+Q_3+Q_7$, $U4+Q_1+Q_3+Q_8$, $U4+Q_1+Q_3+Q_9$, $U4+Q_1+Q_4+Q_5$, $U4+Q_1+Q_4+Q_6$, $U4+Q_1+Q_4+Q_7$, $U4+Q_1+Q_4+Q_5$, $U4+Q_1+Q_4+Q9$, $U4+Q_1+Q_5+Q_6$, $U4+Q_1+Q_5+Q_7$, $U4+Q_1+Q_5+Q_8$, $U4+Q_1+Q_5+Q_9$, $U4+Q_1+Q_6+Q_7$, $U4+Q_1+Q_6+Q_8$, $U4+Q_1+Q_6+Q9$, $U4+Q_1+Q_7+Q_8$, $U4+Q_1+Q_7+Q9$, $U4+Q_1+Q_5+Q9$, $U4+Q_2+Q_3+Q_4$, $U4+Q_2+Q_3+Q_5$, $U4+Q_2+Q_3+Q_6$, $U4+Q_2+Q_3+Q_7$, $U4+Q_2+Q_3+Q_8$, $U4+Q_2+Q_3+Q_9$, $U4+Q_2+Q_4+Q_5$, $U4+Q_2+Q_4+Q_6$, $U4+Q_2+Q_4+Q_7$, $U4+Q_2+Q_4+Q_5$, $U4+Q_2+Q_4+Q9$, $U4+Q_2+Q_5+Q_6$, $U4+Q_2+Q_5+Q_7$, $U4+Q_2+Q_5+Q_8$, $U4+Q_2+Q_5+Q_9$, $U4+Q_2+Q_6+Q_7$, $U4+Q_2+Q_6+Q_8$, $U4+Q_2+Q_6+Q_9$, $U4+Q_2+Q_7+Q_8$, $U4+Q_2+Q_7+Q9$, $U4+Q_2+Q_8+Q9$, $U4+Q_3+Q_4+Q_5$, $U4+Q_3+Q_4+Q_6$, $U4+Q_3+Q_4+Q_7$, $U4+Q_3+Q_4+Q_8$, $U4+Q_3+Q_4+Q9$, $U4+Q_3+Q_5+Q_6$, $U4+Q_3+Q_5+Q_7$, $U4+Q_3+Q_5+Q_8$, $U4+Q_3+Q_5+Q_9$, $U4+Q_3+Q_6+Q_7$, $U4+Q_3+Q_6+Q_8$, $U4+Q_3+Q_6+Q9$, $U4+Q_3+Q_7+Q_8$, $U4+Q_3+Q_7+Q9$, $U4+Q_3+Q_8+Q9$, $U4+Q_4+Q_5+Q_6$, $U4+Q_4+Q_5+Q_7$, $U4+Q_4+Q_5+Q_8$, $U4+Q_4+Q_5+Q_9$, $U4+Q_4+Q_6+Q_7$, $U4+Q_4+Q_5+Q_8$, $U4+Q_4+Q_6+Q_9$, $U4+Q_4+Q_7+Q_8$, $U4+Q_4+Q_7+Q_0$, $U4+Q_4+Q_8+Q_9$, $U4+Q_5+Q_6+Q_7$, $U4+Q_5+Q_6+Q_8$, $U4+Q_5+Q_6+Q_9$, $U4+Q_5+Q_7+Q_8$, $U4+Q_5+Q_7+Q_9$, $U4+Q_5+Q_8+Q_9$, $U4+Q_6+Q_7+Q_8$, $U4+Q_6+Q_7+Q_9$, $U4+Q_6+Q_8+Q_9$, $U4+Q_1+Q_2+Q_3+Q_4$, $U4+Q_4+Q_2+Q_3+Q_5$, $U4+Q_1+Q_2+Q_3+Q_6$, $U4+Q_1+Q_2+Q_3+Q_7$, $U4+Q_4+Q_2+Q_3+Q_8$, $U4+Q_4+Q_2+Q_3+Q9$, $U4+Q_1+Q_3+Q_4+Q_5$, $U4+Q_1+Q_3+Q_4+Q_6$, $U4+Q_4+Q_3+Q_4+Q_7$, $U4+Q_1+Q_3+Q_4+Q_8$, $U4+Q_1+Q_3+Q_4+Q_9$, $U4+Q_4+Q_4+Q_5+Q_6$, $U4+Q_4+Q_4+Q_5+Q_7$, $U4+Q_1+Q_4+Q_5+Q_8$, $U4+Q_1+Q_4+Q_5+Q9$, $U4+Q_4+Q_5+Q_6+Q_7$, $U4+Q_1+Q_5+Q_6+Q_8$, $U4+Q_1+Q_5+Q_6+Q_9$, $U4+Q_4+Q_6+Q_7+Q_8$, $U4+Q_4+Q_6+Q_7+Q9$, $U4+Q_1+Q_7+Q_8+Q_9$, $U4+Q_2+Q_3+Q_4+Q_5$, $U4+Q_2+Q_3+Q_4+Q_6$, $U4+Q_2+Q_3+Q_4+Q_7$, $U4+Q_2+Q_3+Q_4+Q_8$, $U4+Q_2+Q_3+Q_4+Q_9$, $U4+Q_2+Q_3+Q_5+Q_6$, $U4+Q_2+Q_4+Q_5+Q_6$, $U4+Q_2+Q_4+Q_5+Q_7$, $U4+Q_2+Q_4+Q_5+Q_8$, $U4+Q_2+Q_4+Q_5+Q9$, $U4+Q_2+Q_5+Q_6+Q_7$, $U4+Q_2+Q_5+Q_6+Q_8$, $U4+Q_2+Q_5+Q_6+Q_9$, $U4+Q_2+Q_6+Q_7+Q_8$, $U4+Q_2+Q_6+Q_7+Q_9$, $U4+Q_2+Q_7+Q_8+Q_9$, $U4+Q_3+Q_4+Q_5+Q_6$, $U4+Q_3+Q_4+Q_5+Q_7$, $U4+Q_3+Q_4+Q_5+Q_8$, $U4+Q_3+Q_4+Q_5+Q9$, $U4+Q_3+Q_5+Q_6+Q_7$, $U4+Q_3+Q_5+Q_6+Q_8$, $U4+Q_3+Q_5+Q_6+Q_9$, $U4+Q_3+Q_6+Q_7+Q_8$, $U4+Q_3+Q_6+Q_7+Q_9$, $U4+Q_3+Q_7+Q_8+Q_9$, $U4+Q_4+Q_5+Q_6+Q_7$, $U4+Q_4+Q_5+Q6+Q_8$, $U4+Q_4+Q_5+Q_6+Q_9$, $U4+Q_4+Q_6+Q_7+Q_8$, $U4+Q_4+Q_6+Q_7+Q9$, $U4+Q_4+Q_7+Q_8+Q_9$, $U4+Q_5+Q_6+Q_7+Q_8$, $U4+Q_5+Q_6+Q_7+Q_9$, $U4+Q_5+Q_7+Q_8+Q_9$, $U4+Q_1+Q_2+Q_3+Q_4+Q_5$, $U4+Q_4+Q_2+Q_3+Q_4+Q_6$, $U4+Q_4+Q_2+Q_3+Q_4+Q_7$, $U4+Q_1+Q_2+Q_3+Q_4+Q_8$, $U4+Q_1+Q_2+Q_3+Q_4+Q_9$, $U4+Q_1+Q_3+Q_4+Q_5+Q_6$, $U4+Q_1+Q_3+Q_4+Q_5+Q_7$, $U4+Q_4+Q_3+Q_4+Q_5+Q_8$, $U4+Q_1+Q_3+Q_4+Q_5+Q_9$, $U4+Q_1+Q_4+Q_5+Q_6+Q_7$, $U4+Q_1+Q_4+Q_5+Q_6+Q_8$, $U4+Q_1+Q_4+Q_5+Q_6+Q_9$, $U4+Q_1+Q_5+Q_6+Q_7+Q_8$, $U4+Q_1+Q_5+Q_6+Q_7+Q9$, $U4+Q_1+Q_6+Q_7+Q_8+Q_9$, $U4+Q_2+Q_3+Q_4+Q_5+Q_6$, $U4+Q_2+Q_3+Q_4+Q_5+Q_7$, $Q_7+Q_9$, $U4+Q_2+Q_6+Q_7+Q_8+Q_9$, $U4+Q_3+Q_4+Q_5+Q_6+Q_7$, $U4+Q_3+Q_4+Q_5+Q_6+Q_8$, $U4+Q_3+Q_4+Q_5+Q_6+Q_9$, $U4+Q_3+Q_5+Q_6+Q_7+Q_8$, $U4+Q_3+Q_5+Q_6+Q_7+Q9$, $U4+Q_3+Q_6+Q_7+Q_8+Q9$, $U4+Q_4+Q_5+Q_6+Q_7+Q_8$, $U4+Q_4+Q_5+Q_6+Q_7+Q_9$, $U4+Q_4+Q_6+Q_7+Q_8+Q_9$, $U4+Q_5+Q_6+Q_7+Q_8+Q_9$, $U4+Q_1+Q_2+Q_3+Q_4+Q_5+Q_6$, $U4+Q_1+Q_2+Q_3+Q_4+Q_6+Q_7$, $U4+Q_1+Q_2+Q_3+Q_4+Q_5+Q_8$, $U4+Q_1+Q_2+Q_3+Q_4+Q_5+Q_9$, $U4+Q_1+Q_3+Q_4+Q_5+Q_6+Q_7$, $U4+Q_1+Q_3+Q_4+Q_5+Q_6+Q_8$, $U4+Q_1+Q_3+Q_4+Q_5+Q_6+Q_9$, $U4+Q_1+Q_4+Q_5+Q_6+Q_7+Q_8$, $U4+Q_1+Q_4+Q_5+Q_6+Q_7+Q_9$, $U4+Q_1+Q_5+Q_6+Q_7+Q_8+Q_9$, $U4+Q_2+Q_3+Q_4+Q_5+Q_6+Q_7$, $U4+Q_2+Q_3+Q_4+Q_5+Q_6+Q_8$, $U4+Q_2+Q_3+Q_4+Q_5+Q_6+Q_9$, $U4+Q_2+Q_4+Q_5+Q_6+Q_7+Q_8$, $U4+Q_2+Q_4+Q_5+Q_6+Q_7+Q_9$, $U4+Q_2+Q_5+Q_6+Q_7+Q_8+Q_9$, $U4+Q_3+Q_4+Q_5+Q_6+Q_7+Q_8$, $U4+Q_3+Q_4+Q_5+Q_6+Q_7+Q_9$, $U4+Q_3+Q_5+Q_6+Q_7+Q_8+Q_9$, $U4+Q_4+Q_5+Q_6+Q_7+Q_8+Q_9$, $U4+Q_1+Q_2+Q_3+Q_4+Q_5+Q_6+Q_7$, $U4+Q_1+Q_2+Q_3+Q_4+Q_5+Q_6+Q_8$, $U4+Q_1+Q_2+Q_3+Q_4+Q_5+Q_6+Q_9$, $U4+Q_1+Q_3+Q_4+Q_5+Q_6+Q_7+Q_8$, $U4+Q_1+Q_3+Q_4+Q_5+Q_6+Q_8+Q_9$, $U4+Q_1+Q_3+Q_4+Q_5+Q_6+Q_7+Q_9$, $U4+Q_1+Q_4+Q_5+Q_6+Q_7+Q_8+Q_9$, $U4+Q_2+Q_3+Q_4+Q_5+Q_6+Q_7+Q_8$, $U4+Q_2+Q_3+Q_4+Q_5+Q_6+Q_7+Q_9$, $U4+Q_2+Q_3+Q_4+Q_5+Q_6+Q_8+Q_9$, $U4+Q_2+Q_4+Q_5+Q_6+Q7+Q_8+Q_9$, $U4+Q_3+Q_4+Q_5+Q_6+Q_7+Q_8+Q_9$, $U4+Q_1+Q_2+Q_3+Q_4+Q_5+Q_6+Q7+Q_8$, $U4+Q_1+Q_2+Q_3+Q_4+Q_5+Q_6+Q_7+Q_9$, $U4+Q_2+Q_3+Q_4+Q_5+Q_6+Q7+Q_8+Q9$, or $U4+Q_1+Q_2+Q_3+Q_4+Q_5+Q_6+Q_7+Q_8+Q_9$.

In some embodiments of $R_9$, and independently in combination with any embodiments of any other relevant substituent classes, $R_9$ can be —$CH_2$—OH, —$CH_3$, —O—$CH_3$, or —CO—$CH_3$, preferably —$CH_2$—OH. Preferably in these embodiments, $R_8$ is hydrogen.

In some embodiments of C, and independently in combination with any embodiments of any other relevant substituent classes, C can be —$CH_2$—OH, —$CH_3$, —O—$CH_3$, or —CO—$CH_3$, preferably —$CH_2$—OH. Preferably in these embodiments, C is in Formula XVI, B is triazole, and 5 is 1.

In some embodiments of $R^d$, and independently in combination with any embodiments of any other relevant substituent classes, $R^d$ can be —$CH_2$—OH, —$CH_3$, —O—$CH_3$, or —CO—$CH_3$, preferably —$CH_2$—OH. Preferably in these embodiments, $R_{18}$, $R_{19}$, and $R_{20}$ are N, $R_{21}$ and $R_{22}$ are C, and w is 1.

Preferred alkynes for use as reagents in 1,3-dipolarcycloaddition reactions include those shown below.

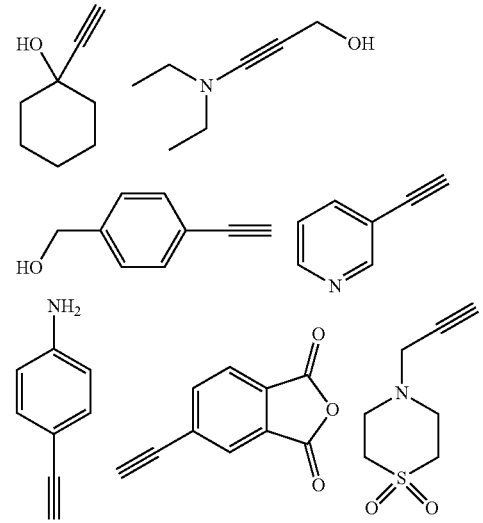

-continued

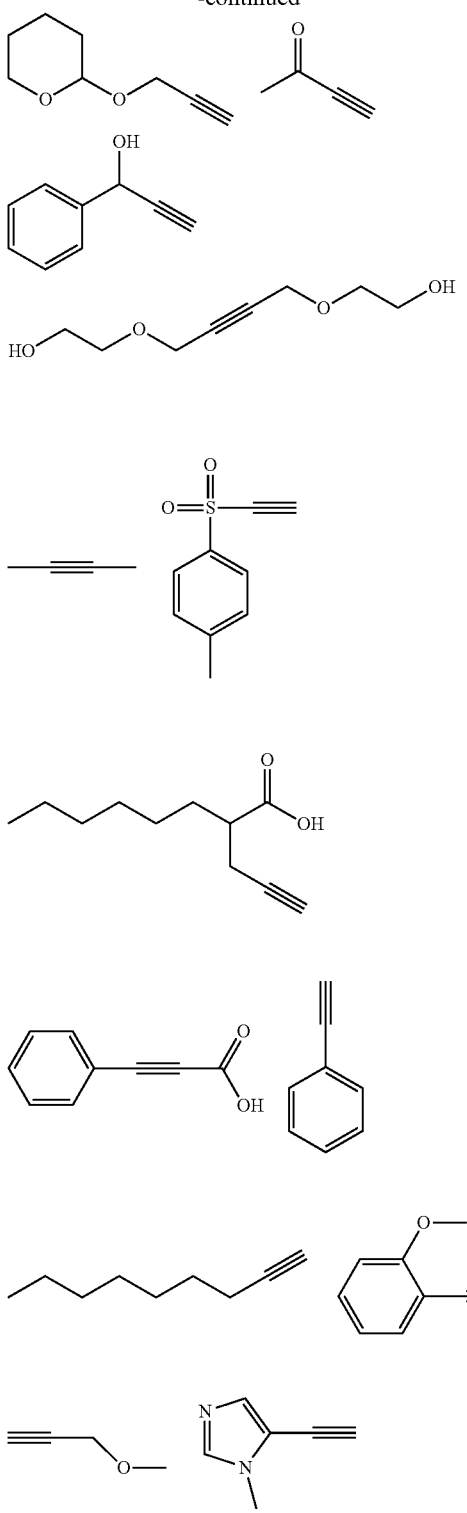

3. Modification Via the Hydroxyl Moiety of the Mannuronate and Guluronate Monomers Mannuronate and guluronate monomers contain hydroxyl moieties which can serve as a point of covalent modification. In preferred embodiments, the hydroxyl moieties of mannuronate and guluronate residues (1) are reacted as shown in Scheme 3.

Scheme 3.

Representative Reaction Conditions: i. I-PO(OR$_5$)$_2$, pyridine; ii. R$_2$—CO—R$_3$, H$^+$.

Mannuronate and guluronate residues (A) can be phosphorylated by a variety of methods known in the art, forming covalently modified monomer I. For example, mannuronate and guluronate residues can be phosphorylated by reaction with I—PO(OR$_5$)$_2$ in the presence of pyridine (Stowell, J. K, and Widlanski, T. S. *Tetrahedron Lett.* 1995; 36(11): 1825-1826.).

Mannuronate and guluronate residues (A) can also be converted to a cyclic acetal using procedures known in the art. For example, a cyclic acetal can be formed by reaction of mannuronate and guluronate residues with any suitable ketone (R$_2$—CO—R$_3$) in acidic conditions.

4. Methods for Preparing Multiply Modified Alginate Polymers

In the case of singularly modified alginate polymers, only a single reaction or sequence of reactions is performed, introducing one type of covalently modified monomer.

In the case of multiply modified alginate polymers, one or more reactions are performed to introduce multiple different types of covalently modified monomers into the modified alginate polymer. In some embodiments, multiply modified alginate polymers are prepared using multiple sequential synthetic reactions. For example, the multiply modified alginate polymer shown below can be prepared using two sequential reactions: (1) amidation of mannuronate and guluronate monomers with methylamine in the presence of CDMT and NMM; and (2) esterification of mannuronate and guluronate residues with ethanol in the presence of CDMT and NMM.

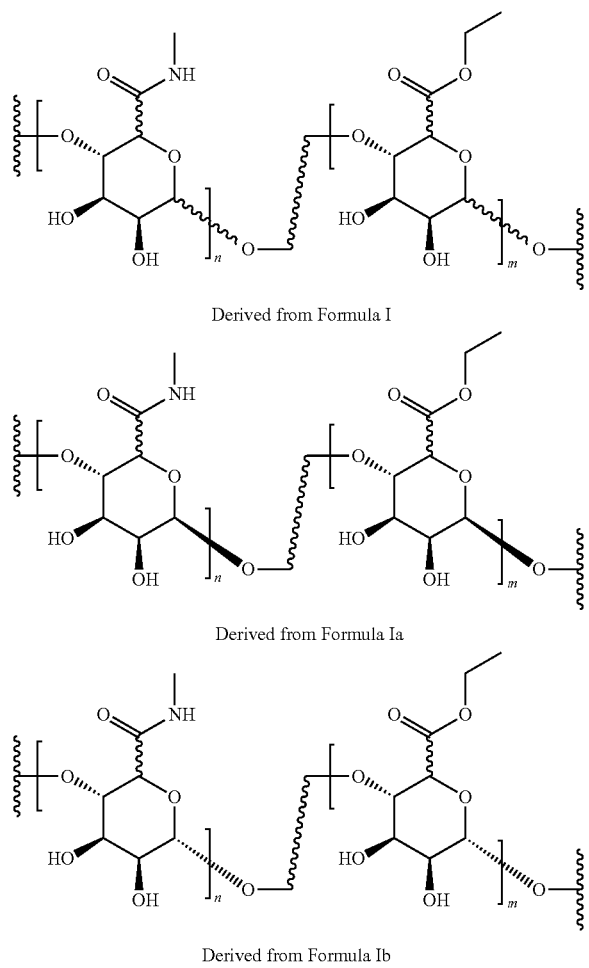

Derived from Formula I

Derived from Formula Ia

Derived from Formula Ib

In alternative embodiments, multiply modified alginate polymers can be prepared using a 'one-pot' synthesis. In these embodiments, multiple covalently modified monomers are introduced into the alginate polymer in a single synthetic step. For example, the multiply modified alginate polymer shown above can alternatively be prepared in a single synthetic step by reacting an alginate polymer with methylamine and ethanol in the presence of CDMT and NMM.

Any type or form of modified alginate, any type or form of alginate modification, and any type or form of reagent for modifying alginate can be, independently and in any combination, specifically included or excluded in any of the disclosed modified alginates, alginate modifications, reagents for alginate modifications, methods, and kits, and in any context, combination, or use. For example, any type or form of esterification reagent, amidation reagent, click reagent, alkyne-containing reagent, azide-containing reagent, phosphorylating reagent, and ketone reagent, such as those described above and in the examples, can be, independently and in any combination, specifically included or excluded from use to modify alginates, and any alginate modifications and any modified alginates that include or are based on such reagents can be, independently and in any combination, specifically included or excluded in any of the disclosed modified alginates, alginate modifications, reagents for alginate modifications, methods, and kits, and in any context, combination, or use.

As another example, any of the reagents described in Table 4 can be, independently and in any combination, specifically included or excluded from use to modify alginates, and any alginate modifications and any modified alginates that include or are based on the reagents described in Table 4 can be, independently and in any combination, specifically included or excluded in any of the disclosed modified alginates, alginate modifications, reagents for alginate modifications, methods, and kits, and in any context, combination, or use. For example, all of the reagents described in Table 4 in combination but excluding reagent Y3 can be specifically included or excluded from use to modify alginates, and any alginate modifications and any modified alginates that include or are based on all the reagents described in Table 4 in combination but excluding reagent Y3 can be specifically included or excluded in any of the disclosed modified alginates, alginate modifications, reagents for alginate modifications, methods, and kits, and in any context, combination, or use.

As another example, any modified alginate, alginate modification, or reagents for alginate modification described in U.S. Patent Application No. 20120308650 can be, independently and in any combination, specifically included or excluded. U.S. Patent Application Publication No. 20120308650 is hereby incorporated herein by reference in its entirety, and specifically for its description of modified alginates, alginate modifications, and reagents for alginate modifications. Any of the R group substituents for any of the R groups described herein can be, independently and in any combination, specifically included or excluded as an option or as the choice for the respective R group.

In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 100% of the residues of the alginates are singly modified using the alcohols, alkynes, amines, or combinations thereof, described herein. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 100% of the residues of the alginates are multiply modified using the alcohols, alkynes, amines, or combinations thereof, described herein.

D. Purification of Alginates

Commercial alginates are generally obtained from algae. Crude alginates from seaweed contain numerous contaminants, including polyphenols, proteins, and endotoxins (de Vos, P, et al. *Biomaterials* 2006; 27: 5603-5617). The presence of these impurities has been shown to limit the biocompatibility of implanted alginates.

To optimize the biocompatibility of the chemically modified alginates described herein, a rigorous purification methodology was developed to eliminate potentially irritating impurities. In preferred embodiments, ultra-pure low viscosity alginate (UPVLVG, FMC Biopolymer) was used as a substrate for covalent modification. Following each covalent modification, the modified alginates were filtered through modified silica columns, for example cyano-modified silica columns, aimed at capturing bulk organic impurities. Finally, after covalent modification of the alginate polymer is complete, the modified alginates are dialyzed to remove any remaining small-molecule or low molecular weight impurities. In a preferred method, the modified alginates are dialyzed against 10,000 molecular weight cut-off (MWCO) membrane to remove any remaining small-molecule impurities.

The purity of the modified alginates can be determined by $^1$H NMR analysis. In such an analysis, the $^1$H NMR spectra of the modified alginate polymer is collected, and peaks corresponding to the modified alginate polymer and to any impurities are integrated to determine the relative quantity of each species in the sample. In some embodiments, the purity of the modified alginate polymer, as determined by $^1$H NMR, is greater than 90%, 91%, 92%, 93%, 94%, 95%, 96%, 97%, 98%, or 99%. In preferred embodiments, the purity of the modified alginate polymer, as determined by $^1$H NMR, is greater than 90%, more preferably greater than 95%.

III. Methods of Assessing Biocompatibility

Biocompatibility of the disclosed hydrogel capsules can be assessed using any suitable techniques. Examples of useful techniques are described below.

A. Assessing Cytotoxicity

The cytotoxicity of the disclosed surface modified hydrogel capsules can be evaluated on HeLa cells. The surface modified hydrogel capsules and can be loaded into containers, such as wells of 96-well plates. The containers can be coated with an attachment molecule, such as poly-L-lysine, if appropriate. Unmodified hydrogel capsule and material and saline can be loaded into conrainers as controls. HeLa cells can then be seeded into the wells and incubated for 3 days at 37° C. in a humidified chamber.

A cell viability assay using 3-(4,5-Dimethylthiazol-2-yl)-2,5-diphenyltetrazolium bromide (MTT) can then be performed, in which the media is aspirated from all containers and an appropriate volume (such as 100 µl for 96-well plate wells) of DMEM media without phenol red and an appropriate volume (such as 10 µl for 96-well plate wells) of MTT (5 mg/ml) added to all of the containers. The containers can then be incubated for 4 hours at 37° C. in a humidified chamber. After incubation, an appropriate volume (such as 85 µl for 96-well plate wells) of solution is aspirated and an appropriate volume (such as 100 µl for 96-well plate wells) of DMSO is added. Purple formazan crystals form during the assay in proportion to the number of viable HeLa cells present in each container. The contents of each container can be pipetted up and down to solubilize the formazan crystals prior to measurement. The containers can then be incubated at 37° C. for 10 minutes after which the bubbles from agitation are removed. The plate can be read using a UV/Vis reader at 540 nm with a reference at 700 nm. The viability can be normalized to cells seeded in containers with no hydrogel capsule or material.

B. Assessing Foreign Body Response/Inflammatory Response

Cathepsin activity, which can be detected by fluorescence, can be used as an indicator of foreign body response (a form of inflammatory response). Mice, such as 8-12 week old male SKH1 mice, can be used to assess foreign body response of the disclosed hydrogel capsules. After injection or implantation of the hydrogel capsule of material, cathepsin activity can be measured using an in vivo fluorescence assay at various times after injection or implantation. For example, imaging can be taken at 7 days after injection or implantation. 24 hours before in vivo fluorescence imaging, 2 nmol of ProSense-680 (VisEn Medical, Woburn, MA, excitation wavelength 680±10 nm, emission 700±10 nm) can be dissolved in 150 µl sterile PBS and injected into the tail vein of each mouse to image cathepsin activity.

In vivo fluorescence imaging can be performed with an in vivo fluorescence imaging system, such as the IVIS-Spectrum measurement system (Xenogen, Hopkinton, MA). The can be maintained under inhaled anesthesia during imaging, using, for example, 1-4% isoflurane in 100% oxygen at a flow rate of 2.5 L/min. Images and data can be collected as appropriate for the imaging device being use. As an example, images can be presented in fluorescence efficiency, which is defined as the ratio of the collected fluorescent intensity to an internal standard of incident intensity at the selected imaging configuration. Regions of interest (ROIs) can be designated around the site of each injection.

Relative cathepsin activity at the point of injection or implantation of hydrogel capsules can be imaged. The fluorescence intensity can be measured and normalized to the fluorescence response measured using the unmodified form of the hydrogel capsule or material in order to quantify the biocompatibility of the surface modified hydrogel capsules as compared to unmodified hydrogel capsules.

Inflammatory response can also be assessed by detecting and measuring a suite of cytokines. The cytokine levels can indicate a high or low inflammatory response. For example, low protein levels of, for example, TNF-α, IL-13, IL-6, G-CSF, GM-CSF, IL-4, CCL2, and CCL4 which are known mediators of the foreign body response and fibrosis (Rodriguez et al., J. Biomed. Mater. Res. A 89:152-159 (2009)), can indicate a lack of or lower foreign body response.

C. Assessing Fibrosis

FACS analysis can be performed on retrieved hydrogel capsules and appropriate times after implantation to characterize the different immune populations that are recruited to the hydrogel capsules compared to control hydrogel capsule or material. For example, the presence of macrophages, neutrophils, myofibroblasts, of a combination thereof, on hydrogel capsules or at the location of the hydrogel capsules indicate a fibrotic response. Cells were tagged with markers for macrophages (CD11b+, CD68+), neutrophils (CD11b+, Ly6 g+), or myofibroblasts (SMA). FACS was used to determine the levels of these fibrosis-associated cell types in proximity to the hydrogel capsule or material.

D. qPCR Analysis of Innate Immune and Firbrosis Markers

Total RNA is isolated from a source, such as capsules or products retrieved from an animal after implantation for a period of time, by snap freezing in liquid nitrogen immediately following excision, using, for example, TRIzol (Invitrogen; Carlsbad, CA) according to the manufacturer's instructions. In addition, to help ensure complete tissue disruption, strong mechanical disruption with a Polytron homogenizer can also be employed. By this process, gene expression signatures are proportional and representative of the entire cell population present on and/or around retrieved materials. Before reverse transcription using, for example, the High Capacity cDNA Reverse Transcription kit (Cat. #4368814; Applied Biosystems, Foster City, CA), all samples are first normalized for comparison by loading the same input total RNA in a set volume (1 µg total RNA in a volume of 20 µl, for example) for each sample. cDNA (4.8 µl; 1:20 dilution in a total volume of 16 µl, for example), including a nucleic acid stain, such as SYBR Green, and PCR primers, is amplified by qPCR with the following appropriate primers (such as the primers shown in Table 1). These primers (Table 1) were designed using Primer Express software (Applied Biosystems, Carlsbad, CA, USA) and evaluated using LaserGene software (DNAStar, Madison, WI, USA) to ensure either mouse or rat (host)-specificity.

Other primers can be designed by similar or equivalent analysis. Samples are incubated, for example, at 95° C. for 10 min followed by 40 cycles of 95° C. for 15 sec and 60° C. for 1 min in, for example, an ABI PRISM 7900HT Sequence Detection System (Applied Biosystems). Results are analyzed using a suitable method, such as the comparative CT (DDCT) method as described by Applied Biosystems. Results are presented, for example, as relative RNA levels compared to the RNA expression in either mock-implanted control cell samples (peripheral intraperitoneal fat tissue, or free floating intraperitoneal lavage cells) after normalization to the β-actin RNA content of each sample.

TABLE 1

Mouse (m) or rat (r)-specific (host) forward and reverse primer sets used for qPCR analysis of RNA levels. Gene names are also shown in parentheses.

| Gene | Primers (5' to 3'): Sense & Antisense |
|---|---|
| Mouse Collagen 1a1 (mColla1) | Forward: 5'-CATGTTCAGCTTTGTGGACCT-3' (SEQ ID NO: 1) Reverse: 5'-GCAGCTGACTTCAGGGATGT-3' (SEQ ID NO: 2) |
| Mouse Collagen 1a2 (mColla2) | Froward: 5'-GCAGGTTCACCTACTCTGTCCT-3' (SEQ ID NO: 3) Reverse: 5'-CTTGCCCCATTCATTTGTCT-3' (SEQ ID NO: 4) |
| Mouse Alpha Smooth Muscle actin (mActa2) | Forward: 5'-CGCTTCCGCTGCCCAGAGACT-3' (SEQ ID NO: 5) Reverse: 5'-TATAGGTGGTTTCGTGGATGCCCGCT-3' (SEQ ID NO: 6) |
| Mouse Myeloid cell Marker CD11b (mItgam) | Forward: 5'-CCAAGAGAATGCAAAAGGCTTT-3' (SEQ ID NO: 7) Reverse: 5'-GGGGGGCTGCAACAACCACA-3' (SEQ ID NO: 8) |
| Mouse Macrophage Marker CD68 (mCD68) | Forward: 5'-GCCCGAGTACAGTCTACCTGG-3' (SEQ ID NO: 9) Reverse: 5'-AGAGATGAATTCTGCGCCAT-3' (SEQ ID NO: 10) |
| Mouse neutrophil Marker Gr1 (mLy6g) | Forward: 5'-TGCCCCTTCTCTGATGGATT-3' (SEQ ID NO: 11) Reverse: 5'-TGCTCTTGACTTGCTTCTGTGA-3' (SEQ ID NO: 12) |
| Mouse β-actin (mActB) | Forward: 5'-GCTTCTTTGCAGCTCCTTCGTT-3' (SEQ ID NO: 13) Reverse: 5'-CGGAGCCGTTCTCGACGACC-3' (SEQ ID NO: 14) |
| Rat Collagen 1a1 (rColla1) | Forward: 5'-CATGTTCAGCTTTGTGGACCT-3' (SEQ ID NO: 15) Reverse: 5'-GCAGCTGACTTCAGGGATGT-3' (SEQ ID NO: 16) |
| Rat Collagen 1a2 (rColla2) | Forward: 5'-CCTGGCTCTCGAGGTGAAC-3' (SEQ ID NO: 17) Reverse: 5'-CAATGCCCAGAGGACCAG-3' (SEQ ID NO: 18) |
| Rat Alpha Smooth Muscle actin (rActa2) | Forward: 5'-TGCCATGTATGTGGCTATTCA-3' (SEQ ID NO: 19) Reverse: 5'-ACCAGTTGTACGTCCAGAAGC-3' (SEQ ID NO: 20) |
| Rat Pdx1 (rPdx1) | Forward: 5'-CTCTCGTGCCATGTGAACC-3' (SEQ ID NO: 21) Reverse: 5'-TTCTCTAAATTGGTCCCAGGAA-3' (SEQ ID NO: 22) |
| Rat β-actin (rActB) | Forward: 5'-ACCTTCTTGCAGCTCCTCCGTC-3' (SEQ ID NO: 23) Reverse: 5'-CGGAGCCGTTGTCGACGACG-3' (SEQ ID NO: 24) |

E. FACS Analysis

Single-cell suspensions from capsules or products freshly excised from an animal after implantation for a period of time (or of tissues freshly excised from an animal) are prepared using, for example, a gentleMACS Dissociator (Miltenyi Biotec, Auburn, CA) according to the manufacturer's protocol. Single-cell suspensions are prepared in a passive PEB dissociation buffer (IX PBS, pH 7.2, 0.5% BSA, and 2 mM EDTA) and suspensions are passed through 70 μm filters (for example, Cat. #22363548, Fisher Scientific, Pittsburgh, PA). This process removes the majority of cells adhered to the surface (>90%). The single-cell populations thus derived are then subjected to red blood cell lysis with 5 ml of 1×RBC lysis buffer (Cat. #00-4333, eBioscience, San Diego, CA, USA) for 5 min at 4° C. The reaction is terminated by the addition of 20 ml of sterile IX PBS. The cells remaining are centrifuged at 300-400 g at 4° C., and resuspended in a minimal volume (~50 μl) of, for example, eBioscience Staining Buffer (Cat. #00-4222) for antibody incubation. All samples are then co-stained in the dark for 25 min at 4° C. with fluorescently tagged monoclonal antibodies specific for the appropriate cell markers, such as for CD68 (for example, CD68-Alexa647, Clone FA-11, Cat. #11-5931, BioLegend at 1 μl (0.5 μg) per sample), Ly-6G (Gr-1) (for example, Ly-6G-Alexa-647, Clone RB6-8C5, Cat. #108418, BioLegend at 1 μl (0.5 μg) per sample), or CD11b (for example, CD11b-Alexa-488, Clone M1/70, Cat. #101217, BioLegend at 1 μl (0.2 μg) per sample). Two ml of, for example, eBioscience Flow Cytometry Staining Buffer (Cat. #00-4222, eBioscience) is then added, and the samples are centrifuged at 400-500 g for 5 min at 4° C. Supernatants are removed by aspiration, and this wash step is repeated two more times with staining buffer. Following the third wash, each sample is resuspended in 500 μl of, for example, FlowCytometry Staining Buffer and run through a 40 μm filter (for example, Cat. #22363547, Fisher Scientific) for eventual FACS analysis using a FACS machine (for example, BD FACSCalibur (cat. #342975), BD Biosciences, San Jose, CA, USA). For proper background and laser intensity settings, unstained, single antibody, and IgG (labeled with, for example, Alexa-488 or Alexa-647, BioLegend) controls can also be run.

F. Fabrication of Alginate Hydrogel Capsules and Cell Encapsulation

All buffers are sterilized by autoclave and alginate solutions are sterilized by filtration through a 0.2 um filter. After solutions are sterilized, aseptic processing is implemented by performing capsule formation in a type II class A2 biosafety cabinet to maintain sterility of manufactured microcapsules/spheres for subsequent implantation. The hydrogel capsules are formed by the following protocol.

To solubilize alginates, SLG20 (NovaMatrix, Sandvika, Norway) is dissolved at 1.4% weight to volume in 0.8% saline. TMTD alginate is initially dissolved at 5% weight to volume in 0.8% saline, and then blended with 3% weight to volume SLG100 (also dissolved in 0.8% saline) at a volume ratio of 80% TMTD alginate to 20% SLG100.

Forming different sized capsules: for 300 μm diameter capsules, a 30 gauge blunt tipped needle (SAI Infusion Technologies) is used with a voltage of 7-8 kV. For 500 μm diameter capsules, a 25 gauge blunt tipped needle (SAI Infusion Technologies) is used with a voltage of 5-7 kV. For 1.5 mm capsules, an 18 gauge blunt tipped needle (SAI Infusion Technologies) is used with a voltage of 5-7 kV.

Cells, such as human islet cells or cultured human cells, are used for encapsulation. Immediately prior to encapsulation, the cultured human cell clusters are centrifuged at 1,400 rpm for 1 minute and washed with Ca-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the human cells are centrifuged again and all supernatant is aspirated. The human cell pellet is then re-suspended in the SLG20 or TMTD alginate solutions at cluster densities of 1,000, 250, and 100 clusters per 0.5 ml alginate solution.

An electrostatic droplet generator is set up as follows: an ES series 0-100 KV, 20 Watt high voltage power generator (Gamma ES series, Gamma High Voltage Research, FL, USA) is connected to the top and bottom of a blunt tipped needle (SAI Infusion Technologies, IL, USA). This needle is attached to a 5 mL lure lock syringe (BD, NJ, USA) which is clipped to a syringe pump (Pump 11 Pico Plus, Harvard Apparatus, MA, USA) that is oriented vertically. The syringe pump pumps alginate out into a glass dish containing a 20 mM barium 5% mannitol solution (Sigma Aldrich, MO, USA). The settings of the PicoPlus syringe pump are 12.06 mm diameter and 0.2 mL/min flow rate. Immediately after crosslinking, the encapsulated human cell clusters are washed 4 times with 50 mL of CMRLM media and cultured overnight in a spinner flask at 37° C. prior to transplantation. Due to an inevitable loss of human cell clusters during the encapsulation process, the total number of encapsulated clusters are recounted post-encapsulation.

G. Analysis of Cell Viability of Encapsulated Cells and/or Protein Secreted from Encapsulated Cells Encapsulated cells are added in 3 ml of fresh medium to each well of a six-well tissue-culture polystyrene plate. Culturing of encapsulated cells is maintained for four days. Afterwards, supernatant samples can be collected and frozen at −20° C. for future analysis, such as by Western blot or ELISA. Encapsulated cells are collected into new plates. Both encapsulated cells are washed in HEPES buffer and subjected to live-dead fluorescent staining (Invitrogen) for viability assessment. The proportion of encapsulated cells that are viable (live) can be calculated. The secretion level of one or more proteins of interest, such as insulin form islet cels or a protein of interest secreted by a recombinant cell, can be assessed by analyzing the supernatant by Western blot or ELISA. The level of secretion can be assessed by, for example, raw level, normalized level (normalized to the level of a housekeeping secreted protein, for example), or either of these compared to the level measured form control cells.

H. Insulin Secretion Analysis

Encapsulated islet cell insulin responses are assessed by loading capsules or product containing encapsulated islet cells into a microfluidic device modified for encapsulated islets (Nourmohammadzadeh et al., Analytical Chem. 85:11240-11249 (2013)). The encapsulated islet cells can be, for example, newly encapsulated or retrieved after implantation into a subject, such as a mouse. Perifusate samples are collected every minute (500 μL/min) by an automated fraction collector (Gilson, model 203B, WI, USA). Insulin concentrations are quantified every other minute using, for example, a chemiluminescent insulin ELISA (Alpco, NH, USA). The following perifusion protocol is used: (1) KRB2 (0-20 min); (2) 20 mM glucose or 30 mM KCl (20-55 min); (3) KRB2 (55-100 min). An appropriate measure of the secreted insulin can be calculated. For example, the area under the curve for each insulin curve can be calculated in order to statistically compare groups using one-way ANOVA (p<0.05 as significant).

Biological and temporal characteristics of the disclosed capsules can be assessed by any suitable analysis. For example, the length of time a capsule implanted into a subject remains acceptably free of fibrotic effects, produces a desired effect, maintains encapsulated cell viability, or combinations thereof can be assessed. Analogously, the suitability of surface modifications for facilitating desirable biological and temporal characteristics of the disclosed capsules can be assessed in similar ways. In some embodiments, a capsule with surface modifications as described herein, if implanted into and retrieved from an immunocompetent animal, such as a C57BL/6J mouse, as described herein, can have one or more of the following properties:

(a) expression of one or more immune and fibrosis markers on the capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(b) expression of one or more immune and fibrosis markers on the capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(c) the cell population of one or more immune- and fibrosis-associated cells on the capsule will be less than 20%, 18%, 15%, 12%, 10%, of 5% of the cell population observed for a control similar capsule lacking the surface modification at least 14 days, 30 days, 60 days, 120 days, 240 days, or 360 days after implantation into the immunocompetent animal as determined by, for example, FACS analysis or ELISA as known in the art or as described herein;

(d) expression of a cell viability marker from cells encapsulated in the capsule will be more than 2-fold higher, 3-fold higher, 3.5-fold higher, 4-fold higher, 5-fold higher, or 10-fold higher observed for similar encapsulated cells comprised in a control similar capsule lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(e) secretion of a protein of interest from cells encapsulated in the capsule will be detectable at least 14 days, 30 days, 60 days, 120 days, 240 days, or 360 days after implantation into the immunocompetent animal as determined by, for example, Western blot analysis or ELISA as known in the art or as described herein;

(f) secretion of insulin from islet cells encapsulated in the capsule will be detectable at least 14 days, 30 days, 60 days, 120 days, 240 days, or 360 days after implantation into the immunocompetent animal as determined by, for example, Western blot analysis or ELISA as known in the art or as described herein; and (g) at least 50%, 45%, 40%, 35%, 30%, 25%, 20%, 15%, or 10% of the cells encapsulated in the capsule will be viable for at least 14 days, 30 days, 60 days, 120 days, 240 days, or 360 days after implantation into the immunocompetent animal as determined by, for example, cell viability analysis as known in the art or as described herein.

The compounds used for the surface modification can be assessed for facilitating desireable biological and temporal characteristics on capsules by, for example, fabricating aliginate capsules modified with the compound to encapsulate human islet cells, implanting the alginate capsules into and retrieving the alginate capsules from a C57BL/6J mouse as described herein, and assessing a suitable property of the retrieved alginate capsules. In some embodiments, the retrieved alginate capsules can have one or more of the following properties:

(a) expression of an islet cell viability marker from the alginate capsules will be more than 2-fold higher, 3-fold higher, 3.5-fold higher, 4-fold higher, 5-fold higher, or 10-fold higher observed for a control similar alginate capsule lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(b) secretion of insulin from the islet cells encapsulated in the alginate capsule will be detectable at least 14 days, 30 days, 60 days, 120 days, 240 days, or 360 days after implantation into the immunocompetent animal as determined by, for example, Western blot analysis or ELISA as known in the art or as described herein;

(c) expression of one or more immune and fibrosis markers on the alginate capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(b) expression of one or more immune and fibrosis markers on the alginate capsule will be less than 3-fold higher, 2.5-fold higher, 2-fold higher, or 1.5-fold higher than in untreated control tissue at least 14 days, 30 days, 60 days, 120 days, 240 days, or 360 days after implantation into the immunocompetent animal as determined by, for example, Western blot analysis, ELISA, or qPCR analysis as known in the art or as described herein;

(c) the cell population of one or more immune- and fibrosis-associated cells on the alginate capsule will be less than 20%, 18%, 15%, 12%, 10%, of 5% of the cell population observed for a control similar capsule lacking the surface modification at least 14 days, 30 days, 60 days, 120 days, 240 days, or 360 days after implantation into the immunocompetent animal as determined by, for example, FACS analysis or ELISA as known in the art or as described herein;

(d) expression of a cell viability marker from the islet cells encapsulated in the alginate capsule will be more than 2-fold higher, 3-fold higher, 3.5-fold higher, 4-fold higher, 5-fold higher, or 10-fold higher observed for similar encapsulated cells comprised in a control similar capsule lacking the surface modification at least 14 days, 30 days, 60 days, 120 days, 240 days, or 360 days after implantation into the immunocompetent animal as determined by, for example, FACS analysis, Western blot analysis, ELISA, histology, or qPCR analysis as known in the art or as described herein;

(e) secretion of a protein of interest from the islet cells encapsulated in the alginate capsule will be detectable at least 14 days, 30 days, 60 days, 120 days, 240 days, or 360 days after implantation into the immunocompetent animal as determined by, for example, Western blot analysis or ELISA as known in the art or as described herein; and (g) at least 50%, 45%, 40%, 35%, 30%, 25%, 20%, 15%, or 10% of the the islet cells encapsulated in the capsule will be viable for at least 14 days, 30 days, 60 days, 120 days, 240 days, or 360 days after implantation into the immunocompetent animal as determined by, for example, cell viability analysis as known in the art or as described herein.

In some embodiments of the capsule, a similar capsule, if implanted into and retrieved from a C57BL/6J mouse as described herein has the following property: expression of one or more immune and fibrosis markers on the capsule will be less than 3-fold higher than in untreated control tissue at least 30 days after implantation into the C57BL/6J mouse as determined by, for example, Western blot analysis, ELISA, or qPCR analysis as known in the art or as described herein.

In some embodiments of the capsule, a similar capsule, if implanted into and retrieved from a C57BL/6J mouse as described herein has the following property: the cell population of one or more immune- and fibrosis-associated cells on the capsule will be less than 20% of the cell population observed for an identical capsule lacking the surface modification at least 14 days after implantation into the C57BL/6J mouse as determined by, for example, FACS analysis, Western blot analysis, ELISA, or histology as known in the art or as described herein.

In some embodiments of the capsule, alginate capsules, (a) fabricated as described herein to encapsulate human islet cells and (b) having the surface modification of the capsule on the outer surface of alginate capsules at a similar density as on the surface of the capsule, provides encapsulated human islet cells that, if implanted into and retrieved from a C57BL/6J mouse as described herein has the following property: expression of an islet cell viability marker from the alginate capsules will be more than 2-fold higher observed for an identical alginate capsule lacking the surface modification at least 30 days after implantation into the C57BL/6J mouse as determined by, for example, FACS analysis, Western blot analysis, ELISA, histology, or qPCR analysis as known in the art or as described herein.

In some embodiments of the capsule, alginate capsules, (a) fabricated as described herein to encapsulate human islet cells and (b) having the surface modification of the capsule on the outer surface of alginate capsules at a similar density as on the surface of the capsule, provides encapsulated human islet cells that, if implanted into and retrieved from a C57BL/6J mouse as described herein has the following property: the encapsulated islet cells will be able to secrete detectable levels of insulin at least 30 days after implantation into the C57BL/6J mouse as determined by, for example, Western blot analysis or ELISA as known in the art or as described herein.

In some embodiments of the capsule, the capsule includes encapsulated cells, where the encapsulated cells, if implanted, via implantation of the capsule, into and retrieved from a C57BL/6J mouse as described herein has the following property: expression of a cell viability marker from the encapsulated cells will be more than 2-fold higher observed for similar encapsulated cells included in an identical capsule lacking the surface modification at least 30 days after implantation into the C57BL/6J mouse as determined by, for example, FACS analysis, Western blot analysis, ELISA, histology or qPCR analysis as known in the art or as described herein.

In some embodiments of the capsule, the capsule includes encapsulated cells expressing and secreting a protein of interest, where the encapsulated cells, if implanted, via implantation of the capsule, into and retrieved from a C57BL/6J mouse as described herein has the following property: the encapsulated islet cells will be able to secrete detectable levels of the protein of interest at least 30 days after implantation into the C57BL/6J mouse as determined by, for example, Western blot analysis or ELISA as known in the art or as described herein.

For testing of a capsule of interest, suitable capsules can be, for example, a capsule identical to the capsule of interest, a corresponding capsule to the capsule of interest, a similar capsule to the capsule of interest, a capsule having identical surface modification as the capsule of interest, a capsule having a corresponding surface modification as the capsule of interest, or a capsule having a similar surface modification as the capsule of interest. For testing of a compound, chemical modification, or surface modification of interest, suitable capsules can be, for example, a capsule surface modified with the compound of interest, a capsule with the chemical modification of interest, or a capsule with the surface modification of interest.

IV. Biological Materials

Biological material for encapsulation in the disclosed alginates can be any biological substance. For example, the biological material can be tissue, cells, biological micromolecules, or biological macromolecules. Examples of biological macromolecules include nucleotides, amino acids, cofactors, and hormones. Examples of biological macromolecules include nucleic acids, polypeptides, proteins, and polysaccharides. Examples of proteins include enzymes, receptors, secretory proteins, structural proteins, signaling proteins, hormones, and ligands. Any class, type, form, or particular biological material can be used together with any other classes, types, forms, or particular biological materials.

A. Cells

The cell type chosen for encapsulation in the disclosed compositions depends on the desired therapeutic effect. The cells may be from the patient (autologous cells), from another donor of the same species (allogeneic cells), or from another species (xenogeneic). Xenogeneic cells are easily accessible, but the potential for rejection and the danger of possible transmission of viruses to the patient restricts their clinical application. Any of these types of cells can be from natural sources, stem cells, derived cells, or genetically engineered cell.

In some embodiments, the cells secrete a therapeutically effective substance, such as a protein or nucleic acid. In some embodiments, the cells produce a metabolic product. In some embodiments, the cells metabolize toxic substances. In some embodiments, the cells form structural tissues, such as skin, bone, cartilage, blood vessels, or muscle. In some embodiments, the cells are natural, such as islet cells that naturally secrete insulin, or hepatocytes that naturally detoxify. In some embodiments, the cells are genetically engineered to express a heterologous protein or nucleic acid and/or overexpress an endogenous protein or nucleic acid.

Types of cells for encapsulation in the disclosed compositions include cells from natural sources, such as cells from xenotissue, cells from a cadaver, and primary cells; stem cells, such as embryonic stem cells, mesenchymal stem cells, and induced pluripotent stem cells; derived cells, such as cells derived from stem cells, cells from a cell line, reprogrammed cells, reprogrammed stem cells, and cells derived from reprogrammed stem cells; and genetically engineered cells, such as cells genetically engineered to express a protein or nucleic acid, cells genetically engineered to produce a metabolic product, and cells genetically engineered to metabolize toxic substances.

Types of cells for encapsulation in the disclosed compositions include hepatocytes, islet cells, parathyroid cells, endocrine cells, cells of intestinal origin, cells derived from the kidney, and other cells acting primarily to synthesize and secret, or to metabolize materials. A preferred cell type is a pancreatic islet cell or other insulin-producing cell. Hormone-producing cells can produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. Genetically engineered cells are also suitable for encapsulation according to the disclosed methods. In some embodiments, the cells are engineered to produce one or more hormones, such as insulin, parathyroid hormone, anti-diuretic hormone, oxytocin, growth hormone, prolactin, thyroid stimulating hormone, adrenocorticotropic hormone, follicle-stimulating hormone, lutenizing hormone, thyroxine, calcitonin, aldosterone, cortisol, epinephrine, glucagon, estrogen, progesterone, and testosterone. In some embodiments, the cells are engineered to secrete blood clotting factors (e.g., for hemophilia treatment) or to secrete growth hormones. In some embodiments, the cells are contained in natural or bioengineered tissue. For example, the cells for encapsulation are in some embodiments a bioartificial renal glomerulus. In some embodiments, the cells are suitable for transplantation into the central nervous system for treatment of neurodegenerative disease.

Cells can be obtained directly from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell viability can be assessed using standard techniques, such as histology and fluorescent microscopy. The function of the implanted cells can be determined using a combination of these techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, pancreatic islet cells and other insulin-producing cells can be implanted to achieve glucose regulation by appropriate secretion of insulin. Other endocrine tissues and cells can also be implanted.

The site, or sites, where cells are to be implanted is determined based on individual need, as is the requisite number of cells. For cells replacing or supplementing organ or gland function (for example, hepatocytes or islet cells), the mixture can be injected into the mesentery, subcutaneous tissue, retroperitoneum, properitoneal space, and intramuscular space.

The amount and density of cells encapsulated in the disclosed compositions, such as capsules and microcapsules, will vary depending on the choice of cell, hydrogel, and site of implantation. In some embodiments, the single cells are present in the hydrogel at a concentration of $0.1 \times 10^6$ to $4 \times 10^6$ cells/ml, preferred $0.5 \times 10^6$ to $2 \times 10^6$ cells/ml. In other embodiments, the cells are present as cell aggregates. For example, islet cell aggregates (or whole islets) preferably contain about 1500-2000 cells for each aggregate of 150 μm diameter, which is defined as one islet equivalent (IE). Therefore, in some embodiments, islet cells are present at a concentration of 100-10000 IE/ml, preferably 200-3,000 IE/ml, more preferably 500-1500 IE/ml.

1. Islet Cells and Other Insulin-Producing Cells

In preferred embodiments, the disclosed compositions contain islet cells or other insulin-producing cells. Methods of isolating pancreatic islet cells are known in the art. Field et al., *Transplantation* 61:1554 (1996); Linetsky et al., *Diabetes* 46:1120 (1997). Fresh pancreatic tissue can be divided by mincing, teasing, comminution and/or collagenase digestion. The islets can then be isolated from contaminating cells and materials by washing, filtering, centrifuging or picking procedures. Methods and apparatus for isolating and purifying islet cells are described in U.S. Pat. No. 5,447,863 to Langley, U.S. Pat. No. 5,322,790 to Scharp et al., U.S. Pat. No. 5,273,904 to Langley, and U.S. Pat. No. 4,868,121 to Scharp et al. The isolated pancreatic cells may optionally be cultured prior to microencapsulation, using any suitable method of culturing islet cells as is known in the art. See e.g., U.S. Pat. No. 5,821,121 to Brothers. Isolated cells may be cultured in a medium under conditions that helps to eliminate antigenic components. Insulin-producing cells can also be derived from stem cells and cell lines and can be cells genetically engineered to produce insulin.

2. Genetically Engineered Cells

In some embodiments, the disclosed compositions contain cells genetically engineered to produce a protein or nucleic acid (e.g., a therapeutic protein or nucleic acid). In these embodiments, the cell can be, for example, a stem cell (e.g., pluripotent), a progenitor cell (e.g., multipotent or oligopotent), or a terminally differentiated cell (i.e., unipotent). Any of the disclosed cell types can be genetically engineered. The cell can be engineered, for example, to contain a nucleic acid encoding, for example, a polynucleotide such miRNA or RNAi or a polynucleotide encoding a protein. The nucleic acid can be, for example, integrated into the cells genomic DNA for stable expression or can be, for example, in an expression vector (e.g., plasmid DNA). The polynucleotide or protein can be selected based on the disease to be treated (or effect to be achieved) and the site of transplantation or implantation. In some embodiments, the polynucleotide or protein is anti-neoplastic. In other embodiments, the polynucleotide or protein is a hormone, growth factor, or enzyme.

B. Hormones

Hormones to be included in the disclosed capsules or, most preferably, produced from cells encapsulated in the disclosed capsules can be any hormone of interest.

Examples of endocrine hormones include Anti-diuretic Hormone (ADH), which is produced by the posterior pituitary, targets the kidneys, and affects water balance and blood pressure; Oxytocin, which is produced by the posterior pituitary, targets the uterus, breasts, and stimulates uterine contractions and milk secretion; Growth Hormone (GH), which is produced by the anterior pituitary, targets the body cells, bones, muscles, and affects growth and development; Prolactin, which is produced by the anterior pituitary, targets the breasts, and maintains milk secretions; Thyroid Stimulating Hormone (TSH), which is produced by the anterior pituitary, targets the thyroid, and regulates thyroid hormones; Adrenocorticotropic Hormone (ACTH), which is produced by the anterior pituitary, targets the adrenal cortex, and regulates adrenal cortex hormones; Follicle-Stimulating Hormone (FSH), which is produced by the anterior pituitary, targets the ovaries/testes, and stimulates egg and sperm production; Lutenizing Hormone (LH), which is produced by the anterior pituitary, targets the ovaries/testes, and stimulates ovulation and sex hormone release; Thyroxine, which is produced by the thyroid, targets the body cells, and regulates metabolism; Calcitonin, which is produced by the thyroid, targets the adrenal cortex, and lowers blood calcium; Parathyroid Hormone, which is produced by the parathyroid, targets the bone matrix, and raises blood calcium; Aldosterone, which is produced by the adrenal cortex, targets the kidney, and regulates water balance; Cortisol, which is produced by the adrenal cortex, targets the body cells, and weakens immune system and stress responses; Epinephrine, which is produced by the adrenal medulla, targets the heart, lungs, liver, and body cells, and affects primary "fight or flight" responses; Glucagon, which is produced by the pancreas, targets the liver body, and raises blood glucose level; Insulin, which is produced by the pancreas, targets body cells, and lowers blood glucose level; Estrogen, which is produced by the ovaries, targets the reproductive system, and affects puberty, menstrual, and development of gonads; Progesterone, which is produced by the ovaries, targets the reproductive system, and affects puberty, menstrual cycle, and development of gonads; and Testosterone, which is produced by the adrenal gland, testes, targets the reproductive system, and affects puberty, development of gonads, and sperm.

V. Assays for the Characterization of Modified Alginate Polymers

The covalent modification of alginate polymers alters the physiochemical properties and biological compatibility of the alginate polymer.

In some embodiments, a hydrogel formation assay is used to quantify the stability of hydrogels formed from alginates or modified alginates. In preferred embodiments, the hydrogel formation assay is used as a screening tool to identify modified alginates capable of forming stable hydrogels.

In vivo assays can be useful to characterize the biocompatibility of modified alginate polymers. In some embodiments, the high throughput in vivo biocompatibility assay described herein is used to identify modified alginates which induce a lower foreign body response than unmodified alginate.

Further described herein is an in vivo method for quantifying the biocompatibility of modified alginates.

The assays can be used to assess the suitability and biocompatibility of both modified and unmodified alginates for certain applications.

A. High Throughput Hydrogel Formation Assay

Covalent modification of the alginates affects the physical properties of the alginate, including the ability of the alginate to form hydrogels suitable for the encapsulation of cells and biomolecules.

The gel-forming assay exploits the ability of hydrogels to trap fluorescent compounds, and differentially retain the fluorophores upon washing based on the stability of the hydrogel. In this assay, a hydrogel formed by ionically crosslinking a candidate modified alginate in aqueous solution containing a dissolved fluorophore. A variety of fluorophores can be used in this assay. In preferred embodiments, the fluorophores possess emission maxima between 480 and 750 nm. In preferred embodiments, the fluorophore is a rhodamine dye possessing an emission maximum between 550 and 600 nm.

After crosslinking, the hydrogel is repeatedly washed with water. Candidate modified alginates which do not efficiently crosslink are washed away along with any fluorophore present. Modified alginates which efficiently crosslink retain the fluorophore during washes. Accordingly, by measuring the fluorescence of modified alginate hydrogels after washing, modified alginates capable of forming stable hydrogels can be readily identified.

In some embodiments, the relative fluorescence intensity values measured for a modified alginate are compared relative to fluorescence levels measured for the negative control and unmodified alginate to determine if the modified alginate is capable of forming hydrogels. In alternative embodiments, the hydrogel formation assay described herein is used to quantify the stability of hydrogels formed from alginates or modified alginates. In these embodiments, the fluorescence intensity measured for a modified alginate is used to indicate the stability of the hydrogel formed by the alginate.

In preferred embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, more preferably between 25,000 and 55,000.

B. High Throughput In Vivo Biocompatibility Assay

Current biocompatibility analysis methods are slow and require histological analysis. Described herein is a high throughput in vivo biocompatibility assay, useful for assessing the relative biocompatibility of alginate polymers.

In the high throughput in vivo biocompatibility assay described herein, modified alginate polymers and an unmodified alginate control are injected in an array format on the back of an animal test subject to facilitate high-throughput screening. In preferred embodiments, the animal test subject is a mouse. After injection, cathepsin activity at the point of injection of the modified alginates was compared to cathepsin activity at the point of injection the unmodified alginate to compare the foreign body response to the implanted alginates using in vivo fluorescence imaging. In preferred embodiments, the biocompatibility of the materials was assessed at 14 days post injection using in vivo fluorescence imaging.

In preferred embodiments, the high throughput in vivo biocompatibility assay described herein is used to identify modified alginates which induce a lower foreign body response than unmodified alginate. The fluorescence intensity measured at the implantation site of modified alginates was compared with the fluorescence intensity measured at the implantation site of an unmodified alginate. In preferred embodiments, modified alginates exhibiting smaller fluorescence intensity at the implantation site than the fluorescence intensity measured at the implantation site of unmodified alginates were qualitatively characterized as biocompatible. Conversely, modified alginates exhibiting greater fluorescence intensity at the implantation site than the fluorescence intensity measured at the implantation site of unmodified alginates were characterized as not biocompatible.

The high throughput in vivo biocompatibility assay described above can also be used to characterize the ability of modified alginates to form mechanically stable hydrogels in vivo. In preferred embodiments, the in vivo stability of the alginate gels was assessed at 28 days post injection.

In preferred embodiments, modified alginates gels which remained at the site of injection after 28 days were characterized as capable of forming mechanically stable hydrogels in vivo. Conversely, modified alginate gels which were not present at the site of injection after 28 days were deemed to not capable of forming mechanically stable hydrogels in vivo.

C. In Vivo Screening of Modified Alginates to Quantify Biocompatibility

Further described herein is an in vivo method for quantifying the biocompatibility of modified alginates.

In this method, a modified alginate polymers is injected on the back of an animal test subject. In preferred embodiments, the animal test subject is a mouse. After injection, cathepsin activity at the point of injection of the modified alginates was measured using in vivo fluorescence assay. In preferred embodiments, the fluorescence assay was conducted at 7 days post injection using in vivo fluorescence imaging. In preferred embodiments, the fluorescence intensity was measured and normalized to the fluorescence response measured using unmodified alginate in order to quantify the biocompatibility of the modified alginates.

In preferred embodiments, the modified alginate polymer induces a lower foreign body response than unmodified alginate (i.e. the fluorescence response normalized to unmodified alginate is less that 100%). In some embodiments, the modified alginate polymer is biocompatible such that the fluorescence response normalized to unmodified alginate measured using the in vivo biocompatibility assay described herein is less than 95%, 90%, 85%, 80%, 75%, 70%, 65%, 60%, 55%, 50%, 45%, or 40%. In preferred embodiments, the modified alginate polymer is biocompatible such that the fluorescence response normalized to unmodified alginate measured using the in vivo biocompatibility assay described herein is less than 75%, more preferably less than 65%, and most preferably less than 50%.

V. Methods of Use

Alginates are used in a variety of applications in the food, pharmaceutical, cosmetic, agriculture, printing, and textile industries. Alginates are widely employed in the food industry as thickening, gelling, stabilizing, bodying, suspending, and emulsifying agents. Alginates can be used as a matrix to control the delivery of therapeutic, prophylactic, and/or diagnostic agents. Alginates can be incorporated in pharmaceutical compositions as excipients, where they can act as viscosifiers, suspension agents, emulsifiers, binders, and disintigrants. Alginate also used as a dental impression material, component of wound dressings, and as a printing agent. One of ordinary skill in the art will recognize that the modified alginates disclosed herein can be used in any application for which alginates are currently employed.

It is specifically contemplated that modified alginates described herein can be used in applications where improved biocompatibility and physical properties (such as being anti-fibrotic), as compared to commercially available alginates, are preferred.

The modified alginates and coated products described herein can be used to treat abroad spectrum of diseases, disorders, and conditions. For example, capsules that include cells or tissues can be used to treat disorders characterized by a need for a product produced by the cell or tissue or of a reaction mediated by a product of the cell. For example, the cell or cell product can metabolize glucocerebroside or detoxify compounds. For type I and III Gaucher's disease, enzyme replacement treatment with intravenous recombinant glucocerebrosidase is generally used to hydrolyze the beta-glucosidic linkage of, an intermediate in glyclipid metabolism. Toxin-specific antibodies can be used in prophylaxis or treatment of infections caused by bacteria such as *Bacillus anthracis* and *Clostridium difficile*. In some embodiments, the cell or tissue can produce a product useful to treat a disorder. For example, where the cell is an islet cell and the disorder is diabetes. In some embodiments, the product can include a cell that metabolizes or modifies a substrate produced by the subject.

TABLE 2

List of disorders and the cells or cell-produced substance that can be used to treat the disorder.

| Cell or Cell-produced Substance | Disorder |
| --- | --- |
| Stem cells | Neurodegenerative diseases, diabetes, heart diseases and many other conditions |
| Pancreatic islet cells | Diabetes |
| Autologous haemopoietic stem cell transplantation | Chronic inflammatory autoimmune diseases including severe forms of scleroderma, multiple sclerosis, and lupus |
| Chimeric antigen receptor T cells | Cancers to be treated include non-solid cancers and solid cacers, for examples, carcinoma, blastoma, and sarcoma, and leukemia or lymphoid malignancies, benign and malignant tumors, and malignancies e.g., sarcomas, carcinomas, and melanomas. |
| Hepatocyte cell therapy | Liver diseases such as cirrhosis, liver cancer and hepatitis. |
| Allogeneic differentiated osteoblastic cells | Orthopedic conditions including impaired fracture, a delayed union fracture, osteonecrosis and osteoporosis. |
| Chemically induced neuron cells from pluripotent cells | neurodegenerative disorder selected from the group consisting of Alzheimer's Disease (AD), Huntington's Disease (HD), Parkinson's Disease (PD) Amyotrophic Lateral Sclerosis (ALS), Multiple Sclerosis (MS) and Cerebral Palsy (CP), Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, |

TABLE 2-continued

List of disorders and the cells or cell-produced substance that can be used to treat the disorder.

| Cell or Cell-produced Substance | Disorder |
|---|---|
| | Spinocerebellar Ataxias, Pick's disease, and dentatorubral-pallidoluysian atrophy |
| | Disorders of Amino Acid Metabolism |
| phenylalanine hydroxylase | Phenylketonuria (PKU) |
| biopterin cofactor | Malignant PKU |
| fumarylacetoacetate hydrolase | Type 1 tyrosinemia |
| tyrosine aminotransferase | Type 2 tyrosinemia |
| protein(s) involved in tyrosine breakdown | Alkaptonuria |
| cystathionine-β-synthase or methylenetetrahydrofolate reductase or protein(s) involved in formation of the methylcobalamin form of vitamin $B_{12}$ | Homocystinuria and Hyperhomocysteinemia |
| branched-chain ketoacid dehydrogenase complex | Maple Syrup Urine disease |
| | Disorders of Organic Acid Metabolism |
| propionyl-CoA carboxylase | Propionic Acidemia |
| pyruvate carboxylase and 3-methylcrotonyl-CoA carboxylase | Multiple Carboxylase deficiency |
| methylmalonyl-CoA mutase; protein(s) involved in vitamin $B_{12}$ metabolism | Methylmalonic Acidemia |
| | Disorders of Fatty Acid Metabolism |
| protein(s) involved in regulation or utilization of lipoproteins | Hyperlipidemia and hypercholesterolemia |
| very long chain acyl-CoA dehydrogenase; long chain hydroxyacyl-CoA dehydrogenase; dehydrogenase; medium chain acyl-CoA dehydrogenase; short chain acyl CoA dehydrogenase; short chain hydroxyacyl-CoA dehydrogenase | Fatty Acid Oxidation disorders |
| protein(s) involved in glycogenolysis | Glycogen Storage diseases |
| galactose-1-phosphate uridyl transferase | Galactosemia |
| enzyme(s) that build the carbohydrate side-chains on proteins | Congenital Disorders of Glycosylation |
| | Disorders of Purine and Pyrimidine Metabolism |
| protein(s) involved in balance between purine synthesis and disposal | Purine Overproduction |
| hypoxanthine phosphoribosyl-transferase | Lesch-Nyhan syndrome |
| | Lysosomal Storage Disorders |
| cerebrosidase | Gaucher disease Types I and II |
| beta-hexosaminidase A | Tay-Sachs disease |
| α-galactosidase | Fabry disease |
| α-iduronidase (Hurler syndrome); iduronate sultatase (Hunter syndrome); iduronate sultatase (Hunter syndrome) | Hurler syndrome, Hunter syndrome |
| enzyme(s) involved in heparan sulfate degradation | Sanfilippo syndrome |
| arylsulfatase B | Maroteaux-Lamy syndrome |
| galactose 6-sulfatase; β-galactosidase | Morquio syndrome |
| carbamyl phosphate synthetase; ornithine transcarbamylase; citrullinemia; argininosuccinic aciduria | Disorders of Urea Formation |

TABLE 2-continued

List of disorders and the cells or cell-produced substance that can be used to treat the disorder.

| Cell or Cell-produced Substance | Disorder |
| --- | --- |
| | Disorders of Peroxisomal Metabolism |
| protein(s) involved in branched-chain fatty acid production and/or breakdown | Refsum disease |
| alanine-glyoxylate transaminase | Alanine-glyoxylate transaminase defect |
| Cellular metabolic enzymes | Enzyme deficiency diseases |
| Muscle cell metabolic enzymes | metabolic disorders of the muscle (e.g. Pompe's disease) |

A. Encapsulation of Cells

Alginate can be ionically cross-linked with divalent cations, in water, at room temperature, to form a hydrogel matrix. See, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete capsules by contact with multivalent cations, then the surface of the capsules is crosslinked with poly amino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N+-\bigvee\!\bigwedge\!\bigvee-+NR_3$ can also be used. Aqueous solutions of the salts of these cations are added to the polymers to form soft, highly swollen hydrogels and membranes. The higher the concentration of cation or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of polymers containing basic sidechains to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of poly cations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One poly cation is poly(L-lysine); examples of synthetic polyamines are: polyethyleneimine, poly(vinylamine), and poly(allyl amine). There are also natural poly cations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In a preferred method, cells are encapsulated in a modified alginate polymer. In a preferred embodiment, modified alginate capsules are fabricated from solution of modified alginate containing suspended cells using the encapsulator (such as an Inotech encapsulator). In some embodiments, modified alginates are ionically crosslinked with a polyvalent cation, such as $Ca^{2+}$, $Ba^{2+}$, or $Sr^{2+}$. In particularly preferred embodiments, the modified alginate is crosslinked using $BaCl_2$. In some embodiments, the capsules are further purified after formation. In preferred embodiments, the capsules are washed with, for example, HEPES solution, Krebs solution, and/or RPMI-1640 medium.

Cells can be obtained directed from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture. In the preferred embodiment, the cells are autologous—i.e., derived from the individual into which the cells are to be transplanted, but may be allogeneic or heterologous.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labeled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials. A preferred cell type is a pancreatic islet cell.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-alginate suspension prior to formation of implant for transplantation. Alternatively, the hydrogel could be modified to bind humoral factors or signal recognition sequences prior to combination with isolated cell suspension.

The techniques described herein can be used for delivery of many different cell types to achieve different tissue structures. In the preferred embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

B. Coating Products and Surfaces

Medical products can be coated with the disclosed modified alginate polymers using a variety of techniques, examples of which include spraying, dipping, and brush coating. Polymer coatings are typically applied to the surface to be coated by dissolving a polymer in an appropriate, preferably organic solvent, and applying by spraying, brushing, dipping, painting, or other similar technique. The coatings are deposited on the surface and associate with the surfaces via non-covalent interactions. The coated products and surfaces that result are specifically contemplated and disclosed.

In some embodiments, the surface may be pretreated with an appropriate solution or suspension to modify the properties of the surface, and thereby strengthen the non-covalent interactions between the modified surface and the coating.

The polymer solution is applied to a surface at an appropriate temperature and for a sufficient period of time to form a coating on the surface, wherein the coating is effective in forming an anti-fibrotic surface. Typical temperatures include room temperature, although higher temperatures may be used. Typical time periods include 5 minutes or less, 30 minutes or less, 60 minutes or less, and 120 minutes or less. In some embodiments the solution can be applied for 120 minutes or longer to form a coating with the desired anti-fibrotic activity. However, preferably shorter time periods are used. Anti-fibrotic activity can be measured in any of the ways disclosed herein or known in the art. Preferably the anti-fibrotic activity can be the foreign body response determined as described herein.

The disclosed modified alginate polymers can be covalently or non-covalently associated with the products, devices, and surfaces. For those embodiments where the modified alginate polymer is covalently associated with the product, device, or surface, the polymer can be attached to the product, device, or surface by, for example, functionalizing the product, device, or surface with a reaction functional group, such as a nucleophilic group, and reacting the nucleophilic group with a reaction functional group on the polymer, such as an electrophilic group. Alternatively, the polymer can be functionalized with a nucleophilic group which is reacted with an electrophilic group on the product, device, or surface.

In particular embodiments, the modified alginate polymer is non-covalently associated with the product, device, or surface. The polymer can be applied to the product, device, or surface by spraying, wetting, immersing, dipping, painting, bonding or adhering or otherwise providing a product, device, or surface with a compound with the modified alginate polymer. In one embodiment, the polymer is applied by spraying, painting, or dipping or immersing. For example, a polymer paint can be prepared by dissolving the modified alginate polymer in a suitable solvent (generally aqueous), and optionally sonicating the solution to ensure the polymer is completely dissolved. The product, device, or surface to be coated can be immersed in the polymer solution for a suitable period of time, e.g., 5 seconds, followed by drying, such as air drying. The procedure can be repeated as many times as necessary to achieve adequate coverage. The thickness of the coating is generally from about 1 nm to about 1 cm, preferably from about 10 nm to 1 mm, more preferably from about 100 nm to about 100 microns.

The coating can be applied at the time the product, device, or surface is manufactured or can be applied subsequent to manufacture of the product, device, or surface. In some embodiments, the coating is applied to the product, device, or surface immediately prior to use of the product, device, or surface. This is referred to an intraoperative coating. "Immediately prior," as used herein, mean within 1, 2, 5, 10, 15, 20, 30, 45, 60, 75, 90, 120, 150, 180 minutes or greater of implantation or use. In some embodiments, the product, device, or surface is coated at the hospital, e.g., in the operating room, with 20, 15, 10, or 5 minutes of implantation or use. Coating immediately prior to use may overcome limitations of products, devices, and surfaces coated at the time of manufacture, such as damage of the coating during storage and/or transportation of the product, device, or surface and/or decrease in the efficacy of the coating over time as the coating is exposed to environmental conditions, which may be harsh (e.g., high temps, humidity, exposure to UV light, etc.).

The coated medical products can be used for the known uses and purposes of uncoated or differently coated forms of the medical products.

I. Medical Products

Medical products useful for coating include any types of medical devices used, at least in part, for implantation in the body of a patient. Examples include, but are not limited to, implants, implantable medical products, implantable devices, catheters and other tubes (including urological and biliary tubes, endotracheal tubes, wound drain tubes, needle injection catheters, peripherably insertable central venous catheters, dialysis catheters, long-term tunneled central venous catheters peripheral venous catheters, short term central venous catheters, arterial catheters, pulmonary catheters, Swan-Ganz catheters, urinary catheters, peritoneal catheters), vascular catheter ports, blood clot filters, urinary devices (including long-term urinary devices, tissue bonding urinary devices, artificial urinary sphincters, urinary dilators), shunts (including ventricular or arterio-venous shunts, stent transplants, biliary stents, intestinal stents, bronchial stents, esophageal stents, ureteral stents, and hydrocephalus shunts), balloons, pacemakers, implantable defibrillators, orthopedic products (including pins, plates, screws, and implants), transplants (including organs, vascular transplants, vessels, aortas, heart valves, and organ replacement parts), prostheses (including breast implants, penile prostheses, vascular grafting prostheses, heart valves, artificial joints, artificial larynxes, otological implants, artificial hearts, artificial blood vessels, and artificial kidneys), aneurysm-filling coils and other coil devices, transmyocardial revascularization devices, percutaneous myocardial revascularization devices, tubes, fibers, hollow fibers, membranes, blood containers, titer plates, adsorber media, dialyzers, connecting pieces, sensors, valves, endoscopes, filters, pump chambers, scalpels, needles, scissors (and other devices used in invasive surgical, therapeutic, or diagnostic procedures), and other medical products and devices intended to have anti-fibrotic properties. The expression "medical products" is broad and refers in particular to products that come in contact with blood briefly (e.g., endoscopes) or permanently (e.g., stents).

Useful medical products are balloon catheters and endovascular prostheses, in particular stents. Stents of a conventional design have a filigree support structure composed of metallic struts. The support structure is initially provided in an unexpanded state for insertion into the body, and is then widened into an expanded state at the application site. The stent can be coated before or after it is crimped onto a balloon. A wide variety of medical endoprostheses or medical products or implants for highly diverse applications and are known. They are used, for example, to support vessels, hollow organs, and ductal systems (endovascular implants), to attach and temporarily affix tissue implants and tissue transplants, and for orthopedic purposes such as pins, plates, or screws.

The modified alginate polymers can be applied to, absorbed into, or coupled to, a variety of different substrates and surfaces. Examples of suitable materials include metals, metallic materials, ceramics, polymers, fibers, inert materials such as silicon, and combinations thereof.

Suitable polymeric materials include, but are not limited to, styrene and substituted styrenes, ethylene, propylene, poly(urethane)s, acrylates and methacrylates, acrylamides and methacrylamides, polyesters, polysiloxanes, polyethers, poly(orthoester), poly(carbonates), poly(hydroxyalkanoate)s, copolymers thereof, and combinations thereof.

Substrates can be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), sensors, pacemaker leads, catheters, stents, contact lenses, bone implants (hip replacements, pins, rivets, plates, bone cement, etc.), or tissue regeneration or cell culture devices, or other medical devices used within or in contact with the body.

Implants coated with modified alginate polymer coatings are described herein. "Implants" are any object intended for placement in the body of a mammal, such as a human, that is not a living tissue. Implants are a form of medical product. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body or that of a mammal, including orthopedic applications, dental applications, ear, nose, and throat ("ENT") applications, and cardiovascular applications.

In some embodiments, "implant" as used herein refers to a macroscopic composition including a device for implantation or a surface of a device for implantation and a modified alginate polymer coating. In these embodiments, the term "implant" does not encompass nanoparticles and/or microparticles. "Macroscopic" as used herein generally refers to devices, implants, or compositions that can be viewed by the unaided eye.

Examples of implantable medical devices and medical devices and mechanical structures that can use a bio-compatible coating include, but are not limited to, stents, conduits, scaffolds, cardiac valve rings, cardiovascular valves, pacemakers, hip replacement devices, implanted sensor devices, esophageal stents, heart implants, bio-compatible linings for heart valves, dialysis equipment and oxygenator tubing for heart-lung by-pass systems.

In general, a stent is a device, typically tubular in shape, that is inserted into a lumen of the body, such as a blood vessel or duct, to prevent or counteract a localized flow constriction. The purpose of a stent, in some cases, is to mechanically prop open a bodily fluid conduit. Stents are often used to alleviate diminished blood flow to organs and extremities in order to maintain adequate delivery of oxygenated blood. The most common use of stents is in coronary arteries, but they are also widely used in other bodily conduits, such as, for example, central and peripheral arteries and veins, bile ducts, the esophagus, colon, trachea, large bronchi, ureters, and urethra. Frequently, stents inserted into a lumen are capable of being expanded after insertion or are self-expanding. For example, metal stents are deployed into an occluded artery using a balloon catheter and expanded to restore blood flow. For example, stainless steel wire mesh stents are commercially available from Boston Scientific, Natick, Mass.

In some embodiments, the implant is an orthopedic implant. An "orthopedic implant" is defined as an implant which replaces bone or provides fixation to bone, replaces articulating surfaces of a joint, provides abutment for a prosthetic, or combinations thereof or assists in replacing bone or providing fixation to bone, replacing articulating surfaces of a joint, providing abutment for a prosthetic, and combinations thereof.

Orthopedic implants can be used to replace bone or provide fixation to bone, replace articulating surfaces of a joint, provide abutment for a prosthetic, or combinations thereof or assist in replacing bone or providing fixation to bone, replacing articulating surfaces of a joint, providing abutment for a prosthetic, including dental applications, and combinations thereof.

Suitable orthopedic implants include, but are not limited to, wire, Kirschner wire, bone plates, screws, pins, tacs, rods, nails, nuts, bolts, washers, spikes, buttons, wires, fracture plates, reconstruction and stabilizer devices, endo- and exoprostheses (articulating and non-articulating), intraosseous transcutaneous prostheses, spacers, mesh, implant abutments, anchors, barbs, clamps, suture, interbody fusion devices, tubes of any geometry, scaffolds, and combinations thereof.

In other embodiments, the implant is an ear, nose, and/or throat ("ENT") implant. Exemplary ENT implants include, but are not limited to, ear tubes, endotracheal tubes, ventilation tubes, cochlear implants and bone anchored hearing devices.

In other embodiments, the implant is a cardiovascular implant. Exemplary cardiovascular implants are cardiac valves or alloplastic vessel wall supports, total artificial heart implants, ventricular assist devices, vascular grafts, stents, electrical signal carrying devices such as pacemaker and neurological leads, defibrillator leads, and the like.

Implants can be prepared from a variety of materials. In some embodiments, the material is biocompatible. In some embodiments, the material is biocompatible and non-biodegradable. Exemplary materials include metallic materials, metal oxides, polymeric materials, including degradable and non-degradable polymeric materials, ceramics, porcelains, glass, allogeneic, xenogenic bone or bone matrix; genetically engineered bone; and combinations thereof.

Suitable metallic materials include, but are not limited to, metals and alloys based on titanium (such as nitinol, nickel titanium alloys, thermo-memory alloy materials), stainless steel, tantalum, palladium, zirconium, niobium, molybdenum, nickel-chrome, or certain cobalt alloys including cobalt-chromium and cobalt-chromium-nickel alloys such as ELGILOY® and PHYNOX®. Useful examples include stainless steel grade 316 (SS 316L) (comprised of Fe, <0.3% C, 16-18.5% Cr, 10-14% Ni, 2-3% Mo, <2% Mn, <1% Si, <0.45% P, and <0.03% S), tantalum, chromium molybdenum alloys, nickel-titanium alloys (such as nitinol) and cobalt chromium alloys (such as MP35N, ASTM Material Designation: 35Co-35Ni-20Cr-10Mo). Typical metals currently in use for stents include SS 316L steel and MP35N. See also, "Comparing and Optimizing Co—Cr Tubing for Stent Applications," Poncin, P, Millet, C., Chevy, J, and Profit, J. L., Materials & Processes for Medical Devices Conference, August 2004, ASM International.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyethylene, polypropylene, polyacetylene, polystyrene, TEFLON®, poly(vinyl chloride) (PVC), polyolefin copolymers, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK®, Teflon® (polytetrafluoroethylene, PTFE), silicones, epoxy resins, Kevlar®, Dacron® (a condensation polymer obtained from ethylene glycol and terephthalic acid), nylon, polyalkenes, phenolic resins, natural and synthetic elastomers, adhesives and sealants, polyolefins, polysulfones, polyacrylonitrile, biopolymers such as polysaccharides and natural latex, collagen, cellulosic polymers (e.g., alkyl celluloses, etc.), polysaccharides, poly(glycolic acid), poly(L-lactic acid) (PLLA), a polydioxanone (PDA), or racemic poly (lactic acid), polycarbonates, (e.g., polyamides (nylon); fluoroplastics, carbon fiber, and blends or copolymers thereof.

The polymer can be covalently or non-covalently associated with the surface; however, in particular embodiments, the polymer is non-covalently associated with the surface. The polymer can be applied by a variety of techniques in the art including, but not limited to, spraying, wetting, immersing, dipping, such as dip coating (e.g., intraoperative dip coating), painting, or otherwise applying a hydrophobic, poly cationic polymer to a surface of the implant.

A surface of a product adapted for use in a medical environment can be capable of sterilization using autoclaving, biocide exposure, irradiation, or gassing techniques, like ethylene oxide exposure. Surfaces found in medical environments include the inner and outer aspects of various instruments and devices, whether disposable or intended for repeated uses. 2. Hydrogels Medical products can also be made of or using hydrogels. The disclosed modified alginate polymers can form hydrogels for this and other purposes. Products made of other hydrogels can also be coated with the disclosed modified alginate polymers. Thus, the disclosed modified alginate polymers can be used as a coating on a product or surface or can be used as the product itself. Hydrogels are three-dimensional, hydrophilic, polymeric networks capable of imbibing large amounts of water or biological fluids (Peppas et al. Eur. J. Pharm. Biopharm. 2000, 50, 27-46). These networks are composed of homopolymers or copolymers, and are insoluble due to the presence of chemical crosslinks or physical crosslinks, such as entanglements or crystallites. Hydrogels can be classified as neutral or ionic, based in the nature of the side groups. In addition, they can be amorphous, semicrystalline, hydrogen-bonded structures, supermolecular structures and hydrocolloidal aggregates (Peppas, N. A. Hydrogels. In: *Biomaterials science: an introduction to materials in medicine*; Ratner, B. D., Hoffman, A. S., Schoen, F. J., Lemons, J. E., Eds; Academic Press, 1996, pp. 60-64; Peppas et al., *Eur. J. Pharm. Biopharm.* 2000, 50, 27-46). Hydrogels can be prepared from synthetic or natural monomers or polymers. Preferred hydrogels herein are the disclosed modified alginate polymers.

Hydrogels can be prepared from synthetic polymers such as poly(acrylic acid) and its derivatives [e.g. poly (hydroxy ethyl methacrylate) (pHEMA)], poly(N-isopropylacrylamide), poly (ethylene glycol) (PEG) and its copolymers and poly (vinyl alcohol) (PVA), among others (Bell and Peppas, *Adv. Polym. Sci.* 722:125-175 (1995); Peppas et al., *Eur. J. Pharm. Biopharm.* 50:27-46 (200); Lee and Mooney, *Chem. Rev.* 707:1869-1879 (2001)). Hydrogels prepared from synthetic polymers are in general non-degradable in physiologic conditions. Hydrogels can also be prepared from natural polymers including, but not limited to, polysaccharides, proteins, and peptides. The disclosed modified alginate polymers are a preferred example. These networks are in general degraded in physiological conditions by chemical or enzymatic means.

In some embodiments, the hydrogel is non-degradable under relevant in vitro and in vivo conditions. Stable hydrogel coatings are necessary for certain applications including central venous catheters coating, heart valves, pacemakers and stents coatings. In other cases, hydrogel degradation may be a preferential approach such as in tissue engineering constructs.

In some embodiments, the hydrogel can be formed by dextran. Dextran is a bacterial polysaccharide, consisting essentially of $\alpha$-1,6 linked D-glucopyranose residues with a few percent of $\alpha$-1,2, $\alpha$-1,3, or $\alpha$-1,4-linked side chains. Dextran is widely used for biomedical applications due to its biocompatibility, low toxicity, relatively low cost, and simple modification. This polysaccharide has been used clinically for more than five decades as a plasma volume expander, peripheral flow promoter and antithrombolytic agent (Mehvar, R. *J. Control. Release* 2000, 69, 1-25). Furthermore, it has been used as macromolecular carrier for delivery of drugs and proteins, primarily to increase the longevity of therapeutic agents in the circulation. Dextran can be modified with vinyl groups either by using chemical or enzymatic means to prepare gels (Ferreira et al. Biomaterials 2002, 23, 3957-3967).

Dextran-based hydrogels prevent the adhesion of vascular endothelial, smooth muscle cells, and fibroblasts (Massia, S. P.; Stark, J. *J. Biomed. Mater. Res.* 2001, 56, 390-399. Ferreira et al. 2004, *J. Biomed. Mater. Res.* 68A, 584-596) and dextran surfaces prevent protein adsorption (Osterberg et al. *J. Biomed. Mat. Res.* 1995, 29, 741-747).

As described herein, the disclosed modified alginate polymers can be used to encapsulate cells. In some embodiments, the encapsulated cells can be fabricated into a macrodevice. For example, in some embodiments, cells encapsulated in modified alginate hydrogel can be coated onto a surface, such as a planar surface. In some embodiments, capsules containing cells can be adhered to tissue of a subject using a biocompatible adhesive. In other embodiments, capsules containing cells can be coated onto a medical device suitable for implantation.

C. Treatment of Diseases or Disorders

Encapsulated cells can be transplanted into a patient in need thereof to treat a disease or disorder. In some embodiments, the encapsulated cells are obtained from a genetically non-identical member of the same species. In alternative embodiments, the encapsulated cells are obtained from a different species than the patient. In preferred embodiments, hormone- or protein-secreting cells are encapsulated and transplanted into a patient to treat a disease or disorder.

In preferred embodiments, the disease or disorder is caused by or involves the malfunction hormone- or protein-secreting cells in a patient. In a preferred embodiment, the disease or disorder is diabetes.

Medical products, devices, and surfaces coated with a modified alginate polymer can be transplanted or implanted into a patient in need thereof to treat a disease or disorder.

The disclosed capsules, products, devices, and surfaces can remain substantially free of fibrotic effects, or can continue to exhibit a reduced foreign body response, for 2 weeks, 3 weeks, 4 weeks, 5 weeks, 6 weeks, 7 weeks, 8 weeks, 9 weeks, 10 weeks, 2 months, 3 months, 4 months, 5 months, 6 months, 7 months, 8, months, 9 months, 10 months, 11 months, 1 year, 2 years, or longer after administration or implantation.

The disclosed capsules, products, devices, and surfaces can be administered or implanted alone or in combination with any suitable drug or other therapy. Such drugs and therapies can also be separately administered (i.e., used in parallel) during the time the capsules, products, devices, and surfaces are present in a patient. Although the disclosed capsules, products, devices, and surfaces reduce fibrosis and immune reaction to the capsules, products, devices, and surfaces, use of anti-inflammatory and immune system suppressing drugs together with or in parallel with the capsules, products, devices, and surfaces is not excluded. In preferred embodiments, however, the disclosed capsules, products, devices, and surfaces are used without the use of anti-inflammatory and immune system suppressing drugs. In preferred embodiments, fibrosis remains reduced after the use, concentration, effect, or a combination thereof, of any anti-inflammatory or immune system suppressing drug that is used falls below an effective level. For example, fibrosis can remain reduced for 2 weeks, 3 weeks, 4 weeks, 5 weeks, 6 weeks, 7 weeks, 8 weeks, 9 weeks, 10 weeks, 2 months, 3 months, 4 months, 5 months, 6 months, 7 months, 8, months, 9 months, 10 months, 11 months, 1 year, 2 years, or longer after the use, concentration, effect, or a combination thereof, of any anti-inflammatory or immune system suppressing drug that is used falls below an effective level.

The present invention will be further understood by reference to the following non-limiting examples.

EXAMPLES

Example 1: Combinatorial Synthesis of Chemically Modified Alginates

The determinate parameters governing material biocompatibility are poorly understood. Accordingly, the rational design and synthesis of modified alginates possessing improved biocompatibility is challenging. In an effort to identify modified alginates with improved biocompatibility and physical properties, a combinatorial approach was used to prepare a library of modified alginates possessing a range of covalent modifications.

I. General Combinatorial Strategy

A pool of twelve alcohols, nine amines, two amines used to introduce an azide moiety (one amine containing an azide moiety and one amine containing an iodide moiety to be converted to an azide moiety subsequent to amidation), and nineteen alkynes with a range of different chemical structures, hydrophobicities/hydrophilicities, hydrogen-bonding potentials, and charge states were selected as reagents for the combinatorial synthesis of modified alginates. With the knowledge that impurities present in alginate polymers have been shown to limit the biocompatibility of implanted alginates, ultra-pure, low viscosity alginate (UPLVG, FMC Biopolymers) was selected as a starting material for modification experiments.

329
Alkynes Used as Reagents for 1,3-Dipolar Cycloaddition
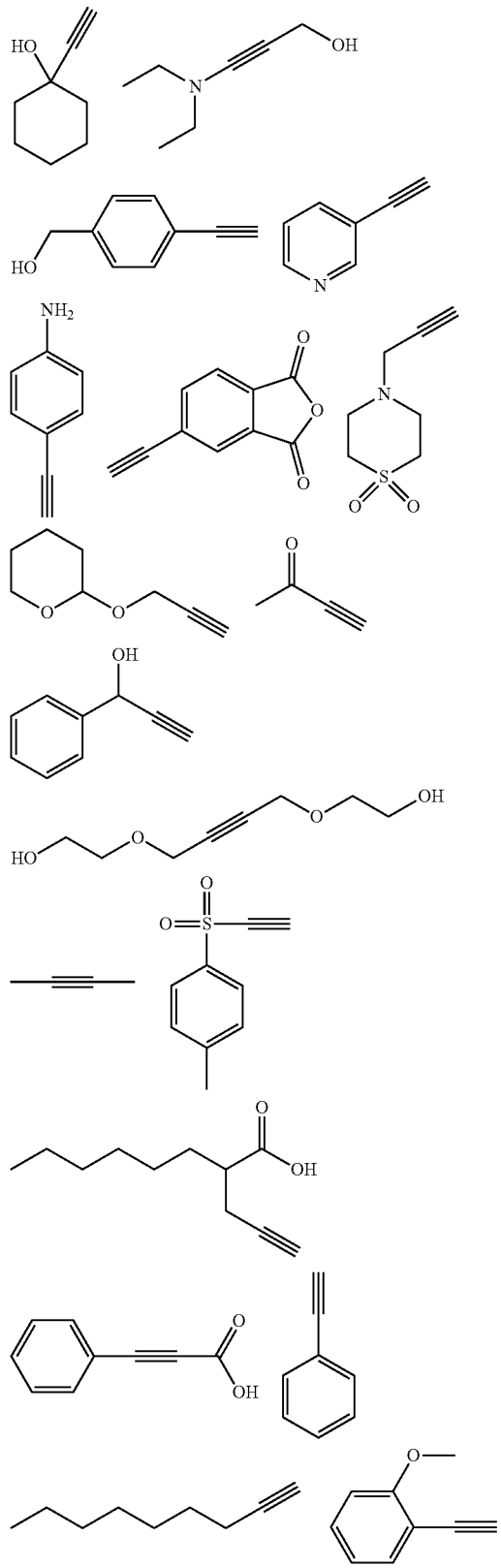
330
-continued
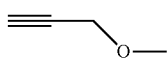
Alcohols Used as Reagents for Esterification
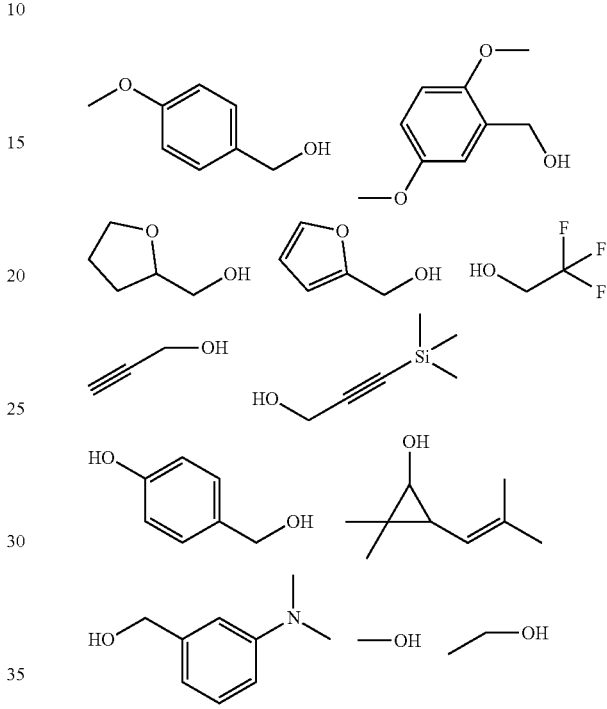
Amines Used as Reagents for Amidation
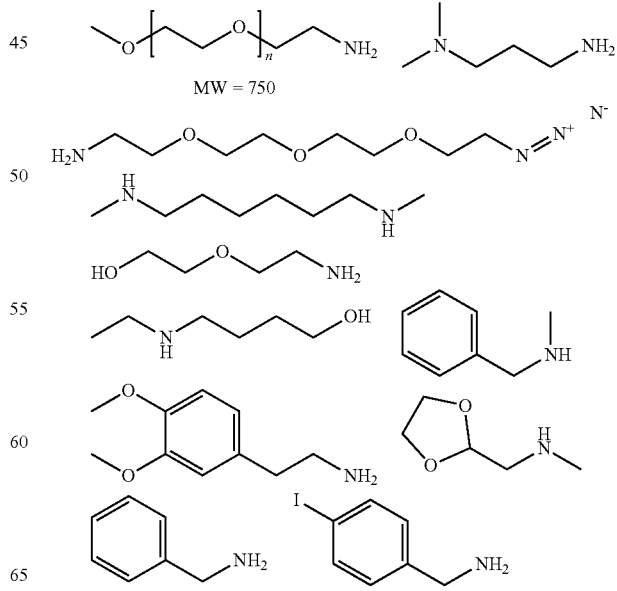

Amines Used as Reagents to Introduce Azide Moieties

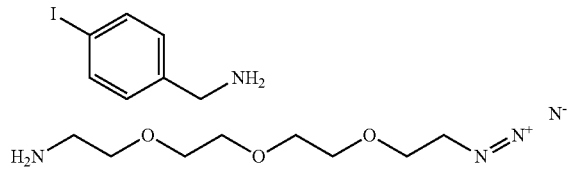

Unmodified alginate polymer was covalently modified by reaction with one, two, or three the esters, amines, and/or alkynes shown above in a combinatorial fashion. FIG. 1 shows the general structure of the modified alginates obtained using this method.

2. Representative Reaction Conditions

Due to the parallel and combinatorial nature of the modification process, synthetic reactions were performed using a robotic core module. UPLVG alginate was selected as a starting material for modification experiments. In the first combinatorial reaction, the unmodified alginate was reacted with one of the alcohols, amines, and amines used to introduce an azide moiety in the presence of 2-Chloro-4,6-dimethoxy-1,3,5-triazine (CDMT) and N-methyl morpholine (NMM). In a second combinatorial step, each of the modified alginate polymers formed above was reacted with another of the alcohols, amines, or amines used to introduce an azide moiety in the presence of 2-Chloro-4,6-dimethoxy-1,3,5-triazine (CDMT) and N-methyl morpholine (NMM). In a final combinatorial step, all members of the library which were reacted with an amine used to introduce an azide moiety were further functionalized using a 1,3-dipolar cycloaddition reaction. Those members of the library which had been reacted with 4-iodobenzylamine were first reacted with sodium azide to convert the iodide moieties to azide moieties. Subsequently, all members of the library which were reacted with an amine used to introduce an azide moiety were reacted with one of the alkynes used as reagents for 1,3-dipolar cycloaddition in the presence of $CuSO_4$/sodium ascorbate.

To optimize the biocompatibility of the chemically modified alginates, a rigorous purification methodology was developed to eliminate potentially irritating impurities. Following each covalent modification, the modified alginates were filtered through a cyano-modified silica column aimed at capturing bulk organic impurities. Finally, after completing all covalent modification steps, the modified alginates were dialyzed against 10,000 MWCO membrane to remove any remaining small-molecule or low molecular weight impurities.

The purity of the modified alginates was determined by $^1$H NMR analysis. The $^1$H NMR spectra of each modified alginate polymer was collected, and peaks corresponding to the modified alginate polymer and to any impurities were integrated to determine the relative quantity of each species in the sample.

Example 2: High Throughput Screening of Modified Alginates Using a Hydrogel Formation Assay Covalent modification of the alginates affects the physical properties of the alginate, including the ability of the alginate to form hydrogels suitable for the encapsulation of cells and biomolecules. To eliminate modified alginates that have lost their ability to form hydrogels and to further focus our screening efforts on stronger candidates, a fluorescence-based crosslinking assay was used to quantify the ability of modified alginates to form hydrogels.

The hydrogel formation assay described herein exploits the ability of hydrogels to trap fluorescent compounds, and differentially retain the fluorophores upon washing based on the stability of the hydrogel. Each of the modified alginates prepared using the combinatorial approach described in Example 1 was dissolved in water. A rhodamine dye that fluoresces at 580 nm was added to each sample. The modified alginate sample was then crosslinked by the addition of a barium or calcium salt, for example $BaCl_2$, to induce formation of a hydrogel. After incubation for 10 minutes, each sample was washed repeatedly with water. The fluorescence intensity of each sample was measured using a fluorimeter.

Each modified alginate was screened three times, and the results obtained in the three trials were averaged. The average fluorescence intensity values for each modified alginate were compared to the fluorescence levels of the negative control (water) and unmodified alginate (UPLVG). Modified alginates yielding fluorescence values below the negative control were considered unusable for applications where hydrogel formation is critical (i.e. the encapsulation of cells).

Example 3: In Vitro Screening of Modified Alginates for Biocompatibility

The cytotoxicity of the modified alginate polymers on HeLa cells was evaluated to screen for biocompatibility in vitro. The modified alginates identified in Example 2 as capable of forming hydrogels were loaded into wells of 96-well plates which were coated with poly-L-lysine. Unmodified alginate and saline were also loaded into wells of 96-well plates which were coated with poly-L-lysine as controls. A 100 mM $BaCl_2$ crosslinking solution was dispensed in all of the wells of the 96-well plate. The excess crosslinker was then aspirated. HeLa cells were seeded into the wells and incubated for 3 days at 37° C. in a humidified chamber.

A cell viability assay using 3-(4,5-Dimethylthiazol-2-yl)-2,5-diphenyltetrazolium bromide (MTT) was performed, in which the media was aspirated from all wells and 100 µl of DMEM media without phenol red and 10 µl MTT (5 mg/ml) were added to all of the wells of the 96-well plate. The plate was incubated for 4 hours at 37° C. in a humidified chamber. After incubation, 85 µl of solution was aspirated and 100 µl DMSO was added. Purple formazan crystals form during the assay in proportion to the number of viable HeLa cells present in each well. The contents of each well were pipetted up and down to solubilize the formazan crystals prior to measurement. The plate was incubated at 37° C. for 10 minutes after which the bubbles from agitation were removed. The plate was read using a UV/Vis plate reader at 540 nm with a reference at 700 nm. The viability was normalized to cells seeded in wells with no alginate.

Figure 3:
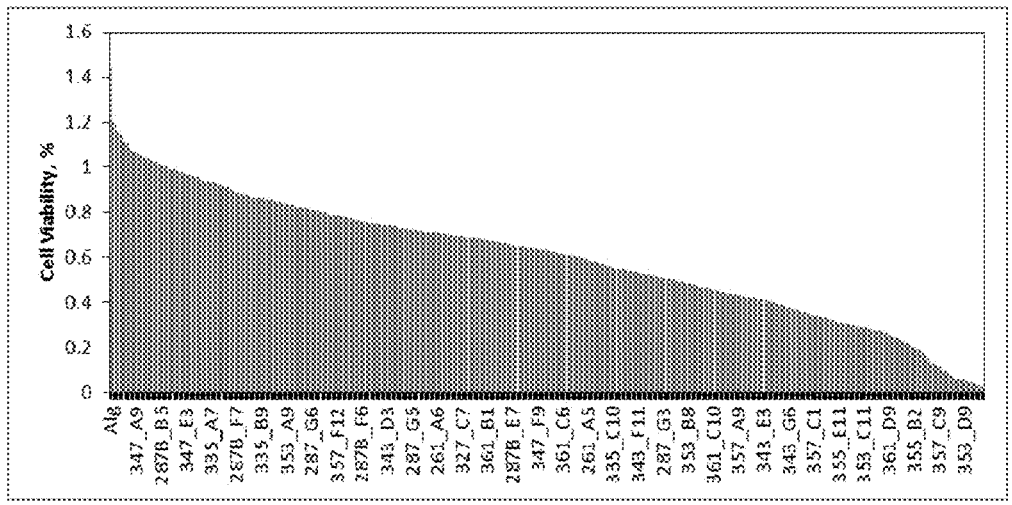
FIG. 3 is a plot showing the effect of selected modified alginates on HeLa cell line viability as compared to the positive control (no alginate). Alginate (Alg) has a viability of 53%. Several polymers are shown to be more cytotoxic than Alg, however, the majority of the library performs as well or better than Alg.

The results of the cell viability are shown in FIG. 3, which plots the effect of selected modified alginates on HeLa cell line viability as compared to the positive control (no alginate). Alginate (Alg) has a viability of 53%. The assay identified modified alginate polymers which displayed decreased cytotoxicity relative to unmodified alginate. These were selected for further analysis.

Example 4: High Throughput In Vivo Screening of Modified Alginates to Assess Biocompatibility Current biocompatibility analysis methods are slow and require histological analysis. In order to screen the large numbers of modified alginates prepared using the combinatorial synthetic methods described herein, a high throughput in vivo biocompatibility assay was used to assess the relative biocompatibility of alginate polymers.

I. High Throughput In Vivo Screening Protocol 8-12 week old male SKH1 mice were obtained from Charles River Laboratories (Wilmington, MA). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 μm filtration. The mice were anesthetized via isoflurane inhalation at a concentration of 1-4% isoflurane/balance $O_2$ to minimize movement. Their backs were scrubbed with 70% isopropyl alcohol and the animals were injected with modified alginates in an array format on the animals' back for high-throughput screening. Six injections were made in each mouse with one of the injections being an unmodified alginate control. Injection volumes were 100 μl.

On days 1, 3, 7, 14, 21, and 28 post-injection, host cell activity in response to the implantation of modified alginates was imaged kinetically using fluorescent whole animal imaging. 24 hours before in vivo fluorescence imaging, 2 nmol of ProSense-680 (VisEn Medical, Woburn, MA, excitation wavelength 680±10 nm, emission 700±10 nm) dissolved in 150 μl sterile PBS was injected into the tail vein of each mouse to image cathepsin activity.

In vivo fluorescence imaging was performed with an IVIS-Spectrum measurement system (Xenogen, Hopkinton, MA). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop—the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Biocompatibility of the materials was examined 14 days post injection. The fluorescence intensity measured at the implantation site of modified alginates was compared with the fluorescence intensity measured at the implantation site of and unmodified alginates. Modified alginates exhibiting smaller fluorescence intensity at the implantation site than the fluorescence intensity measured at the implantation site of unmodified alginates were characterized as biocompatible. Modified alginates exhibiting greater fluorescence intensity at the implantation site than the fluorescence intensity measured at the implantation site of unmodified alginates were characterized as not biocompatible.

The in vivo stability of the alginate gels was assessed at 28 days post injection. Modified alginates which remained at the site of injection after 28 days were characterized as capable of forming mechanically stable hydrogels in vivo. Modified alginates which were not present at the site of injection after 28 days were deemed to not capable of forming mechanically stable hydrogels in vivo, and were classified as 'failures'.

Modified alginates characterized as both biocompatible and capable of forming mechanically stable hydrogels in vivo were identified as 'hits', and selected for further study.

2. Validation of the High Throughput In Vivo Screening Protocol

In order to validate the high throughput in vivo screening assay described above, modified alginates were subcutaneously injected into mice in an array format and crosslinked in situ as described above. Mice were imaged on days 1, 3, 7, 14, 21, and 28 post-injection using fluorescent, whole animal imaging, and tissue samples were collected after imaging for histological analysis. To obtain tissue samples for histological analysis, mice were euthanized via $CO_2$ asphyxiation and the injected biomaterial and surrounding tissue were excised. The tissues were then fixed in 10% formalin, embedded in paraffin, cut into 5 μm sections, and stained using hematoxylin and eosin (H&E) for histological analysis by a board certified pathologist.

Fibrosis was rated on a scale where a zero involved no fibrosis, a one indicated partial coverage with one to two layers of fibrosis, a two is designated a thicker fibrotic layer that nearly covered the implant, and a three denoted concentric fibrotic coverage of the polymer. Both polymorphonuclear (PMN) cells and macrophages were rated on a scale where no observed cells were indicated with a zero, scattered cells scored a one, numerous cells clustering on the sides of the polymer scored a two, and numerous cells surrounding the material resulted in a three. Both the histological score and fluorescence response normalized to alginate were examined for the whole library and materials that outperformed unmodified alginate were judged to be biocompatible. This corresponds to a normalized fluorescent signal of <100% and a fibrosis score of <3.

Data captured using whole animal imaging was demonstrated to displayed similar temporal trends in cellular recruitment of phagocytes to the biomaterials compared to histological analysis. Accordingly, the high throughput in vivo screening method described above was validated.

Example 5: In Vivo Screening of Modified Alginates to Quantify Biocompatibility 8-12 week old male SKH1 mice were obtained from Charles River Laboratories (Wilmington, MA). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 μm filtration. The mice were anesthetized via isoflurane inhalation at a concentration of 1-4% isoflurane/balance $O_2$ to minimize movement. Their backs were scrubbed with 70% isopropyl alcohol and the animals were injected with a modified alginate. The injection volume was 100 μl.

Cathepsin activity was measured 7 days post injection using an in vivo fluorescence assay to quantify the foreign body response to the modified alginate. 24 hours before in vivo fluorescence imaging, 2 nmol of ProSense-680 (VisEn Medical, Woburn, MA, excitation wavelength 680±10 nm, emission 700±10 nm) dissolved in 150 µl sterile PBS was injected into the tail vein of each mouse to image cathepsin activity.

In vivo fluorescence imaging was performed with an IVIS-Spectrum measurement system (Xenogen, Hopkinton, MA). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop—the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Figure 4:
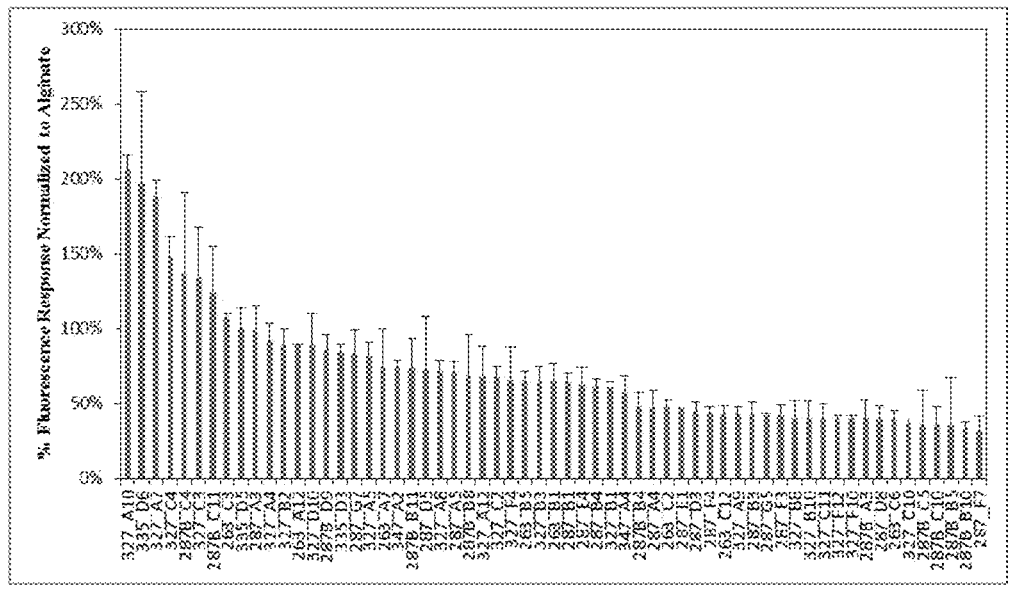
FIG. 4 is a plot obtained using the in vivo method described in Example 5, which quantifies the biocompatibility of selected modified alginates. The fluorescence response obtained for the modified alginates using the in vivo method described in Example 5 was normalized to the fluorescence response measured using unmodified alginate in order to quantify the biocompatibility of the modified alginates in terms of % fluorescence response.

Fluorescence images were captured 7 days post-injection illustrating relative cathepsin activity at the point of injection of selected modified alginates. The fluorescence intensity was measured and normalized to the fluorescence response measured using unmodified alginate in order to quantify the biocompatibility of the modified alginates. The results obtained for selected modified alginates are included in FIG. 4.

Example 6: Treatment of Diabetes in STZ-Induced Diabetic Mice

The transplantation of biocompatible alginate-encapsulated beta cells offers potential as a treatment for diabetes. Pancreatic rat islet cells were encapsulated using fourteen biocompatible modified alginate polymers identified using the assays detailed above (including PF_N287_B_B4, PF_N287_F2, PF_N287_G3, PF_N287_B3, PF_N287_B_B8, PF_N287_A4, PF_N287_B1, PF_N287_E3, PF_N263_C12, PF_N63_A12, PF_N287_E1, PF_N287_D3, PF_N263_A7, and PF_N263_C6). Alginate-encapsulated islets capsules were fabricated from 750 µl of a 4% (w/v) solution of each modified alginate in deionized water containing suspended 1,000 islets suspended using the Inotech encapsulator (Inotech) set to a voltage of 1.05 kV, a vibration of 1225 Hz, and a flow rate of 10-25 ml/min with a 300 µm nozzle. Alginate was crosslinked in a 20 mM $BaCl_2$ solution. After encapsulation, the capsules were washed twice with HEPES solution, four times with Krebs solution, and twice with RPMI-1640 medium.

The encapsulated rat islet cells were transplanted into STZ induced diabetic mice. Prior to transplantation, the mice were anesthetized under continuous flow of 1-4% isofluorane with oxygen at 0.5 L/min. A shaver with size #40 clipper blade will be used to remove hair to reveal an area of about 2 cm×2 cm on ventral midline of the animal abdomen. The entire shaved area was aseptically prepared with a minimum of 3 cycles of scrubbing with povidine, followed by rinsing with 70% alcohol. A final skin paint with povidine was also applied. The surgical site was draped with sterile disposable paper to exclude surrounding hair from touching the surgical site. A sharp surgical blade was used to cut a 0.5-0.75 cm midline incision through the skin and the linea alba into the abdomen. A sterile plastic pipette was used to transfer the alginate capsules into the peritoneal cavity. The abdominal muscle was closed by suturing with 5-0 Ethicon black silk or PDS-absorbable 5.0-6.0 monofilament absorbable thread. The external skin layer was closed using wound clips. These wound clips were removed 7-10d post-surgery after complete healing was confirmed.

Blood glucose levels in the STZ induced diabetic mice were monitored daily for between 20 and 30 days post-transplantation using a drop of blood obtained by scrubbing the tail with 70% isopropyl alcohol and making a superficial cut on the skin of the tail to produce a drop of blood. Mice were restrained during sampling in a rotating tail injector.

Figure 5:
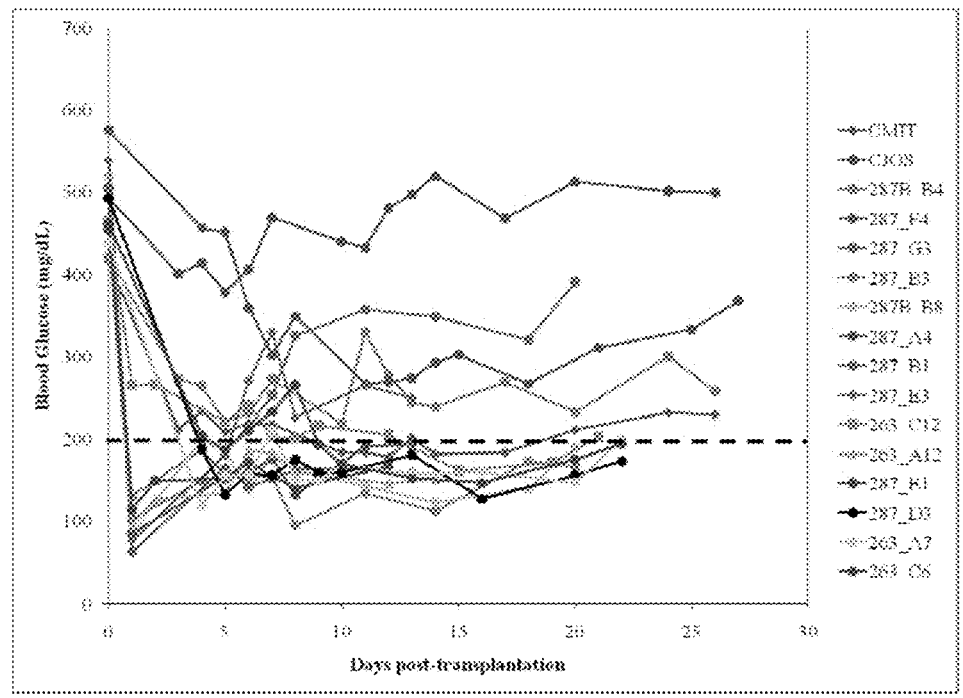
FIG. 5 is a plot detailing the blood glucose level of mice transplanted with rat islets encapsulated in selected modified alginates as well as two different unmodified alginates (CMIT and CJOS). The dashed line represents normoglycemia in mice. At 5 days post-implantation, 287_F4, CJOS, 287_B4, 263_C12, and CMIT are above the dashed line while the others are below the line. At 20 5 days post-implantation, the lines are, from top to bottom: CJOS, 287_G3, 287_F4, 287B_B4, CMIT, 287B_B8, 263_C12, 263_C6, 287_B3, 287_D3, and 263_A7.

The blood glucose levels in the STZ induced diabetic mice following islet transplantation are shown in FIG. 5. The dashed black line represents normoglycemia in mice. Pancreatic rat islet cells that were encapsulated in modified alginates were able to reduce the blood glucose levels in all cases, and in some cases, were even able to induce normoglycemia.

Example 7: Particles Prepared from Mixture of Modified Alginate(s) and Unmodified Alginate The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

A 6% solution of modified alginate (w/w) was combined 1:1 by volume with a 1.15% solution of unmodified alginate (w/w). After mixing, capsules are formed by following this solution through an electrostatic droplet generator, followed by crosslinking of the polymer in a 20 mM aqueous barium chloride solution.

Figure 6:
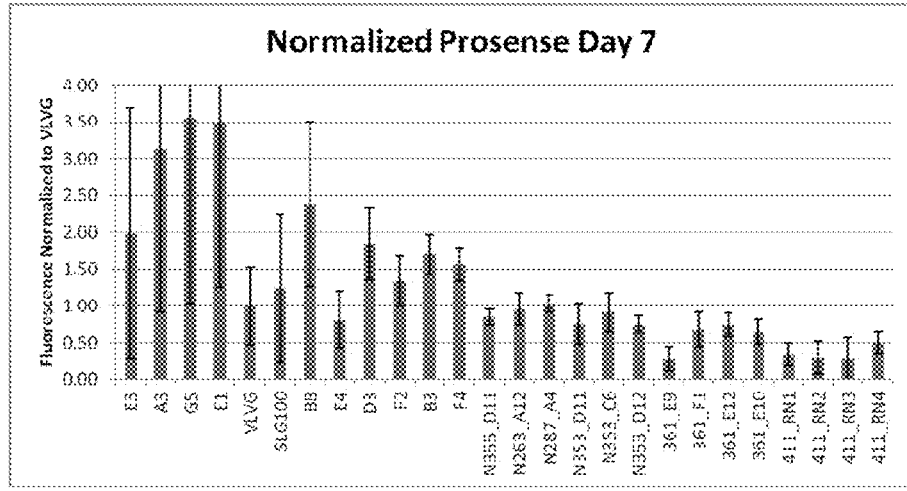
FIG. 6 is a bar graph showing inflammatory response (as measured by fluorescence normalized to VLVG) as a function of modified alginate (combined with unmodified alginate).

Particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations. Quantitative fluorescence analysis with prosense at several time points with modified alginates blended with SLG100 was performed. The results are shown in FIG. 6. Several reformulated modified alginates displayed less inflammatory response at day 7 compared to the control alginate. Initial experiments with large capsules (1.5 mm diameter) show comparably clean capsules after 2 weeks in the IP space of immunocompetent C57BL6 mice.

Data collected to date with these controlled capsules indicates that reformulation and capsule morphology can have a significant effect on inflammation as measured by prosense. An improved inflammation response is observed in some polymers (FIG. 6), while others are impacted negatively.

Example 8: Demonstration of Anti-Fibrotic Activity of Modified Alginates

In this example, a chemical modification approach was taken to mitigate the immune recognition of alginate microspheres in preclinical fibrosis models, including NHPs, which are relevant to translation in humans. The lead materials evade immune recognition and fibrosis in the IP space of both C57BL/6 mice and cynomolgus macaques. This alginate blocks macrophage adhesion, stunting activation of the foreign body response and providing insight to the surface properties necessary to overcome the fibrosis of implanted materials.

I. Methods

A. Alginate Chemical Modification

I. Alginate Amidation

Alginate (Pronova UPVLVG from NovaMatrix, 1 eq., 100 mg=0.52 mmol of COOH available for reaction) was dissolved as a 2% Alginate solution in a 3:2 water:acetonitrile mixture (5 ml total volume). Amine (N1 to N9, Z1, Z2) (1 eq, Sigma Aldrich or TCI America) was then added to the mixture along with the coupling agent 2-chloro-4,6-dimethoxy-1,3,5-triazine (CDMT, 0.5 eq., 45 mg, Sigma Aldrich) and 4-Methylmorpholine (NMM, 1 eq., 56 µl, Sigma Aldrich). The mixture was stirred at 55° C. overnight and the solvent was removed under reduced pressure. The resulting solid was dissolved in water and filtered through cyano modified silica gel (Silicycle) to remove insoluble precipitate. The resulting solution was then dialyzed against a 10,000 MWCO dialysis membrane overnight with DI water to further purify the polymer. The resulting solution was then lyophilized to get purified compound.

2. Alginate Esterification

Alginate (Pronova UPVLVG from NovaMatrix, 1 eq., 100 mg=0.52 mmol of COOH available for reaction) was dissolved as a 2% Alginate solution in a 3:2 water:alcohol (O1 to O12) mixture (5 ml total volume). The coupling agent 2-chloro-4,6-dimethoxy-1,3,5-triazine (CDMT, 0.5 eq., 45 mg, Sigma Aldrich) and 4-Methylmorpholine (NMM, 1 eq., 56 µl, Sigma Aldrich) was then added and the mixture was stirred at 55° C. overnight. The next day the solvent was removed under reduced pressure. The resulting solid was dissolved in water and filtered through cyano modified silica gel (Silicycle) to remove insoluble precipitate. The resulting solution was then dialyzed against a 10,000 MWCO dialysis membrane overnight with DI water to further purify the polymer. The resulting solution was then lyophilized to get purified compound.

3. Huisgen Cycloaddition ("Click")

In a second step, alginates reacted with Z2 were dissolved in a solution of water: methanol 1:1 (5 ml total). Sodium azide (0.25 eq., 19 mg, Sigma Aldrich), sodium L-ascorbate (0.05 eq., 19 mg, Sigma Aldrich), trans-N,N'-Dimethylcyclohexane-1,2-diamine (0.25 eq., typically 20 µl, Sigma Aldrich), Copper(I)-Iodide (0.5 eq., 10 mg, Sigma Aldrich) were added as coupling agents. Then 0.51 mmol of the respective Alkyne (Y1 to Y20) was added and the mixture was stirred at 55° C. overnight. The solvent was removed under reduced pressure. The resulting solid was dissolved in water and filtered through cyano modified silica gel to remove insoluble precipitate. The clear solution was lyophilized and dissolved in 5 ml of water and dialyzed. The resulting solution was then dialyzed against a 10,000 MWCO dialysis membrane overnight with DI water to further purify the polymer. The resulting solution was then lyophilized to get purified compound.

In a second step, alginates reacted with Z1 were dissolved in a solution of water: methanol 1:1 (5 ml total). Tris[(1-benzyl-1H-1,2,3-triazol-4-yl)methyl]amine (TBTA, 0.2 eq., 50 mg, Sigma Aldrich), Trietylamine (0.25 eq., typically 15 µl, Sigma Aldrich), Copper(I)-Iodide (0.25 eq., 5 mg, Sigma Aldrich) were added as coupling agents. Then 0.51 mmol of the respective Alkyne was added and the mixture was stirred at 55° C. overnight. The solvent was removed under reduced pressure. The resulting solid was dissolved in water and filtered through cyano modified silica gel to remove insoluble precipitate. The clear solution was lyophilized, dissolved in 5 ml of water and dialyzed. The resulting solution was then dialyzed against a 10,000 MWCO dialysis membrane overnight with DI water to further purify the polymer. The resulting solution was then lyophilized to get purified compound.

4. Optimized syntheses for preparation of Z2-Y12, Z1-Y15 and Z1-Y19:

Z2-Y12 Amine:

10 g of 2-(2-Propynyloxy) tetrahydopyran (1 eq. 71.36 mmol) was added to a solution of 5.1 g Sodium azide (1.1 eq, 78.5 mmol), 1.41 g Sodium ascorbate (0.1 eq, 7.14 mmol), 2.29 ml Trans-N—N'-Dimethylcyclohexane-1,2-diamine (0.25 eq, 17.83 mmol), 3.4 g Copper(I)-iodide (0.025 eq, 17.83 mmol) in 75 ml methanol. To this mixture 19.97 g of 4 Iodobenzylamide HCl was added. The reaction was stirred overnight at 55° C. The solvent was removed under reduced pressure. The crude reaction was purified by liquid chromatography with dichloromethane:ultra (22% MeOH in DCM with 3% $NH_4OH$) mixture 0%->40% on silica gel. The product was then reacted with alginate as described below.

Z1-Y15 Amine:

3.5 g of 4-Propagylthiomorpholine 1,1-Dioxide (1 eq. 20 mmol) was added to a solution of 2.5 g TBTA (0.2 eq, 4 mmol), 750 µl Triethylamine (0.5 eq, 10 mmol), 250 mg Copper(I)-iodide (0.06 eq, 1.3 mmol) in 50 ml methanol. The mixture was cooled to 0° C. and 5.25 ml of 11-Azido-3,6,9-trioxaundecan-1-amine (1 eq, 20 mmol) was added. The reaction was stirred overnight at 55° C. The solvent was removed under reduced pressure. The crude reaction was purified by liquid chromatography with dichloromethane:ultra (22% MeOH in DCM with 3% $NH_4OH$) mixture 0%->100% on a C18 column. The product was then reacted with alginate as described below.

Z1-Y19 Amine:

3 g of 4-Ethynylaniline (1 eq. 20.2 mmol) was added to a solution of 2.5 g TBTA (0.2 eq, 4 mmol), 750 µl Triethylamine (0.5 eq, 10.1 mmol), 250 mg Copper(I)-iodide (0.06 eq, 1.31 mmol) in 50 ml methanol. The mixture was cooled to 0° C., and 5.25 ml of 11-Azido-3,6,9-trioxaundecan-1-amine (1 eq, 20 mmol) was added. The reaction was stirred overnight at 55° C. The solvent was removed under reduced pressure. The crude reaction was purified by liquid chromatography with dichloromethane:ultra (22% MeOH in DCM with 3% $NH_4OH$) mixture 0%->30% on a cyano functionalized silica column. The product was then reacted with alginate as described below.

Alginate Reaction:

1.5 g of UPVLVG (1 eq) was dissolved in 45 ml of water and 675 mg of 2-Chloro-4,6-dimethoxy-1,3,5-triazine (CDMT, 0.5 eq) and 840 µl of N-Methylmorpholine (NMM, 1 eq) was added. Then 7.65 mmol of the Z2-Y12, Z1-Y15, or Z1-Y19 amine was dissolved in 22.5 ml acetonitrile and added to the mixture. The reaction was stirred overnight at 55° C. The solvent was removed under reduced pressure and the solid was dissolved in water. The solution was filtered through a pad of cyano functionalized silica and the water was removed under reduced pressure to concentrate the solution. It was then dialyzed against a 10,000 MWCO membrane in DI water overnight. The water was removed under reduced pressure to give the functionalized alginate.

B. Capsule Formation

An electrostatic droplet generator was set up as follows: an ES series 0-100 KV, Watt high voltage power generator (Gamma ES series, Gamma High Voltage Research, FL, USA) is connected to the top and bottom of a blunt tipped needle (SAI Infusion Technologies, IL, USA). This needle is attached to a 5 mL lure lock syringe (BD, NJ, USA) which is clipped to a syringe pump (Pump 11 Pico Plus, Harvard Apparatus, MA, USA) that is oriented vertically. The syringe pump pumps alginate out into a glass dish containing a 20 mM barium 5% mannitol solution (Sigma Aldrich, MO, USA). The settings of the PicoPlus syringe pump are 12.06 mm diameter and 0.2 mL/min flow rate. After the capsules are formed, they are then collected and then washed with hepes buffer (NaCl 15.428 g, KCl 0.70 g, MgCl2*6H2O 0.488 g, 50 mL of hepes (1M) buffer solution (Gibco, Life Technologies, California, USA) in 2 L of DiH2O) 4 times. The alginate capsules are left overnight at 4° C. The capsules are then washed 2 times in 0.8% saline and kept at 4° C. until use.

Solubilizing alginates: SLG20 (NovaMatrix, Sandvika, Norway) was dissolved at 1.4% weight to volume in 0.8% saline. SLG100 (NovaMatrix, Sandvika, Norway) was dissolved at 1.2% weight to volume in 0.8% saline. UPVLVG (NovaMatrix, Sandvika, Norway) was dissolved at 5% weight to volume in 0.8% saline. All modified alginates were initially dissolved at 5% weight to volume in 0.8% saline. Modifies were then blended with 3% weight to volume SLG100, dissolved in 0.8% saline (see Table 3 for ratios).

Forming different sized capsules: for 300 μm diameter capsules, a 30 gauge blunt tipped needle (SAI Infusion Technologies) was used with a voltage of 7-8 kV. For 500 μm diameter capsules, a 25 gauge blunt tipped needle (SAI Infusion Technologies) was used with a voltage of 5-7 kV. For 1.5 mm capsules, an 18 gauge blunt tipped needle (SAI Infusion Technologies) was used with a voltage of 5-7 kV.

TABLE 3

Modified Alginate to SLG100 blended volume ratios

| Modified Alginate | % Volume Modified Solution | % Volume SLG100 |
|---|---|---|
| 361_E9 | 70 | 30 |
| 411_RN8 | 80 | 20 |
| 411_OH6 | 60 | 40 |
| 411_OH9 | 60 | 40 |
| 411_OH11 | 50 | 50 |
| 411_OH3 | 80 | 20 |
| 411_RZA15 | 80 | 20 |
| 411_RZA2 | 50 | 50 |
| 411_RZA19 | 70 | 30 |
| 411_RN7 | 80 | 20 |
| VLVG/SLG100* | 80 | 20 |

Table 3 Legend: Modified alginates are blended with SLG100 to make capsules. Modified alginate and SLG100 are drawn into a 5 mL syringe and thoroughly vortexed before encapsulation. Different modified alginates require a different percent volume of SLG100 added to make spherical capsules. *VLVG/SLG100 is a control blend. The unmodified VLVG is blended with SLG100.

C. Transplantation of the Hydrogel Capsules and Other Material Spheres

All animal protocols were approved by the MIT Committee on Animal Care, and all surgical procedures and post-operative care was supervised by MIT Division of Comparative Medicine veterinary staff. Immune-competent male C57BL/6 mice (Jackson Laboratory, Bar Harbor, ME) were anesthetized with 3% isoflurane in oxygen and had their abdomens shaved and sterilized using betadine and isopropanol. A 0.5 mm incision was made along the midline of the abdomen and the peritoneal lining was exposed using blunt dissection. The peritoneal wall was then grasped with forceps and a 0.5-1 mm incision was made along the linea alba. A desired volume of capsules were then loaded into a sterile pipette and transplanted into the peritoneal cavity through the incision. The incision was then closed using 5-0 taper tipped polydioxanone (PDS II) absorbable sutures. The skin was then closed over the incision using a wound clip and tissue glue. Preoperatively, all mice also received a 0.05 mg/kg dose of buprenorphine subcutaneously as a pre-surgical analgesic, along with 0.3 mL of 0.9% saline subcutaneously to prevent dehydration.

D. Retrieval of Cells, Tissues, and Materials

At desired time points post-transplantation, as specified in figures and results, mice were euthanized by $CO_2$ administration, followed by cervical dislocation. In certain instances, 5 ml of ice cold PBS was first injected in order perform an intraperitoneal lavage to rinse out and collect free-floating intraperitoneal immune cells. An incision was then made using the forceps and scissors along the abdomen skin and peritoneal wall, and intraperitoneal lavage volumes were pipetted out into fresh 15 ml falcon tubes (each prepared with 5 ml of RPMI cell culture media). Next, a wash bottle tip was inserted into the abdominal cavity. KREBS buffer was then used to wash out all material capsules from the abdomen and into petri dishes for collection. After ensuring all the capsules were washed out or manually retrieved, if fibrosed directly to intraperitoneal tissues, they were transferred into 50 mL conical tubes for downstream processing and imaging. After intraperitoneal lavage and capsule retrieval, remaining fibrosed intraperitoneal tissues were also excised for downstream FACS and expression analyses.

E. Imaging of the Retrieved Material Capsules

For phase contrast imaging, retrieved materials were gently washed using Krebs buffer and transferred into 35 mm petri dishes for phase contrast microscopy using an Evos X1 microscope (Advanced Microscopy Group).

F. ProSense Assay

Female SKH1 mice (6 weeks old) were utilized for this assay. 100 ul of capsules were resuspended in 200 ul of saline, and injected subcutaneously into the mouse on the left side of upper back. The mice were feeded on AIN-93G purified rodent diet (TD 94045, Harlan) to minimize the fluorescent background after injection. Six days later, 100 ul (4 nmol) of ProSence 750 FAST (NEV11171, PerkinElmer Inc.) per mouse was injected intravenously via tail vein. At day 7 (i.e., 24 hours post the ProSense 750 FAST intravenous administration), the mice were scanned by IVIS Spectrum system (Xenogen, Caliper LifeScience). The mice were anesthetized using 3% isofluorane in oxygen and maintained at the same rate throughout the procedure, and the settings of the IVIS Spectrum system were Exposure=7.50, Binning=Medium, FStop=2, Excitation=605 and Emission=660. The images were analyzed with LivingImage Software, and the right side of upper back on the same mouse was used as control during the signal quantification.

G. Cell Staining and Confocal Immunofluorescence

Retrieved samples were stored in 4% paraformaldehyde overnight (diluted in 1×PBS). Samples were then washed in Krebs Buffer (7.889 g NaCl, 0.35 g KCl, 5.958 g HEPES (Sigma-Aldrich, Montana, USA), 0.163 g KH2PO4, 0.144 g MGSO4*7H2O in 1000 mLs of DiH2O). Samples were washed with 10 mLs of PBS. PBS was aspirated and 20 mL of 1% Triton X-100 (Sigma-Aldrich, Montana, USA) solution was used to permeabilize cells. Samples were incubated for 10 minutes at room temperature. Samples were then incubated in 15 mLs of 1% albumin solution (Sigma-Aldrich, Montana, USA), diluted in 1×PBS for 30 minutes at room temperature. 3 mLs of antibody solution (1:200 CD68488 Anti Mouse (BioLegend California, USA), 1:200 Anti-Mouse Actin, α-Smooth Muscle-Cy3(Sigma-Aldrich, Montana, USA), 1:30 Phalloidin anti mouse 647 (Life Technologies, California, USA), DAPI (NucBlue Live Cell Stain ReadyProbes, Life Technologies, California, USA) 2 drops per mL) all diluted in 1% albumin solution was added to each sample. Samples were incubated in staining solution for 45 minutes at room temperature. Staining solution was then aspirated. Samples were then washed twice with 20 mLs of 0.1% tween 20 solution (Sigma-Aldrich, Montana, USA), diluted in 1×PBS. Samples were then washed twice with 20 mLs of 1×PBS. Samples were then transferred to a 24 well glass bottom plate. Excess PBS was aspirated and 1 mL of 50% glycerol solution (Sigma-Aldrich, Montana, USA) was added. A Zeiss LSM 700 system with ZEN microscope software was used to image and analyze the stained samples. Obtained images where adjusted linearly for presentation using Photoshop (Adobe Inc. Seattle, WA).

H. Protein Extraction

Cells on retrieved capsules were lysed by sonication for 30 seconds on 30 seconds off cycle three times at 70% amplitude (QSonica Sonicator, Model #Q125, QSonica LLC) on ice in NP40 cell lysis buffer (Cat #FNN0021, Invitrogen) at the ratio of 100 ul capsules to 200 ul lysis buffer, with 100 mM PMSF and 1× protease inhibitors (Halt Protease inhibitor single-use cocktail, Cat. #78430, Thermo Scientific). Lysates were centrifuged for 20 min at 12000 rpm at 4° C.; the supernatant which contains proteins was aspirated in a fresh tube kept on ice. The pellets were washed with the same volume of lysis buffer (i.e. the pellet of 100 ul capsules were washed with 200 ul lysis buffer), and then centrifuged for 20 min at 12000 rpm at 4° C., combined the supernatant with the previous one. The proteins were stored at −80° C. for future use.

I. Elispot (Mouse Cytokine Array)

This assay was accomplished with Proteome Profiler Mouse Cytokine Array Panel A kit (Cat #ARY006, R&D system). For each membrane, 200 ul of protein solution was mixed with 100 ul of sample buffer (array buffer 4) and 1.2 ml of block buffer (array buffer 6), then added with 15 ul of reconstituted Mouse Cytokine Array Panel A Detection Antibody Cocktail and incubated at room temperature for 1 hour. The array membrane was incubated with block buffer (array buffer 6) for 2 hours on a rocking platform shaker in the meantime, and then the block buffer was aspirated, the prepared sample/antibody mixture was added onto the membrane and incubated overnight at 4° C. on a rocking platform shaker. The membrane was washed with 20 ml of 1× wash buffer for 10 minutes on a rocking platform shaker for three time and rinsed with deionized water once, then was probed with Fluorophore-conjugated streptavidin (1:5,000 dilution, Cat #926-32230, Li-Cor) at room temperature for 30 minutes on a rocking platform shaker, washed with wash buffer for three times and rinsed with deionized water once again as in above steps. Antibody-antigen complexes were visualized using Odyssey Detection (Li-Cor, Serial No. ODY-2329) at 800 nm wavelengths. The densities of the spots were analyzed by Image J software.

J. Western Blotting 12 ul of protein solution mixed with 1× loading buffer (SDS-Sample buffer, Cat. #BP-111R, Boston BioProducts) for each lane was boiled at 95° C. for 20 min and electrophoresed on SDS polyacrylamide gels (Any Kd 15-well comb mini-gel, Biorad, Cat #456-9036), and 3 ul of Precision Plus Protein Dual Xtra Stands (Cat #161-0377, Bio-rad) was used as ladder to indicate the position of the bands, and then blotted onto nitrocellulose membranes (Biorad, Cat. #162-0213). Blots were probed with anti-αSmooth Muscle actin antibody (1:400 dilution, Rabbit polyclonal to alpha smooth muscle Actin; Cat. #ab5694, AbCam) and anti-βactin antibody (1:4000 dilution, Monoclonal Anti-β-Actin antibody produced in mouse; Cat #A1978, Sigma Aldirch) as a loading control followed by Donkey Anti-Rabbit (1 to 15,000 dilution, Cat #926-32213, Li-Cor) and Goat Anti-Mouse (1 to 15,000 dilution, Cat #926-68070, Li-Cor) Fluorophore-conjugated secondary antibodies. Antibody-antigen complexes were visualized using Odyssey Detection (Li-Cor, Serial No. ODY-2329) at 700 and 800 nm wavelengths. The densities of the bands were analyzed by Image J software.

K. NanoString Analysis

RNAs for mock-transplanted (MT) controls, or for 500 or 1,500 μm alginate capsule-bearing mice (n=5/group) were isolated from tissue samples taken at various time points after transplantation. Respective RNAs were quantified, diluted to the appropriate concentration (100 ng/μl), and then 500 ng of each sample was processed according to NanoString manufacturer protocols for expression analysis via our customized multiplexed 53-gene mouse macrophage subtyping panel. RNA levels (absolute copy numbers) were obtained following nCounter (NanoString Technologies Inc., Seattle, WA) quantification, and group samples were analyzed using nSolver analysis software (NanoString Technologies Inc., Seattle, WA).

L. FACS Analysis

Single-cell suspensions of freshly excised tissues were prepared using a gentleMACS Dissociator (Miltenyi Biotec, Auburn, CA) according to the manufacturer's protocol. Single-cell suspensions were prepared in PEB dissociation buffer (IX PBS, pH 7.2, 0.5% BSA, and 2 mM EDTA) and suspensions were passed through 70 μm filters (Cat. #22363548, Fisher Scientific, Pittsburgh, PA). All tissue and material sample-derived, single-cell populations were then subjected to red blood cell lysis with 5 ml of 1×RBC lysis buffer (Cat. #00-4333, eBioscience, San Diego, CA, USA) for 5 min at 4° C. The reaction was terminated by the addition of 20 ml of sterile IX PBS. The cells remaining were centrifuged at 300-400 g at 4° C., and resuspended in a minimal volume (~50 μl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (1 μl (0.5 μg) per sample; CD68-Alexa647, Clone FA-11, Cat. #11-5931, BioLegend), Ly-6G (Gr-1) (1 μl (0.5 μg) per sample; Ly-6G-Alexa-647, Clone RB6-8C5, Cat. #108418, BioLegend), CD11b (1 μl (0.2 μg) per sample; or CD11b-Alexa-488, Clone M1/70, Cat. #101217, BioLegend). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 µl of Flow Cytometry Staining Buffer and run through a 40 µm filter (Cat. #22363547, Fisher Scientific) for eventual FACS analysis using a BD FACSCalibur (cat. #342975), BD Biosciences, San Jose, CA, USA). For proper background and laser intensity settings, unstained, single antibody, and IgG (labeled with either Alexa-488 or Alexa-647, BioLegend) controls were also run.

M. Intravital Imaging

For intravital imaging, SLG20 hydrogels of 500 µm and 1500 µm sizes were loaded with Qdot 605 (Life technologies, Grand Island, NY) and surgically implanted into C57BL/6-Tg(Csflr-EGFP-NGFR/FKBP1A/TNFRSF6) 2Bck/J mice as described above. After 7 days post transplantation, the mice were placed under isoflurane anesthesia and a small incision was made at the site of the original surgery to expose beads. The mice were placed on an inverted microscope and imaged using a 25×, N.A. 1.05 objective on an Olympus FVB-1000 MP multiphoton microscope at an excitation wavelength of 860 nm. Z-stacks of 200 µm (10 µm steps) were acquired at 2-minute intervals for time series of 20-45 minutes depending on the image. The mice were kept under constant isoflurane anesthesia and monitored throughout the imaging session. Obtained images were analyzed using Velocity 3D Image Analysis Software (Perkin Elmer, Waltham, MA).

N. Confocal Raman Spectroscopy

Sample Preparation: A drop of hydrogel capsules with buffer solution was dried on the quartz coverslip (043210-KJ, Alfa Aesar). In order to remove the salt from dried buffer solution, a drop of distilled water was gently applied on top of the dried sample and immediately absorbed by a tissue. By doing that, dried hydrogel capsules are prepared for Raman mapping.

Instrumentation: A custom-built NIR confocal Raman microscopy system was previously reported (Kang et al., Combined confocal Raman and quantitative phase microscopy system for biomedical diagnosis. Biomed. Opt. Exp. 2(9):2484-2492 (2011); Kang et al., Measuring uptake dynamics of multiple identifiable carbon nanotube species via high-speed confocal Raman imaging of live cells. Nano Letters 12(12):6170-6174 (2012)). Briefly, a 785 nm wavelength Ti: Sapphire laser (3900S, Spectra-Physics) was used for sample excitation. The collimated beam was filtered by a band pass filter (BPF, LL01-785-12.5, Semrock) and redirected to the dual axes galvanometer mirrors. High-speed XY scanning was performed by the galvanometer mirrors (CT-6210, Cambridge Technology). A 1.2 NA water immersion objective lens (Olympus UPLSAPO60XWIR 60X/1.20) was used to both focus the laser light onto the sample and to collect the back-scattered light. A piezo actuator combined with a differential micrometer (DRV517, Thorlabs) was used to perform the coarse and fine adjustments, respectively, of the sample focus. A flip mirror was placed after the tube lens so that the sample focal plane from the incoherent transmission source can be observed using a video camera with 75× magnification. The back-scattered Raman light from the sample passes through two dichroic mirrors (DM1: Semrock LPD01-785RU-25, DM2: Semrock LPD01-785RU-25×36×1.1) and was collected by a multimode fiber (Thorlabs M14L01). The collected signal was delivered to the spectrograph (Holospec f/1.8i, Kaiser Optical Systems) and detected by a thermoelectric-cooled, back-illuminated and deep depleted CCD (PIXIS: 100BR_eXcelon, Princeton Instruments). LabView 8.6 software (National Instruments), data acquisition board (PCI-6251, National Instruments) and MATLAB 2013 software (Mathworks) were used to control the system, acquire the data, and analyze the data.

Raman Spectroscopy Measurement: 60 mW of 785 nm laser power was focused to a micron spot size and used to raster scan the hydrogel samples. 30×30 spectra were acquired from 45 µm×45 µm area with an integration time 1.0 s/pixel. The total measurement time was approximately 15 minutes.

Data Processing: Two Raman images are generated based on the intensities of two Raman bands. These Raman images are resized and overlaid as red and green colors on top of corresponding bright field image from the same area.

II. Polymer and Compound Characterization

N7: $^1$H (400 MHz; $D_2O$): 3.10-4.10 (m, alginate protons), 4.20 (2H, s, $H_2N$—$CH_2$-Ph), 4.40-5.20 (m, alginate protons), 7.41 (2H, m, Phenyl), 7.49 (3H, m, Phenyl)

IR (ATR): 3234, 1579, 1465, 1407, 1368, 1078, 810, 692, 517.

N8: $^1$H (400 MHz; $D_2O$): 3.00-3.20 (m, alginate protons), 3.60 (8H, m, ethoxy), 3.60-5.10 (m, alginate protons).

IR (ATR): 3233, 2927, 2358, 1591, 1405, 1318, 1022, 945, 810.

O3: $^1$H (400 MHz; $D_2O$): 1.90-2.10 (m, 4H, Furfuryl), 3.23 (m, 2H, Furfuryl) 3.26-4.00 (m, alginate protons), 4.03 (3H, m, O—CH2-C[furfuryl]), 4.10-5.20 (m, alginate protons)

IR (ATR): 3202, 3070, 2344, 1711, 1594, 1398, 1021, 715, 549

O6: $^1$H (400 MHz; $D_2O$): 3.60-4.52 (m, alginate protons), 4.59 (2H, m, O—CH2-C[furfuryl]), 4.6-5.2 (m, alginate protons), 6.45 (2H, m, CH—CH=CH-0 Furfuryl), 7.53 (1H, m, CH—CH=CH—O Furfuryl).

IR (ATR): 3232, 2360, 1614, 1410, 1028, 538.

O9: $^1$H (400 MHz; $D_2O$): 0.20 (s, 9H, Furfuryl),) 3.10-5.20 (m, alginate protons).

IR (ATR): 3310, 2939, 2360, 1592, 1406, 1316, 1081, 1020, 902, 770.

O11: $^1$H (400 MHz; $D_2O$): 3.05-4.50 (m, alginate protons), 4.52 (2H, s, O—$CH_2$-Ph), 4.52-5.2 (m, alginate protons), 6.88 (2H, m, Phenyl), 7.26 (2H, m, Phenyl).

IR (ATR): 3370, 3089, 1597, 1517, 1454, 1235, 1207, 989, 835, 801, 561.

Z1-Y2: $^1$H (400 MHz; $D_2O$): 3.05-3.40 (m, alginate protons), 3.40-3.66 (16H, m, ethoxy), 3.75 (3H, s, methoxy) 3.8-5.1 (m, alginate protons), 7.19 (1H, m, Phenyl), 7.50 (1H, m, Phenyl), 7.94 (1H, m, Phenyl), 8.00 (1H, m, Phenyl), 8.49 (1H, s, triazole).

IR (ATR): 3144, 2922, 1592, 1400, 1329 1019, 943.

Z1-Y15: $^1$H (400 MHz; $D_2O$): 3.07 (4H, s, N—$CH_2$—$CH_2$—S), 3.17-3.40 (m, alginate protons), 3.46 (4H, s, N—$CH_2$—$CH_2$—S), 3.50-3.70 (16H, m, ethoxy), 3.7-5.2 (m, alginate protons), 8.08 (1H, s, triazole).

IR (ATR):3268, 2933, 2250, 1602, 1409, 1292, 1119, 1023, 946.

Z1-Y19: $^1$H (400 MHz; $D_2O$): 3.05-3.40 (m, alginate protons), 3.40-3.66 (16H, m, ethoxy), 4.4-5.1 (m, alginate protons), 6.96 (2H, m, Phenyl), 7.63 (3H, m, Phenyl), 8.23 (1H, s, triazole).

IR (ATR): 3234, 2929, 2361, 1593, 1406, 1317 1024, 947, 810.

Z2-Y12: $^1$H (400 MHz; $D_2O$): 1.57-1.78 (m, 6H, pyran), 3.10-4.40 (m, alginate protons), 4.48 (4H, m, pyran), 4.50-5.10 (m, alginate protons), 7.56 (2H, m, Phenyl), 7.76 (3H, m, Phenyl), 8.51 (1H, s, triazole).

IR (ATR): 3235, 2933, 2111, 1592, 1405, 1290, 1023, 946.

N4-N2: ¹H (400 MHz; D₂O): 2.72 (s, 3H, N—CH₃ Dioxolane) 2.77 (s, 3H, N—CH₃ Benzyl), 3.36 (2H, d, N—CH₂-Dioxolane), 3.55-4.20 (m, alginate protons), 4.22 (2H, m, N—CH₂-Ph), 4.50-5.10 (m, alginate protons), 5.19 (1H, m, CH2-CH—O Dioxolane), 7.51 (5H, m, Phenyl).

IR (ATR): 3250, 2894, 1601, 1409, 1127, 1088, 1029, 946.

O3-O10: ¹H (400 MHz; D₂O): 1.60-2.20 (m, 4H, Tetrahydrofurfuryl), 3.55-5.10 (m, alginate protons), 3.78 (2H, m, CH₂—CH₂-0 Tetrahydrofurfuryl), 3.85 (3H, s, COO—CH₃), 4.13-4.30 (3H, m, N—CH₂— Tetrahydrofurfuryl).

IR (ATR): 3448, 2926, 2111, 1618, 1420, 1290, 1096, 948, 904.

N9-O8: ¹H (400 MHz; D₂O): 1.28 (m, 3H, N—CH₂—CH₃), 1.32 (m, 3H, O—CH₂—CH₃), 1.63 (m, 3H, N—CH₂—CH₂—CH₂—CH₂—OH) 1.74 (m, 3H, N—CH₂—CH₂—CH₂—CH₂—OH), 3.09-3.40 (m, 6H, CH₃—CH₂—N—CH₂—CH₂—CH₂—CH₂—OH), 3.55-5.10 (m, alginate protons), 4.06 (m, 3H, O—CH₂—CH₃).

IR (ATR): 3422, 1709, 1655, 1611, 1474, 1395, 1042, 798.

Small Molecule Preparations:
Z2-Y12 Amine:

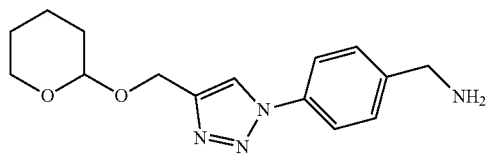 [SMILES: NCc1ccc(-n2cc(COC3CCCCO3)nn2)cc1]

¹H (400 MHz; MeOD): 1.57 (m, 4H, pyran), 1.72 (m, 1H, pyran), 1.82 (m, 1H, pyran) 3.58 (m, 1H, pyran), 3.87 (s, 1H, NH₂—CH₂-Ph), 3.92 (m, 1H, pyran), 4.68 (d, 1H, J=12 Hz, O—CH₂-triazole), 4.79 (m, 1H, O—CH—O pyran), 4.97 (d, 1H, J=12 Hz, O—CH₂-triazole), 7.54 (m, 2H, aromatic), 7.80 (m, 2H, aromatic), 8.49 (s, 1H, triazole). ¹³C (400 MHz; MeOD): 20.3 (CH₂ pyran), 26.5 (CH₂ pyran), 31.5 (CH₂ pyran), 46.1 (NH₂CH₂), 61.0 (O—CH₂—C), 63.3 (CH₂-0 pyran), 99.5 (O—CH—O pyran), 121.6 (CH aromatic), 123.17 (CH triazole), 129.9 (CH aromatic), 137.1 (Cq-N aromatic), 144.9 (Cq-C aromatic), 146.9 (C triazole).
High resolution MS: M+1=289.1665+3.1 ppm.
Z1-Y15 Amine:

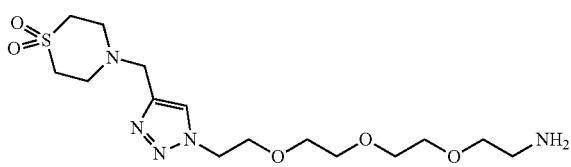 [SMILES: NCCOCCOCCOCCn1cc(CN2CCS(=O)(=O)CC2)nn1]

¹H (400 MHz; D₂O): 2.86 (2H, s, NH₂), 3.01 (4H, m, N—CH₂—CH₂—S), 3.10 (4H, m, N—CH₂—CH₂—S), 3.55 (2H, t, J=5.2 Hz, NH₂—CH₂),3.61 (8H, m, PEG) 3.85 (2H, s, Thiomorpholine-CH₂-Triazole), 3.90 (2H, t, J=5.2 Hz, N—CH₂—CH₂-0), 4.59 (t, 2H, J=5.2, N—CH₂—CH₂-0), 7.99 (1H, s, triazole).
¹³C (400 MHz; MeOH): 41.7 (NH₂—CH₂), 51.42 (N—CH₂), 51.48 (N—CH₂ Thiomorpholine) 52.1 (S—CH₂ Thiomorpholine) 52.4 (Thiomorpholine-CH₂-Triazole), 70.4-72.1 (m, PEG), 126.0 (CH triazole), 144.5 (C triazole).
High resolution MS: M+1=392.1968-6.1 ppm.

Z1-Y19 Amine:

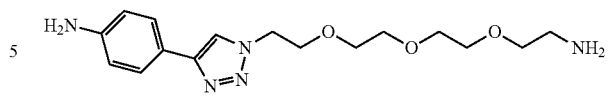

¹H (400 MHz; MeOD): 2.79 (t, 2H, J=5.2 Hz, NH₂—CH₂), 3.46 (t, 2H, J=5.2, NH₂—CH₂—CH₂), 3.53 (m, 4H, PEG), 3.61 (m, 4H, PEG), 3.91 (t, 2H, J=5.2, N—CH₂—CH₂-0), 4.58 (t, 2H, J=5.2, N—CH₂—CH₂-0) 6.76 (m, 2H, aromatic), 7.54 (m, 2H, aromatic), 8.14 (s, 1H, triazole).
¹³C (400 MHz; MeOD): 41.6 (NH₂—CH₂), 51.4 (N—CH₂), 70.3-71.9 (m, PEG), 116.4 (CH aromatic), 121.1 (Cq-C), 121.5 (CH triazole), 127.7 (CH aromatic), 149.4 (C—NH₂ aromatic), 149.5 (C triazole).
High resolution MS: M+1=336.2036-8.3 ppm.

III. Results

The amines and alcohols listed in Table 4 were used to prepare the modified alginates. In the first combinatorial reaction, UPLVG alginate was reacted with one of the compounds in Table 4 in the presence of 2-Chloro-4,6-dimethoxy-1,3,5-triazine (CDMT) and N-methyl morpholine (NMM). In order to prepare multiply modified alginates, the first step was repeated using a different alcohol or amine from Table 4. Alginates modified with amine Z2 were then reacted with sodium azide to prepare the corresponding azide-modified alginate. These alginates, along with alginates modified with amine Z1, were then reacted with one of the alkynes listed in Table 4 in the presence of CuSO₄ and sodium ascorbate in order to prepare tetrazole-modified alginates.

Following each covalent modification, the modified alginates were filtered through a cyano-modified silica column to capture bulk organic impurities. Finally, after completing all covalent modification steps, the modified alginates were dialyzed against 10,000 MWCO membrane to remove any remaining small-molecule or low molecular weight impurities.

The purity of the modified alginates was determined by ¹H NMR analysis. The ¹H NMR spectra of each modified alginate polymer was collected, and peaks corresponding to the modified alginate polymer and to any impurities were integrated to determine the relative quantity of each species in the sample.

TABLE 4

Chemical modifications of the 73 capsule formulations

| Alginate # | Modifications | Alginate # | Modifications |
|---|---|---|---|
| 1 | O1-O7 | 38 | N2-Z2-Y6 |
| 2 | O3-O10 | 39 | N2 |
| 3 | O1-O11 | 40 | O5-O9 |
| 4 | O9-O12 | 41 | Z2-Y15 |
| 5 | O3-O7 | 42 | Z1-Y18 |
| 6 | Z2-Y8 | 43 | O7 |
| 7 | Z1-Y20 | 44 | Z1-Y12 |
| 8 | SLG100 | 45 | N9-Z1-Y18 |
| 9 | Z2-Y16 | 46 | O10 |
| 10 | Z2-Y13 | 47 | Z2-Y7 |
| 11 | Z2-Y17 | 48 | Z1-Y10 |
| 12 | O5 | 49 | N6 |
| 13 | O7-O9 | 50 | Z2-Y13 |
| 14 | Z2-Y15 | 51 | O12 |
| 15 | O8 | 52 | N3 |
| 16 | O4-O1 | 53 | O4 |
| 17 | Z2-Y4 | 54 | Z1-Y11 |
| 18 | N9-Z1-Y16 | 55 | Z1-Y17 |
| 19 | Z1-Y4 | 56 | Z1-Y1 |
| 20 | VLVG | 57 | Z1-Y9 |

TABLE 4-continued

Chemical modifications of the 73 capsule formulations

| Alginate # | Modifications | Alginate # | Modifications |
|---|---|---|---|
| 21 | Z1-Y6 | 58 | Z2-Y6 |
| 22 | Z2-Y11 | 59 | SLG20 |
| 23 | N1 | 60 | N5 |
| 24 | N9 | 61 | Z1-Y3 |
| 25 | Z2-Y3 | 62 | Z2-Y5 |
| 26 | N6-Z1-Y18 | 63 | Z1 |
| 27 | O9-O2 | 64 | O6 |
| 28 | Z2-Y2 | 65 | Z1-Y15 |
| 29 | Z1-Y7 | 66 | Z1-Y2 |
| 30 | O4-O7 | 67 | N8 |
| 31 | N4-N2 | 68 | Z1-Y19 |
| 32 | Z1-Y8 | 69 | O3 |
| 33 | Z2-Y16 | 70 | Z2-Y12 |
| 34 | V/S | 71 | N7 |
| 35 | Z2 | 72 | O9 |
| 36 | Z1-Y14 | 73 | O11 |
| 37 | O9-O3 | | |

Figure 7:
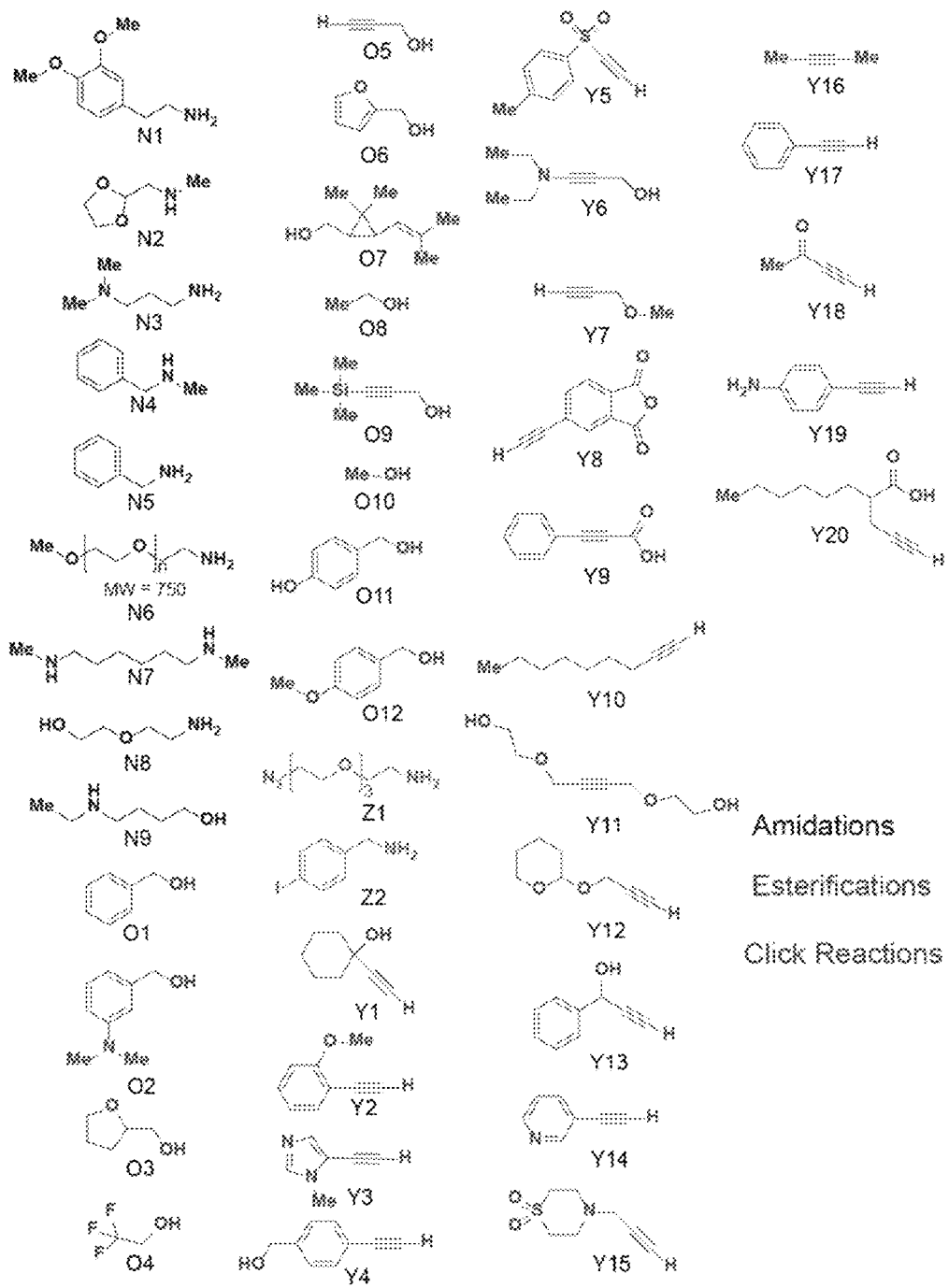
FIG. 7 is a diagram of the structures of amines, alcohols, azides, and alkynes used for the chemical modification of alginate. "N" designation indicates amidation reagents, "O" designations indicate esterification reagents, and "Y" designations indicate click reagents.
Figure 9:
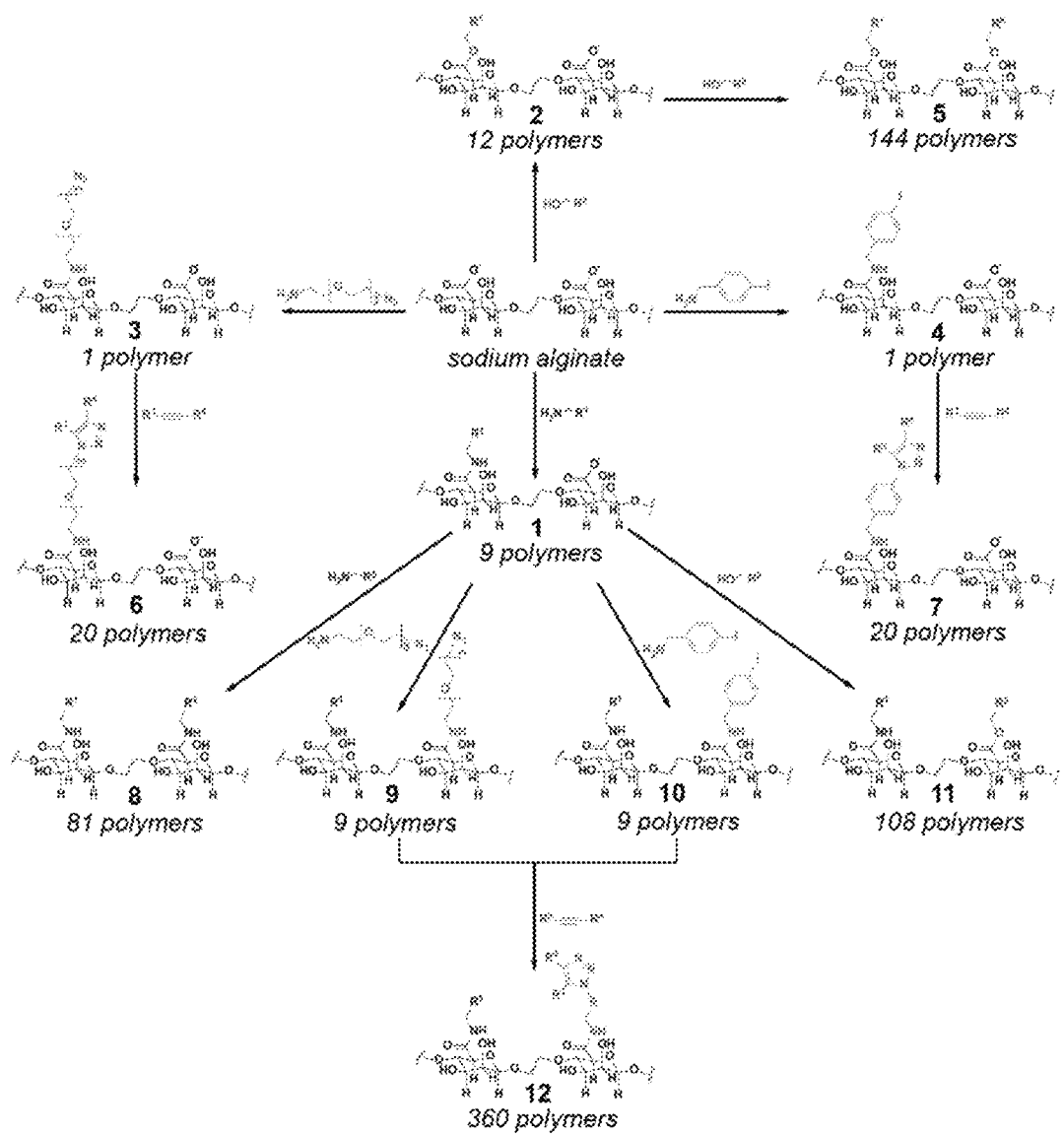
FIG. 9 is a diagram of the scheme for the synthesis of 774 alginate analogues.
Figure 11:
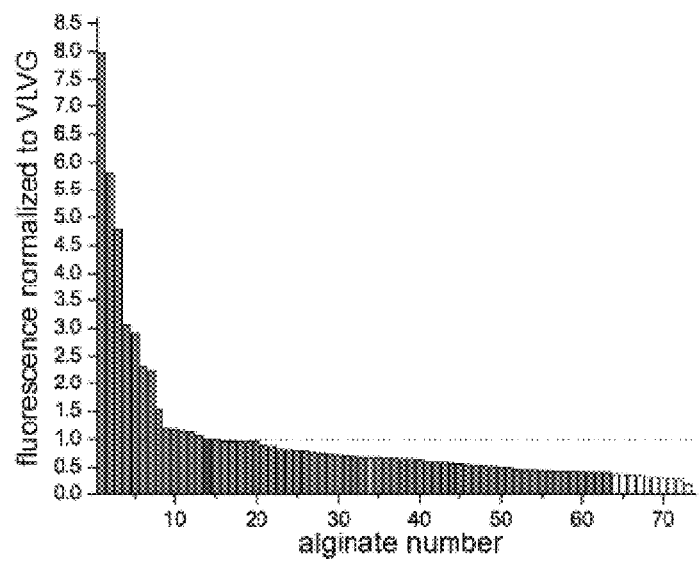
FIG. 11 is a graph showing secondary cathepsin evaluation of 70 top modified alginates from the initial screen formulated as 300 μm capsules. Data normalized to the fluorescence of VLVG capsules. The ten alginate analogue capsules with the lowest cathepsin levels are on the right with lighter shading.

A. Chemical Modification of Alginate Curtails the Foreign Body Response in C57BL/6 mice The physicochemical parameters governing anti-fibrotic properties are currently poorly understood, making rationally designed approaches challenging (Williams, *Biomaterials* 29:2941-2953 (2008)). To better understand which structural features are germane to anti-fibrotic properties, a pool of diverse chemical compounds was selected that can modify latent functionalities and properties on the polymeric alginate backbone (FIG. 7). A 774-membered alginate analogue library was constructed with a variety of amines, alcohols, azides, and alkynes (FIG. 9). Of the 774 alginate analogues, 35 analogues resulted in unacceptably low yields and 634 alginates were determined to be capable of gelation after modification. These alginates were then evaluated as bulk hydrogels in a subcutaneous high-throughput mouse to measure levels of acute inflammation (Tables 5-9). 200 alginate analogues displayed lower levels of cathepsin activity than the control alginate UPVLVG, the alginate used as the starting material for the library synthesis. Component designations refer to the components of Table 4 and FIG. 7. This assay monitors neutrophil activation subcutaneously with an imaging agent which yields increased fluorescence in response to increased neutrophil-mediated cathepsin activity. Two hundred analogues displayed fluorescent levels that were lower than the base unmodified, ultrapure VLVG alginate (FIG. 11).

Figure 12:
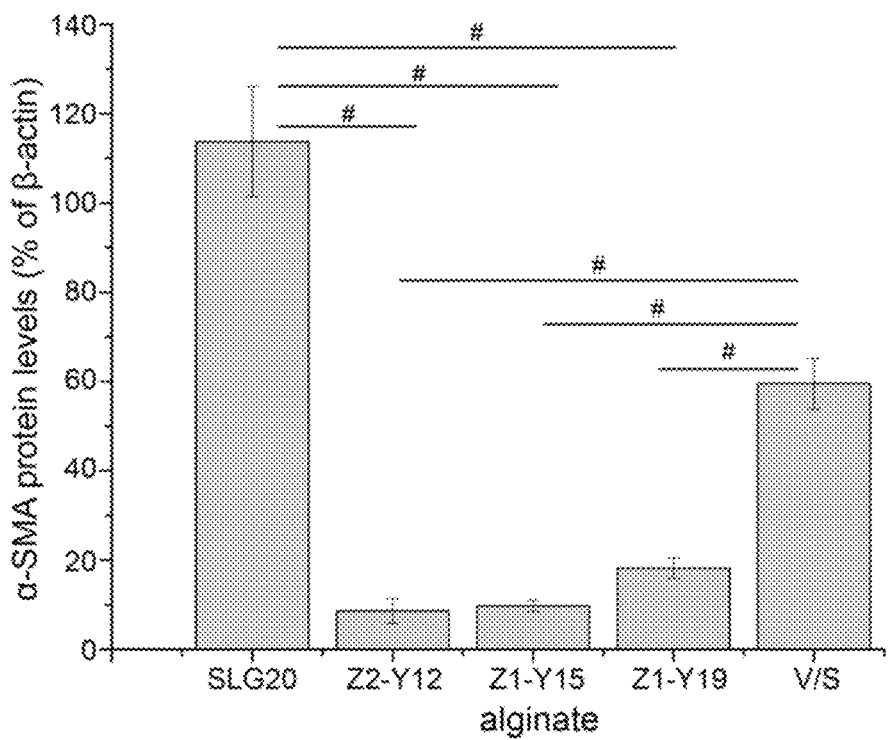
FIG. 12 is a graph of cytokine panel analysis (Elispot) of protein extracted from 300 μm capsules of the top ten alginate analogue capsules and control alginate capsules (SLG20, V/S) retrieved from the IP space of C57BL/6 mice after 14 days. For each cohort n=5. # indicate a significance difference between the means with p<0.01.

Since microcapsules have been the preferred alginate geometry in both drug delivery and cell encapsulation applications, 70 of the top 200 performing polymers (Table 4) from the initial screen were fabricated into 300 μm capsules and re-evaluated in the subcutaneous inflammation assay (FIG. 12). Using chemically-modified alginate proved problematic in constructing microspheres, and good capsule morphology was restored by blending a small amount of ultrapure SLG100 alginate with the alginate analogue solution.

TABLE 5

Cathepsin Activity of Singularly Modified Alginate Polymers

| Moiety | Cathepsin Activity | Moiety | Cathepsin Activity | Moiety | Cathepsin Activity |
|---|---|---|---|---|---|
| N8 | 3.69 | Z2-Y16 | 1.37 | Z1-Y4 | 0.48 |
| N9 | 0.76 | Z2-Y10 | 1.37 | Z1-Y6 | 0.50 |
| N3 | 1.14 | Z2-Y14 | 1.00 | Z1-Y17 | 0.58 |
| N6 | 1.37 | Z2-Y5 | 1.14 | Z1-Y1 | 0.82 |
| N4 | 1.37 | Z2-Y12 | 0.84 | Z1-Y2 | 0.48 |
| N5 | 2040 | Z2-Y7 | 1.37 | Z1-Y11 | 0.64 |
| N2 | 0.96 | Z2-Y6 | 0.71 | Z1-Y10 | 0.54 |
| N1 | 1.57 | Z2-Y8 | 0.97 | Z1-Y12 | 0.84 |
| N7 | 0.39 | Z2-Y20 | 1.57 | Z1-Y13 | 0.76 |
| O6 | — | Z2-Y3 | 1.37 | Z1-Y16 | 0.92 |
| O12 | 0.81 | Z2-Y18 | 1.37 | Z1-Y9 | 0.60 |
| O11 | — | Z2-Y2 | 2.17 | Z1-Y14 | 0.79 |
| O5 | 1.17 | Z2-Y4 | 1.60 | Z1-Y15 | 0.82 |
| O3 | 1.17 | Z2-Y17 | 1.60 | Z1-Y7 | 0.66 |
| O4 | 0.96 | Z2-Y1 | 1.77 | Z1-Y5 | 0.42 |
| O9 | 0.82 | Z2-Y11 | 1.60 | Z1-Y20 | 0.50 |
| O7 | 0.72 | Z2-Y9 | 0.8 | Z1-Y3 | 0.42 |
| O8 | 0.96 | Z2-Y13 | 1.57 | Z1-Y18 | 0.56 |
| O2 | 0.97 | Z2-Y15 | 0.91 | Z1-Y19 | 0.54 |
| O1 | 1.17 | Z2-Y19 | — | Z1-Y8 | 0.58 |
| O10 | 0.69 | | | | |

TABLE 6

Cathepsin Activity of Multiply Modified Alginate Polymers

| | N8 | N9 | N3 | N6 | N4 | N5 | N2 | N1 | N7 |
|---|---|---|---|---|---|---|---|---|---|
| N7 | — | — | 0.20 | — | — | — | — | — | — |
| N9 | 0.51 | — | — | — | 0.42 | 0.54 | 0.92 | — | 1.37 |
| N4 | 1.37 | 0.48 | 2.40 | — | -1.14 | — | 2.17 | 0.76 | 1.17 |
| N2 | — | 0.81 | — | — | 0.86 | 0.80 | -2.40 | — | — |
| N6 | — | 0.60 | — | — | — | — | — | 0.91 | 1.37 |
| N8 | 0.87 | 0.97 | — | 0.72 | 1.17 | 0.86 | — | 0.97 | |
| O3 | 0.71 | 0.88 | 0.60 | 0.72 | 0.6 | 0.58 | 0.58 | 0.64 | 0.76 |
| O2 | 0.63 | 0.99 | 0.78 | 0.69 | 0.91 | 0.64 | 0.75 | 0.72 | 1.17 |
| O10 | 1.17 | 0.72 | 0.95 | 0.78 | 0.92 | 0.88 | 0.82 | 0.88 | 0.69 |
| O1 | 0.97 | 0.91 | 0.80 | 0.76 | 0.92 | 0.89 | 0.88 | 0.88 | 0.75 |
| O8 | 0.87 | 0.92 | 0.81 | 0.93 | 0.78 | 0.80 | 0.84 | 0.81 | 0.89 |
| O12 | 0.76 | 0.88 | 0.79 | 0.87 | 0.81 | 0.75 | 0.82 | 0.75 | 0.76 |
| O9 | 0.88 | 0.92 | 1.17 | 0.85 | 0.84 | 0.78 | 1.17 | 1.17 | 0.89 |
| O7 | 1.17 | 0.97 | 0.99 | 0.96 | 1.17 | 1.17 | 1.17 | 0.84 | 1.37 |
| O4 | 0.89 | 0.71 | 1.17 | 0.78 | 1.37 | 1.14 | 0.76 | 0.91 | 1.60 |
| O5 | — | 0.88 | 0.54 | 0.96 | 0.96 | 1.37 | 0.60 | 0.69 | 1.17 |
| O11 | 1.00 | 1.37 | — | 1.17 | — | — | 0.75 | 0.69 | 1.17 |
| N1 | 2.57 | 1.77 | — | 1.17 | — | 0.56 | — | -0.50 | 1.17 |
| N3 | 1.37 | 1.17 | -0.82 | 0.75 | — | — | 1.57 | — | — |
| N5 | 0.75 | 1.60 | 0.69 | 1.60 | — | — | 0.63 | — | 0.24 |
| O6 | 0.75 | — | 0.63 | — | 0.69 | 0.89 | 0.82 | 0.81 | — |

TABLE 7

Cathepsin Activity of Multiply Modified Alginate Polymers

| | N2 | N1 | N3 | N4 | N5 | N7 | N9 | N8 | N6 |
|---|---|---|---|---|---|---|---|---|---|
| Z2-Y16 | 1.14 | — | 1.17 | 0.60 | 0.75 | 1.17 | 1.37 | 1.57 | 0.93 |
| Z2-Y10 | — | — | 1.37 | 1.37 | — | 1.17 | 1.37 | 1.14 | 1.37 |
| Z2-Y14 | — | — | — | — | 1.60 | 1.97 | 1.77 | 1.77 | 1.77 |
| Z2-Y5 | 1.37 | 1.17 | 0.96 | 1.37 | 0.87 | 0.93 | 0.86 | 0.66 | 0.66 |
| Z2-Y12 | 1.37 | 1.77 | 1.37 | 1.37 | 1.97 | 1.17 | 1.14 | 0.96 | 0.88 |
| Z2-Y7 | 0.75 | 0.66 | 0.99 | 0.76 | 0.81 | — | 0.96 | 0.79 | 0.96 |
| Z2-Y6 | 0.78 | 1.37 | 0.97 | 0.84 | 0.92 | — | 0.82 | 0.54 | 0.97 |
| Z2-Y8 | — | 1.17 | — | — | 1.37 | 1.14 | 1.37 | 1.37 | 1.37 |
| Z2-Y20 | 0.51 | 1.37 | 0.56 | 0.44 | 0.58 | 1.37 | 1.60 | 0.46 | 1.37 |
| Z2-Y3 | 0.79 | 1.17 | 0.69 | 0.94 | 0.92 | 1.57 | 1.37 | 1.37 | 2.00 |
| Z2-Y18 | 1.37 | 0.93 | 1.37 | 1.14 | 1.37 | 0.82 | 1.57 | 1.57 | 1.37 |
| Z2-Y2 | 1.37 | 0.86 | 0.82 | 1.17 | 1.57 | 1.37 | 1.37 | 1.57 | 1.60 |
| Z2-Y4 | 1.14 | 1.37 | 1.37 | — | 1.37 | 1.17 | 1.60 | 1.60 | 1.97 |
| Z2-Y17 | 1.37 | — | 1.37 | 1.17 | 0.94 | 1.37 | 1.00 | 1.17 | 1.37 |
| Z2-Y1 | 1.17 | — | 1.37 | 0.92 | — | 0.93 | 0.80 | 1.37 | 1.37 |
| Z2-Y11 | 0.95 | 1.37 | 1.37 | — | — | 1.37 | — | — | — |

TABLE 7-continued

Cathepsin Activity of Multiply Modified Alginate Polymers

|  | N2 | N1 | N3 | N4 | N5 | N7 | N9 | N8 | N6 |
|---|---|---|---|---|---|---|---|---|---|
| Z2-Y9 | 0.72 | 0.84 | 0.92 | 0.69 | — | 0.75 | 1.77 | 1.37 | 1.37 |
| Z2-Y13 | 1.37 | 1.37 | 1.60 | 0.75 | 1.37 | 1.37 | — | 1.57 | 1.77 |
| Z2-Y15 | 1.57 | 1.17 | 1.00 | — | — | 1.57 | — | — | — |
| Z2-Y19 | — | — | — | — | — | — | — | — | — |

TABLE 8

Cathepsin Activity of Multiply Modified Alginate Polymers

|  | N1 | N4 | N7 | N3 | N2 | N8 | N5 | N9 | N6 |
|---|---|---|---|---|---|---|---|---|---|
| Z1-Y4 | 0.63 | 0.51 | 1.17 | 0.51 | 0.60 | 1.37 | 1.37 | 1.37 | 1.17 |
| Z1-Y6 | 1.17 | 0.88 | 1.17 | 0.84 | 0.75 | 0.87 | 0.75 | 1.57 | 0.99 |
| Z1-Y17 | 0.72 | 0.78 | 0.91 | 0.58 | 0.79 | 0.56 | 0.76 | 0.81 | 0.69 |
| Z1-Y1 | 0.63 | 0.58 | 1.17 | 0.50 | 0.54 | 0.50 | 0.50 | 1.17 | 1.17 |
| Z1-Y2 | 1.00 | 1.37 | 1.17 | 1.37 | 1.37 | 1.37 | 1.37 | 1.37 | 1.37 |
| Z1-Y11 | 1.00 | 1.37 | 1.37 | 1.37 | 1.37 | 1.00 | 1.17 | 1.34 | 1.37 |
| Z1-Y10 | 1.14 | 1.00 | 1.37 | 1.37 | 1.14 | 1.37 | 1.37 | 0.97 | 1.37 |
| Z1-Y12 | 1.37 | 1.17 | 1.37 | 1.37 | 1.37 | 1.17 | 1.37 | 1.17 | 1.17 |
| Z1-Y13 | 1.14 | 0.99 | 1.14 | 1.37 | 1.17 | 1.17 | 1.17 | 1.17 | 1.17 |
| Z1-Y16 | 1.37 | 1.14 | 1.17 | 1.37 | 1.17 | 1.00 | 1.17 | 0.97 | 0.96 |
| Z1-Y9 | 0.97 | 0.94 | 0.94 | 0.97 | 0.93 | 0.84 | 0.96 | 0.87 | 0.84 |
| Z1-Y14 | 0.89 | 0.99 | 0.85 | 0.88 | 1.17 | 0.76 | 0.78 | 0.85 | 0.86 |
| Z1-Y15 | 0.94 | 0.92 | 0.99 | 0.89 | 1.17 | 1.17 | 1.37 | 0.89 | 1.37 |
| Z1-Y7 | 1.37 | 0.77 | 1.00 | 0.76 | 1.37 | 0.76 | 0.75 | 1.14 | 1.17 |
| Z1-Y5 | 1.14 | 0.99 | 1.17 | 0.96 | 1.00 | 1.37 | 1.57 | 1.17 | 1.17 |
| Z1-Y20 | 0.75 | 0.84 | 1.14 | 0.97 | 1.14 | 1.37 | 1.17 | 0.81 | 0.79 |
| Z1-Y3 | 1.37 | 1.17 | 0.86 | 1.17 | 1.37 | 1.37 | 0.94 | 0.58 | 0.96 |
| Z1-Y18 | 0.75 | 0.82 | — | 0.77 | — | — | — | 0.63 | 0.63 |
| Z1-Y19 | 1.17 | — | 0.99 | — | — | — | — | — | 1.17 |
| Z1-Y8 | — | 1.17 | 1.00 | 0.94 | 0.92 | 0.94 | 1.14 | 1.37 | 0.97 |

TABLE 9

Cathepsin Activity of Multiply Modified Alginate Polymers

|  | O6 | O12 | O11 | O5 | O3 | O4 | O9 | O7 | O8 | O2 | O1 | O10 |
|---|---|---|---|---|---|---|---|---|---|---|---|---|
| O7 | 1.37 | 1.17 | — | — | 1.17 | 0.99 | 1.37 | 1.37 | 1.17 | 1.37 | 1.37 | 1.14 |
| O9 | 1.14 | 1.37 | — | — | 1.37 | 1.37 | 1.17 | 1.17 | 1.37 | 1.14 | 1.77 | 1.14 |
| O1 | 0.86 | 0.82 | 1.37 | 1.17 | 1.37 | 0.92 | 0.97 | 0.97 | 1.37 | 0.97 | 1.17 | 1.17 |
| O2 | 1.14 | 0.97 | 1.17 | 1.00 | 0.95 | — | 0.89 | 0.76 | 0.91 | 0.76 | 0.92 | 0.72 |
| O6 | 1.37 | — | — | — | — | 0.99 | 1.37 | 1.17 | 0.85 | 0.79 | 0.78 | 1.37 |
| O12 | 0.99 | 1.77 | 0.89 | 1.37 | 1.37 | 1.17 | 0.75 | 0.96 | — | — | — | — |
| O3 | 1.95 | 1.60 | 1.37 | — | — | 1.17 | 0.87 | 0.80 | 1.14 | — | 0.93 | 0.97 |
| O5 | — | 1.97 | — | — | — | 1.00 | — | — | 1.17 | — | 0.79 | 0.94 |
| O11 | — | 1.17 | 0.95 | — | — | — | — | — | — | 1.17 | 1.37 | 1.14 |
| O4 | — | 1.37 | — | — | — | — | — | — | 0.94 | 0.92 | 0.97 | 1.14 |
| O10 | — | 1.57 | 0.88 | 0.99 | 0.96 | 1.17 | — | 1.17 | — | 0.80 | 1.17 | 1.37 |
| O8 | — | 1.57 | — | 0.71 | 0.72 | 0.85 | 0.80 | 0.92 | 1.37 | 0.69 | 1.37 | 1.14 |

All modified microcapsule formulations required this blending, capsules made from a blended solution of unmodified alginates VLVG and SLG100 (V/S) and the conventional SLG20 capsule formulation served as controls. Of the 70 formulated alginate microcapsules, an improved inflammation response was observed with several polymers (FIG. 12). The top 10 modified microcapsules displayed inflammation levels of 10-40% lower than the control alginates. To see if these lower levels of acute inflammation translated into lower levels of fibrosis, the implant sites of these top 10 alginates were sampled, sectioned, and processed histologically after 28 days. Three modified alginates, Z2-Y12, Z1-Y15, and Z1-Y19, displayed minimal fibrotic overgrowth with capsules able to fully detach from the surrounding tissue.

To test if the subcutaneous results translate into other implantation sites, 300 μm capsules of the top 10 lead modified alginates were implanted in the intraperitoneal (IP) space of C57BL/6 mice. Capsules were retrieved after 14 days and evaluated for the accumulation of cellular and fibrotic tissue. Phase contrast imaging of retrieved control capsules show a robust fibrotic response, with a white fibrous collagenous deposition observed on the capsules with brown capsule clumping. By comparison, the top ten lead modified alginates show varying degrees of fibrosis, with the modified alginates Z2-Y12, Z1-Y15, and Z1-Y19 showing almost no fibrous deposition and emerging as materials with anti-fibrotic properties.

Cellular staining and confocal microscopy of the Z2-Y12, Z1-Y15, and Z1-Y19 capsules showed little to no presence of macrophages (CD68), myofibroblasts (SMA) or general cellular deposition (DAPI). The conventional microcapsule alginate, however, showed significant quantities of these cell populations on the retrieved capsules. Cellular deposition is a key mechanistic component of material recognition and an initiator of collagenous deposition, and the absence of cells on the capsule surface is a further illustration of the anti-fibrotic properties of these modified alginates. To confirm these results, the SMA levels of Z2-Y12, Z1-Y15, Z1-Y19, and the control capsules quantified by Western Blotting. 40 different cytokines from protein samples extracted from the retrieved microcapsules were also profiled. The cytokine profile of Z2-Y12 microcapsules show the lowest cytokine levels of all tested samples, indicative of an overall lower inflammatory response. Importantly, retrieved Z2-Y12 capsules had low protein levels of TNF-α, IL-13, IL-6, G-CSF, GM-CSF, IL-4, CCL2, and CCL4 which are known mediators of the foreign body response and fibrosis (Rodriguez et al., *J. Biomed. Mater. Res. A* 89:152-159 (2009)). Quantification of seventy nine RNA sequences of known inflammation factors and immune cell markers isolated from retrieved capsules also support lower levels of inflammation for Z2-Y12 implants. The RNA profile in the surrounding IP fluid and fat tissue of Z2-Y12 implanted mice also more closely resembled mock treatment than mice implanted with control capsules, further demonstrating the lower inflammatory potential of this material.

B. Anti-Fibrotic Alginates Show Lower Macrophage Adhesion

Figure 8:
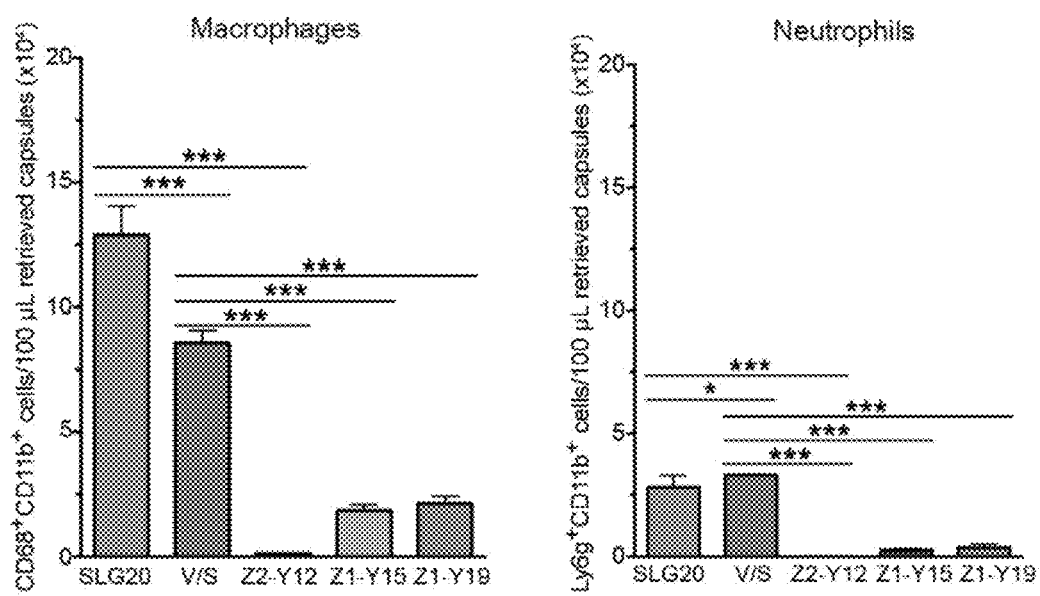
FIG. 8 is a graph of FACS analysis of macrophages (CD11b+, CD68+) and neutrophils (CD11b+, Ly6g+) isolated from Z2-Y12, Z1-Y15, Z1-Y19, SLG20, and V/S capsules retrieved after 14 days in the IP space of C57BL/6 mice. ***=p<0 0001, ns=not significant.

FACS analysis was performed on retrieved capsules after 14 days IP to characterize the different immune populations that are recruited to Z2-Y12 capsules compared to control capsules (FIG. 8). Z2-Y12 capsules displayed significantly lower percentages of macrophage and neutrophil populations, suggesting that Z2-Y12 capsules may be interfering with either the recruitment of immune cell populations or amplification of an inflammatory response. To see if lower macrophage recruitment was evident in vivo, IP intra-vital imaging was performed 7 days after implantation of fluorescent Z2-Y12 capsules in MAFIA mice (where macrophages express GFP) and compared them to fluorescent SLG20 capsules. SLG20 capsules show a large population of macrophages actively aggregating at the surface of these capsules, an indication of foreign-body giant cell formation and a clear step towards fibrosis. Z2-Y12 capsules by comparison showed much lower levels of macrophages near the capsules and there was no visible macrophage aggregation.

The lack of immune cell recruitment/activation to the surface of Z2-Y12 capsules is consistent with the chemical modification of the polymer chains creating differential surfaces. Confocal raman spectroscopic mapping was performed to determine the distribution of the Z2-Y12 chemical modification in the microcapsule. Strikingly, the diagnostic raman signature for the tetrahydropyranyl modification had a higher intensity at the surface of the microcapsule than at the core. Freeze-fracture cryo-SEM was then performed on Z2-Y12 microcapsules to examine both the surface and core topography of the alginate analogue microspheres and compare them to the control capsule formulations. Z2-Y12 capsules display a more variable porosity throughout the capsule core compared to either the blended control or conventional SLG20 capsules, with pores ranging from 1 µm to 10 µm in size. The surface features between the different capsule formulations are quite distinct; the surface of Z2-Y12 capsules show fewer cratered features. These surface differences are likely created by interactions at the boundary layer between the modified polymer chains and the surrounding aqueous solution.

C. Z2-Y12, Z1-Y15, and Z1-Y19 Resist Fibrosis in Non-Human Primates

The lead materials, Z2-Y12, Z1-Y15, and Z1-Y19, were advanced into primate studies to test their anti-fibrotic properties in a NHP model. Previous reports from our lab have established that spheroid size is also a key parameter in mitigating fibrosis, with larger spheres (>1 mm) displaying anti-fibrotic properties. 1.5 mm capsules of the conventional SLG20 capsules and the new Z2-Y12, Z1-Y15, and Z1-Y19 formulated capsules were separately transplanted into non-human primates (n=3 each) using a minimally invasive laparoscopic procedure. Capsules were retrieved by IP lavage at 2 and 4 weeks, with one primate from each cohort allowed to continue for 6 months. By 14 days post-transplant, SLG20 1.5 mm capsules were also largely free and not embedded in tissue at 2 weeks as well. However, numerous capsules were fibrosed and clumped together. The 1.5 mm Z2-Y12, Z1-Y15, and Z1-Y19 retained a high retrieval rate and minimal embedding into the surrounding tissue. At both 2 and 4 weeks Z2-Y12, Z1-Y15, and Z1-Y19 capsules displayed significantly reduced fibrotic responses in phase contrast imaging compared to 1.5 mm SLG20 capsules. Confocal imaging and FACS analysis of retrieved capsules showed large 1.5 mm SLG20 capsules had more extensive immune macrophage and fibrosis-associated activated myofibroblast coverage, consistent with the visible fibrotic overgrowth seen in the phase contrast imaging.

To investigate whether increasing capsule size and/or the modified chemistries would maintain improved anti-fibrotic activity over a longer period of time, confocal staining was also performed on capsules retrieved from NHPs after 6 months. SLG20 capsules showed significant and extensive fibrotic overgrowth, while Z2-Y12 capsules were still clean, showing no associated macrophages or myofibroblasts. FACS analysis displayed similar results with a lower macrophage composition associated with retrieved Z2-Y12 capsules.

The combination of both increased capsule size (1.5 mm) and modified (Z2-Y12) chemistry substantially improved biocompatibility even at the 6 month time point. Large 1.5 mm Z2-Y12 capsules looked to have minimal (almost non-existent) levels of fibrosis throughout all time points, indicating that anti-fibrotic effects of large capsule size synergize with those of modified Z2-Y12 chemistry.

The results in this example demonstrate that chemical modification of one of the most widely used biomaterials, alginate, produces hydrogels that are able to resist foreign body reactions in both rodents and non-human primates. The lead alginate analogues, Z2-Y12, Z1-Y15, and Z1-Y19, show minimal recognition by macrophages and other immune cells, low levels of inflammatory cytokines, and almost no visible fibrous deposition in both rodents and non-human primates even after 6 months (Z2-Y12). The distribution of the Z2-Y12 chemical modification results in a unique hydrogel surface that inhibits macrophage adhesion, effectively mitigating the foreign body response to the biomaterial. The results show that chemical modification of existing biomaterials is a viable strategy to overcome their foreign body responses. These are the first biomaterials to resist the foreign body response in non-human primates and their versatility as alginate-based materials allows its use in multiple biomedical applications.

Example 9: Demonstration of Anti-Fibrotic Activity of Modified Alginates Encapsulating Human Cells in Immunocompetent Animals This example demonstrates the anti-fibrotic properties of the modified alginates encapsulating human cells, which are implanted in robust immunocompetent STZ C57BL/6J mice for a long period of time. The encapsulated human cells are actively secreting xenogeneic substances including, but not limited to, proteins. The xenogeneic substances should elicit an intense immune response from the mice. Therefore, this test represents a severe immune challenge to the implanted modified alginates. Nonetheless, the implanted modified alginates resist foreign body responses and shield the encapsulated human cells from host foreign body responses for long periods of time. As a result, the beneficial effects of the human cells are exerted for long periods of time. This example describes testing of modified alginates encapsulating human cells secreting insulin for their ability to reduce blood glucose levels and maintain normoglycemia in STZ-induced diabetic mice. The implants reduce blood glucose levels and maintain normoglycemia long-term in the STZ C57BL/6J mice without the need for immune suppressants.

Diabetes is a global epidemic afflicting over 300 million people (Shaw et al., Diabetes Res. Clin. Pract. 87:4-14 (2010)). While a rigorous regimen of blood glucose monitoring coupled with daily injections of exogenous insulin remains the leading treatment for type one diabetics, patients still suffer ill effects due to the challenges associated with daily compliance (Pickup et al., N. Engl. J. Med. 366:1616-1624 (2012)). In addition, the regulation of insulin secretion by the beta cells of the pancreatic islets of Langerhans in response to blood glucose level is a highly dynamic process, which is imperfectly simulated by periodic insulin injections (Robertson et al., N. Engl. J. Med. 350:694-705 (2004)). The transplantation of donor tissue, either in the form of a pancreas transplantation or infusion of cadaveric islets, are currently implemented clinically as one strategy to achieve insulin independence for type 1 diabetics (Shapiro et al., N. Engl. J. Med. 355:1318-1330 (2006); Shapiro et al., N. Engl. J. Med. 343:230-238 (2000); $Q_1$ et al., Acta Diabetologica 51:833-843 (2014)). This approach has been limited due to two major drawbacks: (1) the limited supply of available donor tissue, and (2) the adverse effects associated with a lifetime of immunosuppression (Hirshberg et al., Current Diabetes Reports 7:301-303 (2007); Gibly et al., Diabetologia, 54:2494-2505 (2011); O'Sullivan et al., Endocrine Reviews 32:827-844 (2011)). Methods to relieve the need for life long immunosuppression must be developed to allow for the broadest clinical implementation (Hirshberg et al., Current Diabetes Reports 7:301-303 (2007); Shapiro et al., The Review of Diabetic Studies: RDS 9:385-406 (2012); Vogel et al., Diabetologia 56:1605-1614 (2013)).

Cell encapsulation is a promising technology that overcomes the need of immunosuppression by protecting therapeutic tissues from host rejection (Dolgin, Nat. Med. 20:9-11 (2014); Jacobs-Tulleneers-Thevissen et al., Diabetologia 56:1605-1614 (2013)). The most commonly investigated method for islet encapsulation therapy is the formulation of isolated islets into alginate microspheres (Jacobs-Tulleneers-Thevissen et al., Diabetologia 56:1605-1614 (2013); Scharp et al., Advanced Drug Delivery Reviews 67-68:35-73 (2014)). Clinical evaluation of this technology in diabetic patients with cadaveric human islets has only achieved glycemic correction for short periods (Jacobs-Tulleneers-Thevissen et al., Diabetologia 56:1605-1614 (2013); Basta et al., Diabetes Care 34:2406-2409 (2011); Calafiore et al., Diabetes Care 29:137-138, (2006)). Implants from these studies are characterized by strong immune-mediated foreign body responses that result in fibrotic deposition, nutrient isolation, and donor tissue necrosis (de Groot el al., Journal of Surgical Research 121:141-150 (2004); Tuch et al., Diabetes Care 32:1887-1889 (2009)). Similar results are observed with encapsulated xenogeneic islets and pancreatic progenitor cells in preclinical diabetic mouse or non-human primate models, where both the therapeutic efficacy (Hirshberg et al., Current Diabetes Reports 7:301-303 (2007)) of encapsulated cadaveric human islets and pig islets is hampered by immunological responses (Elliot et al., Transplantation Proceedings 37:3505-3508 (2005); Omer et al., Diabetes 52:69-75 (2003); Schneider et al., Diabetes 54:687-693 (2005)).

A major contributor to the performance of encapsulated cell implants is the immune response to the biomaterials used for cell encapsulation (Lim et al., Science 210:908-910 (1980); Jacobs-Tulleneers-Thevissen et al., Diabetologia 56:1605-1614 (2013); Scharp et al., Advanced Drug Delivery Reviews 67-68:35-73 (2014)). Immune-mediated foreign body responses to implanted materials commonly lead to tissue capsule formation that results in implant failure (King et al., Journal of Biomedical Materials Research 57:374-383 (2001)). When implanted into the intraperitoneal space of non-human primates or rodents with robust immune systems such as C57BL/6J, (King et al., Journal of Biomedical Materials Research 57:374-383 (2001); Dang et al., Biomaterials 32, 4464-4470 (2011)) alginate microspheres elicit foreign body reactions and fibrosis (King et al., Journal of Biomedical Materials Research 57:374-383 (2001); Dang et al., Biomaterials 32:4464-4470 (2011)).

Figure 13:
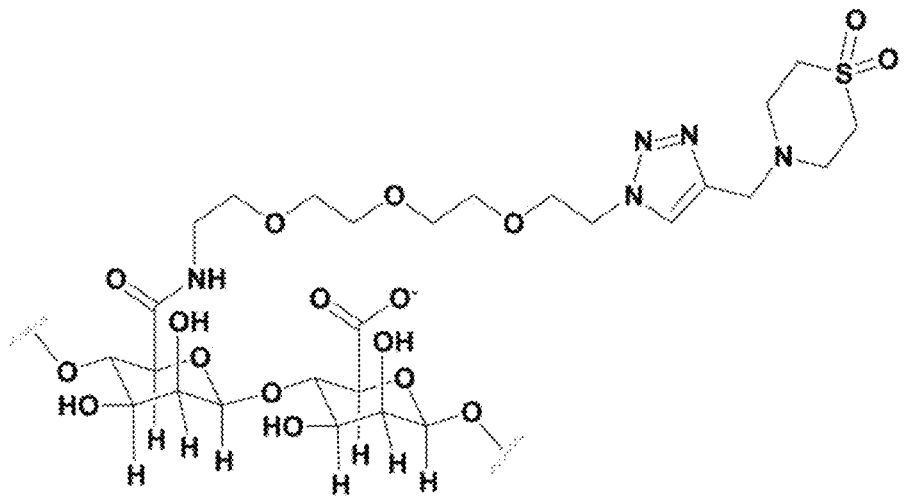
FIG. 13 is a chemical structure of triazole-thiomorpholine dioxide (TMTD) alginate.
Figure 14:
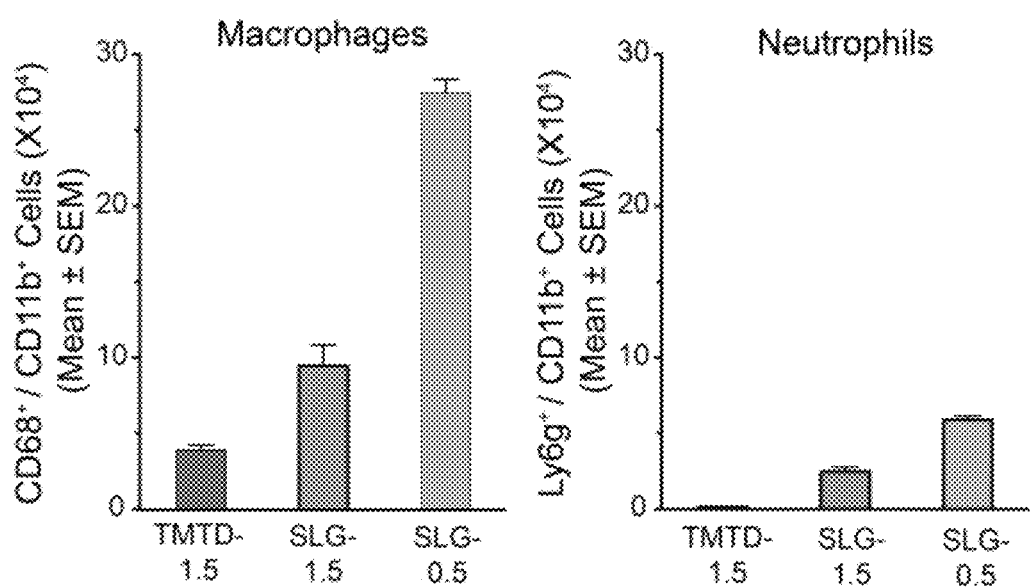
FIG. 14 is graphs of FACS analysis of encapsulated human cell implants retrieved after 14 days IP in C57BL/6 showing macrophages and neutrophils.
Figure 15:
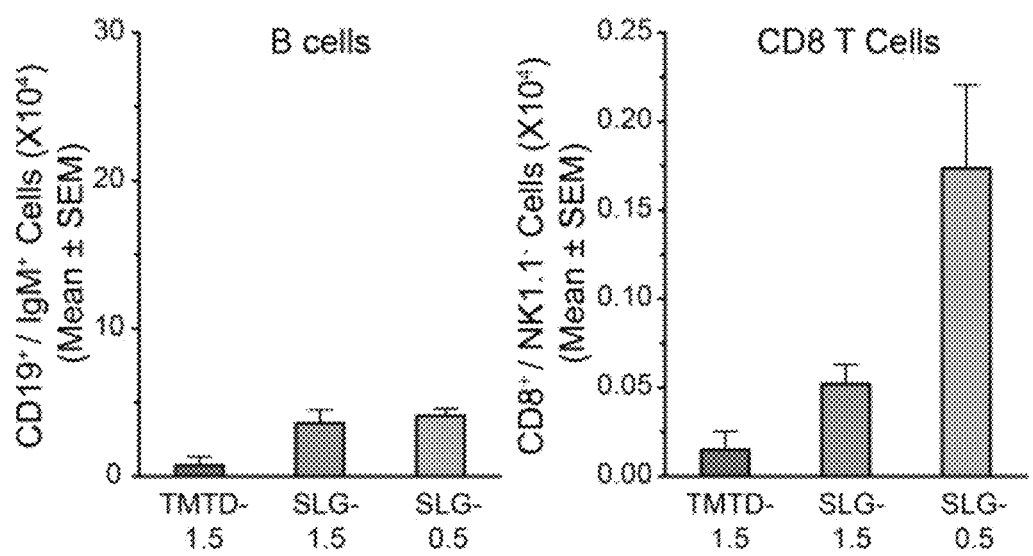
FIG. 15 is graphs of FACS analysis of encapsulated human cell implants retrieved after 14 days IP in C57BL/6 showing B cells and CD8 T cells.

A large library of chemically modified alginates was recently developed and evaluated for their potential to resist implant rejection in both rodent and non-human primate models. This example extends that work to show that triazole-thiomorpholine dioxide (TMTD; FIG. 13) alginate-encapsulating human cells were able to mitigate foreign body responses in immune-competent C57BL/6 mice (FIGS. 14 through 16). As a result, the TMTD alginate-encapsulating human cells are able to provide long-term glycemic correction and glucose-responsiveness. These results demonstrate that these new materials can be used to provide long-term, glycemic correction through implantation of microencapsulated human cell, thus improving therapeutic effect of such implanted cells.

This example demonstrates the successful use potential of encapsulated human cells in immunocompetent animals for the restoration of normoglycemia without immune suppression. This shows the expectation that the disclosed modified alginates can be used to encapsulate cells and coat material and keep immune reactions to the cells and materials at bay in subjects in which they are implanted. To ensure proper biocompatibility assessment in these studies an immunocompetent streptozotocin-induced diabetic C57BL/6 mouse model was used because this strain is known to produce a strong fibrotic and foreign body response similar to observations made in human patients (Kolb et al., J. Respir. Cell. Mol. Biol. 27:141-150 (2002)). Formulations that have shown glycemic correction utilizing other tissue sources, such as conventional microencapsulation with alginate (Lim et al., Science 210; 908-910 (1980); Calafiore el al., Diabetes Care 29:137-138, (2006)) and larger sphere formulations (Veiseh et al., Nat. Mater., DOI: 10.1038/NMAT4290), were unable to support glycemic correction with human cells.

All materials were implanted intraperitoneally and retrieved at specified times from immunocompetent streptozotocin induced diabetic C57BL/6 or B6.129S6-Ccr6tm1 (EGFP)Irw/J mice in accordance with approved protocols and federal guidelines. Sample processing, staining, FACS, and imaging were performed as detailed in below.

I. Materials

All chemicals were obtained from Sigma-Aldrich (St. Louis, MO) and cell culture reagents from Life Technologies (Grand Island, NY), unless otherwise noted. Antibodies: Alexa Fluor 488-conjugated anti-mouse CD68 (Cat. #137012, Clone FA-11) and Alexa Fluor 647-conjugated anti-mouse Ly-6G/Ly-6C (Gr-1) (Cat. #137012, Clone RB6-8C5) were purchased from BioLegend Inc. (San Diego, CA). Cy3-conjugated anti-mouse alpha smooth muscle actin antibody was purchased from Sigma Aldrich (St. Louis MO). Filamentous actin (F-actin)-specific Alexa Fluor 488-conjugated Phalloidin was purchased from Life Technologies (Grand Island, NY). Anti-Glucagon cat #ab82270, Anti-insulin cat #ab7842, Goat Anti-Guinea pig IgG H&L conjugated Alexa Fluor® 488 cat #ab150185, and Goat Anti-Mouse IgG H&L conjugated Alexa Fluor®594 cat #ab150116 were purchased from abeam (Cambridge, MA). Anti-human C-peptide cat #GN-1D4 was purchased from Developmental Studies Hybridoma Bank (University of Iowa, Iowa City, Iowa). A sampling of the spheres used in this study was submitted for endotoxin testing by a commercial vendor (Charles River, Wilmington, MA) and the results showed that spheres contained<0.05 EU/ml of endotoxin levels.

II. Methods

A. Fabrication of Alginate Hydrogel Capsules and Cell Encapsulation

All buffers were sterilized by autoclave and alginate solutions were sterilized by filtration through a 0.2 um filter. After solutions were sterilized, aseptic processing was implemented by performing capsule formation in a type II class A2 biosafety cabinet to maintain sterility of manufactured microcapsules/spheres for subsequent implantation. The hydrogel capsules following the protocol described in Example 8.

To solubilize alginates, SLG20 (NovaMatrix, Sandvika, Norway) was dissolved at 1.4% weight to volume in 0.8% saline. TMTD alginate was initially dissolved at 5% weight to volume in 0.8% saline, and then blended with 3% weight to volume SLG100 (also dissolved in 0.8% saline) at a volume ratio of 80% TMTD alginate to 20% SLG100.

For formation of 0.5 mm spheres were generated with a 25G blunt needle, a voltage of 5 kV and a 200 µl/min flow rate. For formation of 1.5 mm spheres, an 18 gauge blunt tipped needle (SAI Infusion Technologies) was used with a voltage of 5-7 kV.

Cultured human cells were used for encapsulation. Immediately prior to encapsulation, the cultured human cell clusters were centrifuged at 1,400 rpm for 1 minute and washed with Ca-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH≈7.4, ≈290 mOsm). After washing, the human cells were centrifuged again and all supernatant was aspirated. The human cell pellet was then re-suspended in the SLG20 or TMTD alginate solutions (described above) at cluster densities of 1,000, 250, and 100 clusters per 0.5 ml alginate solution. Spheres were crosslinked using a $BaCl_2$ gelling solution and their sizes were controlled as described above. Immediately after crosslinking, the encapsulated human cell clusters were washed 4 times with 50 mL of CMRLM media and cultured overnight in a spinner flask at 37° C. prior to transplantation. Due to an inevitable loss of human cell clusters during the encapsulation process, the total number of encapsulated clusters were recounted post-encapsulation.

B. Transplantation Surgeries

All animal protocols were approved by the MIT Committee on Animal Care, and all surgical procedures and post-operative care was supervised by MIT Division of Comparative Medicine veterinary staff. Immune-competent male STZ-induced diabetic C57BL/6 mice (Jackson Laboratory, Bar Harbor, ME) or male B6.129S6-Ccr6tml(EGFP)Irw/J mice (Jackson Laboratory, Bar Harbor, ME) were anesthetized with 3% isoflurane in oxygen and had their abdomens shaved and sterilized using betadine and isopropanol. Preoperatively, all mice also received a 0.05 mg/kg dose of buprenorphine subcutaneously as a pre-surgical analgesic, along with 0.3 mL of 0.9% saline subcutaneously to prevent dehydration. A 0.5 mm incision was made along the midline of the abdomen and the peritoneal lining was exposed using blunt dissection. The peritoneal wall was then grasped with forceps and a 0.5-1 mm incision was made along the linea alba. A desired volume of spheres (all materials without islets, as well as SLG20 spheres encapsulating rat islets) were then loaded into a sterile pipette and implanted into the peritoneal cavity through the incision. The incision was then closed using 5-0 taper-tipped polydioxanone (PDS II) absorbable sutures. The skin was then closed over the incision using a wound clip and tissue glue.

C. Blood Glucose Monitoring

To create insulin-dependent diabetic mice, healthy C57BL/6 mice were treated with Streptozotocin (STZ) by the vendor (Jackson Laboratory, Bar Harbor, ME) prior to shipment to MIT. The blood glucose levels of all the mice were retested prior to transplantation. Only mice whose non-fasted blood glucose levels were above 400 mg/dL for two consecutive days were considered diabetic and underwent transplantation.

Blood glucose levels were monitored three times a week following transplantation of islet-containing alginate capsules. A small drop of blood was collected from the tail vein using a lancet and tested using a commercial glucometer (Clarity One, Clarity Diagnostic Test Group, Boca Raton, FL). Mice with unfasted blood glucose levels below 200 mg/dL were considered normoglycemic. Monitoring continued until experimental time points had been reached, at which point they were euthanized and the spheres were retrieved.

D. Human c-Peptide Monitoring

Human c-peptide levels were monitored every three weeks following transplantation of human cell-containing alginate capsules. Mice were fasted for 1 hour before blood collection, at which point approximately 100-150 µL of blood was collected retro-orbitally into a serum collection tube. Collected blood was centrifuged for 10 minutes at 13000 rpm, serum was removed, and stored at 20° C. until assayed. Serum was assayed for human c-peptide using the Alpco human c-peptide kit (Catalog #: 80-CPTHU-E10) according to the manufacturer's instructions.

E. Retrieval of Cells, Tissues and Materials

Retrieval of cells, tissues and materials was performed as described above in Example 8.

F. Imaging of the Retrieved Material Spheres

For phase contrast imaging of retrieved materials was performed following the protocol described in Example 8.

For bright-field imaging of retrieved materials, samples were gently washed using Krebs buffer and transferred into 35 mm petri dishes for bright-field imaging using a Leica Stereoscopic microscope.

G. Confocal Immunofluorescence

Immunofluorescence imaging was used to determine immune populations attached to spheres. Materials were retrieved from mice and fixed overnight using 4% paraformaldehyde at 4° C. Samples were then washed twice with KREBS buffer, permeabilized for 30 min using a 0.1% Triton X100 solution, and subsequently blocked for 1 hour using a 1% bovine serum albumin (BSA) solution. Next, the spheres were incubated for 1 hour in an immunostaining cocktail solution consisting of DAPI (500 nM), specific marker probes (1:200 dilution) in BSA. After staining, spheres were washed three times with a 0.1% Tween 20 solution and maintained in a 50% glycerol solution. Spheres were then transferred to glass bottom dishes and imaged using an LSM 700 point scanning confocal microscope (Carl Zeiss Microscopy, Jena Germany) equipped with 5 and 10× objectives. Obtained images were adjusted linearly for presentation using Photoshop (Adobe Inc. Seattle, WA).

H. Proteomic Analysis

1. Reduction, Alkylation and Tryptic Digestion

Retrieved samples were suspended in urea cell lysis buffer (8 M urea, Tris pH 8.0) and incubated at 4° C. overnight. Equivalent amounts of protein were reduced (10 mM dithiothreitol, 56° C. for 45 min) and alkylated (50 mM iodoacetamide, room temperature in the dark for 1 h). Proteins were subsequently digested with trypsin (sequencing grade, Promega, Madison, WI), at an enzyme/substrate ratio of 1:50, at room temperature overnight in 100 mM ammonium acetate pH 8.9. Trypsin activity was quenched by adding formic acid to a final concentration of 5%. Peptides were desalted using C18 SpinTips (Protea, Morgantown, WV) then lyophilized and stored at −80° C.

2. TMT Labeling

Peptides were labeled with TMT 6plex (Thermo) per manufacturer's instructions. Lyophilized samples were dissolved in 70 µL ethanol and 30 µl of 500 mM triethylammonium bicarbonate, pH 8.5, and the TMT reagent was dissolved in 30 µl of anhydrous acetonitrile. The solution containing peptides and TMT reagent was vortexed, incubated at room temperature for 1 h. Samples labeled with the six different isotopic TMT reagents were combined and concentrated to completion in a vacuum centrifuge. For the first analysis samples were labeled using the TMT 6plex channels as follows: 126-RZA 1.5 mm 250 biological replicate 1; 127-RZA 1.5 mm 250 biological replicate 2; 128-SLG201.5 mm 250 biological replicate 1; 129-SLG201.5 mm 250 biological replicate 2; 130-SLG20500 µm 250 biological replicate 1; and 131-SLG20 500 µm 250 biological replicate 2. For the second analysis samples were labeled using the TMT 6plex channels as follows: 126-RZA 1.5 mm 250 biological replicate 3; 127-RZA 1.5 mm 250 biological replicate 4; 128-SLG201.5 mm 250 biological replicate 3; 129-SLG201.5 mm 250 biological replicate 4; 130-SLG20500 µm 250 biological replicate 3; and 131-SLG20500 µm 250 biological replicate 4.

3. LC-MS/MS

Peptides were then loaded on a precolumn and separated by reverse phase HPLC (Thermo Easy nLC1000) over a 140 minute gradient before nanoelectrospray using a QExactive mass spectrometer (Thermo). The mass spectrometer was operated in a data-dependent mode. The parameters for the full scan MS were: resolution of 70,000 across 350-2000 m/z, AGC $3e^6$, and maximum IT 50 ms. The full MS scan was followed by MS/MS for the top 10 precursor ions in each cycle with a NCE of 32 and dynamic exclusion of 30 s. Raw mass spectral data files (.raw) were searched using Proteome Discoverer (Thermo) and Mascot version 2.4.1 (Matrix Science). Mascot search parameters were: 10 ppm mass tolerance for precursor ions; 0.8 Da the fragment ion mass tolerance; 2 missed cleavages of trypsin; fixed modification was carbamidomethylation of cysteine; variable modification was methionine oxidation. TMT quantification was obtained using Proteome Discoverer and isotopically corrected per manufacturer's instructions.

I. Histological Processing for H&E and Masson's Trichrome Staining

Retrieved materials were fixed overnight using 4% paraformaldehyde at 4° C. After fixation, alginate sphere or retrieved tissue samples were washed using 70% alcohol. The materials were then mixed with 4 degrees calcium-cooled Histogel (VWR, CA #60872-486). After the molds hardened, the blocks were processed for paraffin embedding, sectioning and staining according to standard histological methods.

J. Histological Immunostaining

Paraffin embedded sectioned samples were stained for the following: human insulin (Anti-insulin cat #ab7842, abeam), human c-peptide (C-peptide cat #GN-1D4, Developmental Studies Hybridoma Bank, University of Iowa), human glucagon (Anti-Glucagon cat #ab82270, abeam). Cellular nuclei were stained with DAPI (cat #D1306, Life Technologies).

Paraffin slides were deparaffinized through subsequent incubations in the following solvents (Xylene 5 min 2×100% ETOH 2 min×295% 2 min×270% 2 min×2 d-water). Antigen retrieval was done by incubating sections for 30 min in ice cooled PBS, and then blocking with 3% horse serum to block for 30 min. Antibody mixtures were then applied as follows: Primary A—Mix together Glucagon 1 to 200 and c-peptide 1 to 500. Primary B—Mix together Human insulin 1 to 500 and glucagon 1 to 200, incubate for 2 hours and then Wash in PBS 10 min x 4. Secondary A—Add anti-mouse AF5941 to 500 and anti-rat AF4881 to 500. Secondary B—Add anti-guinea pig AF4881 to 500 with anti-mouse AF5941 to 500 incubate for 30 min then wash 10 min 4x. Slides were then stained with DAPI and coverslips mounted using prolong gold antifade (Life Technologies, Carlsbad, CA).

K. Western Blotting

Protein was extracted directly from materials for western blot analysis. For protein analyses, retrieved materials were prepared by immersing materials in Pierce RIPA buffer (Cat. #89901, Thermo Scientific) with protease inhibitors (Halt Protease inhibitor single-use cocktail, Cat. #78430, Thermo Scientific) on ice, and then lysed by sonication (for 30 seconds on, 30 seconds off, twice at 70% amplitude). Samples were then subjected to constant agitation for 2 hours at 4° C. Lysates were then centrifuged for 20 min at 12,000 rpm at 4° C., and protein-containing supernatants were collected in fresh tubes kept on ice. In samples from fat tissue, an excess of fat (a top layer on the supernatant) was first removed before supernatant transfer. 20 µg protein (quantified by BCA assay, Pierce BCA protein assay kit, Cat. #23225, Thermo Scientific) for each lane was boiled at 95° C. for 5 min and electrophoresed on SDS-polyacrylamide gels (Any kD 15-well comb mini-gel, Biorad, Cat. #456-9036) and then blotted onto nitrocellulose membranes (Biorad, Cat. #162-0213). Blots were probed with anti-αSmooth Muscle actin antibody (1:400 dilution, Rabbit polyclonal to alpha smooth muscle actin; Cat. #ab5694, AbCam), anti-PDX1 antibody (1:1000 dilution, Rabbit polyclonal to pancreatic & duodenal homeobox 1; Cat. #06-1379, EMD Millipore), and anti-β-actin antibody (1:4000 dilution, monoclonal anti-β-actin antibody produced in mouse; Cat. #A1978, Sigma Aldrich) as a loading control followed by donkey anti-rabbit (1:15,000 dilution, Cat. #926-32213, Li-Cor) and goat anti-mouse (1:15,000 dilution, Cat. #926-68070, Li-Cor) fluorophore-conjugated secondary antibodies. Antibody-antigen complexes were visualized using Odyssey detection (Li-Cor, Serial No. ODY-2329) at 700 and 800 nm wavelengths.

L. FACS Analysis

Single-cell suspensions of freshly excised tissues were prepared using a gentleMACS Dissociator (Miltenyi Biotec, Auburn, CA) according to the manufacturer's protocol. Single-cell suspensions were prepared in a passive PEB dissociation buffer (IX PBS, pH 7.2, 0.5% BSA, and 2 mM EDTA) and suspensions were passed through 70 µm filters (Cat. #22363548, Fisher Scientific, Pittsburgh, PA). This process removed the majority of cells adhered to the surface (>90%). All tissue and material sample-derived, single-cell populations were then subjected to red blood cell lysis with 5 ml of IX RBC lysis buffer (Cat. #00-4333, eBioscience, San Diego, CA, USA) for 5 min at 4° C. The reaction was terminated by the addition of 20 ml of sterile IX PBS. The cells remaining were centrifuged at 300-400 g at 4° C., and resuspended in a minimal volume (~50 µl) of eBioscience Staining Buffer (cat. #00-4222) for antibody incubation. All samples were then co-stained in the dark for 25 min at 4° C. with two of the fluorescently tagged monoclonal antibodies specific for the cell markers CD68 (1 µl (0.5 µg) per sample; CD68-Alexa647, Clone FA-11, Cat. #11-5931, BioLegend), Ly-6G (Gr-1) (1 µl (0.5 µg) per sample; Ly-6G-Alexa-647, Clone RB6-8C5, Cat. #108418, BioLegend), CD11b (1 µl (0.2 µg) per sample; or CD11b-Alexa-488, Clone M1/70, Cat. #101217, BioLegend), CD19 (1 µl (0.2 µg) per sample; CD19-Alexa-647, Clone HIB19, Cat. #302222, BioLegend), or IgM (1 µl (0.2 µg) per sample; IgM-FITC, Clone RMM-1, Cat. #406505, BioLegend), $CD8^+$ (1 µl (0.2 µg) per sample, BioLegend). Two ml of eBioscience Flow Cytometry Staining Buffer (cat. #00-4222, eBioscience) was then added, and the samples were centrifuged at 400-500 g for 5 min at 4° C. Supernatants were removed by aspiration, and this wash step was repeated two more times with staining buffer. Following the third wash, each sample was resuspended in 500 µl of Flow Cytometry Staining Buffer and run through a 40 µm filter (Cat. #22363547, Fisher Scientific) for eventual FACS analysis using a BD FACSCalibur (cat. #342975), BD Biosciences, San Jose, CA, USA). For proper background and laser intensity settings, unstained, single antibody, and IgG (labeled with either Alexa-488 or Alexa-647, BioLegend) controls were also run.

M. Intravital Imaging

For intravital imaging, human cell-containing hydrogels of 0.5 mm and 1.5 mm sizes were fabricated with Qdot 605 (Life technologies, Grand Island, NY) and surgically implanted into B6A29S6-Ccr6$^{tm1<(EGFP)Irw}$/J mice as described above.

After 14 days post implantation, the mice were placed under isoflurane anesthesia and a small incision was made at the site of the original surgery to expose beads. The mice were placed on an inverted microscope and imaged using a 25×, N.A. 1.05 objective on an Olympus FVB-1000 MP multiphoton microscope at an excitation wavelength of 860 nm. Z-stacks of 200 µm (10 µm steps) were acquired at 2-minute intervals for time series of 20-45 minutes depending on the image. The mice were kept under constant isoflurane anesthesia and monitored throughout the imaging session. Obtained images were analyzed using Velocity 3D Image Analysis Software (Perkin Elmer, Waltham, MA).

N. In Vivo Glucose Challenges (GSIS)

Mice were fasted overnight (12 hours) prior to glucose challenge. On the day of the challenge, fasting blood glucose levels were measured and then mice were injected via tail-vein with a 30 g/L solution of glucose at a dose of 200 mg/kg. Blood glucose was then monitored every 15 minutes for 2 hours.

O. Pancreas Removal and Insulin Quantification

After 174 days, mice treated with human cells encapsulated in TMTD-alginate were euthanized and the pancreas of each mouse removed. Each pancreas was weighed and then placed into vial with a stainless steel ball while keeping samples frozen in liquid nitrogen. A volume of 3 ml of acid ethanol was added to each vial and samples were homogenized on a GenoGrinder at 1000 rpm at 1 min increments until tissue was pulverized. Sample vials are held by aluminum blocks that can be placed in liquid nitrogen between each cycle to keep it cold. Vials were then centrifuged at 2400 rpm at 4° C. for 30 min. The supernatant (now containing insulin) was removed and stored, while the vial is filled with more acid ethanol and vortexed. The vials were left overnight shaking at 4° C. Again, vials were centrifuged at 2400 rpm at 4° C. for 30 min and the supernatant was collected and added to the previously stored supernatant. Acid ethanol was again added to the vials, vortexed, incubated overnight, centrifuged, and supernatant collected and combined. Supernatant solution was evaporated using a Genevac EZ-2 plus. Samples were stored at −80° C. until used. Prior to insulin quantification, samples were resuspended in PBS and quantified using a mouse insulin ELISA kit (Alpco catalog #: 80-INSMS-E10) according to manufacturer's instructions. This same procedure was repeated for healthy, wild type C57BL/6 mice and a STZ treated C57BL/6 mice.

P. Statistical Analysis

Data are expressed as mean±SEM, and N=5 mice per time point and per treatment group. For Rat studies N=3 per treatment. These sample sizes were chosen based on previous literature. All animals were included in analyses except in instances of unforeseen sickness or morbidity. Animal cohorts were randomly selected. Investigators were not blind to performed experiments. FACS data was analyzed for statistical significance either by unpaired, two-tailed t-test, or one-way ANOVA with Bonferroni multiple comparison correction, unless indicated otherwise, as implemented in GraphPad Prism 5; *: $p<0.05$, : $p<0.001$, and *: $p<0.0001$.

Quantified data shown are group mean values±SEM.

II. Results

A. TMTD Alginate Mitigates Immunological Responses to Encapsulated Human Cells.

It has been recently demonstrated that microsphere size can have a beneficial impact on resisting immunological responses to implanted alginates, with spheres of 1.5 mm diameters and larger and TMTD alginates, mitigating fibrotic responses in both rodents and non-human primates (Veiseh et al. in press and Vegas et al. submitted). The chemical structure of TMTD is shown in FIG. 13.

To evaluate the immune responses to these spheres, encapsulated human cells were implanted IP into C57BL/6 mice and were retrieved after 14 days. Cells associated with the outside of the spheres were isolated and analyzed by FACS (FIGS. 14 and 15). Statistically significant lower levels of macrophages, neutrophils, B cells, and CD8+ T cells were measured for TMTD alginate encapsulated human cells (formulation 3) compared to SLG20 controls (formulation 1, 2). Implants retrieved after 80-90 days in STZ-C57BL/6J mice revealed that TMTD alginate spheres had much lower levels of fibrotic deposition. Immunofluorescence staining of these retrieved spheres for cellular deposition (DAPI, F-actin) and myofibroblasts (α-SMA) showed significantly lower levels of cellular deposition on TMTD alginate spheres. Proteomic analysis of these protein extracts detected 18 collagen isoforms, and 10 out of the 18 detected collagen proteins were significantly reduced in TMTD alginate transplants further showing that these materials are able to mitigate fibrotic responses.

Figure 10:
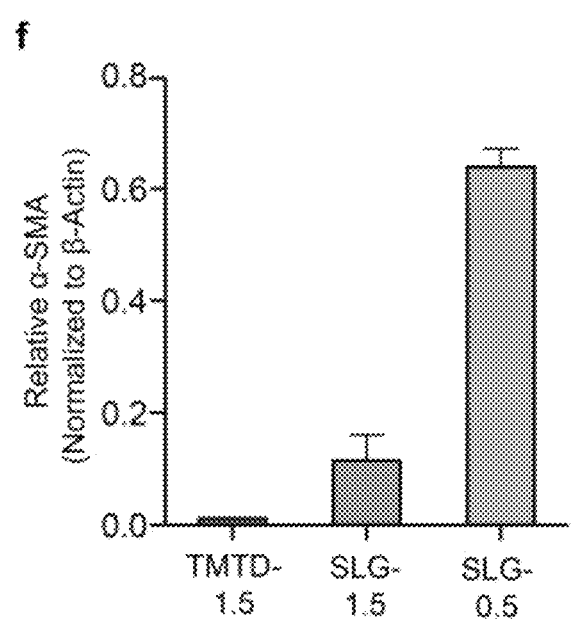
FIG. 10 is a graph of Western blot quantification of α-SMA protein isolated from implants retrieved from the STZ-C57BL/6J.

Western blot quantification of α-SMA protein extracted from the retrieved implants is consistent with lower fibrosis levels on TMTD spheres (FIG. 10).

Finally, consistent with these results, histological processing and immunostaining of TMTD encapsulated human clusters retrieved after over 90 days from STZ-C57BL/6 mice revealed cell clusters with positive co-localized staining of mature human cell markers human insulin and c-peptide. Minimal to no co-localized staining was observed between human c-peptide and glucagon or human insulin and glucagon, consistent with the human cells retaining their differentiation state through the entire study.

The ability of TMTD alginate spheres to provide immunoisolation of the encapsulated human cells was next characterized. Freeze-fracture cryogenic scanning electron microscopy (cryo-SEM) of the spheres display a heterogeneous pore structure with pore sizes ranging from submicron to 1-3 µm in size, a range capable of preventing permeation by cells and large proteins. Intravital imaging of transplanted spheres after 14 days in B6A29S6-Ccr6tm1(EGFP)Irw/J mice (where T, B, and dendritic cells express EGFP) showed localization of CCR6+ cells to regions of spheres containing human cells, but an inability of these cells to make contact and initiate cytotoxic events.

B. Encapsulation of Human Cells with Triazole-Thiomorpholine Dioxide (TMTD) Alginate Enables Glycemic Correction in STZ-C57BL/6J.

To investigate the potential of microencapsulation of human cells to provide glycemic correction, cells were used in three different formulations: (1) 500 μm alginate microcapsules conventionally used for islet encapsulation (Lim et al., Science 210:908-910 (1980); Calafiore et al., Diabetes Care 29:137-138 (2006)), (2) 1.5 mm alginate spheres (Veiseh et al. in press), and (3) 1.5 mm TMTD alginate spheres. Each of these formulations was transplanted in streptozotocin (STZ) treated C57BL/6J mice at three different doses of human cell clusters and evaluated for their ability to restore normoglycemia. Naked, non-encapsulated human cells are unable to provide glycemic correction in this diabetic model regardless of implantation site.

Encapsulation into 500 μm barium alginate microcapsules is a commonly implemented formulation for islet transplantation (Lim et al., Science 210, 908-910 (1980); Calafiore, et al., Diabetes Care 29:137-138, (2006)). Mice transplanted with human cells encapsulated in 500 μm microcapsules showed the lowest levels of glycemic control, with only the highest dose of transplanted clusters able to restore normoglycemia for 15 days. Human cells encapsulated in 1.5 mm alginate spheres performed better than the 500 μm microcapsule formulation with normoglycemia maintained for 20-30 days for the two higher doses, consistent with earlier results obtained using rat islets (Veiseh et al. in press). Sustained normoglycemia was achieved for over 70 days with 1.5 mm TMTD alginate spheres at all three doses tested. Robust human c-peptide levels were measured at 21, 43, and 63 days during the course of this study, consistent with human cell function, with TMTD alginate spheres showing the highest levels of human c-peptide.

C. Encapsulated Human Cells Support Sustained Normoglycemia and Glucose Responsiveness in STZ-C57BL/6J.

To evaluate the capacity of TMTD alginate encapsulated human cell transplants to sustain normoglycemia, a cohort of transplanted diabetic mice was tracked for 6 months. Transplanted mice successfully maintained glycemic correction over the 6-month period, and 5 closely matched the blood glucose levels of wild type C57BL/6J mice tracked over a similar period. In addition, robust human c-peptide levels over 100 pmol/L were recorded at multiple points throughout the study. A glucose challenge was also performed on these mice 150 days post-transplantation, and encapsulated human cells restored normoglycemia comparably to wild type mice. Host pancreas insulin levels for each cohort were also analyzed to confirm the successful STZ treatment and a lack of endogenous pancreas cell regeneration. Human cells implants retrieved after 6 months displayed no signs of fibrotic overgrowth, with little collagenous and cellular deposition evident on the capsule. Since spheres retrieved after 3 months showed minimal levels of fibrosis, this indicates that TMTD alginate mitigates immunological responses by altering the immune recognition/activation kinetics.

The results show that encapsulated human cells can achieve glucose-responsive, long-term glycemic correction (over 170 days) in an immune-competent diabetic animal with no immunosuppression. This result was accomplished by implementing a novel TMTD alginate formulation that mitigates immunological responses to human cell implants, effectively delaying the fibrotic deposition that leads to implant tissue necrosis. This formulation provided sufficient immunoprotection to enable long-term glycemic correction, in spite of the xenogeneic stimulation that these human cells manifest in an immunocompetent rodent recipient. These result support the expectation that human cells encapsulated in the disclosed modified alginates can provide insulin independence for patients suffering from type 1 diabetes. These result support the expectation that human cells encapsulated in the disclosed modified alginates can provide products produced by the encapsulated cells to patients for long periods of time.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a preparation of alginate capsules encapsulating mammalian cells, wherein at least 95% of the capsules in the preparation have a diameter between 1 mm and 4 mm, inclusive, wherein the capsules comprise a singularly modified alginate polymer comprising one or more covalently modified monomers defined by Formula I

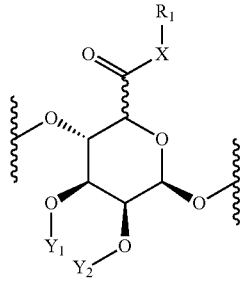

Formula I wherein:

$Y_1$ and $Y_2$ are hydrogen,

—X—$R_1$ is selected from the group consisting of:

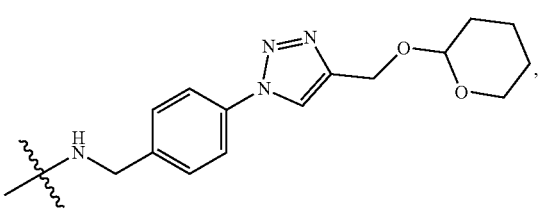

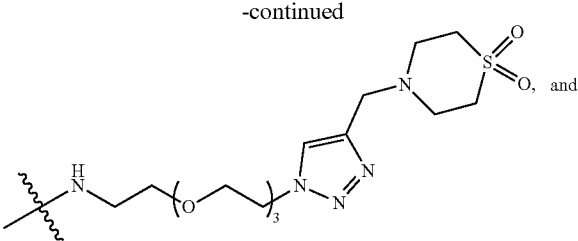, and

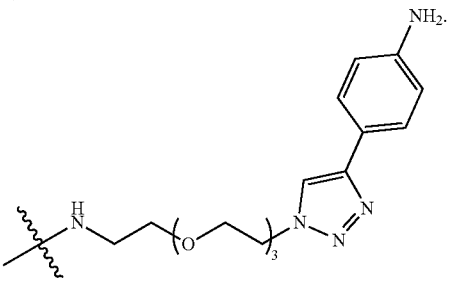

2. The composition of claim 1, wherein —X—$R_1$ is

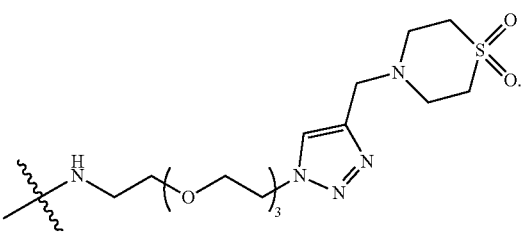

3. The composition of claim 1, wherein the cells comprise stem cells, cells derived from stem cells, cells from a cell line, primary cells, reprogrammed cells, reprogrammed stem cells, cells derived from reprogrammed stem cells, or genetically engineered cells.

4. The composition of claim 1, wherein the cells are neural cells, ganglion cells, retinal epithelial cells, adrenal medulla cells, lung cells, cardiac muscle cells, osteoclast cells, bone marrow cells, spleen cells, thymus cells, glandular cells, blood cells, myogenic cells, keratinocytes, or smooth muscle cells.

5. The composition of claim 1, wherein the cells secrete a therapeutically effective substance.

6. The composition of claim 1, wherein at least 95% of the capsules in the preparation have a diameter of 1 mm to 2 mm, inclusive.

7. The composition of claim 6, wherein the modified alginate polymer is crosslinked ionically.

8. The composition of claim 6, wherein the capsules further comprise an unmodified alginate.

9. The composition of claim 8, wherein at least 95% of the capsules in the preparation have a sphere or sphere-like shape.

10. The composition of claim 9, wherein the cells are genetically engineered to produce a protein or nucleic acid.

11. The composition of claim 10, wherein the protein is a hormone, a growth factor, or an enzyme.

12. The composition of claim 10, wherein the protein is an antigen or an antibody.

13. The composition of claim 10, wherein the protein is a tumor antigen.

14. The composition of claim 10, wherein the protein comprises the antigen binding domain of an antibody.

15. The composition of claim 10, wherein the protein is a blood clotting factor.

16. The composition of claim 10, wherein the protein is an enzyme useful to treat a lysosomal storage disorder.

17. The composition of claim 16, wherein the enzyme is selected from the group consisting of cerebrosidase, beta-hexosaminidase A, alpha-galactosidase, alpha-iduronidase, iduronate sulfatase, an enzyme involved in heparan sulfate degradation, arylsulfatase B, galactose 6-sulfatase, and beta-galactosidase.

18. A method of treating a disease or disorder in a human patient, comprising implanting or transplanting into the human patient a composition according to claim 1.

19. The method of claim 18, wherein the disease is diabetes and the mammalian cells are insulin-producing cells derived from reprogrammed stem cells.

20. The method of claim 18, wherein the disease is hemophilia and the mammalian cells are genetically engineered to produce a blood clotting factor.

21. The method of claim 18, wherein the disease is Fabry disease and the cells are genetically engineered to produce alpha-galactosidase.

22. The method of claim 18, wherein the disease is Hurler syndrome and the cells are genetically engineered to produce alpha-iduronidase.

* * * * *